(12) United States Patent
Tsuruoka et al.

(10) Patent No.: US 7,109,219 B2
(45) Date of Patent: Sep. 19, 2006

(54) NITROGEN-CONTAINING AROMATIC DERIVATIVES

(75) Inventors: Akihiko Tsuruoka, Tsukuba (JP); Tomohiro Matsushima, Ushiku (JP); Masayuki Matsukura, Tsukuba (JP); Kazuki Miyazaki, Tsukuba (JP); Keiko Takahashi, Ushiku (JP); Junichi Kamata, Tsukuba (JP); Yoshio Fukuda, Tsukuba (JP)

(73) Assignee: Eisai Co., Ltd., Tokyo (JP)

( * ) Notice: Subject to any disclaimer, the term of this patent is extended or adjusted under 35 U.S.C. 154(b) by 206 days.

(21) Appl. No.: 10/651,496

(22) Filed: Aug. 29, 2003

(65) Prior Publication Data
US 2005/0187236 A1    Aug. 25, 2005

Related U.S. Application Data

(60) Provisional application No. 60/464,690, filed on Apr. 22, 2003.

(30) Foreign Application Priority Data
Aug. 30, 2002    (JP)    ............................ P2002-253123

(51) Int. Cl.
A61K 31/4439    (2006.01)
C07D 401/12    (2006.01)

(52) U.S. Cl. .................... 514/339; 546/277.4; 514/339

(58) Field of Classification Search ............ 546/277.4; 514/339
See application file for complete search history.

(56) References Cited

FOREIGN PATENT DOCUMENTS

| WO | WO 02/16348 | | 2/2002 |
|---|---|---|---|
| WO | WO- 02/16348 | * | 2/2002 |
| WO | WO 02/32872 | | 4/2002 |
| WO | WO-02032872 | * | 4/2002 |

OTHER PUBLICATIONS

Folkman, J., "What is the Evidence That Tumors are Angiogenesis Dependent?", *Journal of the National Cancer Institute*, 82(1): 4-6, 1990.

Folkman, et al., "Clinical Applications of Research on Angiogenesis", *The New England Journal of Medicine*, 333(26): 1757-1763, 1995.

Folkman, et al., "Angiogenesis", *The Journal of Biological Chemistry*, 267(16): 10931-10934, 1992.

Hayek, et al., "An In Vivo Model for Study of the Angiogenic Effects of Basic Fibroblast Growth Factor", *Biochemical and Biophysical Research Communications*, 147(2): 876-880, 1987.

Jakeman, et al., "Developmental Expression of Binding Sites and Messenger Ribonucleic Acid for Vascular Endothelial Growth Factor Suggests a Role for This Protein in Vasculogenesis and Angiogenesis", *Endocrinology*, 133(2): 848-859, 1993.

* cited by examiner

Primary Examiner—Jospeh K. McKane
Assistant Examiner—Janet L. Coppins
(74) Attorney, Agent, or Firm—Choate, Hall & Stewart LLP; Andrea L. C. Robidoux

(57) ABSTRACT

A compound represented by the general formula:

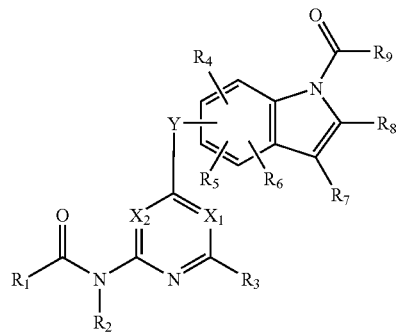

wherein $X_1$ represents a nitrogen atom or a group represented by the formula —$CR_{10}$=; $X_2$ represents a nitrogen atom or a group represented by the formula —$CR_{11}$=; Y represents an oxygen atom or the like; $R_1$ represents a $C_{1-6}$ alkoxy group, an optionally substituted $C_{6-10}$ aryloxy group, a group represented by the formula —$NR_{12a}R_{12b}$ or the like; $R_2$ represents a hydrogen atom, an optionally substituted $C_{1-6}$ alkyl group, or the like; $R_3$, $R_4$, $R_5$, $R_6$, $R_7$, $R_8$, $R_{10}$ and $R_{11}$ each independently represent a hydrogen atom, a halogen atom, an optionally substituted $C_{1-6}$ alkyl group, or the like; $R_9$ represents a group represented by the formula —$NR_{12a}R_{12b}$ or the like; and $R_{12a}$ and $R_{12b}$ each independently represent a hydrogen atom, an optionally substituted $C_{1-6}$ alkyl group, or the like, a salt thereof, or a hydrate of the foregoing.

32 Claims, No Drawings

NITROGEN-CONTAINING AROMATIC DERIVATIVES

This application claims the benefit of U.S. Provisional Application No. 60/464,690, filed Apr. 22, 2003, and Japanese Patent Application No. 2002-253123, filed Aug. 30, 2002, the entire teachings of which are incorporated herein by reference.

DETAILED DESCRIPTION OF THE INVENTION

1. Technical Field to which the Invention Belong

The present invention relates to novel compounds effective for prevention and treatment of various diseases associated with abnormal angiogenesis, and to the medical compositions such as angiogenesis inhibitors and antitumor agents containing the novel compounds.

2. Prior Art

Angiogenesis is an essential biological phenomenon for fetal vascular formation and morphological and functional development of organs. New blood vessels are assembled through several processes including endothelial cell migration, proliferation and tube formation, and the participation of mast cells, lymphocytes, interstitial cells and the like has been shown to be important in this process (non-patent literature 1).

A multiple in vivo angiogenesis-stimulating factors have been identified, particularly Vascular Endothelial Growth Factor (hereinafter abbreviated as "VEGF") and Fibroblast Growth Factor (hereinafter abbreviated as "FGF") are reported to enhance angiogenesis (non-patent literature 2 and 3).

Although physiological angiogenesis occurs at the time of healing of wound or in a female estrous cycle in adult individuals, it is known that pathological increase in angiogenesis in adult individuals is involved in onset or progression of various disease. Specific diseases associated with abnormal angiogenesis include cancer, rheumatoid arthritis, atherosclerosis, diabetic retinopathy, angioma, psoriasis, and the like (non-patent literature 4). In particular, a literature has indicated angiogenesis dependency for solid tumor growth, and angiogenesis inhibitors are therefore promising as new therapeutic agents for intractable solid tumors (non-patent literature 5).

Patent literature 1 and 2 are provided as prior arts with regard to 6-membered nitrogen-containing aromatic derivatives bonded with substituted indole.

Although patent literature 1 describes indole derivatives which suppress VEGF-stimulated angiogenesis based on a selective tyrosine kinase inhibition, the pharmacological test results on their inhibition action are not disclosed. Although patent literature 2 describes pyridine derivatives bonded with indole ring via an oxygen atom at the 4-position, neither the compound according to the present invention nor their inhibiting actions on FGF-stimulated angiogenesis are disclosed.

[patent literature 1] WO 02/16348

[patent literature 2] WO 02/32872

[non-patent literature 1] J. Biol. Chem., 267, 10931, 1992.

[non-patent literature 2] Endocrinology, 133, 848, 1993.

[non-patent literature 3] Biochem. Biophys. Res. Commun., 147, 876, 1987.

[non-patent literature 4] N. Engl. J. Med., 333, 1757, 1995.

[non-patent literature 5] J. Natl. Cancer Inst., 82, 4, 1990.

PROBLEMS TO BE SOLVED BY THE INVENTION

It is an object of the present invention to investigate and discover angiogenesis-inhibiting compounds which: (1) exhibit antitumor activity by strongly suppressing both of angiogenesis included by VEGF and FGF which are major in vivo angiogenesis factors, (2) are highly useful as drug materials in terms of their properties, biokinetics and safety, and (3) are useful for amelioration, prevention and treatment of various diseases associated with abnormal increase in angiogenesis.

MEANS FOR SOLVING THE PROBLEM

As a result of much diligent research in light of the circumstances described above, the present inventors have succeeded in synthesizing novel pyridine derivatives and pyrimidine derivatives represented by the following general formula (I), salts thereof, or hydrates of the foregoing. At the same time, the inventors have completed the present invention upon discovering that these compounds, the salts thereof, or the hydrates of the foregoing exhibit an excellent angiogenesis-inhibiting effect.

Specifically, the present invention provides the followings:

<1> a compound (except N1-cyclopropyl-5-((2-(((2-chloroethylamino)carbonyl)amino)-4-pyridyl)oxy)-1H-1-indolecarboxamide) represented by the general formula:

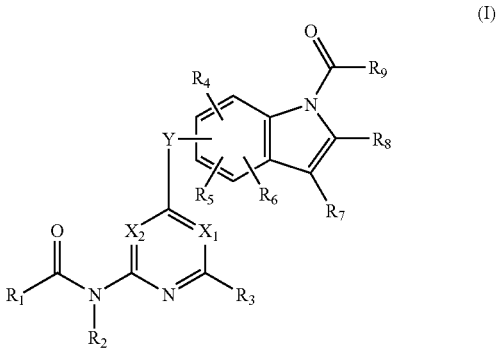

(I)

wherein $X_1$ represents a nitrogen atom or a group represented by the formula $-CR_{10}=$, $X_2$ represents a nitrogen atom or a group represented by the formula $-CR_{11}=$, and $X_1$ and $X_2$ do not represent a nitrogen atom at the same time;

Y represents an oxygen atom, a sulfur atom, a sulfinyl group, a sulfonyl group, or a group represented by the formula $-NR_Y-$ (wherein $R_Y$ represents a hydrogen atom or a $C_{1-6}$ alkyl group);

$R_1$ represents an optionally substituted $C_{1-6}$ alkoxy group, an optionally substituted $C_{6-10}$ aryloxy group, a group represented by the formula $-NR_{12a}R_{12b}$, or a group represented by the formula

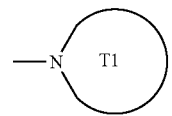

(wherein T1 represents an optionally substituted 5- to 10-membered aromatic heterocycle which may have X in the ring or an optionally substituted 3- to 10-membered heterocycle which may have X in the ring); $R_3$, $R_4$, $R_5$, $R_6$, $R_7$, $R_8$, $R_{10}$ and $R_{11}$ each independently represent a hydrogen atom, a halogen atom, a cyano group, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, a group represented by the formula —CO—$R_{13}$, a group represented by the formula —$NR_{14}$—CO—$R_{13}$, a group represented by the formula —$SO_2$—$R_{15}$, a group represented by the formula —$NR_{14}$—$SO_2$—$R_{15}$, or a group represented by the formula —$NR_{16a}R_{16b}$;

$R_9$ represents a group represented by the formula —$NR_{16a}R_{16b}$ or a group represented by the formula

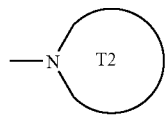

(wherein T2 represents an optionally substituted 5- to 10-membered aromatic heterocycle or an optionally substituted 3- to 10-membered heterocycle);

$R_{12a}$ and $R_{12b}$ each independently represent a hydrogen atom, an optionally substituted $C_{1-6}$ alkyl group, an optionally substituted $C_{3-6}$ alkenyl group, an optionally substituted $C_{3-8}$ cycloalkyl group, an optionally substituted 3- to 10-membered heterocyclic group, or an optionally substituted $C_{1-6}$ alkoxy group; $R_{13}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group, an optionally substituted 3- to 10-membered heterocyclic group, an optionally substituted $C_{1-6}$ alkoxy group, an optionally substituted $C_{6-10}$ aryloxy group, a group represented by the formula —$NR_{12a}R_{12b}$, or a group represented by the formula

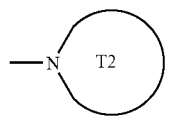

(wherein T2 represents an optionally substituted 5- to 10-membered aromatic heterocycle or an optionally substituted 3- to 10-membered heterocycle); $R_2$ and $R_{14}$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, or a group represented by the formula —CO—$R_{13}$;

$R_{15}$ represents an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group, or an optionally substituted 3- to 10-membered heterocyclic group; $R_{16a}$ and $R_{16b}$ each independently represent a hydrogen atom, an optionally substituted $C_{1-6}$ alkyl group, an optionally substituted $C_{3-6}$ alkenyl group, an optionally substituted $C_{3-6}$ alkynyl group, an optionally substituted $C_{3-8}$ cycloalkyl group, an optionally substituted $C_{6-10}$ aryl group, an optionally substituted 5- to 10-membered heteroaryl group, an optionally substituted 3- to 10-membered heterocyclic group, or an optionally substituted $C_{1-6}$ alkoxy group; and X represents an oxygen atom, a sulfur atom, a carbonyl group, a sulfonyl group, a group represented by the formula —$CR_{X1}R_{X2}$—, or a group represented by the formula —$NR_{X3}$— (wherein $R_{X1}$, $R_{X2}$ and $R_{X3}$ each independently represent a hydrogen atom or a group represented by the formula —$A_1$—$A_2$—$A_3$ (wherein $A_1$ and $A_2$ each independently represent a single bond, an optionally substituted $C_{1-6}$ alkylene group or a carbonyl group; and $A_3$ represents a hydrogen atom, a $C_{3-8}$ cycloalkyl group, a group represented by the formula —$NR_{A1}R_{A2}$, or the formula —$OR_{A3}$ (wherein, $R_{A1}$, $R_{A2}$ and $R_{A3}$ each independently represent a hydrogen atom or a $C_{1-6}$ alkyl group), or an optionally substituted group represented by the formula

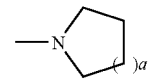

(wherein a represents 1 or 2))), a salt thereof, or a hydrate of the foregoing;

<2> a compound (except N1-cyclopropyl-5-((2-(((2-chloroethylamino)carbonyl)amino)-4-pyridyl)oxy)-1H-1-indole-carboxamide) represented by the general formula:

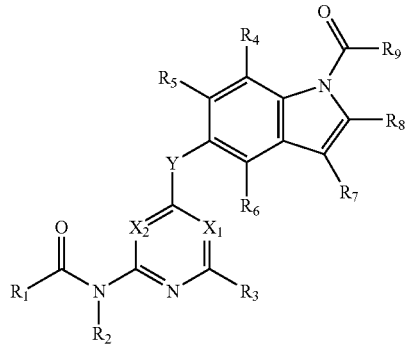

(II)

wherein $X_1$, $X_2$, Y, $R_1$, $R_2$, $R_3$, $R_4$, $R_5$, $R_6$, $R_7$, $R_8$ and $R_9$ represent the same definitions as $X_1$, $X_2$, Y, $R_1$, $R_2$, $R_3$, $R_4$, $R_5$, $R_6$, $R_7$, $R_8$ and $R_9$ in <1>, respectively, a salt thereof, or a hydrate of the foregoing;

<3> a compound according to <1> or <2>, a salt of the compound, or a hydrate of the foregoing, wherein Y represents an oxygen atom;

<4> a compound according to any of <1> to <3>, a salt of the compound, or a hydrate of the foregoing, wherein one of $X_1$ and $X_2$ represents a group represented by the formula —CH= and the other represent a nitrogen atom;

<5> a compound according to any of <1> to <3>, a salt of the compound, or a hydrate of the foregoing, wherein both $X_1$ and $X_2$ represent a group represented by the formula —CH=;

<6> a compound according to any of <1> to <5>, a salt of the compound, or a hydrate of the foregoing, wherein $R_3$, $R_4$, $R_5$, $R_6$ and $R_8$ each represent a hydrogen atom, and $R_7$ represents a hydrogen atom, a halogen atom or an optionally substituted $C_{1-6}$ alkyl group;

<7> a compound according to any of <1> to <6>, a salt of the compound, or a hydrate of the foregoing, wherein $R_9$ represents a group represented by the formula —$NHR_{17}$ (wherein $R_{17}$ represents a $C_{1-6}$ alkyl group, a $C_{3-8}$ cycloalkyl group or a $C_{6-10}$ aryl group);

<8> a compound according to any of <1> to <7>, a salt of the compound, or a hydrate of the foregoing, wherein $R_3$, $R_4$, $R_5$, $R_6$, $R_7$ and $R_8$ each represent a hydrogen atom; <9> a compound according to any of <1> to <8>, a salt of the compound, or a hydrate of the foregoing, wherein $R_2$ represents a hydrogen atom;

<10> a compound according to any of <1> to <9>, a salt of the compound, or a hydrate of the foregoing, wherein $R_9$ represents a group represented by the formula —$NH(CH_3)$;

<11> a compound according to any of <1> to <10>, a salt of the compound, or a hydrate of the foregoing, wherein $R_1$ represents a further optionally substituted group represented by the formula:

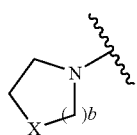

(III)

(wherein b represents 1 or 2; and X represents the same definition as X in <1>);

<12> a compound according to any of <1> to <11>, a salt of the compound, or a hydrate of the foregoing, wherein $R_1$ represents a group represented by the formula:

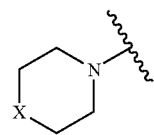

(IV)

(wherein X represents the same definition as X in <1>);

<13> a compound according to <12>, a salt of the compound, or a hydrate of the foregoing, wherein X in the formula (IV) represents an oxygen atom;

<14> a compound according to <12>, a salt of the compound, or a hydrate of the foregoing, wherein X in the formula (IV) represents a group represented by the formula:

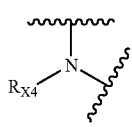

(V)

(wherein $R_{X4}$ represents a hydrogen atom or a group represented by the formula —$A_4$—$A_5$—$A_6$ (wherein $A_4$ and $A_5$ each independently represent a single bond, an optionally substituted $C_{1-6}$ alkylene or a carbonyl group; and $A_6$ represents a hydrogen atom, a $C_{3-8}$ cycloalkyl group or a group represented by the formula —$NR_{44}R_{45}$ or the formula —$OR_{46}$ (wherein $R_{44}$, $R_{45}$ and $R_{46}$ each independently represent a hydrogen atom or a $C_{1-6}$ alkyl group)));

<15> a compound according to <12>, a salt of the compound, or a hydrate of the foregoing, wherein X in the formula (IV) represents a group represented by the formula:

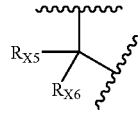

(VI)

(wherein $R_{X5}$ and $R_{X6}$ each independently represent a hydrogen atom or a group represented by the formula —$A_7$—$A_8$—$A_9$ (wherein $A_7$ and $A_8$ each independently represent a single bond, an optionally substituted $C_{1-6}$ alkylene group or a carbonyl group; and $A_9$ represents a hydrogen atom, a $C_{3-8}$ cycloalkyl group, a group represented by the formula —$NR_{47}R_{48}$, or the formula —$OR_{49}$ (wherein $R_{47}$, $R_{48}$, and $R_{49}$ each independently represent a hydrogen atom or a $C_{1-6}$ alkyl group), or a group represented by the formula:

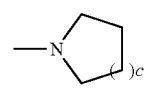

(wherein c represents 1 or 2)));

<16> a compound according to <15>, a salt of the compound, or a hydrate of the foregoing, wherein one of $R_{X5}$ and $R_{X6}$ in the formula (VI) represent a hydroxyl group and the other represents a hydrogen atom or a $C_{1-6}$ alkyl group;

<17> a compound according to <15>, a salt of the compound, or a hydrate of the foregoing, wherein one of $R_{X5}$ or $R_{X6}$ in the formula (VI) represents a hydrogen atom and the other represents a group represented by the formula:

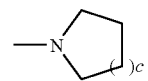

(wherein c represents 1 or 2);

<18> a compound according to any of <1> to <10>, a salt of the compound, or a hydrate of the foregoing, wherein $R_1$ represents a group represented by the formula:

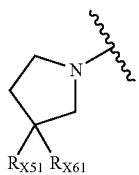

(VII)

wherein $R_{X5}$ and $R_{X6}$ represent the same definitions as $R_{X5}$ and $R_{X6}$ in <15>, respectively;

<19> a compound according to any of <1> to <10>, a salt of the compound, or a hydrate of the foregoing, wherein $R_1$ is a group represented by the formula:

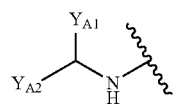

(VIII)

(wherein $Y_{A1}$ and $Y_{A2}$ each independently represent a group represented by the formula —$A_{10}$—$A_{11}$—$A_{12}$ (wherein $A_{10}$ represents a single bond or an optionally substituted $C_{1-6}$ alkylene group; $A_{11}$ represents a single bond, an oxygen atom, a carbonyl group, or a sulfonyl group; and $A_{12}$ represents a hydrogen atom, a $C_{1-6}$ alkyl group, a $C_{6-10}$ aryl group, a group represented by the formula —$NR_{A10}R_{A11}$, or the formula —$OR_{A12}$ (wherein, $R_{A10}$, $R_{A11}$ and $R_{A12}$ each independently represent a hydrogen atom, a $C_{1-6}$ alkyl group or a $C_{3-8}$ cycloalkyl group), or a group represented by the formula:

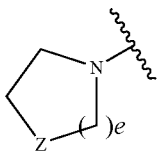

(wherein e represents 1 or 2; and Z represents an oxygen atom or a group represented by the formula —$CR_{X7}R_{X8}$— or the formula —$NR_{X9}$— (wherein $R_{X7}$, $R_{X8}$ and $R_{X9}$ each independently represent a hydrogen atom, a hydroxyl group or a $C_{1-6}$ alkyl group))));

<20> a compound according to <19>, a salt of the compound, or a hydrate of the foregoing, wherein one of $Y_{A1}$ and $Y_{A2}$ in the formula (VIII) represents a hydrogen and the other represents a group represented by the formula —$(CH_2)_2$—$A_{13}$—$A_{14}$ (wherein $A_{13}$ represents a single bond, a carbonyl group or a sulfonyl group; and $A_{14}$ represents a $C_{1-6}$ alkyl group, a group represented by the formula —$NR_{A13}R_{A14}$ (wherein $R_{A13}$ and $R_{A14}$ each independently represent a hydrogen atom, a $C_{1-6}$ alkyl group or a $C_{3-8}$ cycloalkyl group), or a group represented by the formula

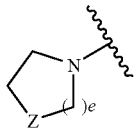

(wherein e and Z represent the same definitions as e and Z in <19>, respectively));

<21> a compound according to any of <1> to <20>, a salt of the compound, or a hydrate of the foregoing, wherein the compound is a compound selected from a group consisting of (1) N1-ethyl-5-(2-((methoxylamino)carbonyl)amino-4-pyrimidyl)oxy-1H-1-indolecarboxamide, (2) 5-(6-(3-(3-diethylaminopropylamino)ureido)pyrimidin-4-yloxy)-1H-indole-1-carboxylic acid methylamide, (3) 5-(6-(((4-hydroxypiperidin-1-yl)carbonyl)amino)-pyrimidin-4-yloxy)-1H-indole-1-carboxylic acid methylamide, (4) 5-(6-((4-pyrrolidin-1-yl)piperidin-1-yl)carbonylamino) pyrimidin-4-yloxy)-1H-indole-1-carboxylic acid methylamide, (5) 5-(2-(3-((1R)-1-carbamoyl-2-phenylethyl)ureido)pyridin-4-yloxy)-1H-indole-1-carboxylic acid methylamide, (6) 5-(2-(3-((1S)-1-carbamoyl-2-phenylethyl)ureido)pyridin-4-yloxy)-1H-indole-1-carboxylic acid methylamide, (7) 5-(2-(3-(2-oxo-2-(pyrrolidin-1-yl)ethyl)ureido)pyridin-4-yloxy)-1H-indole-1-carboxylic acid methylamide, (8) 5-(2-(3-(2-(4-hydroxy-4-methylpiperidin-1-yl)-2-oxoethyl)ureido)pyridin-4-yloxy)-1H-indole-1-carboxylic acid methylamide, (9) 5-(2-(3-((1S)-1-carbamoylethyl)ureido)pyridin-4-yloxy)-1H-indole-1-carboxylic acid methylamide,

(10) 5-(2-(3-((1S)-1-carbamoyl-3-methylbutyl)ureido)pyridin-4-yloxy)-1H-indole-1-carboxylic acid methylamide,

(11) 5-(2-(3-carbamoylmethylureido)pyridin-4-yloxy)-1H-indole-1-carboxylic acid methylamide,

(12) 5-(2-(3-cyclopropylcarbamoylmethylureido)pyridin-4-yloxy)-1H-indole-1-carboxylic acid methylamide,

(13) 5-(2-(3-((1S)-1-carbamoyl-2-hydroxyethyl)ureido)pyridin-4-yloxy)-1H-indole-1-carboxylic acid methylamide,

(14) 5-(2-(3-((1R)-1-carbamoyl-2-hydroxyethyl)ureido)pyridin-4-yloxy)-1H-indole-1-carboxylic acid methylamide,

(15) (2S)-2-(3-(4-(1-methylcarbamoyl-1H-indol-5-yloxy) pyridin-2-yl)ureido)-1,5-pentanedicarboxylic acid diamide,

(16) (2S)-2-(3-(4-(1-methylcarbamoyl-1H-indol-5-yloxy) pyridin-2-yl)ureido)succinamide,

(17) 5-(2-(3-((1S)-1-cyclopropylcarbamoyl-2-hydroxyethyl)ureido)pyridin-4-yloxy)-1H-indole-1-carboxylic acid methylamide,

(18) 5-(2-(3-((1S)-1-hydroxymethyl-2-oxo-2-pyrrolidin-1-ylethyl)ureido)pyridin-4-yloxy)-1H-indole-1-carboxylic acid methylamide,

(19) 5-(2-(3-((1R)-1-hydroxymethyl-2-oxo-2-pyrrolidin-1-ylethyl)ureido)pyridin-4-yloxy)-1H-indole-1-carboxylic acid methylamide,

(20) 5-(2-(3-((1S)-1-hydroxymethyl-2-oxo-2-piperidin-1-ylethyl)ureido)pyridin-4-yloxy)-1H-indole-1-carboxylic acid methylamide,

(21) 5-(2-(3-((1R)-1-hydroxymethyl-2-oxo-2-piperidin-1-ylethyl)ureido)pyridin-4-yloxy)-1H-indole-1-carboxylic acid methylamide,

(22) 5-(2-(3-((1S)-1-hydroxymethyl-2-(4-hydroxypiperidin-1-yl)-2-oxoethyl)ureido)pyridin-4-yloxy)-1H-indole-1-carboxylic acid methylamide,

(23) 5-(2-(3-((1S)-1-hydroxymethyl-2-(morpholin-4-yl)-2-oxoethyl)ureido)pyridin-4-yloxy)-1H-indole-1-carboxylic acid methylamide,

(24) 5-(2-(3-(2-cyclopropylcarbamoylethyl)ureido)pyridin-4-yloxy)-1H-indole-1-carboxylic acid methylamide,

(25) 5-(2-(3-(3-oxo-3-(pyrrolidin-1-yl)propyl)ureido)pyridin-4-yloxy)-1H-indole-1-carboxylic acid methylamide,

(26) 5-(2-(3-(3-(4-hydroxy-4-methylpiperidin-1-yl)-3-oxopropyl)ureido)pyridin-4-yloxy)-1H-indole-1-carboxylic acid methylamide,

(27) N1-ethyl-5-(2-(((2-ethoxyethyl)amino)carbonyl) amino-4-pyridyl)oxy-1H-1-indolecarboxamide,

(28) N1-methyl-5-(2-((4-(2-hydroxy-2-methylpropionyl) piperazino)carbonyl)amino-4-pyridyl)oxy-1H-1-indolecarboxamide,

(29) N1-methyl-5-(2-((3-(diethylamino)propylamino)carbonyl)amino-4-pyridyl)oxy-1H-1-indolecarboxamide,

(30) N1-methyl-5-(2-(((3-(4-hydroxypiperidino)propyl) amino)carbonyl)amino-4-pyridyl)oxy-1H-1-indolecarboxamide,

(31) N1-methyl-5-(2-(((3-(4-methylpiperazino)propyl) amino)carbonyl)amino-4-pyridyl)oxy-1H-1-indolecarboxamide,

(32) 5-(2-(3-(4-oxo-4-(pyrrolidin-1-yl)butyl)ureido)pyridin-4-yloxy)-1H-indole-1-carboxylic acid methylamide,

(33) 5-(2-(3-(cyclopropylcarbamoyl)propyl)ureido)pyridin-4-yloxy)indole-1-carboxylic acid methylamide,

(34) 5-(2-(3-(4-(4-hydroxy-4-methylpiperidin-1-yl)-4-oxobutyl)ureido)pyridin-4-yloxy)-1H-indole-1-carboxylic acid methylamide,
(35) 5-(2-(3-(3-(diethylcarbamoyl)propyl)ureido)pyridin-4-yloxy)-1H-indole-1-carboxylic acid methylamide,
(36) 5-(2-(3-(3-(methylcarbamoyl)propyl)ureido)pyridin-4-yloxy)-1H-indole-1-carboxylic acid methylamide,
(37) N1-methyl-5-(2-(pyrrolidin-1-ylcarbonyl)amino-4-pyridyl)oxy-1H-1-indolecarboxamide,
(38) N1-methyl-5-(2-(piperidin-1-ylcarbonyl)amino-4-pyridyl)oxy-1H-1-indolecarboxamide,
(39) N1-methyl-5-(2-((4-hydroxypiperidino)carbonyl)amino-4-pyridyl)oxy-1H-1-indolecarboxamide,
(40) N1-methyl-5-(2-(4-oxopiperidin-1-ylcarbonyl)amino-4-pyridyl)oxy-1H-1-indolecarboxamide,
(41) 5-(2-(((4-hydroxy-4-methylpiperidin-1-yl)carbonyl)amino)pyridin-4-yloxy)-1H-indole-1-carboxylic acid methylamide,
(42) N1-methyl-5-(2-((4-(1-hydroxy-1-methylethyl)piperidino)carbonyl)amino-4-pyridyl)oxy-1H-1-indolecarboxamide,
(43) 5-(2-(((4-(3-methylcarbamoylpropyl)piperidin-1-yl)carbonyl)amino)pyridin-4-yloxy)-1H-indole-1-carboxylic acid methylamide,
(44) 5-(2-(((4-(3-carbamoylpropyl)piperidin-1-yl)carbonyl)amino)pyridin-4-yloxy)-1H-indole-1-carboxylic acid methylamide,
(45) 5-(2-((4-((pyrrolidin-1-yl)carbonyl)piperidin-1-yl)carbonylamino)pyridin-4-yloxy)-1H-indole-1-carboxylic acid methylamide,
(46) N1-methyl-5-(2-(((4-(pyrrolidin-1-yl)piperidin-1-yl)carbonyl)amino)pyridin-4-yloxy)-1H-1-indolecarboxamide,
(47) N1-methyl-5-(2-(((4-(piperidin-1-yl)piperidin-1-yl)carbonyl)amino)pyridin-4-yloxy)-1H-1-indolecarboxamide,
(48) N1-methyl-5-(2-((4-ethylpiperazino)carbonyl)amino-4-pyridyl)oxy-1H-1-indolecarboxamide,
(49) N1-methyl-5-(2-((4-(2-hydroxyethyl)piperazino)carbonyl)amino-4-pyridyl)oxy-1H-1-indolecarboxamide,
(50) N1-methyl-5-(2-((3-methylsulfonylpropylamino)carbonyl)amino-4-pyridyl)oxy-1H-1-indolecarboxamide,
(51) N1-methyl-5-(2-((4-(2-dimethylaminoacetyl)piperazino)carbonyl)amino-4-pyridyl)oxy-1H-1-indolecarboxamide,
(52) N1-methyl-5-(2-((4-cyclohexylpiperazino)carbonyl)amino-4-pyridyl)oxy-1H-1-indolecarboxamide,
(53) N4-(4-(1-(methylamino)carbonyl-1H-5-indolyl)oxy-2-pyridyl)-4-morpholinecarboxamide,
(54) N1-methyl-5-(2-((1,1-dioxothiomorpholin-4-ylcarbonyl)amino)pyridin-4-yloxy)-1H-1-indolecarboxamide,
(55) 5-(2-(3-((1R)-1-hydroxymethyl-2-oxo-2-pyrrolidin-1-ylethyl)ureido)pyridin-4-yloxy)-1H-indole-1-carboxylic acid ethylamide,
(56) 5-(2-(3-((1S)-1-hydroxymethyl-2-oxo-2-pyrrolidin-1-ylethyl)ureido)pyridin-4-yloxy)-1H-indole-1-carboxylic acid ethylamide,
(57) 5-(2-(3-((1R)-1-hydroxymethyl-2-oxo-2-piperidin-1-ylethyl)ureido)pyridin-4-yloxy)-1H-indole-1-carboxylic acid ethylamide,
(58) 5-(2-(3-((1S)-1-hydroxymethyl-2-oxo-2-piperidin-1-ylethyl)ureido)pyridin-4-yloxy)-1H-indole-1-carboxylic acid ethylamide,
(59) 5-(2-(3-(2-(4-hydroxy-4-methylpiperidin-1-yl)-2-oxoethyl)ureido)pyridin-4-yloxy)-1H-indole-1-carboxylic acid ethylamide,
(60) N1-ethyl-5-(2-((((1-methyl-4-piperidyl)methyl)amino)carbonyl)amino-4-pyridyl)oxy-1H-1-indolecarboxamide,
(61) N1-ethyl-5-(2-(((2-diethylamino)ethyl)amino)carbonyl)amino-4-pyridyl)oxy-1H-1-indolecarboxamide,
(62) N1-ethyl-5-(2-(((2-(morpholin-4-yl)ethyl)amino)carbonyl)amino-4-pyridyl)oxy-1H-1-indolecarboxamide,
(63) N1-ethyl-5-(2-(((2-(4-hydroxypiperidino)ethyl)amino)carbonyl)amino-4-pyridyl)oxy-1H-1-indolecarboxamide,
(64) N1-methyl-5-(2-(((2-(4-hydroxypiperidino)ethyl)amino)carbonyl)amino-4-pyridyl)oxy-1H-1-indolecarboxamide,
(65) N1-ethyl-5-(2-((3-(diethylamino)propylamino)carbonyl)amino-4-pyridyl)oxy-1H-1-indolecarboxamide,
(66) N1-ethyl-5-(2-(((3-(morpholin-4-yl)propyl)amino)carbonyl)amino-4-pyridyl)oxy-1H-1-indolecarboxamide,
(67) N1-ethyl-5-(2-(((3-(4-methylpiperazino)propyl)amino)carbonyl)amino-4-pyridyl)oxy-1H-1-indolecarboxamide,
(68) N1-cyclopropyl-5-(2-(((4-(pyrrolidin-1-yl)piperidin-1-yl)carbonyl)amino)pyridin-4-yloxy)-1H-1-indolecarboxamide,
(69) 5-(2-(3-((1R)-1-hydroxymethyl-2-oxo-2-pyrrolidin-1-ylethyl)ureido)pyridin-4-yloxy)-1H-indole-1-carboxylic acid cyclopropylamide,
(70) 5-(2-(3-((1S)-1-hydroxymethyl-2-oxo-2-pyrrolidin-1-ylethyl)ureido)pyridin-4-yloxy)-1H-indole-1-carboxylic acid cyclopropylamide,
(71) 5-(2-(3-(2-oxo-2-(pyrrolidin-1-yl)ethyl)ureido)pyridin-4-yloxy)-1H-indole-1-carboxylic acid cyclopropylamide,
(72) 5-(2-(3-(3-oxo-3-(pyrrolidin-1-yl)propyl)ureido)pyridin-4-yloxy)-1H-indole-1-carboxylic acid cyclopropylamide,
(73) 5-(2-(3-((1R)-1-hydroxymethyl-2-oxo-2-piperidin-1-ylethyl)ureido)pyridin-4-yloxy)-1H-indole-1-carboxylic acid cyclopropylamide,
(74) 5-(2-(3-((1S)-1-hydroxymethyl-2-oxo-2-piperidin-1-ylethyl)ureido)pyridin-4-yloxy)-1H-indole-1-carboxylic acid cyclopropylamide,
(75) N1-phenyl-5-(2-(((3-(diethylamino)propyl)amino)carbonyl)amino-4-pyridyl)oxy-1H-1-indolecarboxamide,
(76) N1-phenyl-5-(2-(((3-(4-methylpiperazino)propyl)amino)carbonyl)amino-4-pyridyl)oxy-1H-1-indolecarboxamide,
(77) N1-ethyl-5-(2-(((4-(pyrrolidin-1-yl)piperidin-1-yl)carbonyl)amino)pyridin-4-yloxy)-1H-1-indolecarboxamide,
(78) 5-(2-(((4-hydroxy-4-methylpiperidin-1-yl)carbonyl)amino)pyridin-4-yloxy)-1H-indole-1-carboxylic acid ethylamide,
(79) N1-ethyl-5-(2-((4-hydroxypiperidin-1-yl)carbonyl)amino-4-pyridyl)oxy-1H-1-indolecarboxamide,
(80) N1-ethyl-5-(2-(piperidin-1-ylcarbonyl)amino-4-pyridyl)oxy-1H-1-indolecarboxamide,
(81) N1-ethyl-5-((2-((pyrrolidin-1-ylcarbonyl)amino)-4-pyridyl)oxy)-1H-1-indolecarboxamide,
(82) N4-(4-((1-(ethylamino)carbonyl-1H-5-indolyl)oxy-2-pyridyl)-4-morpholinecarboxamide,
(83) N1-ethyl-5-(2-((1,1-dioxothiomorpholin-4-ylcarbonyl)amino)pyridin-4-yloxy)-1H-1-indolecarboxamide,
(84) N1-ethyl-5-(2-((methoxyamino)carbonyl)amino-4-pyridyl)oxy-1H-1-indolecarboxamide,
(85) N1-cyclopropyl-5-(2-((4-hydroxypiperidino)carbonyl)amino-4-pyridyl)oxy-1H-1-indolecarboxamide,
(86) N1-cyclopropyl-5-(2-(((4-hydroxy-4-methylpiperidin-1-yl)carbonyl)amino)pyridin-4-yloxy)-1H-1-indolecarbox-amide,
(87) N4-(4-(1-(cyclopropylamino)carbonyl-1H-5-indolyl)oxy-2-pyridyl)-4-morpholinecarboxamide,
(88) N1-cyclopropyl-5-(2-((pyrrolidin-1-ylcarbonyl)amino)-4-pyridyl)oxy-1H-1-indolecarboxamide,

(89) N1-cyclopropyl-5-(2-(piperidin-1-ylcarbonyl)amino-4-pyridyl)oxy-1H-1-indolecarboxamide,
(90) N4-(4-(1-(cyclopentylamino)carbonyl-1H-5-indolyl)oxy-2-pyridyl)-4-morpholinecarboxamide,
(91) 5-(2-(((4-hydroxypiperidin-1-yl)carbonyl)amino)pyridin-4-yloxy)-1H-indole-1-carboxylic acid cyclopentylamide,
(92) N1-cyclopentyl-5-(2-((4-(pyrrolidin-1-yl)piperidin-1-ylcarbonyl)amino)pyridin-4-yloxy)-1H-1-indolecarboxamide,
(93) N1-(3-methylbutyl)-5-(2-(((4-(pyrrolidin-1-yl)piperidin-1-yl)carbonyl)amino)pyridin-4-yloxy)-1H-1-indolecarboxamide,
(94) N1-(3-methylbutyl)-5-(2-((4-(hydroxypiperidino)carbonyl)amino-4-pyridyl)oxy-1H-1-indolecarboxamide,
(95) N4-(4-(1-((3-methylbutyl)amino)carbonyl-1H-5-indolyl)oxy-2-pyridyl)-4-morpholinecarboxamide,
(96) N1-(1-ethylpropyl)-5-(2-(((4-(pyrrolidin-1-yl)piperidin-1-yl)carbonyl)amino)pyridin-4-yloxy)-1H-1-indolecarboxamide,
(97) N1-(1-ethylpropyl)-5-(2-((4-hydroxypiperidino)carbonyl)amino-4-pyridyl)oxy-1H-1-indolecarboxamide,
(98) N4-(4-(1-((1-ethylpropyl)amino)carbonyl-1H-5-indolyl)oxy-2-pyridyl)-4-morpholinecarboxamide,
(99) N4-(4-(1-((1-pentyl)amino)carbonyl-1H-5-indolyl)oxy-2-pyridyl)-4-morpholinecarboxamide,
(100) N1-(1-pentyl)-5-(2-(((4-hydroxypiperidin-1-yl)carbonyl)amino)pyridin-4-yloxy)-1H-1-indolecarboxamide,
(101) N1-(1-pentyl)-5-(2-((4-(pyrrolidin-1-yl)piperidin-1-ylcarbonyl)amino)pyridin-4-yloxy)-1H-1-indolecarboxamide,
(102) N1-methyl-3-chloro-5-(2-(((3-(diethylamino)propyl)amino)carbonyl)amino-4-pyridyl)oxy-1H-1-indolecarboxamide,
(103) N1-methyl-3-chloro-5-(2-((4-tetrahydro-1H-1-pyrrolylpiperidino)carbonyl)amino-4-pyridyl)oxy-1H-1-indolecarboxamide,
(104) N1-methyl-3-chloro-5-(2-((4-hydroxypiperidino)carbonyl)amino-4-pyridyl)oxy-1H-1-indolecarboxamide,
(105) N1-methyl-3-chloro-5-(2-(((3-(4-hydroxypiperidino)propyl)amino)carbonyl)amino-4-pyridyl)oxy-1H-1-indolecarboxamide,
(106) N1-methyl-3-chloro-5-(2-((4-(2-hydroxyethyl)piperazino)carbonyl)amino-4-pyridyl)oxy-1H-1-indolecarboxamide,
(107) N4-(4-(3-chloro-1-(methylamino)carbonyl-1H-5-indolyl)oxy-2-pyridyl)-4-morpholinecarboxamide,
(108) N1-methyl-3-chloro-5-(2-((4-ethylpiperazino)carbonyl)amino-4-pyridyl)oxy-1H-1-indolecarboxamide,
(109) N1-ethyl-3-chloro-5-(2-((4-hydroxypiperidino)carbonyl)amino-4-pyridyl)oxy-1H-1-indolecarboxamide,
(110) N1-ethyl-3-chloro-5-(2-(((3-(4-hydroxypiperidino)propyl)amino)carbonyl)amino-4-pyridyl)oxy-1H-1-indolecarboxamide,
(111) N1-ethyl-3-chloro-5-(2-(((3-(diethylamino)propyl)amino)carbonyl)amino-4-pyridyl)oxy-1H-1-indolecarboxamide,
(112) N1,3-dimethyl-5-(2-((4-hydroxypiperidino)carbonyl)amino-4-pyridyl)oxy-1H-1-indolecarboxamide,
(113) N1,3-dimethyl-5-(2-((4-tetrahydro-1H-1-pyrrolylpiperidino)carbonyl)amino-4-pyridyl)oxy-1H-1-indolecarboxamide,
(114) N1-cylopropyl-5-(2-((4-hydroxypiperidino)carbonyl)amino-4-pyridyl)oxy-3-methyl-1H-1-indolecarboxamide, and
(115) N1-cylopropyl-5-(2-((4-(2-hydroxyethyl)piperazino)carbonyl)amino-4-pyridyl)oxy-3-methyl-1H-1-indolecarboxamide;

<22> a compound according to any of <1> to <20>, a salt of the compound, or a hydrate of the foregoing, wherein the compound is a compound selected from a group consisting of
(1) 5-(2-(((4-hydroxy-4-methylpiperidin-1-yl)carbonyl)amino)pyridin-4-yloxy)-1H-indole-1-carboxylic acid methylamide,
(2) N1-methyl-5-(2-((4-hydroxypiperidino)carbonyl)amino-4-pyridyl)oxy-1H-1-indolecarboxamide,
(3) N1-methyl-5-(2-(((4-(pyrrolidin-1-yl)piperidin-1-yl)carbonyl)amino)pyridin-4-yloxy)-1H-1-indolecarboxamide,
(4) N1-methyl-5-(2-(((4-(piperidin-1-yl)piperidin-1-yl)carbonyl)amino)pyridin-4-yloxy)-1H-1-indolecarboxyamide, and
(5) N4-(4-(1-(methylamino)carbonyl-1H-5-indolyl)oxy-2-pyridyl)-4-morpholinecarboxamide;

<23> a pharmaceutical composition comprising a compound according to any of <1> to <22> and a pharmaceutical adjuvant;

<24> a prophylactic or therapeutic agent for a disease for which angiogenesis inhibition is effective, comprising as an active ingredient, a compound according to any of <1> to <22>, a salt thereof, or a hydrate of the foregoing;

<25> an angiogenesis inhibitor comprising as an active ingredient, a compound according to any of <1> to <22>, a salt thereof, or a hydrate of the foregoing;

<26> an antitumor agent comprising as an active ingredient, a compound according to any of <1> to <22>, a salt thereof, or a hydrate of the foregoing;

<27> an antitumor agent according to <26>, wherein the tumor is a pancreatic cancer, a gastric cancer, a colon cancer, a breast cancer, a prostate cancer, a lung cancer, a renal cancer, a brain tumor, a blood cancer or an ovarian cancer;

<28> a therapeutic agent for hemangioma comprising as an active ingredient, a compound according to any of <1> to <22>, a salt thereof, or a hydrate of the foregoing;

<29> a cancer metastasis inhibitor comprising as an active ingredient, a compound according to any of <1> to <22>, a salt thereof, or a hydrate of the foregoing;

<30> a therapeutic agent for retinal neovascularization or diabetic retinopathy comprising as an active ingredient, a compound according to any of <1> to <22>, a salt thereof, or a hydrate of the foregoing;

<31> a therapeutic agent for an inflammatory disease comprising as an active ingredient, a compound according to any of <1> to <22>, a salt thereof, or a hydrate of the foregoing;

<32> a therapeutic agent for an inflammatory disease according to <31>, wherein the inflammatory disease is deformant arthritis, rheumatoid arthritis, psoriasis or delayed hypersensitivity reaction;

<33> a therapeutic agent for atherosclerosis comprising as an active ingredient, a compound according to any of <1> to <22>, a salt thereof, or a hydrate of the foregoing;

<34> an angiogenesis inhibition-based antitumor agent comprising as an active ingredient, a compound according to any of <1> to <22>, a salt thereof, or a hydrate of the foregoing;

<35> a prophylactic or therapeutic method for a disease for which angiogenesis inhibition is effective, comprising administering to a patient, a pharmacologically effective dose of a compound according to any of <1> to <22>, a salt thereof, or a hydrate of the foregoing;

<36> use of a compound according to any of <1> to <22>, a salt thereof, or a hydrate of the foregoing for the manufacture of a prophylactic or therapeutic agent for a disease for which angiogenesis inhibition is effective.

The meanings of the terms, symbols or the like used in the specification are described and the present invention is described in detail below.

It should be noted that, although the structural formula of a compound may indicate a certain isomer for convenience's sake in this specification, the present invention include all geometrical isomers generated in the structures of compounds, isomers such as optical isomers based on asymmetric carbon atom, stereoisomers and tautomers, and a mixture of isomers, which are not limited to the descriptions of formulas for convenience's sake, either of isomers or mixtures may be included. Therefore, although optically active compounds and racemic compounds may be existent when they have asymmetric carbon atoms in a molecule, they are not particularly limited in the present invention and any cases are included. In addition, although a variety of crystal morphism are existent, these are not limited similarly. Specifically, any of a single crystal form or mixtures may be included, in addition, anhydrates or hydrates may be included.

In addition, compounds according to the present invention also include compounds which still indicate a desired activity after they are subjected to metabolism such as oxidation, reduction, hydrolysis and conjugation in an organism, and the present invention also include compounds which produce the compounds according to the present invention after they are subjected to metabolism such as oxidation, reduction and hydrolysis.

The term "$C_{1-6}$ alkyl group" as described in the specification represents a linear or branched alkyl group of 1 to 6 carbon atoms, which is a monovalent group derived by removing a hydrogen atom from an aliphatic hydrocarbon of 1 to 6 carbon atoms. As specific examples there may be mentioned methyl group, ethyl group, n-propyl group, i-propyl group, n-butyl group, i-butyl group, sec-butyl group, t-butyl group, n-pentyl group, i-pentyl group, sec-pentyl group, neopentyl group, 1-methylbutyl group, 2-methylbutyl group, 1,1-dimethylpropyl group, 1,2-dimethylpropyl group, n-hexyl group, i-hexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, 1-ethyl-2-methylpropyl group or the like, and preferably methyl group, ethyl group, n-propyl group, i-propyl group, n-butyl group, i-butyl group, sec-butyl group and t-butyl group.

The term "$C_{2-6}$ alkenyl group" as described in the specification represents a linear or branched alkenyl group of 2 to 6 carbon atoms which may contain 1 to 2 double bonds. As specific examples there may be mentioned ethenyl group, 1-propenyl group, 2-propenyl group, 1-butenyl group, 2-butenyl group, 3-butenyl group, 2-methyl-1-propenyl group, pentenyl group, hexenyl group, hexandienyl group or the like, and preferably ethenyl group, 1-propenyl group, 2-propenyl group, 1-butenyl group, 2-butenyl group, 3-butenyl group and 2-methyl-1-propenyl group.

The term "$C_{3-6}$ alkenyl group" as described in the specification represents a linear or branched alkenyl of 3 to 6 carbon atoms which may contain 1 to 2 double bonds. As specific examples there may be mentioned 1-propenyl group, 2-propenyl group, 1-butenyl group, 2-butenyl group, 3-butenyl group, 2-methyl-1-propenyl group, pentenyl group, hexenyl group, hexandienyl group or the like, and preferably 1-propenyl group, 2-propenyl group, 1-butenyl group, 2-butenyl group, 3-butenyl group and 2-methyl-1-propenyl group.

The term "$C_{2-6}$ alkynyl group" as described in the specification represents a linear or branched alkynyl group of 2 to 6 carbon atoms which may contain 1 to 2 triple bonds. As specific examples there may be mentioned ethynyl group, 1-propynyl group, 2-propynyl group, 1-butynyl group, 2-butynyl group, 3-butynyl group, pentynyl group, hexynyl group, hexandiynyl group or the like, and preferably ethynyl group, 1-propynyl group, 2-propynyl group, 1-butynyl group, 2-butynyl group and 3-butynyl group.

The term "$C_{3-6}$ alkynyl group" as described in the specification represents a linear or branched alkynyl group of 3 to 6 carbon atoms which may contain 1 to 2 triple bonds. As specific examples there may be mentioned 1-propynyl group, 2-propynyl group, 1-butynyl group, 2-butynyl group, 3-butynyl group, pentynyl group, hexynyl group, hexandiynyl group or the like, and preferably 1-propynyl group, 2-propynyl group, 1-butynyl group, 2-butynyl group and 3-butynyl group.

The term "$C_{3-8}$ cycloalkyl group" as described in the specification represents a cyclic aliphatic hydrocarbon group of 3 to 8 carbon atoms, and as specific examples there may be mentioned cyclopropyl group, cyclobutyl group, cyclopentyl group, cyclohexyl group, cycloheptyl group, cyclooctyl group or the like, and preferably cyclopropyl group, cyclobutyl group and cyclopentyl group.

The term "$C_{1-6}$ alkylene group" as described in the specification represents a divalent group derived by further removing a hydrogen atom from the aforementioned definition of "$C_{1-6}$ alkyl group." As specific examples there may be mentioned methylene group, ethylene group, methylethylene group, propylene group, ethylethylene group, 1,1-dimethylethylene group, 1,2-dimethylethylene group, tetramethylene group, pentamethylene group, hexamethylene group or the like, and preferably methylene group and ethylene group.

The term "$C_{1-6}$ alkoxy group" as described in the specification represents an oxy group bonded with the aforementioned definition of "$C_{1-6}$ alkyl group." As specific examples there may be mentioned methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, neopentyloxy group, 1-methylbutoxy group, 2-methylbutoxy group, 1,1-dimethylpropoxy group, 1,2-dimethylpropoxy group, n-hexyloxy group, i-hexyloxy group, 1-methylpentyloxy group, 2-menthylpentyloxy group, 3-methylpentyloxy group, 1,1-dimethylbutoxy group, 1,2-dimethylbutoxy group, 2,2-dimethylbutoxy group, 1,3-dimethylbutoxy group, 2,3-dimethylbutoxy group, 3,3-dimethylbutoxy group, 1-ethylbutoxy group, 2-ethylbutoxy group, 1,1,2-trimethylpropoxy group, 1,2,2-trimethylpropoxy group, 1-ethyl-1-methylpropoxy group, 1-ethyl-2-methylpropoxy group or the like, and preferably methoxy group, ethoxy group, n-propoxy group, i-propoxy group, n-butoxy group, i-butoxy group, sec-butoxy group, and t-butoxy group.

The term "$C_{1-6}$ alkylthio group" as described in the specification represents a thio group bonded with the aforementioned definition of "$C_{1-6}$ alkyl group." As specific examples there may be mentioned methylthio group, ethylthio group, n-propylthio group, i-propylthio group, n-buthylthio group, i-buthylthio group, sec-buthylthio group, t-buthylthio group, n-pentylthio group, i-pentylthio group, sec-penthylthio group, neopentylthio group, 1-methylbutylthio group, 2-methylbutylthio group, 1,1-dimethylpropylthio group, 1,2-dimethylpropylthio group, n-hexylthio group, i-hexylthio group, 1-methylpentylthio group, 2-methylpentylthio group, 3-methylpentylthio group, 1,1-dimethylbutylthio group, 1,2-dimethylbutylthio group, 2,2-dimethylbutylthio group, 1,3-dimethylbutylthio group, 2,3-dimethylbutylthio group, 3,3-dimethylbutylthio group, 1-ethylbutylthio group, 2-ethylbutylthio group, 1,1,2-trimethylpropylthio group, 1,2,2-trimethylpropylthio group, 1-ethyl-1-methylpropylthio group, 1-ethyl-2-methylpropylthio group or the like, and preferably methylthio group, ethylthio group, n-propylthio group, i-propylthio group, n-butylthio group, i-butylthio group, sec-butylthio group and t-butylthio group.

The term "$C_{6-10}$ aryl group" as described in the specification represents an aromatic hydrocarbon ring group of 6 to 10 carbon atoms. As specific examples there may be mentioned phenyl group, 1-naphtyl group, 2-naphtyl group, indenyl group, azulenyl group, heptalenyl group or the like, and preferably phenyl group, 1-naphthyl group and 2-naphtyl group.

The term "$C_{6-10}$ aryloxy group" as described in the specification represents an oxy group bonded with the aforementioned definition of "$C_{6-10}$ aryl group." As specific examples there may be mentioned phenoxy group, 1-naphthyloxy group, 2-naphthyloxy group, indenyloxy group, azulenyloxy group, heptalenyloxy group or the like, and preferably phenoxy group, 1-naphthyloxy group and 2-naphthyloxy group.

The term "halogen atom" as described in the specification represents fluorine atom, chlorine atom, bromine atom or iodine atom, and preferably fluorine atom, chlorine atom and bromine atom.

The term "heteroatom" as described in the specification represents nitrogen atom, sulfur atom, or oxygen atom.

The term "5- to 10-membered aromatic heterocycle" as described in the specification represents an aromatic ring in which the number of atoms forming the ring is 5 to 10, and 1 to a plurality of heteroatoms are contained in the atoms forming the ring. Specific examples are pyrrole ring, pyridine ring, pyridazine ring, pyrimidine ring, pyrazine ring, pyrazole ring, imidazole ring, triazole ring, tetrazole ring, indole ring, isoindole ring, indazole ring, quinoline ring, isoquinoline ring, cinnoline ring, quinazoline ring, quinoxaline ring, naphthyridine ring, phthalazine ring, carbazole ring, purine ring, furan ring, thiophene ring, benzimidazole ring, imidazopyridine ring, imidazotriazine ring, pyrrolopyridine ring, pyrrolopyrimidine ring, pyridopyrimidine ring, oxazole ring, isooxazole ring, thiazole ring, isothiazole ring, phenoxazine ring, phenothiazine ring, furopyrrole ring, imidazothiazole ring, benzoxazole ring, benzthiazole ring, pyrazoloxazole ring, pyridoxazine ring, benzofuran ring, benzothiophene ring or the like.

The term "5- to 10-membered heteroaryl group" as described in the specification represents a monovalent group derived by removing a hydrogen atom from the aforementioned definition of "5- to 10-membered aromatic heterocycle."

The term "3- to 10-membered heterocycle" as described in the specification represents, (1) a monocyclic or bicyclic non-aromatic ring (2) having 3 to 10 atoms in the ring, (3) containing 1 to 2 hetero atoms among the atoms of the ring, (4) optionally including 1 to 2 double bonds in the ring, and (5) optionally including 1 to 3 carbonyl groups in the ring.

Specific examples are aziridine ring, azetidine ring, pyrrolidine ring, piperidine ring, homopiperidine ring, piperazine ring, homopiperazine ring, morpholine ring, thiomorpholine ring, pyridone ring, phthalimide ring, succinimide ring or the like, and preferably azetidine ring, pyrrolidine ring, piperidine ring, piperazine ring, morpholine ring and thiomorpholine ring.

The term "3- to 10-membered heterocyclic group" as described in the specification represents a monovalent group derived by removing a hydrogen atom from the aforementioned definition of "3- to 10-membered heterocycle."

The term "optionally substituted" as described in the specification is equivalent in the meaning as in "which may have 1 or a plurality of substitutes by arbitrarily combining them at substitutable positions". As specific examples of such substituents there may be mentioned the following:

(1) a halogen atom, (2) a hydroxyl group, (3) a thiol group, (4) a nitro group, (5) a cyano group, (6) an azido group, (7) a formyl group, (8) a carboxyl group, (9) an amino group, or

(10) a group represented by the formula —$T^1$—$T^2$—T, wherein $T^1$ represents a single bond or a $C_{1-6}$ alkylene group; $T^2$ represents a single bond, a $C_{1-6}$ alkylene group, an oxygen atom, an sulfur atom, a sulfinyl group, a sulfonyl group, a carbonyl group, or a group represented by the formula —O—CO—, the formula —CO—O—, the formula —$NR^{T1}$— the formula —CO—$NR^{T1}$—, the formula —$NR^{T1}$—CO—, the formula —$SO_2$—$NR^{T1}$—, or the formula —$NR^{T1}$—$SO_2$—; $T^3$ each independently represents a hydrogen atom, a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a 5- to 10-membered heteroaryl group, a 3- to 10-membered heterocyclic group or a group represented by the formula —N($R^{T2}$) ($R^{T3}$); $R^{T1}$, $R^{T2}$, or $R^{T3}$ each independently represent a hydrogen atom or a $C_{1-6}$ alkyl group; wherein a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a 5- to 10-membered heteroaryl group and a 3- to 10-membered heterocyclic group in $T^3$ may each independently have 1 to 3 groups selected from a group of the below-mentioned substituent group;

<Substituent Group> a halogen atom, a hydroxyl group, a thiol group, a nitro group, a cyano group, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5- to 10-membered heteroaryl group, a 3- to 10-membered heterocyclic group, a $C_{1-6}$ alkoxy group and a $C_{1-6}$ alkylthio group.

The term "leaving group" as described in the specification may be any group commonly known as a leaving group in organic synthesis, with no special restrictions, and as specific examples there may be mentioned a halogen atom such as a chlorine atom, a bromine atom, an iodine atom; a nitro group; an alkylthio group such as a methylthio group, an ethylthio group and a propylthio group; an arylthio group such as a phenylthio group, a toluylthio group and a 2-pyridylthio group; an alkylsulfonyloxy group such as a methanesulfonyloxy group, a trifluoromethanesulfonyloxy group, an ethanesulfonyloxy group, a propanesulfonyloxy; an arylsulfonyloxy group such as a benzenesulfonyloxy group, a p-toluenesulfonyloxy group; an alkanoyloxy group such as an acetoxy group and a trifluoroacetoxy group; an alkoxy group such as a methoxy group, an ethoxy group and a propoxy group; an alkylamino group such as a methylamino group, an ethylamino group, a propylamino group and a butylamino group; a dialkylamino group such as a dimethylamino group, a diethylamino group, a dipropylamino group, a methylethylamino group, an ethylpropylamino group and a methylpropylamino group; a substituted phosphoryloxy group such as diphenoxyphosphoryloxy group or the like, and preferably a halogen atom such as a chlorine atom, a bromine atom and an iodine atom, a trifluoromethanesulfonyl group or the like.

As a "salt" described in the specification, there may be mentioned, for example, a salt with inorganic acid, a salt with organic acid, a salt with inorganic base, a salt with organic base, a salt with acidic or basic amino acid or the like, preferably a pharmacologically acceptable salt. A slat is formed in an appropriate ratio of 0.1 to 5 molecules of acid or base to one molecule of the compound.

As preferable examples of a salt with inorganic acid, there may be mentioned, for example, a salt with hydrochloric acid, hydrobromic acid, sulfuric acid, nitric acid phosphoric acid, or the like, and as preferable examples of a salt with organic acid, there may be mentioned, for example, a salt with acetic acid, succinic acid, fumaric acid, maleic acid, tartaric acid, citric acid, lactic acid, stearic acid, benzoic acid, methanesulfonic acid, p-toluenesulfonic acid or the like.

As preferable examples of a salt with inorganic base, there may be mentioned, for example, an alkali metal salt such as a sodium salt and a potassium salt, an alkali earth metal salt such as a calcium salt and a magnesium salt, an aluminum salt, an ammonium salt or the like. As preferable examples of a salt with organic base, there may be mentioned, for example, a salt with diethylamine, diethanolamine, meglumine, N,N'-dibenzylethylenediamine or the like.

As preferable examples of a salt with acidic amino acid, there may be mentioned, for example, a salt with aspartic acid, glutamic acid or the like, and as preferable examples of a salt with basic amino acid, there may be mentioned, for example, a salt with arginine, lysine, ornithine or the like.

As a "adjuvant" described in the specification, there may be mentioned, for example, a excipient, a binder, a disintegrator, a lubricant, a coloring agent, a corrective coating, a stabilizer, a emulsifier, a absorbefacient, a surfactant, a pH adjustor, a preservative, an antioxidant or the like.

EMBODIMENT

Production methods for the compounds of the invention will now be described. Various methods may be considered for production of compounds of the invention represented by the general formulas (I) and (II) with synthesis carried out by ordinary organic synthesis means, and the following are representative examples of methods for their production.

[General Synthesis Method]

[Production Method 1]

A typical production method of the compound represented by the formula (Ia)

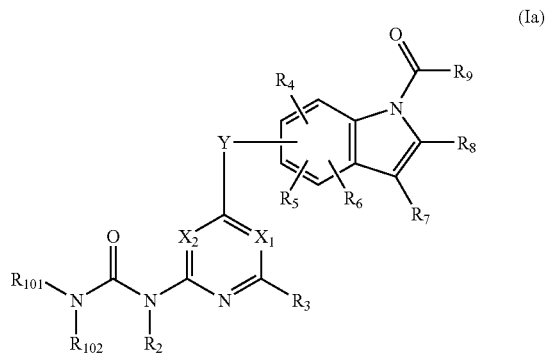

(Ia)

wherein, $R_{101}$, $R_{102}$ may represent the same definitions as the formula $R_{12a}$, $R_{12b}$ ($R_{12a}$ and $R_{12b}$ represent the same definitions as the aforementioned definition), respectively; or $R_{101}$ and $R_{102}$ form a ring, and the formula —$NR_{101}R_{102}$ may represent the same definition as the formula

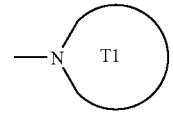

(wherein T1 represents the same definition as the aforementioned definition); other symbols represent the same definitions as the aforementioned definitions.

[Production Method 1-A]

A typical production method of the compound (1e), which is the compounds represented by the formula (Ia), wherein Y represents an oxygen atom, a sulfur atom or a group represented by the formula —$NR_Y$— ($R_Y$ represents a hydrogen atom or a $C_{1-6}$ alkyl group)

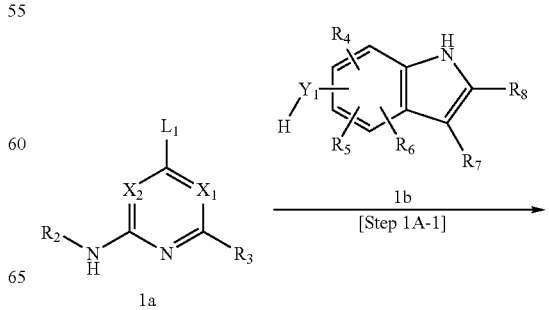

-continued

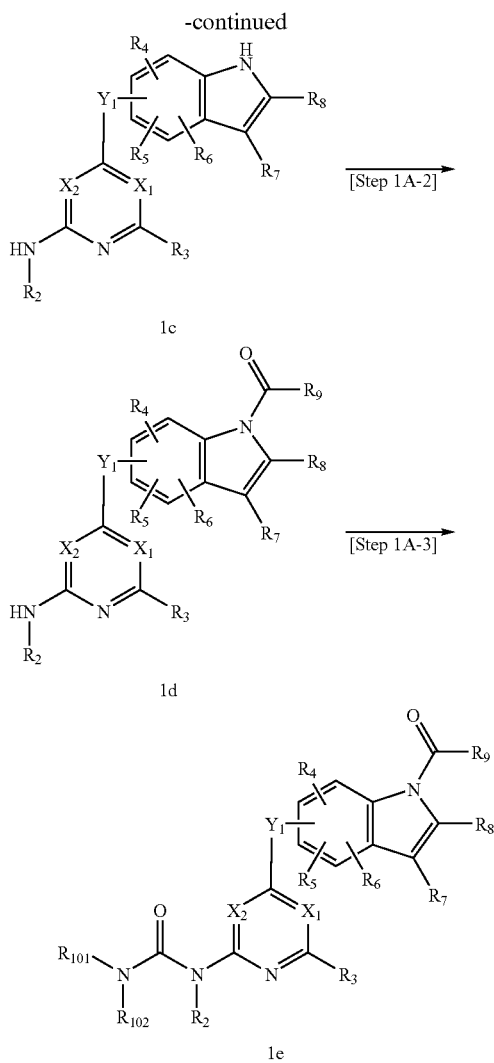

1c

1d

1e wherein, $Y_1$ represents an oxygen atom, a sulfur atom or a group represented by the formula —$NR_{Y'}$— ($R_{Y'}$ represents a hydrogen atom or a $C_{1-6}$ alkyl group); $L_1$ represents a leaving group; other symbols represent the same definitions as the aforementioned definition.

<Step 1A-1>

This is a step for obtaining a compound (1c) by condensing pyrimidine or a pyrimidine derivative (1a) having a leaving group ($L_1$) at the 4-position with an indole derivative (1b). As a reaction solvent, N-methylpyrrolidone, N,N-dimethylformamide, dimethyl sulfoxide, 2-ethoxyethanol, chlorobenzene or the like can be used. A base or an acid may be added thereto, specifically, an organic base such as diisopropylethylamine, an inorganic base such as potassium carbonate, cesium carbonate and sodium hydroxide and an acid such as pyridine hydrochloride and hydrochloric acid can be used. The reaction can be performed at a temperature ranging from room temperature to reflux temperature for a reaction time ranging from 10 minutes to 30 hours. In addition, a compound where a halogen atom which is not as a leaving group is bonded on pyrimidine or pyridine ring may be used as a starting material, and the halogen atom can be reduced by the catalytic reduction method or the like after this step.

<Step 1A-2>

This is a step for obtaining a compound (1d) by carboxyamidating the 1-position of a indole derivative (1c). As a reagent, a carbamate derivative, an isocyanate derivative, a halogenated carbamoyl derivative or the like can be used. As a reaction solvent, chloroform, toluene, N-methylpyrrolidone, N,N-dimethylformamide, dimethyl sulfoxide, chlorobenzene can be used. A base may be added thereto, specifically, an organic base such as pyridine, triethylamine and diisopropylethylamine, an inorganic base such as potassium carbonate, cesium carbonate and sodium hydride can be used, for example. The reaction can be performed for a time of 10 minutes to 30 hours at a temperature of 0° C. to reflux temperature.

<Step 1A-3>

This is a step for converting a compound (1d) into a urea derivative (1e). Carbamate ester derivative is prepared by using phenyl chlorocarbonate or the like as a reagent, for example. After this intermediate is isolated, or not isolated, the intermediate is allowed to react with an amine, thereby a urea derivative can be obtained. Alternatively, by reacting a carbamate derivative or an isocyanate derivative as a reagent, a corresponding urea derivative can be converted into. As a reaction solvent, chloroform, toluene, N-methylpyrrolidone, N,N-dimethylformamide, dimethyl sulfoxide, chlorobenzene or the like can be used. A base may be added thereto, specifically, an organic base such as pyridine, triethylamine, and diisopropylethylamine, an inorganic base such as potassium carbonate, cesium carbonate and sodium hydride can be used, for example. The reaction can be performed for a time of 10 minutes to 30 hours at a temperature of 0° C. to reflux temperature.

It should be noted that a substituent conversion in $R_2$, $R_{101}$, $R_{102}$ can be also performed by suitably using an oxidation reaction, a reduction reaction, a reductive amination reaction, an ester formation reaction, an amide formation reaction, a protecting group introduction reaction, a deprotection reaction, a hydrolysis reaction or the like which are generally used before and/or after each process. Specifically, for example, in the case that $R_2$ is a hydrogen atom in the compounds (1a), (1c) and (1d), the following methods come under the above-mentioned substituent conversions; that is, a method for converting $R_2$ into a $C_{1-6}$ alkyl group by performing a reductive amination reaction with aldehyde or ketone, a method in which, after a corresponding urea derivative is obtained as in <Step 1A-3> from the compound (1c) and an amine having ketone or aldehyde, an amine side chain is introduced into $R_{101}$, $R_{102}$ by further performing a reductive amination reaction with an amine, or the like. In these cases, sodium cyanoborohydride, sodium trimethoxyborohydride or the like can be used as a reducing agent, and methanol, tetrahydrofuran, dichloromethane, dichloroethane or the like can be used as a reaction solvent. In addition, a method that a benzotriazole derivative is prepared and the derivative is reduced by sodium borohydride as reported in Tetrahedron 47, 2683 (1991), or the like is useful. Alternatively, a corresponding urea is formed as in <Step 1A-3> from the compound (1c) and an amine having an ester. After the ester is hydrolyzed by bases such as lithium hydroxide, sodium hydroxide or potassium hydroxide in aqueous ethanol, an amide derivative can be also obtained by using a condensing agent. In this case, N,N-dimethylformamide, tetrahydrofuran or the like can be used as a reaction solvent, and 1-ethyl-3-(3-dimethyl-aminopropyl)carbodiimide hydrochloride, (1H-1,2,3-benzotriazole-1-yloxy)(tri(dimethylamino))phosphonium hexafluorophosphate can be used as a condensing agent. The reaction can be performed for a time of 10 minutes to 30 hours at a temperature of 0° C. to reflux temperature.

[Production Method 1-B]

A production method of the compound (1g), which is the compounds represented by the formula (Ia), wherein Y is a sulfinyl group or a sulfonyl group

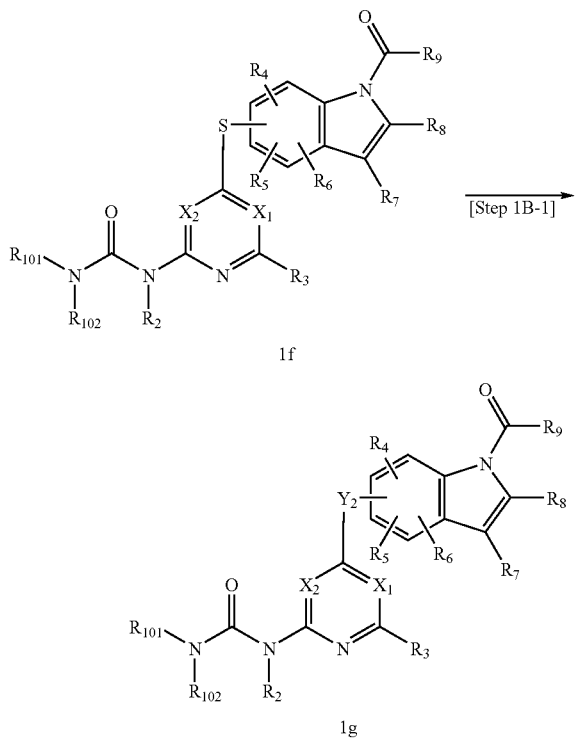

wherein, $Y_2$ represents a sulfinyl group or a sulfonyl group; other symbols represent the same definitions as aforementioned definitions.

<Step 1B-1>

This is a step for oxidation of a compound (1f) to a compound (1g). Hydrogen peroxide, peracetic acid, metha-periodate, 3-chloroperbenzoic acid or the like can be used as an oxidizing agent. Methanol, water, dichloromethane, chloroform or the like can be used as a solvent. The reaction can be performed for a time of 10 minutes to 30 hours at a temperature of 0° C. to reflux temperature.

[Production Method 2]

Another production method of the compound (2c), which is the compound (1c) having a halogen atom, a formyl group, or a cyano group as a substituent at the 3-position in the indole ring

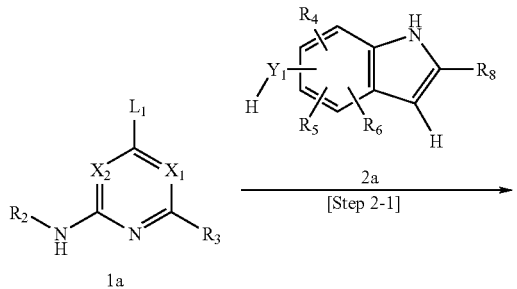

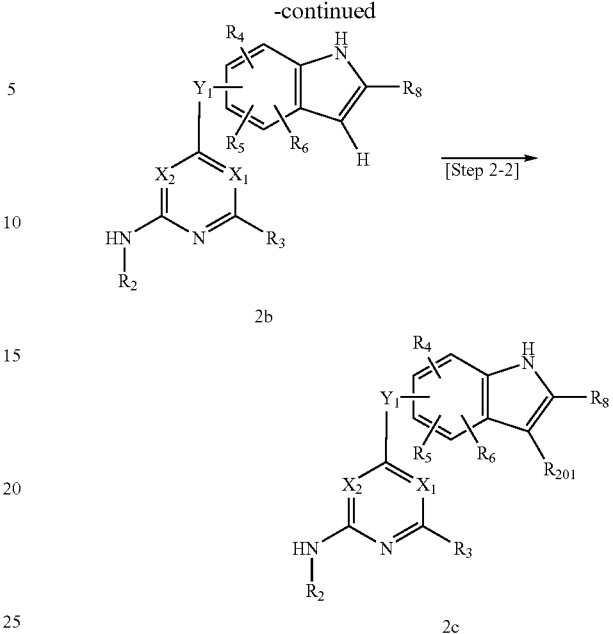

wherein, $R_{201}$ represents a halogen atom, a formyl group or a cyano group; other symbols represent the same definitions as the aforementioned definitions.

<Step 2-1>

This is a step for obtaining a compound (2b) by the condensation of a pyrimidine or pyridine derivative (1a) and a indole derivative (2a) not having a substituent on the 3-position. The compound (2b) can be obtained under the same conditions as <Step 1A-1>.

<Step 2-2>

This is a step in which a substituent is introduced into 3-position of indole in a compound (2b) to obtain a compound substituted at the 3-position of indole (2c). A compound (2c) substituted with a halogen atom, a formyl group, an amino group or the like as the 3-position substituent can be obtained by reacting a compound (2b) with halogenation agents such as N-chlorosuccinimide, N-bromosuccinimide or a mixed reagent of phosphorous oxychloride or thionyl chloride with N,N-dimethylformamide, or after converting the compound into a N-chlorosulfonylcarbamoyl derivative by allowing chlorosulfonyl isocyanate to react with the compound, followed by allowing triethylamine to react with the derivative or the like as reported in Tetrahedron 50, 6549 (1994). As a reaction solvent, 2-propanol, N,N-dimethylformamide, tetrahydrofuran, acetonitrile or the like can be used, and the reaction can be performed for a time of 10 minutes to 30 hours at a temperature of 0° C. to reflux temperature.

[Production Method 3]

Another production method of the compound (1d) via the compounds (3c), (3d), (3g) or (3h)

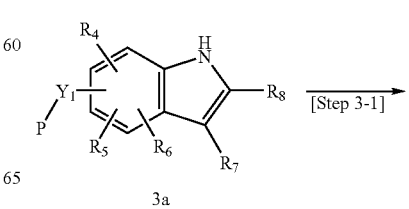

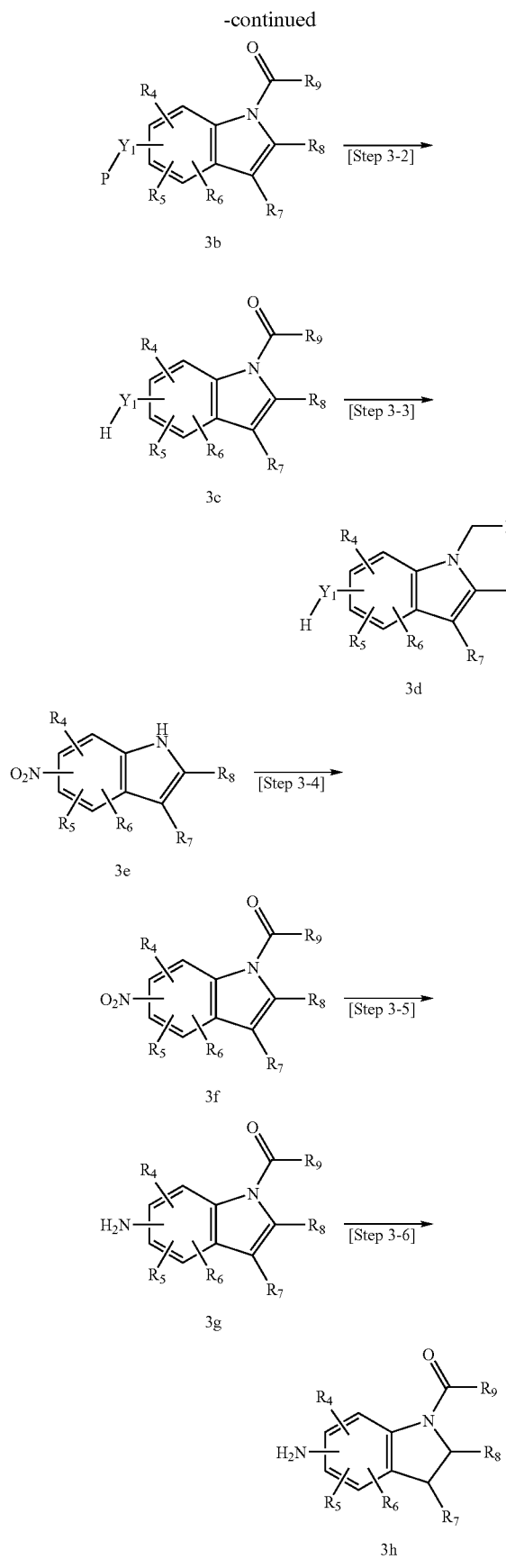

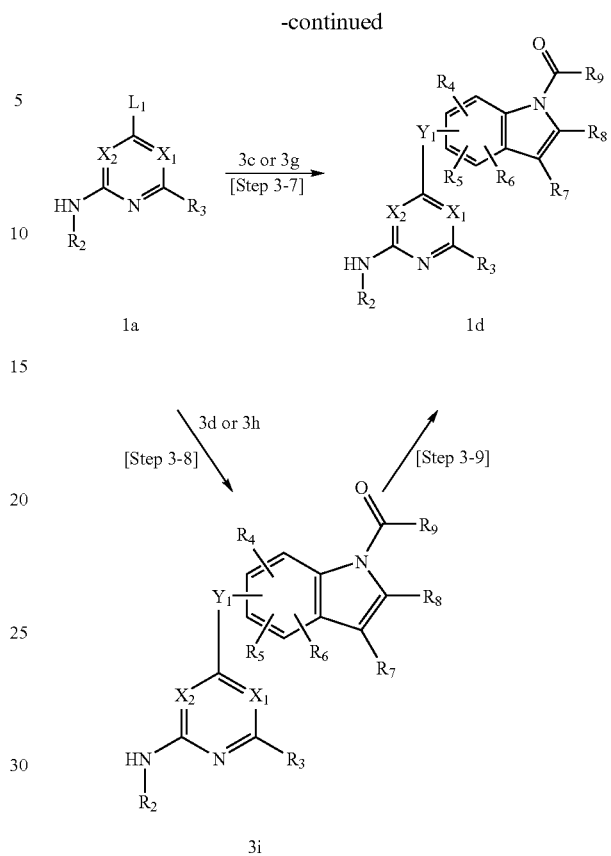

wherein, P represents a protecting group; other symbols represent the same definitions as in the aforementioned definitions.

5<Step 3-1><Step 3-2><Step 3-3>

These are steps for obtaining an indole derivative (3c) or an indoline derivative (3d), both being introduced a carboxamide group at the 1-position, via a compound (3b) from an indole derivative (3a).

<Step 3-1> is a step for conducting carboxamidation of the 1-position of an indole derivative (3a) to obtain a compound (3b), and can be performed in a similar way as <Step 1A-2>. A methyl group, a benzyl group, a substituted benzyl group, a benzyloxycarbonyl group can be used as a protecting group, for example.

<Step 3-2> is a step for obtaining a compound (3c) by deprotecting an indole derivative (3b). Specifically, for example, in the case that $Y_1$ is an oxygen atom, the methods used for ordinal deprotection such as demethylation by using boron tribromide, debenzylation by using trifluoroacetic acid-thioanisole, debenzylation or the debenzyoxycarbonylation by catalytic reduction can be used.

<Step 3-3> is a step for reduction of an indole derivative (3c) to an indoline derivative (3d). Catalytic hydrogenation reaction in the presence of palladium catalyst under ordinal pressure or under pressurization or the like can be applied. Methanol, N,N-dimethylformamide, tetrahydrofuran or the like can be used as a reaction solvent, and the reaction can be performed for a time of 10 minutes to 30 hours at a temperature of 0° C. to reflux temperature.

<Step 3-4><Step 3-5><Step 3-6>

These are steps for obtaining an aminoindole derivative (3g) or an aminoindoline derivative (3h) having a carboxamide group at the 1-position via a compound (3f) from a nitroindole derivative (3e).

<Step 3-4> is a step conducting carboxamidation of the 1-position of a indole derivative (3e) to obtain a compound (3f), and can be performed in the same way as in <Step 1A-2>.

<Step 3-5> is a step for reducing a nitroindole derivative (3f) to an aminoindole derivative (3g). The conditions used for reduction reaction of a nitro group to an amino group generally utilized, specifically, for example, reduction by iron-ammonium chloride or iron-acetic acid or the like, catalytic reduction by palladium hydroxide-hydrogen or the like can be applied. Methanol, ethanol, water, N,N-dimethylformamide, tetrahydrofuran or the like can be used as a reaction solvent, and the reaction can be performed at a temperature of room temperature to reflux temperature for 10 minutes to 30 hours.

<Step 3-6> is a step for reducing an indole derivative (3g) to an indoline derivative (3h) and can be performed in the same way as in <Step 3-3>.

<Step 3-7><Step 3-8>

These are steps for condensing an indole derivative (3c or 3g) or an indoline derivative (3d or 3h) and a compound (1a) to obtain an indole derivative (1d) or an indoline derivative (3i), and can be performed in the same way as in <Step 1A-1>.

<Step 3-9>

This is a step for oxidizing an indoline derivative (3i) to an indole derivative (1d). For example, 2,3-dichloro-5,6-diamino-1,4-benzoquinone (DDQ) or the like can be used as an oxidizing agent, and 1,4-dioxane, toluene, benzene or the like can be used as a solvent. Alternatively, a method in which manganese acetate (III) is used as an oxidizing agent or the like as reported in Tetrahedron Lett. 29, 2151 (1988) can be applied.

In addition, in the case that $Y_1$ is the formula —$NR_Y$— and $R_Y$ is a hydrogen atom in compounds (3g), (3h), (3c) or (3d), a compound (1d), wherein $Y_1$ is the formula —$NR_Y$— and $R_Y$ is a $C_{1-6}$ alkyl group, can be also obtained by converting the hydrogen atom into a $C_{1-6}$ alkyl group by a reductive amination reaction with aldehyde or ketone, and by using these for the respective following reactions. In addition, in the case that $Y_1$ is the formula —$NR_Y$— and $R_Y$ is a hydrogen atom in compounds (3i) or (1d), the compounds can be also similarly converted into the compounds (3i) or (1d), wherein $Y_1$ is the formula —$NR_Y$— and $R_Y$ is a $C_{1-6}$ alkyl group. In this case, sodium cyanoborohydride, sodium trimethoxyborohydride or the like can be used as a reducing agent, and methanol, tetrahydrofuran, dichloromethane, dichloroethane or the like can be used as a reaction solvent. In addition, a method in which a benzotriazole derivative is prepared and is reduced by sodium borohydride as reported in Tetrahedron 47, 2683 (1991) or the like can be applied.

[Production Method 4]

Another production method of the compound (1e)

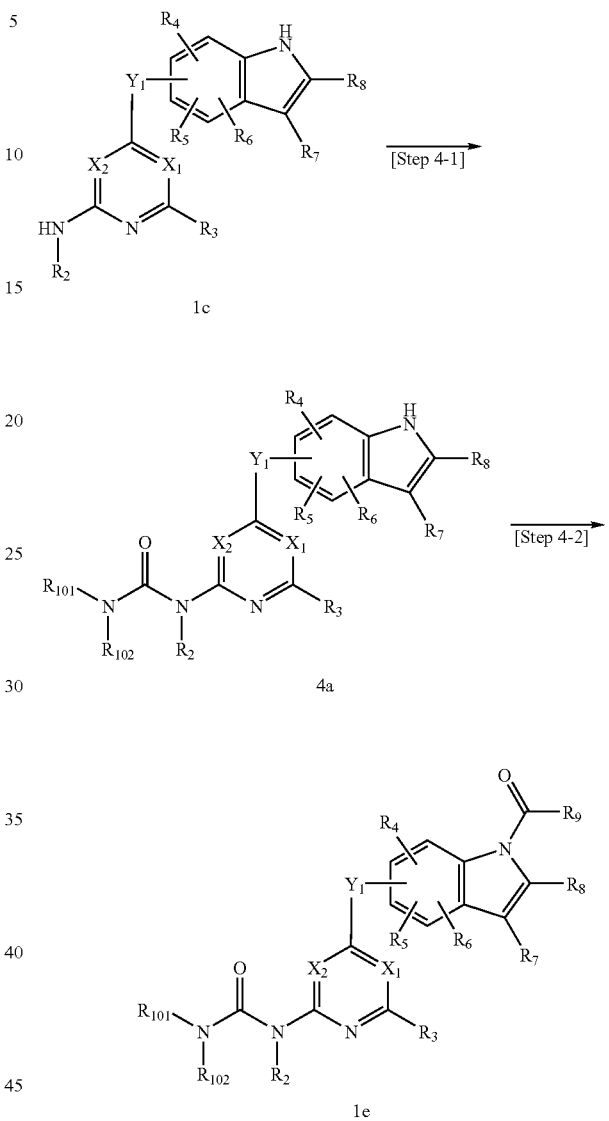

wherein each symbol represents the same definition as the aforementioned definition.

<Step 4-1>

This is a step for converting a compound (1c) to a compound (4a), and can be performed in the same way as in <Step 1A-3>.

<Step 4-2>

This is a step for conducting carboxamidation of the 1-position of an indole derivative (4a) to obtain a compound (1e), and can be performed in the same way as in <Step 1A-2>.

It is to be noted that, as described in [Production method 1-A], a substituent conversion can be also performed in $R_2$, $R_9$, $R_{101}$ and $R_{102}$ by properly performing oxidation reaction, reduction reaction, reductive amination reaction, ester formation reaction, amide formation reaction, protecting group introduction reaction, deprotection reaction, hydrolysis reaction or the like generally utilized after these steps.

[Production Method 5]
Another production method of a compound (1e)

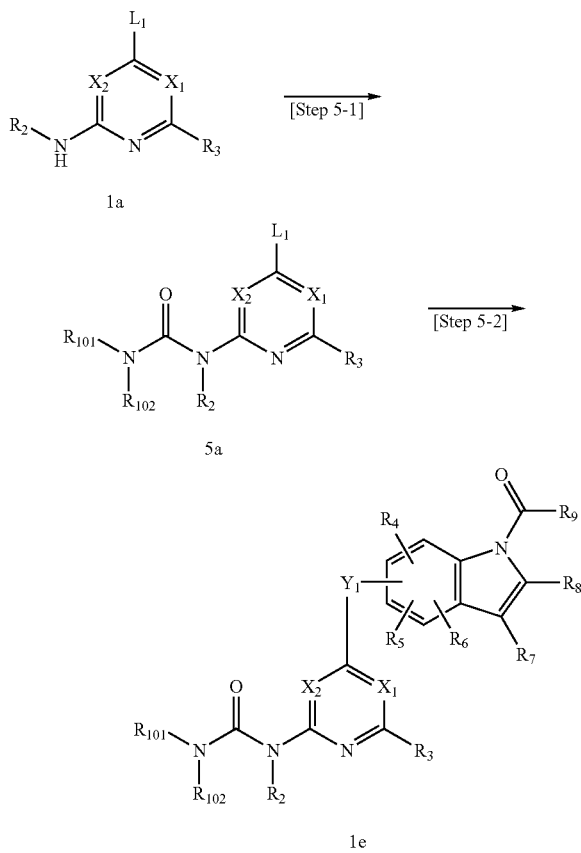

<Step 5-1>

This is a step for converting a pyrimidine or pyridine derivative (1a) into a corresponding urea derivative (5a), and can be performed in the same way as in <Step 1A-3>.

<Step 5-2>

This is a step for obtaining a compound (1e) from a pyrimidine or pyridine derivative (5a) having urea. A method in which the same operations as in <Step 1A-1> and <Step 1A-2> are sequentially performed, a method in which the same operations as in <Step 2-1>, <Step 2-2> and <Step 1A-2> are sequentially performed, a method as in <Step 3-7>, a method in which the same operations as in <Step 3-8> and <Step 3-9> are sequentially performed or the like can be applied.

It is to be noted that, as described in [Production method 1-A], a substituent conversion can be also performed in $R_2$, $R_9$, $R_{101}$ and $R_{102}$ by properly performing oxidation reaction, reduction reaction, reductive amination reaction, ester formation reaction, amide formation reaction, protecting group introduction reaction, deprotection reaction, hydrolysis reaction or the like generally utilized after these steps.

[Production Method 6]
Another manufacturing method of compounds (1c), (1d), (3i)

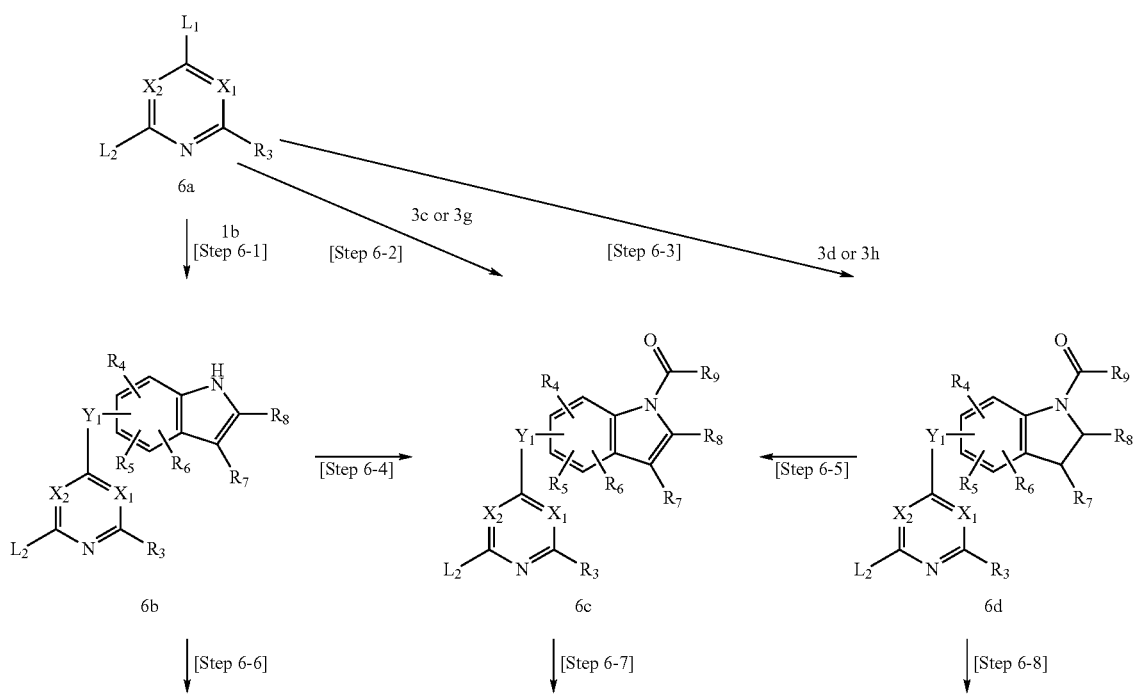

-continued

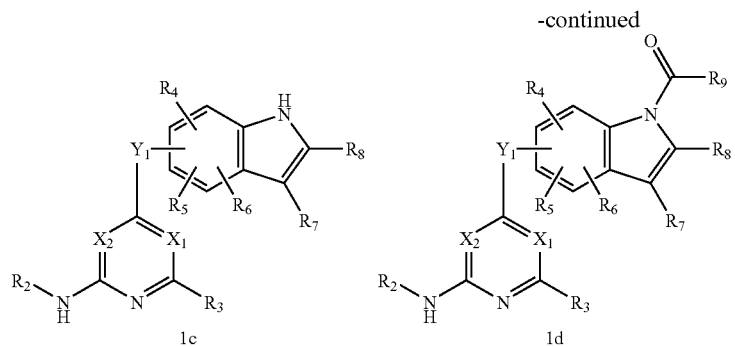

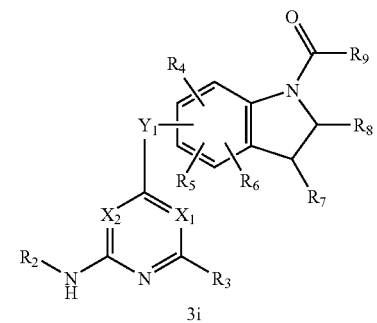

wherein, $L_2$ represents a leaving group; each symbol represents the same definition as the aforementioned definition.

<Step 6-1><Step 6-2><Step 6-3>

These are steps for condensing a pyrimidine or pyridine derivative having leaving groups $L_1$ and $L_2$ and an indole or indoline derivative. In these steps, it is preferable that $L_1$ is a substituent having higher reactivity than that of $L_2$. Specifically, for example, a combination of $L_1$ being a nitro group and $L_2$ being a chlorine atom or the like comes under the category. By using an indole derivative (1b), indole derivatives (3c), (3g) having a carboxamide group at the 1-position, indoline derivatives (3d), (3h) having a carboxamide group at the 1-position, each compound (6b), (6c) and (6d) can be obtained under the same conditions as in <Step 1A-1>.

<Step 6-4>

This is a step for conducting carboxamidation of the 1-position of indole in a compound (6b) to obtain a compound (6c), and can be performed in the same way as in <Step 1A-2>.

<Step 6-5>

This is a step for oxidizing an indoline derivative (6d) to an indole derivative (6c). The same method as in <Step 3-9> can be used.

<Step 6-6><Step 6-7><Step 6-8>

These are steps in which the leaving group $L_2$ of pyrimidine or pyridine derivatives (6b), (6c), or (6d) is converted into a group represented by the formula —$NHR_2$, wherein $R_2$ represents the same definition as the aforementioned definition, to obtain compounds (1c), (1d), or (3i), respectively. For example, an ammonia-ethanol solution or a corresponding primary amine is used, and the reaction can be performed in a sealed tube for a time of 10 minutes to 100 hours at a temperature of 60° C. to reflux temperature.

[Production Method 7]

Another production method of a compound (7j), which is the compound represented by the formula (Ia), wherein Y is an oxygen atom and both 2- and 3-positions of indole ($R_8$, $R_7$) are hydrogen atoms

[Production Method 7-A]

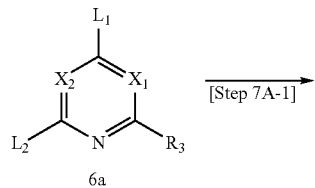

-continued

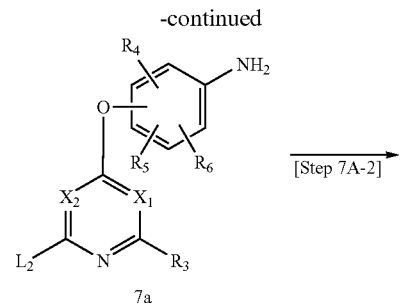

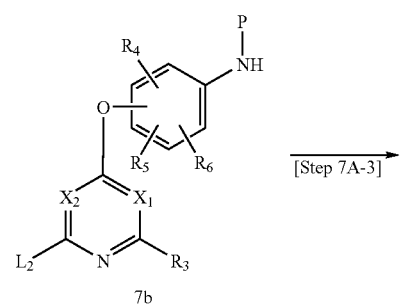

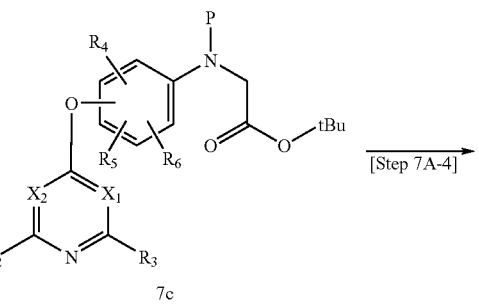

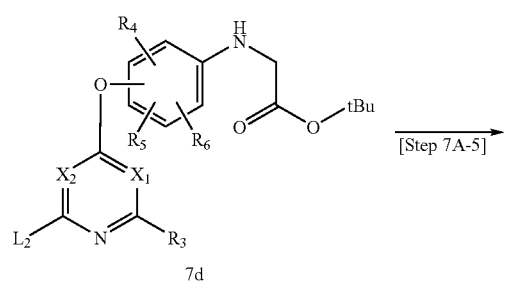

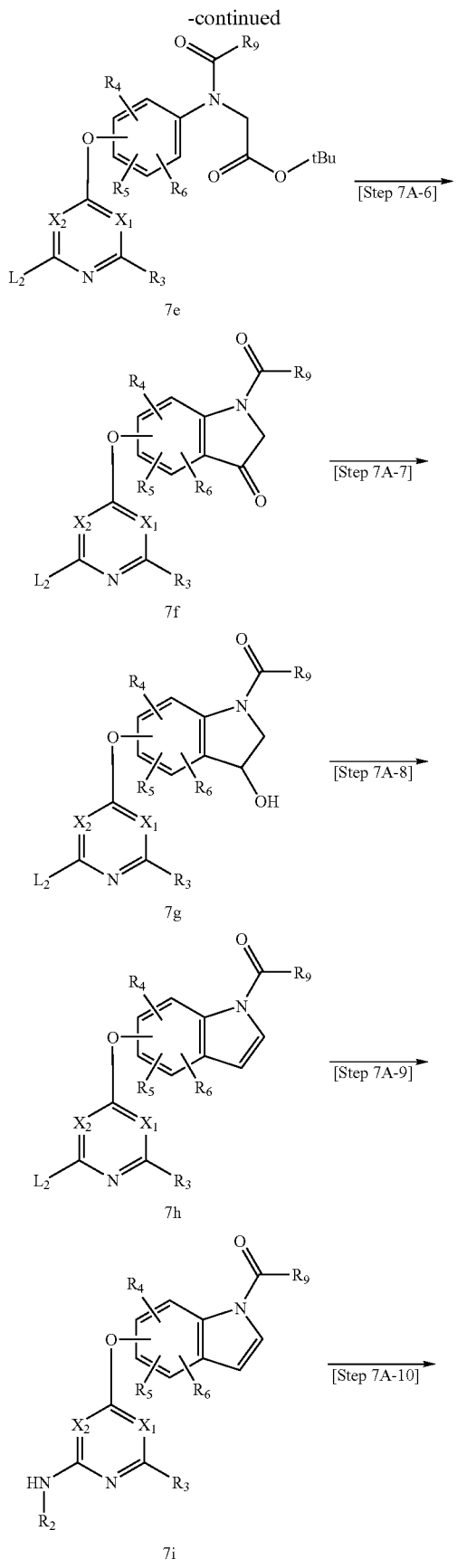

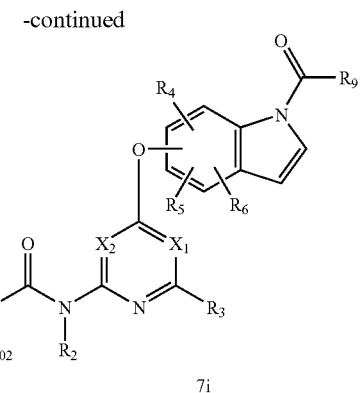

wherein each symbol represents the same definition as the aforementioned definition.

<Step 7A-1>

This is a step for obtaining a compound (7a) by introducing an aminophenoxy group into a compound (6a). It is preferable that in the compound (6a), $L_1$ is a substituent having higher reactivity than that of $L_2$. Specifically, for example, a combination of $L_1$ being a nitro group and $L_2$ being a chlorine atom comes under the category. A compound (7a) can be obtained by using a compound (6a) and an aminophenol derivative in the same method as in <Step 1A-1>. In addition, after these compounds are condensed by using a nitrophenol derivative in the same way as in <Step 1A-1>, a method for reducing a nitro group by catalytic hydrogenation reaction using palladium catalyst or the like, or metal reduction reaction using iron-ammonium chloride, iron-acetic acid or the like can be applied. In the reduction reaction of the nitro group, methanol, ethanol, tetrahydrofuran, N,N-dimethylformamide or the like can be used as a reaction solvent, and the catalytic hydrogenation reaction can be performed at ordinary pressure or under pressurization. The reaction can be performed at a temperature of room temperature to reflux temperature for 10 minutes to 30 hours.

<Step 7A-2>

This is a step for protecting amino group of a compound (7a) to obtain a compound (7b). As a protecting group, for example, a benzyloxycarbonyl group or the like can be introduced by using a corresponding chlorocarbonate ester.

<Step 7A-3>

This is a method for obtaining a compound (7c) from a compound (7b). t-Butyl bromoacetate ester as a reagent, sodium hydroxide or the like as a base, N,N-dimethylformamide, tetrahydrofuran, dimethyl sulfoxide or the like as a reaction solvent can be used. The reaction can be performed at a temperature of room temperature to reflux temperature for 10 minutes to 30 hours.

<Step 7A-4>

This is a step for deprotecting a compound (7c) to obtain a compound (7d). There may be mentioned, for example, deprotection reaction by the catalytic hydrogenation reaction of benzyloxycarbonyl group or the like.

<Step 7A-5>

This is a step for obtaining a compound (7e) by introducing a carboxamide group to a compound (7d). As a reagent, an isocyanate derivative, a carbamate derivative or the like can be used. As a reaction solvent, N,N-dimethylformamide, tetrahydrofuran, dimethyl sulfoxide, toluene or the like can be used, and organic bases such as triethylamine or pyridine can be added thereto as requested. The reaction can be performed for a time of 10 minutes to 30 hours and at a temperature of 0° C. to reflux temperature.

<Step 7A-6>

This is a step for obtaining a compound (7f) from a compound (7e) by cyclization reaction. The reaction is performed in an acidic condition, specifically, for example, in trifluoroacetic acid-trifluoroacetic anhydride or the like. The reaction can be performed for a time of 10 minutes to 30 hours and at a temperature of 0° C. to reflux temperature.

<Step 7A-7><Step 7A-8>

These are steps for converting into an indole derivative (7h) via a compound (7g) from a 3-oxoindoline derivative (7f). A 3-hydroxyindoline derivative (7g) is prepared by reduction of a carbonyl group using sodium borohydride as a reagent, in tetrahydrofuran, methanol, ethanol or the like as a reaction solvent, thereafter a compound (7h) can be obtained by performing dehydration by using camphor sulfonic acid or the like as a reagent, and toluene, dichloroethane or the like as a reaction solvent.

<Step 7A-9><Step 7A-10>

Thereafter, it is possible to lead to a step in which a compound (7j) is prepared under the same conditions in each of <Step 6-6>, <Step 1A-3>

[Production Method 7-B]

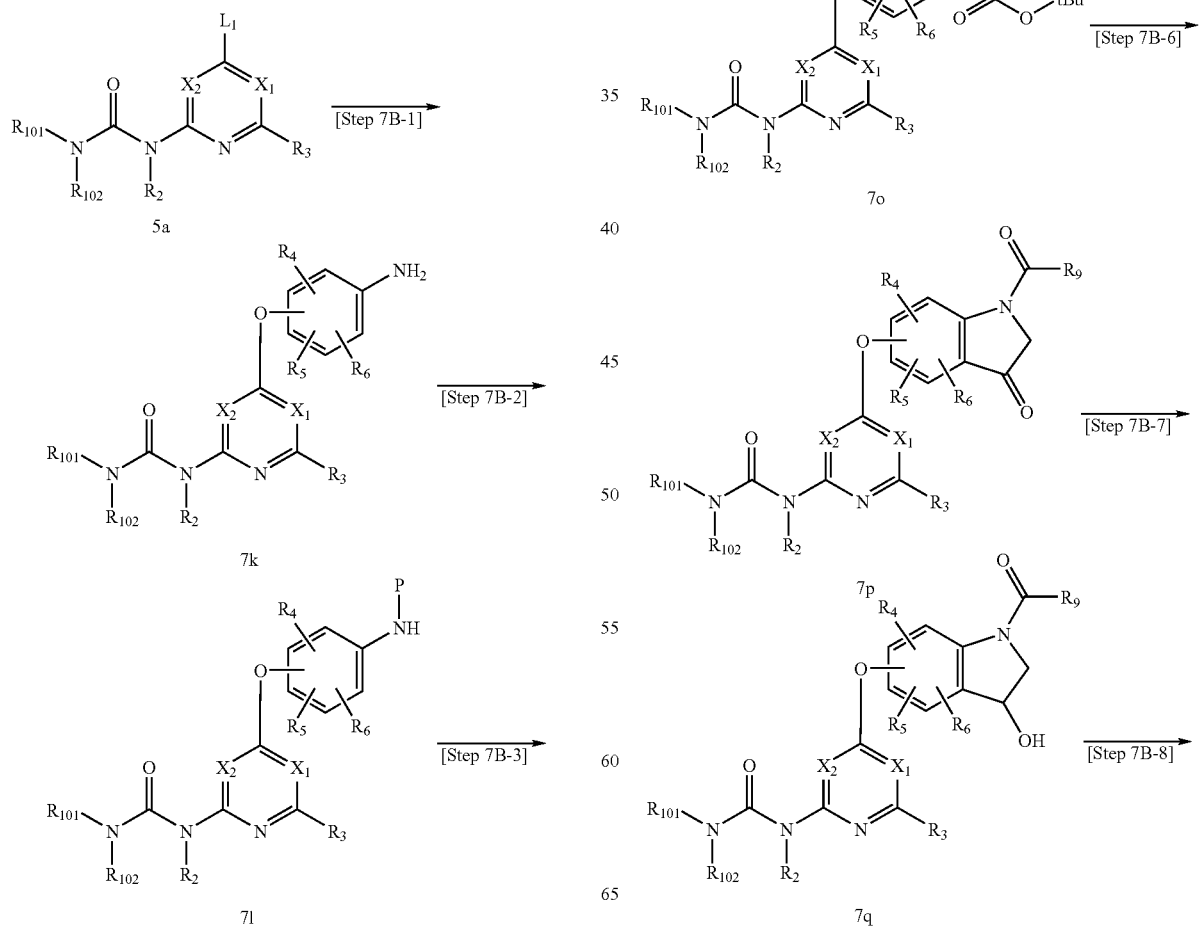

-continued

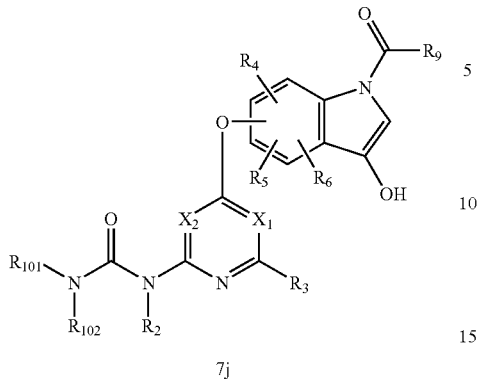

7j wherein, each symbol represents the same definition as the aforementioned definition.

<Step 7B-1>

This is a step for obtaining a compound (7k) from a compound (5a), and can be performed in the same way as in <Step 7A-1>.

<Step 7B-2>

This is a step for protecting an amino group of a compound (7k) to obtain a compound (7l), and can be performed in the same way as in <Step 7A-2>.

15<Step 7B-3>

This is a method for obtaining a compound (7m) from a compound (7l), and can be performed in the same way as in <Step 7A-3>.

<Step 7B-4>

This is a step for deprotecting a compound (7m) to obtain a compound (7n), and can be performed in the same way as in <Step 7A-4>.

<Step 7B-5>

This is a step for introducing a carboxamide group to a compound (7n) to obtain a compound (7o), and can be performed in the same way as in <Step 7A-5>.

<Step 7B-6>

This is a step for obtaining a cyclized compound (7p) from a compound (7o), and can be performed in the same way as in <Step 7A-6>.

<Step 7B-7><Step 7B-8>

These are steps for converting into an indole derivative (7j) via a compound (7q) from a 3-oxoindoline derivative (7p), and can be performed in the same as in <Step 7A-7><Step 7A-8>.

[Production Process 8]

Another production method of a compound (8g), which is the compound represented by the formula (Ia), wherein both 2- and 3-positions of indole ($R_8$, $R_7$) are hydrogen atoms

[Production Method 8-A]

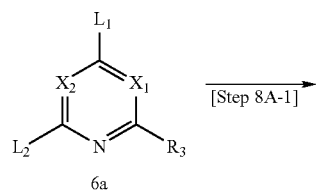

6a

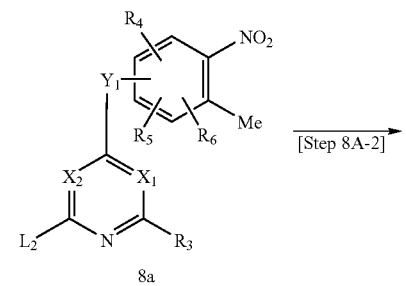

8a

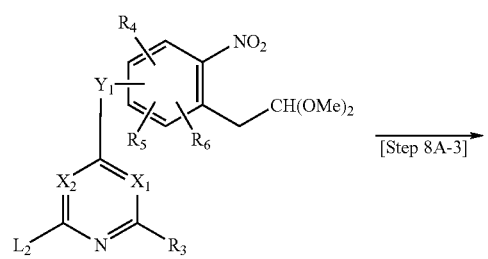

8b

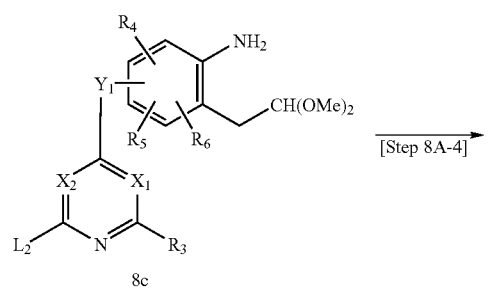

8c

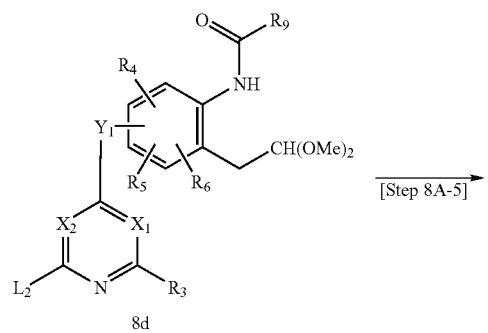

8d

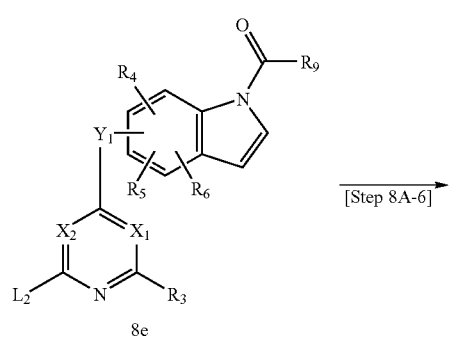

8e

-continued

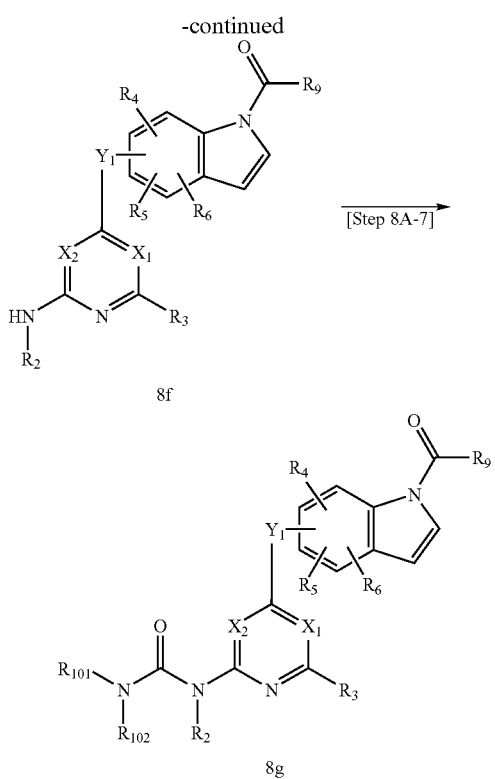

wherein, each symbol represents the same definition as the aforementioned definition.

<Step 8A-1>
This is a coupling reaction of a compound (6a) with a nitrobenzene derivative. A compound (8a) can be obtained under the same conditions as in <Step 1A-1>.

<Step 8A-2>
This is a step for obtaining a compound (8b) from a compound (8a). The reaction can be performed under the conditions as described in Tetrahedron Lett. 39, 71 (1998). Specifically, a dimethylacetal compound can be derived by condensing a nitrotoluene derivative and dimethylformamide dimethylacetal in N,N-dimethylformamide at a temperature of room temperature to reflex temperature for 10 minutes to 30 hours, and by sequentially performing the reaction of the compound in methanol under acidic condition at a temperature of room temperature to reflex temperature for 10 minutes to 30 hours.

<Step 8A-3>
This is a step for reducing a compound (8b) to a compound (8c). Reduction by iron-ammonium chloride, iron-acetic acid or the like can be used. As a reaction solvent, methanol, ethanol, tetrahydrofuran, N,N-dimethylformamide or the like can be used. The reaction can be performed at a temperature of room temperature to reflux temperature for 10 minutes to 30 hours.

<Step 8A-4>
This is a step for converting a compound (8c) into a urea derivative to obtain a compound (8d), and can be performed in the same way as in <Step 7A-5>. Alternatively, tetrahydrofuran or N,N-dimethylformamide is used as a reaction solvent, for example, after a carbamate derivative is prepared by using phenyl chlorocarbonate or the like, and urea can be also introduced by allowing the derivative to react with an amine at a temperature of room temperature to reflux temperature for 10 minutes to 30 hours, while N,N-dimethylformamide, dimethyl sulfoxide are used as a reaction solvent.

<Step 8A-5>
This is a step for cyclizing a compound (8d) to obtain a compound (8e). The reaction can be performed under the conditions as described in Tetrahedron Lett. 39, 71 (1998). Specifically, there may be mentioned a method in which reflux is performed in solvents such as benzene in the presence of catalytic amounts of camphor sulfonic acid and quinoline.

<Step 8A-6>
This is a step for obtaining a compound (8f) from a compound (8e), and can be performed in the same way as in <Step 6-6>.

<Step 8A-7>
This is a step for obtaining a compound (8g) from a compound (8f), and can be performed in the same way as in <Step 7A-10>.

[Production Method 8-B]

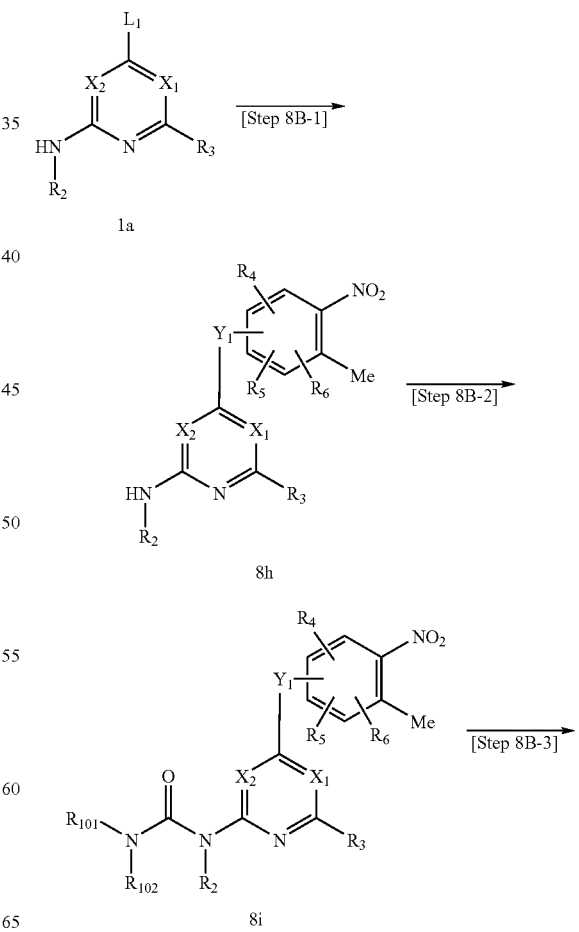

-continued

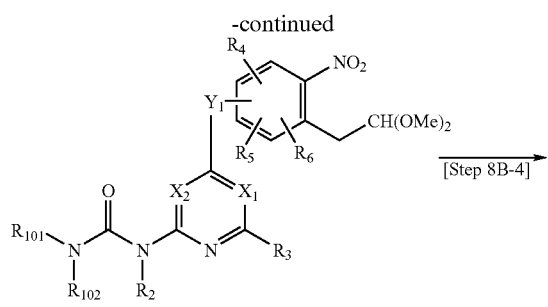

8j

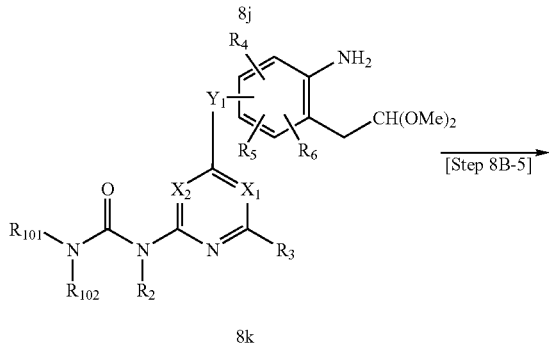

8k

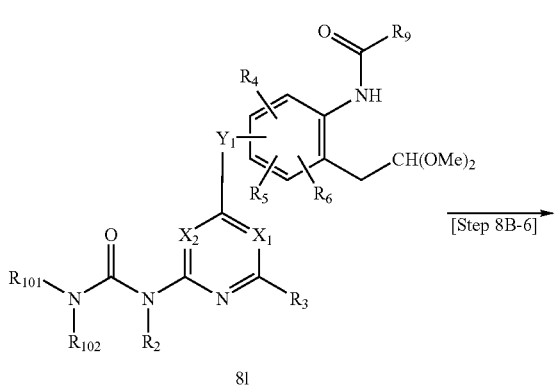

8l

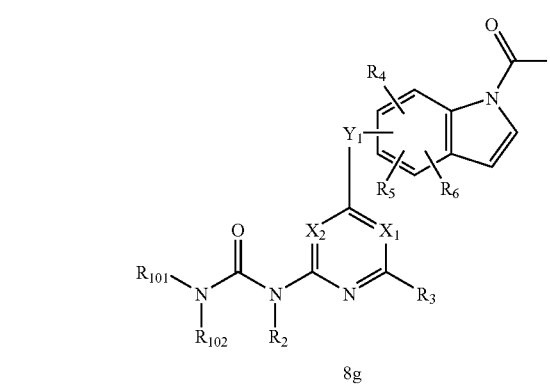

8g wherein, each symbol represents the same definition as in the aforementioned definition.

<Step 8B-1>

This is a step for obtaining a compound (8h) by performing coupling reaction of a compound (1a) with a nitrobenzene derivative, and can be performed in the same way as in <Step 1A-1>.

<Step 8B-2>

This is a step for introducing urea to a compound (8h) to obtain a compound (8i), and can be performed in the same way as in <Step 1A-3>.

<Step 8B-3>

This is a step for condensing a nitrotoluene derivative (8i) and dimethylformamide dimethylacetal, subsequently, for deriving the compound to dimethylacetal compound (8j). The step can be performed in the same way as in <Step 8A-2>.

<Step 8B-4>

This is a step for reducing a nitro group of a compound (8j) to obtain a compound (8k), and can be performed in the same way as in <Step 8A-3>.

<Step 8B-5>

This is a step for obtaining a compound (8l) from a compound (8k) by introducing urea, and can be performed in the same way as in <Step 8A-4>.

<Step 8B-6>

This is a step for cyclizing a compound (8l) to obtain a compound (8g), and can be performed in the same way as in <Step 8A-5>.

[Production Method 9]

Another production method of a compound (7j)

[Production Method 9-A]

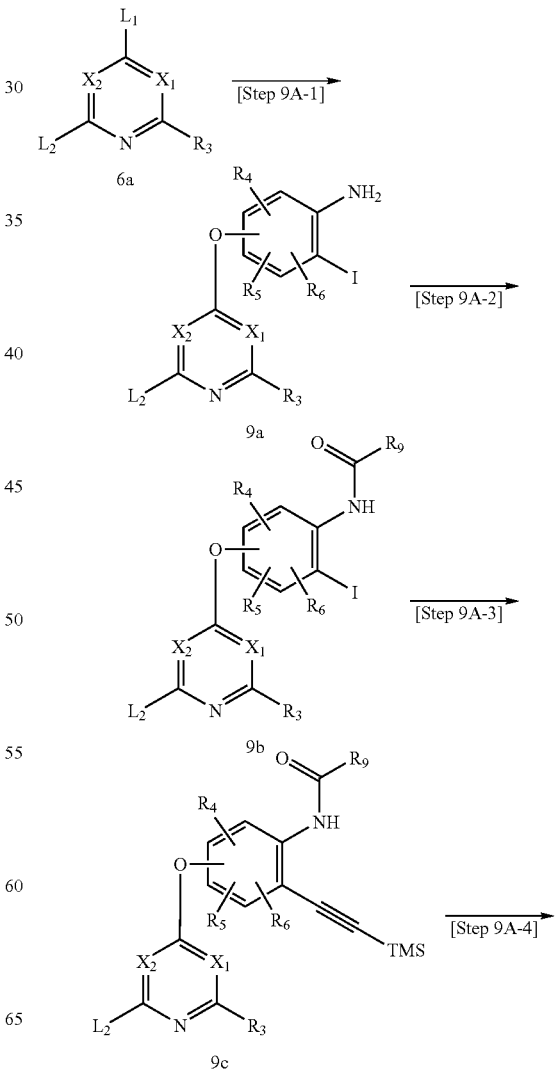

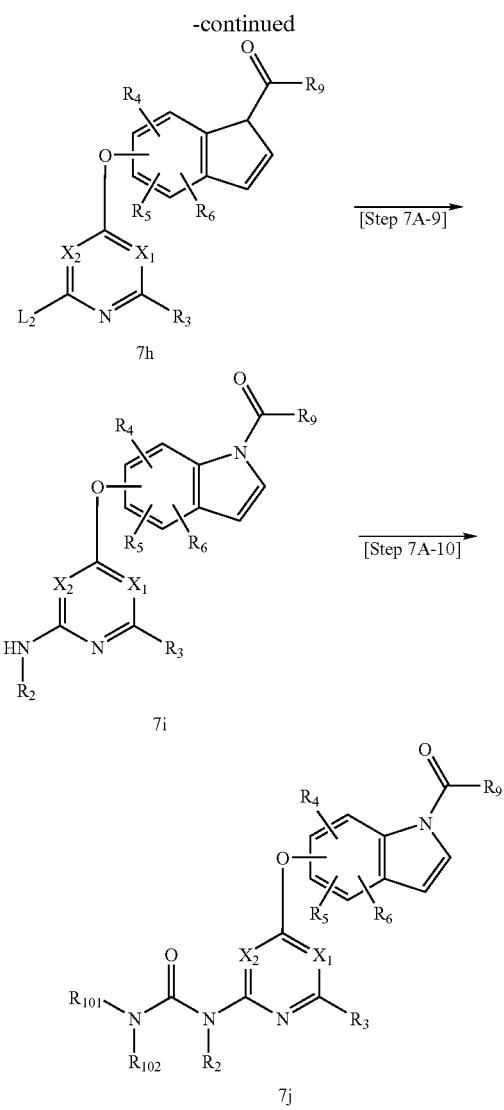

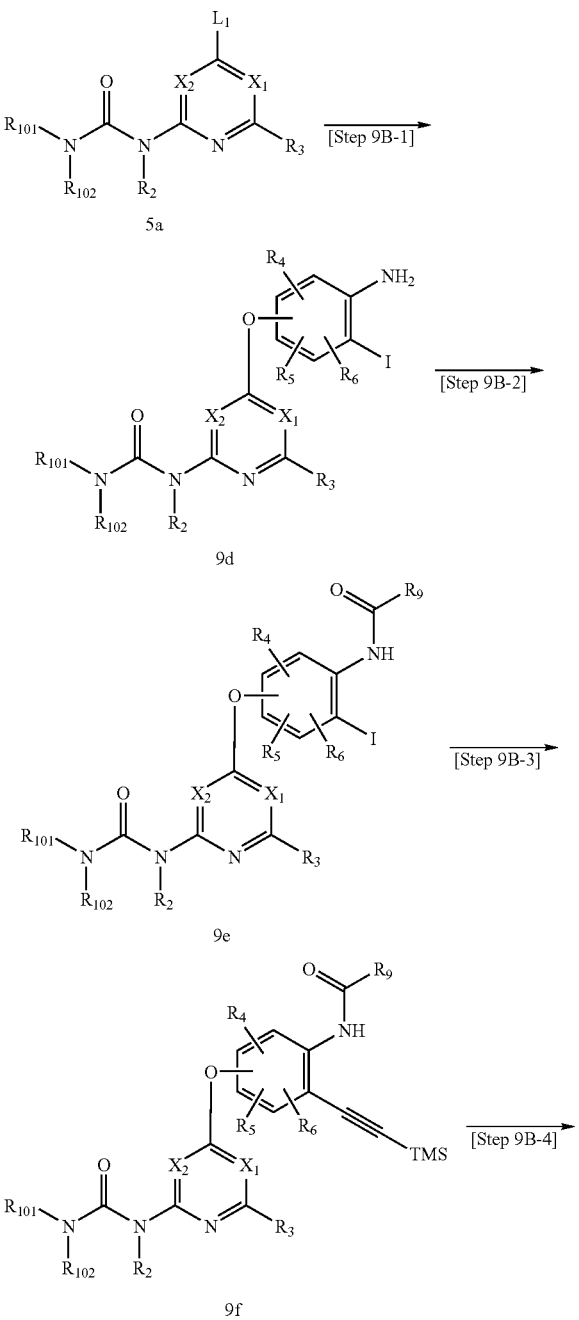

wherein, each symbol represents the same definition as the aforementioned definition.

<Step 9A-1>

This is a step for obtaining a compound (9a) by coupling of a compound (6a) with a phenol derivative. Specifically, for example, a corresponding condensed compound can be obtained under the same conditions as in <Step 1A-1>, by using 4-amino-3-iodophenol obtained from t-butyl(2-iodo-4-((triisopropylsilyl)oxy)phenyl)carbamate obtained by a method as described in J. Org. chem., 62, 6507 (1997) by allowing n-butylammonium fluoride or the like to react therewith.

<Step 9A-2>

This is a step for converting a compound (9a) into a urea derivative to obtain a compound (9b), and can be performed in the same way as in <Step 8A-4>.

<Step 9A-3>

This is a step for obtaining an acetylene derivative (9c) from an iodo compound (9c) using trimethylsilylacetylene. The condensation can be performed in the presence of tetrakis(triphenylphosphine)palladium or dichlorobis(triphenylphosphine)palladium, cuprous iodide. N,N-dimethylformamide or the like can be used as a reaction solvent, and the reaction can be performed at a temperature of room temperature to reflux temperature for 10 minutes to 30 hours.

<Step 9A-4>

This is a step for performing cyclization by heating an acetylene derivative (9c) in the presence of cuprous iodide to obtain an indole derivative (7h). N,N-dimethylformamide or the like can be used as a reaction solvent, and the reaction can be performed at a temperature of 80° C. to reflux temperature for 5 minutes to 10 hours.

Subsequently, a compound (7h) can be converted into a compound (7j) as described in <Step 7A-9>, <Step 7A-10>.

[Production Method 9-B]

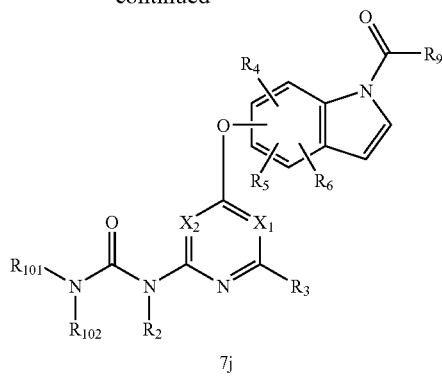

wherein each symbol represents the same definition as in the aforementioned definition.

<Step 9B-1>

This is a step for coupling a compound (5a) with a phenol derivative to obtain a compound (9d), and can be performed in the same way as in <Step 9A-1>.

<Step 9B-2>

This is a step for converting a compound (9d) into a urea derivative to obtain a compound (9e), and can be performed in the same way as in <Step 7A-5>.

<Step 9B-3>

This is a step for obtaining an acetylene derivative (9f) from an iodo compound (9e) by using trimethylsilylacetylene, and can be performed in the same way as in <Step 9A-3>.

<Step 9B-4>

This is a step for cyclizing an acetylene derivative (9f) by heating in the presence of cuprous iodide to obtain an indole derivative (7j). The same conditions as in <Step 9A-4> can be applied.

[Production Method 10]

A typical production method of a compound (10 g), which is the compound represented by the formula (Ia), wherein Y is an oxygen atom, a sulfur atom or a group represented by the formula —NR$_Y$— (wherein R$_Y$ represents a hydrogen atom or a C$_{1-6}$ alkyl group), X$_1$ is a group represented by the formula —C(CN)═, X$_2$ is a group represented by the formula —CH═, R$_2$ is a hydrogen atom, R$_3$ is a hydrogen atom, an optionally substituted C$_{1-6}$ alkyl group or an optionally substituted C$_{3-8}$ cycloalkyl group

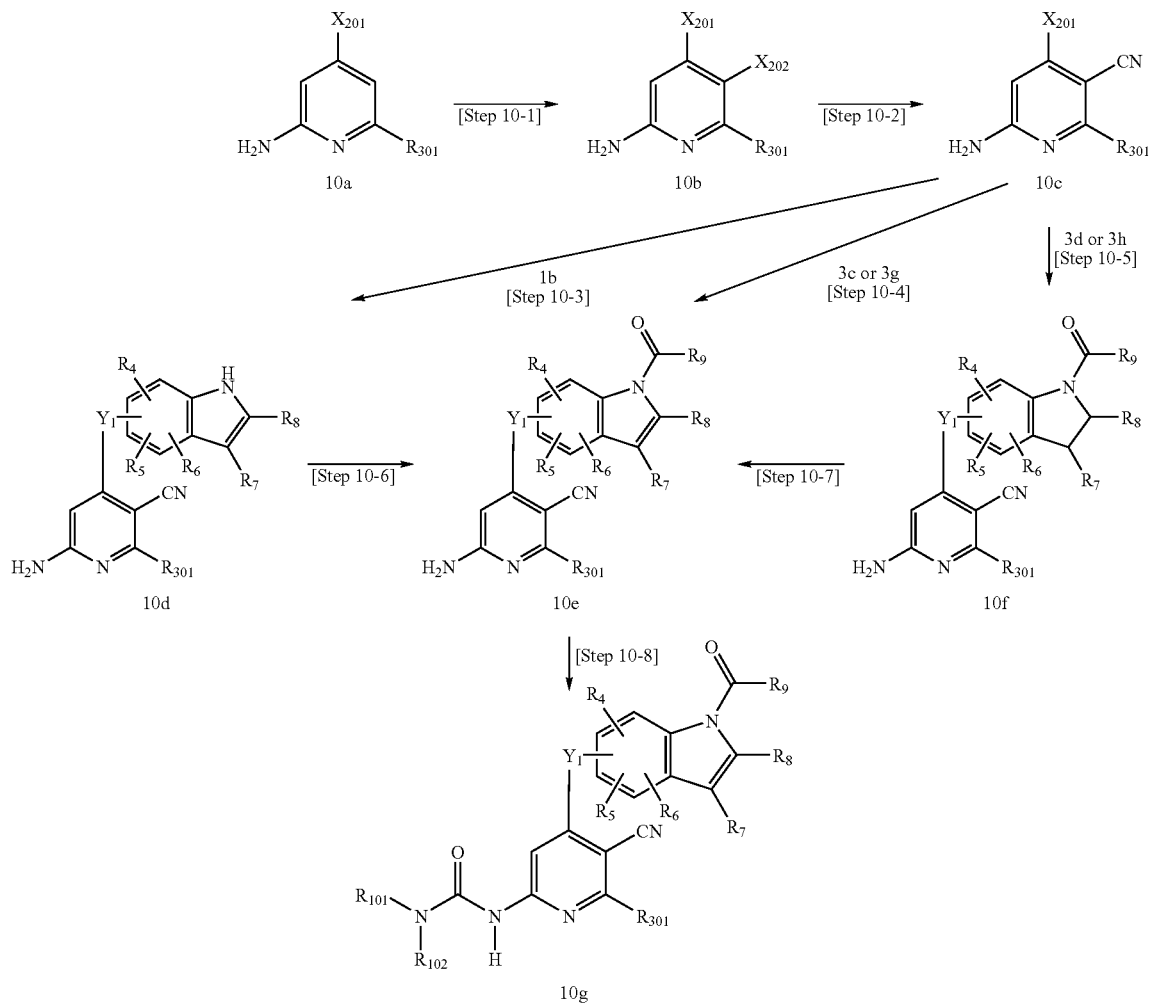

wherein, $X_{201}$ represents a chlorine atom or a bromine atom, $X_{202}$ represents a bromine atom or an iodine atom; $R_{301}$ represents a hydrogen atom, an optionally substituted $C_{1-6}$ alkyl group, or an optionally substituted $C_{3-8}$ cycloalkyl group; it is preferable that as a combination of $X_{201}$ and $X_{202}$, $X_{202}$ is an iodine atom or a bromine atom if $X_{201}$ is a chlorine atom, $X_{202}$ is an iodine atom if $X_{201}$ is a bromine atom; other symbols represent the same definition as the aforementioned definition.

<Step 10-1>

This is a step for bromination or iodination of the 5-position of a 2-aminopyridine derivative (10a) having a chlorine atom or a bromine atom at the 4-position to obtain a compound (10b). For example, halogenation agents such as iodine, N-bromosuccinimide, bromine, N-iodosuccinimide can be used. As a reaction solvent, for example, N,N-dimethylformamide, dimethyl sulfoxide, methylene chloride and acetonitrile can be used. The reaction can be performed at a temperature of 0° C. to reflux temperature for 10 minutes to 48 hours.

<Step 10-2>

This is a step for converting $X_{202}$ of a compound (10b) into a cyano group to obtain a compound (10c).

For example, 0.5 to 0.6 equivalent of zinc cyanide, 1.0 to 1.2 equivalent of potassium cyanide, or trimethylsilylcyanide is reacted with a compound (10b) in the presence of a palladium catalyst such as tetrakis(triphenylphosphine)palladium or dichlorobis(triphenylphosphine)palladium. As a reaction solvent, for example, N,N-dimethylformamide, dioxane and tetrahydrofuran can be used. The reaction can be performed at a temperature of room temperature to reflux temperature for 10 minutes to 10 hours.

<Step 10-3><Step 10-4><Step 10-5>

These are steps for condensing a pyridine derivative (10c) and an indole or indoline derivative. Compounds (10d), (10e) and (10f) can be obtained, respectively, by using an indole derivative (1b), indole derivatives (3c), (3g) having a carboxamide group at the 1-position, and indoline derivatives (3d), (3h) having a carboxamide group at the 1-position under the same conditions as in <Step 1A-1>.

<Step 10-6>

This is a step for conducting carboxamidation of 1-position of indole of a compound (10d) to obtain a compound (10e), and can be performed in the same way as in <Step 1A-2>.

<Step 10-7>

This is a step for oxidizing an indoline derivative (10f) to an indole derivative (10e), and can be performed in the same way as in <Step 3-9>.

<Step 10-8>

This is a step for converting a compound (10e) into a compound (10 g), and can be performed in the same way as in <Step 1A-3>.

[Production Method 11]

Another production method of a compound (10g)

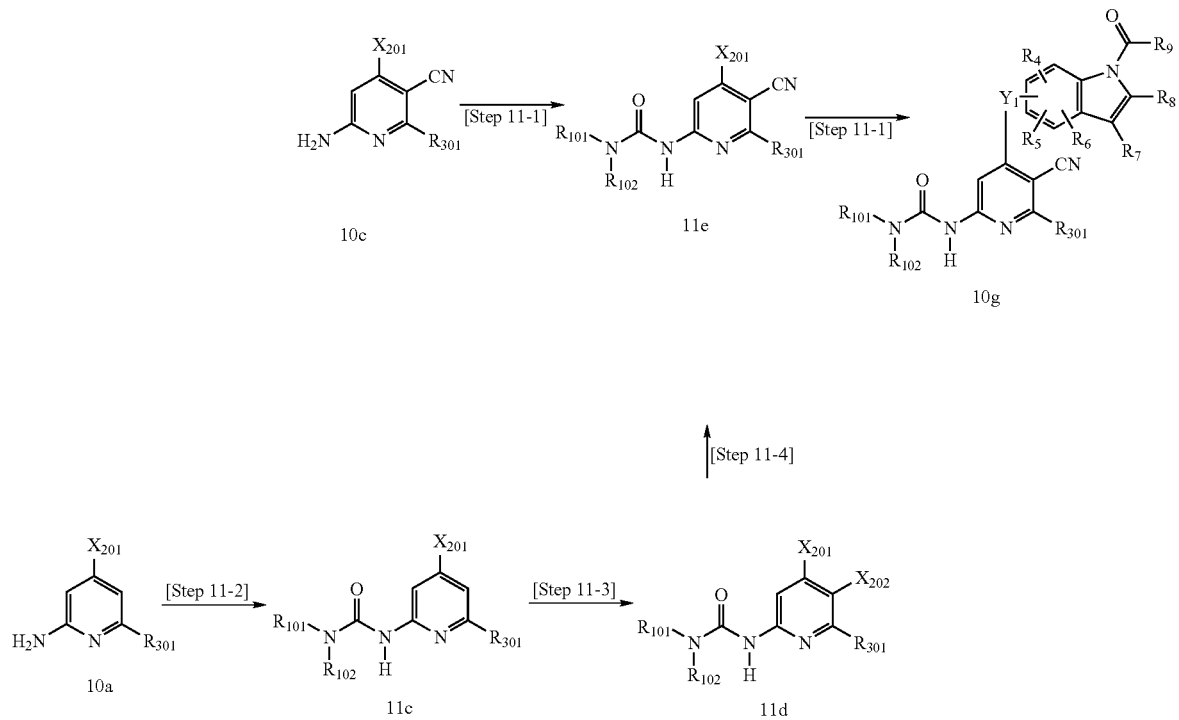

wherein each symbol represents the same definition as the aforementioned definition.

<Step 11-1><Step 11-2>

These are steps for converting aminopyridine derivatives ( c), (10a) into corresponding urea derivatives (11e), (11c), respectively, and can be performed in the same way as in <Step 1A-3>.

<Step 11-3>

This is a step for iodination or bromination of the 5-position of a 2-ureidopyridine derivative (11c) having a chlorine atom or a bromine atom at the 4-position to obtain a compound (11d), and can be performed in the same way as in <Step 10-1>.

<Step 11-4>

This is a step for converting $X_{202}$ of a compound (11d) into a cyano group to obtain a compound (11e), and can be performed in the same way as in <Step 10-2>.

<Step 11-5>

This is a step for obtaining a compound (10g) from a pyridine derivative (11e) having urea, and can be performed in the same way as in <Step 5-2>.

[Production Method 12]

A production method of a compound (12b), which is the compound represented by the formula (Ia), wherein Y is a sulfinyl group or a sulfonyl group, $X_1$ is a group represented by the formula —C(CN)=, and $R_2$ is a hydrogen atom

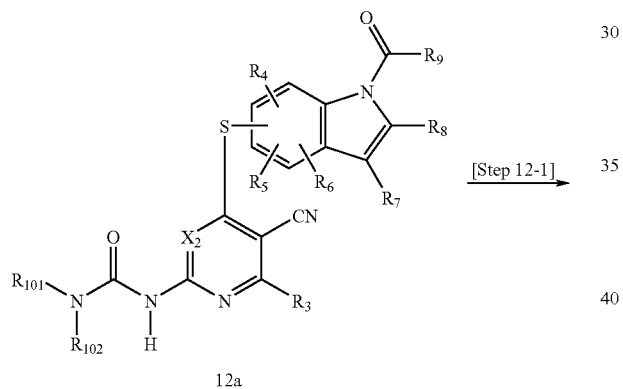

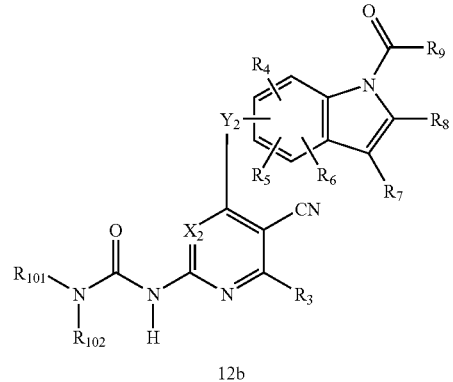

wherein other symbols represent the same definitions as the aforementioned definitions.

<Step 12-1>

This is a step for oxidizing a compound (12a) to a compound (12b), and can be performed in the same way as in <Step 1B-1>.

[Production Method 13]

A production method of a compound (13l), which is the compound represented by the formula (Ia), wherein Y is an oxygen atom, a sulfur atom or the formula —NR$_Y$— (wherein R$_Y$ represents a hydrogen or a $C_1$ to $C_6$ alkyl group), and $X_1$ is a group represented by the formula —C(CN)=

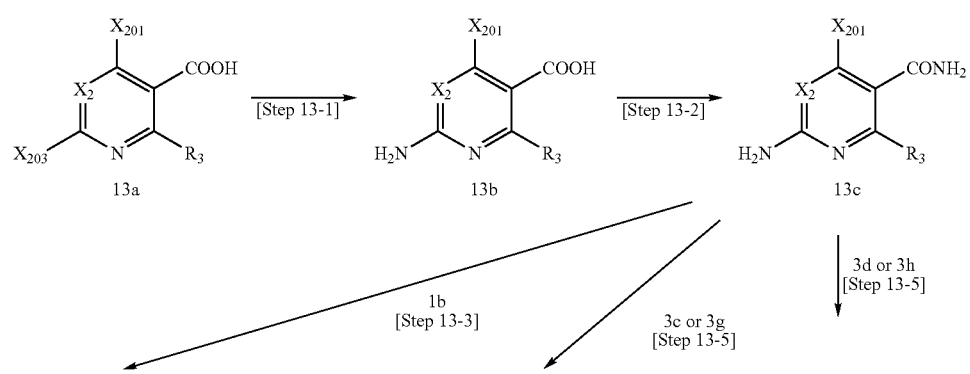

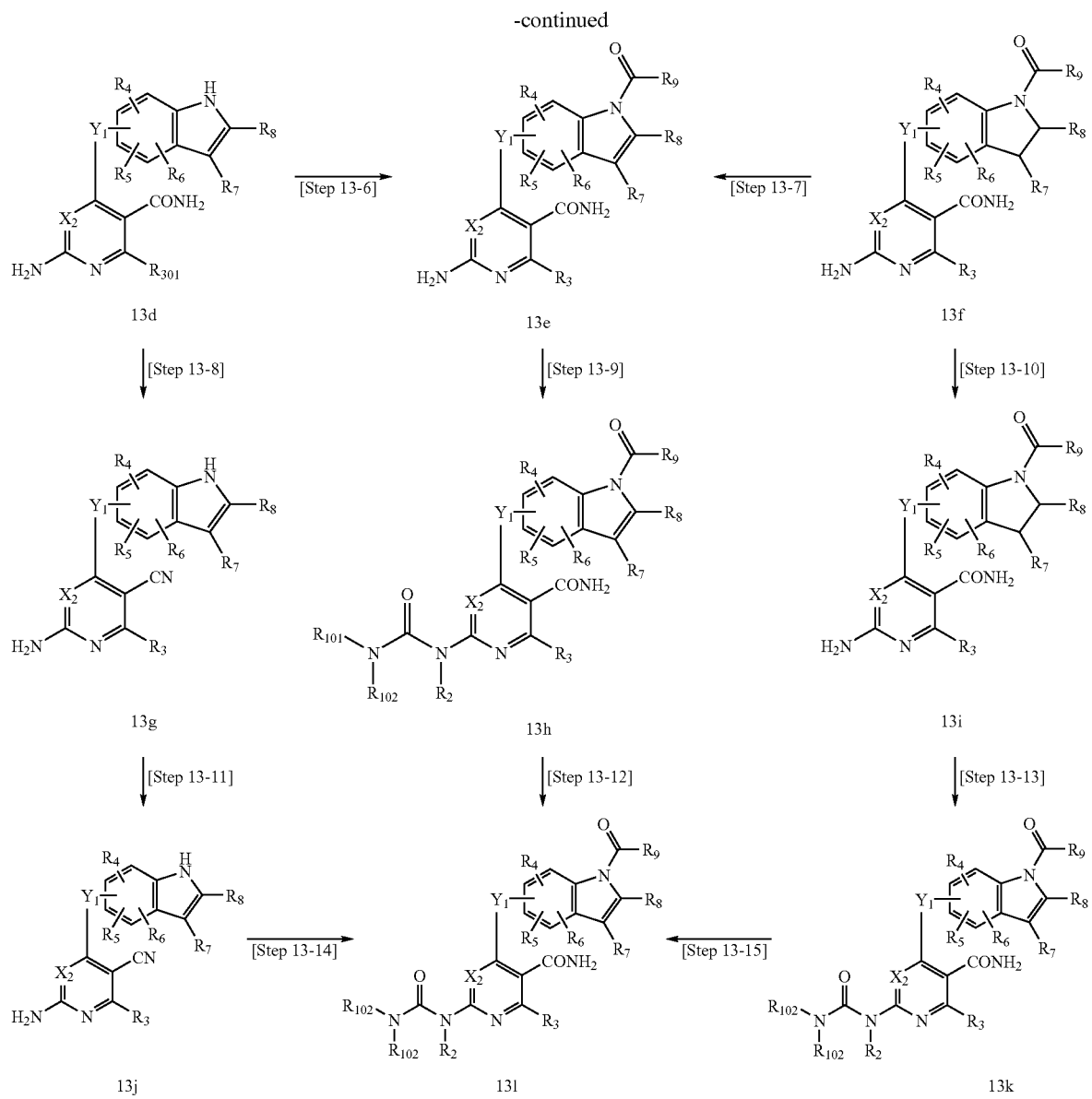

wherein, $X_{203}$ represents a chlorine atom, a bromine atom or an iodine atom; other symbols represent the same definition as the aforementioned definition.

<Step 13-1>

This is a step for converting $X_{203}$ of 4,6-dihalogenated nicotinic acid or its analogous compound (13a) such as 4,6-dichloronicotinic acid as reported in Acad. Nauk Ukr. SSSR, 1986, page 36 into an amino group to obtain a compounds (13b). The reaction can be performed at a temperature of 0° C. to reflux temperature for 10 minutes to 100 hours by using, for example, an ammonia-ethanol solution or the like.

<Step 13-2>

This is a step for obtaining a compound (13c) by converting a carboxyl group of a compound (13b) into a carbamoyl group. For example, a method in which, after oxalyl chloride or thionyl chloride is allowed to react with the compound at a temperature of 0° C. to reflux temperature for 10 minutes to 24 hours, ammonia is allowed to react with the compound, or a method in which diethylcyanophosphate, ammonium chloride, triethylamine are employed as disclosed in Synthesis [SYNTBF], 1998, 1467–1475 or the like can be used.

<Step 13-3><Step 13-4><Step 13-5>

These are steps for condensing a pyridine or pyrimidine derivative (13c) and an indole or indoline derivative. Compounds (13d), (13e), (13f) can be obtained, respectively, by using an indole derivative (1b), indole derivatives (3c), (3g) having a carboxamide group at the 1-position, or indoline derivatives (3d), (3h) having a carboxamide group at the 1-position under the same conditions as in <Step 1A-1>.

<Step 13-6><Step 13-11>

These are steps for conducting carboxamidation of the 1-position of indole of compounds (13d), (13g) to obtain compounds (13e), (13j) and can be performed in the same way as in <Step 1A-2>.

<Step 13-8><Step 13-12><Step 13-15>

These are steps for converting a carbamoyl group of compounds (13d), (13h), (13k) into a cyano group to obtain compounds (13g), (13l). For example, a method in which phosphorus oxychloride, thionyl chloride, trifluoroacetic anhydride are allowed to react with the compounds at a temperature of 0° C. to reflux temperature for 10 minutes to 24 hours can be used.

<Step 13-9><Step 13-10><Step 13-14>

These are steps for converting aminopyridine or aminopyrimidine derivatives (13e), (13f), (13j) into corresponding urea derivatives (13h), (13i), (13l), and can be performed in the same way as in <Step 1A-3>.

<Step 13-7><Step 13-13>

These are steps for oxidizing indoline derivatives (13f), (13i) to indole derivatives (13e), (13k), and can be performed in the same way as in <Step 3-9>.

[Production Method 14]

A typical production method of compounds (14d), (14e), (14f) by halogenation of compounds (14a), (14b), (14c)

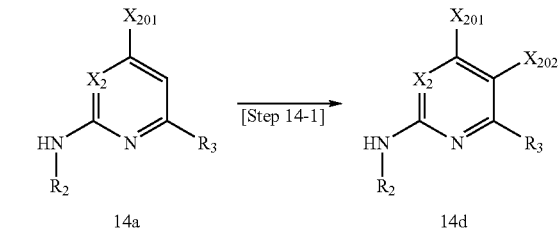

14a → [Step 14-1] → 14d

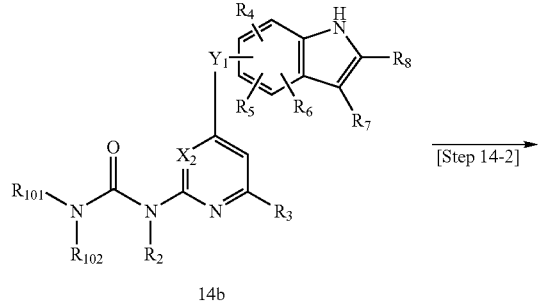

14b → [Step 14-2]

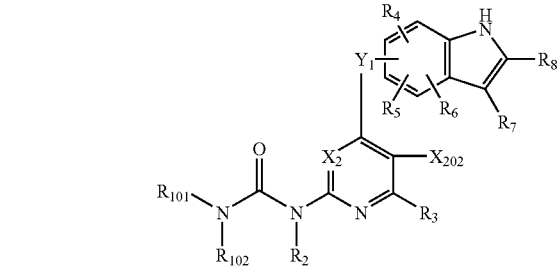

14c

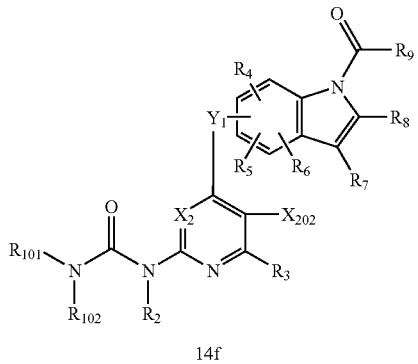

14f wherein, each symbol represents the same definition as the aforementioned definition.

<Step 14-1><Step 14-2><Step 14-3>

These are steps for substituting a substituent in 6-membered heterocycle from a hydrogen atom to a halogen atom. A compound can be obtained from a corresponding compound respectively: a compound (14d) from a compound (14a), a compound (14e) from a compound (14b) and a compound (14f) from a compound (14c) as in <Step 10-1>.

[Production Method 15]

A typical production method of compounds (15a), (15b), (15c) by substituting a halogen atom in 6-membered heterocycle of compounds (14d), (14e), (14f) to a cyano group

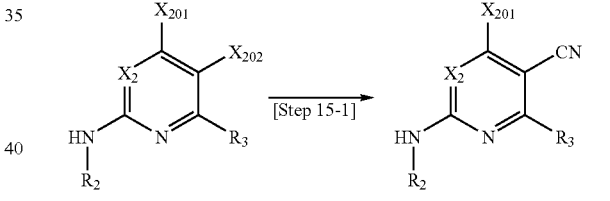

14d → [Step 15-1] → 15a

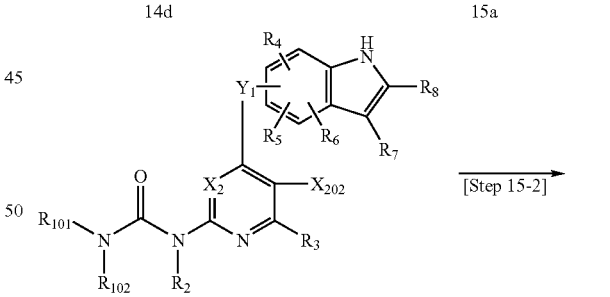

14e → [Step 15-2]

15b

-continued

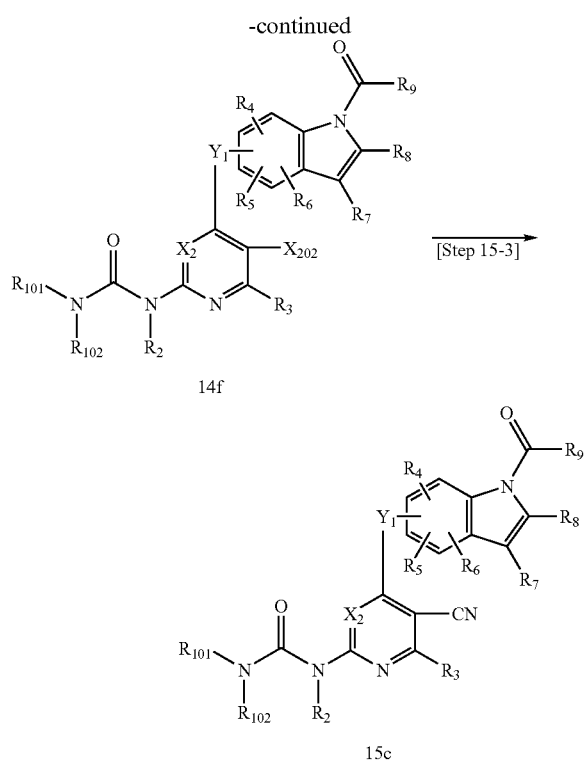

14f

15c wherein, each symbol represents the same definition as the aforementioned definition.

<Step 15-1><Step 15-2><Step 15-3>

These are steps for obtaining a compound from a corresponding compound respectively: a compound (15a) from a compound (14d), a compound (15b) from a compound (14e) and a compound (15c) from a compound (14f) by substituting a substituent in 6-membered heterocycle from a halogen atom to a cyano group. 0.5 to 2.0 equivalent of zinc cyanide or 1.0 to 3.0 equivalent of copper(I) cyanide, potassium cyanide, sodium cyanide, trimethylsilylcyanide or the like to compounds (14d), (14e) and (14f) can be used. In order to accelerate the reaction, as a catalyst, for example, a palladium catalyst such as tetrakis(triphenylphosphine) palladium or dichlorobis(triphenylphosphine)palladium, copper(I) iodide, copper(O) or the like can be used. As a reaction solvent, for example, N,N-dimethylformamide, N-methylpyrrolidone, dimethyl sulfoxide, dioxane, tetrahydrofuran or the like can be used. The reaction can be performed at a temperature of room temperature to reflux temperature for 10 minutes to 2 days.

After completing the aforementioned reactions, purification can be performed by a ordinal treatment method, for example, column chromatography using silica gel or adsorbent resins or the like, or recrystallization from a suitable solvent.

The compounds of the invention, salts thereof or hydrates of the foregoing may be formulated as tablets, powders, fine particles, granules, coated tablets, capsules, syrups, lozenges, inhalants, suppositories, injections, ointments, eye salves, eye drops, nasal drops, ear drops, paps, lotions and the like, by any common methods. The formulation may employ any commonly used excipients, binders, lubricants, coloring agents, corrective coatings, and if necessary, stabilizers, emulsifiers, absorbefacients, surfactants, pH adjustors, preservatives, antioxidants, or the like, in combination with various components that are ordinarily used as raw materials for pharmaceutical formulations. For example, an oral formulation may be prepared by combining a compound of the invention or pharmacologically acceptable salt thereof with an excipient, if necessary adding a binder, disintegrator, lubricant, coloring agent, corrective coating or the like, and forming a powder, fine particles, granules, tablets, coated tablets, capsules, etc. by a common method. As such components there may be mentioned animal and vegetable oils such as soybean oil, beef tallow and synthetic glycerides; hydrocarbons such as liquid paraffin, squalane and solid paraffin; ester oils such as octyldodecyl myristate and isopropyl myristate; higher alcohols such as cetostearyl alcohol and behenyl alcohol; silicone resins; silicone oils; surfactants such as polyoxyethylene fatty acid esters, sorbitan fatty acid esters, glycerin fatty acid esters, polyoxyethylene sorbitan fatty acid esters, polyoxyethylene hydrogenated castor oil and polyoxyethylene-polyoxypropylene block copolymer; water-soluble polymers such as hydroxyethylcellulose, polyacrylic acid, carboxyvinyl polymer, polyethylene glycol, polyvinylpyrrolidone and methylcellulose; lower alcohols such as ethanol and isopropanol; polyhydric alcohols such as glycerin, propylene glycol, dipropylene glycol and sorbitol; sugars such as glucose and sucrose; inorganic powders such as silicic acid anhydride, magnesium aluminum silicate and aluminum silicate, purified water, and the like. Examples of excipients which may be used include lactose, corn starch, white soft sugar, glucose, mannitol, sorbit, crystalline cellulose and silicon dioxide, examples of binders which may be used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, polypropylene glycol/polyoxyethylene block polymer and meglumine, examples of disintegrators which may be used include starch, agar, gelatin powder, crystalline cellulose, calcium carbonate, sodium bicarbonate, calcium citrate, dextrin, pectin and carboxymethylcellulose calcium, examples of lubricants which may be used include magnesium stearate, talc, polyethylene glycol, silica and hydrogenated vegetable oils, examples of coloring agents which may be used include those approved for addition to drugs, and examples of corrective coatings which may be used include cocoa powder, menthol, aromatic powders, *mentha* oil, borneol and powdered cinnamon. The tablets or granules may also be sugar coated or provided with another type of suitable coating if necessary. For preparation of a liquid formulation such as a syrup or injection, a common method may be used to formulate a compound of the invention or a pharmacologically acceptable salt thereof with a pH adjustor, solubilizer, isotonizing agent or the like, as well as a solubilizing aid, stabilizer etc. if necessary. There are no particular restrictions on the method of preparing an external agent, and any common method may be employed. That is, it may be prepared using as base materials any of various raw materials which are ordinarily used in drugs, quasi drugs, cosmetics and the like. As examples of specific base materials there may be mentioned raw materials such as animal and vegetable oils, mineral oils, ester oils, waxes, higher alcohols, fatty acids, silicone oils, surfactants, phospholipids, alcohols, polyhydric alcohols, water-soluble polymers, clay minerals, purified water and the like, and if necessary pH adjustors, antioxidants, chelating agents, antiseptics and fungicides, coloring agents, aromas and the like may also be added, although the base materials for external agents according to the invention are not limited to these. If necessary, there may also be included components such as ingredients having differentiation-inducing activity, circulation promoters, microbicides, antiphlogistic agents, cell activators, vitamins, amino acids, humectants, keratolytic agents and the like. The amounts of the aforementioned base materials may be the concentrations established for preparation of ordinary external agents.

There are no particular restrictions on the compound of the invention, the salt thereof or the hydrate thereof when administered, and either oral or parenteral administration may be carried out according to ordinary methods. For example, it may be prepared and administered in the form of a tablet, powder, a granule, a capsule, syrup, lozenge, inhalant, suppository, injection, ointment, eye salve, eye drop, nasal drop, ear drop, pap, lotion or the like.

Although the dosage of a drug according to the invention will differ depending on severity of symptoms, age, gender, body weight, form of administration, type of disease, etc., it will be generally 100 µg –10 g per day for an adult and such dosages may be administered once or divided over several.

The administration form of the medicine according to the present invention is not particularly restricted, and can be an oral administration or a parenteral administration by a generally employed method.

The biochemical activity and actions and effects (angiogenesis inhibition activity, antitumor activity or the like) as a medicine of the compounds according to the present invention can be evaluated by the following methods.

The following is a list of abbreviations used in the pharmacological test examples described below.

List of Abbreviations

DNA (deoxyribonucleic acid)

VEGFR2 (vascular endothelial growth factor receptor 2)

Hepes (N-[2-Hydroxyethyl]piperazine-N'-[2-ethanesulfonic acid], HEPES (buffer solution))

$MgCl_2$ (Magnesium Chloride)

$MnCl_2$ (Manganese Chloride)

$Na_3VO_4$ (Sodium Orthovanadate (V))

ATP (Adenosine 5'-Triphosphate)

EDTA (Ethylenediaminetetraacetic acid)

HTRF (Homogenous Time-Resolved Fluorescence)

FGFR1 (Fibroblast growth factor receptor 1)

PDGFRβ (Platelet derived growth factor receptor 1)

HGFR (Hepatocyte growth factor receptor)

EGFR (Epidermal growth factor receptor)

Tris (Tris(hydroxymethyl)aminomethane, tris (buffer solution))

NaCl (sodium Chloride)

BSA (Bovine Serum Albumin)

HRP (Horseradish peroxidase)

EGTA (Ethylene glycol bis(2-aminoethyl ether)-N,N,N',N'-tetraacetic acid)

SDS (Sodium Dodecylsulphate)

NP-40 (Nonidet P-40)

PCR: polymerase chain reaction

RT-PCR: reverse transcription-polymerase chain reaction

RNA: ribonucleic acid cDNA: complementary DNA cRNA: complementary RNA dNTP: a mixture composed of dATP, dCTP, dGTP and dTTP UTP: Uridine 5'-triphosphate CTP: Cytidine 5'-triphosphate dATP: 2'-Deoxyadenosine 5'-triphosphate dCTP: 2'-Deoxycytidine 5'-triphosphate dGTP: 2'-Deoxyguanosine 5'-trophosphate dUTP: 2'-Deoxyuridine 5'-tirphosphate GAPDH: glyceraldehydes 3-phosphate dehydrogenase FBS: Fetal bovine serum PBS: Phosphate buffered saline MTT: (3-[4,5-Dimethylthiozol-2-yl]-2,5-diphenyltetrazolium bromide; Thiazolyl blue)

DMSO: Dimethyl sulfoxide

PDGF: Platelet derived growth factor

EGF: Epidermal growth factor

FGF2: Fibroblast growth factor 2

VEGF: Vascular endothelial growth factor

HGF: Hepatocyte growth factor

TNF-α Tumor Necrosis factor alpha

FCS: Fetal Calf Serum

EGM-2: Endothelial Cell Growth Medium-2

Pharmacological Test Example 1

Inhibition Against Sandwich Tube Formation by Vascular Endothelial Cells in Response to Stimulation by Angiogenesis Factor Human Umbilical Vein Endothelial Cells (HUVECs) were isolated according to a reported method (Shinseikagaku Jikken Koza [New Biochemistry Experiment Lectures], "Saibo Baiyo Gijutsu" [Cell Culturing Techniques], p. 197–202), and were cultured in a 5% $CO_2$ incubator (37° C.) using EGM-2 medium (purchased from Clonetics Corp.) until the cells reached confluency.

An ice-cooled mixture of collagen: 5× RPMI 1640: reconstitution buffer (all purchased from Nitta Gelatin, Inc.) at 7:2:1 was dispensed at 0.4 ml into each well of a 24-well plate. After the solution was gelled by being stationed for 40 minutes in a 5% $CO_2$ incubator (37° C.), HUVEC cell suspension was added at 0.4 ml to each well (using 1 to 1.2×10⁵ cells, though the numbers of cells differ slightly according to the HUVEC lot), the HUVEC cell suspension being in human endothelial serum free medium (SFM, purchased from GIBCO BRL) containing added angiogenesis factors [20 ng/ml FGF2 (purchased from GIBCO BRL) and 10 ng/ml EGF (purchased from GIBCO BRL), or 25 ng/ml VEGF (purchased from Wako Pure Chemical Industries Co., Ltd.) and 10 ng/ml EGF, or 30 ng/ml HGF (purchased from R&D Co.) and 10 ng/ml EGF], and cultured overnight in a 5% $CO_2$ incubator (37° C.). On the following day, the medium on the upper layer was aspirated off, and then 0.4 ml of an ice-cooled mixture of collagen: 5× RPMI 1640: reconstitution buffer (all purchased from Nitta Gelatin, Inc.) at 7:2:1 was superposed into each well prior to stationing for 4 hours in a 5% $CO_2$ incubator (37° C.) for gelling. After adding 1.5 ml of an SFM solution containing each of the aforementioned angiogenesis factors and a diluted test substance onto the upper layer, culturing was performed in a 5% $CO_2$ incubator (37° C.). Upon aspirating off the culture supernatant in each well on the 4th day after addition of the test substance, 0.4 ml of a 3.3 mg/ml MTT solution dissolved in PBS (purchased from Sigma Corp.) was added to each well and culturing was performed for approximately 2 hours in a 5% $CO_2$ incubator (37° C.). The tubes formed in the collagen gel of each well were stained by MTT, the tube images were loaded into a computer (Macintosh), and the total length of the tubes was determined by image analysis software "MacScope" (purchased from Mitani Corp.). The ratio of the total length of the tubes formed in the well containing the test substance with respect to the total length of the tubes formed in the well containing no test substance was expressed as a percentage, and the concentration of each test substance required for 50% inhibition of tube formation ($IC_{50}$) was determined from the ratio value. The results are shown Table 1.

TABLE 1

| Example No. | VEGF-stimulated tube formation $IC_{50}$ (nM) | FGF2-stimulated tube formation $IC_{50}$ (nM) |
| --- | --- | --- |
| 39 | 5.1 | 470 |
| 41 | 2.1 | 250 |
| 46 | 7.0 | 470 |
| 47 | 5.8 | 120 |
| 53 | 6.7 | 440 |

Pharmacological Test Example 2

Measurement of Inhibition Against Receptor Tyrosine Kinase Activity

This assay is used to determine inhibition of a test substance on tyrosine kinase activity. DNA coding for the cytoplasmic domain of VEGFR2 is obtained by total cDNA synthesis (Edwards M, International Biotechnology Lab 5(3), 19–25, 1987) or by cloning. Expression in an appropriate expression system can produce a polypeptide with tyrosine kinase activity. The cytoplasmic domain of VEGFR2 obtained by expression of recombinant protein in, for example, insect cells have been found to exhibit intrinsic tyrosine kinase activity. For VEGFR2 (GenBank Accession No. L04947), the 1.7 kb DNA fragment described by Terman et al. (Oncogene, 6(9), 1677–1683, 1991), coding for the cytoplasmic domain, beginning with lysine 791 and including the termination codon, was isolated from a human placental cDNA library (purchased from Clontech Laboratories, Inc.) and cloned in a Baculovirus expression vector (pFastBacHis, purchased from GIBCO BRL). The recombinant construct was transfected into insect cells (Spondoptea frugiperda9 (Sf9)) to prepare a recombinant Baculovirus. (Instructions for preparation and use of recombinant Baculovirus may be found in standard texts, such as "Bac-To-Bac Baculovirus Expression System" (GIBCO BRL).) The cytoplasmic fragment starting from lysine 398 (FGFR1, GenBank Accession No. X52833), the cytoplasmic fragment starting from lysine 558 (PDGFRβ, GenBank Accession No. M21616) or the cytoplasmic fragment starting from lysine 974 (HGFR, GenBank Accession No. J02958) may be cloned and expressed by the same method for use in assays for other tyrosine kinases. EGFR was purchased from Sigma Co. (Product No. E-2645).

For expression of the VEGFR2 tyrosine kinase, Sf9 cells were infected with the VEGFR2 recombinant virus and collected after 48 hours. The collected cells were rinsed with ice-cooled phosphate buffered saline (PBS) and then resuspended using 20 ml of ice-cooled Lysis Buffer (50 mM Tris-HCl (pH 8.5), 5 mM 2-mercaptoethanol, 100 mM KCl, 1 mM phenylmethylsulfonyl fluoride, 1% (v/v) NP-40) per $1.5 \times 10^8$ cells. The suspension was centrifuged at 12,000 rpm for 30 minutes at 4° C. and the supernatant was obtained. The supernatant was added to a Ni-NTA agarose column (3 ml, purchased from Qiagen) equilibrated with Buffer A {20 mM Tris-HCl (pH 8.5), 5 mM 2-mercaptoethanol, 500 mM KCl, 20 mM imidazole, 10% (v/v) glycerol}. The column was washed with 30 ml of Buffer A, and then with 6 ml of Buffer B {20 mM Tris-HCl (pH 8.5), 5 mM 2-mercaptoethanol, 1M KCl, 10% (v/v) glycerol}, and finally with 6 ml of Buffer A. After washing, it was eluted with 6 ml of Buffer C {20 mM Tris-HCl (pH 8.5), 5 mM 2-mercaptoethanol, 100 mM KCl, 100 mM imidazole, 10% (v/v) glycerol}. The eluate was placed on a dialysis membrane (purchased from Spectrum Laboratories) and dialyzed with a dialysis buffer {20 mM Tris-HCl (pH 7.5), 10% (v/v) glycerol, 1 mM dithiothreitol, 0.1 mM $Na_3VO_4$, 0.1 mM EGTA}. After dialysis, it was supplied for SDS-electrophoresis, and the recombinant protein (His6-VEGFR2, cytoplasmic domain of VEGFR2 fused with 6 histidine residues at the N-terminus) detected at a molecular weight of approximately 100 kDa with Coumassie Brilliant Blue staining was assayed using BSA (bovine serum albumin, purchased from Sigma Co.) as the standard substance, and stored at −80° C. until use. Using the same method for the cytoplasmic domains of FGFR1, PDGFRβ and HGFR yielded respective recombinant proteins fused with 6 histidine residues at the N-termini (His6-FGFR1, His6-PDGFRβ or His6-HGFR).

The tyrosine kinase reaction was conducted as follows. In the case of VEGFR2, for example, 10 μl of a kinase reaction solution {200 mM Hepes (pH 7.4), 80 mM $MgCl_2$, 16 mM $MnCl_2$, 2 mM $Na_3VO_4$}, 250 ng of biotin-bound poly(Glu4: Tyr1) (biotin-poly(GT), purchased from CIS Diagnostics Co.) (6 μl of a 15-fold dilution with distilled water), 15 ng of His6-VEGFR2 (10 μl of a 240-fold dilution with 0.4% BSA solution) and the test substance dissolved in dimethylsulfoxide (4 μl of a 100-fold dilution with 0.1% BSA solution) were added into each well of a 96-well round-bottom plate (NUNC Co., Product No. 163320), to a total of 30 μl. Next, 10 μl of 4 μM ATP (diluted with distilled water) was added prior to incubation at 30° C. for 10 minutes, and then 10 μl of 500 mM EDTA (pH 8.0) was added. The tyrosine-phosphorylated biotin-poly(GT) was measured by the Homogenous Time-Resolved Fluorescence (HTRF) method (Analytical Biochemistry, 269, 94–104, 1999). Specifically, the kinase reaction solution was transferred to a 96-well black half-plate (Product No. 3694, Coster, Inc.), 7.5 ng of europium cryptate-labeled anti-phosphotyrosine antibody (Eu(K)-PY20, purchased from CIS Diagnostics Co.) (25 μl of a 250-fold dilution with 20 mM Hepes (pH 7.0), 0.5 M KF, 0.1% BSA solution) and 250 ng of XL665-labeled streptavidin (XL665-SA, purchased from CIS Diagnostics Co.) (25 μl of a 62.5-fold dilution with 20 mM Hepes (pH 7.0), 0.5 M KF and 0.1% BSA solution) were added thereto, the mixture was allowed to stand at room temperature for 30 minutes, and then the fluorescent intensity was measured at 665 nm and 620 nm under irradiation with an excitation wavelength of 337 nm using a Discovery HTRF Microplate Analyzer (Packard Co.). The tyrosine phosphorylation rate for the biotin-poly(GT) was expressed as the delta F % value as described in the HTRF Standard Experiment Methods text by CIS Diagnostics Co. The delta F % value in the presence of the test substance was determined as a ratio (%) with the delta F % value with addition of His6-VEGFR2 in the absence of the test substance defined as 100% and the delta F % value in the absence of both the test substance and His6-VEGFR2 defined as 0%. This ratio (%) was used to calculate the test substance concentration required for 50% inhibition of VEGFR2 kinase activity ($IC_{50}$).

Measurement of inhibition against FGFR1, EGFR and HGFR kinase activity was conducted using 15 ng of His6-FGFR1, 23 ng of EGFR and 30 ng of His6-HGFR, respectively, according to the tyrosine kinase reaction and HTRF method described above. Measurement of inhibition against PDGFRβkinase activity was conducted using 50 ng of His6-PDGFRβ according to the tyrosine kinase reaction described above, followed by detection of tyrosine phosphorylated biotin-poly(GT) by the following method. Specifically, the kinase reaction solution was added to a 96-well streptavidin-coated plate (Product No. 15129, Pierce Chemical) and incubated at room temperature for 30 minutes. After rinsing 3 times with 150 μl of a rinsing solution {20 mM Tris-HCl (pH 7.6), 137 mM NaCl, 0.05% Tween-20, 0.1% BSA}, 701 μl of anti-phosphotyrosine (PY20)-HRP conjugate (Product No. P-11625, Transduction Laboratories) {2000-fold dilution with 20 mM Tris-HCl (pH 7.6), 137 mM NaCl, 0.05% Tween-20, 1% BSA} was added thereto and incubation was performed at room temperature for 1 hour. After incubation, it was rinsed 3 times with 150 μl of the rinsing solution, and 100 μl of TMB Membrane Peroxidase Substrate (Product No. 50-5077-03, Funakoshi Co., Ltd.) was added to initiate the reaction. After stationing at room temperature for 10 minutes, 100 μl of 1 M phosphoric acid was added to suspend the reaction, and the absorbance at 450 nm was measured with a microplate reader (BIO KINETICS READER EL304, Bio-Tek Instruments). The absorbance ratio in the presence of the test substance was determined with respect to 100% as the absorbance with addition of His6-PDGFRβ and no test substance, and 0% as the absorbance without addition of the test substance or His6-PDGFRβ. This absorbance ratio was used to calculate the test substance concentration required for 50% inhibition of PDGFRβkinase activity ($IC_{50}$). The results are shown in Table 2.

TABLE 2

| Example No. | VEGFR2 kinase $IC_{50}$ (nM) | FGFR1 kinase $IC_{50}$ (nM) |
|---|---|---|
| 28 | 4.5 | 4.1 |
| 36 | 3.4 | 16 |
| 37 | 4.8 | 1.2 |
| 39 | 4.5 | 6.3 |
| 41 | 6.1 | 3.2 |
| 46 | 32 | 12 |
| 47 | 40 | 21 |
| 50 | 5.0 | 13 |
| 53 | 3.8 | 2.1 |

Pharmacological Test Example 3

Evaluation of In Vivo Angiogenesis-Inducing Activity Using Mouse Dorsal Air Sac Model

[1] Construction of VEGF (Vascular Endothelial Growth Factor) Expression Vector

PCR was conducted using a human placenta cDNA library (Toyobo Co., Ltd.) as the template and the SEQ ID NO:1 (5'CCGGATCCATGAACTTTCTGCTG3') and SEQ ID NO:2 (5'GTGAATTCTGTATCGATCGTT3') of VEGF as primers. After completion of the PCR reaction, the 5' ends were phosphorylated and an approximately 600 bp DNA band was separated by 1.2% agarose gel electrophoresis. After polymerization by self-ligation, the cDNA was cut with EcoRI and BamHI and inserted into the EcoRI and BamHI sites of vector pUC19. This was used to transform *E. coli* JM83, and plasmids were recovered from the transformed clones. A VEGF cDNA fragment was cut out of the plasmids with HindIII and EcoRI and then inserted into pIRES2-rsGFP vector and obtain pIRES2-rsGFP/VEGF for protein expression.

[2] Preparation of VEGF High-Expressing Strain

After overnight culturing of KP-1 human pancreatic cancer cells ($3\times10^6$ cells) with 10% FCS-containing RPMI 1640 medium, an Effectene Transfection Reagent Kit (Qiagen) was used for introduction of 3 μg of pIRES2-rsGFP/VEGF into the KP-1 cells. After culturing in 10% FCS-containing RPMI 1640 medium containing 600 μg/ml of Geneticin, drug-resistant cells were selected. Furthermore, GFP high-expressing cells were collected by cell sorter (Becton Dickinson) as VEGF high-expressing KP-1 cells (KP-1/VEGF).

[3] Measurement of VEGF Level in Culture Supernatant

The KP-1/VEGF cells were prepared to $5\times10^5$ cells/ml, and 0.5 ml thereof was dispensed into each well of a 24-well plate and cultured at 37° C. for 24 hours. The culture supernatants were collected and the VEGF levels thereof measured using a VEGF measuring kit (IBL Co., Ltd.) for confirmation of high expression.

[4] Evaluation of In Vivo Angiogenesis-Inducing Activity Using Mouse Dorsal Air Sac Model Millipore rings (Nihon Millipore) were sealed with 0.45 μm Durapore filter membranes (Nihon Millipore) to create chambers. KP-1/VEGF human pancreatic cancer cells ($3\times10^6$) suspended in 0.17 ml of collagen gel were injected into each chamber through the injection port, and the chambers were sealed. Approximately 10 ml of air was then injected in the dorsal skin of 6-week-old C57BL/6N female mice under anesthesia to produce pouches, and the prepared chambers were transplanted therein. About 6 hours after completing transplantation, a test substance suspended in 0.5% methylcellulose was orally administered (0.1 ml/10 g body weight), and this was continued once a day for the next 4 days.

On the 4th day after transplanting the chambers, 0.2 ml of $^{51}$Cr (Amersham Pharmacia)-labeled mouse erythrocytes ($2.5\times10^6$ cpm/ml) were injected through the caudal veins of each of the mice with the transplanted chambers. After a prescribed period, the skin in contact with the chamber was excised and frozen, the section in direct contact with the chamber was precisely cut off, and the radioactivity was measured with a γ-counter. The blood volume was calculated from the radioactivity and used as an index of the in vivo angiogenesis-inducing activity. The angiogenesis volume was recorded as this measured blood volume minus the blood volume obtained with transplantation of a chamber containing only collagen gel. The experiment was conducted using 10 mice in the control (solvent-administered) group and 5 mice in each compound-administered group.

Pharmacological Test Example 4

Evaluation of Antitumor Activity on KP-1/VEGF Cells in Subcutaneous Xenograft Models VEGF high-expressing pancreatic cancer cells (KP-1/VEGF) suspended in PBS at a concentration of $1\times10^7$ cells/ml were transplanted under the right flank skin of 6-week-old female Balb/c (nu/nu) mice in a volume of 0.1 ml. When the tumor volume reached approximately 100 mm3, the test substance was orally administered over a period of 2 weeks with a schedule of 5 days per week. The test substance was suspended in 0.5% methylcellulose for an administered volume of 0.1 ml/10 g body weight. The tumor size was measured twice a week using a micrometer caliper. The tumor volume was determined by measuring the long and short diameters of the tumor with a micrometer caliper, and calculating ½×(long diameter×short diameter×short diameter). The experiment was conducted using 10 mice in the control (solvent-administered) group and 5 mice in each test substance-administered group.

Pharmacological Test Examples 5

Evaluation of Angiogenesis Inhibition Activity in Mouse Angiogenesis Model by Using Matrigel The experiment was performed according to the method as already reported in the method (Lab. Invest., 67(4), 519–528, 1992). Specifically, 10 µg/ml of recombinant FGF-2 (purchased from Invitrogen Corporation) dissolved in PBS was added to Matrigel Matrix (purchased from BD Biosciences) to prepare 1 µg/ml. After that, a 300 µl of this mixture of Matrigel Matrix and Recombinant FGF-2 was injected into a subcutaneous tissue on the median line of the abdomen of a 6-week-old Balb/c (nu/nu) mouse.

Subsequently, the test substance suspended in a 0.5% methyl cellulose or the like had been orally administered in succession once a day or twice a day for 7 days.

After 7 days, the implanted Matrigel was taken out, 300 µl of water was added thereto, and cut into pieces with scissors. The resultant substance was allowed to stand at a cool dark place overnight. After hemoglobin in Matrigel was fully extracted, 100 µl of the supernatant obtained by centrifugation and 100 µl of Drabkin's solution (purchased from Sigma Chemical Co., Ltd) were allowed to react at room temperature at a dark place for 1 hour. After that, the absorbance of the reaction solution was measured with measured wavelength of 550 nm and reference wavelength of 660 nm. The hemoglobin quantity (g/ml) in Matrigel was calculated from the calibration curve established by use of designating hemoglobin as a standard.

The experiment was conducted using 8 mice in the control (solvent-administered) group and 6 mice in each compound-administered group.

EXAMPLES

The compounds according to the present invention can be prepared by the methods as described in the following examples, for example. These are, however, exemplary, and the compounds according to the present invention are not limited to the specific examples mentioned below in any cases.

Example 1

N1-Ethyl-5-(2-((methoxylamino)carbonyl)amino-4-pyrimidyl)oxy-1H-indolecarboxamide Similarly to Production example 27-2, a crude product of phenyl N-(4-(1-(ethylamino)carbonyl-1H-5-indolyl)oxy-2-pyrimidyl)carbamate (546 mg, 1.31 mmol, 56.3%) was obtained as pale brown powder from N1-ethyl-5-(2-amino-4-pyrimidyl)oxy-1H-1-indolecarboxamide (691 mg, 2.32 mmol) and phenyl chlorocarbonate. The crude carbamate product (273 mg, 0.65 mmol) was dissolved in tetrahydrofuran (7.0 ml); and triethylamine (0.91 ml, 6.53 mmol) and methoxylamine hydrochloride (273 mg, 3.27 mmol) was added thereto while stirred at room temperature. After the reaction mixture was stirred overnight, the reaction mixture was partitioned between ethyl acetate and water. The organic layer was washed with water and brine, and was dried over anhydrous sodium sulfate. The solvent was distilled off, and the residue was purified by silica gel column chromatography (eluent; ethyl acetate:hexane=1:1). The crystals were precipitated from ethyl acetate-hexane (1:10), filtered off, and dried under aeration to yield the title compound (52.5 mg, 0.14 mmol, 21.7%) as white crystals.

$^1$H-NMR Spectrum (DMSO-$d_6$) δ (ppm): 1.17 (3H, t, J=7.2 Hz), 3.20–3.40 (2H, m), 3.68 (3H, s), 6.45 (1H, d, J=5.6 Hz), 6.67 (1H, d, J=3.6 Hz), 7.09 (1H, dd, J=2.4, 8.8 Hz), 7.43 (1H, d, J=2.4 Hz), 7.54 (1H, d, J=5.6 Hz), 7.89 (1H, d, J=3.6 Hz), 8.21 (1H, m), 8.26 (1H, d, J=8.8 Hz), 8.34 (1H, d, J=5.6 Hz), 9.31 (1H, d, J=10.0 Hz).

The starting materials were synthesized by the following methods.

Production Example 1-1

4-Chloro-6-(1H-5-indolyloxy)-2-pyrimidinamine

Sodium hydride (1.0 g, 25 mmol) was suspended in dimethyl sulfoxide (40 ml) under nitrogen atmosphere, and 5-hydroxyindole (3.33 g, 25 mmol) was gradually added while the reaction mixture was stirred at room temperature. After 20 minutes, 2-amino-4,6-dichloropyrimidine (3.28 g, 20 mmol) was added. The reaction mixture was heated at 100° C. and was stirred for 3 hours. After the reaction mixture was cooled to room temperature, the reaction mixture was partitioned between ethyl acetate and 10% aqueous ammonia solution. The organic layer was washed with water and brine, and dried over anhydrous sodium sulfate. After the solvent was distilled off, the residue was purified by NH silica gel column chromatography (eluent; ethyl acetate:hexane=2:1). The crystals were precipitated from ethyl acetate, filtered off, and dried under aeration to yield the title compound (1.15 g, 4.41 mmol, 22.0%) as white crystals.

$^1$H-NMR Spectrum (CDCl$_3$) δ (ppm): 5.09 (2H, brs), 6.07 (1H, s), 6.57 (1H, m), 6.95 (1H, dd, J=2.4, 8.8 Hz), 7.29 (1H, m), 7.37 (1H, m), 7.41 (1H, d, J=8.8 Hz), 8.28 (1H, brs).

Production Example 1-2

4-(1H-5-Indolyloxy)-2-pyrimidinamine

4-Chloro-6-(1H-5-indolyloxy)-2-pyrimidinamine (1.15 g, 4.41 mmol) was dissolved in tetrahydrofuran (50 ml)-triethylamine (3.07 ml), 10% palladium on carbon (50% wet, 500 mg) was added, and the reaction mixture was stirred overnight under hydrogen atmosphere at atmospheric pressure.

The reaction was purged with nitrogen. After methanol (50 ml) was added and stirred, the catalyst was filtered out. The resultant solution was concentrated under reduced pressure, thus the title compound (826 mg, 3.65 mmol, 82.8%) was obtained as pale gray powder.

$^1$H-NMR Spectrum (CDCl$_3$) δ (ppm): 4.96 (2H, brs), 6.06 (1H, d, J=5.6 Hz), 6.56 (1H, m), 6.97 (1H, dd, J=2.4, 8.8 Hz), 7.26–7.28 (1H, m), 7.38–7.42 (2H, m), 8.08 (1H, d, J=8.8 Hz), 8.29 (1H, brs).

Production Example 1-3

N1-Ethyl-5-(2-amino-4-pyrimidyl)oxy-1H-1-indole-carboxamide

Sodium hydride (157 mg, 3.93 mmol) was suspended in N,N-dimethylformamide (10 ml) under nitrogen atmosphere, and 4-(1H-5-indolyloxy)-2-pyrimidinamine (826 mg, 3.65 mmol) was gradually added while the reaction mixture was stirred at room temperature. After 10 minutes, the reaction mixture was cooled with an ice-water bath, phenyl N-ethylcarbamate (633 mg, 3.83 mmol) was added, the reaction mixture was heated to room temperature, and the solution was stirred for 4 hours. The reaction mixture was partitioned between ethyl acetate and water. The organic layer was washed with water and brine and dried over anhydrous sodium sulfate. The solvent was distilled off, and the residue was purified by silica gel chromatography (eluent; ethyl acetate:hexane=3:1 to 4:1) to yield the title compound (691 mg, 2.32 mmol, 63.7%) as white powder.

$^1$H-NMR Spectrum (CDCl$_3$) δ (ppm): 1.32 (3H, t, J=7.2 Hz), 3.54 (2H, m), 4.94 (2H, brs), 5.50 (1H, brs), 6.11 (1H, dd, J=2.4, 5.6 Hz), 6.62 (1H, d, J=3.6 Hz), 7.09 (1H, dd, J=2.4, 8.8 Hz), 7.34 (1H, d, J=2.4 Hz), 7.46 (1H, d, J=3.6 Hz), 8.11 (1H, d, J=5.6 Hz), 8.15 (1H, d, J=8.8 Hz).

Example 2

5-(6-(3-(3-Diethylaminopropylamino)ureido)pyrimidin-4-yloxy)-1H-indole-1-carboxylic acid methylamide Phenyl(6-(1-methylcarbamoyl-1H-indol-5-yloxy)pyrimidin-4-yl)carbamate (161 mg, 0.400 mmol) was dissolved in N,N-dimethylformamide (1.0 ml), and 3-(diethylamino)propylamine (130 mg, 1.00 mmol) was added while the reaction mixture was stirred at room temperature. After the reaction mixture was stirred overnight, the reaction mixture was partitioned between ethyl acetate and water. The organic layer was washed with water and brine, and dried over anhydrous sodium sulfate. The solvent was distilled off, and the residue was purified by NH silica gel column chromatography (eluent; ethyl acetate:methanol=50:1). The crystals were precipitated from ethyl acetate-hexane, filtered off, and dried under aeration to yield the title compound (123 mg, 0.280 mmol, 70%) as white crystals.

$^1$H-NMR Spectrum (DMSO-d$_6$) δ (ppm): 0.93 (6H, t, J=7.0 Hz), 1.52 (2H, m), 2.32–2.46 (6H, m), 2.84 (3H, d, J=3.6 Hz), 3.12 (2H, m), 6.69 (1H, d, J=3.6 Hz), 6.98 (1H, s), 7.06 (1H, dd, J=2.2, 8.8 Hz), 7.37–7.46 (2H, m), 7.88 (1H, d, J=3.6 Hz), 8.18 (1H, m), 8.27 (1H, d, J=8.8 Hz), 8.37 (1H, s), 9.49 (1H, brs).

The starting materials were synthesized by the following methods.

Production Example 2-1

Phenyl N-methylcarbamate

Methylamine hydrochloride (16.9 g, 250 mmol) was dissolved in N,N-dimethylformamide (250 ml), pyridine (44 ml, 275 mmol) was added thereto, and the reaction mixture was stirred. The reaction mixture was cooled with ice, phenyl chloroformate (35 ml, 275 mmol) was added dropwise thereto, and the reaction mixture was then stirred at room temperature for 24 hours. The reaction mixture was partitioned between ethyl acetate and water. The organic layer was washed with brine, dried over anhydrous magnesium sulfate, and the solvent was distilled off under reduced pressure. The obtained crystals were suspended in diethylether, diluted with hexane, filtered off, washed with the diethylether:hexane=1:1, and dried by evacuation, to yield the title compound (22.3 g, 147 mmol, 59.1%) as colorless crystals.

$^1$H-NMR Spectrum (DMSO-d$_6$) δ (ppm): 2.64 (3H, d, J=3.6 Hz), 7.07 (2H, d, J=8.0 Hz), 7.17 (1H, t, J=8.4 Hz), 7.35 (2H, dd, J=8.0 Hz, 8.4 Hz), 7.58 (1H, d, J=3.6 Hz).

Production Example 2-2

6-(1H-Indol-5-yloxy)pyrimidin-4-ylamine

Sodium hydride (400 mg, 10.0 mmol) was suspended in dimethyl sulfoxide (20 ml) under nitrogen atmosphere, and 5-hydroxyindole (1.33 g, 10.0 mmol) was gradually added while the reaction mixture was stirred at room temperature. After 20 minutes, 6-chloropyrimidin-4-ylamine (1.04 g, 8.00 mmol) was added thereto, the reaction mixture was heated at 100° C. and stirred for 1 hour. After the reaction mixture was naturally cooled to room temperature, the reaction mixture was partitioned between ethyl acetate and water. The organic layer was washed with water and brine, and was dried over anhydrous magnesium sulfate. The solvent was distilled off, and the residue was purified by silica gel column chromatography (eluent; ethyl acetate: hexane=3:1) to yield the title compound (1.07 g, 4.73 mmol, 59%) as a brown oil.

$^1$H-NMR Spectrum (DMSO-d$_6$) δ (ppm): 5.54 (1H, s), 6.43 (1H, m), 6.71 (2H, brs), 6.85 (1H, dd, J=2.4, 8.8 Hz), 7.29 (1H, d, J=2.4 Hz), 7.40–7.45 (2H, m), 8.06 (1H, s), 11.20 (1H, brs).

Production Example 2-3

5-(6-Aminopyrimidin-4-yloxy)-1H-indol-1-carboxylic acid methylamide

Sodium hydride (199 mg, 4.97 mmol) was suspended in N,N-dimethylformamide (10 ml) under nitrogen atmosphere, 6-(1H-indol-5-yloxy)pyrimidin-4-ylamine (1.07 g, 4.73 mmol) synthesized in Production example 2-2 was gradually added while the reaction mixture was stirred at room temperature. After 30 minutes, the reaction mixture was cooled with an ice water bath, then phenyl N-methylcarbamate (751 mg, 4.97 mmol) synthesized in Production example 2-1 was added. The reaction mixture was heated to room temperature and stirred for 1 hour. The reaction mixture was partitioned between ethyl acetate and water. The organic layer was washed with water and brine, and was dried over anhydrous magnesium sulfate. After the solvent was distilled off, the residue was purified by silica gel column chromatography (eluent; ethyl acetate) to yield the title compound (847 mg, 2.99 mmol, 63%) as white crystals.
$^1$H-NMR Spectrum (DMSO-$d_6$) δ (ppm): 2.85 (3H, d, J=4.0 Hz), 5.62 (1H, s), 6.68 (1H, d, J=3.6 Hz), 6.77 (2H, brs), 7.04 (1H, dd, J=2.4, 9.2 Hz), 7.36 (1H, d, J=2.4 Hz), 7.87 (1H, d, J=3.6 Hz), 8.07 (1H, s), 8.15 (1H, q, J=4.0 Hz), 8.27 (1H, d, J=9.2 Hz).

Production Example 2-4

Phenyl(6-(1-methylcarbamoyl-1H-indol-5-yloxy)pyrimidin-4-yl)carbamate 5-(6-Aminopyridin-4-yloxy)-1H-indole-1-cabxylic acid methylamide (847 mg, 2.99 mmol) synthesized in Production example 2-3 was dissolved in N,N-dimethylformamide (10 ml) under nitrogen atmosphere. Pyridine (0.290 ml, 11.5 mmol) and phenyl chlorocarbonate (0.394 ml, 3.15 mmol) were sequentially added dropwise thereto while cooling with an ice water bath. After the reaction mixture was stirred for 30 minutes, triethylamine (0.417 ml, 2.99 mmol) was added, and the reaction mixture was heated to room temperature while stirred. After 30 minutes, the reaction mixture was partitioned between ethyl acetate and water. The organic layer was washed with water and brine, and was dried over anhydrous magnesium sulfate. The solvent was distilled off, and then the residue was purified by silica gel column chromatography (eluent; ethyl acetate:hexane=3:1). The crystals were precipitated from ethyl acetate-hexane, filtered off, and dried under aeration to yield the title compound (504 mg, 1.25 mmol, 42%) as white crystals.
$^1$H-NMR Spectrum (CDCl$_3$) δ (ppm): 3.05 (3H, d, J=4.8 Hz), 5.53 (1H, q, J=4.8 Hz), 6.58 (1H, d, J=4.0 Hz), 7.08 (1H, dd, J=2.4, 8.8 Hz), 7.13–7.19 (2H, m), 7.23–7.29 (1H, m), 7.34 (1H, d, J=2.4 Hz), 7.36–7.44 (3H, m), 7.52 (1H, s), 8.14 (1H, d, J=8.8 Hz), 8.59 (1H, s), 9.99 (1H, brs).

Example 3

5-(6-(((4-Hydroxypiperidin-1-yl)carbonyl)amino)pyrimidin-4-yloxy)-1H-indole-1-carboxylic acid methylamide Similarly to Example 2, the title compound (100 mg, 0.231 mmol, 58%) was obtained as white powder from phenyl(6-(1-methylcarbamoyl-1H-indol-5-yloxy)pyrimidin-4-yl)carbamate (161 mg, 0.400 mmol) and 4-hydroxypiperidine.
$^1$H-NMR Spectrum (DMSO-$d_6$) δ (ppm): 1.24–1.34 (2H, m), 1.64–1.73 (2H, m), 2.85 (3H, d, J=4.0 Hz), 3.02–3.12 (2H, m), 3.64 (1H, m), 3.72–3.80 (2H, m), 4.69 (1H, d, J=4.0 Hz), 6.68 (1H, d, J=3.6 Hz), 7.06 (1H, dd, J=2.4, 8.8 Hz), 7.20 (1H, s), 7.40 (1H, d, J=2.4 Hz), 7.88 (1H, d, J=3.6 Hz), 8.17 (1H, q, J=4.0 Hz), 8.27 (1H, d, J=8.8 Hz), 8.40 (1H, s), 9.72 (1H, brs).

Example 4

5-(6-((4-(Pyrrolidin-1-yl)piperidin-1-yl)carbonylamino)pyrimidin-4-yloxy)-1H-indole-1-carboxylic acid methylamide Similarly to Example 2, the title compound (141 mg, 0.304 mmol, 76%) was obtained as white crystals from phenyl(6-(1-methylcarbamoyl-1H-indol-5-yloxy)pyrimidin-4-yl)carbamate (161 mg, 0.400 mmol) and 4-(1-pyrrolidynyl)piperidine.
$^1$H-NMR Spectrum (DMSO-$d_6$) δ (ppm): 1.23–1.36 (2H, m), 1.63–1.70 (4H, m), 1.74–1.84 (2H, m), 2.08–2.18 (1H, m), 2.42–2.50 (4H, m), 2.82–2.95 (5H, m), 3.90–3.98 (2H, m), 6.68 (1H, d, J=3.6 Hz), 7.06 (1H, dd, J=2.4, 8.8 Hz), 7.20 (1H, s), 7.40 (1H, d, J=2.4 Hz), 7.88 (1H, d, J=3.6 Hz), 8.17 (1H, q, J=4.0 Hz), 8.27 (1H, d, J=8.8 Hz), 8.40 (1H, s), 9.71 (1H, brs).

Example 5

5-(2-(3-((1R)-1-Carbamoyl-2-phenylethyl)ureido)pyridin-4-yloxy)-1H-indole-1-carboxylic acid methylamide Phenyl N-(4-(1-(methylamino)carbonyl-1H-5-indolyloxy)-2-pyridyl)-N-(phenoxycarbonyl)carbamate (104 mg, 0.200 mmol) and triethylamine (1 ml) were dissolved in N,N-dimethylformamide (3 ml), and (2R)-2-amino-3-phenylpropionamide hydrochloride (201 mg, 1.00 mmol) was added, and the reaction mixture was stirred for 18 hours. The reaction mixture was partitioned between ethyl acetate and the saturated aqueous solution of ammonium chloride. The organic layer was washed with water and brine, and was dried over anhydrous magnesium sulfate. The solvent was distilled off, and the residue was purified by silica gel column chromatography (eluent; ethyl acetate:methanol=50:1). The crystals were precipitated from a solvent mixture of ethyl acetate-hexane, filtered off, and dried under aeration to yield the title compound (77.2 mg, 0.152 mmol, 76%) as white crystals.
$^1$H-NMR Spectrum (DMSO-$d_6$) δ (ppm): 2.81 (1H, dd, J=8.0, 13.2 Hz), 2.84 (3H, d, J=4.4 Hz), 3.01 (1H, dd, J=4.8, 13.2 Hz), 4.38 (1H, m), 6.52 (1H, dd, J=2.4, 6.0 Hz), 6.69 (1H, d, J=3.2 Hz), 6.86 (1H, s), 7.01–7.07 (2H, m), 7.15–7.30 (5H, m), 7.37 (1H, d, J=2.4 Hz), 7.50 (1H, s), 7.88 (1H, d, J=3.2 Hz), 8.02 (1H, d, J=6.0 Hz), 8.18 (1H, q, J=4.4 Hz), 8.22–8.34 (2H, m), 9.11 (1H, s).

The starting material, Phenyl N-(4-(1-(methylamino)carbonyl-1H-indol-5-yloxy)pyridin-2-yl)-N-(phenoxycarbonyl) carbamate, was synthesized as follows.

Production Example 5-1

N1-Methyl-5-(2-amino-4-pyridyl)oxy-1H-1-indolecarboxamide

Sodium hydride (430 mg, 10.75 mmol) was suspended in N,N-dimethylformamide (25 ml) under nitrogen atmosphere, and 4-(1H-5-indolyloxy)-2-pyridinamine (2.253 g, 10.00 mmol, CAS No. 417722-11-3) described in WO 02/32872 was gradually added while stirred at room temperature. After 10 minutes, the reaction mixture was cooled with an ice water bath, and then phenyl N-methylcarbamate (1.587 g, 10.50 mmol) was added. The reaction mixture was heated to room temperature and stirred for 2 hours. The reaction mixture was partitioned between ethyl acetate and water. The organic layer was washed with water and brine, and was dried over anhydrous sodium sulfate. The solvent was removed by distilled off. The crystals were precipitated from ethyl acetate, filtered off, and dried under aeration to yield the title compound (2.163 g, 7.66 mmol, 76.6%) as pale brown crystals.
$^1$H-NMR Spectrum (CDCl$_3$) δ (ppm): 3.09 (3H, d, J=4.8 Hz), 4.36 (2H, m), 5.49 (1H, m), 5.92 (1H, d, J=2.0 Hz), 6.30 (1H, dd, J=2.0, 6.0 Hz), 6.61 (1H, d, J=3.6 Hz), 7.07 (1H, dd, J=2.4, 8.8 Hz), 7.30 (1H, d, J=2.4 Hz), 7.45 (1H, d, J=3.6 Hz), 7.92 (1H, d, J=6.0 Hz), 8.17 (1H, d, J=8.8 Hz).

Production Example 5-2 phenyl N-(4-(1-(methylamino)carbonyl-1H-5-indolyloxy)-2-pyridyl)-N-(phenoxycarbonyl)carbamate N1-Methyl-5-(2-amino-pyridyl)oxy-1H-1-indolecarboxamide (2.0 g, 7.1 mmol) was suspended in tetrahydrofuran (140 ml) and N,N-dimethylformamide (1.4 ml) at room temperature, and triethylamine (2.2 ml, 16 mmol) was added while stirred. The reaction mixture was cooled with an ice, and phenyl chloroformate (1.8 ml, 15 mmol) was added, and the reaction mixture was stirred at room temperature for 1.5 hours. Phenyl chloroformate (0.5 ml) was further added, and the reaction mixture was stirred at room temperature for 0.5 hours. Brine was added to the reaction mixture; and this was subjected to extraction with ethyl acetate, washed with brine, dried over anhydrous magnesium sulfate, and concentrated under reduced pressure. Diethyl ether was added to the residue, then the precipitated crystals were filtered off, washed with diethyl ether, and dried under aeration to yield the title compound (3.3 g, 6.3 mmol, 89%) as pale brown crystals.

$^1$H-NMR Spectrum (DMSO-$d_6$) δ (ppm): 3.30 (3H, d, J=4.4 Hz), 6.66 (1H, d, J=3.6 Hz), 6.95 (1H, dd, J=2.4, 6.0 Hz), 7.10 (1H, dd, J=2.4, 8.8 Hz), 7.15–7.18 (4H, m), 7.27–7.31 (2H, m), 7.40–7.45 (5H, m), 7.52 (1H, d, J=2.4 Hz), 7.88 (1H, d, J=3.6 Hz), 8.17 (1H, q, J=4.4 Hz), 8.31 (1H, d, J=8.8 Hz), 8.41 (1H, d, J=6.0 Hz).

N1-methyl-5-(2-amino-4-pyridyl)oxy-1H-1-indolecarboxamide described in Production example 5-1, can be also synthesized as follows.

N1-Methyl-5-(2-amino-4-pyridyl)oxy-1H-1-indolecarboxamide 5-(2-Aminopyridin-4-yloxy)-2,3-dihydro-1H-indole-1-carboxylic acid methylamide (40 mg, 0.14 mmol) was dissolved in acetic acid (0.9 ml), manganese (III) acetate (29 mg, 0.17 mmol) was added thereto and the reaction mixture was stirred at 70° C. for 3.5 hours. Manganese (III) acetate (29 mg, 0.17 mmol) was further added, and the reaction mixture was further stirred at 70° C. for 0.5 hours. After naturally cooled to room temperature, the reaction mixture was partitioned between ethyl acetate and saturated aqueous solution of sodium hydrogencarbonate. The organic layer was washed with brine, dried over anhydrous magnesium sulfate, and concentrated under reduced pressure. The obtained crystals were suspended in diethyl ether:acetone=3:1, filtered off, washed with diethyl ether, and dried under aeration to yield the title compound (24 mg, 0.085 mmol, 61%) as colorless crystals.

The starting material, 5-(2-Aminopyridin-4-yloxy)-2,3-dihydro-1H-indole-1-carboxylic acid methylamide was synthesized as follows.

Production Example 5-3

5-Benzyloxy-1H-indole-1-carboxylic acid methylamide

Sodium hydride (2.212 g, 55.30 mmol, 60% in oil) was suspended in N,N-dimethylformamide (100 ml), 5-benzyloxyindole (10.29 g, 46.09 mmol) was added thereto while stirred at room temperature, and the reaction mixture was stirred at room temperature for 40 minutes. The reaction mixture was cooled with an ice water bath, and phenyl N-methylcarbamate (8.360 g, 55.30 mmol) was added. After the reaction mixture was stirred for 30 minutes, the solution was stirred at room temperature for 2.5 hours. After water was added to the reaction mixture and the reaction mixture was stirred at room temperature for 1 hour, the crystals were sequentially washed with water and diethyl ether, and dried under aeration to yield the title compound (12.07 g, 43.06 mmol, 93.41%) as pale yellow crystals.

$^1$H-NMR Spectrum (DMSO-$d_6$) δ (ppm): 2.80 (3H, d, J=4.4 Hz), 5.10 (2H, s), 6.56 (1H, d, J=3.8 Hz), 6.93 (1H, dd, J=2.4, 9.0 Hz), 7.16 (1H, d, J=2.4 Hz), 7.30 (1H, t, J=7.2 Hz), 7.37 (2H, t, J=7.2 Hz), 7.45 (2H, d, J=7.2 Hz), 7.74 (1H, d, J=3.8 Hz), 8.00 (1H, m), 8.11 (1H, d, J=9.0 Hz).

Production Example 5-4

5-Hydroxy-2,3-dihydro-1H-indole-1-carboxylic acid methylamide

5-Benzyloxy-1H-indole-carboxylic acid methylamide (10.00 g, 35.67 mmol) was dissolved in methanol (200 ml) and tetrahydrofuran (150 ml), 10% palladium on carbon (0.9 g) was added, and the reaction mixture was stirred at room temperature under hydrogen atmosphere for 9 hours. After the catalyst was removed by filtration, the solvent was distilled off under reduced pressure. The residue was dissolved in ethanol (400 ml), 10% palladium on carbon (0.9 g) was added, then the reaction mixture was stirred at room temperature under hydrogen atmosphere for 26 hours. After the catalyst was removed by filtration, the solvent was distilled off under reduced pressure. The obtained crystals were suspended in diethyl ether, filtered off, washed with diethyl ether, and dried under aeration to yield the title compound (6.522 g, 33.93 mmol, 95.12%) as grayish crystals.

$^1$H-NMR Spectrum (DMSO-$d_6$) δ (ppm): 2.61 (3H, d, J=4.4 Hz), 2.99 (2H, t, J=8.6 Hz), 3.76 (2H, t, J=8.6 Hz), 6.33 (1H, d, J=4.4 Hz), 6.43 (1H, dd, J=2.4, 8.4 Hz), 6.54 (1H, d, J=2.4 Hz), 7.58 (1H, d, J=8.4 Hz), 8.82 (1H, s).

Production Example 5-5

5-(2-Aminopyridin-4-yloxy)-2,3-dihydro-1H-indole-1-carboxylic acid methylamide

Sodium hydride (202 mg, 3.89 mmol, 60% in oil) was suspended in dimethyl sulfoxide (5.0 ml), then 5-hydroxy-2,3-dihydro-1H-indole-1-carboxylic acid methylamide (971 mg, 5.06 mmol) and 2-amino-4-chloropyridine (500 mg, 3.89 mmol) were added at room temperature under nitrogen atmosphere, and the reaction mixture was heated and stirred at 160° C. for 12 hours under nitrogen atmosphere. After naturally cooled down to room temperature, the reaction mixture was partitioned between ethyl acetate and water. The organic layer was washed with brine, was dried over anhydrous magnesium sulfate, and was concentrated under reduced pressure. The residue was purified by silica gel column chromatography (Fuji Silysia BW-300; eluent:ethyl acetate, ethyl acetate:methanol=85:10 in this order). The fractions containing the desired compound were concentrated, and the residue was further purified by silica gel column chromatography (Fuji Silysia NH, eluent; from ethyl acetate to ethyl acetate:methanol=90:10). The obtained crystals were suspended in diethyl ether:acetone=3:1, filtered off, washed with diethyl ether, and dried under aeration to yield the title compound (51 mg, 0.18 mmol, 4.6%) as pale green crystals.

¹H-NMR Spectrum (DMSO-d₆) δ (ppm): 2.65 (3H, d, J=4.4 Hz), 3.09 (2H, t, J=8.6 Hz), 3.86 (2H, t, J=8.6 Hz), 5.75 (1H, d, J=2.0 Hz), 5.85 (2H, brs), 6.07 (1H, dd, J=2.0, 6.0 Hz), 6.56 (1H, d, J=4.4 Hz), 6.81 (1H, dd, J=2.4, 8.4 Hz), 6.90 (1H, d, J=2.4 Hz), 7.73 (1H, d, J=6.0 Hz), 7.83 (1H, d, J=8.4 Hz).

Example 6

5-(2-(3-((1S)-1-Carbamoyl-2-phenylethyl)ureido) pyridin-4-yloxy)-1H-indole-1-carboxylic acid methylamide N1-Methyl-5-((2-amino-4-pyridyl)oxy-1H-1-indolcarboxamide (100 mg, 0.354 mmol) synthesized in Production example 5-1 and triethylamine (0.3 ml) were dissolved in N,N-dimethylformamide (3 ml). Phenyl chlorocarbonate (0.0888 ml, 0.708 mmol) was added dropwise thereto at room temperature and the reaction mixture was stirred for 30 minutes. (2S)-2-Amino-3-phenylpropionamide (290 mg, 1.77 mmol) was added and the reaction mixture was stirred for 3 days. The reaction mixture was partitioned between a solvent mixture of ethyl acetate-tetrahydrofuran and water. The organic layer was washed with water and brine, dried over anhydrous magnesium sulfate. The solvent was distilled off, and the residue was purified by silica gel column chromatography (eluent; ethyl acetate:methanol=20:1). The crystals were precipitated from a solvent mixture of ethyl acetate-hexane, filtered off, and dried under aeration to yield the title compound (69.4 mg, 0.147 mmol, 41%) as white crystals.

Example 7

5-(2-(3-(2-Oxo-2-(pyrrolidin-1-yl)ethyl)ureido)pyridin-4-yloxy)-1H-indole-1-carboxylic acid methylamide tert-Butoxycarbonylaminoacetic acid (876 mg, 5.00 mmol) and N-methylmorpholine (506 mg, 5.00 mmol) were dissolved in tetrahydrofuran (20 ml). After isobutyl chloroformate (683 mg, 5.00 mmol) was added dropwise at below −15° C. and the reaction mixture was stirred for 30 minutes, pyrrolidine (782 mg, 11.0 mmol) was added at below −15° C. and the reaction mixture was further stirred at 0° C. for 30 minutes. The reaction mixture was partitioned between ethyl acetate and 1N aqueous solution of sodium hydroxide. The organic layer was washed with 1N hydrochloric acid, a saturated aqueous solution of sodium hydrogencarbonate and brine, and was dried over anhydrous magnesium sulfate. The solvent was distilled off, and the obtained residue was dissolved in a solvent mixture of ethyl acetate (10 ml)-tetrahydrofuran (5 ml). 4N hydrochloric acid Ethyl acetate solution (5 ml) was added and the reaction mixture was stirred at room temperature for 18 hours. After the solvent was distilled off, ethyl acetate was added to the crude product to precipitate crystals; and the crystals were filtered off and dried under aeration to yield 2-amino-1-(pyrrolidin-1-yl)ethanone hydrochloride (573 mg, 4.16 mmol, 84%) as white crystals.

The title compound (74.7 mg, 0.171 mmol, 86%) was obtained as white crystals from phenyl N-(4-(1-(methylamino)carbonyl-1H-5-indolyloxy)-2-pyridyl)-N-(phenoxycarbonyl)carbamate (104 mg, 0.200 mmol) synthesized in Production example 5-2 and the previously obtained 2-amino-1-(pyrrolidin-1-yl)ethanone hydrochloride (165 mg, 1.00 mmol) similarly to Example 5.

¹H-NMR Spectrum (DMSO-d₆) δ (ppm): 1.71–1.81 (2H, m), 1.83–1.93 (2H, m), 2.85 (3H, d, J=4.0 Hz), 3.26–3.40 (4H, m), 3.90 (2H, d, J=4.4 Hz), 6.55 (1H, dd, J=2.0, 6.0 Hz), 6.69 (1H, d, J=3.4 Hz), 6.94 (1H, d, J=2.0 Hz), 7.06 (1H, dd, J=2.0, 9.0 Hz), 7.38 (1H, d, J=2.0 Hz), 7.89 (1H, d, J=3.4 Hz), 8.05 (1H, d, J=6.0 Hz), 8.12–8.26 (2H, m), 8.30 (1H, d, J=9.0 Hz), 9.28 (1H, s).

Example 8

5-(2-(3-(2-(4-Hydroxy-4-methylpiperidin-1-yl)-2-oxoethyl)ureido)pyridin-4-yloxy)-1H-indole-1-carboxylic acid methylamide 4-Hydoxy-4-methylpiperidine hydrochloride (113 mg, 0.745 mmol) was suspended in N,N-dimethylformamide (3 ml), then triethylamine (1 ml) was added; benzotriazole-1-isooxytris(dimethylamino)phosphonium hexafluorophosphate (201 mg, 0.454 mmol) and ((4-(1-methylcarbamoyl-1H-indol-5-yloxy)pyridin-2-yl)aminocarbonylamino)acetic acid (145 mg, 0.378 mmol) were added thereto; and the reaction mixture was stirred at room temperature for 2 hours. After water was added to the reaction mixture, extraction was performed with ethyl acetate-tetrahydrofuran. The organic layer was washed with brine, dried over anhydrous magnesium sulfate, and concentrated under reduced pressure. The residue was purified by silica gel column chromatography (Fuji Silysia NH silica gel; ethyl acetate, ethyl acetate:methanol=20:1, 10:1 in this order). After concentration under reduced pressure, the product was solidified with diethyl ether, suspended, filtered off, washed with diethyl ether, and dried under aeration to yield the title compound (137 mg, 0.285 mmol, 75.4%) as a colorless amorphous solid.

¹H-NMR Spectrum (DMSO-d₆) δ (ppm): 1.10 (3H, s), 1.38–1.44 (4H, m), 2.83 (3H, d, J=3.6 Hz), 3.02 (2H, m), 3.90 (2H, m), 3.96 (2H, d, J=4.0 Hz), 4.37 (1H, s), 6.52 (1H, d, J=5.6 Hz), 6.67 (1H, d, J=3.2 Hz), 6.91 (1H, s), 7.04 (1H, d, J=9.0 Hz), 7.36 (1H, s), 7.87 (1H, d, J=3.2 Hz), 8.03 (1H, d, J=5.6 Hz), 8.17 (2H, m), 8.28 (1H, d, J=9.0 Hz), 9.27 (1H, s).

The starting materials were synthesized as follows.

Production Example 8-1

((4-(1-Methylcarbamoyl-1H-indol-5-yloxy)pyridin-2-yl)aminocarbonylamino)acetic acid Methyl aminoacetate hydrochloride (300 mg, 2.3 mmol) was dissolved in N,N-dimethylformamide (4 ml), and then triethylamine (1 ml) was added. Phenyl N-(4-(1-(methylamino)carbonyl-1H-indol-5-yloxy)-2-pyridyl)-N-(phenoxycarbonyl)carbamate (250 mg, 0.48 mmol) synthesized in Production example 5-2 was added thereto. The reaction mixture was stirred at room temperature for 22 hours. After water was added to the reaction mixture, extraction was performed with a solvent mixture of ethyl acetate-tetrahydrofuran. The organic layer was washed with brine, dried over anhydrous magnesium sulfate, and concentrated under reduced pressure. The residue was purified by silica gel column chromatography (Fuji Silysia BW-300, ethyl acetate). The obtained pale yellow oil was dissolved in a solvent mixture of tetrahydrofuran (2 ml)-methanol (1 ml), then 4N aqueous solution of lithium hydroxide (0.48 ml) was added, and the reaction mixture was stirred at room temperature for 1 hour. After that, 1N hydrochloric acid (2 ml) was added, and this was subjected to extraction with ethyl acetate-tetrahydrofuran. The organic layer was washed with brine and dried over anhydrous magnesium sulfate, and concentrated under reduced pressure to yield the title compound (145 mg, 0.38 mmol, 79%) as colorless crystals.

$^1$H-NMR Spectrum (DMSO-d$_6$) δ (ppm): 2.83 (3H, d, J=3.6 Hz), 3.81 (2H, d, J=5.6 Hz), 6.57 (1H, m), 6.68 (1H, d, J=3.6 Hz), 6.84 (1H, s), 7.05 (1H, dd, J=2.0, 9.2 Hz), 7.38 (1H, d, J=2.0 Hz), 7.88 (1H, d, J=3.6 Hz), 8.05 (1H, d, J=5.6 Hz), 8.16–8.30 (3H, m), 9.33 (1H, brs).

Production Example 8-2

Benzyl(4-hydroxy-4-methylpiperidin-1-yl)carboxylate

Benzyl(4-oxopiperidin-1-yl)carboxylate (4.7 g, 20 mmol) was dissolved in tetrahydrofuran (200 ml); methyllithium-diethylether solution (9.0 ml (1.02 M)+11.6 ml (1.14 M), total 22 mmol) was added dropwise thereto (internal temperature: −60° C. or below) while stirred at −78° C. under nitrogen atmosphere; and then the reaction mixture was stirred for 1.5 hours as it stands. On the other hand, a similar reaction was performed by using piperidin-4-one-1-carboxylate (1.1 g, 5.0 mmol) in another container. After the saturated aqueous solution of ammonium chloride was added to each reaction mixture, the two reaction mixtures were mixed. Extraction was performed with ethyl acetate, washed with brine, dried over anhydrous magnesium sulfate, concentrated under reduced pressure, and purified by silica gel column chromatography (Fuji Silysia BW-300, hexane-ethyl acetate system) to yield the title compound (4.5 g, 18 mmol, 73%) as colorless crystals.

$^1$H-NMR Spectrum (DMSO-d$_6$) δ (ppm): 1.10 (3H, s), 1.32–1.44 (4H, m), 3.17 (2H, m), 3.61 (2H, dt, J=3.6, 9.2 Hz), 4.34 (1H, s), 5.04 (2H, s), 7.27–7.37 (5H, m).

Production Example 8-3

4-Hydroxy-4-methylpiperidine monohydrochloride

Benzyl(4-hydroxy-4-methylpiperidin-1-yl)carboxylate (4.5 g, 18 mmol) was dissolved in methanol (90 ml), 10% palladium on carbon powder (0.60 g) was added, and the reaction mixture was stirred at room temperature under hydrogen atmosphere overnight. The catalyst was removed by filtration and the resultant solution was concentrated under reduced pressure to yield a crude product of 4-hydroxy-4-methylpiperidine as a pale yellow oil (2.1 g). After the product was dissolved in methanol, 1N hydrochloric acid (17.5 ml) was added and the solvent was distilled off under reduced pressure. The obtained crystals were suspended in acetone, the crystals were filtered off, washed with acetone, and dried under aeration to yield the title compound (2.1 g, 14 mmol, 77%) as colorless crystals.

$^1$H-NMR Spectrum (DMSO-d$_6$) δ (ppm): 1.14 (3H, s), 1.55–1.69 (4H, m), 3.00 (4H, m), 4.68 (1H, brs), 8.77 (1H, brs), 8.89 (1H, brs).

Example 9

5-(2-(3-((1S)-1-Carbamoylethyl)ureido)pyridin-4-yloxy)-1H-indole-1-carboxylic acid methylamide N1-Methyl-5-((2-amino-4-pyridyl)oxy-1H-1-indolecarboxamide (100 mg, 0.354 mmol) synthesized in Production example 5-1 and triethylamine (1 ml) were dissolved in tetrahydrofuran (3 ml), then phenyl chlorocarbonate (0.0888 ml, 0.708 mmol) was added dropwise at room temperature, and the reaction mixture was stirred for 2 hours. After the solvent was distilled off under reduced pressure, the residue was dissolved in N,N-dimethylformamide (3 ml). (2S)-2-Aminopropionamide hydrochloride (220 mg, 1.77 mmol) and triethylamine (1 ml) were added and the reaction mixture was stirred for 18 hours. The reaction mixture was partitioned between ethyl acetate and a saturated aqueous solution of ammonium chloride. The organic layer was washed with brine and dried over anhydrous magnesium sulfate. The solvent was distilled off and the residue was purified by silica gel column chromatography (eluent; ethyl acetate:methanol=20:1). The crystals were precipitated from a solvent mixture of ethyl acetate-hexane, filtered off, and dried under aeration to yield the title compound (38.5 mg, 0.0971 mmol, 27%) as white crystals.

$^1$H-NMR Spectrum (DMSO-d$_6$) δ (ppm): 1.21 (3H, d, J=6.8 Hz), 2.85 (3H, d, J=4.0 Hz), 4.17 (1H, m), 6.55 (1H, d, J=5.2 Hz), 6.70 (1H, d, J=3.6 Hz), 6.93 (1H, s), 7.02 (1H, s), 7.06 (1H, dd, J=2.0, 8.8 Hz), 7.39 (1H, d, J=2.0 Hz), 7.46 (1H, s), 7.90 (1H, d, J=3.6 Hz), 8.06 (1H, d, J=5.2 Hz) 8.11 (1H, brs), 8.20 (1H, q, J=4.0 Hz), 8.30 (1H, d, J=8.8 Hz), 9.21 (1H, brs).

Example 10

5-(2-(3-((1S)-1-Carbamoyl-3-methylbutyl)ureido)pyridin-4-yloxy)-1H-indole-1-carboxylic acid methylamide Similarly to Example 9, the title compound (59.5 mg, 0.135 mmol, 38%) was obtained as white crystals from N1-methyl-5-(2-amino-4-pyridyl)oxy-1H-1-indolecarboxamide (100 mg, 0.354 mmol) synthesized in Production example 5-1 and (2S)-2-amino-4-methylpentanamide hydrochloride (295 mg, 1.77 mmol).

$^1$H-NMR Spectrum (DMSO-d$_6$) δ (ppm): 0.83–0.91 (6H, m), 1.35–1.50 (2H, m), 1.58 (1H, m), 2.85 (3H, d, J=4.4 Hz), 4.17 (1H, m), 6.53 (1H, dd, J=2.4, 6.0 Hz), 6.69 (1H, d, J=3.8 Hz), 6.92–7.01 (2H, m), 7.06 (1H, dd, J=2.4, 8.8 Hz), 7.38 (1H, d, J=2.4 Hz), 7.48 (1H, s), 7.89 (1H, d, J=3.8 Hz) 7.98–8.12 (2H, m), 8.19 (1H, q, J=4.4 Hz), 8.30 (1H, d, J=8.8 Hz), 9.09 (1H, s).

Example 11

5-(2-(3-Carbamoylmethylureido)pyridin-4-yloxy)-1H-indole-1-carboxylic acid methylamide Similarly to Example 5, the title compound (52.8 mg, 0.138 mmol, 69%) was obtained as white crystals from phenyl N-(4-(1-(methylamino)carbonyl-1H-5-indolyloxy)-2-pyridyl)-N-(phenoxycarbonyl)carbamate (104 mg, 0.200 mmol) synthesized in Production example 5-2 and glycinamide hydrochloride (111 mg, 1.00 mmol).

$^1$H-NMR Spectrum (DMSO-d$_6$) δ (ppm): 2.85 (3H, d, J=4.0 Hz), 3.70 (2H, d, J=5.2 Hz), 6.53 (1H, dd, J=2.4, 5.8 Hz), 6.69 (1H, d, J=3.4 Hz), 6.92 (1H, d, J=2.4 Hz), 7.01 (1H, s), 7.06 (1H, dd, J=2.4, 9.2 Hz), 7.34–7.42 (2H, m), 7.89 (1H, d, J=3.4 Hz), 8.05 (1H, d, J=5.8 Hz), 8.14–8.26 (2H, m), 8.30 (1H, d, J=9.2 Hz), 9.21 (1H, s).

Example 12

5-(2-(3-Cyclopropylcarbamoylmethylureido)pyridin-4-yloxy)-1H-indole-1-carboxylic acid methylamide Similarly to Example 5, the title compound (50.7 mg, 0.120 mmol, 60%) was obtained as white powder from phenyl N-(4-(1-(methylamino)carbonyl-1H-5-indolyloxy)-2-pyridyl)-N-(phenoxycarbonyl)carbamate (104 mg, 0.200 mmol) synthesized in Production example 5-2 and 2-amino-N-cyclopropylacetamide hydrochloride (151 mg, 1.00 mmol) obtained from tert-butoxycarbonylaminoacetic acid and cyclopropylamine by the method similar to Example 7.

$^1$H-NMR Spectrum (DMSO-$d_6$) δ (ppm): 0.36–0.42 (2H, m), 0.57–0.63 (2H, m), 2.60 (1H, m), 2.85 (3H, d, J=4.4 Hz), 3.68 (2H, d, J=5.2 Hz), 6.53 (1H, dd, J=2.0, 6.0 Hz), 6.69 (1H, d, J=3.6 Hz), 6.91 (1H, d, J=2.0 Hz), 7.06 (1H, dd, J=2.4, 9.0 Hz), 7.38 (1H, d, J=2.4 Hz), 7.89 (1H, d, J=3.6 Hz), 8.00 (1H, d, J=4.0 Hz), 8.06 (1H, d, J=6.0 Hz) 8.14–8.26 (2H, m), 8.30 (1H, d, J=9.0 Hz), 9.21 (1H, s).

Example 13

5-(2-(3-((1S)-1-Carbamoyl-2-hydroxyethyl) ureido)pyridin-4-yloxy)-1H-indole-1-carboxylic acid methylamide Similarly to Example 9, the title compound (52.1 mg, 0.126 mmol, 36%) was obtained as white crystals from N1-methyl-5-(2-amino-4-pyridyl)oxy-1H-1-indolecarboxamide (100 mg, 0.354 mmol) synthesized in Production example 5-1 and (2S)-2-amino-3-hydroxypropionamide hydrochloride (249 mg, 1.77 mmol).

$^1$H-NMR Spectrum (DMSO-$d_6$) δ (ppm): 2.85 (3H, d, J=4.4 Hz), 3.52 (1H, dd, J=4.8, 6.4 Hz), 3.62 (1H, dd, J=4.8, 6.4 Hz), 4.13 (1H, m), 4.94 (1H, brs), 6.53 (1H, dd, J=2.4, 6.0 Hz), 6.69 (1H, d, J=3.6 Hz), 6.99 (1H, s), 7.02–7.10 (2H, m), 7.35 (1H, s), 7.38 (1H, d, J=2.4 Hz), 7.89 (1H, d, J=3.6 Hz), 8.05 (1H, d, J=6.0 Hz), 8.10–8.26 (2H, m), 8.30 (1H, d, J=8.8 Hz), 9.22 (1H, s).

Example 14

5-(2-(3-((R)-1-Carbamoyl-2-hydroxyethyl)ureido)pyridin-4-yloxy)-1H-indole-1-carboxylic acid methylamide Similarly to Example 9, the title compound (56.0 mg, 0.136 mmol, 68%) was obtained as white crystals from phenyl N-(4-(1-(methylamino)carbonyl-1H-5-indolyloxy)-2-pyridyl)-N-(phenoxycarbonyl)carbamate (104 mg, 0.200 mmol) synthesized in Production example 5-2 and (2R)-2-amino-3-hydroxypropioamide hydrochloride (167 mg, 1.00 mmol) obtained from (2R)-2-(tert-butoxycarbonylamino)-3-hydroxypropionic acid and aqueous ammonia by the method similar to Example 7.

Example 15

(2S)-2-(3-(4-(1-Methylcarbamoyl-1H-indol-5-yloxy)pyridin-2-yl)ureido)-1,5-pentanedicarboxylic acid diamide Similarly to Example 6, the title compound (82.5 mg, 0.189 mmol, 51%) was obtained as white powder from N1-methyl-5-(2-amino-4-pyridyl)oxy-1H-1-indolecarboxamide (100 mg, 0.354 mmol) synthesized in Production example 5-1 and (2S)-2-amino-1,5-pentanedicarboxylic acid diamide hydrochloride (321 mg, 1.77 mmol).

$^1$H-NMR Spectrum (DMSO-$d_6$) δ (ppm): 1.66–2.28 (4H, m), 2.85 (3H, d, J=4.4 Hz), 4.17 (1H, m), 6.53 (1H, dd, J=2.4, 6.0 Hz), 6.69 (1H, d, J=3.6 Hz), 6.72 (1H, s), 6.97 (1H, s), 7.01–7.10 (2H, m), 7.30 (1H, s), 7.38 (1H, d, J=2.4 Hz), 7.49 (1H, s), 7.76 (1H, s) 7.89 (1H, d, J=3.6 Hz), 8.06 (1H, d, J=6.0 Hz), 8.18 (1H, q, J=4.4 Hz), 8.30 (1H, d, J=8.8 Hz), 9.13 (1H, s).

Example 16

(2S)-2-(3-(4-(1-Methylcarbamoyl-1H-indol-5-yloxy)pyridin-2-yl)ureido)succinamide Similarly to Example 6, the title compound (65.7 mg, 0.150 mmol, 42%) was obtained as white crystals from N1-methyl-5-(2-amino-4-pyridyl)oxy-1H-1-indolecarboxamide (100 mg, 0.354 mmol) synthesized in Production example 5-1 and (2S)-2-aminosuccinamide hydrochloride (297 mg, 1.77 mmol).

$^1$H-NMR Spectrum (DMSO-$d_6$) δ (ppm): 2.45 (2H, d, J=6.8 Hz), 2.85 (3H, d, J=3.6 Hz), 4.40 (1H, m), 6.53 (1H, dd, J=2.4, 6.0 Hz), 6.69 (1H, d, J=3.6 Hz), 6.88 (1H, s), 6.95 (1H, s), 7.00 (1H, d, J=2.4 Hz), 7.06 (1H, dd, J=2.4, 9.2 Hz), 7.28 (1H, s), 7.35 (1H, s), 7.38 (1H, d, J=2.4 Hz), 7.89 (1H, d, J=3.6 Hz), 8.04 (1H, d, J=6.0 Hz), 8.18 (1H, q, J=4.0 Hz), 8.26 (1H, brs), 8.30 (1H, d, J=9.2 Hz), 9.19 (1H, s).

Example 17

5-(2-(3-((1S)-1-Cyclopropylcarbamoyl-2-hydroxyethyl)ureido)pyridin-4-yloxy)-1H-indole-1-carboxylic acid methylamide Similarly to Example 5, the title compound (72.0 mg, 0.159 mmol, 80%) was obtained as white powder from phenyl N-(4-(1-(methylamino)carbonyl-1H-5-indolyloxy)-2-pyridyl)-N-(phenoxycarbonyl)carbamate (104 mg, 0.200 mmol) synthesized in Production example 5-2 and (2S)-2-amino-N-cyclopropyl-3-hydroxypropionamide hydrochloride (181 mg, 1.00 mmol) obtained from (2S)-2-(tert-butoxycarbonylamino)-3-hydroxypropionic acid and cyclopropylamine by the method similar to Example 7.

$^1$H-NMR Spectrum (DMSO-$d_6$) δ (ppm): 0.35–0.44 (2H, m), 0.54–0.63 (2H, m), 2.62 (1H, m), 2.85 (3H, d, J=4.0 Hz), 3.45–3.58 (2H, m), 4.09 (1H, m), 4.91 (1H, t, J=5.2 Hz), 6.53 (1H, dd, J=2.0, 6.0 Hz), 6.69 (1H, d, J=3.6 Hz), 6.99 (1H, d, J=2.0 Hz), 7.04 (1H, dd, J=2.4, 8.8 Hz), 7.38 (1H, d, J=2.4 Hz), 7.89 (1H, d, J=3.6 Hz), 7.98 (1H, d, J=4.4 Hz), 8.05 (1H, d, J=6.0 Hz), 8.09–8.24 (2H, m), 8.30 (1H, d, J=8.8 Hz), 9.18 (1H, s).

Example 18

5-(2-(3-((1S)-1-Hydroxymethyl-2-oxo-2-pyrrolidin-1-ylethyl)ureido)pyridin-4-yloxy)-1H-indole-1-carboxylic acid methylamide Similarly to Example 5, the title compound (67.6 mg, 0.145 mmol, 73%) was obtained as white powder from phenyl N-(4-(1-(methylamino)carbonyl-1H-5-indolyloxy)-2-pyridyl)-N-(phenoxycarbonyl)carbamate (104 mg, 0.200 mmol) synthesized in Production example 5-2 and (2S)-2-amino-3-hydroxy-1-(pyrrolidin-1-yl)propan-1-one hydrochloride (165 mg, 0.848 mmol) obtained from (2S)-2-(tert-butoxycarbonylamino)-3-hydroxypropionic acid and pyrrolidine by the method similar to Example 7.

¹H-NMR Spectrum (DMSO-d₆) δ (ppm): 1.72–1.81 (2H, m), 1.81–1.90 (2H, m), 2.85 (3H, d, J=4.4 Hz), 3.22–3.36 (2H, m), 3.46–3.60 (4H, m), 4.54 (1H, m), 4.98 (1H, brs), 6.54 (1H, dd, J=2.0, 5.6 Hz), 6.69 (1H, d, J=3.6 Hz), 6.97 (1H, d, J=2.0 Hz), 7.05 (1H, dd, J=2.4, 8.8 Hz), 7.38 (1H, d, J=2.4 Hz), 7.89 (1H, d, J=3.6 Hz), 8.05 (1H, d, J=5.6 Hz), 8.13–8.23 (2H, m), 8.30 (1H, d, J=8.8 Hz), 9.18 (1H, s).

Example 19

5-(2-(3-((1R)-1-Hydroxymethyl-2-oxo-2-pyrrolidin-1-ylethyl)ureido)pyridin-4-yloxy)-1H-indole-1-carboxylic acid methylamide Similarly to Example 5, the title compound (305 mg, 0.654 mmol, 93%) was obtained as white powder from phenyl N-(4-(1-(methylamino)carbonyl-1H-5-indolyloxy)-2-pyridyl)-N-(phenoxycarbonyl)carbamate (366 mg, 0.700 mmol) synthesized in Production example 5-2 and (2R)-2-amino-3-hydroxy-1-(pyrrolidin-1-yl)propan-1-one hydrochloride obtained from (2R)-2-(tert-butoxycarbonylamino)-3-hydroxypropionic acid and pyrrolidine by the method similar to Example 7.

Example 20

5-(2-(3-((1S)-1-Hydroxymethyl-2-oxo-2-piperidin-1-ylethyl)ureido)pyridin-4-yloxy)-1H-indole-1-carboxylic acid methylamide Similarly to Example 5, the title compound (124 mg, 0.258 mmol, 86%) was obtained as white crystals from phenyl N-(4-(1-(methylamino)carbonyl-1H-5-indolyloxy)-2-pyridyl)-N-(phenoxycarbonyl)carbamate (157 mg, 0.300 mmol) synthesized in Production example 5-2 and (2S)-2-amino-3-hydroxy-1-(piperidin-1-yl)propan-1-one hydrochloride (312 mg, 1.50 mmol) obtained from (2S)-2-(tert-butoxycarbonylamino)-3-hydroxypropionic acid and piperidine by the method similar to Example 7.

¹H-NMR Spectrum (DMSO-d₆) δ (ppm): 1.36–1.61 (6H, m), 2.85 (3H, d, J=4.4 Hz), 3.40–3.53 (6H, m), 4.76 (1H, m), 4.92 (1H, brs), 6.54 (1H, dd, J=2.4, 6.0 Hz), 6.69 (1H, d, J=3.6 Hz), 6.97 (1H, d, J=2.4 Hz), 7.06 (1H, dd, J=2.4, 9.0 Hz), 7.38 (1H, d, J=2.4 Hz), 7.89 (1H, d, J=3.6 Hz), 8.05 (1H, d, J=6.0 Hz), 8.10–8.26 (2H, m), 8.30 (1H, d, J=9.0 Hz), 9.21 (1H, s).

Example 21

5-(2-(3-((1R)-1-Hydroxymethyl-2-oxo-2-piperidin-1-ylethyl)ureido)pyridin-4-yloxy)-1H-indole-1-carboxylic acid methylamide (2R)-2-Benzyloxycarbonylamino-3-hydroxypropionic acid (1.91 g, 8.00 mmol) and N-methylmorpholine (809 mg, 8.00 mmol) were dissolved in tetrahydrofuran (20 ml). After isobutyl chloroformate (1.09 g, 8.00 mmol) was added dropwise at −15° C. or below, the reaction mixture was stirred for 30 minutes. Then, pyrrolidine (1.13 g, 16.0 mmol) was added at −15° C. or below, and the reaction mixture was further stirred at 0° C. for 30 minutes. The reaction mixture was partitioned between ethyl acetate and water. The organic layer was washed with 1N hydrochloric acid, 1N aqueous solution of sodium hydroxide, a saturated aqueous solution of sodium hydrogencarbonate, and brine, and dried over anhydrous magnesium sulfate. The solvent was distilled off, and the obtained residue was dissolved in a solvent mixture of methanol (15 ml)-tetrahydrofuran (15 ml). Then, 10% palladium on carbon (wet) (300 mg) was added, and the reaction mixture was stirred at room temperature under the stream of hydrogen for 90 minutes. After the catalyst was removed by filtration, the solvent of the filtrate was distilled off under reduced pressure to yield (2R)-2-amino-3-hydroxy-1-(piperidin-1-yl)propan-1-one (684 mg, 3.97 mmol, 50%) as a colorless oil. Similarly to Example 5, the title compound (107 mg, 0.223 mmol, 74%) was obtained as white crystals from phenyl N-(4-(1-(methylamino)carbonyl-1H-5-indolyloxy)-2-pyridyl)-N-(phenoxycarbonyl)carbamate (157 mg, 0.300 mmol) synthesized in Production example 5-2 and previously obtained (2R)-2-amino-3-hydroxy-1-(piperidin-1-yl)propan-1-one (228 mg, 1.32 mmol).

Example 22

5-(2-(3-((1S)-1-Hydroxymethyl-2-(4-hydroxypiperidin-1-yl)-2-oxoethyl)ureido)pyridin-4-yloxy)-1H-indole-1-carboxylic acid methylamide Similarly to Example 5, the title compound (118 mg, 0.238 mmol, 69%) was obtained as white powder from phenyl N-(4-(1-(methylamino)carbonyl-1H-5-indolyloxy)-2-pyridyl)-N-(phenoxycarbonyl)carbamate (179 mg, 0.343 mmol) synthesized in Production example 5-2 and (2S)-2-amino-3-hydroxy-1-(4-hydroxypiperidin-1-yl)propan-1-one hydrochloride (385 mg, 1.71 mmol) obtained from (2S)-2-(tert-butoxycarbonylamino)-3-hydroxypropionic acid and 4-hydroxypiperidine by the method similar to Example 7.

¹H-NMR Spectrum (DMSO-d₆) δ (ppm): 1.16–1.40 (2H, m), 1.61–1.80 (2H, m), 2.85 (3H, d, J=4.0 Hz), 2.98–3.50 (5H, m), 3.63–3.95 (3H, m), 4.76 (1H, m), 4.92 (1H, brs), 6.55 (1H, dd, J=2.0, 6.0 Hz), 6.69 (1H, d, J=3.6 Hz), 6.96 (1H, d, J=2.0 Hz), 7.06 (1H, dd, J=2.4, 8.8 Hz), 7.38 (1H, d, J=2.4 Hz), 7.90 (1H, d, J=3.6 Hz), 8.05 (1H, d, J=6.0 Hz), 8.08–8.26 (2H, m), 8.30 (1H, d, J=8.8 Hz), 9.26 (1H, s).

Example 23

5-(2-(3-((1S)-1-Hydroxymethyl-2-(morpholin-4-yl)-2-oxoethyl)ureido)pyridin-4-yloxy)-1H-indole-1-carboxylic acid methylamide Similarly to Example 5, the title compound (121 mg, 0.251 mmol, 84%) was obtained as white crystals from phenyl N-(4-(1-(methylamino)carbonyl-1H-5-indolyloxy)-2-pyridyl)-N-(phenoxycarbonyl)carbamate (157 mg, 0.300 mmol) synthesized in Production example 5-2 and (2S)-2-amino-3-hydroxy-1-(morpholin-4-yl)propan-1-one hydrochloride (316 mg, 1.50 mmol) obtained from (2S)-2-(tert-butoxycarbonylamino)-3-hydroxypropionic acid and morpholine by the method similar to Example 7.

¹H-NMR Spectrum (DMSO-d₆) δ (ppm): 2.85 (3H, d, J=4.4 Hz), 3.36–3.62 (10H, m), 4.74 (1H, m), 4.92 (1H, brs), 6.54 (1H, dd, J=2.4, 6.0 Hz), 6.69 (1H, d, J=3.6 Hz), 6.96 (1H, d, J=2.4 Hz), 7.06 (1H, dd, J=2.4, 8.8 Hz), 7.38 (1H, d, J=2.4 Hz), 7.89 (1H, d, J=3.6 Hz), 8.05 (1H, d, J=6.0 Hz), 8.14–8.28 (2H, m), 8.30 (1H, d, J=8.8 Hz), 9.25 (1H, s).

Example 24

5-(2-(3-(2-Cyclopropylcarbamoylethyl)ureido)pyridin-4-yloxy)-1H-indole-1-carboxylic acid methylamide Similarly to Example 5, the title compound (117 mg, 0.268 mmol, 89%) was obtained as white crystals from phenyl N-(4-(1-(methylamino)carbonyl-1H-5-indolyloxy)-2-pyridyl)-N-(phenoxycarbonyl)carbamate (157 mg, 0.300 mmol) synthesized in Production example 5-2 and 3-amino-N-cyclopropylpropionamide hydrochloride (247 mg, 1.50 mmol) obtained from 3-(tert-butoxycarbonylamino)propionic acid and cyclopropylamine by the method similar to Example 7.

$^1$H-NMR Spectrum (DMSO-$d_6$) δ (ppm): 0.32–0.38 (2H, m), 0.54–0.60 (2H, m), 2.19 (2H, t, J=6.4 Hz), 2.60 (1H, m), 2.85 (3H, d, J=4.4 Hz), 3.25–3.33 (2H, m), 6.53 (1H, dd, J=2.0, 6.0 Hz), 6.69 (1H, d, J=3.6 Hz), 6.90 (1H, d, J=2.0 Hz), 7.05 (1H, dd, J=2.4, 9.0 Hz), 7.38 (1H, d, J=2.4 Hz), 7.89 (1H, d, J=3.6 Hz), 7.93 (1H, d, J=4.0 Hz), 7.96–8.06 (2H, m), 8.18 (1H, q, J=4.4 Hz), 8.30 (1H, d, J=9.0 Hz), 9.08 (1H, s).

Example 25

5-(2-(3-(3-oxo-3-(pyrrolidin-1-yl)propyl)ureido)pyridin-4-yloxy)-1H-indole-1-carboxylic acid methylamide Similarly to Example 5, the title compound (122 mg, 0.270 mmol, 90%) was obtained as white crystals from phenyl N-(4-(1-(methylamino)carbonyl-1H-5-indolyloxy)-2-pyridyl)-N-(phenoxycarbonyl)carbamate (157 mg, 0.300 mmol) synthesized in Production example 5-2 and 3-amino-1-(pyrrolidin-1-yl)propan-1-one hydrochloride (268 mg, 1.50 mmol) obtained from 3-(tert-butoxycarbonylamino)propionic acid and pyrrolidine by the same method similar to Example 7.

$^1$H-NMR Spectrum (DMSO-$d_6$) δ (ppm): 1.70–1.78 (2H, m), 1.80–1.88 (2H, m), 2.40 (2H, t, J=6.2 Hz), 2.85 (3H, d, J=4.4 Hz), 3.24–3.38 (6H, m), 6.52 (1H, dd, J=2.0, 5.6 Hz), 6.69 (1H, d, J=3.6 Hz), 6.92 (1H, d, J=2.0 Hz), 7.05 (1H, dd, J=2.4, 9.0 Hz), 7.38 (1H, d, J=2.4 Hz), 7.89 (1H, d, J=3.6 Hz), 7.98–8.10 (2H, m), 8.18 (1H, q, J=4.4 Hz), 8.30 (1H, d, J=9.0 Hz), 9.10 (1H, s).

Example 26

5-(2-(3-(3-(4-Hydroxy-4-methylpiperidin-1-yl)-3-oxopropyl)ureido)pyridin-4-yloxy)-1H-indole-1-carboxylic acid methylamide The title compound (177 mg, 0.358 mmol, 71.1%) was obtained as colorless crystals by performing the reaction similar to Example 8 using 3-(3-(4-(1-methylcarbamoyl-1H-indol-5-yloxy)pyridin-2-yl)ureido)propionic acid (200 mg, 0.503 mmol) and 4-hydroxy-4-methylpiperidine monohydrochloride (114 mg, 0.755 mmol, Production example 8-3).

$^1$H-NMR Spectrum (DMSO-$d_6$) δ (ppm): 1.07 (3H, s), 1.23–1.41 (4H, m), 2.44 (2H, d, J=4.8 Hz), 2.83 (3H, d, J=4.4 Hz), 2.98 (1H, m), 3.23–3.30 (3H, m), 3.46 (1H, m), 3.93 (1H, m), 4.32 (1H, s), 6.49 (1H, dd, J=2.0, 6.0 Hz), 6.67 (1H, d, J=3.4 Hz), 6.90 (1H, s), 7.03 (1H, dd, J=2.0, 8.8 Hz), 7.35 (1H, d, J=2.0 Hz), 7.87 (1H, d, J=3.4 Hz), 8.00 (2H, m), 8.15 (1H, d, J=4.4 Hz), 8.28 (1H, d, J=8.8 Hz), 9.06 (1H, s).

The starting material was synthesized by the following methods.

Production Example 26-1

3-(3-(4-(1-Methylcarbamoyl-1H-indol-5-yloxy)pyridin-2-yl)ureido)propionic acid Ethyl 4-aminopropionate hydrochloride (588 mg, 3.8 mmol) was suspended in N,N-dimethylformamide (3.0 ml), and then 5N aqueous solution of sodium hydroxide (0.77 ml, 3.8 mmol) was added, and the reaction mixture was stirred at room temperature. Phenyl N-(4-(1-(methylamino)carbonyl-1H-indol-5-yloxy)-pyridin-2-yl)-N-(phenoxycarbonyl) carbamate (400 mg, 0.77 mmol, Production example 5-2) was added thereto, and the reaction mixture was stirred at room temperature for 0.75 hours. Water was added to the reaction mixture, and this was subjected to extraction with ethyl acetate-tetrahydrofuran, dried over anhydrous magnesium sulfate, and concentrated under reduced pressure. The residue was purified by silica gel column chromatography (Fuji Silysia BW-300, ethyl acetate) to yield a pale brown oil. This oil was dissolved in tetrahydrofuran (4.0 ml) and methanol (2.0 ml), 4N aqueous solution of lithium hydroxide (0.77 ml) was added at room temperature, and the reaction mixture was stirred at room temperature for 1.5 hours. To the reaction mixture, 1N hydrochloric acid (3.1 ml) was added while stirred at room temperature; and this was subjected to extraction with ethyl acetate-tetrahydrofuran, washed with brine, dried over anhydrous magnesium sulfate, and concentrated under reduced pressure. A small amount of acetone was added to the obtained amorphous solid, and this solution was diluted with diethyl ether. The crystals were filtered off, washed with diethyl ether, and dried under aeration to yield the title compound (200 mg, 0.50 mmol, 66%) as colorless crystals.

$^1$H-NMR Spectrum (DMSO-$d_6$) δ (ppm): 2.39 (2H, t, J=6.2 Hz), 2.84 (3H, d, J=4.0 Hz), 3.30 (2H, m), 6.51 (1H, d, J=5.8 Hz), 6.68 (1H, d, J=3.2 Hz), 6.87 (1H, s), 7.05 (1H, d, J=9.0 Hz), 7.37 (1H, s), 7.88 (1H, d, J=3.2 Hz), 8.01 (1H, d, J=5.8 Hz), 8.16 (1H, m), 8.17 (1H, d, J=4.0 Hz), 8.29 (1H, d, J=9.0 Hz), 9.10 (1H, s), 12.24 (1H, s).

Example 27

N1-Ethyl-5-(2-(((2-ethoxyethyl)amino)carbonyl)amino-4-pyridyl)oxy-1H-1-indolecarboxamide Phenyl N-(4-(1-(ethylamino)carbonyl-1H-5-indolyl)oxy-2-pyridyl)carbamate (100 mg, 0.24 mmol) was dissolved in N,N-dimethylformamide (1.0 ml), and 2-ethoxyethylamine (0.063 ml, 0.6 mmol) was added while stirred at room temperature. After 1 hour, the reaction mixture was partitioned between ethyl acetate and water. The organic layer was washed with water and brine, and dried over anhydrous sodium sulfate. After the solvent was distilled off, the crystals were precipitated from ethyl acetate-hexane (1:5), filtered off, and dried under aeration to yield the title compound (100 mg, 0.24 mmol, quantitative) as white crystals.

$^1$H-NMR Spectrum (DMSO-$d_6$) δ (ppm): 1.09 (3H, t, J=7.2 Hz), 1.17 (3H, t, J=7.2 Hz), 3.21–3.45 (8H, m), 6.50 (1H, dd, J=2.4, 5.6 Hz), 6.67 (1H, d, J=3.6 Hz), 6.87 (1H, brs), 7.03 (1H, dd, J=2.4, 8.8 Hz), 7.36 (1H, d, J=2.4 Hz), 7.91 (1H, d, J=3.6 Hz), 8.01 (1H, d, J=5.6 Hz), 8.12 (1H, m), 8.22 (1H, t, J=4.8 Hz), 8.28 (1H, d, J=8.8 Hz), 9.08 (1H, s).

The starting materials were synthesized by the following methods.

Production Example 27-1

N1-Ethyl-5-(2-amino-4-pyridyl)oxy-1H-1-indolecarboxamide

Sodium hydride (573 mg, 14.32 mmol) was suspended in N,N-dimethylformamide (30 ml) under nitrogen atmosphere. 4-(1H-5-Indolyloxy)-2-pyridinamine (3.00 g, 13.32 mmol, CAS No. 417722-11-3) described in WO 02/32872 was gradually added thereto while stirred at room temperature. After 10 minutes, the reaction mixture was cooled with an ice water bath, and phenyl N-ethylcarbamate (2.31 g, 13.98 mmol) was added. The reaction mixture was heated to room temperature and was stirred for 2 hours. The reaction mixture was partitioned between ethyl acetate and water. The organic layer was washed with water and brine, and dried over anhydrous sodium sulfate. The solvent was distilled off, then the crystals were precipitated from ethyl acetate, filtered off, and dried under aeration to yield the title compound (3.168 g, 10.69 mmol, 80.3%) as pale brown crystals.

$^1$H-NMR Spectrum (DMSO-$d_6$) δ (ppm): 1.32 (3H, t, J=7.2 Hz), 2.40–2.50 (2H, m), 5.74 (1H, d, J=2.4 Hz), 5.83 (2H, brs), 6.12 (1H, dd, J=2.4, 5.6 Hz), 6.66 (1H, d, J=3.6 Hz). 7.01 (1H, dd, J=2.4, 8.8 Hz), 7.32 (1H, d, J=2.4 Hz), 7.75 (1H, d, J=5.6 Hz), 7.88 (1H, d, J=3.6 Hz), 8.19 (1H, t, J=5.6 Hz), 8.26 (1H, d, J=8.8 Hz).

Production Example 27-2

Phenyl N-(4-(1-(ethylamino)carbonyl-1H-5-indolyl)oxy-2-pyridyl)carbamate

N1-ethyl-5-(2-amino-4-pyridyl)oxy-1H-1-indolecarboxamide (3.168 g, 10.69 mmol) synthesized in Production example 27-1 was dissolved in N,N-dimethylformamide (30 ml) under nitrogen atmosphere. Pyridine (1.25 ml, 15.40 mmol) and phenyl chlorocarbonate (1.61 ml, 12.83 mmol) were sequentially added dropwise while cooled with an ice water bath. The reaction mixture was heated to room temperature while stirred. After 1 hour, the reaction mixture was partitioned between ethyl acetate and water. The organic layer was washed with water and brine, and dried over anhydrous sodium sulfate. The solvent was distilled off, and the crystals were precipitated from ethyl acetate, filtered off, and dried under aeration to yield the title compound (1.530 g, 3.67 mmol, 34.4%) as white crystals.

$^1$H-NMR Spectrum (CDCl$_3$) δ (ppm): 1.32 (3H, t, J=7.2 Hz), 3.53 (2H, m), 5.48 (1H, m), 6.58 (1H, d, J=4.0 Hz), 6.62 (1H, dd, J=2.4, 5.6 Hz), 7.06 (1H, dd, J=2.4, 8.8 Hz), 7.15 (2H, m), 7.20–7.27 (1H, m), 7.30 (1H, d, J=2.4 Hz), 7.37 (2H, m), 7.45 (1H, d, J=4.0 Hz), 7.52 (1H, d, J=2.4 Hz), 8.10–8.15 (3H, m).

Example 28

N1-Methyl-5-(2-((4-(2-hydroxy-2-methylpropionyl)piperazino)carbonyl)amino-4-pyridyl)oxy-1H-1-indolecarboxamide N1-Methyl-5-(2-amino-4-pyridyl)oxy-1H-1-indolecarboxamide (150 mg, 0.53 mmol) synthesized in Production example 5-1 was dissolved in tetrahydrofuran (3 ml). Triethylamine (0.37 ml, 2.66 mmol) and phenyl chlorocarbonate (0.15 ml, 1.2 mmol) were sequentially added dropwise at room temperature, and the reaction mixture was stirred for 30 minutes. 1-(2-Hydroxy-2-methylpropionyl)piperazine (412 mg, 2.39 mmol) and N,N-dimethylformamide (3 ml) were added and the reaction mixture was stirred for 3 days. The reaction mixture was partitioned between ethyl acetate and water. The organic layer was washed with water and brine, and dried over anhydrous sodium sulfate. The solvent was distilled off, and the residue was purified by silica gel column chromatography (eluent; ethyl acetate:methanol=95:5). The crystals were precipitated from diethyl ether-hexane (1:2), filtered off, and dried under aeration to yield the title compound (189.4 mg, 0.39 mmol, 74.2%) as white crystals.

$^1$H-NMR Spectrum (DMSO-$d_6$) δ (ppm): 1.28 (6H, s), 2.83 (3H, d, J=4.0 Hz), 3.10–3.50 (8H, m), 5.43 (1H, s), 6.56 (1H, dd, J=2.4, 5.6 Hz), 6.67 (1H, d, J=3.6 Hz), 7.03 (1H, dd, J=2.4, 8.8 Hz), 7.30 (1H, d, J=2.4 Hz), 7.36 (1H, d, J=2.4 Hz), 7.87 (1H, d, J=3.6 Hz), 8.08 (1H, d, J=5.6 Hz), 8.16 (1H, q, J=4.0 Hz), 8.28 (1H, d, J=8.8 Hz), 9.21 (1H, s).

1-(2-Hydroxy-2-methylpropionyl)piperazine was synthesized by the following methods.

Production Example 28-1

Benzyl 4-(2-hydroxy-2-methylpropionyl)piperazine-1-carboxylate

Benzyl piperazine-1-carbamate (2.203 g, 10.0 mmol) was dissolved in tetrahydrofuran (50 ml); 2-hydroxy-2-methylpropionic acid (1.25 g, 12.0 mmol), 1-ethyl-3-(3-dimethylaminopropyl)carbodiimide hydrochloride (2.30 g, 12.0 mmol), 1-hydroxy-1H-benzotriazole monohydrate (1.84 g, 12.0 mmol) and triethylamine (3.35 ml, 24.0 mmol) were added; and the reaction mixture was stirred at room temperature for 7 hours. The reaction mixture was partitioned between ethyl acetate and 1N hydrochloric acid. The organic layer was washed with water, a saturated aqueous solution of sodium hydrogencarbonate and brine, and dried over anhydrous sodium sulfate. The solvent was distilled off, and dried under reduced pressure to yield the title compound (2.823 g, 9.21 mmol, 92.1%) as a colorless oil.

$^1$H-NMR Spectrum (CDCl$_3$) δ (ppm): 1.50 (6H, s), 3.52–3.55 (4H, m), 3.60–3.70 (4H, m), 3.93 (1H, s), 5.16 (2H, s), 7.34–7.38 (5H, m).

Production Example 28-2

1-(2-Hydroxy-2-methylpropionyl)piperazine

Benzyl 4-(2-hydroxy-2-methylpropionyl)piperazine-1-carbamate (2.82 g, 9.20 mmol) synthesized in Production example 28-1 was dissolved in methanol (100 ml) under nitrogen atmosphere; 10% palladium on carbon (50% wet, 1.96 g) was added thereto, the reaction system was purged with hydrogen at atmospheric pressure; and the reaction mixture was stirred overnight. After the reaction system was purged with nitrogen, the catalyst was filtered out, and washed with methanol, then the solvent, together with the filtrate and the washing solution, was distilled off. The residue was dried under reduced pressure to yield the title compound (1.58 g, 9.20 mmol, quantitative) as a colorless oil.

$^1$H-NMR Spectrum (CDCl$_3$) δ (ppm): 1.49 (6H, s), 2.84–2.94 (4H, m), 3.49 (1H, s), 3.62–3.70 (4H, m).

Example 29

N1-Methyl-5-(2-((3-diethylamino)propylamino)carbonyl)amino-4-pyridyl)oxy-1H-1-indolecarboxamide Similarly to Example 27, the title compound (96.4 mg, 0.22 mmol, 73.3%) was obtained as white crystals from phenyl N-(4-(1-(methylamino)carbonyl-1H-5-indolyl)oxy-2-pyridyl)carbamate (121 mg, 0.30 mmol) and 3-(diethylamino)propylamine.

$^1$H-NMR Spectrum (DMSO-$d_6$) δ (ppm): 0.91 (6H, t, J=7.2 Hz), 1.50 (2H, m), 2.30–2.44 (6H, m), 2.83 (3H, d, J=4.4 Hz), 3.23 (2H, m), 6.50 (1H, dd, J=2.4, 6.0 Hz), 6.68 (1H, d, J=3.6 Hz), 6.82 (1H, s), 7.04 (1H, dd, J=2.4, 8.8 Hz), 7.37 (1H, d, J=2.4 Hz), 7.87 (1H, d, J=3.6 Hz), 8.01 (1H, d, J=6.0 Hz), 8.10–8.17 (2H, m), 8.29 (1H, d, J=8.8 Hz), 9.04 (1H, s).

The starting material was synthesized as follows.

Production Example 29-1

Phenyl N-(4-(1-(methylamino)carbonyl-1H-5-indolyl)oxy-2-pyridyl)carbamate

N1-Methyl-5-(2-amino-4-pyridyl)oxy-1H-1-indolecarboxamide (2.163 g, 7.66 mmol) synthesized in Production example 5-1 was dissolved in N,N-dimethylformamide (50 ml) under nitrogen atmosphere; pyridine (0.93 ml, 11.5 mmol), triethylamine (2.4 ml, 17.24 mmol) and phenyl chlorocarbonate (1.44 ml, 11.5 mmol) were sequentially added dropwise while cooled with an ice water bath; and the reaction mixture was heated to room temperature while stirred. After 1 hour, the reaction mixture was partitioned between ethyl acetate and water. The organic layer was washed with water and brine, and dried over anhydrous sodium sulfate. The solvent was distilled off, and then the residue was purified by silica gel column chromatography (eluent; ethyl acetate), precipitated from ethyl acetate-hexane (1:10), filtered off, and dried under aeration to yield the title compound (2.731 g, 6.79 mmol, 88.6%) as white crystals.

$^1$H-NMR Spectrum (CDCl$_3$) δ (ppm): 3.09 (3H, d, J=4.8 Hz), 5.52 (1H, m), 6.62 (1H, d, J=3.6 Hz), 6.98 (1H, dd, J=2.4, 5.6 Hz), 7.01 (1H, d, J=2.4 Hz), 7.11 (1H, dd, J=2.4, 8.8 Hz), 7.14–7.40 (7H, m), 7.47 (1H, d, J=3.6 Hz), 8.24 (1H, d, J=8.8 Hz), 8.41 (1H, d, J=5.6 Hz).

Example 30

N1-Methyl-5-(2-(((3-4-hydroxypiperidino)propyl)amino)carbonyl)amino-4-pyridyl)oxy-1H-1-indolecarboxamide Similarly to Example 27, the title compound (51.3 mg, 0.11 mmol, 29.5%) was obtained as white crystals from phenyl N-(4-(1-(methylamino)carbonyl-1H-5-indolyl)oxy-2-pyridyl)carbamate (150 mg, 0.37 mmol, Production example 29-1) and 1-(3-aminopropyl)-4-hydroxypiperidine.

$^1$H-NMR Spectrum (DMSO-$d_6$) δ (ppm): 1.29–1.38 (2H, m), 1.50–1.55 (2H, m), 1.64–1.68 (2H, m), 1.88–1.92 (2H, m), 2.20–2.24 (2H, m), 2.62–2.66 (2H, m), 2.83 (3H, d, J=4.4 Hz), 3.06–3.12 (2H, m), 3.39 (1H, m), 4.49 (1H, d, J=4.0 Hz), 6.50 (1H, dd, J=2.4, 5.6 Hz), 6.67 (1H, d, J=3.6 Hz), 6.84 (1H, s), 7.03 (1H, dd, J=2.4, 8.8 Hz), 7.36 (1H, s), 7.87 (1H, d, J=3.6 Hz), 8.01 (1H, d, J=5.6 Hz), 8.05 (1H, m), 8.16 (1H, q, J=4.4 Hz), 8.28 (1H, d, J=8.8 Hz), 9.02 (1H, s).

Example 31

N1-Methyl-5-(2-(((3-(4-methylpiperazino)propyl)amino)carbonyl)amino-4-pyridyl)oxy-1H-1-indolecarboxamide Similarly to Example 27, the title compound (133.2 mg, 0.29 mmol, 76.8%) was obtained as white crystals from phenyl N-(4-(1-(methylamino)carbonyl-1H-5-indolyl)oxy-2-pyridyl)carbamate (150 mg, 0.37 mmol, Production example 29-1) and 1-(3-aminopropyl)-4-methylpiperazine.

$^1$H-NMR Spectrum (DMSO-$d_6$) δ (ppm): 1.53 (2H, m), 2.11 (3H, s), 2.11–2.40 (10H, m), 2.83 (3H, d, J=4.0 Hz), 3.09 (2H, m), 6.50 (1H, dd, J=2.4, 5.6 Hz), 6.67 (1H, d, J=3.6 Hz), 6.84 (1H, s), 7.03 (1H, dd, J=2.4, 8.8 Hz), 7.36 (1H, d, J=2.4 Hz), 7.87 (1H, d, J=3.6 Hz), 8.01 (1H, d, J=5.6 Hz), 8.05 (1H, m), 8.16 (1H, q, J=4.0 Hz), 8.28 (1H, d, J=8.8 Hz), 9.01 (1H, s).

Example 32

5-(2-(3-(4-Oxo-4-(pyrrolidin-1-yl)butyl)ureido)pyridin-4-yloxy)-1H-indole-1-carboxylic acid methylamide The title compound (113 mg, 0.24 mmol, 77%) was obtained as colorless crystals by performing the reaction similar to Example 8 using 4-((4-(1-methylcarbamoyl-1H-indol-5-yloxy)pyridin-2-yl)aminocarbonylamino)butyric acid (130 mg, 0.31 mmol) and pyrrolidine (0.053 ml, 0.63 mmol).

$^1$H-NMR Spectrum (DMSO-$d_6$) δ (ppm): 1.64 (2H, m), 1.71 (2H, m), 1.82 (2H, m), 2.20 (2H, t, J=6.8 Hz), 2.83 (3H, d, J=4.0 Hz), 3.09 (2H, q, J=6.8 Hz). 3.22 (2H, t, J=6.8 Hz), 3.33 (2H, m), 6.50 (1H, dd, J=2.4, 5.8 Hz), 6.67 (1H, d, J=3.6 Hz), 6.86 (1H, d, J=2.4 Hz), 7.03 (1H, dd, J=2.4, 9.0 Hz), 7.36 (1H, d, J=2.4 Hz), 7.87 (1H, d, J=3.6 Hz), 8.00 (1H, m), 8.03 (1H, d, J=5.8 Hz), 8.16 (1H, m), 8.28 (1H, d, J=9.0 Hz), 9.00 (1H, s).

The starting material was synthesized by the following methods.

Production Example 32-1

4-((4-(1-Methylcarbamoyl-1H-indol-5-yloxy)pyridin-2-yl)aminocarbonylamino)butyric acid Ethyl 4-aminobutyrate hydrochloride (1.0 g, 6.0 mmol) was suspended in N,N-dimethylformamide (6.7 ml), 5N aqueous solution of sodium hydroxide (1.2 ml, 6.0 mmol) was added and the reaction mixture was stirred at room temperature. Phenyl N-(4-(1-(methylamino)carbonyl-1H-indol-5-yloxy)pyridin-2-yl)-N-(phenoxycarbonyl)carbamate (700 mg, 1.3 mmol, Production example 5-2) was added thereto and the reaction mixture was stirred at room temperature for 1.2 hours. The reaction mixture was partitioned between ethyl acetate and water. The organic layer was dried over anhydrous magnesium sulfate, concentrated under reduced pressure. The residue was purified by silica gel column chromatography (Fuji Silysia BW-300, ethyl acetate) to yield a pale yellow oil. This oil was dissolved in tetrahydrofuran (6.0 ml) and methanol (3.0 ml); 4N lithium hydroxide (1.1 ml) was added thereto at room temperature; and the reaction mixture was stirred at room temperature for 3.5 hours. Moreover, 1N hydrochloric acid (4.4 ml) and water (2 ml) were added thereto while stirred at room temperature; and this was subjected to extraction with ethyl acetate, washed with brine, dried over anhydrous magnesium sulfate, and concentrated under reduced pressure. After the precipitated crystals were suspended in diethyl ether:hexane=1:1, the crystals were filtered off, washed with diethyl ether, and dried under aeration to yield the title compound (411 mg, 1.0 mmol, 75%) as colorless crystals.

$^1$H-NMR Spectrum (DMSO-$d_6$) δ (ppm): 1.63 (2H, m), 2.20 (2H, t, J=7.4 Hz), 2.83 (3H, d, J=4.0 Hz), 3.10 (2H, m), 6.52 (1H, d, J=5.4 Hz), 6.68 (1H, d, J=3.6 Hz), 6.87 (1H, s), 7.04 (1H, dd, J=2.4, 9.0 Hz), 7.37 (1H, d, J=2.4 Hz), 7.88 (1H, d, J=3.6 Hz), 8.03 (2H, m), 8.17 (1H, d, J=4.0 Hz), 8.29 (1H, d, J=9.0 Hz), 9.03 (1H, s), 12.05 (1H, s).

Example 33

5-(2-(3-(3-(Cyclopropylcarbamoyl)propyl)ureido)pyridin-4-yloxy)indole-1-carboxylic acid methylamide The title compound (166 mg, 0.37 mmol, 76%) was obtained as colorless crystals by performing the reaction similar to Example 8 using 4-((4-(1-methylcarbamoyl-1H-indol-5-yloxy)pyridin-2-yl)aminocarbonylamino)butyric acid (200 mg, 0.49 mmol, Production example 32-1) and cyclopropylamine (0.028 ml, 0.58 mmol).

$^1$H-NMR Spectrum (DMSO-$d_6$) δ (ppm): 0.33–0.37 (2H, m), 0.54–0.59 (2H, m), 1.62 (2H, m), 2.02 (2H, t, J=7.4 Hz), 2.58 (1H, m), 2.85 (3H, m), 3.08 (2H, m), 6.53 (1H, dd, J=2.4, 6.0 Hz), 6.70 (1H, d, J=3.6 Hz), 6.88 (1H, d, J=2.4 Hz), 7.06 (1H, dd, J=2.4, 8.8 Hz), 7.39 (1H, d, J=2.4 Hz), 7.86 (1H, d, J=3.6 Hz), 7.90 (1H, d, J=3.6 Hz), 8.04 (1H, m), 8.05 (1H, d, J=6.0 Hz), 8.19 (1H, d, J=4.2 Hz), 8.31 (1H, d, J=8.8 Hz), 9.04 (1H, s).

Example 34

5-(2-(3-(4-(4-Hydroxy-4-methylpiperidin-1-yl)-4-oxobutyl)ureido)pyridin-4-yloxy)-1H-indole-1-carboxylic acid methylamide The title compound (195 mg, 0.383 mmol, 78.9%) was obtained as colorless crystals by performing the reaction similar to Example 8 using 4-((4-(1-methylcarbamoyl-1H-indol-5-yloxy)pyridin-2-yl)aminocarbonylamino)butyric acid (200 mg, 0.486 mmol, Production example 32-1) and 4-hydroxy-4-methylpiperidine monohydrochloride (110 mg, 0.729 mmol).

$^1$H-NMR Spectrum (DMSO-$d_6$) δ (ppm): 1.08 (3H, s), 1.22–1.44 (4H, m), 1.62 (2H, m), 2.27 (2H, t, J=7.4 Hz), 2.83 (3H, d, J=4.0 Hz), 2.97 (1H, m), 3.08 (2H, m), 3.29 (1H, m), 3.47 (1H, m), 3.89 (1H, m), 4.33 (1H, s), 6.50 (1H, d, J=6.0 Hz), 6.67 (1H, d, J=3.6 Hz), 6.87 (1H, s), 7.04 (1H, d, J=9.2 Hz), 7.36 (1H, s), 7.87 (1H, d, J=3.6 Hz), 8.01 (1H, m), 8.02 (1H, d, J=6.0 Hz), 8.16 (1H, m), 8.28 (1H, d, J=9.2 Hz), 9.00 (1H, m).

Example 35

5-(2-(3-(3-(Diethylcarbamoyl)propyl)ureido)pyridin-4-yloxy)-1H-indole-1-carboxylic acid methylamide The title compound (94 mg, 0.20 mmol, 64%) was obtained as colorless crystals by performing the reaction similar to Example 8 using 4-((4-(1-methylcarbamoyl-1H-indol-5-yloxy)pyridin-2-yl)aminocarbonylamino)butyric acid (130 mg, 0.31 mmol, Production example 32-1) and diethylamine (0.066 ml, 0.63 mmol).

$^1$H-NMR Spectrum (DMSO-$d_6$) δ (ppm): 0.96 (3H, t, J=7.2 Hz), 1.04 (3H, t, J=7.2 Hz), 1.63 (2H, m), 2.25 (2H, t, J=7.2 Hz), 2.83 (3H, d, J=4.4 Hz), 3.09 (2H, m), 3.22 (4H, m), 6.51 (1H, dd, J=2.0, 5.6 Hz), 6.67 (1H, d, J=3.4 Hz), 6.86 (1H, d, J=2.0 Hz), 7.03 (1H, dd, J=2.4, 8.8 Hz), 7.36 (1H, d, J=2.4 Hz), 7.87 (1H, d, J=3.4 Hz), 8.02 (2H, m), 8.16 (1H, d, J=4.4 Hz), 8.29 (1H, d, J=8.8 Hz), 9.00 (1H, s).

Example 36

5-(2-(3-(3-(Methylcarbamoyl)propyl)ureido)pyridin-4-yloxy)-1H-indole-1-carboxylic acid methylamide The title compound (107 mg, 0.25 mmol, 69%) was obtained as colorless crystals by performing the reaction similar to Example 8 using 4-((4-(1-methylcarbamoyl-1H-indol-5-yloxy)pyridin-2-yl)aminocarbonylamino)butyric acid (150 mg, 0.36 mmol, Production example 32-1) and methylamine hydrochloride (49 mg, 0.73 mmol).

$^1$H-NMR Spectrum (DMSO-$d_6$) δ (ppm): 1.61 (2H, m), 2.03 (2H, t, J=7.6 Hz), 2.51 (3H, d, J=4.4 Hz), 2.83 (3H, d, J=4.0 Hz), 3.06 (2H, q, J=6.4 Hz), 6.50 (1H, dd, J=2.4, 5.6 Hz), 6.67 (1H, d, J=3.6 Hz), 6.86 (1H, d, J=2.4 Hz), 7.03 (1H, dd, J=2.4, 9.2 Hz), 7.36 (1H, d, J=2.4 Hz), 7.71 (1H, m), 7.87 (1H, d, J=3.6 Hz), 8.03 (2H, m), 8.16 (1H, d, J=4.4 Hz), 8.28 (1H, d, J=9.2 Hz), 9.01 (1H, s).

Example 37

N1-Methyl-5-(2-(pyrrolidin-1-ylcarbonyl)amino-4-pyridyl)oxy-1H-1-indolecarboxamide Similarly to Example 5, the title compound (265 mg, 0.70 mmol, 69%) was obtained as white crystals from phenyl N-(4-(1-(methylamino)carbonyl-1H-5-indolyloxy)-2-pyridyl)-N-(phenoxycarbonyl)carbamate (532 mg, 1.02 mmol) synthesized in Production example 5-2 and pyrrolidine (0.42 ml, 5.0 mmol).

MS Spectrum (ESI): 380 (M+1), 759 (2M+1)

$^1$H-NMR Spectrum (DMSO-$d_6$) δ (ppm): 1.78–1.84 (4H, m), 2.83 (3H, d, J=4.5 Hz), 3.22–3.36 (4H, m), 6.54 (1H, dd, J=2.3, 5.6 Hz), 6.67 (1H, d, J=3.6 Hz), 7.03 (1H, dd, J=2.3, 8.7 Hz), 7.35 (1H, d, J=2.3 Hz), 7.41 (1H, d, J=2.3 Hz), 7.87 (1H, d, J=3.6 Hz), 8.04 (1H, d, J=5.6 Hz), 8.16 (1H, m), 8.28 (1H, t, J=8.7 Hz), 8.59 (1H, s).

Example 38

N1-Methyl-5-(2-(piperidin-1-ylcarbonyl)amino-4-pyridyl)oxy-1H-1-indolecarboxamide Similarly to Example 5, the title compound (265 mg, 0.674 mmol, 76%) was obtained as white crystals from phenyl N-(4-(1-(methylamino)carbonyl-1H-5-indolyloxy)-2-pyridyl)-N-(phenoxycarbonyl)carbamate (463 mg, 0.885 mmol) synthesized in Production example 5-2 and piperidine (0.44 ml, 4.4 mmol).

MS Spectrum (ESI): 394 (M+1), 787 (2M+1)

$^1$H-NMR Spectrum (DMSO-$d_6$) δ (ppm): 1.37–1.57 (6H, m), 2.83 (3H, d, J=4.4 Hz), 3.26–3.45 (4H, m), 6.54 (1H, dd, J=2.4, 5.4 Hz), 6.67 (1H, d, J=3.4 Hz), 7.03 (1H, dd, J=2.4, 8.8 Hz), 7.30 (1H, d, J=2.4 Hz), 7.36 (1H, d, J=2.4 Hz), 7.87 (1H, d, J=3.4 Hz), 8.05 (1H, d, J=5.4 Hz), 8.16 (1H, m), 8.28 (1H, t, J=8.8 Hz), 9.05 (1H, s).

Example 39

N1-Methyl-5-(2-((4-hydroxypiperidino)carbonyl)amino-4-pyridyl)oxy-1H-1-indolecarboxamide Similarly to Example 27, the title compound (86.7 mg, 0.21 mmol, 21.2%) was obtained as white powder from phenyl N-(4-(1-(methylamino)carbonyl-1H-5-indolyl)oxy-2-pyridyl)carbamate (402 mg, 1.0 mmol) synthesized in Production example 29-1 and 4-hydroxypiperidine.

$^1$H-NMR Spectrum (DMSO-$d_6$) δ (ppm): 1.60–1.70 (2H, m), 1.75 (1H, m), 2.83 (3H, d, J=4.4 Hz), 2.95–3.01 (2H, m), 3.55–3.65 (2H, m), 3.71–3.76 (2H, m), 4.64 (1H, d, J=4.0 Hz), 6.53 (1H, dd, J=2.4, 5.6 Hz), 6.67 (1H, d, J=3.6 Hz), 7.03 (1H, dd, J=2.4, 8.8 Hz), 7.32 (1H, d, J=2.4 Hz), 7.36 (1H, d, J=2.4 Hz), 7.87 (1H, d, J=3.6 Hz), 8.06 (1H, d, J=5.6 Hz), 8.16 (1H, q, J=4.4 Hz), 8.28 (1H, d, J=8.8 Hz), 9.10 (1H, s).

Example 40

N1-Methyl-5-(2-(4-oxopiperidin-1-ylcarbonyl)amino-4-pyridyl)oxy-1H-1-indolecarboxamide Phenyl N-(4-(1-(methylamino)carbonyl-1H-5-indolyloxy)-2-pyridyl)-N-(phenoxycarbonyl)carbamate (440 mg, 0.841 mmol) synthesized in Production example 5-2 was dissolved in N,N-dimethylformamide (5 ml); triethylamine (0.543 ml, 3.90 mmol) and 4-piperidone hydrochloride monohydrate (0.530 g, 3.93 mmol) were added thereto; and the reaction mixture was stirred for 2 hours. The reaction mixture was partitioned between ethyl acetate and water. The organic layer was concentrated to yield the title compound (0.202 g, 0.496 mmol, 59%) as a colorless amorphous solid.

$^1$H-NMR Spectrum (DMSO-$d_6$) δ (ppm): 2.32 (4H, t, J=4.9 Hz), 2.82 (3H, d, J=4.3 Hz), 3.68 (4H, t, J=4.9 Hz), 6.55 (1H, dd, J=2.3, 5.6 Hz), 6.67 (1H, d, J=3.6 Hz), 7.03 (1H, dd, J=2.3, 8.6 Hz), 7.37 (2H, s), 7.87 (1H, d, J=3.6 Hz), 8.09 (1H, d, J=5.6 Hz), 8.17 (1H, s), 8.28 (1H, t, J=8.6 Hz), 9.37 (1H, s).

Example 41

5-(2-(((4-Hydroxy-4-methylpiperidin-1-yl)carbonyl)amino)pyridin-4-yloxy)-1H-1-indole-1-carboxylic acid methylamide 4-Hydroxy-4-methylpiperidine monohydrochloride (508 mg, 3.83 mmol, Production example 8-3) was dissolved in N,N-dimethylformamide (8 ml); triethylamine (2 ml) was added; and the reaction mixture was stirred at room temperature. Phenyl N-(4-(1-(methylamino)carbonyl-1H-indol-5-yloxy)pyridin-2-yl)-N-(phenoxycarbonyl)carbamate (500 mg, 0.957 mmol, Production example 5-2) was added and the reaction mixture was stirred at room temperature for 8 hours. The reaction mixture was partitioned between ethyl acetate and water. The organic layer was dried over anhydrous magnesium sulfate, and concentrated under reduced pressure; and the residue was purified by silica gel column chromatography (Fuji Silysia BW-300, ethyl acetate, ethyl acetate:methanol=20:1 then 10:1). The obtained amorphous solid was crystallized by adding diethyl ether:acetone=2:1. Thus obtained crystals were filtered off, washed with diethyl ether, and dried under aeration to yield the title compound (385 mg, 0.909 mmol, 95.0%).

$^1$H-NMR Spectrum (DMSO-$d_6$) δ (ppm): 1.08 (3H, s), 1.33–1.40 (4H, m), 2.83 (3H, d, J=4.4 Hz), 3.14 (2H, m), 3.63 (2H, m), 4.27 (1H, s), 6.53 (1H, dd, J=2.4, 5.6 Hz), 6.67 (1H, d, J=3.4 Hz), 7.03 (1H, dd, J=2.4, 8.8 Hz), 7.32 (1H, d, J=2.4 Hz), 7.35 (1H, d, J=2.4 Hz), 7.87 (1H, d, J=3.4 Hz), 8.06 (1H, d, J=5.6 Hz), 8.16 (1H, m), 8.28 (1H, d, J=8.8 Hz), 9.04 (1H, s).

Example 42

N1-Methyl-5-(2-((4-(1-hydroxy-1-methylethyl)piperidino)carbonyl)amino-4-pyridyl)oxy-1H-1-indolecarboxamide Similarly to Example 28, the title compound (71.1 mg, 0.16 mmol, 29.7%) was obtained as white crystals from N1-ethyl-5-((2-amino-4-pyridyl)oxy)-1H-1-indolecarboxamide (150 mg, 0.53 mmol) synthesized in Production example 5-1 and 4-(1-hydroxy-1-methylethyl)piperidine (342 mg, 2.39 mmol).

$^1$H-NMR Spectrum (DMSO-$d_6$) δ (ppm): 0.99 (6H, s), 1.03–1.09 (2H, m), 1.30 (1H, m), 1.60–1.64 (2H, m), 2.54–2.61 (2H, m), 2.83 (3H, d, J=4.4 Hz), 4.08 (1H, s), 4.10–4.15 (2H, m), 6.53 (1H, dd, J=2.4, 5.6 Hz), 6.67 (1H, d, J=3.6 Hz), 7.03 (1H, dd, J=2.4, 8.8 Hz), 7.32 (1H, d, J=2.4 Hz), 7.36 (1H, d, J=2.4 Hz), 7.87 (1H, d, J=3.6 Hz), 8.06 (1H, d, J=5.6 Hz), 8.16 (1H, q, J=4.0 Hz), 8.27 (1H, d, J=8.8 Hz), 9.04 (1H, s).

4-(1-Hydroxy-1-methylethyl)piperidine was synthesized in the following methods.

Production Example 42-1

Benzyl 4-ethoxycarbonylpiperidine-1-carboxylate

4-Ethoxycarbonylpiperidine (1.572 g, 10.0 mmol) was dissolved in tetrahydrofuran (50 ml); triethylamine (2.79 ml, 20.0 mmol) and benzyl chlorocarbonate (1.71 ml, 12.0 mmol) were added dropwise while cooled with an ice water bath; and the reaction mixture was stirred at room temperature overnight. The reaction mixture was partitioned between ethyl acetate and the saturated aqueous solution of sodium hydrogencarbonate. The organic layer was washed with brine and dried over anhydrous sodium sulfate. The solvent was distilled off, and the residue was purified by silica gel column chromatography (eluent; ethyl acetate:hexane=1:3) to yield the title compound (2.315 g, 7.95 mmol, 79.5%) as a colorless oil.

$^1$H-NMR Spectrum (CDCl$_3$) δ (ppm): 1.26 (3H, t, J=7.2 Hz), 1.60–1.70 (2H, m), 1.80–2.00 (2H, m), 2.46 (1H, m), 2.80–3.00 (2H, m), 4.00–4.20 (2H, m), 4.15 (2H, q, J=7.2 Hz), 5.13 (2H, s), 7.29–7.38 (5H, m).

Production Example 42-2

Benzyl 4-(1-hydroxy-1-methylethyl)piperidine-1-carboxylate

Benzyl 4-ethoxycarbonylpiperidine-1-carboxylate (2.315 g, 7.95 mmol) synthesized in Production example 42-1 was dissolved in tetrahydrofuran (25 ml) under nitrogen atmosphere; methyl magnesium bromide (0.93 M) in tetrahydrofuran (32.5 ml, 30.2 mmol) was added dropwise while cooled with an ice water bath; and the reaction mixture was stirred at room temperature overnight. The reaction mixture was partitioned between ethyl acetate and the saturated aqueous solution of ammonium chloride. The organic layer was washed with brine and dried over anhydrous sodium sulfate. The solvent was distilled off, and the residue was purified by silica gel column chromatography (eluent; ethyl acetate:hexane=1:1) to yield the title compound (1.786 g, 6.44 mmol, 81%) as a colorless oil.

$^1$H-NMR Spectrum (CDCl$_3$) δ (ppm): 1.18 (6H, s), 1.18–1.27 (2H, m), 1.40–1.48 (1H, m), 1.74–1.78 (2H, m), 2.60–2.80 (2H, m), 4.20–4.40 (2H, m), 5.13 (2H, s), 7.27–7.37 (5H, m).

Production Example 42-3

4-(1-Hydroxy-1-methylethyl)piperidine

Benzyl 4-(1-hydroxy-1-methylethyl)piperidine-1-carboxylate (1.786 g, 6.44 mmol) synthesized in Production example 42-2 was dissolved in methanol (100 ml) under nitrogen atmosphere; 10% palladium on carbon (50% wet, 1.37 g) was added; the reaction system was purged with hydrogen at atmospheric pressure; and the reaction mixture was stirred overnight. After the reaction system was purged with nitrogen, the catalyst was filtered out, and washed with methanol; the solvent, together with the filtrate and the washing solution, was distilled off; and the residue was dried under reduced pressure to yield the title compound (922 mg, 6.44 mmol, quantitative) as pale gray crystals.

$^1$H-NMR Spectrum (CDCl$_3$) δ (ppm): 1.18 (6H, s), 1.26–1.42 (3H, m), 1.74–1.80 (2H, m), 2.57–2.64 (2H, m), 3.14–3.22 (2H, m), 3.48 (1H, s).

Example 43

5-(2-(((4-(3-Methylcarbamoylpropyl)piperidin-1-yl)carbonyl)amino)pyridin-4-yloxy)-1H-indole-1-carboxylic acid methylamide 4-(1-((4-(1-Methylcarbamoyl-1H-indol-5-yloxy)pyridin-2-yl)aminocarbonyl)piperidin-4-yl)butyric acid (170 mg, 0.35 mmol) was dissolved in N,N-dimethylformamide (7.0 ml); methylamine hydrochloride (48 mg, 0.71 mmol), benzotriazol-1-yloxy-tris(dimethylamino)phosphonium hexafluorophosphate (314 mg, 0.71 mmol) and triethylamine (0.35 ml) were added thereto; and the reaction mixture was stirred at room temperature for 2 hours. The reaction mixture was partitioned between ethyl acetate and water. The organic layer was washed with brine, dried over anhydrous magnesium sulfate, and concentrated under reduced pressure. The residue was purified by silica gel column chromatography (Fuji Silysia NH silica gel, hexane-ethyl acetate-methanol system). After a small amount of acetone and ethyl acetate were added to the obtained amorphous solid; this solution was diluted with diethyl ether; and the solid portion was filtered off, washed with diethyl ether, and dried under aeration to yield the title compound (30 mg, 0.061 mmol, 17%) as a colorless amorphous solid.

$^1$H-NMR Spectrum (DMSO-d$_6$) δ (ppm): 0.87–1.00 (2H, m), 1.13 (2H, m), 1.33 (1H, m), 1.46 (2H, m), 1.57 (2H, m), 1.99 (2H, t, J=7.4 Hz), 2.52 (3H, d, J=4.4 Hz), 2.65 (2H, m), 2.83 (3H, d, J=4.0 Hz), 4.03 (2H, m), 6.53 (1H, d, J=6.0 Hz), 6.67 (1H, d, J=3.4 Hz), 7.03 (1H, d, J=9.0 Hz), 7.31 (1H, s), 7.35 (1H, s), 7.66 (1H, m), 7.87 (1H, d, J=3.4 Hz), 8.06 (1H, d, J=4.0 Hz), 8.16 (1H, d, J=4.0 Hz), 8.27 (1H, d, J=9.0 Hz), 9.05 (1H, s).

The starting materials were synthesized as follows.

Production Example 43-1 tert-Butyl 4-(3-ethoxycarbonylpropyl)piperidine-1-carboxylate tert-Butyl 4-(2-(toluene-4-sulfonyloxy)ethyl)piperidine-1-carboxylate (7.55 g, 19.7 mmol, CAS No. 89151-45-1) as described in WO 02/32872 was dissolved in ethanol; diethyl malonate (3.3 ml, 21.3 mmol) and sodium ethoxide (1.45 g, 21.3 mmol) were added; and the reaction mixture was heated to reflux under nitrogen atmosphere for 2.5 hours. After naturally cooled to room temperature, the saturated aqueous solution of ammonium chloride was added; this was subjected to extraction with ethyl acetate, washed with brine, dried over anhydrous magnesium sulfate, and concentrated under reduced pressure. After the residue was dissolved in dimethyl sulfoxide (20 ml); lithium chloride (1.7 g, 40 mmol) and water (0.36 ml, 20 mmol) were added; and the reaction mixture was stirred at 185° C. for 1.5 hours and further stirred at 195° C. for 2 hours. After naturally cooled to room temperature, the reaction mixture was partitioned between ethyl acetate-brine. The organic layer was washed with brine, dried over anhydrous magnesium sulfate, and concentrated under reduced pressure. The residue was purified by silica gel column chromatography (Fuji Silysia BW-300, hexane-ethyl acetate system) to yield the title compound (2.60 g, 8.7 mmol, 43%) as a pale yellow oil.

$^1$H-NMR Spectrum (CDCl$_3$) δ (ppm): 1.02–1.13 (2H, m), 1.23–1.29 (5H, m), 1.39 (1H, m), 1.45 (9H, s), 1.62–1.69 (4H, m), 2.29 (2H, t, J=7.4 Hz), 2.67 (2H, m), 4.07 (2H, m), 4.13 (2H, q, J=7.2 Hz).

Production Example 43-2

Ethyl 4-(piperidin-4-yl)butyrate tert-Butyl 4-(3-ethoxycarbonylpropyl)piperidine-1-carboxylate (1.2 g, 4.0 mmol, Production example 43-1) was dissolved in trifluoroacetic acid (30 ml), and the reaction mixture was stirred at room temperature for 20 minutes. This was concentrated under reduced pressure, and was further azeotropically distilled with toluene. The obtained residue was partitioned between ethyl acetate and a saturated aqueous solution of sodium hydrogencarbonate. The organic layer was dried over anhydrous magnesium sulfate. In addition, the aqueous layer was concentrated under reduced pressure to dryness; the obtained solid was suspended in tetrahydrofuran; insoluble portion were filtered off, and this solution was added to the previously obtained organic layer. This was purified by silica gel column chromatography (Fuji Silysia NH, hexane-ethyl acetate-methanol system) to yield the title compound (1.15 g, quantitative) as a yellow oil.

$^1$H-NMR Spectrum (CDCl$_3$) δ (ppm): 1.26 (3H, m), 1.28–1.37 (2H, m), 1.40–1.52 (3H, m), 1.64 (2H, m), 1.86 (2H, m), 2.29 (2H, t, J=7.4 Hz), 2.82 (2H, m), 3.35 (2H, m), 4.13 (2H, m).

Production Example 43-3

5-(2-(((4-(3-Ethoxycarbonylpropyl)piperidin-1-yl)carbonyl)amino)pyridin-4-yloxy)-1H-indole-1-carboxylic acid methylamide Ethyl 4-(piperidin-4-yl)butyrate (650 mg, 2.0 mmol, Production example 43-2) was suspended in N,N-dimethylformamide (3.35 ml); phenyl N-(4-(1-(methylamino)carbonyl-1H-indol-5-yloxy)-pyridin-2-yl)-N-(phenoxycarbonyl)

carbamate (350 mg, 0.67 mmol, Production example 5-2) was added; and the reaction mixture was stirred at room temperature for 1 hour. The reaction mixture was partitioned between ethyl acetate and water. The organic layer was dried over anhydrous magnesium sulfate, concentrated under reduced pressure. The residue was purified by silica gel column chromatography (Fuji Silysia BW-300, hexane-ethyl acetate-methanol system) to yield the title compound (271 mg, 0.54 mmol, 80%) as a pale yellow oil.

$^1$H-NMR Spectrum (CDCl$_3$) δ (ppm): 1.05–1.16 (2H, m), 1.22–1.28 (5H, m), 1.43 (1H, m), 1.62 (2H, m), 1.71 (2H, m), 2.27 (2H, t, J=7.4 Hz), 2.80 (2H, m), 2.95 (3H, d, J=4.4 Hz), 3.99 (2H, m), 4.12 (2H, q, J=7.2 Hz), 6.09 (1H, d, J=4.4 HZ), 6.46 (1H, d, J=3.4 Hz), 6.58 (1H, dd, J=2.0, 5.6 Hz), 7.04 (1H, dd, J=2.0, 8.8 Hz), 7.24 (1H, s), 7.28 (1H, d, J=2.0 Hz), 7.32 (1H, d, J=3.4 Hz), 7.54 (1H, d, J=2.0 Hz), 8.03 (1H, d, J=5.6 Hz), 8.20 (1H, d, J=8.8 Hz).

Production Example 43-4

4-(1-((4-(1-Methylcarbamoyl-1H-indol-5-yloxy) pyridin-2-yl)aminocarbonyl)piperidin-4-yl)butyric acid 5-(2-((4-(3-Ethoxycarbonylpropyl)piperidin-1-yl)carbonyl)amino)pyridin-4-yloxy)-1H-indole-1-carboxylic acid methylamide (271 mg, 0.54 mmol, Production example 43-3) was dissolved in tetrahydrofuran (3.0 ml) and methanol (1.5 ml); 4N lithium hydroxide (0.54 ml) was added; and the reaction mixture was stirred at room temperature for 3.5 hours. 1N hydrochloric acid (2.2 ml) was added thereto while the stirred at room temperature. After the precipitated crystals were filtered off, the crystals were washed with water and diethyl ether sequentially, and dried under aeration to yield the title compound (170 mg, 0.35 mmol, 66%) as colorless crystals.

$^1$H-NMR Spectrum (DMSO-d$_6$) δ (ppm): 0.93 (2H, m), 1.16 (2H, m), 1.36 (1H, m), 1.47 (2H, m), 1.58 (2H, m), 2.15 (2H, t, J=7.4 Hz), 2.66 (2H, m), 2.83 (3H, d, J=4.2 Hz), 4.02 (2H, m), 6.53 (1H, d, J=6.0 Hz), 6.67 (1H, d, J=3.4 Hz), 7.03 (1H, d, J=9.2 Hz), 7.31 (1H, s), 7.35 (1H, s), 7.86 (1H, d, J=3.4 Hz), 8.05 (1H, d, J=6.0 Hz), 8.15 (1H, d, J=4.2 Hz), 8.27 (1H, d, J=9.2 Hz), 9.02 (1H, s).

Example 44

5-(2-(((4-(3-Carbamoylpropyl)piperidin-1-yl)carbonyl)amino)pyridin-4-yloxy)-1H-indole-1-carboxylic acid methylamide 4-(Piperidin-4-yl)butanamide (547 mg, 1.41 mmol) was dissolved in N,N-dimethylformamide (3 ml); phenyl N-(4-(1-(methylamino)carbonyl-1H-indol-5-yloxy)-pyridin-2-yl)-N-(phenoxycarbonyl)carbamate (210 mg, 0.402 mmol, the product of Production example 5-2) was added thereto; and the reaction mixture was stirred at room temperature for 1.5 hour. The reaction mixture was partitioned between ethyl acetate and water; the organic layer was dried over anhydrous magnesium sulfate, and concentrated under reduced pressure; and the residue was purified by silica gel column chromatography (Fuji Silysia NH, ethyl acetate-methanol system). The obtained amorphous solid was crystallized by adding diethyl ether. After addition of a small amount of ethanol to make a suspension, this was diluted with hexane. After separation by filtration to obtain crystals, these were rinsed with diethyl ether and dried under aeration. Thus, the title compound was obtained as colorless crystals (157 mg, 0.328 mmol, 81.7%).

$^1$H-NMR Spectrum (DMSO-d$_6$) δ (ppm): 0.87–1.00 (2H, m), 1.10–1.16 (2H, m), 1.35 (1H, m), 1.42–1.50 (2H, m), 1.58 (2H, m), 1.98 (2H, t, J=7.4 Hz), 2.65 (2H, m), 2.83 (3H, d, J=4.0 Hz), 4.03 (2H, m), 6.53 (1H, dd, J=2.0, 5.6 Hz), 6.67 (2H, m), 7.03 (1H, dd, J=2.0, 9.0 Hz), 7.20 (1H, s), 7.31 (1H, d, J=2.0 Hz), 7.35 (1H, d, J=2.0 Hz), 7.87 (1H, d, J=3.2 Hz), 8.06 (1H, d, J=5.6 Hz), 8.16 (1H, m), 8.28 (1H, d, J=9.0 Hz), 9.05 (1H, s).

The starting materials were synthesized as follows.

Production Example 44-1 tert-Butyl 4-(3-carbamoylpropyl)piperidine-1-carboxylate tert-Butyl 4-(3-ethoxycarbonylpropyl)piperidine-1-carboxylate (0.60 g, 2.0 mmol, the product of Production example 43-1) and formamide (0.27 ml, 6.7 mmol) were dissolved in N,N-dimethylformamide (1.0 ml); sodium ethoxide (0.095 g, 1.4 mmol) was added thereto while stirred and heated at 100° C.; the reaction mixture was stirred for 2 hours under nitrogen atmosphere. After cooled to room temperature, the reaction mixture was partitioned between water and ethyl acetate. The organic layer was washed with brine, dried over anhydrous magnesium sulfate, and then the solvent was distilled off under reduced pressure. The residue was purified by silica gel chromatography (eluent; hexane-ethyl acetate=95:5 to 85:15). The title compound was obtained as a colorless oil (0.38 g, 1.4 mmol, 70%).

$^1$H-NMR Spectrum (CDCl$_3$) δ (ppm): 1.03–1.14 (2H, m), 1.26–1.31 (2H, m), 1.35–1.45 (1H, m), 1.46 (9H, s), 1.63–1.71 (4H, m), 2.22 (2H, t, J=7.6 Hz), 2.67 (2H, m), 4.07 (2H, brs), 5.30 (1H, brs), 5.39 (1H, brs).

Production Example 44-2

4-(Piperidin-4-yl)butylamine tert-Butyl 4-(3-carbamoylpropyl)piperidine-1carboxylate (0.38 g, 1.4 mmol, Production example 44-1) was dissolved in trifluoroacetic acid (2 ml) and the reaction mixture was stirred at room temperature for 20 minutes. The reaction mixture was concentrated under reduced pressure and then azeotropically distilled with toluene. The residue was partitioned between tetrahydrofuran and a saturated aqueous solution of sodium hydrogencarbonate; and the organic layer was dried over anhydrous magnesium sulfate and concentrated under reduced pressure; and the residue was purified by silica gel chromatography (Fuji Silysia NH, ethyl acetate-methanol system) to yield the title compound (0.55 g, quantitative) as pale yellow oil.

$^1$H-NMR Spectrum (DMSO-d$_6$) δ (ppm): 0.90–1.01 (2H, m), 1.09–1.15 (2H, m), 1.26 (1H, m), 1.45 (2H, m), 1.55 (2H, m), 1.98 (2H, t, J=7.4 Hz), 2 43 (2H, m), 2.91 (2H, m), 6.65 (1H, s), 7.20 (1H, s).

Example 45

5-(2-((4-Pyrrolidin-1-yl)carbonyl)piperidin-1-yl) carbonylamino)pyridin-4-yloxy)-1H-indole-1-carboxylic acid methylamide Similarly to Example 5, the title compound (134 mg, 0.273 mmol, 91%) was obtained as white crystals from phenyl N-(4-(1-(methylamino)carbonyl-1H-5-indolyloxy)-2-pyridyl)-N-(phenoxycarbonyl)carbamate (157 mg, 0.300 mmol) synthesized in Production example 5-2 and (piperidin-4-yl)-(pyrrolidin-1-yl)methanone (328 mg, 1.50 mmol) obtained from N-benzyloxycarbonylisonipecotic acid and pyrrolidine by the method similar to Example 21.

$^1$H NMR Spectrum (DMSO-d$_6$) δ (ppm): 1.35–1.48 (2H, m), 1.56–1.65 (2H, m), 1.71–1.80 (2H, m), 1.82–1.91 (2H, m), 2.61 (1H, m), 2.73–2.84 (2H, m), 2.85 (3H, d, J=4.4 Hz), 3.22–3.28 (2H, m), 3.44–3.50 (2H, m), 4.04–4.12 (2H, m), 6.56 (1H, d, J=6.0 Hz), 6.69 (1H, d, J=3.6 Hz), 7.06 (1H, dd, J=2.4, 9.2 Hz), 7.34 (1H, s), 7.38 (1H, d, J=2.4 Hz), 7.89 (1H, d, J=3.6 Hz), 8.09 (1H, d, J=6.0 Hz) 8.18 (1H, q, J=4.4 Hz), 8.30 (1H, d, J=9.2 Hz), 9.16 (1H, s).

Example 46

N1-Methyl-S-(2-(((4-(pyrrolidin-1-yl)piperidin-1-yl) carbonyl)amino)pyridin-4-yloxy)-1H-1-indolecarboxamide Similarly to Example 27, the title compound (88.5 mg, 0.19 mmol, 63.8%) was obtained as white crystals from phenyl N-(4-(1-(methylamino)carbonyl-1H-5-indolyl)oxy-2-pyridyl)carbamate (121 mg, 0.30 mmol, Production example 29-1) and 4-tetrahydro-1H-1-pyrrolylpiperidine.

Phenyl N1-methyl-5-(2-(((4-(pyrrolidin-1-yl)piperidin-1-yl)carbonyl)amino)pyridin-4-yloxy)-1H-1-indolecarboxamide may be synthesized by the following methods.

Phenyl N-(4-(1-(methylamino)carbonyl-1H-5-indolyloxy)-2-pyridyl)-N-(phenoxycarbonyl)carbamate (12.1 g, 23.2 mmol) synthesized in Production example 5-2 was dissolved in dimethylformamide (150 ml); 4-tetrahydro-1H-1-pyrrolylpiperidine (14.4 g, 93.3 mmol) was added thereto; and the reaction mixture was stirred at room temperature for 16 hours. The reaction mixture was partitioned between ethyl acetate and water. The organic layer was washed with brine and concentrated to about 100 ml. The residue was allowed to be kept cool at 5° C. for overnight to precipitate crystals. The crystals were filtered off, washed with ethyl acetate to yield the title compound (7.8 g, 16.9 mmol, 73%) as white crystals.

$^1$H NMR Spectrum (DMSO-d$_6$) δ (ppm): 1.20–1.33 (2H, m), 1.60–1.70 (4H, m), 1.70–1.80 (2H, m), 2.40–2.60 (5H, m), 2.77–2.84 (5H, m), 3.90–4.00 (2H, m), 6.54 (1H, dd, J=2.4, 5.6 Hz), 6.67 (1H, d, J=3.6 Hz) 7.03 (1H, dd, J=2.4, 8.8 Hz), 7.31 (1H, s), 7.35 (1H, d, J=2.4 Hz), 7.87 (1H, d, J=3.6 Hz), 8.06 (1H, d. J=5.6 Hz), 8.16 (1H, m), 8.28 (1H, d, J=8.8 Hz), 9.11 (1H, s).

Example 47

N1-Methyl-5-(2-(((4-(piperidin-1-yl)piperidin-1-yl) carbonyl)amino)pyridin-4-yloxy)-1H-1-indolecarboxamide Similarly to Example 27, the title compound (94.6 mg, 0.20 mmol, 66.2%) as white crystals was obtained from phenyl N-(4-(1-(methylamino)carbonyl-1H-5-indolyl)oxy-2-pyridyl)carbamate (121 mg, 0.30 mmol, Production example 29-1) and 4-piperidinopiperidine.

N1-Methyl-5-(2-(((4-(piperidin-1-yl)piperidin-1-yl)carbonyl)amino)pyridin-4-yloxy)-1H-1-indolecarboxamide may be prepared by the following methods.

Phenyl N-(4-(1-(methylamino)carbonyl-1H-5-indolyloxy)-2-pyridyl)-N-(phenoxycarbonyl)carbamate (15.5 g, 29.7 mmol) synthesized in Production example 5-2 was dissolved in dimethylformamide (180 ml); 4-piperidinopiperidine (20.0 g, 119 mmol) was added thereto; and the reaction mixture was stirred at room temperature for 9 hours. The reaction mixture was partitioned between ethyl acetate and water. The organic layer was washed with brine and concentrated to about 100 ml. The residue was allowed to be kept cool at 5° C. overnight to precipitate crystals. The crystals were filtered off and washed with ethyl acetate to yield the title compound (4.0 g, 8.4 mmol, 28%) as white crystals.

$^1$H NMR Spectrum (DMSO-d$_6$) δ (ppm): 1.20–1.65 (10H, m), 2.31–2.40 (5H, m), 2.66 (2H, m), 2.83 (3H, d, J=4.4 Hz), 4.08 (2H, m), 6.53 (1H, dd, J=2.4, 5.6 Hz), 6.67 (1H, d, J=3.6 Hz), 7.03 (1H, dd, J=2.4, 8.8 Hz), 7.31 (1H, d, J=2.4 Hz), 7.35 (1H, d, J=2.4 Hz), 7.87 (1H, d, J=3.6 Hz), 8.06 (1H, d, J=5.6 Hz), 8.16 (1H, q, J=4.4 Hz), 8.28 (1H, d, J=8.8 Hz), 9.09 (1H, s).

Example 48

N1-Methyl-5-(2-((4-ethylpiperazino)carbonyl) amino-4-pyridyl)oxy-1H-1-indolecarboxamide Similarly to Example 27, the title compound (73.2 mg, 0.17 mmol, 57.8%) was obtained as white powder from phenyl N-(4-(1-(methylamino)carbonyl-1H-5-indolyl)oxy-2-pyridyl)carbamate (121 mg, 0.30 mmol, Production example 29-1) and 1-ethylpiperazine.

$^1$H NMR Spectrum (DMSO-d$_6$) δ (ppm): 0.97 (3H, t, J=7.2 Hz), 2.25–2.32 (6H, m), 2.83 (3H, d, J=4.0 Hz), 3.20–3.40 (4H, m), 6.55 (1H, dd, J=2.4, 5.6 Hz), 6.67 (1H, d, J=3.6 Hz), 7.04 (1H, dd, J=2.4, 8.8 Hz), 7.31 (1H, d, J=2.4 Hz), 7.36 (1H, d, J=2.4 Hz), 7.87 (1H, d, J=3.6 Hz), 8.07 (1H, d, J=5.6 Hz), 8.16 (1H, q, J=4.0 Hz), 8.28 (1H, d, J=8.8 Hz), 9.13 (1H, s).

Example 49

N1-Methyl-5-(2-((4-(2-hydroxyethyl)piperazino) carbonyl)amino-4-pyridyl)oxy-1H-1-indolecarboxamide Similarly to Example 27, the title compound (97.6 mg, 0.22 mmol, 59.7%) was obtained as pale pink powder from phenyl N-(4-(1-(methylamino)carbonyl-1H-5-indolyl)oxy-2-pyridyl)carbamate (150 mg, 0.37 mmol, Production example 29-1) and 1-(2-hydroxyethyl)piperazine.

$^1$H NMR Spectrum (DMSO-d$_6$) δ (ppm): 2.30–2.40 (6H, m), 2.83 (3H, d, J=4.0 Hz), 3.20–3.40 (4H, m), 3.46 (2H, m), 4.39 (1H, t, J=5.6 Hz), 6.55 (1H, dd, J=2.4, 5.6 Hz), 6.67 (1H, d, J=3.6 Hz), 7.03 (1H, dd, J=2.4, 8.8 Hz), 7.31 (1H, d, J=2.4 Hz), 7.35 (1H, d, J=2.4 Hz), 7.87 (1H, d, J=3.6 Hz), 8.06 (1H, d, J=5.6 Hz), 8.16 (1H, q, J=4.0 Hz), 8.27 (1H, d, J=8.8 Hz), 9.12 (1H, s).

Example 50

N1-Methyl-5-(2-((3-methylsulfonylpropylamino) carbonyl)amino-4-pyridyl)-oxy-1H-1-indolecarboxamide Similarly to Example 28, the title compound (166.8 mg, 0.37 mmol, 70.5%) was obtained as white crystals from N1-methyl-5-(2-amino-4-pyridyl)oxy-1H-1-indolecarboxamide (150 mg, 0.53 mmol, Production example 5-1) and 3-methylsulfonylpropylamine hydrochloride (410 mg, 2.36 mmol).

$^1$H NMR Spectrum (DMSO-d$_6$) δ (ppm): 1.70–1.90 (2H, m), 2.83 (3H, d, J=4.4 Hz), 2.94 (3H, s), 3.04–3.09 (2H, m), 3.17–3.24 (2H, m), 6.52 (1H, dd, J=2.4, 5.6 Hz), 6.67 (1H, d, J=3.6 Hz), 6.86 (1H, s), 7.03 (1H, dd, J=2.4, 8.8 Hz), 7.36 (1H, s), 7.87 (1H, d, J=3.6 Hz), 8.03 (1H, d, J=5.6 Hz), 8.10–8.17 (2H, m), 8.28 (1H, d, J=8.8 Hz), 9.07 (1H, s).

Example 51

N1-Methyl-5-(2-((4-(2-dimethylaminoacetyl)piperazino)carbonyl)amino-4-pyridyl)oxy-1H-1-indolecarboxamide Similarly to Example 28, the title compound (189.8 mg, 0.40 mmol, 74.5%) was obtained as white powder from N1-methyl-5-(2-amino-4-pyridyl)oxy-1H-1-indolecarboxamide (150 mg, 0.53 mmol, Production example 5-1) and 1-(2-dimethylaminoacetyl)piperazine (500 mg, 2.92 mmol).

$^1$H-NMR Spectrum (DMSO-$d_6$) δ (ppm): 2.14 (6H, s), 3.04 (3H, d, J=4.0 Hz), 3.29 (2H, s), 3.20–3.49 (8H, m), 6.56 (1H, dd, J=2.4, 5.6 Hz), 6.67 (1H, d, J=3.6 Hz), 7.03 (1H, dd, J=2.4, 8.8 Hz) 7.30 (1H, d, J=2.4 Hz), 7.36 (1H, d, J=2.4 Hz), 7.87 (1H, d, J=3.6 Hz), 8.08 (1H, d, J=5.6 Hz), 8.16 (1H, q, J=4.0 Hz), 8.28 (1H, d, J=8.8 Hz), 9.24 (1H, s).

1-(2-Dimethylaminoacetyl)piperazine was prepared by the following methods.

Production Example 51-1

Benzyl 4-(2-dimethyaminoacetyl)piperazine-1-carboxylate

Benzyl piperazine-1-carbamate (2.203 g, 10.0 mmol) was dissolved in tetrahydrofuran (50 ml); 2-dimethylaminoacetic acid (1.24 g, 12.0 mmol), 1-ethyl-3-(3-dimethylaminopropyl)carbodiimide hydrochloride (2.30 g, 12.0 mmol), 1-hydroxy-1H-benzotriazole monohydrate (1.84 g, 12.0 mmol) and triethylamine (3.35 ml, 24.0 mmol) were added thereto; and the reaction mixture was stirred at room temperature for 7 hours. The reaction mixture was partitioned between ethyl acetate and a saturated aqueous solution of sodium hydrogencarbonate. The organic layer was washed with a saturated aqueous solution of sodium hydrogencarbonate, water and brine, dried over anhydrous sodium sulfate, and the residue was purified by NH silica gel column chromatography (eluent; ethyl acetate:hexane=3:1) to yield the title compound (954 mg, 3.12 mmol, 31.2%) as a colorless oil.

$^1$H-NMR Spectrum (CDCl$_3$) δ (ppm): 2.26 (6H, s), 3.11 (2H, s), 3.45–3.65 (8H, m), 5.15 (2H, s), 7.32–7.38 (5H, m).

Production Example 51-2

1-(2-Dimethylaminoacetyl)piperazine

Benzyl 4-(2-dimethyaminoacetyl)piperazine-1-carbamate (954 mg, 3.12 mmol) synthesized in Production example 51-1 was dissolved in methanol (50 ml) under nitrogen atmosphere; 10% palladium on carbon (50% wet, 665 mg) was added thereto; the reaction system was purged with hydrogen at atmospheric pressure; and the reaction mixture was stirred overnight. After the reaction system was purged with nitrogen, the catalyst was filtered out, and washed with methanol. The solvent, together with the filtrate and washing solution, was distilled off, and the residue was dried under reduced pressure to yield the title compound (508 mg, 2.97 mmol, 95.0%) as a colorless oil.

$^1$H-NMR Spectrum (CDCl$_3$) δ (ppm): 2.28 (6H, s), 2.80–2.88 (4H, m), 3.11 (2H, s), 3.52–3.62 (4H, m).

Example 52

N1-Methyl-5-(2-((4-cyclohexylpiperazino)carbonyl)amino-4-pyridyl)oxy-1H-1-indolecarboxamide Similarly to Example 27, the title compound (121.3 mg, 0.25 mmol, 68.2%) was obtained as white crystals from phenyl N-(4-(1-methylamino)carbonyl-1H-5-indolyl)oxy-2-pyridyl)carbamate (150 mg, 0.37 mmol, Production example 29-1) and 1-cyclohexylpiperazine.

$^1$H-NMR Spectrum (DMSO-$d_6$) δ (ppm): 1.00–1.20 (6H, m), 1.53 (2H, m), 1.60–1.80 (4H, m), 2.19 (2H, m), 2.30–2.45 (5H, m), 2.83 (3H, d, J=4.0 Hz), 6.54 (1H, dd, J=2.4, 5.6 Hz), 6.67 (1H, d, J=3.6 Hz), 7.03 (1H, dd, J=2.4, 8.8 Hz), 7.31 (1H, d, J=2.4 Hz), 7.35 (1H, d, J=2.4 Hz), 7.87 (1H, d, J=3.6 Hz), 8.06 (1H, d, J=5.6 Hz), 8.16 (1H, q, J=4.0 Hz), 8.27 (1H, d, J=8.8 Hz), 9.09 (1H, s).

Example 53

N4-(4-(1-(Methylamino)carbonyl-1H-5-indolyl)oxy-2-pyridyl)-4-morpholinecarboxamide Similarly to Example 27, the title compound (58.6 mg, 0.15 mmol, 49.4%) was obtained as white powder from phenyl N-(4-((1-((methylamino)carbonyl)-1H-5-indolyl)oxy-2-pyridyl)carbamate (121 mg, 0.30 mmol, Production example 29-1) and morpholine.

N4-(4-(1-(Methylamino)carbonyl-1H-5-indolyl)oxy-2-pyridyl)-4-morpholinecarboxamide may be prepared by the following methods.

Phenyl N-(4-(1-(methylamino)carbonyl-1H-5-indolyloxy)-2-pyridyl)-N-(phenoxycarbonyl)carbamate (20 g, 38 mmol) synthesized in Production example 5-2 was dissolved in N,N-dimethylformamide (190 ml); morpholine (13.3 mg, 153 mmol) was added thereto; and the reaction system was stirred at room temperature for 9 hours. The reaction mixture was partitioned between ethyl acetate and water; and the organic layer was washed with brine, dried over anhydrous magnesium sulfate, and concentrated under reduced pressure. The obtained residue was dissolved in ethyl acetate and a small amount of tetrahydrofuran; this suspension was filtrated with silica gel; and ethyl acetate and three different ratio of solvent mixtures of ethyl acetate:methanol=20:1, 10:1, and 5:1 were eluted through the gel. The filtrate was concentrated under reduced pressure. The residue was dissolved in diethyl ether (40 ml); hexane (200 ml) was added thereto; and precipitated insoluble syrupy portion was removed from the solution; and the resultant solution was concentrated again under reduced pressure. The residue was dissolved in ethyl acetate (300 ml) and was allowed to stand at room temperature. After the crystals were precipitated, the crystals were filtered off, washed with ethyl acetate, and dried to yield the crude crystals of the title compound (10.3 g). 9 g of this crude crystals was suspended in a mixture of tetrahydrofuran (3 ml) and N,N-dimethylformamide (3 ml each); this suspension was diluted with ethanol (60 ml); and the crystals were filtered off, washed with ethanol and dried to yield the title compound as colorless crystals (7.70 g, 19 mmol).

$^1$H-NMR Spectrum (DMSO-$d_6$) δ (ppm): 2.83 (3H, d, J=4.4 Hz), 3.34–3.38 (4H, m), 3.50–3.53 (4H, m), 6.56 (1H, dd. J=2.4, 5.6 Hz), 6.67 (1H, d, J=3.6 Hz), 7.04 (1H, dd, J=2.4, 8.8 Hz), 7.31 (1H, d, J=2.4 Hz), 7.36 (1H, d, J=2.4 Hz), 7.87 (1H, d, J=3.6 Hz), 8.08 (1H, d, J=5.6 Hz), 8.17 (1H, q, J=4.4 Hz), 8.28 (1H, d, J=8.8 Hz), 9.19 (1H, s).

Example 54

N1-Methyl-5-(2-((1,1-dioxothiomorpholin-4-ylcarbonyl)amino)pyridin-4-yloxy)-1H-1-indolecarboxamide Phenyl N-(4-(1-(methylamino)carbonyl-1H-indol-5-yloxy)-pyridin-2-yl)-N-(phenoxycarbonyl)carbamate (150 mg, 0.278 mmol, Production example 5-2) was dissolved in N,N-dimethylformamide (1.5 ml); 5N aqueous solution of sodium hydroxide (0.29 ml) and 1,1-dioxothiomorpholine hydrochloride (246 mg, 1.44 mmol) were added thereto; and the reaction mixture was stirred at room temperature for 5 hours. The reaction mixture was partitioned between ethyl acetate and water. The organic layer was dried over anhydrous magnesium sulfate and concentrated under reduced pressure. The residue was purified by silica gel column chromatography (Fuji Silysia BW-300, ethyl acetate). Diethyl ether was added to this to allow to crystallize; and the crystals were filtered off, washed with diethyl ether, and dried under aeration to yield the title compound as colorless crystals (100 mg, 0.226 mmol, 78.5%).

$^1$H-NMR Spectrum (DMSO-$d_6$) δ (ppm): 2.83 (3H, d, J=3.6 Hz), 3.10 (4H, m), 3.81 (4H, m), 6.57 (1H, dd, J=1.2, 5.6 Hz), 6.67 (1H, d, J=3.2 Hz), 7.03 (1H, dd, J=2.0, 9.2 Hz), 7.32 (1H, m), 7.36 (1H, d, J=2.0 Hz), 7.87 (1H, d, J=3.2 Hz), 8.09 (1H, d, J=5.6 Hz), 8.16 (1H, d, J=3.6 Hz), 8.28 (1H, d, J=9.2 Hz), 9.54 (1H, s).

The starting material was synthesized by the following methods.

Production Examples 54-1 tert-Butyl thiomorpholine-4-carboxylate

Thiomorpholine (5.0 ml, 53 mol) was dissolved in tetrahydrofuran (200 ml); triethylamine (8.1 ml, 58 ml) was added thereto; and the reaction mixture was stirred at room temperature. tert-Butoxycarbonyl dicarbonate (13.3 ml, 58 mmol) was added thereto and the reaction mixture was stirred at room temperature for 10 hours. The reaction mixture was concentrated under reduced pressure; and the residue was purified by silica gel column (eluent; hexane: ethyl acetate=from 80:20, 75:25 to 70:30) to yield the title compound as colorless crystals (10.4 g, 51 mmol).

$^1$H-NMR Spectrum (CDCl$_3$) δ (ppm): 1.46 (9H, s), 2.57 (4H, m), 3.69 (4H, m).

Production Example 54-2 tert-Butyl 1,1-dioxothiomorpholine-4-carboxylate tert-Butyl thiomorpholine-4-carboxylate (1.91 g, 9.42 mol) was dissolved in dichloromethane (50 ml); m-chloroperbenzoic acid (5.0 g, 19 mmol) was gradually added while cooled with ice bath, stirred, and under nitrogen atmosphere; and the reaction mixture was stirred at room temperature for 12 hours. After addition of a saturated aqueous solution of sodium thiosulfate, the reaction mixture was kept stirred for a while; and this was subjected to extraction with ethyl acetate, washed with brine, dried over anhydrous sodium sulfate, and concentrated under reduced pressure. Triethylamine (8.1 ml, 58 ml) were added to the obtained crystals; and the reaction mixture was stirred at room temperature. tert-Butoxycarbonyl dicarbonate (13.3 ml, 58 mmol) was added thereto; and the reaction mixture was stirred at room temperature for 10 hours. The reaction mixture was concentrated under reduced pressure; and the obtained crystals were suspended with a solvent mixture of diethyl ether: ethanol=10:1, filtered off, washed with diethyl ether and dried under aeration to yield the title compound as colorless crystals (2.03 g, 8.63 mmol, 91.6%).

$^1$H-NMR Spectrum (DMSO-$d_6$) δ (ppm): 1.40 (9H, s), 3.09 (4H, t, J=5.2 Hz), 3.72 (4H, t, J=5.2 Hz).

Production Example 54-3

Thiomorpholine 1,1-dioxide monohydrochloride tert-Butyl 1,1-dioxothiomorpholine-4-carboxylate (2.03 g, 8.63 mmol) was dissolved in a mixture of hydrochloric acid-methanol 10 (20 ml) and tetrahydrofuran (20 ml); hydrochloric acid (4.0 ml) was added thereto during stirring at room temperature; and the reaction mixture was stirred at room temperature for 3 hours. The reaction mixture was concentrated; methanol (20 ml), tetrahydrofuran (20 ml) and hydrochloric acid (4.0 ml) were added to the obtained crystals. Furthermore, water (10 ml) was added to this solution to perfectly dissolve the crystals; and this solution was stirred at room temperature for 1 hour. The solvent was concentrated under reduced pressure; and the obtained crystals were suspended in methanol, filtered off, washed with methanol, and dried under aeration to yield the title compound as colorless crystals (1.49 g, 8.65 mmol, quantitative).

$^1$H-NMR Spectrum (DMSO-$d_6$) δ (ppm): 3.54 (8H, m), 9.83 (2H, brs).

Example 55

5-(2-(3-((1R)-1-Hydroxymethyl-2-oxo-2-pyrrolidin-1-ylethyl)ureido)pyridin-4-yloxy)-1H-indole-1-carboxylic acid ethylamide Similarly to Example 5, the title compound (118 mg, 0.246 mmol, 82%) was obtained as white crystals from phenyl N-(4-(1-(ethylamino)carbonyl-1H-5-indolyloxy-2-pyridyl)-N-(phenoxycarbonyl)carbamate (161 mg, 0.300 mmol), and (2R)-2-amino-3-hydroxy-1-(pyrrolidin-1-yl) propan-1-one (265 mg, 1.67 mmol) obtained by the method similar to Example 21 from (2R)-2-benzyloxycarbonylamino-3-hydroxypropionic acid and pyrrolidine.

$^1$H-NMR Spectrum (DMSO-$d_6$) δ (ppm): 1.19 (3H, t, J=7.2 Hz), 1.70–1.90 (4H, m), 3.20–3.60 (8H, m), 4.54 (1H, m), 4.98 (1H, brs), 6.55 (1H, d, J=6.0 Hz), 6.69 (1H, d, J=3.6 Hz), 6.97 (1H, s), 7.05 (1H, dd, J=2.4, 8.8 Hz), 7.39 (1H, d, J=2.4 Hz), 7.92 (1H, d, J=3.6 Hz), 8.05 (1H, d, J=6.0 Hz), 8.08–8.28 (2H, m), 8.30 (1H, d, J=8.8 Hz), 9.21 (1H, s).

The starting material was synthesized as follows.

Production Example 55-1

Phenyl N-(4-(1-(ethylamino)carbonyl-1H-5-indolyloxy)-2-pyridyl)-N-(phenoxycarbonyl)carbamate The reaction similar to Production example 5-2 was performed by using N1-ethyl-5-(2-aminopyridin-4-yloxy)-1H-indole-1-carboxamide (2.9 g, 9.9 mmol, Production example 27-1), tetrahydrofuran, triethylamine and phenyl chloroformate; the extraction and washing was performed; the obtained residue was crystallized by addition of a solvent mixture of diethyl ether:hexane=1:1; and the obtained crystals were filtered off, washed with diethyl ether, and dried under aeration to yield the title compound as pale pink crystals (3.7 g, 6.9 mmol, 70%).

$^1$H-NMR Spectrum (DMSO-$d_6$) δ (ppm): 1.17 (3H, t, J=7.2 Hz), 3.29 (2H, m), 6.66 (1H, d, J=3.4 Hz), 6.96 (1H, dd, J=2.0, 5.8 Hz), 7.09 (1H, dd, J=2.0, 8.0 Hz), 7.17 (4H, d, J=8.0 Hz), 7.29 (2H, d, J=8.0 Hz), 7.41–7.44 (5H, m), 7.51 (1H, d. J=2.0 Hz), 7.92 (1H, d, J=3.4 Hz), 8.22 (1H, m), 8.31 (1H, d, J=8.8 Hz), 8.42 (1H, d, J=5.8 Hz).

Example 56

5-(2-(3-((1S)-1-Hydroxymethyl-2-oxo-2-pyrrolidin-1ylethyl)ureido)pyridin-4-yloxy)-1H-indole-1-carboxylic acid ethylamide Similarly to Example 5, the title compound (132 mg, 0.275 mmol, 92%) was obtained as white crystals from phenyl N-(4-(1-(ethylamino)carbonyl-1H-5-indolyloxy)-2-pyridyl)-N-(phenoxycarbonyl)carbamate (161 mg, 0.300 mmol) synthesized in Production example 55-1 and (2S)-2-amino-3-hydroxy-1-(pyrrolidin-1-yl)propan-1-one hydrochloride (synthesized as an intermediate in Example 18).

Example 57

5-(2-(3-((1R)-1-Hydroxymethyl-2-oxo-2-piperidin-1-ylethyl)ureido)pyridin-4-yloxy)-1H-indole-1-carboxylic acid ethylamide Similarly to Example 5, the title compound (127 mg, 0.257 mmol, 86%) was obtained as white crystals from phenyl N-(4-(1-(ethylamino)carbonyl-1H-5-indolyloxy)-2-pyridyl)-N-(phenoxycarbonyl)carbamate (161 mg, 0.300 mmol) and (2R)-2-amino-3-hydroxy-1-(piperidin-1-yl)propan-1-one (228 mg, 1.32 mmol, synthesized as an intermediate in Example 21).

$^1$H-NMR Spectrum (DMSO-$d_6$) δ (ppm): 1.19 (3H, t, J=7.2 Hz), 1.38–1.61 (6H, m), 3.25–3.53 (8H, m), 4.75 (1H, m), 4.92 (1H, brs), 6.54 (1H, dd, J=2.4, 6.0 Hz), 6.69 (1H, d, J=3.6 Hz), 6.97 (1H, d, J=2.4 Hz), 7.05 (1H, dd, J=2.4, 9.0 Hz), 7.38 (1H, d, J=2.4 Hz), 7.92 (1H, d, J=3.6 Hz), 8.05 (1H, d, J=6.0 Hz), 8.08–8.27 (2H, m), 8.30 (1H, d, J=9.0 Hz), 9.21 (1H, s).

Example 58

5-(2-(3-((1S)-1-Hydroxymethyl-2-oxo-2-piperidin-1-ylethyl)ureido)pyridin-4-yloxy)-1H-indole-1-carboxylic acid ethylamide Similarly to Example 5, the title compound (54.4 mg, 0.110 mmol, 73%) was obtained as white crystals from phenyl N-(4-(1-(ethylamino)carbonyl-1H-5-indolyloxy)-2-pyridyl)-N-(phenoxycarbonyl)carbamate (80.1 mg, 0.150 mmol) synthesized in Production example 55-1 and (2S)-2-amino-3-hydroxy-1-(piperidin-1-yl)propan-1-one hydrochloride (156 mg, 0.748 mmol, synthesized as an intermediate in Example 20).

Example 59

5-(2-(3-(2-(4-Hydroxy-4-methylpiperidin-1-yl)-2-oxoethyl)ureido)pyridin-4-yloxy)-1H-indole-1-carboxylic acid ethylamide The reaction similar to Example 5 was performed by using ((4-(1-ethylcarbamoyl-1H-indol-5-yloxy)pyridin-2-yl)aminocarbonylamino)acetic acid (149 mg, 0.37 mmol) and 4-hydroxy-4-methylpiperidine monohydrochloride (68 mg, 0.45 mmol, Production example 8-3); purification was performed by silica gel column chromatography (Fuji Silysia BW-300, eluent, ethyl acetate:methanol=9:1; Fuji Silysia NH, eluent, ethyl acetate:methanol=10:1; and again Fuji Silysia BW-300, eluent, ethyl acetate-methanol system); and the obtained crystals were suspended in diethyl ether and filtered off, washed with diethyl ether and dried under aeration to yield the title compound as colorless crystals (40 mg, 0.081 mmol, 22%).

$^1$H-NMR Spectrum (DMSO-$d_6$) δ (ppm): 1.10 (3H, s), 1.16 (3H, t, J=7.2 Hz), 1.43 (4H, m), 3.01 (2H, m), 3.36 (2H, m), 3.89 (2H, m), 3.96 (2H, d, J=4.4 Hz), 4.37 (1H, s), 6.52 (1H, d, J=5.6 Hz), 6.67 (1H, d, J=3.6 Hz), 6.91 (1H, s), 7.03 (1H, d, J=9.0 Hz), 7.37 (1H, s), 7.90 (1H, d, J=3.6 Hz), 8.03 (1H, d, J=5.6 Hz), 8.17 (1H, m), 8.22 (1H, m), 8.28 (1H, d, J=9.0 Hz), 9.27 (1H, s).

The starting material was synthesized as follows.

Production Example 59-1

((4-(1-Ethylcarbamoyl-1H-indol-5-yloxy)pyridin-2-yl)aminocarbonylamino)acetic acid Methyl aminoacetate hydrochloride (292 mg, 2.33 mmol) was suspended in a solvent mixture of N,N-dimethylformamide (4 ml) and triethylamine (1 ml); phenyl N-(4-(1-(ethylamino)carbonyl-1H-5-indolyloxy)-2-pyridyl)-N-(phenoxycarbonyl)carbamate (250 mg, 0.466 mmol, Production example 55-1) was added thereto; and the reaction mixture was stirred at room temperature for 2 days. The reaction mixture was partitioned between ethyl acetate and water; and the organic layer was washed with brine, dried over anhydrous sodium sulfate, and concentrated under reduced pressure. The obtained residue was dissolved in a solvent mixture of tetrahydrofuran (2 ml) and methanol (1 ml); and 4N aqueous solution of sodium hydroxide was added thereto while stirred at room temperature; and the reaction mixture was stirred for 1.5 hour at room temperature. After 1N hydrochloric acid was added, extraction was performed with ethyl acetate-tetrahydrofuran, washed with brine, dried over anhydrous sodium sulfate, and concentrated under reduced pressure. The obtained crystals were suspended in diethyl ether, filtered off, washed with dimethyl ether, and dried under aeration to yield the title compound as colorless crystals (149 mg, 0.375 mmol, 80.5%).

$^1$H-NMR Spectrum (DMSO-$d_6$) δ (ppm): 1.17 (3H, t, J=7.0 Hz), 3.36 (2H, d, J=7.0 Hz), 3.81 (2H, d, J=5.2 Hz), 6.54 (1H, d, J=5.6 Hz), 6.67 (1H, d, J=3.4 Hz), 6.85 (1H, s), 7.04 (1H, dd, J=2.0, 8.8 Hz), 7.37 (1H, d, J=2.0 Hz), 7.90 (1H, d, J=3.4 Hz), 8.05 (1H, d, J=5.6 Hz), 8.20–8.30 (3H, m), 9.27 (1H, s), 12.55 (1H, s).

Example 60

N1-Ethyl-5-(2-((((1-methyl-4-piperidyl)methyl)amino)carbonyl)amino-4-pyridyl)oxy-1H-1-indole-carboxamide Similarly to Example 27, a crude product of tert-butyl 4-(((((4-((1-(ethylamino)carbonyl-1H-5-indolyl)oxy)-2-pyridyl)amino)carbonyl)amino)methyl)piperidin-1-carboxylate was obtained from phenyl N-(4-(1-(ethylamino)carbonyl)-1H-5-indolyl)oxy)-2-pyridyl)carbamate (150 mg, 0.36 mmol, Production example 27-2) and tert-butyl 4-aminomethyl-1-piperidine carboxylate. Trifluoroacetic acid was added to this at room temperature; the solution was stirred for 30 minutes; trifluoroacetic acid was distilled off; triethylamine-methanol was added to the residue to neutralize; and the solvent was distilled off again under reduced pressure. The residue was dissolved in tetrahydrofuran (4.0 ml)-methanol (4.0 ml); acetic acid (0.1 ml), 37% aqueous formaldehyde solution (0.5 ml) and sodium cyanoborohydride (90.5 mg, 1.44 mmol) were added at room temperature; and the reaction mixture was stirred for 1 hour. The reaction mixture was partitioned between ethyl acetate and water; and the organic layer was washed with water and brine, dried over anhydrous sodium sulfate. The solvent was distilled off, and the residue was purified by NH silica gel column chromatography (eluent; ethyl acetate:methanol=98:2). The crystals were precipitated from diethyl ether, filtered off, and dried under aeration to yield the title compound as white crystals (197.0 mg, 0.44 mmol, 60.7%).

$^1$H-NMR Spectrum (DMSO-$d_6$) δ (ppm): 1.08–1.19 (5H, m), 1.30 (1H, m), 1.54 (2H, m), 1.75 (2H, m), 2.09 (3H, m), 2.70 (2H, m), 2.98 (2H, m), 3.20–3.40 (2H, m), 6.49 (1H, dd, J=2.4, 5.6 Hz), 6.67 (1H, d, J=3.6 Hz), 6.85 (1H, s), 7.03 (1H, dd, J=2.4, 8.8 Hz), 7.36 (1H, d, J=3.6 Hz), 7.90 (1H, d, J=2.4 Hz), 8.02 (1H, d, J=5.6 Hz), 8.08 (1H, m), 8.22 (1H, m), 8.28 (1H, d, J=8.8 Hz), 9.00 (1H, s).

Example 61

N1-Ethyl-5-(2-(((2-(diethylamino)ethyl)amino)carbonyl)amino-4-pyridyl)oxy-1H-1-indolecarboxamide Similarly to Example 27, the title compound (140.9 mg, 0.32 mmol, 89.2%) was obtained as white crystals from phenyl N-(4-(1-(ethylamino)carbonyl-1H-5-indolyl)oxy-2-pyridyl)carbamate (150 mg, 0.36 mmol, Production example 27-2) and 2-(diethylamino)ethylamine.

$^1$H-NMR Spectrum (DMSO-$d_6$) δ (ppm): 0.93 (6H, t, J=7.2 Hz), 1.17 (3H, t, J=7.2 Hz), 2.40–2.49 (6H, m), 3.13 (2H, m), 3.20–3.40 (2H, m), 6.49 (1H, dd, J=2.4, 5.6 Hz), 6.67 (1H, d, J=3.6 Hz), 6.82 (1H, s), 7.03 (1H, dd, J=2.4, 8.8 Hz), 7.36 (1H, d, J=2.4 Hz), 7.90 (1H, d, J=3.6 Hz), 8.00 (1H, d, J=5.6 Hz), 8.20–8.25 (2H, m), 8.28 (1H, d, J=8.8 Hz), 9.11 (1H, s).

Example 62

N1-Ethyl-5-(2-(((2-(morpholin-4-yl)ethyl)amino)carbonyl)amino-4-pyridyl)oxy-1H-1-indolecarboxamide Similarly to Example 27, the title compound (155.0 mg, 0.34 mmol, 95.1%) was obtained as white crystals from phenyl N-(4-(1-(ethylamino)carbonyl-1H-5-indolyl)oxy-2-pyridyl)carbamate (150 mg, 0.36 mmol, Production example 27-2) and 4-(2-aminoethyl)morpholine.

$^1$H-NMR Spectrum (DMSO-$d_6$) δ (ppm): 1.67 (3H, t, J=7.2 Hz), 2.30–2.40 (6H, m), 3.20 (2H, m), 3.20–3.40 (2H, m), 3.54–3.57 (4H, m), 6.50 (1H, dd, J=2.4, 5.6 Hz), 6.67 (1H, d, J=3.6 Hz), 6.84 (1H, s), 7.03 (1H, dd, J=2.4, 8.8 Hz), 7.36 (1H, d, J=3.6 Hz), 7.90 (1H, d, J=2.4 Hz), 8.02 (1H, d, J=5, 6 Hz), 8.10–8.25 (2H, m), 8.28 (1H, d, J=8.8 Hz), 9.11 (1H, s).

Example 63

N1-Ethyl-5-(2-(((2-(4-hydroxypiperidino)ethyl)amino)carbonyl)amino-4-pyridyl)oxy-1H-1-indole-carboxamide Similarly to Example 27, the title compound (49.1 mg, 0.11 mmol, 35.1%) was obtained as white crystals from phenyl N-(4-(1-(ethylamino)carbonyl-1H-5-indolyl)oxy-2-pyridyl)carbamate (125 mg, 0.30 mmol, Production example 27-2) and 1-(2-aminoethyl)-4-hydroxypiperidine dihydrochloride.

$^1$H-NMR Spectrum (DMSO-$d_6$) δ (ppm): 1.17 (3H, t, J=7.2 Hz), 1.36 (2H m), 1.66–1.70 (2H, m), 2.00 (2H, m), 2.32 (2H, m), 2.65–2.69 (2H, m), 3.16 (2H, m), 3.20–3.40 (2H, m), 3.40 (1H, m), 4.53 (1H, d, J=4.0 Hz), 6.50 (1H, dd, J=2.4, 5.6 Hz), 6.67 (1H, d, J=3.6 Hz), 6.83 (1H, s), 7.03 (1H, dd. J=2.4, 8.8 Hz), 7.36 (1H, d, J=2.4 Hz), 7.90 (1H, d, J=3.6 Hz), 8.01 (1H, d, J=5.6 Hz), 8.10–8.23 (2H, m), 8.28 (1H, d, J=8.8 Hz), 9.11 (1H, s).

Example 64

N1-Methyl-5-(2-(((2-(4-hydroxypiperidino)ethyl)amino)carbonyl)amino-4-pyridyl)oxy-1H-1-indole-carboxamide Similarly to Example 27, the title compound (114.3 mg, 0.25 mmol, 25.3%) was obtained as white crystals from phenyl N-(4-(1-(methylamino)carbonyl-1H-5-indolyl)oxy-2-pyridyl)carbamate (402 mg, 1.0 mmol, Production example 29-1) and 1-(2-aminoethyl)-4-hydroxypiperidine dihydrochloride.

$^1$H-NMR Spectrum (DMSO-$d_6$) δ (ppm): 1.32–1.38 (2H, m), 1.60–1.70 (2H, m), 1.96–2.03 (2H, m), 2.31–2.34 (2H, m), 2.60–2.70 (2H, m), 2.83 (3H, d, J=4.4 Hz), 3.15–3.18 (2H, m), 3.42 (1H, m), 4.53 (1H, d, J=4.0 Hz), 6.51 (1H, dd, J=2.4, 5.6 Hz), 6.67 (1H, d, J=3.6 Hz), 6.84 (1H, s), 7.04 (1H, dd, J=2.4, 8.8 Hz), 7.36 (1H, d, J=2.4 Hz), 7.87 (1H, d, J=3.6 Hz), 8.01 (1H, d, J=5.6 Hz), 8.14–8.16 (2H, m), 8.28 (1H, d, J=8.8 Hz), 9.11 (1H, s).

Example 65

N1-Ethyl-5-(2-((3-(diethylamino)propylamino)carbonyl)amino-4-pyridyl)oxy-1H-1-indolecarboxamide Similarly to Example 27, the title compound (159.9 mg, 0.35 mmol, 98.1%) was obtained as white crystals from phenyl N-(4-(1-(ethylamino)carbonyl-1H-5-indolyl)oxy-2-pyridyl)carbamate (150 mg, 0.36 mmol, Production example 27-2) and 3-(diethylamino)propylamine.

$^1$H-NMR Spectrum (DMSO-$d_6$) δ (ppm): 0.91 (6H, t, J=7.2 Hz), 1.17 (3H, t, J=7.2 Hz), 1.50 (2H, m), 2.32–2.41 (6H, m), 3.10 (2H, m), 3.20–3.40 (2H, m), 6.50 (1H, dd, J=2.4, 5.6 Hz), 6.67 (1H, d, J=3.6 Hz), 6.81 (1H, s), 7.03 (1H, dd, J=2.4, 8.8 Hz), 7.36 (1H, d, J=3.6 Hz), 7.90 (1H, d, J=2.4 Hz), 8.00 (1H, d, J=5.6 Hz), 8.12 (1H, m), 8.22 (1H, t, J=5.2 Hz), 8.28 (1H, d, J=8.8 Hz), 9.03 (1H, s).

Example 66

N1-Ethyl-5-(2-(((3-(morpholin-4-yl)propyl)amino)carbonyl)amino-4-pyridyl)oxy-1H-1-indolecarboxamide Similarly to Example 27, the title compound (135.0 mg, 0.29 mmol, 96.4%) was obtained as white crystals from phenyl N-(4-(1-(ethylamino)carbonyl-1H-5-indolyl)oxy-2-pyridyl)carbamate (125 mg, 0.30 mmol, Production example 27-2) and 4-(3-aminopropyl)morpholine.

¹H-NMR Spectrum (DMSO-d₆) δ (ppm): 1.17 (3H, t, J=7.2 Hz), 1.55 (2H, m), 2.20–2.40 (6H, m), 3.11 (2H, m), 3.20–3.40 (2H, m), 3.51–3.55 (4H, m), 6.50 (1H, dd, J=2.4, 5.6 Hz), 6.67 (1H, d, J=3.6 Hz), 6.84 (1H, s), 7.03 (1H, dd, J=2.4, 8.8 Hz), 7.36 (1H, d, J=2.4 Hz), 7.90 (1H, d, J=3.6 Hz), 8.01 (1H, d, J=5.6 Hz), 8.04 (1H, m), 8.21 (1H, t, J=5.6 Hz), 8.28 (1H, d, J=8.8 Hz), 9.02 (1H, s).

Example 67

N1-Ethyl-5-(2-(((3-(4-methylpiperazino)propyl)amino)carbonyl)amino-4-pyridyl)oxy-1H-1-indole-carboxamide Similarly to Example 27, the title compound (141.9 mg, 0.30 mmol, 98.6%) was obtained as white crystals from phenyl N-(4-(1-(ethylamino)carbonyl-1H-5-indolyl)oxy-2-pyridyl)carbamate (125 mg, 0.30 mmol, Production example 27-2) and 1-(3-aminopropyl)-4-methylpiperazine.

¹H-NMR Spectrum (DMSO-d₆) δ (ppm): 1.17 (3H, t, J=7.2 Hz), 1.54 (2H, m), 2.11 (3H, s), 2.11–2.40 (10H, m), 3.08 (2H, m), 3.20–3.40 (2H, m), 6.50 (1H, dd, J=2.4, 5.6 Hz), 6.67 (1H, d, J=3.6 Hz), 6.84 (1H, s), 7.03 (1H, dd, J=2.4, 8.8 Hz), 7.36 (1H, d, J=2.4 Hz), 7.90 (1H, d, J=3.6 Hz), 8.01 (1H, d, J=5.6 Hz), 8.04 (1H, m), 8.22 (1H, t, J=5.6 Hz), 8.28 (1H, d, J=88 Hz), 9.01 (1H, s).

Example 68

N1-Cyclopropyl-5-(2-(((4-(pyrrolidin-1-yl)piperidin-1-yl)carbonyl)amino)pyridin-4-yloxy)-1H-1-indole-carboxamide Tetrahydrofuran (30 ml) and triethylamine (3.87 ml, 27.8 mmol) were added to N1-cyclopropyl-5-(2-amino-4-pyridyl)oxy-1H-1-indolecarboxamide (2.85 g, 9.25 mmol, CAS No. 417722-12-4) which was described in WO 02/32872; phenyl chloroformate (2.57 ml, 20.4 mmol) was added thereto at 0° C. while stirred; and the reaction mixture was stirred at room temperature for 2 hours. The reaction mixture was partitioned between ethyl acetate and water; and the organic layer was concentrated to yield 3.30 g of the mixture of phenyl N-(4-(1-(cyclopropylamino)carbonyl-1H-5-indolyl)-oxy-2-pyridyl)carbamate and phenyl N-(4-(1-cyclopropylaminocarbonyl-1H-5-indolyl)oxy-2-pyridyl)-N-(phenoxycarbonyl)carbamate. A portion of 0.524 g of the mixture was dissolved in N,N-dimethylformamide (5 ml); 4-(1-pyrrolidinyl)piperidine (0.736 g, 4.80 mmol) was added thereto; the reaction mixture was stirred for 5 hours; the reaction mixture was partitioned between ethyl acetate and water; and the organic layer was concentrated to yield the title compound as white crystals (280 mg, 0.57 mmol).

MS Spectrum (ESI): 489 (M+1).

¹H-NMR Spectrum (DMSO-d₆) δ (ppm): 0.57–0.75 (4H, m), 1.18–1.30 (2H, m), 1.58–1.80 (6H, m), 2.03–2.12 (1H, m), 2.38–2.48 (4H, m), 2.72–2.87 (3H, m), 3.88–3.96 (2H, m), 6.53 (1H, dd, J=2.7, 6.1 Hz), 6.64 (1H, d, J=3.4 Hz), 7.03 (1H, dd, J=2.7, 8.9 Hz), 7.30 (1H, d, J=2.7 Hz), 7.35 (1H, d, J=2.7 Hz), 7.86 (1H, d, J=3.4 Hz), 8.06 (1H, d, J=6.1 Hz), 8.24–8.29 (2H, m), 9.08 (1H, s).

Example 69

5-(2-(3-((1R)-1-Hydroxymethyl-2-oxo-2-pyrrolidin-1-ylethyl)ureido)pyridin-4-yloxy)-1H-indole-1-carboxylic acid cyclopropylamide Similarly to Example 5, the title compound. (113 mg, 0.229 mmol) was obtained as white crystals from a mixture (165 mg) of N-(4-(1-cyclopropylaminocarbonyl-1H-5-indolyloxy)-2-pyridyl)-N-(phenoxycarbonyl)carbamate and phenyl N-(4-(1-cyclopropylaminocarbonyl-1H-5-indolyloxy)-2-pyridyl)carbamate, intermediates in Example 68, and (2R)-2-amino-3-hydroxy-1-(pyrrolidin-1-yl)propan-1-one (265 mg, 1.67 mmol, synthesized as an intermediate in Example 55).

¹H-NMR Spectrum (DMSO-d₆) δ (ppm): 0.58–0.66 (2H, m), 0.70–0.78 (2H, m), 1.72–1.90 (4H, m), 2.78 (1H, m), 3.20–3.60 (6H, m), 4.54 (1H, m), 4.98 (1H, t, J=5.6 Hz), 6.53 (1H, dd, J=2.0, 6.0 Hz), 6.67 (1H, d, J=3.6 Hz) 6.97 (1H, d, J=2.0 Hz), 7.06 (1H, dd, J=2.4, 8.8 Hz), 7.37 (1H, d, J=2.4 Hz), 7.88 (1H, d, J=3.6 Hz), 8.05 (1H, d, J=6.0 Hz), 8.16 (1H, brs), 8.25–8.34 (2H, m), 9.18 (1H, s).

Example 70

5-(2-(3-((1S)-1-Hydroxymethyl-2-oxo-2-pyrrolidin-1-ylethyl)ureido)pyridin-4-yloxy)-1H-indole-1-carboxylic acid cyclopropylamide Similarly to Example 5, the title compound (117 mg, 0.237 mmol) was obtained as white crystals from a mixture (165 mg) of phenyl N-(4-(1-cyclopropylaminocarbonyl-1H-5-indolyloxy)-2-pyridyl)-N-(phenoxycarbonyl)carbamate and phenyl N-(4-(1-cyclopropylaminocarbonyl-1H-5-indolyloxy)-2-pyridyl)carbamate, intermediates in Example 68, and (2S)-2-amino-3-hydroxy-1-(pyrrolidin-1-yl)propan-1-one hydrochloride (synthesized as an intermediate in Example 18).

Example 71

5-(2-(3-(2-Oxo-2-(pyrrolidin-1-yl)ethyl)ureido)pyridin-4-yloxy)-1H-indole-1-carboxylic acid cyclopropylamide Similarly to Example 5, the title compound (90.9 mg, 0.197 mmol) was obtained as white crystals from a mixture (165 mg) of phenyl N-(4-(1-cyclopropylaminocarbonyl-1H-5-indolyloxy)-2-pyridyl)-N-(phenoxycarbonyl)carbamate and phenyl N-(4-(1-cyclopropylaminocarbonyl-1H-5-indolyloxy)-2-pyridyl)carbamate, intermediates in Example 68, and 2-amino-1-(pyrrolidin-1-yl)ethanone hydrochloride (247 mg, 1.50 mmol, synthesized as an intermediate in Example 7).

¹H-NMR Spectrum (DMSO-d₆) δ (ppm): 0.58–0.66 (2H, m), 0.71–0.79 (2H, m), 1.72–1.80 (2H, m), 1.83–1.91 (2H, m), 2.78 (1H, m), 3.28–3.40 (4H, m), 3.89 (2H, d, J=4.4 Hz), 6.54 (1H, dd, J=2.0, 6.0 Hz), 6.67 (1H, d, J=3.6 Hz), 6.94 (1H, d, J=2.0 Hz), 7.06 (1H, dd, J=2.4, 8.8 Hz), 7.38 (1H, d, J=2.4 Hz), 7.88 (1H, d, J=3.6 Hz), 8.05 (1H, d, J=6.0 Hz), 8.17 (1H, brs), 8.26–8.35 (2H, m), 9.28 (1H, s).

Example 72

5-(2-(3-(3-Oxo-3-(pyrrolidin-1-yl)propyl)ureido)pyridin-4-yloxy)-1H-indole-1-carboxylic acid cyclopropylamide Similarly to Example 5, the title compound (113 mg, 0.237 mmol) was obtained as white crystals from a mixture (165 mg) of phenyl N-(4-(1-cyclopropylaminocarbonyl-1H-5-indolyloxy)-2-pyridyl)-N-(phenoxycarbonyl)carbamate and phenyl N-(4-(1-cyclopropylaminocarbonyl-1H-5-indolyloxy)-2-pyridyl)carbamate, intermediates in Example 68, and 3-amino-1-(pyrrolidin-1-yl)propan-1-one hydrochloride (268 mg, 1.50 mmol, synthesized as an intermediate in Example 25).

¹H-NMR Spectrum (DMSO-d₆) δ (ppm): 0.58–0.66 (2H, m), 0.71–0.79 (2H, m), 1.70–1.79 (2H, m), 1.79–1.88 (2H, m), 2.40 (2H, t, J=6.4 Hz), 2.78 (1H, m), 3.24–3.38 (6H, m), 6.51 (1H, dd, J=2.0, 6.0 Hz), 6.67 (1H, d, J=3.8 Hz), 6.93 (1H, d, J=2.0 Hz), 7.05 (1H, dd, J=2.4, 8.8 Hz), 7.37 (1H, d, J=2.4 Hz), 7.88 (1H, d, J=3.8 Hz), 7.98–8.10 (2H, m), 8.26–8.34 (2H, m), 9.09 (1H, s).

Example 73

5-(2-(3-((1R)-1-Hydroxymethyl-2-oxo-2-piperidin-1-ylethyl)ureido)pyridin-4-yloxy)-1H-indole-1-carboxylic acid cyclopropylamide Similarly to Example 5, the title compound (106 mg, 0.209 mmol) was obtained as white crystals from a mixture (165 mg) of phenyl N-(4-(1-cyclopropylaminocarbonyl-1H-5-indolyloxy)-2-pyridyl)-N-(phenoxycarbonyl)carbamate and phenyl N-(4-(1-cyclopropylaminocarbonyl-1H-5-indolyloxy)-2-pyridyl)carbamate, intermediates in Example 68, and (2R)-2-amino-3-hydroxy-1-(piperidin-1-yl)propan-1-one (228 mg, 1.32 mmol, synthesized as an intermediate in Example 57).

¹H-NMR Spectrum (DMSO-d₆) δ (ppm): 0.58–0.66 (2H, m), 0.70–0.78 (2H, m), 1.38–1.62 (6H, m), 2.79 (1H, m), 3.38–3.53 (6H, m), 4.75 (1H, m), 4.93 (1H, t, J=5.8 Hz), 6.54 (1H, dd, J=2.0, 6.0 Hz), 6.67 (1H, d, J=3.6 Hz), 6.97 (1H, d, J=2.0 Hz), 7.06 (1H, dd, J=2.4, 8.8 Hz), 7.37 (1H, d, J=2.4 Hz), 7.88 (1H, d, J=3.6 Hz), 8.05 (1H, d, J=6.0 Hz), 8.10–8.34 (3H, m), 9.20 (1H, s).

Example 74

5-(2-(3-((1S)-1-Hydroxymethyl-2-oxo-2-piperidin-1-ylethyl)ureido)pyridin-4-yloxy)-1H-indole-1-carboxylic acid cyclopropylamide Similarly to Example 5, the title compound (66.8 mg, 0.132 mmol) was obtained as white crystals from a mixture (82.3 mg) of phenyl N-(4-(1-cyclopropylaminocarbonyl-1H-5-indolyloxy)-2-pyridyl)-N-(phenoxycarbonyl)carbamate and phenyl N-(4-(1-cyclopropylaminocarbonyl-1H-5-indolyloxy)-2-pyridyl)carbamate, intermediates in Example 68, and (2S)-2-amino-3-hydroxy-1-(piperidin-1-yl)propan-1-one hydrochloride (156 mg, 0.748 mmol, synthesized as an intermediate in Example 20).

Example 75

N1-Phenyl-5-(2-(((3-(diethylamino)propyl)amino)carbonyl)amino-4-pyridyl)-oxy-1H-1-indolecarboxamide The title compound was obtained from N1-phenyl-5-(2-amino-4-pyridyl)oxy-1H-1-indolecarboxamide (CAS No. 417721-87-0) which was written in the description of WO 02/32872 and 3-diethylaminopropylamine using a procedure analogous to that described for Example 28.

¹H-NMR Spectrum (DMSO-d₆) δ (ppm): 0.91 (6H, t, J=7.2 Hz), 1.47–1.53 (2H, m), 2.30–2.44 (6H, m), 3.05–3.14 (2H, m), 6.52 (1H, dd, J=6.0, 2.0 Hz), 6.76 (1H, d, J=3.6 Hz), 6.84 (1H, d, J=2.0H), 7.09 (1H, dd, J=9.2, 2.4 Hz), 7.13 (1H, t, J=7.6 Hz), 7.38 (2H, dd, J=7.6, 7.6 Hz), 7.42 (1H, d, J=2.4 Hz), 7.64 (2H, d, J=7.6 Hz), 8.02 (1H, d, J=6.0 Hz), 8.10–8.14 (2H, m), 8.27 (1H, d, J=9.2 Hz), 9.05 (1H, brs), 10.10 (1H, brs).

Example 76

N1-Phenyl-5-(2-(((3-(4-methylpiperazin-1-yl)propyl)amino)carbonyl)amino-4-pyridyl)oxy-1H-1-indolecarboxamide Similarly to Example 28, the title compound was obtained from N1-phenyl-5-(2-amino-4-pyridyl)oxy-1H-1-indolecarboxamide (CAS No. 417721-87-0) which was described in WO 02/32872 and 1-(3-aminopropyl)-4-methylpiperazine.

¹H-NMR Spectrum (DMSO-d₆) δ (ppm): 1.52–1.59 (2H, m), 2.13 (3H, s), 2.15–2.45 (10H, m), 3.08–3.15 (2H, m), 6.54 (1H, dd, J=6.0, 2.0 Hz), 6.79 (1H, d, J=3.6 Hz), 6.89 (1H, brs), 7.10 (1H, dd, J=2.4, 9.2 Hz), 7.15 (1H, t, J=7.6 Hz), 7.40 (2H, t, J=7.6 Hz), 7.44 (1H, d, J=2.4 Hz), 7.66 (2H, d, J=7.6 Hz), 8.03–8.07 (2H, m), 8.14 (1H, d, J=3.6 Hz), 8.29 (1H, d, J=9.2 Hz), 9.05 (1H, brs), 10.10 (1H, brs).

Example 77

N1-Ethyl-5-(2-(((4-(pyrrolidin-1-yl)piperidin-1-yl)carbonyl)amino)pyridin-4-yloxy)-1H-1-indolecarboxamide Tetrahydrofuran (20 ml) and triethylamine (2.70 ml, 19.4 mmol) were added to N1-ethyl-5-(2-amino-4-pyridyl)oxy-1H-1-indolecarboxamide (1.91 g, 6.45 mmol, Production example 27-1); phenyl chloroformate (1.79 ml, 14.2 mmol) was added thereto at 0° C. while stirred; and the reaction mixture was stirred at room temperature for 2 hours. The reaction mixture was partitioned between ethyl acetate and water; the organic layer was concentrated to yield a mixture (2.95 g) of phenyl N-(4-(1-(ethylamino)carbonyl-1H-5-indolyl)oxy-2-pyridyl)carbamate and phenyl N-(4-(1-(ethylamino)carbonyl-1H-5-indolyl)oxy-2-pyridyl)-N-(phenoxycarbonyl)carbamate. A portion of 0.454 g of the mixture was dissolved in N,N-dimethylformamide (5 ml); and 4-tetrahydro-1H-1-pyrrolylpiperidine (0.522 g, 3.39 mmol) was added; and the reaction mixture was stirred for 5 hours. The reaction mixture was partitioned between ethyl acetate and water; the organic layer was concentrated to yield a solid; the obtained solid was washed with hexane:diethyl ether=1:1 to yield the title compound as crystals (205 mg, 0.43 mmol).

MS Spectrum (ESI): 477 (M+1), 953 (2M+1).

¹H-NMR Spectrum (DMSO-d₆) δ (ppm): 1.12–1.22 (5H, m), 1.57–1.81 (6H, m), 2.05–2.15 (1H, m), 2.38–2.50 (4H, m), 2.77–2.78 (2H, m), 3.28–3.37 (2H, m), 3.87–3.97 (2H, m), 6.53 (1H, dd, J=2.5, 5.4 Hz), 6.66 (1H, d, J=3.5 Hz), 7.02 (1H, dd, J=2.5, 8.9 Hz), 7.30 (1H, d, J=2.5 Hz), 7.36 (1H, d, J=2.5 Hz), 7.89 (1H, d, J=3.5 Hz), 8.05 (1H, d, J=5.4 Hz), 8.20 (1H, m), 8.27 (1H, t, J=8.9 Hz), 9.08 (1H, s).

Example 78

5-(2-(((4-Hydroxy-4-methylpiperidin-1-yl)carbonyl)amino)pyridin-4-yloxy)-1H-indole-1-carboxylic acid ethylamide Similarly to Example 41, the title compound was obtained as colorless crystals (124 mg, 0.283 mmol, 89.4%) from 4-hydroxy-4-methylpiperidine monohydrochloride (216 mg, 1.42 mmol, Production example 8-3) and phenyl N-(4-(1-(ethylaminocarbonyl-1H-indol-5-yloxy)-pyridin-2-yl)-N-(phenoxycarbonyl)carbamate (170 mg, 0.317 mmol, Production example 55-1).

¹H-NMR Spectrum (DMSO-d₆) δ (ppm): 1.08 (3H, s), 1.17 (3H, t, J=7.2 Hz), 1.38–1.44 (4H, m), 3.13 (2H, m), 3.30 (2H, m), 3.63 (2H, m), 4.27 (1H, s), 6.53 (1H, dd, J=2.4, 6.0 Hz), 6.67 (1H, d, J=3.6 Hz), 7.03 (1H, dd, J=2.4, 8.8 Hz), 7.32 (1H, d, J=2.4 Hz), 7.35 (1H, d, J=2.4 Hz), 7.90 (1H, d, J=3.0 Hz), 8.05 (1H, d, J=6.0 Hz), 8.21 (1H, t, J=5.4 Hz), 8.27 (1H, d, J=8.8 Hz), 9.04 (1H, s).

Example 79

N1-Ethyl-5-(2-((4-hydroxypiperidin-1-yl)carbonyl)amino-4-pyridyl)oxy-1H-1-indolecarboxamide Similarly to Example 27, the title compound was obtained as white powder (18.7 mg, 0.044 mmol, 14.7%) from phenyl N-(4-(1-(ethylamino)carbonyl-1H-5-indolyl)oxy-2-pyridyl)carbamate (125 mg, 0.30 mmol, Production example 27-2) and 4-hydroxypiperidine.

¹H-NMR Spectrum (DMSO-d₆) δ (ppm): 1.13–1.27 (5H, m), 1.63–1.67 (2H, m), 2.98 (2H, m), 3.20–3.40 (2H, m), 3.60 (1H, m), 3.74 (2H, m), 4.64 (1H, d, J=4.4 Hz), 6.53 (1H, dd, J=2.4, 5.6 Hz), 6.67 (1H, d, J=3.6 Hz), 7.03 (1H, dd, J=2.4, 8.8 Hz), 7.31 (1H, d, J=2.4 Hz), 7.35 (1H, d, J=2.4 Hz), 7.90 (1H, d, J=3.6 Hz), 8.06 (1H, d, J=5.6 Hz), 8.21 (1H, t, J=5.2 Hz), 8.27 (1H, d, J=8.8 Hz), 9.09 (1H, s).

Example 80

N1-Ethyl-5-(2-(piperidin-1-ylcarbonyl)amino-4-pyridyl)oxy-1H-1-indolecarboxamide N,N-Dimethylformamide (4 ml) and piperidine (0.31 ml, 3.13 mmol) were added to a mixture (0.336 g) of phenyl N-(4-(1-(ethylamino)carbonyl-1H-5-indolyl)oxy-2-pyridyl)carbamate and phenyl N-(4-(1-(ethylamino)carbonyl-1H-5-indolyl)oxy-2-pyridyl)-N-(phenoxycarbonyl)carbamate obtained in Example 77; the reaction mixture was stirred overnight; the reaction mixture was partitioned between ethyl acetate and water; and the organic layer was concentrated to yield the title compound as crystals (182 mg, 0.45 mmol).

MS Spectrum (ESI): 408 (M+1), 815 (2M+1).

¹H-NMR Spectrum (DMSO-d₆) δ (ppm): 1.18 (3H, t, J=7.6 Hz), 1.35–1.57 (6H, m), 3.23–3.33 (6H, m), 6.52 (1H, dd, J=2.4, 5.4 Hz), 6.67 (1H, d, J=3.4 Hz), 7.03 (1H, dd, J=2.4, 8.7 Hz), 7.30 (1H, d, J=2.4 Hz), 7.36 (1H, d, J=2.4 Hz), 7.90 (1H, d, J=3.4 Hz), 8.06 (1H, d, J=5.5 Hz), 8.21 (1H, t, J=5.5 Hz), 8.27 (1H, d, J=8.7 Hz), 9.05 (1H, s).

Example 81

N1-Ethyl-5-((2-((pyrrolidin-1-ylcarbonyl)amino)-4-pyridyl)oxy)-1H-1-indolecarboxamide N,N-Dimethylformamide (5 ml) and pyrrolidine (0.36 ml, 4.3 mmol) were added to a mixture (0.461 g) of phenyl N-(4-(1-(ethylamino)carbonyl)-1H-5-indolyl)oxy-2-pyridyl)carbamate and phenyl N-(4-(1-(ethylamino)carbonyl-1H-5-indolyl)oxy-2-pyridyl)-N-(phenoxycarbonyl)carbamate obtained in Example 77; the reaction mixture was stirred overnight; the reaction mixture was partitioned between ethyl acetate and water; and the organic layer was concentrated to yield the title compound as crystals (245 mg, 0.623 mmol).

MS Spectrum (ESI): 394 (M+1), 787 (2M+1).

¹H-NMR Spectrum (DMSO-d₆) δ (ppm): 1.16 (3H, t, J=7.6 Hz), 1.70–1.82 (4H, m), 3.22–3.40 (6H, m), 6.54 (1H, dd, J=2.4, 5.5 Hz), 6.67 (1H, d, J=3.4 Hz), 7.03 (1H, dd, J=2.4, 8.7 Hz), 7.35 (1H, d, J=2.4 Hz), 7.41 (1H, d, J=2.4 Hz), 7.90 (1H, d, J=3.4 Hz), 8.06 (1H, d, J=5.5 Hz), 8.21 (1H, t, J=5.5 Hz), 8.27 (1H, d, J=8.7 Hz), 8.59 (1H, s).

Example 82

N4-(4-((1-(Ethylamino)carbonyl-1H-5-indolyl)oxy)-2-pyridyl)-4-morpholinecarboxamide N,N-Dimethylformamide (5 ml) and morpholine (0.326 ml, 3.73 mmol) were added to a mixture (0.401 g) of phenyl N-(4-(1-(ethylamino)carbonyl)-1H-5-indolyl)oxy-2-pyridyl)carbamate and phenyl N-(4-(1-(ethylamino)carbonyl-1H-5-indolyl)oxy)-2-pyridyl)-N-(phenoxycarbonyl)carbamate obtained in Example 77; the reaction mixture was stirred overnight; the reaction mixture was partitioned between ethyl acetate and water; the organic layer was concentrated; and the obtained solid was washed with a solvent mixture of hexane:diethyl ether=1:1 to yield the title compound (255 mg, 0.62 mmol).

MS Spectrum (ESI): 410 (M+1), 819 (2M+1).

¹H-NMR Spectrum (DMSO-d₆) δ (ppm): 1.17 (3H, t, J=7.7 Hz), 3.25–3.42 (6H, m), 3.48–3.53 (4H, m), 6.55 (1H, dd, J=2.6, 5.6 Hz), 6.67 (1H, d, J=3.6 Hz), 7.02 (1H, dd, J=2.6, 8.7 Hz), 7.29 (1H, d, J=2.6 Hz), 7.35 (1H, d, J=2.4 Hz), 7.90 (1H, d, J=3.6 Hz), 8.08 (1H, d, J=5.6 Hz), 8.20 (1H, t, J=5.6 Hz), 8.28 (1H, t, J=5.6 Hz), 9.19 (1H, s).

Example 83

N1-Ethyl-5-(2-((1,1-dioxothiomorpholin-4-ylcarbonyl)amino)pyridin-4-yloxy)-1H-1-indolecarboxamide Similarly to Example 54, the title compound was obtained as colorless crystals (116 mg, 0.253 mmol, 80.0%) from 1,1-dioxothiomorpholine hydrochloride (248 mg, 1.42 mmol, Production example 54-3) and phenyl N-(4-(1-(ethylamino)carbonyl-1H-indol-5-yloxy)-pyridin-2-yl)-N-(phenoxycarbonyl)carbamate (170 mg, 0.317 mmol, Production example 55-1).

¹H-NMR Spectrum (DMSO-d₆) δ (ppm): 1.17 (3H, t, J=7.2 Hz), 3.10 (4H, m), 3.29 (2H, m), 3.80 (4H, m), 6.58 (1H, dd, J=2.0, 5.6 Hz), 6.67 (1H, d, J=3.4 Hz), 7.03 (1H, dd, J=2.0, 9.0 Hz), 7.31 (1H, d, J=2.0 Hz), 7.36 (1H, d, J=2.0 Hz), 7.90 (1H, d, J=3.4 Hz), 8.10 (1H, d, J=5.6 Hz), 8.22 (1H, t, J=5.4 Hz), 8.28 (1H, d, J=9.0 Hz), 9.54 (1H, s).

Example 84

N1-Ethyl-5-(2-((methoxylamino)carbonyl)amino-4-pyridyl)oxy-1H-1-indolecarboxamide Similarly to Example 27, the title compound was obtained as white crystals (94.3 mg, 0.26 mmol, 70.9%) from phenyl N-(4-(1-(ethylamino)carbonyl-1H-5-indolylyl)oxy-2-pyridinyl)carbamate (150 mg, 0.36 mmol, Production example 27-2) and methoxylamine hydrochloride.

¹H-NMR Spectrum (DMSO-d₆) δ (ppm): 1.17 (3H, t, J=7.2 Hz), 3.20–3.40 (2H, m), 3.59 (3H, s), 6.57 (1H, dd, J=2.4, 5.6 Hz), 6.67 (1H, d, J=3.6 Hz), 7.05 (1H, dd, J=2.4, 8.8 Hz), 7.16 (1H, s), 7.38 (1H, d, J=2.4 Hz), 7.90 (1H, d, J=3.6 Hz), 8.08 (1H, d, J=5.6 Hz), 8.21 (1H, m), 8.28 (1H, d, J=8.8 Hz), 8.95 (1H, s), 10.15 (1H, s).

Example 85

N1-Cyclopropyl-5-(2-((4-hydroxypiperidino)carbonyl)amino-4-pyridyl)oxy-1H-1-indolecarboxamide N,N-Dimethylformamide (5 ml) and 4-hydroxypiperidine (433 mg, 4.29 mmol) were added to a mixture (470 mg) of phenyl N-(4-(1-cyclopropylaminocarbonyl-1H-5-indolyl)oxy-2-pyridyl)carbamate and phenyl N-(4-(1-cyclopropylaminocarbonyl-1H-5-indolyl)oxy-2-pyridyl)-N-(phenoxycarbonyl)carbamate obtained in Example 68; the reaction mixture was stirred overnight; the reaction mixture was partitioned between ethyl acetate and water; and the organic layer was concentrated to yield the title compound as white crystals (220 mg, 0.51 mmol, 39%).

MS Spectrum (ESI): 436 (M+1), 871 (2M+1).

$^1$H-NMR Spectrum (DMSO-$d_6$) δ (ppm): 0.58–0.63 (2H, m), 0.69–0.76 (2H, m), 1.18–1.30 (2H, m), 1.60–1.70 (2H, m), 2.70–2.80 (1H, m), 2.93–3.02 (2H, m), 3.55–3.64 (1H, m), 3.69–3.77 (2H, m), 4.63 (1H, d, J=4.4 Hz), 6.53 (1H, dd, J=2.4, 5.8 Hz), 6.64 (1H, d, J=3.6 Hz), 7.04 (1H, dd, J=2.4, 8.5 Hz), 7.31 (1H, d, J=2.4 Hz), 7.35 (1H, d, J=2.4 Hz), 7.86 (1H, d, J=3.6 Hz), 8.06 (1H, d, J=5.8 Hz), 8.24–8.29 (2H, m), 9.08 (1H, s).

Example 86

N1-Cyclopropyl-5-(2-(((4-hydroxy-4-methylpiperidin-1-yl)carbonyl)amino)pyridin-4-yloxy)-1H-1-indolecarboxamide Similarly to Example 41, the title compound was obtained as colorless crystals (109 mg, 0.242 mmol) from 4-hydroxy-4-methylpiperidine monohydrochloride (221 mg, 1.46 mmol, Production example 8-3) and a mixture (200 mg, intermediates in Example 68) of phenyl N-(4-(1-cyclopropylaminocarbonyl-1H-5-indolyloxy)-2-pyridyl)-N-(phenoxycarbonyl)carbamate and phenyl N-(4-(1-cyclopropylaminocarbonyl-1H-5-indolyloxy)-2-pyridyl)carbamate.

$^1$H-NMR Spectrum (DMSO-$d_6$) δ (ppm): 0.61 (2H, m), 0.73 (2H, m), 1.08 (3H, s), 1.30–1.41 (4H, m), 2.76 (1H, m), 3.14 (2H, m), 3.63 (2H, m), 4.27 (1H, s), 6.53 (1H, d, J=5.4 Hz), 6.65 (1H, d, J=3.4 Hz), 7.03 (1H, d, J=8.8 Hz), 7.32 (1H, s), 7.35 (1H, s), 7.86 (1H, d. J=3.4 Hz), 8.06 (1H, d, J=5.4 Hz), 8.27 (2H, m), 9.04 (1H, s).

Example 87

N4-(4-(1-(Cyclopropylamino)carbonyl)-1H-5-indolyl)oxy-2-pyridyl)-4-morpholinecarboxamide N,N-Dimethylformamide (5 ml) and morpholine (0.373 ml, 4.28 mmol) were added to a mixture (470 mg) of phenyl N-(4-(1-cyclopropylaminocarbonyl-1H-5-indolyl)oxy-2-pyridyl)carbamate and phenyl N-(4-(1-cyclopropylaminocarbonyl-1H-5-indolyl)oxy-2-pyridyl)-N-(phenoxycarbonyl)carbamate obtained in Example 68; and the reaction mixture was stirred overnight; the reaction mixture was partitioned between ethyl acetate and water; the organic layer was concentrated; and the obtained solid was washed with a solvent mixture of hexane:diethyl ether=1:1 to yield the title compound (255 mg, 0.58 mmol, 95%).

MS Spectrum (ESI): 422 (M+1), 843 (2M+1).

$^1$H-NMR Spectrum (DMSO-$d_6$) δ (ppm): 0.58–0.75 (4H, m), 2.72–2.81 (1H, m), 3.26–3.40 (4H, m), 3.50 (4H, t, J=4.8 Hz), 6.56 (1H, dd, J=2.5, 5.6 Hz), 6.65 (1H, d, J=3.4 Hz), 7.04 (1H, dd. J=2.5, 8.8 Hz), 7.30 (1H, d, J=2.5 Hz), 7.36 (1H, d, J=2.5 Hz), 7.86 (1H, d, J=3.4 Hz), 8.08 (1H, d, J=5.5 Hz), 8.24–8.30 (2H, m), 9.18 (1H, s).

Example 88

N1-Cyclopropyl-5-(2-((pyrrolidin-1-ylcarbonyl)amino)-4-pyridyl)oxy-1H-1-indolecarboxamide N,N-Dimethylformamide (5 ml) and pyrrolidine (0.35 ml, 4.2 mmol) were added to a mixture (470 mg) of phenyl N-(4-(1-cyclopropylaminocarbonyl-1H-5-indolyl)oxy-2-pyridyl)carbamate and phenyl N-(4-(1-cyclopropylaminocarbonyl-1H-5-indolyl)oxy-2-pyridyl)-N-(phenoxycarbonyl)carbamate obtained in Example 68; the reaction mixture was stirred overnight; the reaction mixture was partitioned between ethyl acetate and water; and the organic layer was concentrated to yield the title compound as white crystals (200 mg, 0.49 mmol).

MS Spectrum (ESI): 406 (M+1), 811 (2M+1).

$^1$H-NMR Spectrum (DMSO-$d_6$) δ (ppm): 0.58–0.78 (4H, m), 1.70–1.83 (4H, m), 2.73–2.81 (1H, m), 3.23–3.45 (4H, m), 6.55 (1H, dd, J=2.2, 5.7 Hz), 6.65 (1H, d, J=3.5 Hz), 7.03 (1H, dd, J=2.2, 8.7 Hz), 7.36 (1H, d, J=2.2 Hz), 7.41 (1H, d, J=2.2 Hz), 7.86 (1H, d, J=3.5 Hz), 8.06 (1H, d, J=5.7 Hz), 8.16–8.30 (2H, m), 8.59 (1H, s).

Example 89

N1-Cyclopropyl-5-(2-(piperidin-1-ylcarbonyl)amino-4-pyridyl)oxy-1H-1-indolecarboxamide N,N-Dimethylformamide (5 ml) and piperidine (0.42 ml, 4.2 mmol) were added to a mixture (467 mg) of phenyl N-(4-(1-cyclopropylaminocarbonyl-1H-5-indolyl)oxy-2-pyridyl)carbamate and phenyl N-(4-(1-cyclopropylaminocarbonyl-1H-5-indolyl)oxy-2-pyridyl)-N-(phenoxycarbonyl)carbamate obtained in Example 68; and the reaction mixture was stirred overnight; the reaction mixture was partitioned between ethyl acetate and water; the organic layer was concentrated; the obtained solid was washed with a solvent mixture of hexane:diethyl ether=1:1 to yield the title compound as crystals (241 mg, 0.57 mmol).

MS Spectrum (ESI): 420 (M+1), 839 (2M+1).

$^1$H-NMR Spectrum (DMSO-$d_6$) δ (ppm): 0.58–0.77 (4H, m), 1.34–1.55 (6H, m), 2.72–2.81 (1H, m), 3.27–3.40 (4H, m), 6.52 (1H, dd, J=2.6, 5.6 Hz), 6.64 (1H, d, J=3.6 Hz), 7.03 (1H, dd, J=2.6, 8.7 Hz), 7.30 (1H, d, J=2.6 Hz), 7.35 (1H, d, J=2.6 Hz), 7.87 (1H, d, J=3.6 Hz), 8.06 (1H, d, J=5.6 Hz), 8.23–8.30 (2H, m), 9.03 (1H, s).

Example 90

N4-(4-(1-(Cyclopentylamino)carbonyl-1H-5-indolyl)oxy-2-pyridyl)-4-morpholinecarboxamide Phenyl N-(4-(1-cyclopentylaminocarbonyl-1H-indol-5-yloxy)-2-pyridyl)-N-(phenoxycarbonyl)carbamate (200 mg, 0.35 mmol) was dissolved in N,N-dimethylformamide (1.5 ml) and morpholine (0.15 ml, 1.73 mmol); and the reaction mixture was stirred at room temperature overnight. The reaction mixture was partitioned between ethyl acetate and water; and the organic layer was washed with brine, dried over anhydrous magnesium sulfate, and concentrated under reduced pressure. The residue was purified by silica gel column chromatography (Fuji Silysia BW-300; ethyl acetate, ethyl acetate:methanol=10:1 in this order); the obtained colorless oil was crystallized by addition of diethyl ether; and the crystals were filtered off, washed with diethyl ether, and dried under aeration to yield the title compound as colorless crystals (140 mg, 0.31 mmol, 90%).

$^1$H-NMR Spectrum (DMSO-d$_6$) δ (ppm): 1.48–1.64 (4H, m), 1.66–1.76 (2H, m), 1.88–1.98 (2H, m), 3.35 (4H, m), 3.51 (4H, m), 4.14 (1H, m), 6.56 (1H, d, J=6.0 Hz), 6.65 (1H, d, J=3.6 Hz), 7.02 (1H, d, J=8.8 Hz), 7.30 (1H, s), 7.35 (1H, s), 7.96 (1H, d, J=3.6 Hz), 8.00 (1H, d, J=6.8 Hz), 8.08 (1H, d, J=6.0 Hz), 8.25 (1H, d, J=8.8 Hz), 9.18 (1H, s).

The starting materials were synthesized as follows.

Production Example 90-1

Phenyl N-cyclopentylcarbamate

Cyclopentylamine (9.9 ml, 100 mmol) was dissolved in tetrahydrofuran (400 ml); pyridine (8.9 ml, 110 mmol) was added thereto; and the reaction mixture was stirred. The reaction mixture was cooled with ice; phenyl chloroformate (13.8 ml, 110 mmol) was added dropwise for 5 minutes while stirring; and the reaction mixture was stirred at room temperature for 24.5 hours. The reaction mixture was partitioned between ethyl acetate and water; and the organic layer was washed with brine, dried over anhydrous sodium sulfate, and concentrated under reduced pressure. The obtained crystals were suspended in a solvent mixture of hexane:ethyl acetate=5:1, filtered off, washed with hexane, and dried under aeration to yield the title compound as colorless crystals (16.6 g, 81 mmol, 81%).

$^1$H-NMR Spectrum (DMSO-d$_6$) δ (ppm): 1.47 (4H, m), 1.63 (2H, m), 1.81 (2H, m), 3.81 (1H, m), 7.07 (2H, d, J=7.6 Hz), 7.17 (1H, t, J=7.6 Hz), 7.35 (2H, t, J=7.6 Hz), 7.75 (1H, d, J=6.8 Hz).

Production Example 90-2

N1-Cyclopentyl-5-(2-aminopyridin-4-yloxy)-1H-1-indolecarboxamide 4-(1H-5-Indolyloxy)-2-pyridinamine (2.50 g, 11.1 mmol, CAS No. 417722-11-3), which was described in WO 02/32872, was dissolved in N,N-dimethylformamide (30 ml); sodium hydride (0.530 g, 13.3 mmol) was added thereto at room temperature; and the reaction mixture was stirred for 30 minutes. Phenyl N-cyclopentylcarbamate (2.50 g, 12.2 mmol) was added thereto at room temperature while stirring; and the reaction mixture was stirred for 30 minutes. Water was added to the reaction mixture; and the precipitated crystals were filtered off, and washed with water. This crystals were dissolved in methanol, and purified by silica gel column chromatography (Fuji Silysia NH; hexane:ethyl acetate=1:1, ethyl acetate, ethyl acetate:methanol=98:2 in this order). The obtained crystals were suspended in hexane:ethanol=10:1, filtered off, washed with hexane, and dried under aeration to yield the title compound as colorless crystals (2.08 g, 6.18 mmol, 55.7%).

$^1$H-NMR Spectrum (DMSO-d$_6$) δ (ppm): 1.56 (4H, m), 1.71 (2H, m), 1.92 (2H, m), 4.14 (1H, m), 5.74 (1H, d, J=2.0 Hz), 5.83 (2H, s), 6.12 (1H, dd, J=2.0, 5.6 Hz), 6.64 (1H, d, J=3.4 Hz), 7.00 (1H, dd, J=2.0, 8.8 Hz), 7.32 (1H, d, J=2.0 Hz), 7.75 (1H, d, J=5.6 Hz), 7.94 (1H, d, J=3.4 Hz), 7.97 (1H, d, J=6.4 Hz), 8.23 (1H, d, J=8.8 Hz).

Production Example 90-3

Phenyl N-(4-(1-cyclopentylaminocarbonyl-1H-indol-5-yloxy)-2-pyridyl)-N-(phenoxycarbonyl)carbamate N1-Cyclopentyl-5-(2-aminopyridin-4-yloxy)-1H-1-indolecarboxamide (1.55 g, 4.58 mmol) was dissolved in tetrahydrofuran (90 ml); triethylamine (1.43 ml, 10.31 mmol) and pyridine (0.56 ml, 6.88 mmol) were added thereto; and the reaction mixture was stirred. The reaction mixture was cooled with ice; phenyl chloroformate (1.44 ml, 11.45 mmol) was added dropwise; and the reaction mixture was stirred at room temperature for 2.5 hours. The reaction mixture was partitioned between ethyl acetate and water; and the organic layer was washed with brine, dried over anhydrous sodium sulfate, and concentrated under reduced pressure. The residue was purified by silica gel column chromatography (Fuji Silysia BW-300; hexane:ethyl acetate=1:1, 1:3 in this order) to yield the title compound as a colorless amorphous solid (2.516 g, 4.36 mmol, 95.2%).

$^1$H-NMR Spectrum (DMSO-d$_6$) δ (ppm): 1.50–1.63 (4H, m), 1.66–1.74 (2H, m), 1.88–1.98 (2H, m), 4.15 (1H, m), 6.65 (1H, d, J=3.8 Hz), 6.95 (1H, dd, J=2.4, 5.6 Hz), 7.09 (1H, dd, J=2.4, 8.8 Hz), 7.16 (4H, d, J=7.6 Hz), 7.29 (2H, d, J=7.6 Hz), 7.42 (4H, d, J=7.6 Hz), 7.44 (1H, d, J=2.4 Hz), 7.51 (1H, d, J=2.4 Hz), 7.98 (1H, d, J=3.8 Hz), 8.01 (1H, d, J=6.8 Hz), 8.28 (1H, d, J=8.8 Hz), 8.42 (1H, d, J=5.6 Hz).

Example 91

5-(2-(((4-Hydroxypiperidin-1-yl)carbonyl)amino) pyridin-4-yloxy)-1H-indole-1-carboxylic acid cyclopentylamide Similarly to Example 90, the title compound was obtained as colorless crystals (129 mg, 0.278 mmol, 80.2%) from phenyl N-(4-(1-cyclopentylaminocarbonyl-1H-indol-5-yloxy)-2-pyridyl)-N-(phenoxycarbonyl)carbamate (200 mg, 0.346 mmol, Production example 90-3) and 4-hydroxypiperidine (175 mg, 1.73 mmol).

$^1$H-NMR Spectrum (DMSO-d$_6$) δ (ppm): 1.23 (2H, m), 1.48–1.77 (8H, m), 1.92 (2H, m), 2.98 (2H, m), 3.59 (1H, m), 3.73 (2H, m), 4.15 (1H, m), 4.64 (1H, d, J=4.4 Hz), 6.53 (1H, dd, J=2.0, 5.6 Hz), 6.65 (1H, d, J=3.6 Hz), 7.02 (1H, dd, J=2.0, 9.0 Hz), 7.31 (1H, d, J=2.0 Hz), 7.35 (1H, d, J=2.0 Hz), 7.96 (1H, d, J=3.6 Hz), 7.99 (1H, d, J=6.8 Hz), 8.06 (1H, d, J=5.6 Hz), 8.24 (1H, d, J=9.0 Hz), 9.09 (1H, s).

Example 92

N1-Cyclopentyl-5-(2-((4-(pyrrolidin-1-yl)piperidin-1-ylcarbonyl)amino)pyridin-4-yloxy)-1H-1-indolecarboxamide Similarly to Example 90, the title compound was obtained as colorless crystals (83 mg, 0.161 mmol, 46.3%) from phenyl N-(4-(1-cyclopentylaminocarbonyl-1H-indol-5-yloxy)-2-pyridyl)-N-(phenoxycarbonyl)carbamate (200 mg, 0.346 mmol, Production example 90-3) and 4-(1-pyrrolidinyl)piperidine (268 mg, 1.73 mmol).

$^1$H-NMR Spectrum (DMSO-d$_6$) δ (ppm): 1.18–1.30 (2H, m), 1.50–1.80 (12H, m), 1.87–1.98 (2H, m), 2.08 (1H, m), 2.43 (4H, m), 2.81 (2H, m), 3.91 (2H, m), 4.15 (1H, m), 6.53 (1H, dd, J=2.0, 5.6 Hz), 6.65 (1H, d, J=3.6 Hz), 7.02 (1H, dd, J=2.0, 9.0 Hz), 7.31 (1H, d, J=2.0 Hz), 7.35 (1H, d, J=2.0

Hz), 7.96 (1H, d, J=3.6 Hz), 7.99 (1H, d, J=6.8 Hz), 8.06 (1H, d, J=5.6 Hz), 8.25 (1H, d, J=9.0 Hz), 9.08 (1H, s).

Example 93

N1-(3-Methylbutyl)-5-(2-(((4-(pyrrolidin-1-yl)piperidin-1-yl)carbonyl)amino)pyridin-4-yloxy)-1H-1-indolecarboxamide N,N-dimethylformamide (30 ml), pyridine (0.52 ml, 6.4 mmol) and triethylamine (1.35 ml, 9.69 mmol) were added to N1-(3-methylbutyl)-5-((2-amino-4-pyridyl)oxy)-1H-1-indolecarboxamide (1.45 g, 4.29 mmol); phenyl chloroformate (0.81 ml, 6.4 mmol) was added at 0° C. while stirring; and the reaction mixture was stirred at room temperature for 1 hour. The reaction mixture was partitioned between ethyl acetate and water; and the organic layer was concentrated and subjected to silica gel column chromatography to yield a mixture (2.0 g) of phenyl N-(4-(1-((3-methylbutyl)amino)carbonyl-1H-5-indolyl)oxy-2-pyridyl)carbamate and phenyl N-(4-(1-((3-methylbutyl)amino)carbonyl-1H-5-indolyl)oxy-2-pyridyl)-N-(phenoxycarbonyl)carbamate. A portion of 0.4 g of the mixture was dissolved in N,N-dimethylformamide (4 ml); 4-tetrahydro-1H-1-pyrrolylpiperidine (0.43 g, 2.8 mmol) was added thereto; and the reaction mixture was stirred for 2 hours. The reaction mixture was partitioned between ethyl acetate and water; the organic layer was concentrated; and the residue was purified by silica gel column chromatography (Fuji Silysia NH, ethyl acetate:methanol=10:1) to yield the title compound as white crystals (275 mg, 0.53 mmol).

MS Spectrum (ESI): 519 (M+1).

$^1$H-NMR Spectrum (DMSO-d$_6$) δ (ppm): 0.91 (6H, d, J=7.6 Hz), 1.18–1.30 (3H, m), 1.47 (2H, q, J=7.6 Hz), 1.57–1.80 (6H, m), 2.03–2.22 (1H, m), 2.37–2.48 (4H, m), 2.76–2.85 (2H, m), 3.25–3.36 (2H, m), 3.88–3.97 (2H, m), 6.53 (1H, dd, J=2.4, 5.4 Hz), 6.66 (1H, d, J=3.6 Hz), 7.02 (1H, dd, J=2.4, 8.7 Hz), 7.31 (1H, d, J=2.4 Hz), 7.35 (1H, d, J=2.4 Hz), 7.90 (1H, d, J=3.6 Hz), 8.06 (1H, d, J=5.4 Hz), 8.16 (1H, t, J=5.4 Hz), 8.27 (1H, d, J=8.7 Hz), 9.08 (1H, s).

The starting materials were synthesized as follows.

Production Example 93-1

N1-(3-Methylbutyl)-5-((2-amino-4-pyridyl)oxy)-1H-1-indolecarboxamide 4-(1H-5-Indolyloxy)-2-pyridinamine (2.0 g, 8.9 mmol, CAS No. 417722-11-3) which was described in WO 02/32872 was dissolved in N,N-dimethylformamide (20 ml); and sodium hydride (426 mg, 10.7 mmol) was added thereto at room temperature while stirring. The reaction mixture was cooled with ice bath after 30 minutes; phenyl N-(3-methylbutyl)carbamate (2.02 g, 9.75 mmol) was added thereto; and the reaction mixture was stirred for 3 hours at room temperature. The reaction mixture was partitioned between ethyl acetate and water; the organic layer was washed with water and brine, dried over anhydrous sodium sulfate, and concentrated; and the residue was purified by NH-silica gel column chromatography (hexane:ethyl acetate=3:1) to yield the title compound as crystals (1.45 g, 4.3 mmol, 48%).

$^1$H-NMR Spectrum (DMSO-d$_6$) δ (ppm): 0.89–0.93 (6H, m), 1.40–1.70 (3H, m), 3.25–3.40 (2H, m), 5.72–5.75 (1H, m), 5.83 (2H, s), 6.10–6.40 (1H, m), 6.64–6.68 (1H, m), 6.98–7.02 (1H, m), 7.30–7.34 (1H, m), 7.75 (1H, dd, J=1.5, 6.0 Hz), 7.86–7.90 (1H, m), 8.14 (1H, t, J=4.5 Hz), 8.25 (1H, d, J=9.0 Hz).

Production Example 93-2

Phenyl N-(3-methylbutyl)carbamate

Phenyl chloroformate (14.8 ml, 0.117 mol) was dissolved in tetrahydrofuran (200 ml); triethylamine (18.0 ml, 0.129 mol) and isoamylamine (15.0 ml, 0.129 mol) were added thereto at room temperature while stirring; and the reaction mixture was stirred overnight. The reaction mixture was partitioned between ethyl acetate and water; and the organic layer was concentrated and dried under reduced pressure to yield the title compound as crystals (14 g, 0.068 mol, 58%).

$^1$H-NMR Spectrum (DMSO-d$_6$) δ (ppm): 0.89 (6H, d, J=7.9 Hz), 1.36 (2H, q, J=7.9 Hz), 1.55–1.69 (1H, m), 3.05 (2H, q, J=7.9 Hz), 7.03–7.09 (2H, m), 7.14–7.19 (1H, m), 7.31–7.38 (2H, m), 7.68 (1H, t, J=4.8 Hz).

Example 94

N1-(3-Methylbutyl)-5-(2-((4-hydroxypiperidino)carbonyl)amino-4-pyridyl)oxy-1H-1-indolecarboxamide N,N-dimethylformamide (2.5 ml) and 4-hydroxypiperidine (213 mg, 2.11 mmol) were added to a mixture (243 mg) of phenyl N-(4-(1-((3-methylbutyl)amino)carbonyl-1H-5-indolyl)oxy-2-pyridyl)-carbamate and phenyl N-(4-(1-((3-methylbutyl)amino)carbonyl-1H-5-indolyl)oxy-2-pyridyl)-N-(phenoxycarbonyl)carbamate synthesized in Example 93; and the reaction mixture was stirred for 2 hours. The reaction mixture was partitioned between ethyl acetate and water; the organic layer was concentrated; and the residue was purified by NH-silica gel column chromatography (ethyl acetate:methanol=10:1) to yield the title compound as white crystals (150 mg, 0.322 mmol).

$^1$H-NMR Spectrum (DMSO-d$_6$) δ (ppm): 0.91 (6H, d, J=7.2 Hz), 1.18–1.30 (2H, m), 1.46 (2H, q, J=7.2 Hz), 1.60–1.70 (3H, m), 2.97 (2H, m), 3.25–3.35 (2H, m), 3.55–3.64 (1H, m), 3.69–3.80 (2H, m), 4.63 (1H, d, J=3.4 Hz), 6.53 (1H, dd, J=2.3, 5.8 Hz), 6.66 (1H, d, J=3.5 Hz), 7.02 (1H, dd, J=2.3, 8.6 Hz), 7.31 (1H, d, J=2.3 Hz), 7.35 (1H, d, J=2.3 Hz), 7.90 (1H, d, J=3.5 Hz), 8.06 (1H, d, J=5.8 Hz), 8.16 (1H, t, J=5.8 Hz), 8.26 (1H, t, J=8.6 Hz), 9.08 (1H, s).

Example 95

N4-(4-(1-((3-Methylbutyl)amino)carbonyl-1H-5-indolyl)oxy-2-pyridyl)-4-morpholinecarboxamide N,N-dimethylformamide (5 ml) and morpholine (0.163 ml, 1.87 mmol) were added to a mixture (0.6 g) of phenyl N-(4-(1-((3-methylbutyl)amino)carbonyl-1H-5-indolyl)oxy-2-pyridyl)carbamate and phenyl N-(4-(1-((3-methylbutyl)amino)carbonyl-1H-5-indolyl)oxy-2-pyridyl)-N-(phenoxycarbonyl)carbamate synthesized in Example 93; and the reaction mixture was stirred for 2 hours. The reaction mixture was partitioned between ethyl acetate and water; the organic layer was concentrated; and the residue was purified by silica gel column chromatography (Fuji Silysia NH, ethyl acetate:methanol=10:1) to yield the title compound as white crystals (0.202 g, 0.447 mmol).

$^1$H-NMR Spectrum (DMSO-d$_6$) δ (ppm): 0.92 (6H, dd, J=1.7, 7.3 Hz), 1.47 (2H, q, J=7.3 Hz), 1.58–1.70 (1H, m), 3.25–3.60 (10H, m), 6.55–6.59 (1H, m), 6.65–6.70 (1H, m), 7.00–7.07 (1H, m), 7.32 (1H, s), 7.37 (1H, m), 7.90 (1H, m), 8.07 (1H, m), 8.17 (1H, t, J=5.2 Hz), 8.27 (1H, d, J=8.3 Hz), 9.18 (1H, s).

Example 96

N1-(1-Ethylpropyl)-5-(2-(((4-(pyrrolidin-1-yl)piperidin-1-yl)carbonyl)amino)pyridin-4-yloxy)-1H-1-indolecarboxamide Tetrahydrofuran (20 ml) and triethylamine (1.73 ml, 12.4 mmol) were added to N1-(1-ethylpropyl)-5-(2-amino-4-pyridyl)oxy-1H-1-indolecarboxamide (1.45 g, 4.29 mmol); phenyl chloroformate (1.15 ml, 9.1 mmol) was added thereto at 0° C. while stirring; and the reaction mixture was stirred at room temperature for 1 hour. The reaction mixture was partitioned between ethyl acetate and water; and the organic layer was concentrated and subjected to silica gel column chromatography to yield a mixture (1.8 g) of phenyl N-(4-(1-((1-ethylpropyl)amino)carbonyl-1H-5-indolyl)oxy-2-pyridyl)carbamate and phenyl N-(4-(1-((1-ethylpropyl)amino)carbonyl-1H-5-indolyl)-oxy-2-pyridyl)-N-(phenoxycarbonyl)carbamate. A portion of 0.6 g of the mixture was dissolved in N,N-dimethylformamide (5 ml); 4-tetrahydro-1H-1-pyrrolylpiperidine (0.7 g, 4.7 mmol) and stirred for 2 hours; the reaction mixture was partitioned between ethyl acetate and water; the organic layer was concentrated; and the residue was purified by silica gel column chromatography (Fuji Silysia NH, ethyl acetate:methanol=10:1) to yield as white crystals (202 mg, 0.391 mmol).

MS Spectrum (ESI): 519 (M+1).

$^1$H-NMR Spectrum (DMSO-$d_6$) δ (ppm): 0.90 (6H, t, J=7.5 Hz), 1.20–1.30 (3H, m), 1.47–1.80 (9H, m), 2.03–2.12 (1H, m), 2.40–2.47 (4H, m), 2.77–2.86 (2H, m), 3.62–3.72 (1H, m), 3.88–3.95 (2H, m), 6.53 (1H, dd, J=2.4, 5.9 Hz), 6.66 (1H, d, J=3.5 Hz), 7.02 (1H, dd, J=2.4, 8.8 Hz), 7.11 (1H, d, J=2.4 Hz), 7.35 (1H, d, J=2.4 Hz), 7.78 (1H, d, J=8.8 Hz), 7.99 (1H, d, J=3.5 Hz), 8.06 (1H, d, J=5.9 Hz), 8.25 (1H, t, J=8.8 Hz), 9.08 (1H, s).

The starting materials were synthesized by following methods.

Production Example 96-1

N1-(1-Ethylpropyl)-5-(2-amino-4-pyridyl)oxy-1H-1-indolecarboxamide 4-(1H-5-Indolyloxy)-2-pyridinamine (1.85 g, 8.2 mmol, CAS No. 417722-11-3) which was described in WO 02/32872 was dissolved in N,N-dimethylformamide (20 ml); and sodium hydride (394 mg, 9.84 mmol) was added thereto while stirring at room temperature. The reaction mixture was cooled with ice bath after 30 minutes; phenyl N-(1-ethylpropyl)carbamate (1.87 g, 9.03 mmol); and the reaction mixture was stirred at room temperature for 3 hours. The reaction mixture was partitioned between ethyl acetate and water; the organic layer was washed with water and brine, dried over anhydrous sodium sulfate, concentrated; and the residue was purified by silica gel column chromatography (Fuji Silysia NH, hexane:ethyl acetate=3:1) to yield the title compound as crystals (1.95 g, 5.8 mmol, 71%).

$^1$H-NMR Spectrum (DMSO-$d_6$) δ (ppm): 0.89 (6H, t, J=7.5 Hz), 1.44–1.63 (4H, m), 3.60–3.72 (1H, m), 5.73 (1H, d, J=2.6 Hz), 5.80 (2H, s), 6.12 (1H, dd, J=2.6, 6.0 Hz), 6.67 (1H, d, J=4.3 Hz), 7.00 (1H, dd, J=2.6, 8.6 Hz), 7.32 (1H, d, J=2.6 Hz), 7.75 (1H, d, J=6.0 Hz), 7.98 (1H, d, J=4.3 Hz), 8.23 (1H, d, J=8.6 Hz), 9.30 (1H, s).

Production Example 96-2

Phenyl N-(1-ethylpropyl)carbamate

1-Ethylpropylamine (11.6 ml, 100 mmol) was dissolved in tetrahydrofuran (400 ml); pyridine (8.9 ml, 110 mmol) was added thereto at room temperature; and the reaction mixture was stirred. The reaction mixture was cooled with ice bath; phenyl chloroformate (13.8 ml, 110 mmol) was added dropwise; and the reaction mixture was stirred at room temperature for 24 hours. Water was added to the reaction mixture; the reaction mixture was partitioned between ethyl acetate and water; and the organic layer was washed with brine, dried over anhydrous sodium sulfate, and the solvent was distilled off under reduced pressure. The obtained crystals were washed with diethyl ether:hexane=1:5 to yield the title compound as crystals (22.3 g, 147 mmol, 59.1%).

$^1$H-NMR Spectrum (DMSO-$d_6$) δ (ppm): 0.87 (6H, t, J=7.5 Hz), 1.30–1.56 (4H, m), 3.20–3.34 (1H, m), 7.03–7.08 (2H, m), 7.14–7.19 (1H, m), 7.32–7.38 (2H, m), 7.51 (1H, d, J=8.7 Hz).

Example 97

N1-(1-Ethylpropyl)-5-(2-((4-hydroxypiperidino)carbonyl)amino-4-pyridyl)oxy-1H-1-indolecarboxamide N,N-Dimethylformamide (4 ml) and 4-hydroxypiperidine (360 mg, 3.56 mmol) were added to a mixture (456 mg) of phenyl N-(4-(1-((1-ethylpropyl)amino)carbonyl-1H-5-indolyl)oxy-2-pyridyl)-carbamate and phenyl N-(4-(1-((1-ethylpropyl)amino)carbonyl-1H-5-indolyl)oxy-2-pyridyl)-N-(phenoxycarbonyl)carbamate synthesized in Example 96; and the reaction mixture was stirred for 2 hours. The reaction mixture was partitioned between ethyl acetate and water; the organic layer was concentrated; and the residue was purified by silica gel column chromatography (Fuji Silysia NH, ethyl acetate:methanol=10:1) to yield the title compound as white crystals (1.37 mg, 0.294 mmol).

$^1$H-NMR Spectrum (DMSO-$d_6$) δ (ppm): 0.90 (6H, t, J=7.5 Hz), 1.18–1.30 (3H, m), 1.45–1.70 (6H, m), 2.92–3.02 (2H, m), 3.55–3.80 (3H, m), 4.63 (1H, d, J=5.1 Hz), 6.53 (1H, m), 6.66 (1H, d, J=3.5 Hz), 7.02 (1H, dd, J=2.5, 8.8 Hz), 7.31 (1H, d, J=2.5 Hz), 7.36 (1H, d, J=2.5 Hz), 7.78 (1H, d, J=8.8 Hz), 7.98 (1H, d, J=3.5 Hz), 8.06 (1H, d, J=5.7 Hz), 8.24 (1H, t, J=8.8 Hz), 9.08 (1H, s).

Example 98

N4-(4-(1-((1-Ethylpropyl)amino)carbonyl-1H-5-indolyl)oxy-2-pyridyl)-4-morpholinecarboxamide N,N-dimethylformamide (3 ml) and morpholine (0.22 ml, 2.5 mmol) were added to a mixture (0.324 g) of phenyl N-(4-(1-((1-ethylpropyl)amino)carbonyl-1H-5-indolyl)oxy-2-pyridyl)carbamate and phenyl N-(4-(1-((1-ethylpropyl)amino)carbonyl-1H-5-indolyl)oxy-2-pyridyl)-N-(phenoxycarbonyl)carbamate synthesized in Example 96; and the reaction mixture was stirred for 2 hours. The reaction mixture was partitioned between ethyl acetate and water; the organic layer was concentrated; and the residue was purified by silica gel column chromatography (Fuji Silysia NH, ethyl acetate:methanol=10:1) to yield the title compound as white crystals (95 mg, 0.21 mmol).

¹H-NMR Spectrum (DMSO-d₆) δ (ppm): 0.91 (6H, t, J=7.5 Hz), 1.45–1.65 (4H, m), 3.37–3.40 (4H, m), 3.48–3.58 (4H, m), 3.62–3.72 (1H, m), 6.56 (1H, dd, J=2.6, 5.8 Hz), 6.68 (1H, d, J=3.5 Hz), 7.02 (1H, dd, J=2.6, 8.8 Hz), 7.31 (1H, d, J=2.6 Hz), 7.36 (1H, d, J=2.6 Hz), 7.80 (1H, d, J=9.1 Hz), 8.00 (1H, d, J=3.5 Hz), 8.08 (1H, d, J=5.8 Hz), 8.26 (1H, d, J=8.8 Hz), 9.18 (1H, s).

Example 99

N4-(4-(1-((1-Pentyl)amino)carbonyl-1H-5-indolyl)oxy-2-pyridyl)-4-morpholinecarboxamide Similarly to Example 90, the title compound was obtained as colorless crystals (131 mg, 0.29 mmol, 84%) from phenyl N-(4-(1-(1-pentylamino)carbonyl-1H-indol-5-yloxy)-2-pyridyl)-N-(phenoxycarbonyl)carbamate (200 mg, 0.35 mmol) and morpholine (0.15 ml, 1.7 mmol).

¹H-NMR Spectrum (DMSO-d₆) δ (ppm): 0.88 (3H, t, J=6.0 Hz), 1.31 (4H, m), 1.56 (2H, m), 3.26 (2H, m), 3.35 (4H, m), 3.51 (4H, m), 6.56 (1H, d, J=5.6 Hz), 6.67 (1H, d, J=3.0 Hz), 7.03 (1H, d, J=8.0 Hz), 7.31 (1H, s), 7.36 (1H, s), 7.91 (1H, d, J=3.0 Hz), 8.08 (1H, d, J=5.6 Hz), 8.20 (1H, t, J=5.6 Hz), 8.26 (1H, d, J=8.0 Hz), 9.18 (1H, s).

The starting materials were synthesized by following procedures.

Production Example 99-1

Phenyl N-(1-pentyl)carbamate

Similarly to Example 90-1, the title compound was obtained as pale yellow crystals (20.5 g, 99 mmol, 99%) from 1-pentylamine (11.6 ml, 100 mmol), pyridine (8.9 ml, 110 mmol) and phenyl chloroformate (13.8 ml, 110 mmol).

¹H-NMR Spectrum (CDCl₃) δ (ppm): 0.92 (3H, t, J=6.8 Hz), 1.36 (4H, m), 1.58 (2H, m), 3.26 (2H, q, J=6.8 Hz), 5.00 (1H, brs), 7.13 (2H, d, J=7.6 Hz), 7.19 (1H, t, J=7.6 Hz), 7.35 (2H, t, J=7.6 Hz).

Production Example 99-2

N1-(1-Pentyl)-5-(2-aminopyridin-4-yloxy)-1H-1-indolecarboxamide 4-(1H-5-Indolyloxy)-2-pyridinamine (5.0 g, 22 mmol, CAS No. 417722-11-3) which was described in WO 02/32872 was dissolved in N,N-dimethylformamide (60 ml); sodium hydride (1.06 g, 27 mmol) was added thereto at room temperature; and the reaction mixture was stirred for 30 minutes. Phenyl N-n-pentylcarbamate (5.06 g, 24 mmol) while stirring at room temperature; and the reaction mixture was stirred for 30 minutes. The reaction mixture was partitioned between water and ethyl acetate (insoluble portions were perfectly dissolved by adding a small amount of methanol); and the organic layer was washed with brine, dried over anhydrous sodium sulfate, concentrated under reduced pressure. The residue was purified by silica gel column chromatography (Fuji Silysia NH; hexane:ethyl acetate=1:1, ethyl acetate, ethyl acetate:methanol=95:5 in this order). The obtained crystals were suspended in hexane:ethanol=10:1, filtered off, washed with hexane, and dried under aeration to yield the title compound as colorless crystals (1.55 g, 4.58 mmol, 21%).

¹H-NMR Spectrum (DMSO-d₆) δ (ppm): 0.87 (3H, t, J=6.6 Hz), 1.31 (4H m), 1.56 (2H, m), 3.25 (2H, m), 5.74 (1H, d, J=2.8 Hz), 5.83 (2H, s), 6.12 (1H, dd, J=2.8, 5.8 Hz), 6.65 (1H, d, J=3.6 Hz), 7.00 (1H, dd, J=2.0, 8.8 Hz), 7.32 (1H, d, J=2.0 Hz), 7.75 (1H, d, J=5.8 Hz), 7.89 (1H, d, J=3.6 Hz), 8.17 (1H, t, J=5.4 Hz), 8.25 (1H, d, J=8.8 Hz).

Production Example 99-3

Phenyl N-(4-((1-pentyl)aminocarbonyl-1H-indol-5-yloxy)-2-pyridyl)-N-(phenoxycarbonyl)carbamate Similarly to Example 90-3, the title compound was obtained as a colorless amorphous solid (2.39 g, 4.13 mmol, 90.1%) from N1-(1-pentyl)-5-(2-aminopyridin-4-yloxy)-1H-1-indolecarboxamide (1.55 g, 4.58 mmol), triethylamine (1.43 ml, 10.31 mmol), pyridine (0.56 ml, 6.88 mmol), and phenyl chloroformate (1.44 ml, 11.45 mmol).

¹H-NMR Spectrum (DMSO-d₆) δ (ppm): 0.87 (3H, t, J=6.4 Hz), 1.31 (4H, m), 1.56 (2H, m), 3.27 (2H, m), 6.56 (1H, d, J=3.6 Hz), 6.96 (1H, dd, J=2.4, 5.4 Hz), 7.09 (1H, dd, J=2.4, 9.0 Hz), 7.16 (4H, d, J=7.6 Hz), 7.29 (2H, t, J=7.6 Hz), 7.43 (5H, m), 7.51 (1H, d, J=2.4 Hz), 7.93 (1H, d, J=2.4 Hz), 8.21 (1H, t, J=5.6 Hz), 8.31 (1H, d, J=9.0 Hz), 8.42 (1H, d, J=5.4 Hz).

Example 100

N1-(1-Pentyl)-5-(2-(((4-hydroxypiperidin-1-yl)carbonyl)amino)pyridin-4-yloxy)-1H-1-indolecarboxamide Similarly to Example 90, the title compound was obtained as colorless crystals (149 mg, 0.320 mmol, 92.6%) from phenyl N-(4-(1-(1-pentyl)aminocarbonyl-1H-indol-5-yloxy)-2-pyridyl)-N-(phenoxycarbonyl)carbamate (200 mg, 0.346 mmol, Production example 99-3) and 4-hydroxypiperidine (174 mg, 1.73 mmol).

¹H-NMR Spectrum (DMSO-d₆) δ (ppm): 0.87 (3H, m), 1.15–1.40 (6H, m), 1.50–1.70 (4H, m), 2.98 (2H, m), 3.36 (2H, m), 3.59 (1H, m), 3.74 (2H, m), 4.64 (1H, d, J=4.0 Hz), 6.53 (1H, d, J=5.2 Hz), 6.70 (1H, d, J=3.6 Hz), 7.03 (1H, d, J=8.6 Hz), 7.31 (1H, s), 7.35 (1H, s), 7.91 (1H, d, J=3.6 Hz), 8.06 (1H, d, J=5.2 Hz), 8.19 (1H, m), 8.26 (1H, d, J=8.6 Hz), 9.09 (1H, s).

Example 101

N1-(1-Pentyl)-5-(2-((4-(pyrrolidin-1-yl)piperidin-1-ylcarbonyl)amino)pyridin-4-yloxy)-1H-1-indolecarboxamide Similarly to Example 90, the title compound was obtained as colorless crystals (124 mg, 0.239 mmol, 69.2%) from phenyl N-(4-(1-(1-pentyl)aminocarbonyl-1H-indol-5-yloxy)-2-pyridyl)-N-(phenoxycarbonyl)carbamate (200 mg, 0.346 mmol, Production example 99-3) and 4-(1-pyrrolidinyl)piperidine (267 mg, 1.73 mmol).

¹H-NMR Spectrum (DMSO-d₆) δ (ppm): 0.87 (3H, t, J=6.8 Hz), 1.20–1.35 (6H, m), 1.52–1.67 (6H, m), 1.74 (2H, m), 2.08 (1H, m), 2.43 (2H, m), 2.81 (2H, t, J=7.6 Hz), 3.23–3.29 (4H, m), 3.92 (2H, m), 6.53 (1H, dd, J=2.4, 5.6 Hz), 6.67 (1H, d, J=3.8 Hz), 7.03 (1H, dd, J=2.4, 9.2 Hz), 7.31 (1H, d, J=2.4 Hz), 7.35 (1H, d, J=2.4 Hz), 7.91 (1H, t, J=3.8 Hz), 8.06 (1H, d, J=5.6 Hz), 8.19 (1H, d, J=5.4 Hz), 8.26 (1H, d, J=9.2 Hz), 9.09 (1H, s).

Example 102

N1-Methyl-3-chloro-5-(2-(((3-(diethylamino)propyl) amino)carbonyl)amino-4-pyridyl)oxy-1H-1-indolecarboxamide Phenyl N-(4-(3-chloro-1-(methylamino)carbonyl-1H-5-indolyl)oxy-2-pyridyl)carbamate (160 mg), 3-(diethylamino)propylamine (120 mg), N,N-dimethylformamide (5 ml) were mixed together and stirred at room temperature for 10 minutes. After the addition of aqueous sodium hydrogencarbonate, extraction was performed with ethyl acetate. The purification by silica gel column chromatography (Fuji Silysia NH, ethyl acetate and sequentially ethyl acetate: methanol=10:1) to yield the title compound as a white solid (86 mg).

$^1$H-NMR Spectrum (DMSO-$d_6$) δ (ppm): 0.90 (6H, t, J=7.2 Hz), 1.46–1.56 (2H, m), 2.32–2.46 (6H, m), 2.83 (3H, d, J=4.4 Hz), 3.08–3.15 (2H, m), 6.52 (1H, dd, J=5.6, 2.4 Hz), 6.84 (1H, d, J=2.4 Hz), 7.16 (1H, dd, J=8.8, 2.4 Hz), 7.28 (1H, d, J=2.4 Hz), 8.02 (1H, d, J=5.6 Hz), 8.09 (2H, s), 8.21 (1H, q, J=4.4 Hz), 8.33 (1H, d, J=8.8 Hz), 9.04 (1H, s).

The starting materials were synthesized as follows.

Production Example 102-1

N1-Methyl-5-(2-amino-4-pyridyl)oxy-3-chloro-1H-indolecarboxamide 5-((2-amino-4-pyridyl)oxy)-3-chloro-1H-1-indole (4.0 g, 15 mmol, CAS No. 417721-98-3) which was described in WO 02/32872 was dissolved in N,N-dimethylformamide (20 ml); sodium hydride (0.68 g, 60% in oil) and phenyl N-methylcarbamate (2.6 g, the product of Production example 2-1) were added thereto; and the reaction mixture was stirred at room temperature for 1 hour. The reaction mixture was partitioned between ethyl acetate and water; and the organic layer was concentrated under reduced pressure. The residue was purified by silica gel column chromatography (Fuji Silysia NH, hexane:ethyl acetate=1:2) to yield the title compound as a colorless amorphous solid (1.5 g).

$^1$H-NMR Spectrum (DMSO-$d_6$) δ (ppm): 2.83 (3H, d, J=4.0 Hz), 5.78 (1H, d, J=2.0 Hz), 5.88 (2H, brs), 6.14 (1H, dd, J=2.0, 5.8 Hz), 7.14 (1H, dd, J=2.4, 9.0 Hz), 7.23 (1H, d, J=2.4 Hz), 7.78 (1H, d, J=5.8 Hz), 8.08 (1H, s), 8.19 (1H, m), 8.32 (1H, d, J=9.0 Hz).

Production Example 102-2

Phenyl N-(4-(3-chloro-1-(methylamino)carbonyl-1H-5-indolyl)oxy-2-pyridyl)carbamate While a mixture of N1-methyl-5-(2-amino-4-pyridyl)oxy-3-chloro-1H-1-indolecarboxamide (850 mg, Production example 102-1), triethylamine (0.37 ml), pyridine (320 mg) and N,N-dimethylformamide (10 ml) was cooled with ice and sodium chloride, phenyl chloroformate (630 mg) was added dropwise to the mixture. Aqueous solution of sodium hydrogencarbonate was added thereto after stirring for 20 minutes; extraction was performed with ethyl acetate; and purification was performed by silica gel column chromatography (ethyl acetate). The crystals precipitated by adding ethyl acetate to the residue were filtered off to yield the title compound as white crystals (160 mg).

$^1$H-NMR Spectrum (DMSO-$d_6$) δ (ppm): 2.80 (3H, d, J=4.4 Hz), 6.70 (1H, dd, J=5.6, 2.4 Hz), 7.10–7.25 (4H, m), 7.26–7.40 (4H, m), 8.07 (1H, s), 8.18 (2H, m), 8.31 (1H, d, J=8.8 Hz), 10.77 (1H, s).

Example 103

N1-Methyl-3-chloro-5-(2-((4-tetrahydro-1H-1-pyrrolylpiperidino)carbonyl)amino-4-pyridyl)oxy-1H-1-indolecarboxamide A mixture of N1-methyl-5-(2-amino-4-pyridyl)oxy-3-chloro-1H-1-indolecarboxamide (278 mg, Production example 102-1), triethylamine (0.37 ml), tetrahydrofuran (5 ml) was ice-cooled and stirred; phenyl chloroformate (0.33 ml) was added dropwise to the mixture; and the reaction mixture was further stirred for 10 minutes. Water was added thereto; extraction was performed with ethyl acetate; and purification by silica gel column chromatography was performed to yield a 373 mg of residue. A portion of 245 mg of the residue was dissolved in N,N-dimethylformamide (2 ml); 4-(1-pyrrolidinyl)piperidine (345 mg) was added thereto; and the reaction mixture was stirred at room temperature for 30 minutes. Extraction was performed with ethyl acetate after the addition of water; and the organic layer was washed with water and brine, dried over anhydrous sodium sulfate, and concentrated under reduced pressure. The residue was purified by silica gel column chromatography (Fuji Silysia NH) to yield the title compound (154 mg).

$^1$H-NMR Spectrum (DMSO-$d_6$) δ (ppm): 1.19–1.30 (2H, m), 1.58–1.68 (4H, m), 1.70–1.78 (2H, m), 2.03–2.13 (1H, m), 2.36–2.46 (4H, m), 2.77–2.87 (5H, m), 3.88–3.97 (2H, m), 6.55 (1H, d, J=5.6 Hz), 7.16 (1H, dd. J=9.2, 2.4 Hz), 7.27 (1H, d, J=2.4 Hz), 7.32 (1H, s), 8.08 (1H, d, J=5.6 Hz), 8.10 (1H, s), 8.19–8.22 (1H, m), 8.33 (1H, d, J=9.2 Hz), 9.13 (1H, brs).

Example 104

N1-Methyl-3-chloro-5-(2-((4-hydroxypiperidino) carbonyl)amino-4-pyridyl)oxy-1H-1-indolecarboxamide A mixture of N1-methyl-5-(2-amino-4-pyridyl)oxy-3-chloro-1H-1-indolecarboxamide (480 mg, Production example 102-1), triethylamine (0.63 ml), tetrahydrofuran (15 ml) was ice-cooled and stirred; phenyl chloroformate (710 mg) was added dropwise to the mixture; and the reaction mixture was further stirred for 10 minutes. Extraction was performed with ethyl acetate after addition of water; and purification was performed by silica gel column chromatography (hexane:ethyl acetate=1:1). The obtained residue was dissolved in N,N-dimethylformamide (5 ml); 4-hydroxypiperidine (450 mg) was added thereto; and the reaction mixture was stirred at room temperature overnight. Water was added to the reaction mixture; extraction was performed with ethyl acetate; and purification was performed by silica gel column chromatography (Fuji Silysia NH, ethyl acetate:methanol=40:1) to yield the title compound as colorless powder (78 mg).

$^1$H-NMR Spectrum (DMSO-$d_6$) δ (ppm): 1.20–1.30 (2H, m), 1.61–1.79 (2H, m), 2.82 (3H, d, J=4.4 Hz), 2.94–3.03 (2H, m), 3.56–3 63 (1H, m), 3.70–3.78 (2H, m), 4.64 (1H, d, J=4.0 Hz), 6.55 (1H, dd, J=5.6, 2.4 Hz), 7,16 (1H, dd, J=8.8, 2.4 Hz), 7.27 (1H, d, J=2.4 Hz), 7.32 (1H, d, J=2.4

Hz), 8.08 (1H, d, J=5.6 Hz), 8.09 (1H, s), 8.21 (1H, q, J=4.4 Hz), 8.32 (1H, d, J=8.8 Hz), 9.13 (1H, s).

Example 105

N1-Methyl-3-chloro-5-(2-(((3-(4-hydroxypiperidino)propyl)amino)carbonyl)amino-4-pyridyl)oxy-1H-1-indolecarboxamide Similarly to Example 103, the title compound was obtained as white crystals from 1-(3-aminopropyl)-4-hydroxypiperidine.

$^1$H-NMR Spectrum (DMSO-d$_6$) δ (ppm): 1.25–1.38 (2H, m), 1.48–1.58 (2H, m), 1.62–1.70 (2H, m), 1.86–1.97 (2H, m), 2.18–2.25 (2H, m), 2.60–2.68 (2H, m), 2.83 (3H, d, J=3.6 Hz), 3.02–3.13 (2H, m), 3.34–3.42 (1H, m), 4.49 (1H, d, J=4.0 Hz), 6.52 (1H, dd, J=6.0, 2.4 Hz), 6.84–6.86 (1H, m), 7.17 (1H, dd, J=8.8, 2.4 Hz), 7.28 (1H, d, J=2.4 Hz), 8.01–8.05 (2H, m), 8.10 (1H, s), 8.19–8.24 (1H, m), 8.33 (1H, d, J=8.8 Hz), 9.04 (1H, brs).

The starting materials were synthesized as follows.

Production Example 105-1

2-(3-(4-Hydroxypiperidino)propyl)isoindolin-1,3-dione

N-(3-bromopropyl)phthalimide (26.8 g), 4-hydroxypiperidine (15.0 g) and potassium carbonate (27.6 g) were added to N,N-dimethylformamide; and the reaction mixture was stirred at room temperature overnight. After the addition of water, extraction was performed with ethyl acetate; the organic layer was washed with water and brine, dried over anhydrous sodium sulfate, and concentrated under reduced pressure to yield the title compound (13.9 g).

$^1$H-NMR Spectrum (CDCl$_3$) δ (ppm): 1.40–2.05 (6H, m), 2.10–2.60 (4H, m), 2.70–2.90 (2H, m), 3.60–3.85 (3H, m), 7.70–7.75 (2H, m), 7.82–7.87 (2H, m).

Production Example 105-2

Benzyl N-(3-(4-hydroxypiperidino)propyl)carbamate

Ethanol (100 ml) and hydrazine hydrate (1.5 g) were added to hydroxypiperidino)propyl)isoindolin-1,3-dione (4.5 g); the reaction mixture was heated to reflux for 2.5 hours; and the produced crystals were filtered off. N-Methylmorpholine (2.5 ml) and N-(benzyloxycarbonyloxy)succinimide (5.2 g) were added to the filtrate; and the reaction mixture was stirred at room temperature overnight. Aqueous solution of sodium hydrogencarbonate was added to the reaction mixture; extraction was performed with ethyl acetate; and the organic layer was washed with water and brine, dried over anhydrous sodium sulfate, and concentrated under reduced pressure. The residue was purified by silica gel column chromatography to yield the title compound (2.96 g).

$^1$H-NMR Spectrum (CDCl$_3$) δ (ppm): 1.52–2.10 (6H, m), 2.10–2.60 (4H, m), 2.78–2.90 (2H, m), 3.24–3.33 (2H, m), 3.53–3.86 (1H, m), 5.09 (2H, s), 5.88–5.96 (1H, m), 7.28–7.38 (5H, m).

Production Example 105-3

1-(3-Aminopropyl)-4-hydroxypiperidine

Ethanol (200 ml) and palladium carbon (2.5 g) were added to benzyl N-(3-(4-hydroxypiperidino)propyl)carbamate (2.96 g); and the reaction mixture was stirred vigorously under hydrogen atmosphere overnight. Palladium carbon was removed by filtration, and the filtrate was concentrated to yield the title compound (1.5 g).

$^1$H-NMR Spectrum (DMSO-d$_6$) δ (ppm): 1.25–1.38 (2H, m), 1.41–1.49 (2H, m), 1.61–1.69 (2H, m), 1.84–1.95 (2H, m), 2.18–2.25 (2H, m), 2.49–2.57 (2H, m), 2.58–2.69 (2H, m), 3.30-3.42 (1H, m).

Example 106

N1-Methyl-3-chloro-5-(2-((4-(2-hydroxyethyl)piperazino)carbonyl)amino-4-pyridyl)oxy-1H-1-indolecarboxamide Similarly to Example 104, the title compound was obtained from 4-(2-hydroxyethyl)piperazine.

$^1$H-NMR Spectrum (DMSO-d$_6$) δ (ppm): 2.30–2.48 (6H, m), 2.82 (3H, d, J=4.4 Hz), 3.30–3.40 (4H, m), 3.46 (2H, q, J=5.6 Hz), 4.38 (1H, t, J=5.6 Hz), 6.57 (1H, dd, J=5.6, 2.4 Hz), 7.16 (1H, dd, J=8.8, 2.4 Hz), 7.29 (1H, d, J=2.4 Hz), 7.32 (1H, d, J=2.4 Hz), 8.07–8.13 (2H, m), 8.21 (1H, q, J=4.4 Hz), 8.32 (1H, d, J=8.8 Hz), 9.15 (1H, s).

Example 107

N4-(4-(3-Chloro-1-(methylamino)carbonyl-1H-5-indolyl)oxy-2-pyridyl)-4-morpholinecarboxamide Similarly to Example 104, the title compound was obtained from morpholine.

$^1$H-NMR Spectrum (DMSO-d$_6$) δ (ppm): 2.82 (3H, d, J=4.4 Hz), 3.33–3.40 (4H, m), 3.49–3.56 (4H, m), 6.58 (1H, dd, J=5.6, 2.4 Hz), 7.16 (1H, dd, J=8.8, 2.4 Hz), 7.27 (1H, d, J=2.4 Hz), 7.32 (1H, d, J=2.4 Hz), 8.06–8.13 (2H, m), 8.21 (1H, q, J=4.4 Hz), 8.32 (1H, d, J=8.8 Hz), 9.22 (1H, s).

Example 108

N1-Methyl-3-chloro-5-(2-((4-ethylpiperazino)carbonyl)amino-4-pyridyl)oxy-1H-1-indolecarboxamide Similarly to Example 103, the title compound was obtained from N-ethylpiperazine.

$^1$H-NMR Spectrum (DMSO-d$_6$) δ (ppm): 0.96 (3H, t, J=7.2 Hz), 2.24–2.32 (6H, m), 2.82 (3H, d, J=4.0 Hz), 3.34–3.39 (4H, m), 6.57 (1H, dd, J=6.0, 2.4 Hz), 7.17 (1H, dd, J=9.2, 2.4 Hz), 7.27 (1H, d, J=2.4 Hz), 7.32 (1H, d, J=2.4 Hz), 8.07–8.10 (2H, m), 8.18–8.25 (1H, m), 8.33 (1H, d, J=9.2 Hz), 9.17 (1H, brs).

Example 109

N1-Ethyl-3-chloro-5-(2-((4-hydroxypiperidino)carbonyl)amino-4-pyridyl)oxy-1H-1-indolecarboxamide Similarly to Example 104, the title compound was obtained as a colorless amorphous solid from N1-ethyl-5-(2-amino-4-pyridyl)oxy-3-chloro-1H-1-indolecarboxamide.

¹H-NMR Spectrum (DMSO-d₆) δ (ppm): 1.15 (2H, m), 1.61 (3H, t, J=7.2 Hz), 1.60–1.70 (2H, m), 2.94–3.02 (2H, m), 3.26–3.36 (2H, m), 3.56–3.63 (1H, m), 3.70–3.78 (2H, m), 4.64 (1H, d, J=4.4 Hz), 6.55 (1H, dd, J=5.6, 2.4 Hz), 7.16 (1H, dd, J=8.8, 2.4 Hz), 7.27 (1H, d, J=2.4 Hz), 7.32 (1H, d, J=2.4 Hz), 8.08 (1H, d, J=5.6 Hz), 8.13 (1H, s), 8.22–8.27 (1H, m), 8.32 (1H, d, J=8.8 Hz), 9.12 (1H, s).

The starting material was synthesized as follows.

Production Example 109-1

N1-Ethyl-5-(2-amino-4-pyridyl)oxy-3-chloro-1H-1-indolecarboxamide

Phenyl N-ethylcarbamate was added to a solution of 5-(2-amino-4-pyridyl)oxy-3-chloro-1H-1-indole (1.35 g, CAS No. 417721-98-3) which was described in WO 02/32872, sodium hydride (210 mg) and N,N-dimethylformamide; and the reaction mixture was stirred for 1 hour. An aqueous solution of ammonium chloride was added to the reaction mixture; extraction was performed with ethyl acetate; and purification by silica gel column chromatography (Fuji Silysia NH, hexane:ethyl acetate=1:2) to yield the title compound as a colorless oil (1.07 g).

¹H-NMR Spectrum (DMSO-d₆) δ (ppm): 1.15 (3H, t, J=7.2 Hz), 3.25–3.35 (2H, m), 5.76 (1H, d, J=2.4 Hz), 5.87 (2H, s), 6.14 (1H, dd, J=5.6, 2.4 Hz), 7.13 (1H, dd, J=8.8, 2.4 Hz), 7.23 (1H, d, J=2.4 Hz), 7.77 (1H, d, J=5.6 Hz), 8.11 (1H, s), 8.20–8.25 (1H, m), 8.31 (1H, d, J=8.8 Hz).

Example 110

N1-Ethyl-3-chloro-5-(2-(((3-(4-hydroxypiperidino)propyl)amino)carbonyl)amino-4-pyridyl)oxy-1H-1-indolecarboxamide Similarly to Example 103, the title compound was obtained as white crystals from N1-ethyl-5-(2-amino-4-pyridyl)oxy-3-chloro-1H-1-indolecarboxamide and 1-(3-aminopropyl)-4-hydroxypiperidine.

¹H-NMR Spectrum (DMSO-d₆) δ (ppm): 1.16 (3H, t, J=7.2 Hz), 1.26–1.38 (2H, m), 1.48–1.57 (2H, m), 1.63–1.70 (2H, m), 1.86–1.97 (2H, m), 2.18–2.25 (2H, m), 2.60–2.68 (2H, m), 3.05–3.13 (2H, m), 3.26–3.34 (2H, m), 3.34–3.42 (1H, m), 4.49 (1H, d, J=4.0 Hz), 6.52 (1H, dd, J=6.0, 2.4 Hz), 6.84–6.86 (1H, m), 7.16 (1H, dd, J=8.8, 2.4 Hz), 7.28 (1H, d, J=2.4 Hz), 7.98–8.05 (2H, m), 8.14 (1H, s), 8.22–8.28 (1H, m), 8.33 (1H, d, J=8.8 Hz), 9.03 (1H, brs).

Example 111

N1-Ethyl-3-chloro-5-(2-(((3-(diethylamino)propyl)amino)carbonyl)amino-4-pyridyl)oxy-1H-1-indolecarboxamide Similarly to Example 104, the title compound was obtained from N1-ethyl-5-(2-amino-4-pyridyl)oxy-3-chloro-1H-1-indolecarboxamide and 3-(diethylamino)propylamine.

¹H-NMR Spectrum (DMSO-d₆) δ (ppm): 0.90 (6H, t, J=7.2 Hz), 1.16 (3H, t, J=7.2 Hz), 1.46–1.54 (2H, m), 2.33–2.44 (6H, m), 3.07–3.14 (2H, m), 3.26–3.34 (2H, m), 6.52 (1H, dd, J=5.6, 2.4 Hz), 6.83 (1H, s), 7.16 (1H, dd, J=8.8, 2.4 Hz), 7.28 (1H, d, J=2.4 Hz), 8.02 (1H, d, J=5.6 Hz), 8.04–8.13 (1H, brs), 8.14 (1H, s), 8.23–8.27 (1H, m), 8.33 (1H, d, J=8.8 Hz), 9.04 (1H, s).

Example 112

N1,3-Dimethyl-5-(2-((4-hydroxypiperidino)carbonyl)amino-4-pyridyl)oxy-1H-1-indolecarboxamide Similarly to Example 104, the title compound was obtained as a colorless amorphous solid from N1,3-dimethyl-5-(2-amino-4-pyridyl)oxy-1H-1-indolecarboxamide.

¹H-NMR Spectrum (DMSO-d₆) δ (ppm): 1.17–1.30 (2H, m), 1.61–1.70 (2H, m), 2.19 (3H, s), 2.80 (3H, d, J=4.0 Hz), 2.94–3.03 (2H, m), 3.56–3.64 (1H, m), 3.70–3.78 (2H, m), 4.64 (1H, d, J=4.0 Hz), 6.52 (1H, dd, J=5.6, 2.4 Hz), 7.02 (1H, dd, J=8.8, 2.4 Hz), 7.29–7.33 (2H, m), 7.66 (1H, s), 8.00 (1H, q, J=4.0 Hz), 8.05 (1H, d, J=5.6 Hz), 8.25 (1H, d, J=8.8 Hz), 9.08 (1H, s).

The starting materials were synthesized as follows.

Production Example 112-1

4-(3-Methyl-1H-5-indolyl)oxy-2-pyridinamine

A mixture of 5-hydroxy-3-methylindole (4.7 g), 2-amino-4-chloropyridine (4.1 g), sodium hydride (1.3 g), and dimethyl sulfoxide (40 ml) was stirred at 160° C. for 15 hours. Water was added thereto; extraction was performed with ethyl acetate; and purification was performed by silica gel column chromatography (ethyl acetate, sequentially, ethyl acetate:methanol=20:1). The solvent was distilled off to yield the title compound as a brown solid (1.6 g).

¹H-NMR Spectrum (DMSO-d₆) δ (ppm): 2.29 (3H, s), 5.70 (1H, d, J=2.4 Hz), 5.77 (2H, s), 6.10 (1H, dd, J=5.6, 2.4 Hz), 6.80 (1H, dd, J=8.8, 2.4 Hz), 7.15 (1H, s), 7.17 (1H, d, J=2.4 Hz), 7.35 (1H, d, J=8.8 Hz), 7.72 (1H, d, J=5.6 Hz), 10.83 (1H, s).

Production Example 112-2

N1,3-Dimethyl-5-(2-amino-4-pyridyl)oxy-1H-1-indolecarboxamide

Phenyl N-methylcarbamate (350 mg, Production example 2-1) was added to a solution of 4-(3-methyl-1H-5-indolyl)oxy-2-pyridinamine (500 mg), sodium hydride (93 mg) and N,N-dimethylformamide (5 ml) at room temperature; and the reaction mixture was stirred for 2 hours and 45 minutes. Water was added to the reaction mixture; extraction was performed with ethyl acetate; and purification was performed by NH-silica gel column chromatography (Fuji Silysia, hexane:ethyl acetate=1:2, sequentially, ethyl acetate) to yield the title compound as a pale yellow amorphous solid (365 mg).

¹H-NMR Spectrum (DMSO-d₆) δ (ppm): 2.19 (3H, s), 2.80 (3H, d, J=4.0 Hz), 5.73 (1H, d, J=2.4 Hz), 5.83 (2H, s), 6.12 (1H, dd, J=5.6, 2.4 Hz), 7.00 (1H, dd, J=8.8, 2.4 Hz), 7.27 (1H, d, J=2.4 Hz), 7.64 (1H, s), 7.75 (1H, d, J=5.6 Hz), 7.98 (1H, q, J=4.0 Hz), 8.24 (1H, d, J=8.8 Hz).

Example 113

N1,3-Dimethyl-5-(2-((4-tetrahydro-1H-pyrrolylpiperidino)carbonyl)amino-4-pyridyl)oxy-1H-1-indolecarboxamide Similarly to Example 104, the title compound was obtained as a colorless amorphous solid from N1,3-dimethyl-5-(2-amino-4-pyridyl)oxy-1H-1-indolecarboxamide and 4-(1-pyrrolidinyl)piperidine.

¹H-NMR Spectrum (DMSO-d₆) δ (ppm): 1.17–1.79 (2H, m), 1.60–1.67 (4H, m), 1.70–1.79 (2H, m), 2.03–2.13 (1H, m), 2.19 (3H, s), 2.40–2.57 (4H, m), 2.77–2.86 (5H, m), 3.88–3.96 (2H, m), 6.52 (1H, dd, J=5.6, 2.4 Hz), 7.02 (1H, dd, J=8.8, 2.4 Hz), 7.28–7.85 (2H, m), 7.66 (1H, s), 8.00 (1H, q, J=4.0 Hz), 8.05 (1H, d, J=5.6 Hz), 8.25 (1H, d, J=8.8 Hz), 9.08 (1H, s).

Example 114

N1-Cyclopropyl-5-(2-((4-hydroxypiperidino)carbonyl)amino-4-pyridyl)oxy-3-methyl-1H-1-indolecarboxamide Similarly to Example 104, the title compound was obtained as a colorless amorphous solid from N1-cyclopropyl-5-(2-amino-4-pyridyl)oxy-3-methyl-1H-1-indolecarboxamide.

¹H-NMR Spectrum (DMSO-d₆) δ (ppm): 0.56–0.60 (2H, m), 2.67–2.73 (2H, m), 1.19–1.29 (2H, m), 1.61–1.70 (2H, m), 2.18 (3H, s), 2.72–2.78 (1H, m), 2.94–3.03 (2H, m), 3.56–3.63 (1H, m), 3.70–3.77 (2H, m), 4.64 (1H, d, J=4.0 Hz), 6.51 (1H, dd, J=5.6, 2.4 Hz), 7.02 (1H, dd, J=8.8, 2.4 Hz), 7.28–7.32 (2H, m), 7.65 (1H, s), 8.05 (1H, d, J=5.6 Hz), 8.11 (1H, d, J=2.4 Hz), 8.24 (1H, d, J=8.8 Hz), 9.08 (1H, s).

The starting material was synthesized as follows.

Production Example 114-1

N1-Cyclopropyl-5-(2-amino-4-pyridyl)oxy-3-methyl-1H-1-indolecarboxamide

Similarly to Production example 112-2, the title compound was obtained as a colorless amorphous solid from phenyl N-cyclopropylcarbamate.

¹H-NMR Spectrum (DMSO-d₆) δ (ppm): 0.55–0.60 (2H, m), 0.68–0.73 (2H, m), 2.18 (3H, s), 2.70–2.79 (1H, m), 5.73 (1H, d, J=2.4 Hz), 5.83 (2H, s), 6.12 (1H, dd, J=5.6, 2.4 Hz), 7.00 (1H, dd, J=8.8, 2.4 Hz), 7.26 (1H, d, J=2.4 Hz), 7.63 (1H, s), 7.75 (1H, d, J=5.6 Hz), 8.09 (1H, d, J=2.4 Hz), 8.23 (1H, d, J=8.8 Hz).

Example 115

N1-Cyclopropyl-5-(2-((4-(2-hydroxyethyl)piperazino)carbonyl)amino-4-pyridyl)oxy-3-methyl-1H-1-indolecarboxamide Similarly to Example 104, the title compound was obtained as a colorless amorphous solid from N1-cyclopropyl-5-(2-amino-4-pyridyl)oxy-3-methyl-1H-1-indolecarboxamide and 1-(2-hydroxyethyl)piperazine.

¹H-NMR Spectrum (DMSO-d₆) δ (ppm): 0.57–0.60 (2H, m), 0.67–0.74 (2H, m), 2.18 (3H, s), 2.30–2.37 (6H, m), 2.70–2.78 (1H, m), 3.30–3.38 (4H, m), 3.46 (2H, q, J=6.4 Hz), 4.38 (1H, t, J=6.4 Hz), 6.53 (1H, dd, J=5.6, 2.4 Hz), 7.02 (1H, dd, J=8.8, 2.4 Hz), 7.28–7.32 (2H, m), 7.65 (1H, s), 8.06 (1H, d, J=5.6 Hz), 8.11 (1H, d, J=2.4 Hz), 8.24 (1H, d, J=8.8 Hz), 9.10 (1H, s).

Example 116

N1-Methyl-5-(2-((methylamino)carbonyl)amino-4-pyridyl)oxy-1H-1-indolecarboxamide Similarly to Example 5, the title compound was obtained as white crystals (19.5 mg, 0.058 mmol, 58%) from phenyl N-(4-(1-(methylamino)carbonyl-1H-indol-5-yloxy)-pyridin-2-yl)-N-(phenoxycarbonyl)carbamate (52 mg, 0.1 mmol) synthesized in Production example 5-2 and 40% methylamine in methanol.

¹H-NMR Spectrum (DMSO-d₆) δ (ppm): 2.64 (3H, d, J=4.4 Hz), 2.83 (3H, d, J=4.4 Hz), 6.50 (1H, dd, J=2.4, 5.6 Hz), 6.67 (1H, d, J=3.6 Hz), 6.82 (1H, d, J=2.4 Hz), 7.04 (1H, dd, J=2.4, 8.8 Hz), 7.36 (1H, d, J=2.4 Hz), 7.87 (1H, d, J=3.6 Hz), 7.95 (1H, m), 8.02 (1H, d, J=5.6 Hz), 8.16 (1H, m), 8.28 (1H, d, J=8.8 Hz), 9.07 (1H, s).

Example 117

N1-Methyl-5-(2-((ethylamino)carbonyl)amino-4-pyridyl)oxy-1H-1-indolecarboxamide

Similarly to Example 5, the title compound was obtained as white crystals (15.0 mg, 0.042 mmol, 42%) from phenyl N-(4-(1-(methylamino)carbonyl-1H-indol-5-yloxy)-pyridin-2-yl)-N-(phenoxycarbonyl)carbamate (52 mg, 0.1 mmol) synthesized in Production example 5-2 and 2.0 M ethylamine in tetrahydrofuran.

¹H-NMR Spectrum (DMSO-d₆) δ (ppm): 1.02 (3H, t, J=7.2 Hz), 2.83 (3H, d, J=4.0 Hz), 3.10 (2H, m), 6.50 (1H, dd, J=2.4, 5.6 Hz), 6.67 (1H, d, J=3.6 Hz), 6.86 (1H, d, J=2.4 Hz), 7.03 (1H, dd, J=2.4, 8.8 Hz), 7.36 (1H, d, J=2.4 Hz), 7.87 (1H, d, J=3.6 Hz), 7.96 (1H, m), 8.02 (1H, d, J=5.6 Hz), 8.17 (1H, m), 8.28 (1H, d, J=8.8 Hz), 8.99 (1H, s).

Example 118

N1-Methyl-5-(2-((cyclopropylamino)carbonyl)amino-4-pyridyl)oxy-1H-1-indolecarboxamide Similarly to Example 5, the title compound was obtained as white crystals from phenyl N-(4-(1-(methylamino)carbonyl-1H-indol-5-yloxy)-pyridin-2-yl)-N-(phenoxycarbonyl)carbamate (52 mg, 0.1 mmol) synthesized in Production example 5-2 and cyclopropylamine.

¹H-NMR Spectrum (CDCl₃) δ (ppm): 0.58–0.62 (2H, m), 0.71–0.79 (2H, m), 2.70 (1H, m), 3.07 (3H, d, J=4.8 Hz), 5.64 (1H, m), 6.26 (1H, m), 6.41 (1H, m), 6.58 (1H, d, J=3.6 Hz), 7.03 (1H, dd, J=2.4, 8.8 Hz), 7.20–7.30 (2H, m), 7.42–7.53 (2H, m), 7.90 (1H, d, J=5.6 Hz), 8.19 (1H, d, J=8.8 Hz).

Example 119

N1-Methyl-5-(2-((diethylamino)carbonyl)amino-4-pyridyl)oxy-1H-1-indolecarboxamide Similarly to Example 5, the title compound was obtained as white crystals (24.7 mg, 0.065 mmol, 65%) from phenyl N-(4-(1-(methylamino)carbonyl-1H-indol-5-yloxy)-pyridin-2-yl)-N-(phenoxycarbonyl)carbamate (52 mg, 0.1 mmol) synthesized in Production example 5-2 and diethylamine.

¹H-NMR Spectrum (DMSO-d₆) δ (ppm): 1.01 (6H, t, J=7.2 Hz), 2.82 (3H, d, J=4.4 Hz), 3.20–3.50 (4H, m), 6.54 (1H, dd, J=2.4, 5.6 Hz), 6.67 (1H, d, J=3.6 Hz), 7.04 (1H, dd, J=2.4, 8.8 Hz), 7.36 (1H, d, J=2.4 Hz), 7.40 (1H, d, J=2.4 Hz), 7.78 (1H, d, J=3.6 Hz), 8.06 (1H, d, J=5.6 Hz), 8.16 (1H, m), 8.28 (1H, d, J=8.8 Hz), 8.59 (1H, s).

Example 120

N1-Methyl-5-(2-((1-propylamino)carbonyl)amino-4-pyridyl)oxy-1H-1-indolecarboxamide Similarly to Example 5, the title compound (28.0 mg, 0.076 mmol, 76%) was obtained as white crystals from phenyl N-(4-(1-(methylamino)carbonyl-1H-indol-5-yloxy)-pyridin-2-yl)-N-(phenoxycarbonyl)carbamate (52 mg, 0.1 mmol) synthesized in Production example 5-2 and 1-propylamine.

$^1$H-NMR Spectrum (DMSO-d$_6$) δ (ppm): 0.83 (3H, t, J=7.2 Hz), 1.40 (2H, m), 2.83 (3H, d, J=4.4 Hz), 3.04 (2H, m), 6.49 (1H, dd, J=2.4, 5.6 Hz), 6.67 (1H, d, J=3.6 Hz), 6.86 (1H, s), 7.04 (1H, dd, J=2.4, 8.8 Hz), 7.36 (1H, d, J=2.4 Hz), 7.87 (1H, d, J=3.6 Hz), 8.01–8.03 (2H, m), 8.16 (1H, m), 8.28 (1H, d, J=8.8 Hz), 9.00 (1H, s).

Example 121

N1-Methyl-5-(2-((2-propylamino)carbonyl)amino-4-pyridyl)oxy-1H-1-indolecarboxamide Similarly to Example 5, the title compound (20.7 mg, 0.056 mmol, 56%) was obtained as white crystals from phenyl N-(4-(1-(methylamino)carbonyl-1H-indol-5-yloxy)-pyridin-2-yl)-N-(phenoxycarbonyl)carbamate (52 mg, 0.1 mmol) synthesized in Production example 5-2 and 2-propylamine.

$^1$H-NMR Spectrum (DMSO-d$_6$) δ (ppm): 1.06 (6H, d, J=6.8 Hz), 2.83 (3H, d, J=4.4 Hz), 3.74 (1H, m), 6.49 (1H, dd, J=2.4, 5.6 Hz), 6.67 (1H, d, J=3.6 Hz), 6.89 (1H, d, J=2.4 Hz), 7.03 (1H, dd, J=2.4, 8.8 Hz), 7.36 (1H, d, J=2.4 Hz), 7.81 (1H, m), 7.87 (1H, d, J=3.6 Hz), 8.02 (1H, d, J=5.6 Hz), 8.16 (1H, m), 8.28 (1H, d, J=8.8 Hz), 8.90 (1H, s).

Example 122

N1-Methyl-5-(2-((cyclopentylamino)carbonyl)amino-4-pyridyl)oxy-1H-1-indolecarboxamide Similarly to Example 5, the title compound (30.7 mg, 0.078 mmol, 78%) was obtained as white crystals from phenyl N-(4-(1-(methylamino)carbonyl-1H-indol-5-yloxy)-pyridin-2-yl)-N-(phenoxycarbonyl)carbamate (52 mg, 0.1 mmol) synthesized in Production example 5-2 and cyclopentylamine.

$^1$H-NMR Spectrum (DMSO-d$_6$) δ (ppm): 1.10–1.90 (8H, m), 2.83 (3H, d, J=4.4 Hz), 3.89 (1H, m), 6.50 (1H, d, J=2.4, 5.6 Hz), 6.68 (1H, d, J=3.6 Hz), 6.90 (1H, d, J=2.4 Hz), 7.03 (1H, dd, J=2.4, 8.8 Hz), 7.36 (1H, d, J=2.4 Hz), 7.87 (1H, m), 7.93 (1H, d, J=3.6 Hz), 8.00 (1H, d, J=5.6 Hz), 8.15 (1H, m), 8.28 (1H, d, J=8.8 Hz), 8.89 (1H, s).

Example 123

N1-Methyl-5-(2-((cyclohexylamino)carbonyl)amino-4-pyridyl)oxy-1H-1-indolecarboxamide Similarly to Example 5, the title compound (32.5 mg, 0.080 mmol, 80%) was obtained as white crystals from phenyl N-(4-(1-(methylamino)carbonyl-1H-indol-5-yloxy)-pyridin-2-yl)-N-(phenoxycarbonyl)carbamate (52 mg, 0.1 mmol) synthesized in Production example 5-2 and cyclohexylamine.

$^1$H-NMR Spectrum (CDCl$_3$) δ (ppm): 1.00–2.00 (8H, m), 2.83 (3H, d, J=4.4 Hz), 3.40–3.60 (2H, m), 3.75 (1H, m), 6.11 (1H, s), 6.43 (1H, m), 6.60 (1H, d, J=3.6 Hz), 6.95 (1H, m), 7.04 (1H, m), 7.20–7.30 (2H, m), 7.44 (1H, d, J=3.6 Hz), 7.95 (1H, d, J=5.6 Hz), 8.20 (1H, d, J=8.8 Hz), 9.20 (1H, m).

Example 124

N1-Methyl-S-(2-((2-propenylamino)carbonyl)amino-4-pyridyl)oxy-1H-1-indolecarboxamide Similarly to Example 5, the title compound (18.5 mg, 0.051 mmol, 51%) was obtained as white crystals from phenyl N-(4-(1-(methylamino)carbonyl-1H-indol-5-yloxy)-pyridin-2-yl)-N-(phenoxycarbonyl)carbamate (52 mg, 0.1 mmol) synthesized in Production example 5-2 and allylamine.

$^1$H-NMR Spectrum (DMSO-d$_6$) δ (ppm): 2.85 (3H, d, J=4.8 Hz), 3.75 (2H, m), 5.06 (1H, dd, J=1.6, 10.4 Hz), 5.14 (1H, dd, J=1.6, 17.2 Hz), 5.87 (1H, m), 6.54 (1H, dd, J=2.4, 5.6 Hz), 6.69 (1H, d, J=3.6 Hz), 6.87 (1H, d, J=2.4 Hz), 7.06 (1H, dd, J=2.4, 8.8 Hz), 7.39 (1H, d, J=2.4 Hz), 7.89 (1H, d, J=3.6 Hz), 8.05 (1H, d, J=5.6 Hz), 8.16–8.19 (2H, m), 8.30 (1H, d, J=8.8 Hz), 9.13 (1H, s).

Example 125

N1-Methyl-5-(2-((2-propynylamino)carbonyl)amino-4-pyridyl)oxy-1H-1-indolecarboxamide Similarly to Example 5, the title compound (16.8 mg, 0.046 mmol, 46%) was obtained as white crystals from phenyl N-(4-(1-(methylamino)carbonyl-1H-indol-5-yloxy)-pyridin-2-yl)-N-(phenoxycarbonyl)carbamate (52 mg, 0.1 mmol) synthesized in Production example 5-2 and propargylamine.

$^1$H-NMR Spectrum (DMSO-d$_6$) δ (ppm): 2.85 (3H, d, J=4.4 Hz), 3.12 (1H, m), 3.92 (2H, m), 6.56 (1H, dd, J=2.4, 5.6 Hz), 6.70 (1H, d, J=3.6 Hz), 6.87 (1H, d, J=2.4 Hz), 7.06 (1H, dd, J=2.4, 8.8 Hz), 7.39 (1H, d, J=2.4 Hz), 7.89 (1H, d, J=3.6 Hz), 8.07 (1H, d, J=5.6 Hz), 8.18 (1H, m), 8.29–8.31 (2H, m), 9.21 (1H, s).

Example 126

N1-Methyl-5-(2-((benzylamino)carbonyl)amino-4-pyridyl)oxy-1H-1-indolecarboxamide Similarly to Example 5, the title compound (26.1 mg, 0.063 mmol, 63%) was obtained as white crystals from phenyl N-(4-(1-(methylamino)carbonyl-1H-indol-5-yloxy)-pyridin-2-yl)-N-(phenoxycarbonyl)carbamate (52 mg, 0.1 mmol) synthesized in Production example 5-2 and benzylamine.

$^1$H-NMR Spectrum (DMSO-d$_6$) δ (ppm): 2.85 (3H, d, J=4.4 Hz), 4.34 (2H, d, J=5.6 Hz), 6.53 (1H, dd, J=2.4, 5.6 Hz), 6.69 (1H, d, J=3.6 Hz), 6.90 (1H, d, J=2.4 Hz), 7.06 (1H, dd, J=2.4, 8.8 Hz), 7.20–7.35 (5H, m), 7.39 (1H, d, J=2.4 Hz), 7.89 (1H, d, J=3.6 Hz), 8.04 (1H, d, J=5.6 Hz), 8.17 (1H, m), 8.30 (1H, d, J=8.8 Hz), 8.51 (1H, m), 9.17 (1H, s).

Example 127

N1-Methyl-5-(2-((furfurylamino)carbonyl)amino-4-pyridyl)oxy-1H-1-indolecarboxamide Similarly to Example 5, the title compound (9.1 mg, 0.022 mmol, 22%) was obtained as white powder from phenyl N-(4-(1-(methylamino)carbonyl-1H-indol-5-yloxy)-pyridin-2-yl)-N-(phenoxycarbonyl)carbamate (52 mg, 0.1 mmol) synthesized in Production example 5-2 and furfurylamine.

$^1$H-NMR Spectrum (DMSO-d$_6$) δ (ppm): 2.85 (3H, d, J=4.4 Hz), 4.32 (2H, d, J=5.2 Hz), 6.24 (1H, s), 6.38 (1H, s), 6.54 (1H, m), 6.69 (1H, d, J=3.6 Hz), 6.90 (1H, s), 7.06 (1H, m), 7.39 (1H, s), 7.57 (1H, s), 7.89 (1H, d, J=2.4 Hz), 8.05 (1H, d, J=5.6 Hz), 8.18 (1H, m), 8.31 (1H, d, J=8.8 Hz), 8.38 (1H, m), 9.15 (1H, s).

Example 128

N1-Methyl-5-(2-((thiophen-2-ylmethylamino)carbonyl)amino-4-pyridyl)oxy-1H-1-indolecarboxamide Similarly to Example 5, the title compound (22.6 mg, 0.054 mmol, 54%) was obtained as white powder from phenyl N-(4-(1-(methylamino)carbonyl-1H-indol-5-yloxy)-pyridin-2-yl)-N-(phenoxycarbonyl)carbamate (52 mg, 0.1 mmol) synthesized in Production example 5-2 and 2-thiophenemethylamine.

$^1$H-NMR Spectrum (DMSO-d$_6$) δ (ppm): 2.85 (3H, d, J=4.4 Hz), 4.50 (2H, d, J=5.6 Hz), 6.54 (1H, dd, J=2.4, 5.6 Hz), 6.69 (1H, d, J=3.6 Hz), 6.88–6.98 (3H, m), 7.06 (1H, dd, J=2.4, 8.8 Hz), 7.35–7.39 (2H, m), 7.89 (1H, d, J=3.6 Hz), 8.04 (1H, d, J=5.6 Hz), 8.18 (1H, m), 8.30 (1H, d, J=8.8 Hz), 8.55 (1H, m), 9.18 (1H, s).

Example 129

N1-Ethyl-5-(2-((ethylamino)carbonyl)amino-4-pyridyl)oxy-1H-1-indolecarboxamide

Similarly to Example 27, the title compound (23.1 mg, 0.063 mmol, 63%) was obtained as white crystals from phenyl N-(4-(1-(ethylamino)carbonyl-1H-5-indolyl)oxy-2-pyridyl)carbamate (42 mg, 0.1 mmol) synthesized in Production example 27-2 and 2.0 M ethylamine in tetrahydrofuran.

$^1$H-NMR Spectrum (DMSO-d$_6$) δ (ppm): 1.04 (3H, t, J=7.2 Hz), 1.18 (3H, t, J=7.2 Hz), 3.12 (2H, m), 3.31 (2H, m), 6.52 (1H, dd, J=2.4, 5.6 Hz), 6.69 (1H, d, J=3.6 Hz), 6.88 (1H, d, J=2.4 Hz), 7.05 (1H, dd, J=2.4, 8.8 Hz), 7.38 (1H, d, J=2.4 Hz), 7.92 (1H, d, J=3.6 Hz), 7.97 (1H, m), 8.04 (1H, d, J=5.6 Hz), 8.23 (1H, m), 8.30 (1H, d, J=8.8 Hz), 9.01 (1H, s).

Example 130

N1-Ethyl-5-(2-((diethylamino)carbonyl)amino-4-pyridyl)oxy-1H-1-indolecarboxamide Similarly to Example 27, the title compound (25.8 mg, 0.065 mmol, 65%) was obtained as white crystals from phenyl N-(4-(1-(ethylamino)carbonyl-1H-5-indolyl)oxy-2-pyridyl)carbamate (42 mg, 0.1 mmol) synthesized in Production example 27-2 and diethylamine.

$^1$H-NMR Spectrum (DMSO-d$_6$) δ (ppm): 1.03 (6H, t, J=7.2 Hz), 1.19 (3H, t, J=7.2 Hz), 3.20–3.40 (6H, m), 6.55 (1H, dd, J=2.4, 5.6 Hz), 6.69 (1H, d, J=3.6 Hz), 7.05 (1H, dd, J=2.4, 8.8 Hz), 7.38 (1H, s), 7.43 (1H, d, J=2.4 Hz), 7.92 (1H, d, J=3.6 Hz), 8.08 (1H, d, J=5.6 Hz), 8.23 (1H, m), 8.30 (1H, d, J=8.8 Hz), 8.62 (1H, s).

Example 131

N1-Dimethyl-5-(2-((methylamino)carbonyl)amino-4-pyridyl)oxy-1H-1-indolecarboxamide Similarly to Example 28, the title compound (17.5 mg, 0.05 mmol, 35%) was obtained as white powder from N1-dimethyl-5-(2-amino-4-pyridyl)oxy-1H-1-indolecarboxamide (42 mg, 0.14 mmol) and 40% methylamine in methanol.

$^1$H-NMR Spectrum (DMSO-d$_6$) δ (ppm): 2.67 (3H, d, J=4.4 Hz), 3.05 (6H, s), 6.53 (1H, dd, J=2.4, 5.6 Hz), 6.67 (1H, d, J=3.6 Hz), 6.83 (1H, d, J=2.4 Hz), 7.04 (1H, dd, J=2.4, 8.8 Hz), 7.40 (1H, d, J=2.4 Hz), 7.68–7.71 (2H, m), 8.00–8.05 (2H, m), 9.10 (1H, s).

The starting materials were synthesized by the following methods.

Production Example 131-1

Phenyl N,N-dimethylcarbamate

Similarly to Production example 2-1, the title compound (6.27 g, 0.038 mol, 38%) was obtained as a colorless oil from 2.0 M diethylamine in tetrahydrofuran (50 ml, 0.1 mol), phenyl chloroformate (13.8 ml, 0.11 mol) and pyridine (8.9 ml, 0.11 mol).

$^1$H-NMR Spectrum (CDCl$_3$) δ (ppm): 3.02 (3H, s), 3.11 (3H, s), 7.09–7.39 (5H, m).

Production Example 131-2

N1-Dimethyl-5-(2-amino-4-pyridyl)oxy-1H-1-indolecarboxamide

Similarly to Production example 1-3, the title compound (128 mg, 0.43 mmol, 43%) was obtained as white crystals from 4-(1H-5-indolyloxy)-2-pyridinamine (225 mg, 1.0 mmol) and phenyl N,N-dimethylcarbamate.

$^1$H-NMR Spectrum (CDCl$_3$) δ (ppm): 3.13 (6H, s), 4.36 (2H, brs), 5.92 (1H, d, J=2.4 Hz), 6.31 (1H, dd, J=2.4, 5.6 Hz), 6.59 (1H, d, J=3.6 Hz), 7.03 (1H, dd, J=2.4, 8.8 Hz), 7.30 (1H, d, J=2.4 Hz), 7.37 (1H, d, J=3.6 Hz), 7.70 (1H, d, J=8.8 Hz), 7.91 (1H, d, J=5.6 Hz).

Example 132

N1-Dimethyl-5-(2-((ethylamino)carbonyl)amino-4-pyridyl)oxy-1H-1-indolecarboxamide Similarly to Example 28, the title compound (21.4 mg, 0.058 mmol, 41%) was obtained as white powder from N1-dimethyl-5-(2-amino-4-pyridyl)oxy-1H-1-indolecarboxamide (42 mg, 0.14 mmol) and 2.0 M ethylamine in tetrahydrofuran.

$^1$H-NMR Spectrum (DMSO-d$_6$) δ (ppm): 1.05 (3H, t, J=7.2 Hz), 3.05 (6H, s), 3.13 (2H, m), 6.52 (1H, dd, J=2.4, 5.6 Hz), 6.67 (1H, d, J=3.6 Hz), 6.87 (1H, d, J=2.4 Hz), 7.04 (1H, dd, J=2.4, 8.8 Hz), 7.40 (1H, d, J=2.4 Hz), 7.68–7.71 (2H, m), 8.00–8.05 (2H, m), 9.02 (1H, s).

Example 133

N1-Dimethyl-5-(2-((dimethylamino)carbonyl)amino-4-pyridyl)oxy-1H-1-indolecarboxamide Similarly to Example 28, the title compound (15.1 mg, 0.041 mmol, 29%) was obtained as white powder from N1-dimethyl-5-(2-amino-4-pyridyl)oxy-1H-1-indolecarboxamide (42 mg, 0.14 mmol) and 2.0 M dimethylamine in tetrahydrofuran.

$^1$H-NMR Spectrum (DMSO-$d_6$) δ (ppm): 2.85 (6H, s), 3.03 (6H, s), 6.54 (1H, d, J=5.6 Hz), 6.65 (1H, d, J=3.6 Hz), 7.02 (1H, d, J=8.8 Hz), 7.30–7.50 (2H, m), 7.60–7.69 (2H, m), 8.06 (1H, d, J=5.6 Hz), 8.81 (1H, s).

Example 134

N1-Benzyl-5-(2-((methylamino)carbonyl)amino-4-pyridyl)oxy-1H-1-indolecarboxamide Similarly to Example 28, the title compound (12.5 mg, 0.030 mmol, 24%) was obtained as white powder from N1-benzyl-5-(2-amino-4-pyridyl)oxy-1H-1-indolecarboxamide (45 mg, 0.13 mmol) and 40% methylamine in methanol.

$^1$H-NMR Spectrum (DMSO-$d_6$) δ (ppm) 2.66 (3H, d, J=4.4 Hz), 4.51 (2H, d, J=5.6 Hz), 6.52 (1H, dd, J=2.4, 5.6 Hz), 6.72 (1H, d, J=3.6 Hz), 6.84 (1H, d, J=2.4 Hz), 7.06 (1H, dd, J=2.4, 8.8 Hz), 7.20–7.44 (6H, m), 7.96 (1H, m), 8.00–8.05 (2H, m), 8.31 (1H, d, J=8.8 Hz), 8.83 (1H, t, J=5.6 Hz), 9.09 (1H, s).

The starting material was synthesized by the following methods.

Production Example 134-1

N1-Benzyl-5-(2-amino-4-pyridyl)oxy-1H-1-indolecarboxamide

Similarly to Production example 1-3, the title compound (45 mg, 0.13 mmol, 13%) was obtained as white powder from 4-(1H-5-indolyloxy)-2-pyridinamine (225 mg, 1.0 mmol) and phenyl N-benzylcarbamate.

$^1$H-NMR Spectrum (CDCl$_3$) δ (ppm): 4.38 (2H, brs), 4.68 (2H, d, J=4.0 Hz), 5.82 (1H, m), 5.92 (1H, m), 6.30 (1H, m), 6.61 (1H, d, J=3.6 Hz), 7.07 (1H, dd, J=2.4, 8.8 Hz), 7.26–7.47 (7H, m), 7.91 (1H, d, J=5.6 Hz), 8.19 (1H, d, J=8.8 Hz).

Example 135

5-(2-((Methylamino)carbonyl)amino-4-pyridyl)oxy-1H-1-indole-1-carboxylic acid pyrrolidin-1-ylamide Similarly to Example 28, the title compound (21.1 mg, 0.056 mmol, 27%) was obtained as white powder from 5-(2-amino-4-pyridyl)oxy-1H-1-indole-1-carboxylic acid pyrrolidin-1-ylamide (67 mg, 0.21 mmol) and 40% methylamine in methanol.

$^1$H-NMR Spectrum (DMSO-$d_6$) δ (ppm): 1.80–2.00 (4H, m), 2.67 (3H, d, J=4.4 Hz), 3.40–3.60 (4H, m), 6.53 (1H, dd, J=2.4, 5.6 Hz), 6.66 (1H, d, J=3.6 Hz), 6.85 (1H, d, J=2.4 Hz), 7.03 (1H, dd, J=2.4, 8.8 Hz), 7.39 (1H, d, J=2.4 Hz), 7.80 (1H, d, J=3.6 Hz), 7.83 (1H, d, J=8.8 Hz), 8.00 (1H, m), 8.04 (1H, d, J=5.6 Hz), 9.10 (1H, s).

The starting materials were synthesized by the following methods.

Production Example 135-1

Phenyl pyrrolidin-1-ylcarboxylate

Similarly to Production example 2-1, the title compound (2.68 g, 0.014 mol, 14%) was obtained as white crystals from pyrrolidine (8.3 ml, 0.1 mol), phenyl chloroformate (13.8 ml, 0.11 mol) and pyridine (8.9 ml, 0.11 mol).

$^1$H-NMR Spectrum (CDCl$_3$) δ (ppm): 1.90–1.99 (4H, m), 3.46–3.59 (4H, m), 7.20–7.37 (5H, m).

Production Example 135-2

5-(2-Amino-4-pyridyl)oxy-1H-1-indole-1-carboxylic acid pyrrolidin-1-ylamide

Similarly to Production example 1-3, the title compound (146 mg, 0.45 mmol, 60%) was obtained as white powder from 4-(1H-5-indolyloxy)-2-pyridinamine (170 mg, 0.76 mmol) and phenyl pyrrolidin-1-ylcarboxylate.

$^1$H-NMR Spectrum (CDCl$_3$) δ (ppm): 1.96–2.02 (4H, m), 3.60–3.67 (4H, m), 4.35 (2H, brs), 5.91 (1H, d, J=2.4 Hz), 6.31 (1H, dd, J=2.4, 5.6 Hz), 6.57 (1H, d, J=3.6 Hz), 7.03 (1H, dd, J=2.4, 8.8 Hz), 7.29 (1H, d, J=2.4 Hz), 7.43 (1H, d, J=3.6 Hz), 7.88 (1H, d, J=8.8 Hz), 7.91 (1H, d, J=5.6 Hz).

Example 136

5-(2-((Pyrrolidin-1-ylamino)carbonyl)amino-4-pyridyl)oxy-1H-1-indole-1-carboxylic acid pyrrolidin-1-ylamide Similarly to Example 28, the title compound (6.2 mg, 0.015 mmol, 9.2%) was obtained as white powder from 5-(2-amino-4-pyridyl)oxy-1H-1-indole-1-carboxylic acid pyrrolidin-1-ylamide (52 mg, 0.16 mmol) and pyrrolidine.

$^1$H-NMR Spectrum (DMSO-$d_6$) δ (ppm): 1.70–1.90 (8H, m), 3.20–3.40 (4H, m), 3.50–3.70 (4H, m), 6.56 (1H, dd, J=2.4, 5.6 Hz), 6.66 (1H, d, J=3.6 Hz), 7.03 (1H, dd, J=2.4, 8.8 Hz), 7.38 (1H, d, J=2.4 Hz), 7.45 (1H, d, J=2.4 Hz), 7.80 (1H, d, J=3.6 Hz), 7.84 (1H, d, J=8.8 Hz), 8.08 (1H, d, J=5.6 Hz), 8.61 (1H, s).

Example 137

N1-(2-Propynyl)-5-(2-((ethylamino)carbonyl)amino-4-pyridyl)oxy-1H-1-indolecarboxamide Similarly to Example 28, the title compound (16.5 mg, 0.044 mmol, 25%) was obtained as white crystals from N1-(2-propynyl)-5-(2-amino-4-pyridyl)oxy-1H-1-indolecarboxamide (54 mg, 0.18 mmol) and 2.0 M ethylamine in tetrahydrofuran.

$^1$H-NMR Spectrum (DMSO-$d_6$) δ (ppm): 1.04 (3H, t, J=7.2 Hz), 3.12 (2H, m), 3.23 (1H, m), 4.10 (2H, m), 6.52 (1H, dd, J=2.4, 5.6 Hz), 6.53 (1H, d, J=3.6 Hz), 6.88 (1H, d, J=2.4 Hz), 7.08 (1H, dd, J=2.4, 8.8 Hz), 7.40 (1H, d, J=2.4 Hz), 7.92 (1H, d, J=3.6 Hz), 8.00 (1H, m), 8.04 (1H, d, J=5.6 Hz), 8.31 (1H, d, J=8.8 Hz), 8.73 (1H, m), 9.02 (1H, s).

The starting materials were synthesized by the following methods.

Production Example 137-1

Phenyl N-(2-propynyl)carbamate

Similarly to Production example 2-1, the title compound (7.64 g, 0.044 mol, 87%) was obtained as white crystals from 2-propynylamine (3.43 ml, 0.05 mol), phenyl chloroformate (6.9 ml, 0.055 mol) and pyridine (4.45 ml, 0.055 mol).

$^1$H-NMR Spectrum (CDCl$_3$) δ (ppm): 2.30 (1H, t, J=2.8 Hz), 4.05–4.15 (2H, m), 5.22 (1H, brs), 7.10–7.40 (5H, m).

Production Example 137-2

N1-(2-Propynyl)-5-(2-amino-4-pyridyl)oxy-1H-1-indolecarboxamide

Similarly to Production example 1-3, the title compound (169 mg, 0.55 mmol, 28%) was obtained as white crystals from 4-(1H-5-indolyloxy)-2-pyridinamine (450 mg, 2.0 mmol) and phenyl N-(2-propynyl)carbamate.

$^1$H-NMR Spectrum (CDCl$_3$) δ (ppm): 2.35 (1H, m), 4.20–4.40 (4H, m), 5.72 (1H, brs), 5.92 (1H, d, J=2.4 Hz), 6.30 (1H, dd, J=2.4, 5.6 Hz), 6.63 (1H, d, J=3.6 Hz), 7.08 (1H, dd, J=2.4, 8.8 Hz), 7.30 (1H, d, J=2.4 Hz), 7.46 (1H, d, J=3.6 Hz), 7.92 (1H, d, J=5.6 Hz), 8.20 (1H, d, J=8.8 Hz).

Example 138

N1-(2-Propynyl)-5-(2-((diethylamino)carbonyl)amino-4-pyridyl)oxy-1H-1-indolecarboxamide Similarly to Example 28, the title compound (27.9 mg, 0.069 mmol, 39%) was obtained as white crystals from N1-(2-propynyl)-5-(2-amino-4-pyridyl)oxy-1H-1-indolecarboxamide (54 mg, 0.18 mmol) and N,N-diethylamine.

$^1$H-NMR Spectrum (DMSO-d$_6$) δ (ppm): 1.03 (6H, t, J=7.2 Hz), 3.23 (1H, m), 3.25–3.40 (4H, m), 4.01 (2H, m), 6.56 (1H, dd, J=2.4, 5.6 Hz), 6.72 (1H, d, J=3.6 Hz), 7.08 (1H, dd, J=2.4, 8.8 Hz), 7.39 (1H, d, J=2.4 Hz), 7.43 (1H, d, J=2.4 Hz), 7.92 (1H, d, J=3.6 Hz), 8.08 (1H, d, J=5.6 Hz), 8.31 (1H, d, J=8.8 Hz), 8.63 (1H, s), 8.73 (1H, m).

Example 139

N1-(2-Propynyl)-5-(2-((pyrrolidin-1-yl)carbonyl)amino-4-pyridyl)oxy-1H-1-indolecarboxamide Similarly to Example 28, the title compound (25.1 mg, 0.062 mmol, 35%) was obtained as white crystals from N1-(2-propynyl)-5-(2-amino-4-pyridyl)oxy-1H-1-indolecarboxamide (54 mg, 0.18 mmol) and pyrrolidine.

$^1$H-NMR Spectrum (DMSO-d$_6$) δ (ppm): 1.70–1.90 (4H, m), 3.22 (1H, m), 3.25–3.40 (4H, m), 4.10 (2H, m), 6.56 (1H, dd, J=2.4, 5.6 Hz), 6.71 (1H, d, J=3.6 Hz), 7.07 (1H, dd, J=2.4, 8.8 Hz), 7.39 (1H, d, J=2.4 Hz), 7.44 (1H, d, J=2.4 Hz), 7.92 (1H, d, J=5.6 Hz), 8.08 (1H, d, J=5.6 Hz), 8.30 (1H, d, J=8.8 Hz), 8.62 (1H, s), 8.72 (1H, m).

Example 140

N1-Methyl-5-(6-((morpholin-4-yl)carbonyl)aminopyrimidin-4-yl)amino-1H-1-indolecarboxamide Similarly to Example 28, the title compound (12.5 mg, 0.032 mmol, 12%) was obtained as pale yellow powder from N1-methyl-5-(6-aminopyrimidin-4-yl)amino-1H-1-indolecarboxamide (73 mg, 0.26 mmol) and morpholine.

$^1$H-NMR Spectrum (DMSO-d$_6$) δ (ppm): 2.83 (3H, d, J=3.6 Hz), 3.43–3.45 (4H, m), 3.55–3.58 (4H, m), 6.63 (1H, d, J=3.6 Hz), 7.26 (1H, s), 7.32 (1H, d, J=8.8 Hz), 7.77 (1H, d, J=3.6 Hz), 7.90 (1H, s), 8.05 (1H, m), 8.14 (1H, d, J=8.8 Hz), 8.29 (1H, s), 9.21 (1H, s), 9.34 (1H, s).

The starting materials were synthesized by the following methods.

Production Example 140-1

6-Chloro-4-(1H-5-indolylamino)pyrimidine 4,6-Dichloropyrimidine (5.89 g, 40 mmol), 5-aminoindole (6.27 g, 47 mmol) and N,N-diisopropylethylamine (20.6 ml, 0.12 mol) were dissolved in N-methylpyrrolidone (80 ml), and the reaction mixture was stirred at 50° C. for 2.5 hours. The reaction mixture was partitioned between ethyl acetate and water; the aqueous layer was subjected to re-extraction with ethyl acetate; and the combined organic layer was washed with brine, and dried over anhydrous sodium sulfate. The solvent was distilled off under reduced pressure; a small amount of ethyl acetate was added to the residue to crystallize; and the crystals were filtered off, washed with diethyl ether, and dried under aeration to yield the title compound (3.70 g, 15 mmol, 38%) as white crystals.

$^1$H-NMR Spectrum (DMSO-d$_6$) δ (ppm): 6.42 (1H, m), 6.62 (1H, brs), 7.11 (1H, d, J=8.0 Hz), 7.35–7.40 (2H, m), 7.72 (1H, brs), 8.38 (1H, s), 9.68 (1H, s), 11.11 (1H, s).

Production Example 140-2

6-Amino-4-(1H-5-indolylamino)pyrimidine

A 7N ammonia in methanol (60 ml) was added to 6-chloro-4-(1H-5-indolylamino)pyrimidine (2.455 g, 10 mmol); and the reaction mixture was heated in a sealed tube at 130° C. for 90 hours. The solvent was distilled off under reduced pressure; the residue was purified by silica gel column chromatography (eluent; ethyl acetate:tetrahydrofuran=1:1); diethyl ether was added to crystallize; and the crystals were filtered off, washed with diethyl ether, and dried under aeration to yield the title compound (1.563 g, 6.9 mmol, 69%) as pale brown crystals.

$^1$H-NMR Spectrum (CDCl$_3$) δ (ppm): 4.50 (2H, brs), 5.66 (1H, m), 6.55 (1H, m), 6.68 (1H, brs), 7.07 (1H, dd, J=2.4, 8.8 Hz), 7.25–7.28 (1H, m), 7.40 (1H, d, J=8.8 Hz), 7.52 (1H, d, J=2.4 Hz), 8.19 (1H, s), 8.29 (1H, brs).

Production Example 140-3

N1-Methyl-5-(6-aminopyrimidin-4-yl)amino-1H-1-indolecarboxamide

Similarly to Production example 2-3, the title compound (295 mg, 1.05 mmol, 52%) was obtained as white crystals from 6-amino-4-(1H-5-indolylamino)pyrimidine (450.5 mg, 2.0 mmol) and phenyl N-methylcarbamate.

$^1$H-NMR Spectrum (CDCl$_3$) δ (ppm): 3.09 (3H, d, J=4.0 Hz), 4.56 (2H, brs), 5.52 (1H, m), 5.73 (1H, m), 6.61 (1H, d, J=3.6 Hz), 6.66 (1H, brs), 7.19 (1H, dd, J=2.4, 8.8 Hz), 7.43 (1H, d, J=3.6 Hz), 7.48 (1H, d, J=2.4 Hz), 8.13 (1H, d, J=2.4 Hz), 8.21 (1H, s).

Example 141

N1-Methyl-5-(6-((4-(pyrrolidin-1-yl)piperidin-1-yl)carbonyl)aminopyrimidin-4-yl)amino-1H-1-indolecarboxamide Similarly to Example 28, the title compound (20.6 mg, 0.045 mmol, 17%) was obtained as white crystals from N1-methyl-5-(6-aminopyrimidin-4-yl)amino-1H-1-indolecarboxamide (73 mg, 0.26 mmol) and 4-(pyrrolidin-1-yl)piperidine.

$^1$H-NMR Spectrum (DMSO-$d_6$) δ (ppm): 1.20–1.36 (2H, m), 1.60–1.70 (4H, m), 1.70–1.85 (2H, m), 2.40–2.60 (5H, m), 2.83 (3H, d, J=4.4 Hz), 2.85–2.95 (2H, m), 3.95–4.05 (2H, m), 6.63 (1H, d, J=3.6 Hz), 7.24 (1H, s), 7.31 (1H, dd, J=2.4, 8.8 Hz), 7.77 (1H, d, J=3.6 Hz), 7.90 (1H, s), 8.05 (1H, m), 8.14 (1H, d, J=8.8 Hz), 8.28 (1H, s), 9.14 (1H, s), 9.31 (1H, s).

Example 142

N1-Ethyl-5-(6-((ethylamino)carbonyl)aminopyrimidin-4-yl)amino-1H-1-indolecarboxamide Sodium hydride (69 mg, 1.73 mmol) was suspended in N,N-dimethylformamide (3 ml); 6-amino-4-(1H-5-indolylamino)pyrimidine (311 mg, 1.38 mmol) was added thereto at room temperature under nitrogen stream; the reaction mixture was stirred for 30 minutes; phenyl N-ethylcarbamate (286 mg, 1.73 mmol) was added thereto; and the reaction mixture was stirred overnight. The reaction mixture was partitioned between a solvent mixture of ethyl acetate-tetrahydrofuran (1:1) and a saturated aqueous solution of sodium hydrogencarbonate; the organic layer was washed with water and brine, and dried over anhydrous sodium sulfate; the solvent was distilled off; the residue was purified by silica gel column chromatography (eluent; ethyl acetate: tetrahydrofuran=1:1); eluted fractions were concentrated; ethyl acetate was added to the residue to crystallize; and the crystals were filtered off, and dried under aeration to yield the title compound (14.3 mg, 0.039 mmol, 2.8%) as white crystals.

$^1$H-NMR Spectrum (DMSO-$d_6$) δ (ppm): 1.07 (3H, t, J=7.2 Hz), 1.18 (3H, t, J=7.2 Hz), 3.11–3.40 (4H, m), 6.64 (1H, d, J=3.6 Hz), 6.87 (1H, s), 7.29 (1H, dd, J=2.4, 8.8 Hz), 7.62 (1H, m), 7.80 (1H, d, J=3.6 Hz), 7.86 (1H, s), 8.09–8.17 (2H, m), 8.27 (1H, s), 9.06 (1H, s), 9.35 (1H, s).

Furthermore, the eluted fractions obtained in the above chromatography were concentrated; the residue was purified again by silica gel column chromatography (eluent; ethyl acetate:methanol=95:5); eluted fractions were concentrated; ethyl acetate was added to the residue to crystallize; and the crystals were filtered off, and dried under aeration to yield N1-ethyl-5-(6-aminopyrimidin-4-yl)amino-1H-1-indolecarboxamide (210 mg, 0.71 mmol, 51%) as white crystals.

$^1$H-NMR Spectrum (DMSO-$d_6$) δ (ppm): 1.18 (3H, t, J=7.2 Hz), 3.20–3.40 (2H, m), 5.72 (1H, m), 6.24 (2H, brs), 6.61 (1H, d, J=3.6 Hz), 7.21 (1H, dd, J=2.4, 8.8 Hz), 7.76 (1H, s), 7.79 (1H, d, J=3.6 Hz), 8.01 (1H, s), 8.07–8.14 (2H, m), 8.74 (1H, s).

Example 143

N1-Ethyl-5-(6-((diethylamino)carbonyl)aminopyrimidin-4-yl)amino-1H-1-indolecarboxamide Similarly to Example 28, the title compound (24.5 mg, 0.062 mmol, 26%) was obtained as white crystals from N1-ethyl-5-(6-aminopyrimidin-4-yl)amino-1H-1-indolecarboxamide (70 mg, 0.24 mmol) and diethylamine.

$^1$H-NMR Spectrum (DMSO-$d_6$) δ (ppm): 1.07 (6H, t, J=7.2 Hz), 1.18 (3H, t, J=7.2 Hz), 3.20–3.50 (6H, m), 6.63 (1H, d, J=3.6 Hz), 7.31–7.33 (2H, m), 7.80 (1H, d, J=3.6 Hz), 7.91 (1H, s), 8.09–8.15 (2H, m), 8.28 (1H, s), 8.66 (1H, s), 9.33 (1H, s).

Example 144

N1-Ethyl-5-(6-((4-(pyrrolidin-1-yl)piperidin-1-yl)carbonyl)aminopyrimidin-4-yl)amino-1H-1-indolecarboxamide Similarly to Example 28, the title compound (43.3 mg, 0.091 mmol, 39%) was obtained as white crystals from N1-ethyl-5-(6-aminopyrimidin-4-yl)amino-1H-1-indolecarboxamide (70 mg, 0.24 mmol) and 4-(pyrrolidin-1-yl)piperidine.

$^1$H-NMR Spectrum (DMSO-$d_6$) δ (ppm): 1.18 (3H, t, J=7.2 Hz), 1.20–1.36 (2H, m), 1.60–1.70 (4H, m), 1.70–1.85 (2H, m), 2.40–2.60 (5H, m), 2.85–2.95 (2H, m), 3.20–3.50 (2H, m), 3.95–4.05 (2H, m), 6.63 (1H, d, J=3.6 Hz), 7.24 (1H, s), 7.31 (1H, d, J=8.0 Hz), 7.80 (1H, d, J=3.6 Hz), 7.90 (1H, s), 8.10–8.15 (2H, m), 8.28 (1H, s), 9.14 (1H, s), 9.31 (1H, s).

Example 145

N1-Ethyl-5-(6-((2-(N,N-diethylamino)ethylamino)carbonyl)aminopyrimidin-4-yl)amino-1H-1-indolecarboxamide Similarly to Example 28, the title compound (43.0 mg, 0.098 mmol, 42%) was obtained as white crystals from N1-ethyl-5-(6-aminopyrimidin-4-yl)amino-1H-1-indolecarboxamide (70 mg, 0.24 mmol) and 2-(N,N-diethylamino)ethylamine.

$^1$H-NMR Spectrum (DMSO-$d_6$) δ (ppm): 0.96 (6H, t, J=7.2 Hz), 1.18 (3H, t, J=7.2 Hz), 2.30–2.60 (6H, m), 3.10–3.40 (4H, m), 6.64 (1H, d, J=3.6 Hz), 6.87 (1H, s), 7.29 (1H, d, J=8.8 Hz), 7.71 (1H, m), 7.80 (1H, d, J=3.6 Hz), 7.88 (1H, s), 8.09–8.20 (2H, m), 8.25 (1H, s), 9.21 (1H, s), 9.34 (1H, s).

Example 146

N1-Phenyl-5-(6-((diethylamino)carbonyl)aminopyrimidin-4-yl)amino-1H-1-indolecarboxamide Similarly to Example 28, the title compound (27.5 mg, 0.062 mmol, 27%) was obtained as white crystals from N1-phenyl-5-(6-aminopyrimidin-4-yl)amino-1H-1-indolecarboxamide (80 mg, 0.23 mmol) and diethylamine.

$^1$H-NMR Spectrum (DMSO-$d_6$) δ (ppm): 1.08 (6H, t, J=7.2 Hz), 3.20–3.40 (4H, m), 6.74 (1H, d, J=3.6 Hz), 7.13 (1H, dd, J=2.4, 8.8 Hz), 7.33–7.42 (4H, m), 7.64–7.67 (2H, m), 7.98–8.03 (2H, m), 8.13 (1H, d, J=8.8 Hz), 8.31 (1H, s), 8.69 (1H, s), 9.39 (1H, s), 10.00 (1H, s).

The starting material was synthesized by the following method.

Production Example 146-1

N1-Phenyl-5-(6-aminopyrimidin-4-yl)amino-1H-1-indolecarboxamide

Similarly to Production example 2-3, the title compound (160 mg, 0.46 mmol, 35%) was obtained as pale brown powder from 6-amino-4-(1H-5-indolylamino)pyrimidine (300 mg, 1.33 mmol) and phenyl isocyanate.
$^1$H-NMR Spectrum (CDCl$_3$) δ (ppm): 4.61 (2H, brs), 5.76 (1H, m), 6.68 (1H, d, J=3.6 Hz), 6.77 (1H, s), 7.22–7.25 (2H, m), 7.35–7.45 (3H, m), 7.50–7.60 (4H, m), 8.16 (1H, d, J=8.8 Hz), 8.22 (1H, s).

Example 147

N1-Phenyl-5-(6-((3-(N,N-diethylamino)propylamino)carbonyl)aminopyrimidin-4-yl)amino-1H-1-indolecarboxamide Similarly to Example 28, the title compound (56.2 mg, 0.11 mmol, 48%) was obtained as white powder from N1-phenyl-5-(6-aminopyrimidin-4-yl)amino-1H-1-indolecarboxamide (80 mg, 0.23 mmol) and 3-(N,N-diethylamino)propylamine.
$^1$H-NMR Spectrum (DMSO-d$_6$) δ (ppm): 0.80–1.00 (6H, m), 1.40–1.65 (2H, m), 2.20–2.60 (6H, m), 3.00–3.40 (2H, m), 6.70–6.88 (2H, m), 7.10–7.17 (1H, m), 7.30–7.49 (3H, m), 7.60–7.80 (3H, m), 7.90–8.40 (4H, m), 9.10–9.40 (2H, m), 10.00–10.14 (1H, m).

Example 148

N1-Cyclopropyl-5-(6-((4-(piperidin-1-yl)piperidin-1-yl)carbonyl)aminopyrimidin-4-yl)amino-1H-1-indolecarboxamide Similarly to Production example 2-3, a crude product of N1-cyclopropyl-5-(6-aminopyrimidin-4-yl)amino-1H-1-indolecarboxamide (132 mg) was obtained as white powder from 6-amino-4-(1H-5-indolylamino)pyrimidine (300 mg, 1.33 mmol) and phenyl N-cyclopropylcarbamate.
$^1$H-NMR Spectrum (DMSO-d$_6$) δ (ppm): 0.60–0.63 (2H, m), 0.70–0.74 (2H, m), 2.76 (1H, m), 5.73 (1H, s), 6.24 (2H, brs), 6.59 (1H, d, J=3.6 Hz), 7.02 (1H, dd, J=2.4, 8.8 Hz), 7.74–7.76 (2H, m), 8.01 (1H, s), 8.12 (1H, d, J=8.8 Hz), 8.15 (1H, d, J=2.4 Hz), 8.75 (1H, s).
Similarly to Example 28, the title compound (20.6 mg, 0.041 mmol, 3.1% in 2 processes) was obtained as white crystals from the above crude product.
$^1$H-NMR Spectrum (DMSO-d$_6$) δ (ppm): 0.59–0.63 (2H, m), 0.70–0.76 (2H, m), 1.20–1.60 (8H, m), 1.60–1.80 (2H, m), 2.30–2.80 (8H, m), 4.05–4.20 (2H, m), 6.61 (1H, d, J=3.6 Hz), 7.24 (1H, s), 7.32 (1H, dd, J=2.4, 8.8 Hz), 7.76 (1H, d, J=3.6 Hz), 7.90 (1H, s), 8.13 (1H, d, J=8.8 Hz), 8.17 (1H, d, J=2.4 Hz), 8.28 (1H, s), 9.15 (1H, s), 9.32 (1H, s).

Example 149

N1-Dimethyl-5-(6-((4-(pyrrolidin-1-yl)piperidin-1-yl)carbonyl)aminopyrimidin-4-yl)amino-1H-1-indolecarboxamide Similarly to Example 28, the title compound (19.2 mg, 0.040 mmol, 21%) was obtained as white powder from N1-dimethyl-5-(6-aminopyrimidin-4-yl)amino-1H-1-indolecarboxamide (56 mg, 0.19 mmol) and 4-(pyrrolidin-1-yl)piperidine.
$^1$H-NMR Spectrum (DMSO-d$_6$) δ (ppm): 1.20–1.36 (2H, m), 1.60–1.70 (4H, m), 1.70–1.85 (2H, m), 2.40–2.60 (5H, m), 2.85–2.95 (2H, m), 3.00 (6H, s), 3.95–4.05 (2H, m), 6.60 (1H, d, J=3.2 Hz), 7.22 (1H, d, J=1.2 Hz), 7.30 (1H, dd, J=2.0, 8.8 Hz), 7.50–7.55 (2H, m), 7.88 (1H, brs), 8.26 (1H, d, J=1.2 Hz), 9.13 (1H, s), 9.29 (1H, s).
The starting material was synthesized by the following method.

Production Example 149-1

N1-Dimethyl-5-(6-aminopyrimidin-4-yl)amino-1H-1-indolecarboxamide

Similarly to Production example 2-3, the title compound (101 mg, 0.34 mmol, 34%) was obtained as white crystals from 6-amino-4-(1H-5-indolylamino)pyrimidine (225.3 mg, 1.0 mmol) and phenyl N,N-dimethylcarbamate.
$^1$H-NMR Spectrum (DMSO-d$_6$) δ (ppm): 3.02 (6H, s), 5.71 (1H, s), 6.23 (2H, brs), 6.60 (1H, d, J=3.6 Hz), 7.22 (1H, dd, J=2.0, 8.8 Hz), 7.50–7.55 (2H, m), 7.74 (1H, d, J=2.0 Hz), 8.00 (1H, s), 8.73 (1H, s).

Example 150

N1-Dimethyl-5-(6-((3-diethylaminopropyl)carbonyl)aminopyrimidin-4-yl)amino-1H-1-indolecarboxamide Similarly to Example 28, the title compound (55.3 mg, 0.12 mmol, 66%) was obtained as white crystals from N1-dimethyl-5-(6-aminopyrimidin-4-yl)amino-1H-1-indolecarboxamide (55 mg, 0.19 mmol) and 3-diethylaminopropylamine.
$^1$H-NMR Spectrum (DMSO-d$_6$) δ (ppm): 0.92 (6H, t, J=7.2 Hz), 1.50–1.55 (2H, m), 2.30–2.45 (6H, m), 3.00 (6H, s), 3.10–3.15 (2H, m), 6.60 (1H, dd, J=0.8, 3.6 Hz), 6.82 (1H, brs), 7.28 (1H, dd, J=2.0, 8.8 Hz), 7.50–7.55 (2H, m), 7.71 (1H, m), 7.84 (1H, brs), 8.23 (1H, d, J=0.8 Hz), 9.08 (1H, s), 9.32 (1H, s).

Example 151

5-(6-((4-(Pyrrolidin-1-yl)piperidin-1-yl)carbonyl)amino-4-pyrimidyl)amino-1H-1-indole-1-carboxylic acid pyrrolidin-1-ylamide Similarly to Example 28, the title compound (13.1 mg, 0.026 mmol, 14%) was obtained as white crystals from 5-(6-amino-4-pyrimidyl)amino-1H-1-indole-1-carboxylic acid pyrrolidin-1-ylamide (61 mg, 0.19 mmol) and 4-(pyrrolidin-1-yl)piperidine.
$^1$H-NMR Spectrum (DMSO-d$_6$) δ (ppm): 1.20–1.36 (2H, m), 1.60–1.70 (4H, m), 1.70–1.90 (6H, m), 2.40–2.60 (5H, m), 2.85–2.95 (2H, m), 3.40–3.60 (4H, m), 3.95–4.05 (2H, m), 6.59 (1H, d, J=3.2 Hz), 7.22 (1H, brs), 7.28 (1H, dd, J=2.0, 8.8 Hz), 7.60–7.70 (2H, m), 7.87 (1H, m), 8.26 (1H, d, J=1.2 Hz), 9.12 (1H, s), 9.28 (1H, s).
The starting material was synthesized by the following method.

Production Example 151-1

5-(6-Amino-4-pyrimidyl)amino-1H-1-indole-1-carboxylic acid pyrrolidin-1-ylamide

Similarly to Production example 2-3, the title compound (122 mg, 0.38 mmol, 38%) was obtained as white crystals from 6-amino-4-(1H-5-indolylamino)pyrimidine (225.3 mg, 1.0 mmol) and phenyl pyrrolidin-1-ylcarboxylate.
$^1$H-NMR Spectrum (DMSO-d$_6$) δ (ppm): 1.80–1.95 (4H, m), 3.50–3.60 (4H, m), 5.71 (1H, s), 6.23 (2H, brs), 6.59

(1H, d, J=3.6 Hz), 7.20 (1H, dd, J=2.0, 8.8 Hz), 7.64–7.69 (2H, m), 7.74 (1H, d, J=2.0 Hz), 8.00 (1H, s), 8.73 (1H, s).

Example 152

5-(6-((Morpholin-4-yl)carbonyl)amino-4-pyrimidyl) amino-1H-1-indole-1-carboxylic acid pyrrolidin-1-ylamide Similarly to Example 28, the title compound (30.3 mg, 0.070 mmol, 37%) was obtained as white powder from 5-(6-amino-4-pyrimidyl)amino-1H-1-indole-1-carboxylic acid pyrrolidin-1-ylamide (61 mg, 0.19 mmol) and morpholine.
$^1$H-NMR Spectrum (DMSO-$d_6$) δ (ppm): 1.80–1.90 (4H, m), 3.40–3.50 (4H, m), 3.50–3.60 (8H, m), 6.59 (1H, d, J=2.8 Hz), 7.24 (1H, d, J=2.0 Hz), 7.28 (1H, dd, J=2.0, 8.8 Hz), 7.63–7.69 (2H, m), 7.88 (1H, brs), 8.27 (1H, d, J=2.8 Hz), 9.19 (1H, s), 9.31 (1H, s).

Example 153

N1-(2-Propyl)-5-(6-((2-propylamino)carbonyl)aminopyrimidin-4-yl)amino-1H-1-indolecarboxamide Sodium hydride (48 mg, 1.2 mmol) was suspended in N,N-dimethylformamide (2.5 ml); 6-amino-4-(1H-5-indolylamino)pyrimidine (225.3 mg, 1.0 mmol) was added thereto at room temperature under nitrogen stream; the reaction mixture was stirred for 30 minutes; phenyl N-(2-propyl) carbamate (215 mg, 1.2 mmol) was added thereto; and the reaction mixture was stirred overnight. The reaction mixture was partitioned between a solvent mixture of ethyl acetate-tetrahydrofuran (1:1) and a saturated aqueous solution of sodium hydrogencarbonate; and the organic layer was washed with water and brine, and dried over anhydrous sodium sulfate. After the solvent was distilled off, the residue was purified by silica gel column chromatography (eluent; ethyl acetate); eluted fractions were concentrated; ethyl acetate was added to the residue to crystallize; and the crystals were filtered off, and dried under aeration to yield the title compound (31.3 mg, 0.079 mmol, 7.9%) as white crystals.
$^1$H-NMR Spectrum (DMSO-$d_6$) δ (ppm): 1.09 (6H, d, J=6.8 Hz), 1.20 (6H, d, J=6.8 Hz), 3.75 (1H, m), 4.00 (1H, m), 6.60 (1H, d, J=3.6 Hz), 6.89 (1H, s), 7.27 (1H, dd, J=2.0, 8.8 Hz), 7.45 (1H, m), 7.80–7.90 (3H, m), 8.11 (1H, d, J=8.8 Hz), 8.24 (1H, s), 8.91 (1H, s), 9.31 (1H, s).

The above chromatography was further performed by eluting ethyl acetate:methanol=95:5; the eluted fractions were concentrated; ethyl acetate-hexane (1:5) was added to the residue to crystallize; and the crystals were filtered off, and dried under aeration to yield N1-(2-propyl)-5-(6-aminopyrimidin-4-yl)amino-1H-1-indolecarboxamide (77.8 mg, 0.25 mmol, 25%) as white crystals.
$^1$H-NMR Spectrum (DMSO-$d_6$) δ (ppm): 1.29 (6H, d, J=6.8 Hz), 3.98 (1H, m), 5.70 (1H, s), 6.21 (2H, brs), 6.57 (1H, d, J=2.8 Hz), 7.18 (1H, d, J=8.8 Hz), 7.72 (1H, s), 7.79–7.82 (2H, m), 7.98 (1H, s), 8.08 (1H, d, J=8.8 Hz), 8.72 (1H, s).

Example 154

N1-(2-Propyl)-5-(6-((4-(pyrrolidin-1-yl)piperidin-1-yl)carbonyl)aminopyrimidin-4-yl)amino-1H-1-indolecarboxamide Similarly to Example 28, the title compound (36.3 mg, 0.074 mmol, 60%) was obtained as white powder from N1-(2-propyl)-5-(6-aminopyrimidin-4-yl)amino-1H-1-indolecarboxamide (38 mg, 0.12 mmol) and 4-(pyrrolidin-1-yl)piperidine.
$^1$H-NMR Spectrum (DMSO-$d_6$) δ (ppm): 1.20 (6H, d, J=6.8 Hz), 1.20–1.36 (2H, m), 1.60–1.70 (4H, m), 1.70–1.85 (2H, m), 2.40–2.60 (5H, m), 2.85–2.95 (2H, m), 3.90–4.10 (3H, m), 6.60 (1H, d, J=3.6 Hz), 7.22 (1H, s), 7.29 (1H, d, J=8.0 Hz), 7.80–8.00 (3H, m), 8.10 (1H, d, J=8.0 Hz), 8.26 (1H, s), 9.13 (1H, s), 9.29 (1H, s).

Example 155

N1-(2-Propyl)-5-(6-((3-diethylaminopropyl)carbonyl)aminopyrimidin-4-yl)amino-1H-1-indolecarboxamide Similarly to Example 28, the title compound (27.3 mg, 0.059 mmol, 48%) was obtained as white crystals from N1-(2-propyl)-5-(6-aminopyrimidin-4-yl)amino-1H-1-indolecarboxamide (38 mg, 0.12 mmol) and 3-diethylaminopropylamine.
$^1$H-NMR Spectrum (DMSO-$d_6$) δ (ppm): 0.91 (6H, t, J=6.8 Hz), 1.20 (6H, d, J=6.8 Hz), 1.40–1.60 (2H, m), 2.20–2.50 (6H, m), 3.10–3.20 (2H, m), 4.00 (1H, m), 6.60 (1H, d, J=3.6 Hz), 6.82 (1H, s), 7.26 (1H, d, J=8.8 Hz), 7.70 (1H, m), 7.80–7.85 (3H, m), 8.11 (1H, d, J=8.8 Hz), 8.24 (1H, s), 9.08 (1H, s), 9.32 (1H, s).

Example 156

N1-Methyl-4-(6-((4-(pyrrolidin-1-yl)piperidin-1-yl)carbonyl)aminopyrimidin-4-yl)amino-1H-1-indolecarboxamide Similarly to Example 28, the title compound (21.0 mg, 0.045 mmol, 31%) was obtained as white powder from N1-methyl-4-(6-aminopyrimidin-4-yl)amino-1H-1-indolecarboxamide (41 mg, 0.15 mmol) and 4-(pyrrolidin-1-yl)piperidine.
$^1$H-NMR Spectrum (DMSO-$d_6$) δ (ppm): 1.20–1.40 (2H, m), 1.60–1.70 (4H, m), 1.70–1.85 (2H, m), 2.40–2.60 (5H, m), 2.81 (3H, d, J=4.4 Hz), 2.85–2.95 (2H, m), 3.90–4.10 (2H, m), 6.85 (1H, m), 7.18 (1H, t, J=8.0 Hz), 7.35 (1H, d, J=4.0 Hz), 7.55 (1H, d, J=8.0 Hz), 7.64 (1H, d, J=8.0 Hz), 7.70 (1H, d, J=4.0 Hz), 7.93 (1H, d, J=8.0 Hz), 8.08 (1H, m), 8.26 (1H, s), 9.19 (1H, s).

The starting materials were synthesized by the following methods.

Production Example 156-1

6-Chloro-4-(1H-4-indolylamino)pyrimidine 4,6-Dichloropyrimidine (1.01 g, 6.6 mmol), 4-aminoindole (900 mg, 6.6 mmol) and N,N-diisopropylethylamine (3.14 ml, 18 mmol) were dissolved in N,N-dimethylformamide (20 ml), and the reaction mixture was stirred at 80° C. for 6 hours. The reaction mixture was partitioned between ethyl acetate and water; the aqueous layer was subjected to re-extraction with ethyl acetate, and the combined organic layer was washed with brine, and dried over anhydrous sodium sulfate. The solvent was distilled off under reduced pressure; and a small amount of methanol was added to the residue to crystallize; and the crystals were filtered off, washed with methanol and ethyl acetate, and dried under aeration to yield the title compound (599 mg, 2.5 mmol, 37%) as pale brown crystals.

¹H-NMR Spectrum (DMSO-d₆) δ (ppm): 6.49 (1H, brs), 6.75 (1H, brs), 7.10 (1H, m), 7.25 (1H, d, J=8.0 Hz), 7.33–7.40 (2H, m), 8.42 (1H, s), 9.71 (1H, brs), 11.24 (1H, brs).

Production Example 156-2

6-Amino-4-(1H-4-indolylamino)pyrimidine

A 7N methanol solution of ammonia (50 ml) and tetrahydrofuran (20 ml) were added to 6-chloro-4-(1H-4-indolylamino)pyrimidine (599 mg, 2.5 mmol) and the reaction mixture was heated in a sealed tube at 130° C. for 137 hours. The solvent was distilled off under reduced pressure; the residue was purified by silica gel column chromatography (eluent; ethyl acetate:tetrahydrofuran=1:1); diethyl ether was added to the residue to crystallize; the crystals were filtered off, washed with diethyl ether, and dried under aeration to yield the title compound (454 mg, 2.0 mmol, 82%) as pale brown crystals.

¹H-NMR Spectrum (DMSO-d₆) δ (ppm): 5.74 (1H, s), 6.20 (2H, brs), 6.50 (1H, m), 7.00 (1H, t, J=8.0 Hz), 7.09 (1H, d, J=8.0 Hz), 7.15–7.30 (2H, m), 7.98 (1H, s), 8.55 (1H, s), 11.06 (1H, brs).

Production Example 156-3

N1-Methyl-4-(6-aminopyrimidin-4-yl)amino-1H-1-indolecarboxamide

Similarly to Production example 2-3, the title compound (124.7 mg, 0.44 mmol, 44%) was obtained as pale brown crystals from 6-amino-4-(1H-5-indolylamino)pyrimidine (225.3 mg, 1.0 mmol) and phenyl N-methylcarbamate.

¹H-NMR Spectrum (DMSO-d₆) δ (ppm): 2.81 (3H, d, J=4.0 Hz), 5.75 (1H, s), 6.27 (2H, brs), 6.76 (1H, d, J=4.0 Hz), 7.17 (1H, t, J=8.0 Hz), 7.43 (1H, d, J=8.0 Hz), 7.70 (1H, d, J=4.0 Hz), 7.92 (1H, d, J=8.0 Hz), 8.00 (1H, s), 8.06 (1H, m), 8.70 (1H, s).

Example 157

N1-Methyl-4-(6-((4-(piperidin-1-yl)piperidin-1-yl)carbonyl)aminopyrimidin-4-yl)amino-1H-1-indolecarboxamide Similarly to Example 28, the title compound (7.7 mg, 0.016 mmol, 11%) was obtained as white powder from N1-methyl-4-(6-aminopyrimidin-4-yl)amino-1H-1-indolecarboxamide (41 mg, 0.15 mmol) and 4-(piperidin-1-yl)piperidine.

¹H-NMR Spectrum (DMSO-d₆) δ (ppm): 1.20–1.60 (8H, m), 1.60–1.80 (2H, m), 2.30–2.80 (7H, m), 2.81 (3H, d, J=4.4 Hz), 4.05–4.20 (2H, m), 6.85 (1H, m), 7.18 (1H, t, J=8.0 Hz), 7.35 (1H, d, J=4.0 Hz), 7.55 (1H, d, J=8.0 Hz), 7.65–7.70 (2H, m), 7.92 (1H, d, J=8.0 Hz), 8.06 (1H, m), 8.26 (1H, s), 9.18 (1H, s).

Example 158

N1-Methyl-4-(6-((3-diethylaminopropylamino)carbonyl)aminopyrimidin-4-yl)amino-1H-1-indolecarboxamide Similarly to Example 28, the title compound (23.3 mg, 0.053 mmol, 37%) was obtained as white crystals from N1-methyl-4-(6-aminopyrimidin-4-yl)amino-1H-1-indolecarboxamide (41 mg, 0.15 mmol) and 3-diethylaminopropylamine.

¹H-NMR Spectrum (DMSO-d₆) δ (ppm): 0.92 (6H, t, J=6.8 Hz), 1.40–1.60 (2H, m), 2.20–2.50 (6H, m), 2.82 (3H, d, J=4.4 Hz), 3.10–3.20 (2H, m), 6.80 (1H, m), 6.93 (1H, d, J=6.8 Hz), 7.19 (1H, t, J=8.0 Hz), 7.55 (1H, d, J=8.0 Hz), 7.60–7.70 (2H, m), 7.95 (1H, d, J=8.0 Hz), 8.08 (1H, m), 8.23 (1H, s), 9.11 (1H, s), 9.26 (1H, s).

Example 159

N1-(4-Fluorophenyl)-4-(6-((3-diethylaminopropylamino)carbonyl)aminopyrimidin-4-yl)amino-1H-1-indolecarboxamide Similarly to Example 28, the title compound (28.6 mg, 0.055 mmol, 40%) was obtained as white powder from N1-(4-fluorophenyl)-4-(6-aminopyrimidin-4-yl)amino-1H-1-indolecarboxamide (50 mg, 0.14 mmol) and 3-diethylaminopropylamine.

¹H-NMR Spectrum (DMSO-d₆) δ (ppm): 0.93 (6H, t, J=6.8 Hz), 1.40–1.60 (2H, m), 2.30–2.50 (6H, m), 3.10–3.15 (2H, m), 6.90 (1H, d, J=3.6 Hz), 6.97 (1H, m), 7.18–7.26 (3H, m), 7.60–7.70 (4H, m), 7.90–8.00 (2H, m), 8.25 (1H, s), 9.13 (1H, s), 9.32 (1H, s), 10.09 (1H, brs).

The starting material was synthesized by the following method.

Production Example 159-1

N1-(4-Fluorophenyl)-4-(6-aminopyrimidin-4-yl)amino-1H-1-indolecarboxamide

Similarly to Production example 2-3, the title compound (109 mg, 0.30 mmol, 30%) was obtained as pale yellow powder from 6-amino-4-(1H-4-indolylamino)pyrimidine (225.3 mg, 1.0 mmol) and phenyl N-(4-fluorophenyl)carbamate.

¹H-NMR Spectrum (DMSO-d₆) δ (ppm): 5.78 (1H, s), 6.29 (2H, brs), 6.86 (1H, d, J=3.6 Hz), 7.15–7.30 (3H, m), 7.51 (1H, d, J=8.0 Hz), 7.60–7.70 (2H, m), 7.89 (1H, d, J=8.0 Hz), 7.92 (1H, d, J=3.6 Hz), 8.01 (1H, s), 8.76 (1H, s), 10.07 (1H, s).

Example 160

N1-(4-Fluorophenyl)-4-(6-((2-diethylaminoethylamino)carbonyl)aminopyrimidin-4-yl)amino-1H-1-indolecarboxamide Similarly to Example 28, the title compound (36.1 mg, 0.072 mmol, 52%) was obtained as white crystals from N1-(4-fluorophenyl)-4-(6-aminopyrimidin-4-yl)amino-1H-1-indolecarboxamide (50 mg, 0.14 mmol) and 2-diethylaminoethylamine.

¹H-NMR Spectrum (DMSO-d₆) δ (ppm): 0.95 (6H, t, J=6.8 Hz), 2.30–2.50 (6H, m), 3.10–3.20 (2H, m), 6.91 (1H, d, J=3.6 Hz), 6.99 (1H, m), 7.18–7.26 (3H, m), 7.60–7.75 (4H, m), 7.90–8.00 (2H, m), 8.25 (1H, s), 9.24 (1H, s), 9.31 (1H, s), 10.09 (1H, brs).

Example 161

N1-Methyl-6-(6-((4-(pyrrolidin-1-yl)piperidin-1-yl)carbonyl)aminopyrimidin-4-yl)amino-1H-1-indolecarboxamide Similarly to Example 28, the title compound (35.6 mg, 0.077 mmol, 43%) was obtained as white crystals from N1-methyl-6-(6-aminopyrimidin-4-yl)amino-1H-1-indolecarboxamide (51 mg, 0.18 mmol) and 4-(pyrrolidin-1-yl)piperidine.

$^1$H-NMR Spectrum (DMSO-$d_6$) δ (ppm): 1.20–1.40 (2H, m), 1.60–1.70 (4H, m), 1.70–1.85 (2H, m), 2.40–2.60 (5H, m), 2.81 (3H, d, J=4.0 Hz), 2.85–2.95 (2H, m), 3.90–4.10 (2H, m), 6.57 (1H, d, J=3.6 Hz), 7.23 (1H, s), 7.39–7.50 (2H, m), 7.68 (1H, d, J=3.6 Hz), 8.02 (1H, m), 8.26 (1H, s), 8.51 (1H, s), 9.13 (1H, s), 9.40 (1H, s).

The starting materials were synthesized by the following methods.

Production Example 161-1

6-Chloro-4-(1H-6-indolylamino)pyrimidine

The title compound (1.229 g, 5.0 mmol, 46%) was obtained as pale yellow crystals from 4,6-dichloropyrimidine (1.69 g, 11 mmol), 6-aminoindole and N,N-diisopropylethylamine by the method similar to the synthesis of 6-chloro-4-(1H-5-indolylamino)pyrimidine.

$^1$H-NMR Spectrum (DMSO-$d_6$) δ (ppm): 6.39 (1H, s), 6.74 (1H, s), 7.02 (1H, dd, J=2.8, 8.8 Hz), 7.30 (1H, t, J=2.8 Hz), 7.50 (1H, d, J=8.8 Hz), 7.83 (1H, m), 8.43 (1H, s), 9.78 (1H, s), 11.07 (1H, brs).

Production Example 161-2

6-Amino-4-(1H-6-indolylamino)pyrimidine

A 7N ammonia in methanol solution (75 ml) was added to 6-chloro-4-(1H-6-indolylamino)pyrimidine (1.229 g, 5.0 mmol); and the reaction mixture was heated in a sealed tube at 130° C. for 6 days. The solvent was distilled off under reduced pressure; the residue was purified by silica gel column chromatography (eluent; ethyl acetate:tetrahydrofuran=1:1); diethyl ether was added to the residue to crystallize; the crystals were filtered off, and washed with diethyl ether, and dried under aeration to yield the title compound (883 mg, 3.9 mmol, 78%) as pale yellow crystals.

$^1$H-NMR Spectrum (DMSO-$d_6$) δ (ppm): 5.71 (1H, s), 6.19 (2H, brs), 6.32 (1H, s), 6.92 (1H, dd, J=1.2, 8.0 Hz), 7.20 (1H, m), 7.40 (1H, d, J=8.0 Hz), 7.65 (1H, s), 7.98 (1H, s), 8.65 (1H, s), 10.91 (1H, s).

Production Example 161-3

N1-Methyl-6-(6-aminopyrimidin-4-yl)amino-1H-1-indolecarboxamide

Similarly to Production example 2-3, the title compound (105 mg, 0.37 mmol, 48%) was obtained as pale brown crystals from 6-amino-4-(1H-6-indolylamino)pyrimidine (175 mg, 0.78 mmol) and phenyl N-methylcarbamate.

$^1$H-NMR Spectrum (DMSO-$d_6$) δ (ppm): 2.80 (3H, d, J=4.4 Hz), 5.73 (1H, s), 6.24 (2H, brs), 6.56 (1H, d, J=2.8 Hz), 7.33 (1H, d, J=8.4 Hz), 7.44 (1H, d, J=8.4 Hz), 7.66 (1H, d, J=2.8 Hz), 7.90–8.10 (2H, m), 8.33 (1H, s), 8.84 (1H, s).

Example 162

N1-Methyl-6-(6-((3-diethylaminopropylamino)carbonyl)aminopyrimidin-4-yl)amino-1H-1-indolecarboxamide Similarly to Example 28, the title compound (37.3 mg, 0.085 mmol, 47%) was obtained as white crystals from N1-methyl-6-(6-aminopyrimidin-4-yl)amino-1H-1-indolecarboxamide (51 mg, 0.18 mmol) and 3-diethylaminopropylamine.

$^1$H-NMR Spectrum (DMSO-$d_6$) δ (ppm): 0.92 (6H, t, J=6.8 Hz), 1.40–1.60 (2H, m), 2.20–2.40 (6H, m), 2.81 (3H, d, J=4.0 Hz), 3.05–3.20 (2H, m), 6.58 (1H, d, J=4.0 Hz), 6.83 (1H, s), 7.38 (1H, d, J=8.0 Hz), 7.46 (1H, d, J=8.0 Hz), 7.60–7.80 (2H, m), 8.03 (1H, m), 8.23 (1H, s), 8.46 (1H, s), 9.10 (1H, s), 9.43 (1H, s).

Example 163

N1-(2-Propyl)-6-(6-((4-(pyrrolidin-1-yl)piperidin-1-yl)carbonyl)aminopyrimidin-4-yl)amino-1H-1-indolecarboxamide Similarly to Example 28, the title compound (40.4 mg, 0.082 mmol, 54%) was obtained as white crystals from N1-(2-propyl)-6-(6-aminopyrimidin-4-yl)amino-1H-1-indolecarboxamide (47 mg, 0.15 mmol) and 4-(pyrrolidin-1-yl)piperidine.

$^1$H-NMR Spectrum (DMSO-$d_6$) δ (ppm): 1.20 (6H, d, J=6.8 Hz), 1.20–1.36 (2H, m), 1.60–1.70 (4H, m), 1.70–1.85 (2H, m), 2.40–2.60 (5H, m), 2.80–3.00 (2H, m), 3.90–4.10 (3H, m), 6.56 (1H, d, J=3.6 Hz), 7.24 (1H, s), 7.30–7.50 (2H, m), 7.74 (1H, d, J=3.6 Hz), 7.81 (1H, d, J=8.8 Hz), 8.26 (1H, s), 8.50 (1H, s), 9.13 (1H, s), 9.39 (1H, s).

The starting material was synthesized by the following method.

Production Example 163-1

N1-(2-Propyl)-6-(6-aminopyrimidin-4-yl)amino-1H-1-indolecarboxamide

Similarly to Production example 2-3, the title compound (95.3 mg, 0.31 mmol, 40%) was obtained as pale brown crystals from 6-amino-4-(1H-6-indolylamino)pyrimidine (175 mg, 0.78 mmol) and phenyl N-(2-propyl)carbamate.

$^1$H-NMR Spectrum (DMSO-$d_6$) δ (ppm): 1.20 (6H, d, J=6.4 Hz), 4.00 (1H, m), 5.73 (1H, s), 6.24 (2H, brs), 6.55 (1H, d, J=3.6 Hz), 7.33 (1H, dd, J=2.0, 8.0 Hz), 7.44 (1H, d, J=8.0 Hz), 7.73 (1H, d, J=3.6 Hz), 7.80 (1H, d, J=8.0 Hz), 7.98 (1H, s), 8.33 (1H, s), 8.84 (1H, s).

Example 164

N1-(2-Propyl)-6-(6-((3-diethylaminopropylamino)carbonyl)aminopyrimidin-4-yl)amino-1H-1-indolecarboxamide Similarly to Example 28, the title compound (40.1 mg, 0.086 mmol, 57%) was obtained as white crystals from N1-(2-propyl)-6-(6-aminopyrimidin-4-yl)amino-1H-1-indolecarboxamide (47 mg, 0.15 mmol) and 3-diethylaminopropylamine.

$^1$H-NMR Spectrum (DMSO-$d_6$) δ (ppm): 0.92 (6H, t, J=6.8 Hz), 1.20 (6H, d, J=6.4 Hz), 1.40–1.60 (2H, m), 2.20–2.50 (6H, m), 3.05–3.20 (2H, m), 4.00 (1H, m), 6.57

(1H, d, J=3.6 Hz), 6.84 (1H, s), 7.36 (1H, dd, J=8.0 Hz), 7.46 (1H, d, J=8.0 Hz), 7.12 (1H, m), 7.76 (1H, d, J=3.6 Hz), 7.82 (1H, d, J=8.0 Hz), 8.23 (1H, s), 8.44 (1H, s), 9.10 (1H, s), 9.43 (1H, s).

Example 165

N1-(4-Fluorophenyl)-6-(6-((3-diethylaminopropylamino)carbonyl)aminopyrimidin-4-yl)amino-1H-1-indolecarboxamide Similarly to Example 28, the title compound (22.9 mg, 0.044 mmol, 24%) was obtained as white crystals from N1-(4-fluorophenyl)-6-(6-aminopyrimidin-4-yl)amino-1H-1-indolecarboxamide (67 mg, 0.19 mmol) and 3-diethylaminopropylamine.

$^1$H-NMR Spectrum (DMSO-$d_6$) δ (ppm): 0.92 (6H, t, J=6.8 Hz), 1.40–1.60 (2H, m), 2.20–2.40 (6H, m), 3.05–3.20 (2H, m), 6.68 (1H, d, J=3.6 Hz), 6.87 (1H, s), 7.24 (2H, t, J=8.8 Hz), 7.43 (1H, dd, J=2.0, 8.4 Hz), 7.52 (1H, d, J=8.4 Hz), 7.60–7.80 (4H, m), 7.89 (1H, d, J=3.6 Hz), 8.23 (1H, s), 8.48 (1H, s), 9.11 (1H, s), 9.45 (1H, s).

The starting material was synthesized by the following method.

Production Example 165-1

N1-(4-Fluorophenyl)-6-(6-aminopyrimidin-4-yl)amino-1H-1-indolecarboxamide

Similarly to Production example 2-3, the title compound (137 mg, 0.38 mmol, 49%) was obtained as pale brown crystals from 6-amino-4-(1H-6-indolylamino)pyrimidine (175 mg, 0.78 mmol) and phenyl N-(4-fluorophenyl)carbamate.

$^1$H-NMR Spectrum (DMSO-$d_6$) δ (ppm): 5.75 (1H, s), 6.26 (2H, brs), 6.66 (1H, d, J=3.6 Hz), 7.22 (2H, t, J=8.8 Hz), 7.39 (1H, dd, J=2.0, 8.4 Hz), 7.49 (1H, d, J=8.4 Hz), 7.60–7.70 (2H, m), 7.87 (1H, d, J=3.6 Hz), 7.99 (1H, s), 8.36 (1H, s), 8.91 (1H, s), 10.01 (1H, s).

Example 166

N1-(4-Fluorophenyl)-6-(6-((2-diethylaminoethylamino)carbonyl)aminopyrimidin-4-yl)amino-1H-1-indolecarboxamide Similarly to Example 28, the title compound (11.1 mg, 0.022 mmol, 12%) was obtained as white crystals from N1-(4-fluorophenyl)-6-(6-aminopyrimidin-4-yl)amino-1H-1-indolecarboxamide (67 mg, 0.19 mmol) and 2-diethylaminoethylamine.

$^1$H-NMR Spectrum (DMSO-$d_6$) δ (ppm): 0.80–1.00 (6H, m), 2.20–2.50 (6H, m), 3.00–3.20 (2H, m), 6.74 (1H, s), 6.84 (1H, d, J=3.6 Hz), 7.03 (1H, d, J=8.0 Hz), 7.20 (2H, t, J=8.8 Hz), 7.50–7.70 (3H, m), 7.70 (1H, d, J=8.0 Hz), 8.00 (1H, s), 8.12 (1H, d, J=3.6 Hz), 8.37 (1H, s), 9.23 (1H, s), 9.41 (1H, s), 10.12 (1H, s).

Example 167

N1-Dimethyl-6-(6-((4-(pyrrolidin-1-yl)piperidin-1-yl)carbonyl)aminopyrimidin-4-yl)amino-1H-1-indolecarboxamide Similarly to Example 28, the title compound (16.1 mg, 0.034 mmol, 17%) was obtained as pale yellow powder from N1-dimethyl-6-(6-aminopyrimidin-4-yl)amino-1H-1-indolecarboxamide (58 mg, 0.20 mmol) and 4-(pyrrolidin-1-yl)piperidine.

$^1$H-NMR Spectrum (DMSO-$d_6$) δ (ppm): 1.20–1.36 (2H, m), 1.60–1.70 (4H, m), 1.70–1.85 (2H, m), 2.40–2.60 (5H, m), 2.80–3.00 (2H, m), 3.02 (6H, s), 3.90–4.10 (2H, m), 6.55 (1H, s), 7.26 (1H, s), 7.30 (1H, d, J=8.0 Hz), 7.40–7.50 (2H, m), 8.01 (1H, s), 8.29 (1H, s), 9.16 (1H, s), 9.41 (1H, s).

The starting material was synthesized by the following method.

Production Example 167-1

N1-Dimethyl-6-(6-aminopyrimidin-4-yl)amino-1H-1-indolecarboxamide

Similarly to Production example 2-3, the title compound (58.3 mg, 0.20 mmol, 25%) was obtained as pale brown crystals from 6-amino-4-(1H-6-indolylamino)pyrimidine (175 mg, 0.78 mmol) and phenyl N,N-dimethylcarbamate.

$^1$H-NMR Spectrum (DMSO-$d_6$) δ (ppm): 3.01 (6H, s), 5.72 (1H, s), 6.26 (2H, brs), 6.54 (1H, d, J=3.6 Hz), 7.24 (1H, dd, J=2.0, 8.0 Hz), 7.40–7.50 (2H, m), 7.84 (1H, s), 8.01 (1H, s), 8.86 (1H, s).

Example 168

N1-Diethyl-5-(2-((pyrrolidin-1-ylamino)carbonyl)aminopyrimidin-4-yl)amino-1H-1-indolecarboxamide Similarly to Example 28, the title compound (91.0 mg, 0.22 mmol, 38%) was obtained as pale yellow powder from N1-diethyl-5-(2-aminopyrimidin-4-yl)amino-1H-1-indolecarboxamide (186 mg, 0.57 mmol) and pyrrolidine.

$^1$H-NMR Spectrum (DMSO-$d_6$) δ (ppm): 1.15 (6H, t, J=6.8 Hz), 1.60–1.90 (4H, m), 3.20–3.50 (8H, m), 6.28 (1H, d, J=6.0 Hz), 6.52 (1H, d, J=3.6 Hz), 7.40–7.50 (3H, m), 7.96 (1H, d, J=6.0 Hz), 8.24 (1H, brs), 8.67 (1H, s), 9.35 (1H, s).

The starting materials were synthesized by the following methods.

Production Example 168-1

2-Amino-4-(1H-5-indolylamino)pyrimidine

A mixture of 2-amino-4,6-dichloropyrimidine (1.64 g, 10 mmol), 5-aminoindole (1.32 g, 10 mmol), diisopropylethylamine (5.23 ml, 30 mmol) and N,N-dimethylformamide (30 ml) was heated at 60° C. and stirred overnight under nitrogen atmosphere. The reaction mixture was partitioned between ethyl acetate and water after cooled to room temperature; and the organic layer was washed with water and brine, and dried over anhydrous sodium sulfate. The solvent was distilled off; the obtained residue was dissolved in tetrahydrofuran (100 ml); 10% Palladium on carbon (50% wet, 1.0 g) was added thereto under nitrogen atmosphere; and the reaction mixture was stirred for 4 days under hydrogen atmosphere at atmospheric pressure. The reaction system was purged with nitrogen; the catalyst was filtered off; the filtrate was concentrated under reduced pressure; the residue was purified by NH silica gel column chromatography (eluent; ethyl acetate:methanol=95:5); diethyl ether was added to the residue to crystallize; and the crystals were filtered off, and dried under aeration to yield the title compound (852 mg, 3.8 mmol, 38%) as pale brown crystals.

¹H-NMR Spectrum (DMSO-d₆) δ (ppm): 5.89 (1H, d, J=5.6 Hz), 5.99 (2H, brs), 6.34 (1H, s), 7.12 (1H, d, J=8.4 Hz), 7.20–7.40 (2H, m), 7.70 (1H, d, J=5.6 Hz), 7.79 (1H, s), 8.73 (1H, s), 10.95 (1H, s).

Production Example 168-2

N1-Diethyl-5-(2-aminopyrimidin-4-yl)amino-1H-1-indolecarboxamide

Similarly to Production example 2-3, the title compound (1.22 g, 3.8 mmol, quantitative) was obtained as pale brown powder from 2-amino-4-(1H-5-indolylamino)pyrimidine (852 mg, 3.8 mmol) and diethylcarbamyl chloride.

¹H-NMR Spectrum (CDCl₃) δ (ppm): 1.26 (6H, t, J=7.2 Hz), 3.49 (4H, q, J=7.2 Hz), 4.78 (2H, brs), 6.03 (1H, d, J=5.6 Hz), 6.57 (1H, d, J=3.6 Hz), 6.66 (1H, s), 7.16 (1H, dd, J=2.0, 8.8 Hz), 7.31 (1H, d, J=3.6 Hz), 7.53 (1H, d, J=2.0 Hz), 7.65 (1H, d, J=8.8 Hz), 7.88 (1H, d, J=5.6 Hz).

Example 169

N1-Diethyl-5-(5-iodo-2-((pyrrolidin-1-ylamino)carbonyl)aminopyrimidin-4-yl)amino-1H-1-indolecarboxamide Similarly to Example 28, the title compound (37.3 mg, 0.068 mmol, 26%) was obtained as white powder from N1-diethyl-5-(2-amino-5-iodopyrimidin-4-yl)amino-1H-1-indolecarboxamide (117 mg, 0.26 mmol) and pyrrolidine.

¹H-NMR Spectrum (DMSO-d₆) δ (ppm): 1.15 (6H, t, J=6.8 Hz), 1.60–1.80 (4H, m), 3.30–3.50 (8H, m), 6.54 (1H, s), 7.30–7.60 (3H, m), 8.09 (1H, s), 8.15 (1H, s), 8.33 (1H, s), 8.82 (1H, s).

The starting material was synthesized by the following method.

Production Example 169-1

N1-Diethyl-5-(2-amino-5-iodopyrimidin-4-yl)amino-1H-1-indolecarboxamide

N1-Diethyl-5-(2-aminopyrimidin-4-yl)amino-1H-1-indolecarboxamide (1.06 g, 3.27 mmol) was dissolved in N,N-dimethylformamide (10 ml) under nitrogen atmosphere; N-iodosuccinimide (920 mg, 4.08 mmol) was added thereto while cooling with an ice water bath; and the reaction mixture was stirred at room temperature overnight. The reaction mixture was partitioned between ethyl acetate and water; and the organic layer was washed with water and brine, and dried over anhydrous sodium sulfate. The solvent was distilled off; and the residue was purified by silica gel column chromatography (eluent; ethyl acetate) to yield the title compound (1.00 g, 2.33 mmol, 68%) as yellow powder.

¹H-NMR Spectrum (CDCl₃) δ (ppm): 1.26 (6H, t, J=7.2 Hz), 3.49 (4H, q, J=7.2 Hz), 4.84 (2H, brs), 6.58 (1H, d, J=3.6 Hz), 6.95 (1H, s), 7.27–7.40 (2H, m), 7.63 (1H, d, J=8.8 Hz), 7.82 (1H, s), 8.16 (1H, s).

Example 170

N1-Diethyl-5-(5-cyano-2-((pyrrolidin-1-ylamino)carbonyl)aminopyrimidin-4-yl)amino-1H-1-indolecarboxamide Similarly to Example 28, the title compound (35.3 mg, 0.079 mmol, 28%) was obtained as white crystals from N1-diethyl-5-(2-amino-5-cyanopyrimidin-4-yl)amino-1H-1-indolecarboxamide (100 mg, 0.29 mmol) and pyrrolidine.

¹H-NMR Spectrum (DMSO-d₆) δ (ppm): 1.15 (6H, t, J=6.8 Hz), 1.60–1.80 (4H, m), 3.20–3.50 (8H, m), 6.56 (1H, s), 7.40–7.60 (3H, m), 8.03 (1H, s), 8.49 (1H, s), 9.43 (1H, s), 9.50 (1H, s).

The starting material was synthesized as follows.

Production Example 170-1

N1-Diethyl-5-(2-amino-5-cyanopyrimidin-4-yl)amino-1H-1-indolecarboxamide

N1-Diethyl-5-(2-amino-5-iodopyrimidin-4-yl)amino-1H-1-indolecarboxamide (882 mg, 1.96 mmol) was dissolved in N,N-dimethylformamide (10 ml) under nitrogen atmosphere; zinc cyanide (253 mg, 2.15 mmol) and tetrakis(triphenylphosphine)palladium (226 mg, 0.2 mmol) was added thereto; the reaction mixture was stirred at 100° C. for 2 hours. The reaction mixture was partitioned between ethyl acetate and water; and the organic layer was washed with water and brine, and dried over anhydrous sodium sulfate. The solvent was distilled off; and the residue was purified by silica gel column chromatography (eluent; ethyl acetate) to yield the title compound (493 mg, 1.41 mmol, 72%) as white crystals.

¹H-NMR Spectrum (CDCl₃) δ (ppm): 1.26 (6H, t, J=7.2 Hz), 3.49 (4H, q, J=7.2 Hz), 5.26 (2H, brs), 6.59 (1H, d, J=3.6 Hz), 7.05 (1H, s), 7.27–7.35 (2H, m), 7.66 (1H, d, J=8.8 Hz), 7.78 (1H, m), 8.27 (1H, s).

Example 171

5-(2-(3-Ethylureido)pyridin-4-yloxy)indole-1-carboxylic acid (2-diethylaminoethyl)amide Similarly to Production example 5-1, a crude product of 5-(2-aminopyridin-4-yloxy)indole-1-carboxylic acid (2-diethylaminoethyl)amide (81 mg) was obtained as a pale yellow oil from 4-(1H-5-indolyloxy)-2-pyridinamine (225 mg, 1.00 mmol, WO 02/32872), sodium hydride (80 mg, 2.00 mmol, 60% in oil), and phenyl N-(2-diethylaminoethyl)carbamate (314 mg, 1.50 mmol). Similarly to Production example 5-2, a mixture of phenyl(4-(1-(2-diethylaminoethyl)carbamoyl-1H-indol-5-yloxy)pyridin-2-yl)-N-(phenoxycarbonyl)carbamate and phenyl(4-(1-(2-diethylaminoethyl)carbamoyl-1H-indol-5-yloxy)pyridin-2-yl)carbamate (32 mg) was obtained as a pale yellow oil from the crude product obtained above, phenyl chloroformate (0.041 ml, 0.33 mmol) and triethylamine (0.049 ml, 0.35 mmol). Similarly to Example 5, the title compound (11 mg, 0.025 mmol, 12%) was obtained as pale yellow crystals from the mixture obtained above, ethylamine hydrochloride (30 mg, 0.26 mmol) and triethylamine (0.5 ml).

¹H-NMR Spectrum (DMSO-d₆) δ (ppm): 0.97 (6H, t, J=7.0 Hz), 1.02 (3H, t, J=7.0 Hz), 2.44–2.60 (8H, m), 3.10 (2H, m), 6.50 (1H, dd, J=1.6, 6.0 Hz), 6.68 (1H, d, J=3.6 Hz), 6.86 (1H, d, J=1.6 Hz), 7.03 (1H, dd, J=2.0, 8.8 Hz), 7.36 (1H, d, J=2.0 Hz), 7.89 (1H, d, J=3.6 Hz), 7.97 (1H, m), 8.02 (1H, d, J=6.0 Hz), 8.17 (1H, m) 8.28 (1H, d, J=8.8 Hz), 9.00 (1H, s).

ESI-MS: 439.30 (M+H).

The starting material was synthesized as follows.

Production Example 171-1

Phenyl N-(2-diethylaminoethyl)carbamate

Similarly to Production example 2-1, a crude product was obtained from 2-diethylaminoethylamine (7.3 ml, 50 mmol) and phenyl chloroformate (6.9 ml, 55 mmol). The crude product was purified by silica gel column chromatography (Fuji Silysia NH, ethyl acetate), and further purified by silica gel column chromatography (Fuji Silysia NH; hexane:ethyl acetate=3:1, 1:1, ethyl acetate in this order) to yield the title compound (1.3 g, 6.4 mmol, 13%) as a colorless oil.

$^1$H-NMR Spectrum (CDCl$_3$) δ (ppm): 1.04 (6H, t, J=7.2 Hz), 2.52–2.62 (6H, m), 3.31 (2H, q, J=5.6 Hz), 5.62 (1H, brs), 7.13 (2H, d, J=7.6 Hz), 7.18 (1H, t, J=7.6 Hz), 7.35 (2H, t, J=7.6 Hz).

Example 172

5-(2-(3,3-Diethylureido)pyridin-4-yloxy)indole-1-carboxylic acid (2-ethoxyethyl)amide Similarly to Production example 5-2, a mixture of phenyl (4-(1-(2-ethoxyethyl)carbamoyl-1H-indol-5-yloxy)pyridin-2-yl)-N-(phenoxycarbonyl)carbamate and phenyl(4-(1-(2-ethoxyethyl)carbamoyl-1H-indol-5-yloxy)pyridin-2-yl)carbamate (3.42 g) was obtained as a pale yellow oil from 5-(2-aminopyridin-4-yloxy)indole-1-carboxylic acid (2-ethoxyethyl)amide (1.86 g, 5.46 mmol), phenyl chloroformate (1.51 ml, 12.0 mmol) and triethylamine (1.90 ml, 13.7 mmol). Similarly to Example 5, the title compound was obtained as pale pink crystals (84 mg, 0.19 mmol) from this intermediates (174 mg) and diethylamine (0.16 ml, 1.5 mmol).

$^1$H-NMR Spectrum (DMSO-d$_6$) δ (ppm): 1.01 (6H, t, J=7.2 Hz), 1.11 (3H, t, J=7.2 Hz), 3.26–3.31 (4H, m), 3.42–3.50 (4H, m), 3.53 (2H, m), 6.54 (1H, dd, J=2.4, 5.6 Hz), 6.68 (1H, d, J=3.6 Hz), 7.04 (1H, dd, J=2.4, 9.0 Hz), 7.36 (1H, d, J=2.4 Hz), 7.41 (1H, d, J=2.4 Hz), 7.93 (1H, d, J=3.6 Hz), 8.06 (1H, d, J=5.6 Hz), 8.28 (1H, d, J=9.0 Hz), 8.31 (1H, m), 8.60 (1H, s).

ESI-MS: 440.47 (M+H).

The starting materials were synthesized as follows.

Production Example 172-1

Phenyl N-(2-ethoxyethyl)carbamate

Similarly to Example 5, a crude product was obtained from 2-ethoxyethylamine (5.2 ml, 50 mmol), phenyl chloroformate (6.9 ml, 55 mmol), and pyridine (4.5 ml, 55 mmol). The obtained crude product was purified by silica gel column chromatography (Fuji Silysia BW-300, hexane:ethyl acetate=85:15 to 50:50) to yield the title compound (8.38 g, 40.4 mmol, 80.9%) as a pale yellow oil.

$^1$H-NMR Spectrum (CDCl$_3$) δ (ppm): 1.23 (3H, t, J=7.0 Hz), 3.44–3.48 (2H, m), 3.52–3.58 (4H, m), 5.41 (1H, brs), 7.13 (2H, d, J=7.6 Hz), 7.19 (1H, t, J=7.6 Hz), 7.35 (2H, t, J=7.6 Hz).

Production Example 172-2

5-(2-Aminopyridin-4-yloxy)indole-1-carboxylic acid (2-ethoxyethyl)amide

Similarly to Production example 5-1, the title compound (1.86 g, 5.46 mmol, 61.5%) was obtained as a pale brown oil from 4-(1H-5-indolyloxy)-2-pyridinamine (2.00 g, 8.88 mmol, WO 02/32872), sodium hydride (462 mg, 11.5 mmol, 60% in oil), and phenyl N-(2-ethoxyethyl)carbamate (2.23 g, 10.7 mmol).

$^1$H-NMR Spectrum (DMSO-d$_6$) δ (ppm): 1.11 (3H, t, J=7.2 Hz), 3.42 (2H, m), 3.47 (2H, q, J=7.2 Hz), 3.53 (2H, t, J=6.0 Hz), 5.74 (1H, d, J=2.0 Hz), 5.84 (2H, m), 6.12 (1H, dd, J=2.0, 6.0 Hz), 6.67 (1H, d, J=3.8 Hz), 7.01 (1H, dd, J=2.0, 8.8 Hz), 7.33 (1H, d, J=2.0 Hz), 7.75 (1H, d, J=6.0 Hz), 7.91 (1H, d, J=6.0 Hz), 8.26 (1H, d, J=8.8 Hz), 8.28 (1H, m).

Example 173

5-(2-(3-Ethylureido)pyridin-4-yloxy)indole-1-carboxylic acid (2-ethoxyethyl)amide A mixture (3.42 g) of phenyl(4-(1-(2-ethoxyethyl)carbamoyl-1H-indol-5-yloxy)pyridin-2-yl)-N-(phenoxycarbonyl)carbamate and phenyl(4-(1-(2-ethoxyethyl)carbamoyl-1H-indol-5-yloxy)pyridin-2-yl)carbamate, which was obtained as an intermediate in Example 172, was obtained. Similarly to Example 5, the title compound was obtained as colorless crystals (84 mg, 0.204 mmol) from a mixture of these intermediates (174 mg), ethylamine hydrochloride (122 mg, 1.50 mmol) and triethylamine (0.5 ml).

$^1$H-NMR Spectrum (DMSO-d$_6$) δ (ppm): 1.02 (3H, t, J=7.0 Hz), 1.12 (3H, t, J=7.0 Hz), 3.10 (2H, m), 3.40–3.49 (4H, m), 3.53 (2H, t, J=5.8 Hz), 6.50 (1H, dd, J=2.4, 5.8 Hz), 6.68 (1H, d, J=3.6 Hz), 6.86 (1H, d, J=2.4 Hz), 7.04 (1H, dd, J=2.4, 8.8 Hz), 7.37 (1H, d, J=2.4 Hz), 7.93 (1H, d, J=3.6 Hz), 7.96 (1H, m), 8.02 (1H, d, J=5.8 Hz), 8.28 (1H, d, J=8.8 Hz), 8.31 (1H, m), 9.00 (1H, s).

ESI-MS: 412.18 (M+H).

Example 174

5-(2-(3-Ethylureido)pyridin-4-yloxy)indole-1-carboxylic acid (3-ethoxypropyl)amide Similarly to Production example 5-2, a mixture of phenyl (4-(1-(3-ethoxypropyl)carbamoyl-1H-indol-5-yloxy)pyridin-2-yl)-N-(phenoxycarbonyl)carbamate and phenyl(4-(1-(3-ethoxypropyl)carbamoyl-1H-indol-5-yloxy)pyridin-2-yl)carbamate was obtained as a pale brown oil (720 mg) from 5-(2-Aminopyridin-4-yloxy)indole-1-carboxylic acid (3-ethoxypropyl)amide (900 mg, 2.54 mmol), phenyl chloroformate (0.669 ml, 5.33 mmol) and triethylamine (0.885 ml, 6.35 mmol). Similarly to Example 5, the title compound was obtained as pale pink crystals (41 mg, 0.096 mmol) from this intermediate (174 mg) ethylamine hydrochloride (122 mg, 1.50 mmol) and triethylamine (0.5 ml).

$^1$H-NMR Spectrum (DMSO-d$_6$) δ (ppm): 1.02 (3H, t, J=7.2 Hz), 1.10 (3H, t, J=7.2 Hz), 1.79 (2H, m), 3.10 (2H, m), 3.34 (2H, m), 3.42 (4H, m), 6.50 (1H, dd, J=2.4, 5.8 Hz), 6.67 (1H, d, J=3.8 Hz), 6.86 (1H, d, J=2.4 Hz), 7.03 (1H, dd, J=2.4, 9.2 Hz), 7.36 (1H, d, J=2.4 Hz), 7.90 (1H, d, J=3.8 Hz), 7.95 (1H, m), 8.02 (1H, d, J=5.8 Hz), 8.20 (1H, m), 8.28 (1H, m), 8.99 (1H, s).

ESI-MS: 426.39 (M+H).

The starting material was synthesized as follows.

Production Example 174-1

5-(2-Aminopyridin-4-yloxy)indol-1-carboxylic acid (3-ethoxypropyl)amide

Similarly to Production example 5-1, the title compound (900 mg, 2.54 mmol, 57.2%) was obtained as a pale brown oil from 4-(1H-5-indolyloxy)-2-pyridinamine (1.00 g, 4.44 mmol, WO 02/32872), sodium hydride (213 mg, 5.33 mmol, 60% in oil), and phenyl N-(3-ethoxypropyl)carbamate (1.19 g, 5.33 mmol, WO 02/32872).

$^1$H-NMR Spectrum (DMSO-$d_6$) δ (ppm): 1.07–1.13 (3H, m), 1.81 (2H, m), 3.33–3.47 (6H, m), 5.76 (1H, d, J=2.4 Hz), 5.85 (2H, s), 6.14 (1H, dd, J=2.4, 6.0 Hz), 6.68 (1H, d, J=3.6 Hz), 7.03 (1H, dd, J=2.4, 8.8 Hz), 7.34 (1H, d, J=2.4 Hz), 7.77 (1H, d, J=6.0 Hz), 7.90 (1H, d, J=3.6 Hz), 8.20 (1H, m), 8.27 (1H, d, J=8.8 Hz).

Example 175

5-(2-(3-Ethylureido)pyridin-4-yloxy)indole-1-carboxylic acid (3-methylsulphanylpropyl)amide Similarly to Production example 5-1, a crude product of 5-(2-aminopyridin-4-yloxy)indole-1-carboxylic acid (3-methylsulfanylpropyl)amide (105 mg) was obtained as a pale yellow oil from 4-(1H-5-indolyloxy)-2-pyridinamine (125 mg, 0.555 mmol, WO 02/32872), sodium hydride (28 mg, 0.694 mmol, 60% in oil), and phenyl N-(3-methylsulfanylpropyl)carbamate (156 mg, 0.694 mmol, WO 02/32872). Similarly to Production Example 5-2, a mixture of phenyl (4-(1-(3-methylsulfanylpropyl)carbamoyl-1H-indol-5-yloxy)pyridin-2-yl)-N-(phenoxycarbonyl)carbamate and phenyl(4-(1-(3-methylsulfanylpropyl)carbamoyl-1H-indol-5-yloxy)pyridin-2-yl)carbamate was obtained as a pale yellow oil from the crude product obtained above, phenyl chloroformate (0.10 ml, 0.76 mmol) and triethylamine (0.12 ml, 0.83 mmol). Similarly to Example 5, the title compound (17 mg, 0.040 mmol) was obtained as colorless crystals from the mixture obtained above, ethylamine hydrochloride (141 mg, 1.73 mmol) and triethylamine (0.5 ml).

$^1$H-NMR Spectrum (DMSO-$d_6$) δ (ppm): 1.02 (3H, t, J=7.2 Hz), 1.83 (2H, m), 2.05 (3H, s), 2.52 (2H, t, J=7.6 Hz), 3.10 (2H, m), 3.35 (2H, m), 6.50 (1H, d, J=5.6 Hz), 6.68 (1H, d, J=3.4 Hz), 6.86 (1H, s), 7.03 (1H, d, J=9.2 Hz), 7.36 (1H, s), 7.91 (1H, d, J=3.4 Hz), 7.94 (1H, m), 8.02 (1H, d, J=5.6 Hz), 8.24 (1H, m), 8.27 (1H, d, J=9.2 Hz), 8.99 (1H, s).

Example 176

5-(2-(3,3-Diethylureido)pyridin-4-yloxy)indole-1-carboxylic acid thiazol-2-ylamide Similarly to Production example 5-2, a mixture (267 mg) of phenyl(4-(1-(thiazol-2-yl)carbamoyl-1H-indol-5-yloxy)pyridin-2-yl)-N-(phenoxycarbonyl)carbamate and phenyl(4-(1-(thiazol-2-yl)carbamoyl-1H-indol-5-yloxy)pyridin-2-yl)carbamate was obtained as a pale yellow oil from 5-(2-aminopyridin-4-yloxy)indole-1-carboxylic acid thiazol-2-ylamide (145 mg, 0.413 mmol), phenyl chloroformate (0.110 ml, 0.909 mmol), and triethylamine (0.140 ml, 1.03 mmol). Similarly to Example 5, the title compound (74 mg, 0.16 mmol) was obtained as pale pink crystals from the intermediate obtained above (131 mg) and diethylamine (0.120 ml, 1.11 mmol).

$^1$H-NMR Spectrum (DMSO-$d_6$) δ (ppm): 1.01 (6H, t, J=6.8 Hz), 3.28 (4H, m), 6.56 (1H, dd, J=2.0, 5.6 Hz), 6.66 (1H, m), 7.06 (2H, m), 7.37 (1H, d, J=2.0 Hz), 7.43 (1H, s), 7.47 (1H, d, J=4.4 Hz), 8.05 (1H, m), 8.07 (1H, d, J=5.6 Hz), 8.60 (2H, m).

ESI-MS: 451.15 (M+H).

The starting material was synthesized as follows.

Production Example 176-1

5-(2-Aminopyridin-4-yloxy)indole-1-carboxylic acid thiazol-2-ylamide

Similarly to Production example 5-1, the title compound (145 mg, 0.413 mmol, 57.2%) was obtained as a pale brown oil from 4-(1H-5-indolyloxy)-2-pyridinamine (225 mg, 1.00 mmol, WO 02/32872), sodium hydride (120 mg, 3.00 mmol, 60% in oil) and phenyl N-(thiazol-2-yl)carbamate (286 mg, 1.30 mmol, WO 02/32872).

$^1$H-NMR Spectrum (DMSO-$d_6$) δ (ppm): 5.77 (1H, d, J=2.4 Hz), 5.87 (2H, brs), 6.15 (1H, dd, J=2.4, 5.6 Hz), 6.65 (1H, d, J=3.6 Hz), 7.03 (1H, dd, J=2.4, 9.0 Hz), 7.07 (1H, d, J=4.6 Hz), 7.34 (1H, d, J=2.4 Hz), 7.46 (1H, d, J=4.6 Hz), 7.77 (1H, d, J=5.6 Hz), 8.04 (1H, d, J=3.6 Hz), 8.58 (1H, d, J=9.0 Hz).

Example 177

5-(2-(3-Ethylureido)pyridin-4-yloxy)indole-1-carboxylic acid thiazol-2-ylamide Similarly to Example 5, the title compound (71 mg, 0.168 mmol) was obtained as colorless crystals from a mixture (135 mg) of phenyl(4-(1-(thiazol-2-yl)carbamoyl-1H-indol-5-yloxy)pyridin-2-yl)-N-(phenoxycarbonyl)carbamate and phenyl(4-(1-(thiazol-2-yl)carbamoyl-1H-indol-5-yloxy)pyridin-2-yl)carbamate obtained in Example 176, ethylamine hydrochloride (91 mg, 1.1 mmol), and triethylamine (0.5 ml).

$^1$H-NMR Spectrum (DMSO-$d_6$) δ (ppm): 1.07 (3H, t, J=7.2 Hz), 3.07–3.14 (2H, m), 6.51 (1H, dd, J=2.0, 6.0 Hz), 6.61 (1H, s), 7.01 (2H, m), 7.35 (1H, s), 7.41 (1H, m), 8.01–8.06 (3H, m), 8.05 (1H, m), 8.62 (1H, d, J=9.2 Hz), 9.00 (1H, s).

ESI-MS: 423.23 (M+H).

Example 178

1-Ethyl-3-(4-(1-((4-methylpiperazin-1-yl)carbonyl)-1H-indol-5-yloxy)pyridin-2-yl)urea Similarly to Production example 5-2, a mixture (1.09 g) of phenyl(4-(1-((4-methylpiperazin-1-yl)carbonyl)-1H-indol-5-yloxy)pyridin-2-yl)-(N-phenoxycarbonyl)carbamate and phenyl(4-(1-((4-methylpiperazin-1-yl)carbonyl)-1H-indol-5-yloxy)pyridin-2-yl)carbamate was obtained as a colorless amorphous solid from (5-(2-aminopyridin-4-yloxy)indol-1-yl)-(4-methylpiperazin-1-yl)methanone (0.66 g, 1.9 mmol), phenyl chloroformate (0.52 ml, 4.2 mmol), and triethylamine (0.66 ml, 4.8 mmol). Similarly to Example 5, the title compound (41 mg, 0.097 mmol) was obtained as colorless crystals from the intermediate obtained above (177 mg), ethylamine hydrochloride (0.122 g, 1.50 mmol) and triethylamine (0.5 ml).

$^1$H-NMR Spectrum (DMSO-$d_6$) δ (ppm): 1.03 (3H, t, J=6.0 Hz), 2.21 (3H, s), 2.39 (4H, m), 3.12 (2H, m), 3.51 (4H, m), 6.51 (1H, dd, J=2.4, 5.6 Hz), 6.67 (1H, d, J=3.4

Hz), 6.86 (1H, d, J=2.4 Hz), 7.04 (1H, dd, J=2.4, 8.8 Hz), 7.39 (1H, d, J=2.4 Hz), 7.61 (1H, d, J=3.4 Hz), 7.70 (1H, d, J=8.8 Hz), 8.02 (1H, m), 8.03 (1H, d, J=8.8 Hz), 9.00 (1H, s).

ESI-MS: 423.27 (M+H).

The starting materials were synthesized as follows.

Production Example 178-1

Phenyl(4-methylpiperazin-1-yl)carboxylate

Similarly to Production example 2-1, crystals were obtained from 1-methylpiperazine (5.5 ml, 50 mmol), phenyl chloroformate (6.9 ml, 55 mmol), and pyridine (4.5 ml, 55 mmol). The obtained crystals were suspended in diethylether:hexane=2:1, filtered off, washed with hexane, and dried to yield the title compound (9.7 g, 44 mmol, 88%) as an oil with pale orange color.

$^1$H-NMR Spectrum (DMSO-d$_6$) δ (ppm): 2.20 (3H, s), 2.34 (4H, m), 3.40 (2H, m), 3.56 (2H, m), 7.09 (2H, d, J=7.6 Hz), 7.20 (1H, t, J=7.6 Hz), 7.36 (2H, t, J=7.6 Hz).

Production Example 178-2

(5-(2-Aminopyridin-4-yloxy)indol-1-yl)-(4-methylpiperazin-1-yl)methanone

Similarly to Production example 5-1, a crude product was obtained from 4-(1H-5-indolyloxy)-2-pyridinamine (2.00 g, 8.88 mmol, WO 02/32872), sodium hydride (462 mg, 11.5 mmol, 60% in oil) and phenyl(4-methylpiperazin-1-yl)carboxylate (2.35 g, 10.7 mmol). The obtained crude product was purified by silica gel column chromatography (Fuji Silysia NH; hexane:ethyl acetate=3:7, ethyl acetate, ethyl acetate:methanol=9:1 in this order) to yield the title compound (0.66 g, 1.9 mmol, 21%) as a colorless amorphous solid.

$^1$H-NMR Spectrum (DMSO-d$_6$) δ (ppm): 2.20 (3H, s), 2.39 (4H, m), 3.51 (4H, m), 5.75 (1H, d, J=2.0 Hz), 5.84 (2H, m), 6.13 (1H, dd, J=2.0, 6.0 Hz), 6.66 (1H, d, J=3.2 Hz), 7.02 (1H, dd, J=2.4, 8.8 Hz), 7.36 (1H, d, J=2.4 Hz), 7.59 (1H, d, J=3.2 Hz), 7.68 (1H, d, J=8.8 Hz), 7.76 (1H, d, J=6.0 Hz).

Example 179

1-Ethyl-3-(4-(1-(morpholin-4-ylcarbonyl)-1H-indol-5-yloxy)pyridin-2-yl)urea

Similarly to Production example 5-2, a crude product was obtained from 5-(2-aminopyridin-4-yloxy)indol-1-yl)-(morpholin-4-yl)methanone (0.60 g, 1.8 mmol), phenyl chloroformate (0.49 ml, 3.9 mmol), and triethylamine (0.62 ml, 4.4 mmol). The obtained crude product was filtrated by silica gel filtration (Fuji Silysia BW-300, ethyl acetate) and concentrated under reduced pressure to yield a mixture (1.11 g) of phenyl(4-(1-(morpholin-4-ylcarbonyl)-1H-indol-5-yloxy) pyridin-2-yl)-N-(phenoxycarbonyl)carbamate and phenyl(4-(1-(morpholine-4-ylcarbonyl)-1H-indol-5-yloxy)pyridin-2-yl)carbamate as a pale yellow oil. Similarly to Example 5, the title compound (73 mg, 0.178 mmol) was obtained as colorless crystals from the intermediate obtained above (173 mg), ethylamine hydrochloride (122 mg, 1.50 mmol) and triethylamine (0.5 ml).

$^1$H-NMR Spectrum (DMSO-d$_6$) δ (ppm): 1.03 (3H, t, J=7.2 Hz), 3.07–3.14 (2H, m), 3.52 (4H, m), 3.68 (4H, m), 6.50 (1H, dd, J=2.4, 6.0 Hz), 6.68 (1H, d, J=3.2 Hz), 6.87 (1H, d, J=2.4 Hz), 7.05 (1H, dd, J=2.4, 8.8 Hz), 7.40 (1H, d, J=2.4 Hz), 7.64 (1H, d, J=3.2 Hz), 7.73 (1H, d, J=8.8 Hz), 8.00 (1H, m), 8.03 (1H, d, J=6.0 Hz), 9.01 (1H, s).

ESI-MS: 410.57 (M+H).

The starting materials were synthesized as follows.

Production Example 179-1

Phenyl(morpholin-4-yl)carboxylate

Similarly to Production example 2-1, a crude product was obtained from morpholine (4.4 ml, 50 mmol), phenyl chloroformate (6.9 ml, 55 mmol), and pyridine (4.5 ml, 55 mmol). The obtained crude product was purified by silica gel column chromatography (Fuji Silysia BW-300; hexane:ethyl acetate=85:15, 60:40 in this order) to yield the title compound (8.9 g, 43 mmol, 86%) as colorless crystals.

$^1$H-NMR Spectrum (CDCl$_3$) δ (ppm): 3.57 (2H, brs), 3.68 (2H, brs), 3.75 (4H, m), 7.11 (2H, d, J=7.6 Hz), 7.21 (1H, t, J=7.6 Hz), 7.37 (2H, t, J=7.6 Hz).

Production Example 179-2

(5-(2-Aminopyridin-4-yloxy)indol-1-yl)-(morpholin-4-yl)methanone

Similarly to Production example 5-1, a crude product was obtained from 4-(1H-5-indolyloxy)-2-pyridinamine (2.00 g, 8.88 mmol, WO 02/32872), sodium hydride (462 mg, 11.5 mmol, 60% in oil) and phenyl (morpholin-4-yl)carboxylate (2.21 g, 10.7 mmol). The obtained crude product was purified by silica gel column chromatography (Fuji Silysia NH, hexane:ethyl acetate=2:3 or ethyl acetate), and further purified by silica gel column chromatography (Fuji Silysia BW-300, hexane:ethyl acetate=2:3, ethyl acetate, or ethyl acetate:methanol=9:1) to yield the title compound (0.60 g, 1.8 mmol, 20%) as colorless crystals.

$^1$H-NMR Spectrum (DMSO-d$_6$) δ (ppm): 3.52 (4H, m), 3.68 (4H, m), 5.77 (1H, d, J=2.4 Hz), 5.83 (2H, brs), 6.13 (1H, dd, J=2.4, 5.6 Hz), 6.67 (1H, d, J=3.2 Hz), 7.02 (1H, dd, J=2.4, 8.8 Hz), 7.36 (1H, d, J=2.4 Hz), 7.61 (1H, d, J=3.2 Hz), 7.71 (1H, d, J=8.8 Hz), 7.76 (1H, d, J=5.6 Hz).

Example 180

1,1-Diethyl-3-(4-(1-(morpholin-4-ylcarbonyl)-1H-indol-5-yloxy)pyridin-2-yl)urea

Similarly to Example 5, the title compound (85 mg, 0.194 mmol) was obtained as colorless crystals from a mixture (173 mg) of phenyl(4-(1-(morpholin-4-ylcarbonyl)-1H-indol-5-yloxy)pyridin-2-yl)-N-(phenoxycarbonyl)carbamate and phenyl(4-(1-(morpholin-4-ylcarbonyl)-1H-indol-5-yloxy)pyridin-2-yl)carbamate synthesized as intermediate in Example 179, and diethylamine (0.16 ml, 1.50 mmol).

$^1$H-NMR Spectrum (DMSO-d$_6$) δ (ppm): 1.01 (6H, t, J=6.8 Hz), 3.30 (4H, m), 3.53 (4H, m), 3.68 (4H, m), 6.54 (1H, d, J=6.0 Hz), 6.68 (1H, d, J=3.4 Hz), 7.05 (1H, dd, J=2.0, 8.8 Hz), 7.39 (1H, d, J=2.0 Hz), 7.43 (1H, s), 7.64 (1H, d, J=3.4 Hz), 7.73 (1H, d, J=8.8 Hz), 8.07 (1H, d, J=6.0 Hz), 8.62 (1H, s).

ESI-MS: 438.25 (M+H).

Example 181

5-(2-(3-Ethylureido)pyridin-4-yloxy)indole-1-carboxylic acid piperidin-4-ylamide Similarly to Production example 5-1, a crude product of t-butyl 4-((5-(2-aminopyridin-4-yloxy)indole-1-carbonyl)amino)piperidine-1-carboxylate was obtained from 4-(1H-5-indolyloxy)-2-pyridinamine (144 mg, 0.639 mmol, WO 02/32872), sodium hydride (29 mg, 0.735 mmol, 60% in oil), and t-butyl(4-phenoxycarbonylaminopiperidin-1-yl)carboxylate (215 mg, 0.671 mmol). A reaction similar to Production example 5-2 was performed using the entire amount of this crude product, phenyl chloroformate (0.20 ml, 1.6 mmol) and triethylamine (0.22 ml); and the solvent was distilled off under reduced pressure after the reaction was completed. A reaction similar to Example 5 was performed using the entire amount of the residue, ethylamine hydrochloride (260 mg, 3.92 mmol) and triethylamine (0.5 ml); the organic layer was partitioned between ethyl acetate and water, washed with brine, and dried over anhydrous sodium sulfate; and the solvent was distilled off under reduced pressure. The residue was dissolved in trifluoroacetate (3.0 ml); the reaction mixture was stirred at room temperature for 15 minutes, and concentrated; and the residue was partitioned between ethyl acetate and water. The organic layer was washed with brine and dried over anhydrous sodium sulfate; the solvent was distilled off under reduced pressure; the residue was purified by silica gel column chromatography (Fuji Silysia NH, ethyl acetate:methanol=98:2 to 75:25). The obtained crystals were suspended in diethyl ether and filtered off, washed with diethyl ether, and dried to yield the title compound (43 mg, 0.10 mmol, 16%) as colorless crystals.

$^1$H-NMR Spectrum (DMSO-$d_6$) δ (ppm): 1.02 (3H, t, J=7.2 Hz), 1.37–1.49 (2H, m), 1.80 (2H, m), 2.48 (2H, m), 2.95 (2H, m), 3.10 (2H, m), 3.71 (1H, m), 6.50 (1H, dd, J=2.4, 6.0 Hz), 6.66 (1H, d, J=3.4 Hz), 6.86 (1H, d, J=2.4 Hz), 7.03 (1H, dd, J=2.4, 8.8 Hz), 7.36 (1H, d, J=2.4 Hz), 7.90–8.01 (3H, m), 8.02 (1H, d, J=6.0 Hz), 8.26 (1H, d, J=8.8 Hz), 8.99 (1H, s).

ESI-MS: 423.26 (M+H).

The starting material was synthesized as follows.

Production Example 181-1 t-Butyl(4-phenoxycarbonylaminopiperidin-1-yl)carboxylate

A reaction similar to Production example 2-1 using t-Butyl 4-aminopiperidin-1-ylcarboxylate (328 mg, 1.64 mmol), phenyl chloroformate (0.226 ml, 1.80 mmol) and pyridine (0.146 ml, 1.80 mmol); and the obtained crystals were suspended in hexane:ethyl acetate=4:1, filtered off, and the filtrate was purified by silica gel column chromatography (Fuji Silysia BW-300, hexane:ethyl acetate=4:1 to 1:1). The purified crystals were then suspended in hexane:ethyl acetate=4:1 and filtered off. The title compound (215 mg, 0.617 mmol, 40.9%) was obtained as colorless crystals, together with the previously obtained crystals.

$^1$H-NMR Spectrum (DMSO-$d_6$) δ (ppm): 1.22–1.34 (2H, m), 1.38 (9H, s), 1.77 (2H, m), 2.83 (2H, m), 3.51 (1H, m), 3.84 (2H, m), 7.08 (2H, d, J=7.6 Hz), 7.18 (1H, t, J=7.6 Hz), 7.35 (2H, t, J=7.6 Hz), 7.78 (1H, d, J=8.0 Hz).

ESI-MS: 343.15 (M+Na).

Example 182

5-(2-(3-Ethylureido)pyridin-4-yloxy)indole-1-carboxylic acid (1-methylpiperidin-4-yl)amide 5-(2-(3-Ethylureido)pyridin-4-yloxy)indole-1-carboxylic acid piperidin-4-ylamide (36 mg, 0.085 mmol, Example 181) was dissolved in tetrahydrofuran (2.0 ml) and methanol (1.0 ml); and a 37% aqueous formaldehyde solution (0.036 ml, 0.43 mmol) and acetic acid (0.0098 ml, 0.17 mmol) were added thereto. While stirring at room temperature, sodium trimethoxyborohydride (27 mg, 0.13 mmol) was added; and the reaction mixture was stirred for 30 minutes. The reaction mixture was partitioned between ethyl acetate and a saturated aqueous solution of sodium hydrogencarbonate; and the organic layer was washed with brine and dried over anhydrous sodium sulfate. The solvent was distilled off under reduced pressure; the obtained crystals were suspended in diethyl ether, filtered off, washed with diethyl ether, and dried to yield the title compound (25 mg, 0.057 mmol, 67%) as colorless crystals.

$^1$H-NMR Spectrum (DMSO-$d_6$) δ (ppm): 1.02 (3H, t, J=7.2 Hz), 1.54–1.68 (2H, m), 1.83 (2H, m), 1.96 (2H, m), 2.16 (3H, s), 2.78 (2H, m), 3.10 (2H, m), 3.64 (1H, m), 6.50 (1H, dd, J=2.4, 6.0 Hz), 6.66 (1H, d, J=3.6 Hz), 6.86 (1H, d, J=2.4 Hz), 7.03 (1H, dd, J=2.4, 8.8 Hz), 7.36 (1H, d, J=2.4 Hz), 7.95 (1H, d, J=3.6 Hz), 7.97 (2H, m), 8.02 (1H, d, J=6.0 Hz), 8.25 (1H, d, J=8.8 Hz), 8.99 (1H, m).

ESI-MS: 437.37 (M+H).

Example 183

5-(2-(N-Methyl-(4-(pyrrolidin-1-yl)piperidin-1-yl)carbonyl)amino)pyridin-4-yloxy)indole-1-carboxylic acid methylamide 5-(2-(Methylamino)pyridin-4-yloxy)indole-1-carboxylic acid methylamide (70 mg, 0.24 mmol) was dissolved in tetrahydrofuran (7.0 ml); triethylamine (0.039 ml) and 4-nitrophenylchloroformate (57 mg, 0.28 mmol) were added thereto one by one; and the reaction mixture was stirred at room temperature for 2 hours. The reaction mixture was partitioned between ethyl acetate and water; and the organic layer was washed with a saturated aqueous solution of sodium hydrogencarbonate and brine, then dried over anhydrous sodium sulfate, and concentrated under reduced pressure. The residue was dissolved in N,N-dimethylformamide (2.0 ml); 4-(pyrrolidin-1-yl)piperidine (43 mg, 0.28 mmol) was added thereto; and the reaction mixture was stirred at room temperature for 24 hours. The reaction mixture was partitioned between ethyl acetate and water; and the organic layer was washed with brine, dried over anhydrous sodium sulfate, and concentrated under reduced pressure. The residue was purified by silica gel column chromatography (Fuji Silysia NH, hexane-ethyl acetate-methanol system); the obtained oil was solidified with hexane; the obtained solid was then suspended in hexane, filtered off, washed with hexane, and dried to yield the title compound (51 mg, 0.11 mmol, 45%) as pale yellow crystals.

$^1$H-NMR Spectrum (DMSO-$d_6$) δ (ppm): 1.13–1.30 (2H, m), 1.65 (6H, m), 2.02 (1H, m), 2.42 (4H, m), 2.72 (2H, m), 2.83 (3H, d, J=4.0 Hz), 3.08 (3H, s), 3.53 (2H, m), 6.23 (1H, s), 6.51 (1H, d, J=6.0 Hz), 6.66 (1H, d, J=3.4 Hz), 7.04 (1H, d, J=9.0 Hz), 7.36 (1H, s), 7.87 (1H, d, J=3.4 Hz), 8.11 (1H, d, J=6.0 Hz), 8.15 (1H, m), 8.29 (1H, d, J=9.0 Hz).

ESI-MS: 477.38 (M+H).

The starting material was synthesized as follows.

Production Example 183-1

5-(2-(Methylamino)pyridin-4-yloxy)indole-1-carboxylic acid methylamide

N1-Methyl-5-(2-aminopyridin-4-yl)oxy-1H-1-indolecarboxamide (5.00 g, 17.7 mmol, Production example 5-1) was dissolved in ethanol (170 ml) and N,N-dimethylformamide (40 ml); 1H-benzotriazole-1-methanol (2.64 g, 17.7 mmol) was added thereto; and the reaction mixture was heated to reflux for 2 hours. After allowing to be cooled to room temperature, sodium borohydride (1.49 g, 35.4 mmol) was added to the reaction mixture; the reaction mixture was stirred at room temperature for 2 hours. The reaction mixture was partitioned between ethyl acetate and water; and the organic layer was washed with brine, dried over anhydrous sodium sulfate, and concentrated under reduced pressure. The residue was purified by silica gel column chromatography (Fuji Silysia BW-300, hexane-ethyl acetate-methanol system). The obtained crystals were suspended in acetone: diethyl ether=1:3, filtered off, washed with hexane, and dried to yield the title compound (1.05 g, 3.55 mmol, 20.1%) as pale yellow crystals.

$^1$H-NMR Spectrum (DMSO-$d_6$) δ (ppm): 2.66 (3H, d, J=4.8 Hz), 2.82 (3H, d, J=4.0 Hz), 5.76 (1H, d, J=2.0 Hz), 6.10 (1H, dd, J=2.0, 6.0 Hz), 6.36 (1H, m), 6.65 (1H, d, J=4.0 Hz), 7.00 (1H, dd, J=2.4, 8.8 Hz), 7.31 (1H, d, J=2.4 Hz), 7.83 (2H, m), 8.13 (1H, m), 8.26 (1H, d, J=8.8 Hz).

Example 184

5-(2-(1-Methylureido)pyridin-4-yloxy)indole-1-carboxylic acid methylamide

4-Nitrophenyl N-methyl-(4-(1-methylcarbamoyl-indol-5-yloxy)pyridin-2-yl)carbamate (105 mg, 0.228 mmol) was dissolved in N,N-dimethylformamide (2.5 ml); aqueous ammonia (0.5 ml, 28.0%) was added thereto; the reaction mixture was stirred at room temperature for 10.5 hours. The reaction mixture was partitioned between ethyl acetate and water; and the organic layer was washed with brine, dried over anhydrous sodium sulfate, and concentrated under reduced pressure. The obtained crystals were suspended in ethanol: diethyl ether=1:1 (6 ml), filtered off, washed with diethyl ether, and dried to yield the title compound (37 mg, 0.11 mmol, 48%) as pale yellow crystals.

$^1$H-NMR Spectrum (DMSO-$d_6$) δ (ppm): 2.83 (3H, d, J=4.0 Hz), 3.19 (3H, s), 6.51 (1H, d, J=5.6 Hz), 6.67 (1H, d, J=3.6 Hz), 6.84 (1H, s), 7.07 (1H, d, J=9.0 Hz), 7.39 (1H, s), 7.87 (1H, d, J=3.6 Hz), 8.14 (2H, m), 8.29 (1H, d, J=9.0 Hz).

ESI-MS: 340.07 (M+H).

The starting material was synthesized as follows.

Production Example 184-1

4-Nitrophenyl N-methyl-(4-(1-methylcarbamoyl-indol-5-yloxy)pyridin-2-yl)carbamate 5-(2-(Methylamino)pyridin-4-yloxy)indole-1-carboxylic acid methylamide (200 mg, 0.675 mmol) synthesized in Production example 183-1 was dissolved in tetrahydrofuran (20 ml); triethylamine (0.100 ml, 0.742 mmol) and 4-nitrophenylchloroformate (150 mg, 0.742 mmol) was added thereto one by one; and the reaction mixture was stirred at room temperature for 2 hours. The reaction mixture was partitioned between ethyl acetate and water; and the organic layer was washed with a saturated aqueous solution of sodium hydrogencarbonate and with brine, dried over anhydrous sodium sulfate, and concentrated under reduced pressure. The residue was purified by silica gel column chromatography (Fuji Silysia BW-300, hexane-ethyl acetate system) to yield the title compound (210 mg, 0.455 mmol, 67.4%) as a pale yellow oil.

$^1$H-NMR Spectrum (DMSO-$d_6$) δ (ppm): 2.82 (3H, d, J=4.4 Hz), 3.46 (3H, s), 6.62 (1H, d, J=3.6 Hz), 6.83 (1H, dd, J=2.0, 5.6 Hz), 7.03 (1H, dd, J=2.0, 8.4 Hz), 7.24 (1H, d, J=2.0 Hz), 7.37 (1H, d, J=2.0 Hz), 7.41 (2H, d, J=9.2 Hz), 7.85 (1H, d, J=3.6 Hz), 8.14 (1H, m), 8.22 (2H, d, J=9.2 Hz), 8.23 (1H, d, J=8.4 Hz), 8.32 (1H, d, J=5.6 Hz).

Example 185

5-(2-(3,3-Diethyl-1-methylureido)pyridin-4-yloxy)indole-1-carboxylic acid methylamide Similarly to Example 184, the title compound (14 mg, 0.035 mmol, 16%) was obtained as a colorless amorphous solid from 4-nitrophenyl N-methyl-(4-(1-methylcarbamoyl-indol-5-yloxy)pyridin-2-yl)carbamate (105 mg, 0.228 mmol, Production example 184-1) and diethylamine (0.028 ml, 0.27 mmol).

$^1$H-NMR Spectrum (DMSO-$d_6$) δ (ppm): 0.80 (6H, t, J=6.4 Hz), 2.83 (3H, d, J=3.2 Hz), 3.03 (3H, s), 3.07 (4H, m), 6.11 (1H, s), 6.49 (1H, m), 6.66 (1H, s), 7.02 (1H, d, J=9.0 Hz), 7.35 (1H, s), 7.86 (1H, s), 8.09 (1H, d, J=5.6 Hz), 8.15 (1H, m), 8.28 (1H, d, J=9.0 Hz).

ESI-MS: 396.18 (M+H).

Example 186

5-(2-(3-Ethyl-1-methylureido)pyridin-4-yloxy)indole-1-carboxylic acid methylamide Similarly to Production example 27-2, phenyl N-methyl-(4-(1-methylcarbamoyl-indol-5-yloxy)pyridin-2-yl)carbamate (324 mg, 0.778 mmol) was obtained as a colorless amorphous solid from 5-(2-(methylamino)pyridin-4-yloxy)indole-1-carboxylic acid methylamide (500 mg, 1.69 mmol), phenyl chloroformate (0.23 ml, 1.9 mmol) and triethylamine (0.26 ml, 1.9 mmol). This intermediate (125 mg, 0.300 mmol) was dissolved in N,N-dimethylformamide (2.5 ml)-triethylamine (0.5 ml); ethylamine hydrochloride (122 mg, 1.50 mmol) was added thereto; and the reaction mixture was stirred at room temperature overnight, and then stirred at 80° C. for 1.5 hours. Ethylamine hydrochloride (122 mg, 1.50 mmol) was added thereto; the reaction mixture was stirred at 80° C. for 2 hours; ethylamine hydrochloride (122 mg, 1.50 mmol) and triethylamine (0.5 ml) were further added thereto; and the reaction mixture was stirred at 80° C. for 0.5 hours, and then stirred at room temperature for 2 days. The reaction mixture was partitioned between ethyl acetate (100 ml) and water (50 ml); and the organic layer was washed with brine, dried over anhydrous sodium sulfate, and concentrated under reduced pressure. The residue was purified by silica gel column chromatography (Fuji Silysia BW-300, hexane:ethyl acetate=3:2, then ethyl acetate); the obtained crystals were suspended in diethyl ether (10 ml)-hexane (50 ml), filtered off, and dried to yield the title compound (41 mg, 0.11 mmol) as colorless crystals.

$^1$H-NMR Spectrum (DMSO-$d_6$) δ (ppm): 1.04 (3H, t, J=7.2 Hz), 2.83 (3H, d, J=4.4 Hz), 3.15 (2H, m), 3.19 (3H, s), 6.51 (1H, dd, J=2.4, 6.6 Hz), 6.67 (1H, d, J=4.0 Hz), 6.77 (1H, d, J=2.4 Hz), 7.07 (1H, dd, J=2.4, 8.8 Hz), 7.39 (1H, d, J=2.4 Hz), 7.87 (1H, d, J=4.0 Hz), 8.15 (1H, d, J=6.0 Hz), 8.16 (1H, m), 8.29 (1H, d, J=8.8 Hz), 9.27 (1H, m).
ESI-MS: 368.13 (M+H).

Example 187

6-(2-(3-Ethylureido)pyridin-4-yloxy)indole-1-carboxylic acid methylamide

Similarly to Example 5, the title compound (54 mg, 0.15 mmol, 80%) was obtained as colorless crystals from phenyl (4-(1-methylcarbamoyl-1H-indol-6-yloxy)pyridin-2-yl)-N-(phenoxycarbonyl)carbamate (100 mg, 0.19 mmol), ethylamine hydrochloride (78 mg, 0.96 mmol) and triethylamine (0.5 ml).
$^1$H-NMR Spectrum (DMSO-d$_6$) δ (ppm): 1.03 (3H, t, J=7.2 Hz), 2.79 (3H, d, J=4.4 Hz), 3.07–3.14 (2H, m), 6.52 (1H, dd, J=2.4, 5.8 Hz), 6.71 (1H, d, J=3.6 Hz), 6.88 (1H, d, J=2.4 Hz), 6.99 (1H, dd, J=2.4, 8.4 Hz), 7.65 (1H, d, J=8.4 Hz), 7.84 (1H, d, J=3.6 Hz), 7.96 (2H, m), 8.04 (1H, d, J=5.8 Hz), 8.16 (1H, m), 9.02 (1H, s).
ESI-MS: 354.15 (M+H), 376.16 (M+Na).
The starting materials were synthesized as follows.

Production Example 187-1

4-(1H-Indol-6-yloxy)pyridin-2-ylamine

Sodium hydride (1.04 g, 26.0 mmol, 60% in oil) was suspended in dimethyl sulfoxide (2.5 ml); 6-hydroxyindole (3.46 g, 26.0 mmol) and 2-amino-4-chloropyridine (2.57 g, 20.0 mmol, WO 02/332872) were subsequently added thereto at room temperature under nitrogen stream; and the reaction mixture was stirred at 160° C. for 8.5 hours. After cooled down to room temperature, the reaction mixture was partitioned between ethyl acetate (150 ml) and a solvent mixture of aqueous ammonia:water=1:1 (50 ml); the organic layer was washed with a solvent mixture of aqueous ammonia:water=1:1, and with brine, dried over anhydrous sodium sulfate, and concentrated. The residue was purified by silica gel column chromatography (Fuji Silysia BW-300, ethyl acetate, or ethyl acetate:methanol=93:7); and the obtained crystals were suspended in diethyl ether, filtered off, washed with diethyl ether, and dried to yield the title compound (477 mg, 2.12 mmol, 10.6%) as pale yellow crystals.
$^1$H-NMR Spectrum (DMSO-d$_6$) δ (ppm): 5.76 (1H, s), 5.82 (2H, brs), 6.13 (1H, d, J=6.0 Hz), 6.44 (1H, s), 6.75 (1H, d, J=8.4 Hz), 7.10 (1H, s), 7.34 (1H, s), 7.56 (1H, d, J=8.4 Hz), 7.75 (1H, d, J=6.0 Hz), 11.12 (1H, brs).

Production Example 187-2

6-(2-Aminopyridin-4-yloxy)indole-1-carboxylic acid methylamide

Similarly to Production example 5-1, the title compound (315 mg, 1.12 mmol, 87.9%) was obtained as colorless crystals from 4-(1H-indol-6-yloxy)pyridin-2-ylamine (285 mg, 1.27 mmol), sodium hydride (63 mg, 1.58 mmol, 60% in oil) and phenyl N-methylcarbamate (239 mg, 1.58 mmol).
$^1$H-NMR Spectrum (DMSO-d$_6$) δ (ppm): 2.80 (3H, d, J=4.4 Hz), 5.77 (1H, d, J=2.0 Hz), 5.85 (2H, m), 6.14 (1H, dd, J=2.0, 5.6 Hz), 6.69 (1H, d, J=3.6 Hz), 6.96 (1H, dd, J=2.0, 8.4 Hz), 7.63 (1H, d, J=8.4 Hz), 7.77 (1H, d, J=5.6 Hz), 7.81 (1H, d, J=3.6 Hz), 7.94 (1H, d, J=2.0 Hz), 8.13 (1H, d, J=4.4 Hz).

Production Example 187-3

Phenyl(4-(1-methylcarbamoyl-1H-indol-6-yloxy)pyridin-2-yl)-N-(phenoxycarbonyl)carbamate Similarly to Production example 5-2, the title compound (404 mg, 0.77 mmol, 69%) was obtained as pale pink crystals from 6-(2-aminopyridin-4-yloxy)indole-1-carboxylic acid methylamide (315 mg, 1.12 mmol), triethylamine (0.51 ml, 3.7 mmol), and phenyl chloroformate (0.42 ml, 3.4 mmol).
$^1$H-NMR Spectrum (DMSO-d$_6$) δ (ppm): 2.78 (3H, d, J=4.4 Hz), 6.74 (1H, d, J=3.6 Hz), 7.02 (1H, dd, J=2.4, 5.6 Hz), 7.05 (1H, dd, J=2.4, 8.4 Hz), 7.16 (4H, d, J=7.8 Hz), 7.29 (2H, t, J=7.8 Hz), 7.42 (4H, t, J=7.8 Hz), 7.52 (1H, m), 7.69 (1H, d, J=8.4 Hz), 7.86 (1H, d, J=3.6 Hz), 8.04 (1H, d, J=2.4 Hz), 8.15 (1H, m), 8.44 (1H, d, J=5.6 Hz).

Example 188

6-(2-(3,3-Diethylureido)pyridin-4-yloxy)indole-1-carboxylic acid methylamide

Similarly to Example 5, the title compound (55 mg, 0.14 mmol, 76%) was obtained as colorless crystals from phenyl (4-(1-methylcarbamoyl-1H-indol-6-yloxy)pyridin-2-yl)-N-(phenoxycarbonyl)carbamate (100 mg, 0.19 mmol) and diethylamine (0.10 ml, 0.96 mmol).
$^1$H-NMR Spectrum (DMSO-d$_6$) δ (ppm): 1.01 (6H, t, J=7.2 Hz), 2.79 (3H, d, J=4.4 Hz), 3.26–3.32 (4H, m), 6.56 (1H, dd, J=2.0, 5.6 Hz), 6.71 (1H, d, J=3.6 Hz), 6.99 (1H, dd, J=2.0, 8.8 Hz), 7.42 (1H, d, J=2.0 Hz), 7.65 (1H, d, J=8.8 Hz), 7.84 (1H, d, J=3.6 Hz), 7.96 (1H, d, J=2.0 Hz), 8.08 (1H, d, J=5.6 Hz), 8.15 (1H, m), 8.63 (1H, s).
ESI-MS: 382.21 (M+H).

Example 189

6-(2-(3-(2-Diethylaminoethyl)ureido)pyridin-4-yloxy)indole-1-carboxylic acid methylamide Similarly to Example 5, the title compound (51 mg, 0.12 mmol, 63%) was obtained as pale yellow crystals from phenyl(4-(1-methylcarbamoyl-1H-indol-6-yloxy)pyridin-2-yl)-N-(phenoxycarbonyl)carbamate (100 mg, 0.19 mmol) and 2-diethylaminoethylamine (0.14 ml, 0.96 mmol).
$^1$H-NMR Spectrum (DMSO-d$_6$) δ (ppm): 0.93 (6H, t, J=7.6 Hz), 2.41–2.49 (6H, m), 2.79 (3H, d, J=4.0 Hz), 3.14 (2H, m), 6.51 (1H, dd, J=2.4, 6.0 Hz), 6.71 (1H, d, J=3.6 Hz), 6.84 (1H, d, J=2.4 Hz), 6.99 (1H, dd, J=2.4, 8.2 Hz), 7.65 (1H, d, J=8.2 Hz), 7.84 (1H, d, J=3.6 Hz), 7.96 (1H, d, J=2.4 Hz), 8.02 (1H, d, J=6.0 Hz), 8.16 (2H, m), 9.13 (1H, s).
ESI-MS: 425.29 (M+H).

Example 190

6-(2-(((4-(Pyrrolidin-1-yl)piperidin-1-yl)carbonyl)amino)pyridin-4-yloxy)indole-1-carboxylic acid methylamide Similarly to Example 5, the title compound (72 mg, 0.16 mmol, 82%) was obtained as colorless crystals from phenyl (4-(1-methylcarbamoyl-1H-indol-6-yloxy)pyridin-2-yl)-N-(phenoxycarbonyl)carbamate (100 mg, 0.19 mmol) and 4-(pyrrolidin-1-yl)piperidine (148 mg, 0.96 mmol).

¹H-NMR Spectrum (DMSO-d₆) δ (ppm): 1.19–1.31 (2H, m), 1.63 (4H, m), 1.76 (2H, m), 2.09 (1H, m), 2.44 (4H, m), 2.79 (3H, d, J=4.0 Hz), 2.82 (2H, m), 3.92 (2H, m), 6.55 (1H, dd, J=2.4, 5.6 Hz), 6.71 (1H, d, J=3.8 Hz), 6.98 (1H, dd, J=2.4, 8.8 Hz), 7.32 (1H, d, J=2.4 Hz), 7.65 (1H, d, J=8.8 Hz), 7.84 (1H, d, J=3.8 Hz), 7.96 (1H, d, J=2.4 Hz), 8.08 (1H, d, J=5.6 Hz), 8.15 (1H, m), 9.12 (1H, s).
ESI-MS: 436.32 (M+H).

Example 191

6-(6-(3-Ethylureido)pyrimidin-4-yloxy)indole-1-carboxylic acid methylamide

Similarly to Production example 5-2, an intermediate, phenyl(4-(1-methylcarbamoyl-1H-indol-6-yloxy)pyrimidin-6-yl)-N-(phenoxycarbonyl)carbamate, was obtained as pale yellow crystals (597 mg) from 6-(6-aminopyrimidin-4-yloxy)indole-1-carboxylic acid methylamide (245 mg, 0.865 mmol), triethylamine (0.40 ml, 2.9 mmol), and phenyl chloroformate (0.33 ml, 2.6 mmol). Similarly to Example 5, the title compound (43 mg, 0.12 mmol) was obtained as colorless crystals from this intermediate (143 mg), ethylamine hydrochloride (88 mg, 1.1 mmol), and triethylamine (0.5 ml).
¹H-NMR Spectrum (DMSO-d₆) δ (ppm): 1.03 (3H, t, J=6.8 Hz), 2.80 (3H, s), 3.10 (2H, m), 6.71 (1H, s), 6.99 (1H, d, J=8.4 Hz), 7.01 (1H, s), 7.04 (1H, m), 7.62 (1H, d, J=8.4 Hz), 7.84 (1H, s), 7.98 (1H, s), 8.16 (1H, m), 8.36 (1H, s), 9.45 (1H, s).
ESI-MS: 355.27 (M+H), 377.26 (M+Na).
The starting material was synthesized as follows.

Production Example 191-1

6-(1H-Indol-6-yloxy)pyrimidin-4-ylamine

Sodium hydride (200 mg, 5.00 mmol) was suspended in dimethyl sulfoxide (8 ml); while stirring at room temperature, 6-hydroxyindole (666 mg, 5.00 mmol) and 6-amino-4-chloropyrimidine (518 mg, 4.00 mmol) were added thereto one by one; and the reaction mixture was stirred at 60° C. for 2 hours, at 80° C. for 1 hour, and at 100° C. for 1.5 hours. After cooled down to room temperature, the reaction mixture was partitioned between ethyl acetate and water; and the organic layer was washed with brine, dried over anhydrous sodium sulfate, and concentrated. The residue was purified by silica gel column chromatography (Fuji Silysia BW-300, hexane:ethyl acetate=1:1, ethyl acetate, then ethyl acetate:methanol=98:2); the obtained crystals were suspended in ethyl acetate (50 ml) and stirred at room temperature overnight, filtered off, washed with diethyl ether, and dried to yield the title compound (322 mg, 1.42 mmol, 35.6%) as pale yellow crystals.
¹H-NMR Spectrum (DMSO-d₆) δ (ppm): 5.56 (1H, s), 6.44 (1H, s), 6.72 (2H, s), 6.76 (1H, d, J=8.4 Hz), 7.12 (1H, s), 7.34 (1H, s), 7.55 (1H, d, J=8.4 Hz), 8.05 (1H, s), 11.13 (1H, brs).

Production Example 191-2

6-(6-Aminopyrimidin-4-yloxy)indole-1-carboxylic acid methylamide

Similarly to Production example 5-1, the title compound (245 mg, 0.865 mmol, 61.3%) was obtained as colorless crystals from 6-(1H-indol-6-yloxy)pyrimidin-4-ylamine (320 mg, 1.41 mmol), sodium hydride (68 mg, 1.7 mmol, 60% in oil), and phenyl N-methylcarbamate (257 mg, 1.70 mmol).
¹H-NMR Spectrum (DMSO-d₆) δ (ppm): 2.80 (3H, d, J=4.4 Hz), 5.64 (1H, s), 6.69 (1H, d, J=3.6 Hz), 6.77 (2H, s), 6.96 (1H, dd, J=2.0, 8.4 Hz), 7.61 (1H, d, J=8.4 Hz), 7.81 (1H, d, J=3.6 Hz), 7.94 (1H, d, J=2.0 Hz), 8.05 (1H, s), 8.12 (1H, m).

Example 192

6-(6-(3,3-Diethylureido)pyrimidin-4-yloxy)indole-1-carboxylic acid methylamide

Similarly to Example 5, the title compound (63 mg, 0.16 mmol) was obtained as milky white crystals from the intermediate obtained in Example 191 (149 mg) and diethylamine (0.11 ml, 1.1 mmol).
¹H-NMR Spectrum (DMSO-d₆) δ (ppm): 1.03 (6H, t, J=7.2 Hz), 2.80 (3H, d, J=4.4 Hz), 3.33 (4H, q, J=7.2 Hz), 6.71 (1H, d, J=3.8 Hz), 7.00 (1H, dd, J=2.0, 8.4 Hz), 7.31 (1H, s), 7.62 (1H, d, J=8.4 Hz), 7.83 (1H, d, J=3.8 Hz), 7.98 (1H, d, J=2.0 Hz), 8.15 (1H, m), 8.38 (1H, s), 9.31 (1H, s).
ESI-MS: 383.23 (M+H), 405.26 (M+Na).

Example 193

6-(6-(3-(2-Diethylaminoethyl)ureido)pyrimidin-4-yloxy)indole-1-carboxylic acid methylamide Similarly to Example 5, the title compound (63 mg, 0.15 mmol) was obtained as grayish white crystals from the intermediate obtained in Example 191 (164 mg) and 2-diethylaminoethylamine (0.15 ml, 1.1 mmol).
¹H-NMR Spectrum (DMSO-d₆) δ (ppm): 0.93 (6H, t, J=7.0 Hz), 2.44 (6H, m), 2.80 (3H, d, J=4.0 Hz), 3.13 (2H, m), 6.70 (1H, d, J=3.6 Hz), 6.90 (2H, m), 7.43 (1H, brs), 7.62 (1H, d, J=8.4 Hz), 7.83 (1H, d, J=3.6 Hz), 7.98 (1H, d, J=1.6 Hz), 8.15 (1H, m), 8.34 (1H, s), 9.63 (1H, s).
ESI-MS: 426.31 (M+H).

Example 194

6-(6-(((4-Pyrrolidin-1-yl)piperidin-1-ylcarbonyl)amino)pyrimidin-4-yloxy)indole-1-carboxylic acid methylamide Similarly to Example 5, the title compound (59 mg, 0.13 mmol) was obtained as colorless crystals from the intermediate obtained in Example 191 (141 mg) and 4-(pyrrolidin-1-yl)piperidine (167 mg, 1.08 mmol).
¹H-NMR Spectrum (DMSO-d₆) δ (ppm): 1.22–1.34 (2H, m), 1.64 (4H, m), 1.78 (2H, m), 2.12 (1H, m), 2.44 (4H, m), 2.80 (3H, d, J=4.0 Hz), 2.88 (2H, m), 3.93 (2H, m), 6.70 (1H, d, J=3.6 Hz), 6.99 (1H, dd, J=2.0, 8.4 Hz), 7.20 (1H, s), 7.62 (1H, d, J=8.4 Hz), 7.83 (1H, d, J=3.6 Hz), 7.97 (1H, d, J=2.0 Hz), 8.15 (1H, m), 8.38 (1H, s), 9.73 (1H, s).
ESI-MS: 464.36 (M+H).

Example 195

4-(6-(3-Ethylureido)pyrimidin-4-yloxy)indole-1-carboxylic acid methylamide

Similarly to Production example 5-2, an intermediate (a mixture of phenyl(4-(1-methylcarbamoyl-1H-indol-4-yloxy)pyrimidin-6-yl)-N-(phenoxycarbonyl)carbamate and phenyl(4-(1-methylcarbamoyl-1H-indol-4-yloxy)pyrimidin-6-yl)carbamate, 379 mg) was obtained as pale yellow crystals from 4-(6-Aminopyrimidin-4-yloxy)indole-1-carboxylic acid methylamide (245 mg, 0.865 mmol), triethylamine (0.40 ml, 2.9 mmol) and phenyl chloroformate (0.33 ml, 2.6 mmol). Similarly to Example 5, the title compound (41 mg, 0.12 mmol) was obtained as a colorless crystal from this intermediate (94 mg), ethylamine hydrochloride (78 mg, 0.96 mmol), and triethylamine (0.5 ml).

$^1$H-NMR Spectrum (DMSO-$d_6$) δ (ppm): 1.03 (3H, t, J=7.4 Hz), 2.82 (3H, d, J=4.0 Hz), 3.12 (2H, m), 6.40 (1H, d, J=3.8 Hz), 6.98 (1H, d, J=8.0 Hz), 7.05 (1H, s), 7.28 (1H, t, J=8.0 Hz), 7.31 (1H, m), 7.76 (1H, d, J=3.8 Hz), 8.14 (1H, d, J=8.0 Hz), 8.17 (1H, m), 8.33 (1H, m), 9.48 (1H, s).

ESI-MS: 355.20 (M+H), 377.25 (M+Na).

The starting materials were synthesized as follows.

Production Example 195-1

6-(1H-Indol-4-yloxy)pyrimidin-4-ylamine

The title compound (568 mg, 2.51 mmol, 41.8%) was obtained as grayish white crystals by performing a reaction similar to that in Production example 191-1 using 6-amino-4-chloropyrimidine (777 mg, 6.00 mmol), 4-hydroxyindole (999 mg, 7.50 mmol) and sodium hydride (300 mg, 7.50 mmol) at 100° C. for 6 hours.

$^1$H-NMR Spectrum (DMSO-$d_6$) δ (ppm): 5.56 (1H, s), 6.13 (1H, m), 6.70 (2H, brs), 6.74 (1H, d, J=8.0 Hz), 7.09 (1H, t, J=8.0 Hz), 7.29 (2H, m), 8.05 (1H, s), 11.28 (1H, s).

Production Example 195-2

4-(6-Aminopyrimidin-4-yloxy)indole-1-carboxylic acid methyl amide

Similarly to Production example 5-1, the title compound (279 mg, 0.985 mmol, 74.0%) was obtained as colorless crystals from 6-(1H-indol-4-yloxy)pyrimidin-4-ylamine (300 mg, 1.33 mmol), sodium hydride (83 mg, 2.1 mmol, 60% in oil), and phenyl N-methylcarbamate (314 mg, 2.07 mmol).

$^1$H-NMR Spectrum (DMSO-$d_6$) δ (ppm): 2.82 (3H, d, J=4.4 Hz), 5.64 (1H, s), 6.39 (1H, d, J=3.6 Hz), 6.77 (2H, brs), 6.94 (1H, d, J=8.0 Hz), 7.27 (1H, t, J=8.0 Hz), 7.75 (1H, d, J=3.6 Hz), 8.04 (1H, s), 8.12 (1H, d, J=8.0 Hz), 8.15 (1H, m).

Example 196

4-(6-(3,3-Diethylureido)pyrimidin-4-yloxy)indole-1-carboxylic acid methylamide

Similarly to Example 5, the title compound (54 mg, 0.14 mmol) was obtained as colorless crystals from the intermediate obtained in Example 195 (94 mg) and diethylamine (0.10 ml, 0.96 mmol).

$^1$H-NMR Spectrum (DMSO-$d_6$) δ (ppm): 1.04 (6H, t, J=6.8 Hz), 2.82 (3H, d, J=4.0 Hz), 3.34 (4H, q, J=6.8 Hz), 6.41 (1H, d, J=3.8 Hz), 6.98 (1H, d, J=8.0 Hz), 7.28 (1H, t, J=8.0 Hz), 7.36 (1H, s), 7.76 (1H, d, J=3.8 Hz), 8.14 (1H, d, J=8.0 Hz), 8.17 (1H, m), 8.35 (1H, s), 9.34 (1H, S).

ESI-MS: 383.31 (M+H), 405.22 (M+Na).

Example 197

4-(6-(3-(2-Diethylaminoethyl)ureido)pyrimidin-4-yloxy)indole-1-carboxylic acid methylamide Similarly to Example 5, the title compound (49 mg, 0.12 mmol) was obtained as colorless crystals from the intermediate obtained in Example 195 (94 mg) and 2-diethylaminoethylamine (0.14 ml, 0.96 mmol).

$^1$H-NMR Spectrum (DMSO-$d_6$) δ (ppm): 0.93 (6H, t, J=7.0 Hz), 2.45 (6H, m), 2.82 (3H, d, J=4.0 Hz), 3.14 (2H, m), 6.40 (1H, d, J=3.4 Hz), 6.98 (1H, d, J=8.0 Hz), 7.04 (1H, s), 7.28 (1H, t, J=8.0 Hz), 7.45 (1H, m), 7.76 (1H, d, J=3.4 Hz), 8.14 (1H, d, J=8.0 Hz), 8.17 (1H, m), 8.32 (1H, s), 8.65 (1H, brs).

ESI-MS: 426.27 (M+H).

Example 198

4-(6-(((4-(Pyrrolidin-1-yl)piperidin-1-yl)carbonyl)amino)pyrimidin-4-yloxy)indole-1-carboxylic acid methylamide Similarly to Example 5, the title compound (57 mg, 0.12 mmol) was obtained as colorless crystals from the intermediate obtained in Example 195 (94 mg) and 4-(pyrrolidin-1-yl)piperidine (148 mg, 0.96 mmol).

$^1$H-NMR Spectrum (DMSO-$d_6$) δ (ppm): 1.22–1.35 (2H, m), 1.64 (4H, m), 1.78 (2H, m), 2.13 (1H, m), 2.45 (4H, m), 2.82 (3H, d, J=3.2 Hz), 2.89 (2H, m), 3.94 (2H, m), 6.40 (1H, m), 6.98 (1H, d, J=8.0 Hz), 7.26 (1H, s), 7.28 (1H, t, J=8.0 Hz), 7.76 (1H, m), 8.13 (1H, d, J=8.0 Hz), 8.16 (1H, m), 8.35 (1H, s), 9.35 (1H, s).

ESI-MS: 464.35 (M+H).

Example 199

5-(2-(3-(3-Diethylaminopropyl)ureido)pyridin-4-ylamino)indole-1-carboxylic acid methylamide 1-(4-Chloropyridin-2-yl)-3-(3-diethylaminopropyl)urea (30 mg, 0.11 mmol) was dissolved in ethoxyethanol (1.1 ml); pyridine hydrochloride (24 mg, 0.22 mmol) and 5-aminoindole-1-carboxylic acid methylamide (22 mg, 0.12 mmol, Production example 218-2) was added thereto; and the reaction mixture was stirred at 130° C. for 2 hours. After cooled down to room temperature, the reaction mixture was partitioned between a saturated aqueous solution of sodium hydrogencarbonate and ethyl acetate; and the organic layer was washed with brine, dried over anhydrous magnesium sulfate, and concentrated under reduced pressure. The residue was purified by silica gel column chromatography (Fuji Silysia NH, hexane:ethyl acetate=1:3, ethyl acetate, ethyl acetate:methanol=93:7 in this order) to yield the title compound (8 mg, 0.018 mmol, 17%) as pale yellow powder.

$^1$H-NMR Spectrum (DMSO-$d_6$) δ (ppm): 0.94 (6H, t, J=6.8 Hz), 1.54 (2H, m), 2.37–2.46 (6H, m), 2.83 (3H, d, J=3.6 Hz), 3.16 (2H, m), 6.42 (1H, d, J=5.8 Hz), 6.63 (1H, d, J=3.2 Hz), 6.73 (1H, s), 7.07 (1H, d, J=8.8 Hz), 7.37 (1H, s), 7.76 (1H, d, J=5.8 Hz), 7.80 (1H, m), 8.08 (1H, m), 8.19 (1H, d, J=8.8 Hz), 8.66 (1H, s), 8.81 (1H, m), 8.86 (1H, s).

ESI-MS: 438.36 (M+H).

The starting materials were synthesized as follows.

Production Example 199-1

Phenyl(4-chloropyridin-2-yl)-N-(phenoxycarbonyl) carbamate

2-Amino-4-chloropyridine (5.00 g, 38.9 mmol, WO 02/32872) was dissolved in tetrahydrofuran (200 ml); and triethylamine (17.9 ml, 128 mmol) was added thereto. While stirring with a waterbath, phenyl chloroformate (14.6 ml, 117 mmol) was added thereto dropwise; the reaction mixture was stirred at room temperature for 1.5 hours. The reaction mixture was partitioned between water and ethyl acetate; the organic layer was washed with brine, dried over anhydrous sodium sulfate, and concentrated under reduced pressure. The obtained residue was filtered by silica gel; the crystals obtained after the concentration were suspended in diethyl ether, filtered off, washed with diethyl ether, and dried to yield the title compound (3.77 g, 10.2 mmol, 26.3%) as pale yellow crystals. The mother liquor was concentrated under reduced pressure, which was then treated by the similar methods to yield the title compound (3.98 g, 10.5 mmol, 27.1%) as pale yellow crystals (secondary crystals).

$^1$H-NMR Spectrum (DMSO-$d_6$) δ (ppm): 7.20 (4H, d, J=7.6 Hz), 7.30 (2H, t, J=7.6 Hz), 7.44 (4H, t, J=7.6 Hz), 7.68 (1H, dd, J=1.6, 5.2 Hz), 8.21 (1H, d, J=1.6 Hz), 8.60 (1H, d, J=5.2 Hz).

Production Example 199-2

1-(4-Chloropyridin-2-yl)-3-(3-diethylaminopropyl) urea

Phenyl(4-chloropyridin-2-yl)-N-(phenoxycarbonyl)carbamate (738 mg, 2.00 mmol) was dissolved in N,N-dimethylformamide (8.0 ml); N,N-diethyl-1,3-diaminopropane (1.57 ml, 10.0 mmol) was added thereto; and the reaction mixture was stirred at room temperature for 1 hour. The reaction mixture was partitioned between water and ethyl acetate; and the organic layer was washed with brine, dried over anhydrous sodium sulfate, and concentrated under reduced pressure. The residue was purified by silica gel column chromatography (Fuji Silysia NH, hexane-ethyl acetate-methanol system) to yield the title compound (309 mg, 1.09 mmol, 54.3%) as a pale brown oil.

$^1$H-NMR Spectrum (DMSO-$d_6$) δ (ppm): 0.92 (6H, t, J=7.0 Hz), 1.54 (2H, m), 2.35–2.44 (6H, m), 3.16 (2H, m), 7.02 (1H, d, J=5.6 Hz), 7.54 (1H, s), 7.73 (1H, brs), 8.13 (1H, d, J=5.6 Hz), 9.31 (1H, m).

Example 200

5-(N-(2-(3-(3-Diethylaminopropyl)ureido)pyridin-4-yl)-N-methylamino)indole-1-carboxylic acid methylamide Similarly to Example 199, the title compound (6 mg, 0.013 mmol, 12%) was obtained as pale yellow powder from 5-(N-methylamino)indol-1-carboxylic acid methylamide (22 mg, 0.11 mmol), 1-(4-chloropyridin-2-yl)-3-(3-diethylaminopropyl)urea (30 mg, 0.11 mmol, Production Example 199-2) and pyridine hydrochloride (25 mg, 0.22 mmol).

$^1$H-NMR Spectrum (DMSO-$d_6$) δ (ppm): 0.91 (6H, t, J=7.0 Hz), 1.51 (2H, m), 2.34–2.43 (6H, m), 2.83 (3H, d, J=4.0 Hz), 3.13 (2H, m), 3.23 (3H, s), 6.11 (1H, d, J=6.0 Hz), 6.40 (1H, s), 6.70 (1H, d, J=3.6 Hz), 7.10 (1H, d, J=8.6 Hz), 7.44 (1H, s), 7.69 (1H, d, J=6.0 Hz), 7.84 (1H, d, J=3.6 Hz), 8.14 (1H, m), 8.27 (1H, d, J=8.6 Hz), 8.76 (1H, s), 8.78 (1H, brs).

ESI-MS: 452.38 (M+H).

The starting material was synthesized as follows.

Production Example 200-1

5-(N-Methylamino)indole-1-carboxylic acid methylamide

5-Aminoindole-1-carboxylic acid methylamide (22 mg, 0.11 mmol, Production example 218-2) was dissolved in methanol (5.5 ml); and benzotriazol-1-ylmethanol (434 mg, 2.91 mmol) was added thereto. Because crystals were precipitated immediately, methanol (5.5 ml) was added to dissolve the precipitation, and the reaction mixture was stirred at room temperature for 1.25 hours. Then, the reaction mixture was heated and stirred at 60° C. for an hour. After cooled to room temperature, precipitated crystals were filtered off, washed by methanol, and dried to yield colorless crystals (421 mg). The crystals were dissolved in a solvent mixture of N,N-dimethylformamide (4.2 ml) and methanol (21 ml); sodium borohydride (99 mg, 2.63 mmol) was added while stirring at room temperature; and the reaction mixture was stirred for 1.5 hours. Sodium borohydride (99 mg, 2.63 mmol) was further added thereto; and the reaction mixture was stirred at room temperature for 12 hours. A similar reaction was performed using the residue obtained by the concentration of the mother liquor the crystals were previously given from under reduced pressure, and sodium borohydride (342 mg, 9.02 mmol). Both reaction mixtures mentioned above were partitioned between a saturated aqueous solution of sodium hydrogencarbonate and ethyl acetate; both organic layers are combined, washed with a saturated aqueous solution of sodium hydrogencarbonate, dried over anhydrous sodium sulfate, and concentrated under reduced pressure. The residue was purified by silica gel column chromatography (Fuji Silysia BW-300, hexane-ethyl acetate-methanol system). The obtained crystals were suspended in ethyl acetate, filtered off, washed with ethyl acetate, and dried to yield the title compound (255 mg, 1.25 mmol, 43.1%) was obtained as pale pink crystals.

$^1$H-NMR Spectrum (DMSO-$d_6$) δ (ppm): 2.66 (3H, s), 2.78 (3H, d, J=4.4 Hz), 5.32 (1H, brs), 6.42 (1H, d, J=3.6 Hz), 6.56 (1H, d, 2.4 Hz), 6.57 (1H, dd, J=2.4, 9.0 Hz), 7.61 (1H, d, J=3.6 Hz), 7.84 (1H, d, J=4.4 Hz), 7.93 (1H, d, J=9.0 Hz).

Example 201

5-(2-(3,3-Diethylureido)pyridin-4-ylamino)indole-1-carboxylic acid phenylamide 5-(2-Aminopyridin-4-ylamino)indole-1-carboxylic acid phenylamide (69 mg, 0.20 mmol) was dissolved in tetrahydrofuran (14 ml); triethylamine (0.055 ml, 0.40 mmol) was added thereto; and phenyl chloroformate (0.038 ml, 0.30 mmol) was added thereto while cooling with ice and stirring. A portion of 7.0 ml of the reaction mixture was transferred to another vessel and concentrated under reduced pressure. After the residue was dissolved in N,N-dimethylformamide (1.0 ml), the similar reaction to Example 27 was performed by use of diethylamine (0.031 ml, 0.30 mmol). The obtained crude product was purified by TLC plate (Fuji Silysia NH, developing solvent: ethyl acetate) to yield the title compound (2.0 mg, 0.005 mmol) as pale yellow crystals.

$^1$H-NMR Spectrum (DMSO-$d_6$) δ (ppm): 1.07 (6H, t, J=7.0 Hz), 3.33 (4H, m), 6.52 (1H, m), 6.72 (1H, m), 7.14

(2H, m), 7.40 (3H, m), 7.52 (1H, s), 7.66 (2H, d, J=7.6 Hz), 7.83 (1H, d, J=6.4 Hz), 8.04 (1H, d, J=2.8 Hz), 8.18 (2H, m), 8.65 (1H, s), 10.03 (1H, s).

ESI-MS: 443.28 (M+H).

The starting materials were synthesized as follows.

Production Example 201-1

5-Nitroindole-1-carboxilic acid phenylamide

Sodium hydride (802 mg, 20.0 mmol, 60% in oil) was suspended in N,N-dimethylformamide (40 ml); 5-nitroindole (2.50 g, 15.4 mmol) was added thereto; and the reaction mixture was stirred at room temperature for 30 minutes. Phenyl isocyanate (2.01 ml, 1.23 mmol) was added thereto, and the reaction mixture was stirred at room temperature for 1.5 hours. Water (80 ml) was added to the reaction mixture; the reaction mixture was stirred at room temperature for 30 minutes; and the precipitated crystals were filtered off, washed by water and diethyl ether one by one, and dried by means of suction to yield the title compound (3.53 g, 12.3 mmol, 79.8%) as pale yellow crystals.

$^1$H-NMR Spectrum (DMSO-$d_6$) δ (ppm): 7.00 (1H, d, J=3.6 Hz), 7.16 (1H, t, J=8.0 Hz), 7.40 (2H, t, J=8.0 Hz), 7.65 (2H, d, J=8.0 Hz), 8.17 (1H, dd, J=2.4, 9.2 Hz), 8.25 (1H, d, J=3.6 Hz), 8.36 (1H, d, J=9.2 Hz), 8.62 (1H, d, J=2.4 Hz), 10.30 (1H, s).

Production Example 201-2

5-Aminoindole-1-carboxylic acid phenylamide

5-Nitroindole-1-carboxylic acid phenylamide (3.53 g, 12.3 mmol) was dissolved in ethanol (250 ml); water (50 ml), electrolytic iron powder (2.75 g, 49.2 mmol), ammonium chloride (5.26 g, 98.4 mmol) were added thereto; and the reaction mixture was heated and stirred at 80° C. for 2 hours. After cooling to room temperature, the reaction mixture was filtered off; insoluble portions were washed with ethyl acetate; and the filtrate was concentrated under reduced pressure. The residue was partitioned between water and a solvent mixture of ethyl acetate and tetrahydrofuran; and the organic layer was washed with brine, dried over anhydrous sodium sulfate, and concentrated under reduced pressure. The residue was solidified by diethyl ether; the crystals were suspended in diethyl ether, filtered off, washed with diethyl ether, and dried to yield the title compound as pale red powder (681 mg, 2.71 mmol, 22.0%). The mother liquor was concentrated under reduced pressure, which was then treated by the similar methods to yield the title compound (590 mg, 2.35 mmol, 19.1%) as pale red powder (secondary crystals).

$^1$H-NMR Spectrum (DMSO-$d_6$) δ (ppm): 4.80 (2H, s), 6.48 (1H, d, J=3.4 Hz), 6.59 (1H, dd, J=2.4, 8.8 Hz), 6.71 (1H, d, J=2.4 Hz), 7.09 (1H, t, J=7.6 Hz), 7.34 (2H, t, J=7.6 Hz), 7.61 (2H, d, J=7.6 Hz), 7.84 (1H, d, J=3.4 Hz), 7.88 (1H, d, J=8.8 Hz), 9.79 (1H, s).

Production Example 201-3

5-(2-Aminopyridin-4-ylamino)indole-1-carboxylic acid phenylamide

2-Amino-4-chloropyridine (500 mg, 0.446 mmol) was dissolved in N-methylpyrrolidone (5.0 ml); pyridine hydrochloride (750 mg) and 5-aminoindole-1-carboxylic acid phenylamide (408 mg, 1.62 mmol) was added thereto; the reaction mixture was stirred at 100° C. for 6.5 hours. After cooling to room temperature, the reaction mixture was partitioned between saturated aqueous solution of sodium hydrogencarbonate and ethyl acetate; the organic layer was washed with brine, dried over anhydrous magnesium sulfate, and concentrated under reduced pressure. The residue was purified by silica gel column chromatography (Fuji Silysia NH, hexane-ethyl acetate-methanol system). The obtained pale yellow oil was solidified with diethyl ether; and the crystals were suspended in diethyl ether, filtered off, washed with diethyl ether, and dried to yield the title compound (188 mg, 0.464 mmol, 35.7%) as pale yellow crystals.

$^1$H-NMR Spectrum (DMSO-$d_6$) δ (ppm): 5.45 (2H, m), 5.99 (1H, d, J=2.0 Hz), 6.10 (1H, dd, J=2.0, 6.0 Hz), 6.69 (1H, d, J=3.6 Hz), 7.07 (1H, dd, J=2.0, 8.6 Hz), 7.12 (1H, t, J=7.6 Hz), 7.37 (3H, m), 7.56 (1H, d, J=6.0 Hz), 7.63 (2H, d, J=7.6 Hz), 8.00 (1H, d, J=3.6 Hz), 8.14 (1H, d, J=8.6 Hz), 8.26 (1H, s), 9.98 (1H, s).

Example 202

5-(2-(3-(3-Diethylaminopropyl)ureido)pyridin-4-ylamino)indole-1-carboxylic acid phenylamide 5-(2-Aminopyridin-4-ylamino)indole-1-carboxylic acid phenylamide (69 mg, 0.20 mmol, Production example 201-3) was dissolved in tetrahydrofuran (14 ml); triethylamine (0.055 ml, 0.40 mmol) was added thereto; and phenyl chloroformate (0.038 ml, 0.30 mmol) was added while stirring and cooled by ice. A portion of 7.0 ml of this reaction mixture was transferred to another vessel; and the remaining portion of the reaction mixture was concentrated under reduced pressure. The residue was dissolved in N,N-dimethylformamide (1.0 ml); the similar reaction to Example 201 was performed using N,N-diethyl-1,3-diaminopropane (0.047 ml, 0.30 mmol); the crude product obtained was purified by a TLC plate (Fuji Silysia NH, developing solvent:ethyl acetate/ethanol=10/1); and the obtained crystals were suspended in ethyl acetate, filtered off, and dried to yield the title compound (3 mg, 0.006 mmol) as colorless crystals.

$^1$H-NMR Spectrum (DMSO-$d_6$) δ (ppm): 0.93 (6H, t, J=7.0 Hz), 1.53 (2H, m), 2.42 (6H, m), 3.18 (2H, m), 6.43 (1H, d, J=5.6 Hz), 6.70 (1H, s), 6.75 (1H, s), 7.12 (2H, m), 7.38 (3H, m), 7.64 (2H, d, J=8.0 Hz), 7.76 (1H, d, J=5.6 Hz), 8.03 (1H, s), 8.16 (1H, d, J=9.2 Hz), 8.70 (1H, s), 8.78 (1H, m), 8.86 (1H, s), 10.01 (1H, s).

ESI-MS: 500.54 (M+H).

Example 203

5-(5-Cyano-2-(3-(2-diethylaminoethyl)ureido)pyridin-4-ylamino)indole-1-carboxylic acid phenylamide A reaction similar to Production example 5-2 was performed using 5-(2-amino-5-cyanopyridin-4-ylamino)indole-1-carboxylic acid phenylamide (60 mg, 0.16 mmol), triethylamine (0.056 ml, 0.41 mmol), and phenyl chloroformate (0.082 ml, 0.66 mmol); the solvent was concentrated under reduced pressure. Similarly to Example 5, the title compound (63 mg, 0.12 mmol, 76%) was obtained as pale yellow crystals from the residue obtained above, and 2-diethylaminoethylamine (0.115 ml, 0.81 mmol).

$^1$H-NMR Spectrum (DMSO-$d_6$) δ (ppm): 0.92 (6H, t, J=7.0 Hz), 2.38–2.46 (6H, m), 3.09 (2H, m), 6.75 (1H, d, J=3.8 Hz), 7.03 (1H, brs), 7.13 (1H, dd, J=6.8, 7.6 Hz), 7.18

(1H, dd, J=2.0, 8.8 Hz), 7.38 (2H, t, J=7.6 Hz), 7.48 (1H, d, J=2.0 Hz), 7.65 (3H, m), 8.07 (1H, d, J=3.8 Hz), 8.21 (1H, d, J=8.8 Hz), 8.25 (1H, s), 8.87 (1H, s), 9.21 (1H, brs), 10.06 (1H, s).

ESI-MS: 511.53 (M+H).

The starting material was synthesized as follows.

Production Example 203-1

5-(2-Amino-5-cyanopyridin-4-ylamino)indole-1-carboxylic acid phenylamide

2-Amino-4-chloro-5-cyanopyridine (200 mg, 1.30 mmol, Production example 215-3) was dissolved in ethoxyethanol (13.0 ml); 5-aminoindole-1-carboxylic acid phenylamide (408 mg, 1.62 mmol, Production example 201-2) and pyridine hydrochloride (315 mg, 2.73 mmol) were added thereto; and the reaction mixture was heated and stirred at 130° C. for 4 hours. After cooling to room temperature, the reaction mixture was partitioned between a saturated aqueous solution of sodium hydrogencarbonate and ethyl acetate; the organic layer was washed with brine, dried over anhydrous sodium sulfate, and concentrated under reduced pressure. The residue was purified by silica gel column chromatography (Fuji Silysia NH, hexane:ethyl acetate=2:3, ethyl acetate, ethyl acetate:methanol=95:5 in this order). The pale yellow oil obtained was solidified with diethyl ether; the crystals were suspended with diethyl ether, filtered off, washed with diethyl ether, and dried to yield the title compound (171 mg, 0.464 mmol, 35.7%) as colorless crystals.

$^1$H-NMR Spectrum (DMSO-d$_6$) δ (ppm): 5.77 (1H, s), 6.40 (2H, brs), 6.74 (1H, d, J=3.6 Hz), 7.13 (1H, t, J=7.6 Hz), 7.17 (1H, dd, J=2.4, 8.8 Hz), 7.38 (2H, t, J=7.6 Hz), 7.46 (1H, d, J=2.4 Hz), 7.64 (2H, d, J=7.6 Hz), 8.04 (1H, s), 8.05 (1H, d, J=3.6 Hz), 8.20 (1H, d, J=8.8 Hz), 8.35 (1H, s), 10.04 (1H, s).

Example 204

5-(5-Cyano-2-(((4-(pyrrolidin-1-yl)piperidin-1-yl)carbonyl)amino)pyridin-4-ylamino)indole-1-carboxylic acid phenylamide Similarly to Example 203, the title compound (73 mg, 0.13 mmol, 82%) was obtained as colorless crystals from 5-(2-amino-5-cyanopyridin-4-ylamino)indole-1-carboxylic acid phenylamide (60 mg, 0.16 mmol, Production example 203-1), triethylamine (0.056 ml, 0.41 mmol), phenyl chloroformate (0.082 ml, 0.66 mmol), and 4-(pyrrolidin-1-yl)piperidine (126 mg, 0.81 mmol).

$^1$H-NMR Spectrum (DMSO-d$_6$) δ (ppm): 1.17–1.28 (2H, m), 1.62 (4H, m), 1.73 (2H, m), 2.07 (1H, m), 2.42 (4H, m), 2.80 (2H, m), 3.87 (2H, m), 6.75 (1H, d, J=3.6 Hz), 7.13 (1H, t, J=7.6 Hz), 7.18 (1H, d, J=8.8 Hz), 7.38 (3H, m), 7.48 (1H, s), 7.64 (2H, d, J=7.6 Hz), 8.07 (1H, d, J=3.6 Hz), 8.20 (1H, d, J=8.8 Hz), 8.30 (1H, s), 8.87 (1H, s), 9.20 (1H, brs), 10.06 (1H, s).

ESI-MS: 549.48 (M+H).

Example 205

5-(N-(2-(3-(3-Diethylaminopropyl)ureido)-5-cyanopyridin-4-yl)-N-methylamino)indole-1-carboxylic acid methylamide Similarly to Example 203, the title compound (13 mg, 0.027 mmol, 67%) was obtained as colorless crystals from 5-(N-(2-amino-5-cyanopyridin-4-yl)-N-methylamino)indole-1-carboxylic acid methylamide (13 mg, 0.041 mmol), phenyl chloroformate (0.011 ml, 0.089 mmol), triethylamine (0.014 ml, 0.10 mmol), and N,N-diethyl-1,3-diaminopropane (0.032 ml, 0.21 mmol).

$^1$H-NMR Spectrum (DMSO-d$_6$) δ (ppm): 0.92 (6H, t, J=7.0 Hz), 1.53 (2H, m), 2.41 (6H, m), 2.82 (3H, d, J=4.0 Hz), 3.14 (2H, m), 3.29 (3H, s), 6.65 (1H, d, J=3.6 Hz), 7.09 (1H, s), 7.13 (1H, dd, J=2.0, 8.8 Hz), 7.45 (1H, d, J=2.0 Hz), 7.74 (1H, brs), 7.84 (1H, d, J=3.6 Hz), 8.10 (1H, s), 8.15 (1H, m), 8.23 (1H, d, J=8.8 Hz), 9.27 (1H, s).

ESI-MS: 477.40 (M+H).

The starting material was synthesized as follows.

Production Example 205-1

5-(N-(2-Amino-5-cyanopyridin-4-yl)-N-methylamino)indole-1-carboxylic acid methylamide Similarly to Production example 203, the title compound (13 mg, 0.041 mmol, 35.7%) was obtained as colorless crystals from 2-amino-4-chloro-5-cyanopyridine (27 mg, 0.18 mmol, Production example 215-3), 5-(N-methylamino)indole-1-carboxylic acid methylamide (30 mg, 0.15 mmol), and pyridine hydrochloride (38 mg, 0.38 mmol).

$^1$H-NMR Spectrum (DMSO-d$_6$) δ (ppm): 5.77 (1H, s), 6.40 (2H, brs), 6.74 (1H, d, J=3.6 Hz), 7.13 (1H, t, J=7.6 Hz), 7.17 (1H, dd, J=2.4, 8.8 Hz), 7.38 (2H, t, J=7.6 Hz), 7.46 (1H, d, J=2.4 Hz), 7.64 (2H, d, J=7.6 Hz), 8.04 (1H, s), 8.05 (1H, d, J=3.6 Hz), 8.20 (1H, d, J=8.8 Hz), 8.35 (1H, s), 10.04 (1H, s).

Example 206

N1-Methyl-5-(2-(azetidin-1-ylcarbonyl)amino-4-pyridyl)oxy-1H-1-indolecarboxamide Azetidine hydrochloride (104 mg, 1.11 mmol) and triethylamine (0.155 ml, 1.11 mmol) were added to a dimethylformamide (1 ml) solution of phenyl N-(4-(1-(methylamino)carbonyl-1H-5-indolyloxy)-2-pyridyl)-N-(phenoxycarbonyl)carbamate (116 mg, 0.222 mmol) synthesized in Production example 5-2; and the reaction mixture was stirred overnight at room temperature. The reaction mixture was partitioned between ethyl acetate and water; the organic layer was dried over anhydrous sodium sulfate, and concentrated under reduced pressure. The residue was washed with a solvent mixture of ether-hexane=1:1; and the resultant solid was filtered off to yield the title compound (50 mg) as crystals.

$^1$H-NMR Spectrum (DMSO-d$_6$) δ (ppm): 2.03–2.13 (2H, m), 2.83 (3H, d, J=6.2 Hz), 3.99 (4H, t, J=7.9 Hz), 6.54 (1H, dd, J=2.2, 6.7 Hz), 6.68 (1H, d, J=3.9 Hz), 7.03 (1H, dd, J=2.2, 8.3 Hz), 7.35 (1H, d, J=2.2 Hz), 7.41 (1H, d, J=2.2 Hz), 7.87 (1H, d, J=3.9 Hz), 8.04 (1H, d, J=6.7 Hz), 8.03–8.20 (1H, m), 8.28 (1H, t, J=8.3 Hz), 8.88 (1H, s).

Example 207

N1-Ethyl-5-(2-(azetidin-1-ylcarbonyl)amino-4-pyridyl)oxy-1H-1-indolecarboxamide

Similarly to Example 206, the title compound (50 mg) was obtained as white crystals from phenyl N-(4-(1-(ethylamino)carbonyl-1H-5-indolyloxy)-2-pyridyl)-N-(phenoxycarbonyl)carbamate (120 mg, 0.224 mmol) synthesized in Production example 55-1, dimethylformamide (1 ml), azetidine hydrochloride (105 mg, 1.12 mmol), and triethylamine (0.156 ml, 1.12 mmol).

$^1$H-NMR Spectrum (DMSO-d$_6$) δ (ppm): 1.19 (3H, t, J=7.9 Hz), 2.04–2.13 (2H, m), 3.27–3.36 (2H, m), 3.90 (4H, t, J=7.0 Hz), 6.52 (1H, dd, J=1.9, 6.5 Hz), 6.67 (1H, d, J=3.9 Hz), 7.02 (1H, dd, J=1.9, 8.4 Hz), 7.34 (1H, d, J=1.9 Hz), 7.42 (1H, d, J=1.9 Hz), 7.90 (1H, d, J=3.9 Hz), 8.05 (1H, d, J=6.5 Hz), 8.21 (1H, t, J=6.5 Hz), 8.28 1H, d, J=8.4 Hz), 8.88 (1H, s).

Example 208

N1-Cyclopropyl-5-(2-(azetidin-1-ylcarbonyl)amino-4-pyridyl)oxy-1H-1-indolecarboxamide Similarly to Example 206, the title compound (80 mg) was obtained as white crystals from a mixture (228 mg) of phenyl N-(4-(1-cyclopropylaminocarbonyl-1H-5-indolyl)oxy-2-pyridyl)carbamate and phenyl N-(4-(1-cyclopropylaminocarbonyl-1H-5-indolyl)oxy-2-pyridyl)-N-(phenoxycarbonyl)carbamate obtained by a similar method to Example 68, N,N-dimethylformamide (2 ml), azetidine hydrochloride (194 mg, 2.07 mmol), and triethylamine (0.29 ml, 2.08 mmol).

$^1$H-NMR Spectrum (DMSO-d$_6$) δ (ppm): 0.59–0.65 (2H, m), 0.70–0.78 (2H, m), 2.03–2.13 (2H, m), 2.73–2.82 (1H, m), 3.89 (4H, t, J=7.1 Hz), 6.52 (1H, dd, J=2.0, 6.6 Hz), 6.64 (1H, d, J=3.9 Hz), 7.02 (1H, dd, J=2.0, 8.5 Hz), 7.34 (1H, d, J=2.0 Hz), 7.41 (1H, d, J=2.0 Hz), 7.87 (1H, d, J=3.9 Hz), 8.05 (1H, d, J=6.6 Hz), 8.23–8.30 (2H, m), 8.87 (1H, s).

Example 209

N1-Methyl-5-(2-(((4-(morpholin-4-yl)piperidin-1-yl)carbonyl)amino)pyridin-4-yloxy)-1H-1-indolecarboxamide Morpholine (228 mg, 1.64 mmol), sodium triacetoxyborohydride (372 mg, 1.76 mmol), and acetic acid (0.134 ml, 2.34 mmol) were added to a dichloromethane (3.5 ml) solution of N1-methyl-5-(2-(4-oxopiperidin-1-ylcarbonyl)amino-4-pyridyl)oxy-1H-1-indolecarboxamide (476 mg) synthesized in Example 40, and stirred overnight at room temperature. The reaction mixture was partitioned between ethyl acetate and water; and the organic layer was dried over anhydrous sodium sulfate. The solution was concentrated under reduced pressure; and the residue was purified by silica gel column chromatography (Fuji Silysia NH, ethyl acetate-methanol system). The resultant was washed with a solvent mixture of ether-hexane=1:1; and the solid was filtered off to yield the title compound (110 mg) as crystals.

MS Spectrum (ESI): 479 (M+1), 958 (2M+1).

Example 210

N1-Methyl-5-(2-(((4-(azetidin-1-yl)piperidin-1-yl)carbonyl)amino)pyridin-4-yloxy)-1H-1-indolecarboxamide Azetidine hydrochloride (179 mg, 2.00 mmol) and sodium triacetoxyborohydride (434 mg, 2.05 mmol) were added to a dichloromethane (3.7 ml) solution of N1-methyl-5-(2-(4-oxopiperidin-1-ylcarbonyl)amino-4-pyridyl)oxy-1H-1-indolecarboxamide (555 mg, 1.36 mmol) synthesized in Example 40, and stirred overnight at room temperature. The reaction mixture was partitioned between ethyl acetate and water; and the organic layer was dried over anhydrous sodium sulfate. The solution was concentrated under reduced pressure; and the residue was purified by use of silica gel column chromatography (Fuji Silysia NH, ethyl acetate-methanol system). The resultant was washed with a solvent mixture of ether-hexane=1:1; and the solid was filtered off to yield crystals of the title compound (5 mg), and a mixture (410 mg) including the title compound.

MS Spectrum (ESI): 449 (M+1), 897 (2M+1).

Example 211

N1-Methyl-5-(2-(((4-(diethylamino)piperidin-1-yl)carbonyl)amino)pyridin-4-yloxy)-1H-1-indolecarboxamide Similarly to Example 209, the title compound (20 mg) was obtained as crystals from a dichloromethane (4 ml) solution of N1-methyl-5-(2-(4-oxopiperidin-1-ylcarbonyl)amino-4-pyridyl)oxy-1H-1-indolecarbox-amide (558 mg) synthesized in Example 40, diethylamine (0.199 ml, 1.92 mmol), sodium triacetoxyborohydride (436 mg, 2.06 mmol) and acetic acid (0.157 ml, 2.74 mmol). A mixture (180 mg) including the title compound was also obtained.

MS Spectrum (ESI): 465 (M+1).

Example 212

N1-Methyl-5-(2-(((4-(4-hydroxypiperidin-1-yl)piperidin-1-yl)carbonyl)amino)pyridin-4-yloxy)-1H-1-indolecarboxamide Similarly to Example 209, the title compound (100 mg) was obtained as crystals from a dichloromethane (3.5 ml) solution of N1-methyl-5-(2-(4-oxopiperidin-1-ylcarbonyl)-amino-4-pyridyl)oxy-1H-1-indolecarboxamide (500 mg) synthesized in Example 40, 4-hydroxypiperidine (174 mg, 1.72 mmol), sodium triacetoxyborohydride (389 mg, 1.84 mmol) and acetic acid (0.141 mg, 2.46 mmol).

MS Spectrum (ESI): 493 (M+1), 985 (2M+1).

Example 213

N1-Propyl-5-(2-(pyrrolidin-1-ylcarbonyl)amino-4-pyridyl)oxy-1H-1-indolecarboxamide N1-Propyl-5-(2-amino-4-pyridyl)oxy-1H-1-indolecarboxamide (477 mg, 1.54 mmol) was suspended in tetrahydrofuran (5 ml) at room temperature; triethylamine (0.536 mg, 3.08 mmol) and phenyl chloroformate (0.389 ml, 3.85 mmol) was added thereto while stirring; and the reaction mixture was stirred at room temperature for 2 hours. Water was added to the reaction mixture; this was subjected to extraction with ethyl acetate, washed with brine, dried over anhydrous sodium sulfate and concentrated under reduced pressure. N,N-dimethylformamide (3 ml) and pyrrolidine (0.27 ml, 3.23 mmol) was added to the residue; and the reaction mixture was stirred at room temperature overnight. The reaction mixture was partitioned between ethyl acetate and water; and the organic layer was dried over anhydrous sodium sulfate. The solution was concentrated under reduced pressure; the residue was purified by silica gel column chromatography (Fuji Silysia NH, ethyl acetate-methanol). The resultant was washed with a solvent mixture of ether:hexane=1:1; and the solid was filtered off to yield crystals (40 mg) of the title compound.

$^1$H-NMR Spectrum (DMSO-d$_6$) δ (ppm): 0.93 (3H, t, J=7.1 Hz), 1.52–1.65 (2H, m), 1.74–1.82 (4H, m), 3.20–3.40

(6H, m), 6.56 (1H, dd, J=2.7, 6.3 Hz), 6.68 (1H, d, J=3.6 Hz), 7.04 (1H, dd, J=2.7, 7.6 Hz), 7.37 (1H, d, J=2.7 Hz), 7.44 (1H, d, J=2.7 Hz), 7.94 (1H, d, J=3.6 Hz), 8.08 (1H, d, J=6.3 Hz), 8.23 (1H, t, J=7.1 Hz), 8.28 (1H, d, J=7.6 Hz), 8.61 (1H, s).

The starting materials were synthesized as follows.

Production Example 213-1

N1-Propyl-5-(2-amino-4-pyridyl)oxy-1H-1-indole-carboxamide

Sodium hydride (60% in oil, 104 mg, 2.6 mmol) was gradually added at room temperature under nitrogen atmosphere to a N,N-dimethylformamide (7 ml) solution of 4-(1H-5-indolyloxy)-2-pyridinamine (487 mg, 2.16 mmol, CAS No. 417722-11-3) which was described in WO 02/32872. After the reaction mixture was stirred for 2 hours, phenyl N-propylcarbamate (465 mg, 2.6 mmol) was added thereto, and the reaction mixture was stirred for 4 hours. The reaction mixture was partitioned between ethyl acetate and water; and the organic layer was washed with water and brine, dried over anhydrous sodium sulfate. The solution was concentrated under reduced pressure; and the residue was filtrated by silica gel column chromatography (Fuji Silysia NH, ethyl acetate-methanol) to yield a mixture (500 mg) including the title compound.

MS Spectrum (ESI): 311 (M+1).

Example 214

N1-Isopropyl-5-(2-(pyrrolidin-1-ylcarbonyl)amino-4-pyridyl)oxy-1H-1-indolecarboxamide N1-Isopropyl-5-(2-amino-4-pyridyl)oxy-1H-1-indolecarboxamide (90 mg, 0.29 mmol) was suspended in tetrahydrofuran (2 ml) at room temperature; triethylamine (0.121 mg, 0.868 mmol) and phenyl chloroformate (0.08 ml, 0.633 mmol) was added thereto while stirring; and the reaction mixture was stirred at room temperature for 2 hours. Water was added to the reaction mixture; this was subjected to extraction with ethyl acetate, washed with brine, dried over anhydrous sodium sulfate and concentrated under reduced pressure. N,N-Dimethylformamide (1 ml) and pyrrolidine (0.2 ml, 2.39 mmol) was added to the residue, and stirred at room temperature overnight. The reaction mixture was partitioned between ethyl acetate and water; the organic layer was dried over anhydrous sodium sulfate. This solution was concentrated under reduced pressure; and the residue was purified by silica gel column chromatography (Fuji Silysia NH, ethyl acetate-methanol). The resultant was washed with a solvent mixture (ether:hexane=1:1); and the solid was filtered off to yield the title compound as crystals (65 mg).

$^1$H-NMR Spectrum (DMSO-d$_6$) δ (ppm): 1.23 (6H, d, J=6.8 Hz), 1.75–1.82 (4H, m), 3.28–3.46 (4H, m), 3.98–4.09 (1H, m), 6.56 (1 h, dd, J=2.4, 6.0 Hz), 6.68 (1H, d, J=3.6 Hz), 7.04 (1H, dd, J=2.4, 8.8 Hz), 7.37 (1H, d, J=2.4 Hz), 7.42 (1H, d, J=2.4 Hz), 7.84–8.00 (2H, m), 8.08 (1H, d, J=6.0 Hz), 8.28 (1H, d, J=8.8 Hz), 8.61 (1H, s).

The starting materials were synthesized as follows.

Production Example 214-1

N1-Isopropyl-5-(2-amino-4-pyridyl)oxy-1H-1-indolecarboxamide

Similarly to Production example 213-1, the title compound was obtained as crystals (220 mg) from 4-(1H-5-indolyloxy)-2-pyridinamine (482 mg, 2.16 mmol, CAS No. 417722-11-3), which was described in WO 02/32872, N,N-dimethylformamide (7 ml), sodium hydride (60% in oil, 94 mg, 2.57 mmol), and phenyl N-isopropylcarbamate (460 mg, 2.57 mmol) under nitrogen atmosphere.

$^1$H-NMR Spectrum (DMSO-d$_6$) δ (ppm): 1.22 (6H, d, J=6.8 Hz), 3.97–4.08 (1H, m), 5.76 (1H, d, J=2.0 Hz), 5.85 (2H, s), 6.14 (1H, dd, J=2.0, 5.6 Hz), 6.67 (1H, d, J=3.6 Hz), 7.02 (1H, dd, J=2.0, 8.8 Hz), 7.34 (1H, d, J=2.4 Hz), 7.77 (1H, d, J=6.0 Hz), 7.94–7.96 (2H, m), 8.27 (1H, d, J=8.8 Hz).

Example 215

N1-Methyl-5-(2-(methylaminocarbonyl)amino-5-cyano-4-pyridyl)oxy-1H-1-indolecarboxamide Production Example 215-1

N1-Methyl-5-(2-amino-5-cyano-4-pyridyl)oxy-1H-1-indolecarboxamide

6-Amino-4-(1H-5-indolyloxy)nicotinonitrile (63 mg, 0.252 mmol) was dissolved in N,N-dimethylformamide (1 ml); and sodium hydride (60% in oil, 11.6 mg, 0.29 mmol) was gradually added thereto while stirring at room temperature. After the reaction mixture was stirred for 30 minutes, phenyl N-propylcarbamate (49.5 mg, 0.277 mmol) was added thereto; and the reaction mixture was stirred for 3 hours. A saturated aqueous solution of ammonium chloride was added thereto; this was subjected to extraction with ethyl acetate, and dried over anhydrous sodium sulfate. This solution was concentrated under reduced pressure. The residue was purified by silica gel column chromatography (Fuji Silysia NH, ethyl acetate-methanol) to yield the title compound (12 mg) and N1-methyl-5-(2-amino-5-cyano-4-pyridyl)oxy-1H-1-indolecarboxamide (17 mg).

N1-Methyl-5-(2-(methylaminocarbonyl)amino-5-cyano-4-pyridyl)oxy-1H-1-indolecarboxamide;

$^1$H-NMR Spectrum (DMSO-d$_6$) δ (ppm): 2.58 (3H, d, J=4.6 Hz), 2.86 (3H, d, J=4.6 Hz), 7.15 (1H, dd, J=2.0, 8.3 Hz), 7.20–7.28 (1H, m), 7.51 (1H, d, J=2.0 Hz), 7.93 (1H, d, J=3.0 Hz), 8.22 (1H, q, J=4.6 Hz), 8.34 (3H, d, J=8.3 Hz), 8.59 (1H, s), 9.51 (1H, s).

N1-Methyl-5-(2-amino-5-cyano-4-pyridyl)oxy-1H-1-indolecarboxamide;

$^1$H-NMR Spectrum (DMSO-d$_6$) δ (ppm): 2.85 (3H, d, J=4.9 Hz), 5.59 (1H, s), 6.72 (1H, d, J=2.6 Hz), 6.87 (2H, brs), 7.13 (1H, dd, J=1.6, 8.5 Hz), 7.49 (1H, d, J=1.6 Hz), 7.92 (1H, d, J=2.6 Hz), 8.21 (1H, q, J=4.9 Hz), 8.28 (1H, s), 8.34 (1H, d, J=8.5 Hz).

Production Example 215-2

2-Amino-4-chloro-5-iodopyridine

N,N-Dimethylformamide (47 ml) and N-iodosuccinimide (10.7 g, 47.6 mmol) were added to 2-amino-4-chloropyridine (4.72 g, 36.7 mmol); and the reaction mixture was stirred overnight. An aqueous solution of sodium thiosulfate and ethyl acetate were added thereto; the organic layer was separated, concentrated, and dried over anhydrous sodium sulfate. This was concentrated under reduced pressure; a solvent mixture (ether: hexane=1:1) was added to the residue; and the solid was filtered off to yield the title compound (7.0 g, 27.5 mmol).

$^1$H-NMR Spectrum (CDCl$_3$) δ (ppm): 4.56 (2H, brs), 6.68 (1H, s), 8.32 (1H, s).

Production Example 215-3

2-Amino-4-chloro-5-cyanopyridine

1-Methyl-2-pyrrolidone (20 ml), zinc cyanide (0.49 g, 4.17 mmol) and tetrakis(triphenylphosphine)palladium (1.3 g, 1.12 mmol) were added to 2-amino-4-chloro-5-iodopyridine (1.93 g, 7.58 mmol) synthesized in Production example 215-2; and the reaction mixture was stirred at 130-135° C. for 5 hours. Approximately 0.28% of aqueous ammonium (100 ml) and ethyl acetate was added to the reaction mixture; and the organic layer was separated, washed with brine, and dried over anhydrous sodium sulfate. This was concentrated under reduced pressure and the residue was filtrated by silica gel column chromatography (Fuji Silysia NH, ethyl acetate). After concentration under reduced pressure, a solvent mixture (ether:hexane=1:1) was added to the residue, and stirred; and the solid was filtered off to yield the title compound as crystals (680 mg).
$^1$H-NMR Spectrum (CDCl$_3$) δ (ppm): 5.03 (2H, brs), 6.58 (1H, s), 8.32 (1H, s).
MS Spectrum (EI): 153 (M).

Production Example 215-4

6-Amino-4-(1H-5-indolyloxy)nicotinonitrile

5-Hydroxyindole (313 mg, 2.35 mmol) was dissolved in dimethyl sulfoxide (3 ml); and sodium hydride (90 mg, 2.25 mmol) was gradually added thereto while stirring at room temperature. After the reaction mixture was stirred for 1 hour, 2-amino-4-chloro-5-cyanopyridine (300 mg, 1.96 mmol) synthesized in Production example 215-3 was added thereto; and the reaction mixture was heated and stirred at 120° C. for 4 hours. After allowing to be cooled to room temperature, the reaction mixture was partitioned between ethyl acetate and water; and the organic layer was washed with water and brine, and dried over anhydrous sodium sulfate. The solvent was distilled off; the residue was subjected to silica gel column chromatography (Fuji Silysia NH, ethyl acetate-methanol); fractions containing the desired compound was concentrated under reduced pressure; ether was added thereto; and the solid was filtered off, and dried under reduced pressure to yield the title compound (95 mg, 0.38 mmol, 59%).
$^1$H-NMR Spectrum (DMSO-d$_6$) δ (ppm) 5.59 (1H, s), 6.48 (1H, s), 6.82 (2H, s), 6.92 (1H, dd, J=2.0, 9.0 Hz), 7.40 (1H, d, J=2.0 Hz), 7.46 (1H, t, J=2.0 Hz), 7.50 (1H, d, J=9.0 Hz), 8.26 (1H, s), 11.30 (1H, s).

Example 216

N1-Methyl-5-(2-(pyrrolidin-1-ylcarbonyl)amino-5-cyano-4-pyridyl)oxy-1H-1-indolecarboxamide N1-Methyl-5-(2-amino-5-cyano-4-pyridyl)oxy-1H-1-indolecarboxamide (20 mg) synthesized in Example 215 was suspended in tetrahydrofuran (0.5 ml) at room temperature; triethylamine (0.121 ml, 0.868 mmol) and phenyl chloroformate (0.08 ml, 0.633 mmol) was added thereto while stirring; and the reaction mixture was stirred at room temperature for 2 hours. Water was added to the reaction mixture; this was subjected to extraction with ethyl acetate, washed with brine, dried over anhydrous sodium sulfate, and concentrated under reduced pressure. N,N-Dimethylformamide and pyrrolidine (0.013 ml) was added to a portion of the residue (14 mg); and the reaction mixture was stirred overnight. The reaction mixture was partitioned between ethyl acetate and water; and the organic layer was dried over anhydrous sodium sulfate, and concentrated under reduced pressure. The residue was purified by silica gel column chromatography (Fuji Silysia NH, ethyl acetate-methanol). The resultant was washed with a solvent mixture (ether:hexane=1:1) to yield the title compound as crystals (6 mg).
$^1$H-NMR Spectrum (DMSO-d$_6$) δ (ppm): 1.74 (4H, brs), 2.85 (3H, d, J=4.4 Hz), 3.15–3.40 (4H, m), 6.72 (1H, d, J=4.7 Hz), 7.15 (1H, dd, J=1.9, 8.4 Hz), 7.37 (1H, s), 7.50 (1H, d, J=1.9 Hz), 7.93 (1H, d, J=4.7 Hz), 8.20–8.26 (1H, m), 8.33 (1H, d, J=8.4 Hz), 8.63 (1H, s), 9.28 (1H, brs).

Example 217

N1-Methyl-5-(2-((4-(pyrrolidin-1-yl)piperidin-1-yl)carbonyl)amino-5-cyano-4-pyridyl)oxy-1H-1-indolecarboxamide N1-Methyl-5-(2-amino-5-cyano-4-pyridyl)oxy-1H-1-indolecarboxamide (15 mg, 0.049 mmol) synthesized in Example 215 was suspended in tetrahydrofuran (0.5 ml) at room temperature; triethylamine (17 μl, 0.122 mmol) and phenyl chloroformate (14 μl, 0.072 mmol) was added thereto while stirring; and the reaction mixture was stirred at room temperature for 2 hours. Water was added to the reaction mixture, this was subjected to extraction with ethyl acetate, washed with brine, dried over anhydrous sodium sulfate, and concentrated under reduced pressure. N,N-Dimethylformamide (0.5 ml) and 4-(1-pyrrolidinyl)piperidine (28 mg, 0.18 mmol) was added to a portion of the residue (14 mg); and the reaction mixture was stirred at room temperature overnight. The reaction mixture was partitioned between ethyl acetate and water; and the organic layer was dried over anhydrous sodium sulfate. This was concentrated under reduced pressure; and the residue was purified by silica gel column chromatography (Fuji Silysia NH, ethyl acetate-methanol). The resultant was washed with a solvent mixture (ether:hexane=1:1); and the solid was filtered off to yield the title compound as crystals (6 mg).
MS Spectrum (ESI): 488 (M+1), 975 (2M+1).

Example 218

N1-Methyl-5-(2-((4-(pyrrolidin-1-yl)piperidin-1-yl)carbonyl)amino-5-cyano-4-pyridyl)amino-1H-1-indolecarboxamide N1-Methyl-5-(2-amino-5-cyano-4-pyridyl)amino-1H-1-indolecarboxamide (50 mg, 0.16 mmol) was suspended in tetrahydrofuran (1 ml) at room temperature; triethylamine (0.057 ml, 0.41 mmol) and phenyl chloroformate (0.041 ml, 0.325 mmol) was added thereto while stirring; and the reaction mixture was stirred at room temperature for 2 hours. Water was added to the reaction mixture; this was subjected to extraction with ethyl acetate, washed with brine, dried over anhydrous sodium sulfate, and concentrated under reduced pressure. N,N-Dimethylformamide (0.5 ml) and 4-(1-pyrrolidinyl)piperidine (100 mg, 0.648 mmol) was added to the residue; and the reaction mixture was stirred at room temperature overnight. The reaction mixture was partitioned between ethyl acetate and water; and the organic layer was dried over anhydrous sodium sulfate. This was concentrated under reduced pressure; and the residue was purified by silica gel column chromatography (Fuji Silysia NH, ethyl acetate-methanol) to yield the title compound (65 mg, 0.134 mmol).

MS Spectrum (ESI): 487 (M+1).

The starting materials were synthesized as follows.

Production Example 218-1

N1-Methyl-5-nitro-1H-1-indolecarboxamide

Sodium hydride (60% in oil, 228 mg, 5.7 mmol) was gradually added to a N,N-dimethylformamide (0.5 ml) solution of 5-nitroindole (0.841 g, 5.19 mmol) while stirring at room temperature; phenyl N-methylcarbamate (1.02 g, 6.74 mmol) was added thereto; and the reaction mixture was stirred overnight. The reaction mixture was partitioned between ethyl acetate and water; and the organic layer was washed with water and brine, dried over anhydrous sodium sulfate. This was concentrated under reduced pressure; and the residue was purified by silica gel column chromatography (hexane-ethyl acetate, sequentially ethyl acetate) to yield the title compound (600 mg).

$^1$H-NMR Spectrum (DMSO-$d_6$) δ (ppm): 2.88 (3H, d, J=4.4 Hz), 6.94 (1H, d, J=3.6 Hz), 8.03 (1H, d, J=3.6 Hz), 8.15 (1H, dd, J=2.4, 9.2 Hz), 8.35–8.43 (2H, m), 8.59 (1H, d, J=2.4 Hz).

Production Example 218-2

N1-Methyl-5-amino-1H-1-indolecarboxamide

Methanol (6 ml), water (2 ml), iron (0.32 g) and ammonium chloride (0.64 g) were added to N1-methyl-5-nitro-1H-1-indolecarboxamide (0.32 g, 1.46 mmol) synthesized in Production example 218-1; and the reaction mixture was heated to reflux for 2 hours. The reaction mixture was partitioned between ethyl acetate and water; the organic layer was washed with water and brine, and dried over anhydrous sodium sulfate. The residue was filtrated with celite, and concentrated under reduced pressure to yield the title compound (210 mg).

$^1$H-NMR Spectrum (DMSO-$d_6$) δ (ppm): 2.79 (3H, d, J=4.4 Hz), 4.73 (2H, brs), 6.48 (1H, d, J=3.6 Hz), 6.56 (1H, dd, J=2.4, 8.8 Hz), 6.68 (1H, d, J=1.6 Hz), 7.60 (1H, d, J=3.6 Hz), 7.80–7.88 (1H, m), 7.89 (1H, d, J=8.8 Hz).

Production Example 218-3

N1-Methyl-5-(2-amino-5-cyano-4-pyridyl)amino-1H-1-indolecarboxamide

2-Amino-4-chloro-5-cyanopyridine (123 mg, 0.80 mmol) synthesized in Production example 215-3, ethoxyethanol (3 ml) and pyridine hydrochloride (186 mg, 1.60 mmol) were added to N1-methyl-5-amino-1H-1-indolecarboxamide (198 mg, 1.05 mmol) synthesized in Production example 218-2; and the reaction mixture was stirred at 130° C. for 3 hours. After allowing to be cooled to room temperature, the reaction mixture was partitioned between a saturated aqueous solution of sodium hydrogencarbonate and ethyl acetate; and the organic layer was washed with water and brine, dried over anhydrous sodium sulfate. The solvent was distilled off, and the residue was purified by silica gel column chromatography (hexane-ethyl acetate, ethyl acetate in this order) to yield the title compound (110 mg, 0.359 mmol).

MS Spectrum (ESI): 307 (M+1).

$^1$H-NMR Spectrum (DMSO-$d_6$) δ (ppm): 2.84 (3H, d, J=4.4 Hz), 5.75 (1H, s), 6.39 (2H, s), 6.66 (1H, d, J=3.2 Hz), 7.13 (1H, dd, J=2.0, 8.8 Hz), 7.42 (1H, d, J=2.0 Hz), 7.82 (1H, d, J=3.2 Hz), 8.04 (1H, s), 8.08–8.14 (1H, m), 8.23 (1H, d, J=8.8 Hz), 8.30 (1H, s).

Example 219

N1-Methyl-5-(2-(3-(2-diethylaminoethyl)ureido) amino-5-cyano-4-pyridyl)amino-1H-1-indolecarboxamide N1-Methyl-5-(2-amino-5-cyano-4-pyridyl)amino-1H-1-indolecarboxamide (36 mg, 0.12 mmol) synthesized in Production example 218-3 was suspended in tetrahydrofuran (2 ml) at room temperature; triethylamine (0.1 ml, 0.72 mmol) and phenyl chloroformate (0.037 ml, 0.29 mmol) were added thereto while stirring; and the reaction mixture was stirred at room temperature for 2 hours. Water was added to the reaction mixture; this was subjected to extraction with ethyl acetate, washed with brine, dried over anhydrous sodium sulfate, and concentrated under reduced pressure. N,N-Dimethylformamide (0.5 ml) and N,N-diethylaminoethylamine (0.1 ml) were added to the residue; and the reaction mixture was stirred at room temperature overnight. The reaction mixture was partitioned between ethyl acetate and water; the organic layer was washed with brine, dried over anhydrous sodium sulfate. This was concentrated under reduced pressure; and the residue was purified by silica gel column chromatography (Fuji Silysia NH, ethyl acetate-methanol) to yield the title compound (25 mg, 0.056 mmol).

MS Spectrum (ESI): 449 (M+1).

$^1$H-NMR Spectrum (DMSO-$d_6$) δ (ppm): 0.93 (6H, t, J=6.8 Hz), 2.37–2.50 (6H, m), 2.84 (3H, d, J=4.4 Hz), 3.10 (2H, q, J=6.8 Hz), 6.68 (1H, d, J=3.2 Hz), 7.05 (1H, s), 7.15 (1H, dd, J=2.4, 8.8 Hz), 7.44 (1H, d, J=3.2 Hz), 7.70 (1H, brs), 7.84 (1H, d, J=4.0 Hz), 8.14 (1H, d, J=4.4 Hz), 8.24 (1H, d, J=8.8 Hz), 8.25 (1H, s), 8.84 (1H, s), 9.21 (1H, s).

Example 220

N1-Diethyl-2-methyl-5-(2-((4-(pyrrolidin-1-yl)piperidin-1-yl)carbonyl)amino-5-cyano-4-pyridyl) amino-1H-1-indolecarboxamide N1-Diethyl-2-methyl-5-(2-amino-5-cyano-4-pyridyl) amino-1H-1-indolecarboxamide (84 mg, 0.249 mmol) was suspended in tetrahydrofuran (1 ml) at room temperature; triethylamine (0.2 ml, 1.43 mmol) and phenyl chloroformate (0.079 ml, 0.626 mmol) were added thereto while stirring; and the reaction mixture was stirred at room temperature for 2 hours. Water was added to the reaction mixture; and this was subjected to extraction with ethyl acetate, washed with brine, dried over anhydrous sodium sulfate, and concentrated under reduced pressure. N,N-Dimethylformamide (0.5 ml) and 4-(1-pyrrolidinyl)piperidine (173 mg, 0.111 mmol) was added to a portion (80 mg) of the obtained residue (120 mg), and the reaction mixture was stirred at room temperature overnight. The reaction mixture was partitioned between ethyl acetate and water; and the organic layer was dried over anhydrous sodium sulfate. This was concentrated under reduced pressure; and the residue was purified by silica gel column chromatography (Fuji Silysia NH, ethyl acetate-methanol system) to yield the title compound (45 mg, 0.083 mmol).

MS Spectrum (ESI): 543.5 (M+1).

The starting materials were synthesized as follows.

Production Example 220-1

N1-Diethyl-2-methyl-5-nitro-1H-1-indolecarboxamide

Sodium hydride (60% in oil, 94 mg) was gradually added to a N,N-dimethylformamide (0.5 ml) solution of 2-methyl-5-nitroindole (0.841 g, 5.19 mmol) while stirring at room temperature; diethylcarbamoyl chloride (0.341 ml) was added thereto; and the reaction mixture was heated and stirred at 70° C. for 4 hours. After cooling down to room temperature, the reaction mixture was partitioned between ethyl acetate and water; the organic layer was washed with water and brine, and dried over anhydrous sodium sulfate. This was concentrated under reduced pressure; and the residue was purified by silica gel column chromatography (Fuji Silysia NH; hexane-ethyl acetate, ethyl acetate in this order) to yield the title compound (420 mg).

MS Spectrum (ESI): 330 (M+55).

Production Example 220-2

N1-Diethyl-2-methyl-5-amino-1H-1-indolecarboxamide

Methanol (8 ml), water (2 ml), iron powder (0.42 g) and ammonium chloride (0.84 g) were added to N1-methyl-5-nitro-1H-1-indolecarboxamide (415 g, 1.46 mmol) synthesized in Production example 220-1; and the reaction mixture was heated to reflux for 2 hours. The reaction mixture was partitioned between ethyl acetate and water; and the organic layer was washed with water and brine, and dried over anhydrous sodium sulfate. The filtration with celite, and concentration under reduced pressure yield the title compound (322 mg).

MS Spectrum (ESI): 246 (M+1).

$^1$H-NMR Spectrum (DMSO-$d_6$) $\delta$ (ppm): 1.10 (6H, t, J=7.2 Hz), 2.28 (3H, s), 3.25–3.40 (4H, m), 4.92 (2H, brs), 6.10 (1H, t, J=0.8 Hz), 6.51 (1H, dd, J=2.4, 8.4 Hz), 6.64 (1H, d, J=2.4 Hz), 6.89 (1H, d, J=8.4 Hz).

Production Example 220-3

N1-Diethyl-2-methyl-5-(2-amino-5-cyano-4-pyridyl)amino-1H-1-indolecarboxamide 2-Amino-4-chloro-5-cyanopyridine (140 mg, 0.92 mmol) synthesized in Production example 215-3, ethoxyethanol (2.5 ml), and pyridine hydrochloride (223 mg, 1.92 mmol) was added to N1-diethyl-2-methyl-5-amino-1H-1-indolecarboxamide (320 mg, 1.31 mmol) synthesized in Production example 220-2; and the reaction mixture was stirred at 130° C. for 3 hours. After cooling down to room temperature, the reaction mixture was partitioned between a saturated aqueous solution of sodium hydrogencarbonate and ethyl acetate; and the organic layer was washed with water and brine, and dried over anhydrous sodium sulfate. The solvent was distilled off; and the residue was purified by silica gel column chromatography (hexane-ethyl acetate, sequentially ethyl acetate) to yield the title compound (110 mg, 0.359 mmol).

MS Spectrum (ESI): 363 (M+1).

$^1$H-NMR Spectrum (DMSO-$d_6$) $\delta$ (ppm): 1.05–1.20 (6H, m), 2.36 (3H, s), 3.25–3.40 (4H, m), 5.68 (1H, s), 6.35–6.37 (3H, m), 7.02 (1H, dd, J=2.0, 8,4 Hz), 7.19 (1H, d, J=8.4 Hz), 7.30 (1H, d, J=2.0 Hz), 8.01 (1H, s), 8.22 (1H, s).

Example 221

5-(5-Iodo-2-(3-methylureido)pyrimidin-4-yloxy)-1H-indole-1-carboxylic acid methylamide Phenyl N-(5-iodo-4-(1-methylaminocarbonyl-1H-indol-5-yloxy)pyrimidin-2-yl)-N-(phenoxycarbonyl)carbamate (597 mg, 0.919 mmol) was dissolved in dimethylformamide (3.0 ml); a 40% methanol solution of methylamine (1.0 ml) was added while stirring at 0° C.; and the reaction mixture was further stirred for 30 minutes keeping the temperature. Water (10 ml) was added to the reaction mixture after the completion of the reaction; the precipitated crystals were filtered off, washed with water, methanol and diethyl ether, and dried under warm aeration to yield the title compound as white crystals (367 mg, 0.787 mmol, 86%).

$^1$H-NMR Spectrum (DMSO-$d_6$) $\delta$ (ppm): 2.04 (3H, D, J=4.8 Hz), 2.85 (3H, d, J=4.0 Hz), 6.73 (1H, d, J=3.6 Hz), 7.16 (1H, dd, J=2.4, 8.8 Hz), 7.52 (1H, d, J=2.4 Hz), 7.61 (1H, m), 7.92 (1H, d, J=3.6 Hz), 8.20 (1H, m), 8.35 (1H, d, J=8.8 Hz), 8.69 (1H, s), 9.78 (1H, brs).

The starting materials were synthesized as follows.

Production Example 221-1

N1-Methyl-5-(2-amino-4-pyrimidyl)oxy-1H-1-indolecarboxamide

Similarly to Production example 1-3, the title compound was obtained as white powder from 4-(1H-5-indolyloxy)-2-pyrimidinamine (413 mg, 1.83 mmol) synthesized in Production example 1-2 and phenyl N-methylcarbamate (332 mg, 2.20 mmol) synthesized in Production example 2-1.

$^1$H-NMR Spectrum (DMSO-$d_6$) $\delta$ (ppm): 2.84 (3H, d, J=4.0 Hz), 6.06 (1H, d, J=5.6 Hz), 6.57 (2H, brs), 6.67 (1H, d, J=3.6 Hz), 7.04 (1H, dd, J=2.4, 8.8 Hz), 7.36 (1H, d, J=2.4 Hz), 7.85 (1H, d, J=3.6 Hz), 8.08 (1H, d, J=5.6 Hz), 8.14 (1H, m), 8.25 (1H, d, J=8.8 Hz).

Production Example 221-2

N1-Methyl-5-(2-amino-5-iodo-4-pyrimidyl)oxy-1H-1-indolecarboxamide

N1-Methyl-5-(2-amino-4-pyrimidyl)oxy-1H-1-indolecarboxamide (302 mg, 1.07 mmol) and N-iodosuccinimide (301 mg, 1.34 mmol) were dissolved in N,N-dimethylformamide (3.0 ml); and the reaction mixture was stirred at room temperature for 1 hour. The reaction mixture was partitioned between ethyl acetate and water; and the organic layer was washed with water and brine, and was dried over anhydrous magnesium sulfate. The solvent was distilled off; and the residue was purified by silica gel column chromatography (eluent; ethyl acetate:hexane=2:1) to yield the title compound as yellow crystals (224 mg, 0.547 mmol, 51%).

$^1$H-NMR Spectrum (DMSO-$d_6$) $\delta$ (ppm): 2.84 (3H, d, J=4.4 Hz), 6.67 (1H, d, J=3.6 Hz), 6.72 (2H, brs), 7.04 (1H, dd, J=2.4, 8.8 Hz), 7.36 (1H, d, J=2.4 Hz), 7.85 (1H, d, J=3.6 Hz), 8.15 (1H, m), 8.24 (1H, d, J=8.8 Hz), 8.33 (1H, s).

Production Example 221-3

Phenyl N-(5-iodo-4-(1-methylaminocarbonyl-1H-indol-5-yloxy)pyrimidin-2-yl)-N-(phenoxycarbonyl)carbamate N1-Methyl-5-(2-amino-5-iodo-4-pyrimidyl)oxy-1H-1-indolecarboxamide (205 mg, 0.500 mmol) was suspended in tetrahydrofuran (5.0 ml); triethylamine (0.209 ml, 1.50 mmol) was added thereto while stirring. The suspension was cooled with ice; phenyl chloroformate (0.188 ml, 1.50 mmol) was added thereto; and the reaction mixture was stirred at room temperature for 3 hours. The reaction mixture was partitioned between ethyl acetate and a saturated aqueous solution of sodium hydrogencarbonate; and the organic layer was washed with a saturated aqueous solution of sodium hydrogencarbonate and brine, and was dried over anhydrous magnesium sulfate. After solvent distillation, the obtained crude product was crystallized from ethyl acetate-hexane; and the crystals were filtered off, and dried under aeration to yield the title compound as white crystals (207 mg, 0.319 mmol, 64%).

$^1$H-NMR Spectrum (CDCl$_3$) δ (ppm): 3.09 (3H, d, J=4.8 Hz), 5.56 (1H, m), 6.56 (1H, d, J=3.6 Hz), 6.98–7.14 (4H, m), 7.17–7.34 (6H, m), 7.36–7.42 (2H, m), 7.68 (1H, s), 8.12 (1H, d, J=8.8 Hz), 8.74 (1H, s).

The structural formulas of the compounds obtained in Production examples and Examples above are shown in Tables 3 to 15 below.

TABLE 3

PRODUCTION EXAMPLE 1-1

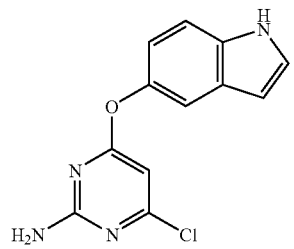

PRODUCTION EXAMPLE 1-2

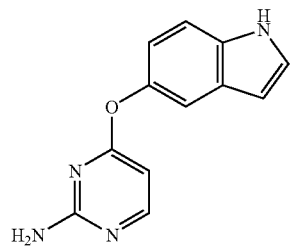

PRODUCTION EXAMPLE 1-3

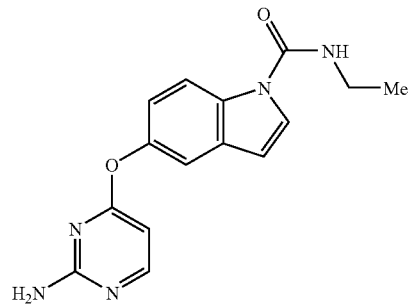

PRODUCTION EXAMPLE 2-1

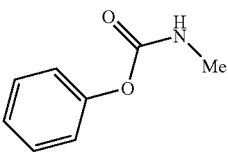

TABLE 3-continued
PRODUCTION
EXAMPLE 2-2
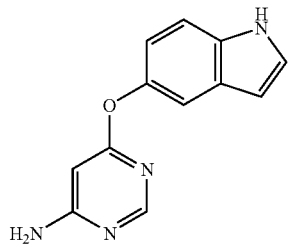
PRODUCTION
EXAMPLE 2-3
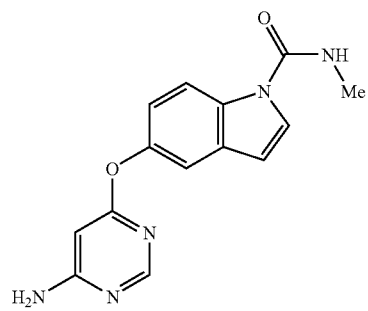
PRODUCTION
EXAMPLE 2-4
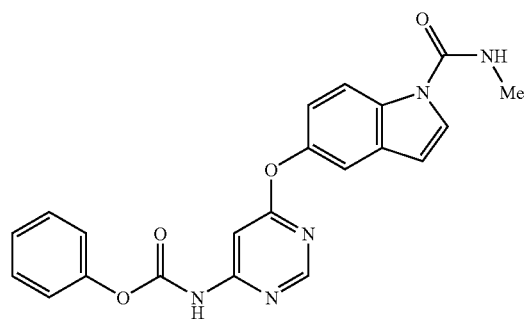
PRODUCTION
EXAMPLE 5-1
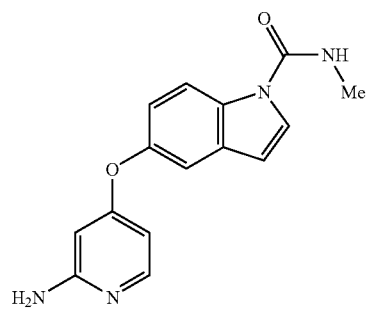

TABLE 3-continued
PRODUCTION EXAMPLE 5-2
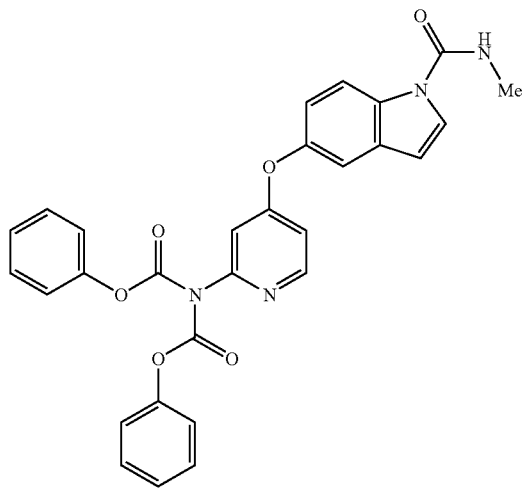
PRODUCTION EXAMPLE 5-3
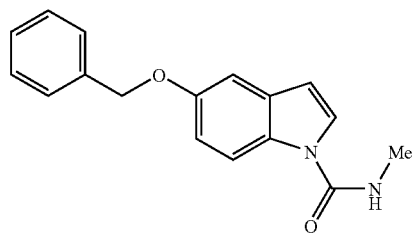
PRODUCTION EXAMPLE 5-4
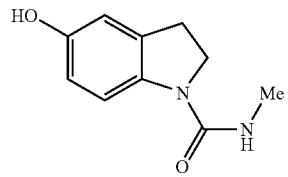
PRODUCTION EXAMPLE 5-5
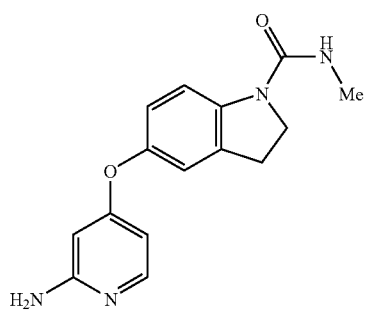

TABLE 3-continued
PRODUCTION
EXAMPLE 8-1
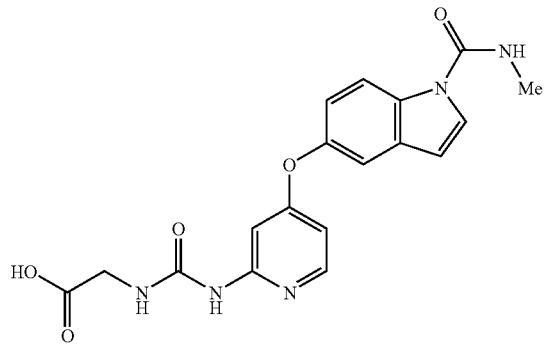
PRODUCTION
EXAMPLE 8-2
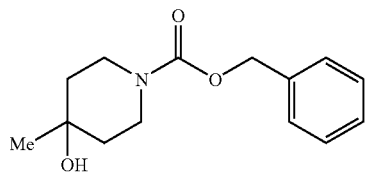
PRODUCTION
EXAMPLE 8-3
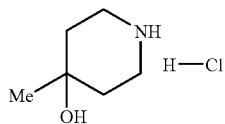
PRODUCTION
EXAMPLE 26-1
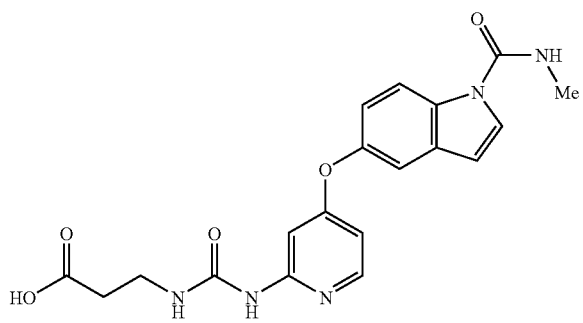
PRODUCTION
EXAMPLE 27-1
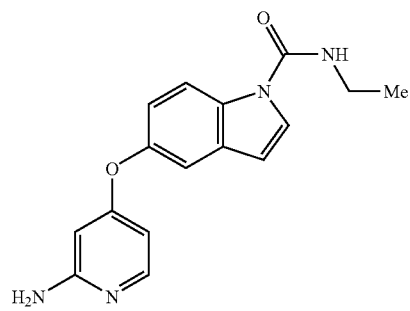

TABLE 3-continued
PRODUCTION
EXAMPLE 27-2
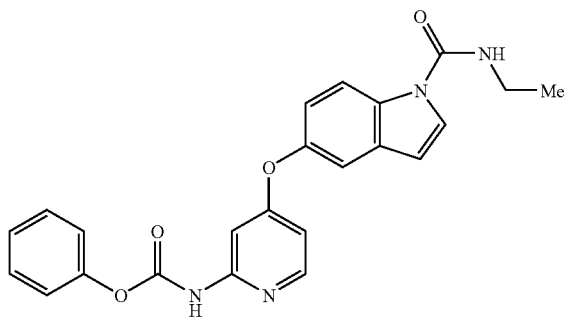
PRODUCTION
EXAMPLE 28-1
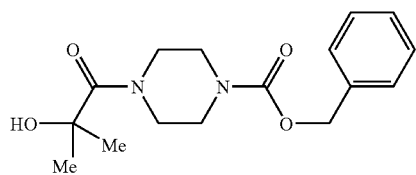
PRODUCTION
EXAMPLE 28-2
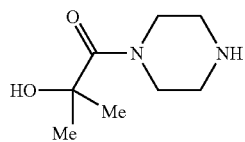
PRODUCTION
EXAMPLE 29-1
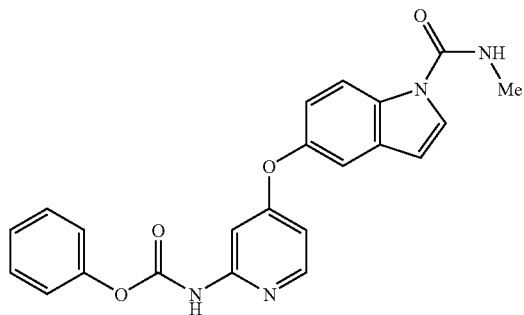

TABLE 3-continued
PRODUCTION
EXAMPLE 32-1
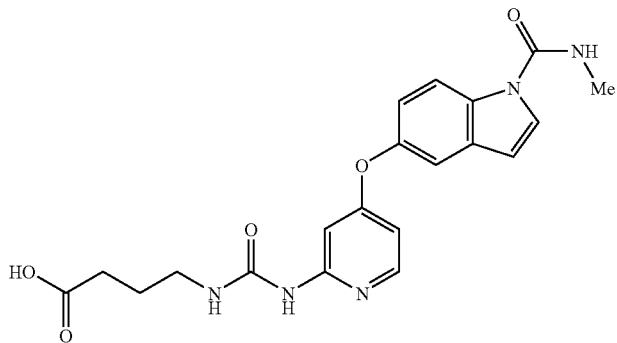
PRODUCTION
EXAMPLE 42-1
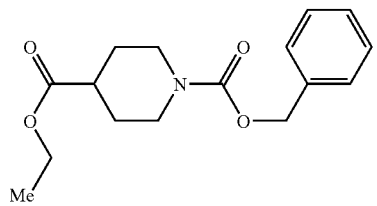
PRODUCTION
EXAMPLE 42-2
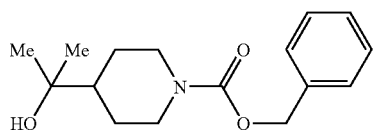
PRODUCTION
EXAMPLE 42-3
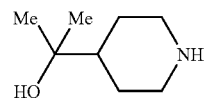
PRODUCTION
EXAMPLE 43-1
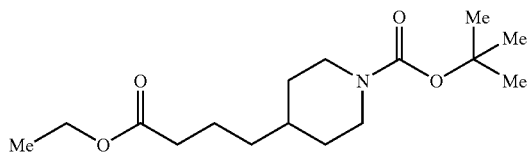
PRODUCTION
EXAMPLE 43-2
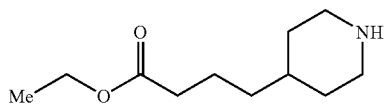

PRODUCTION
EXAMPLE 43-3
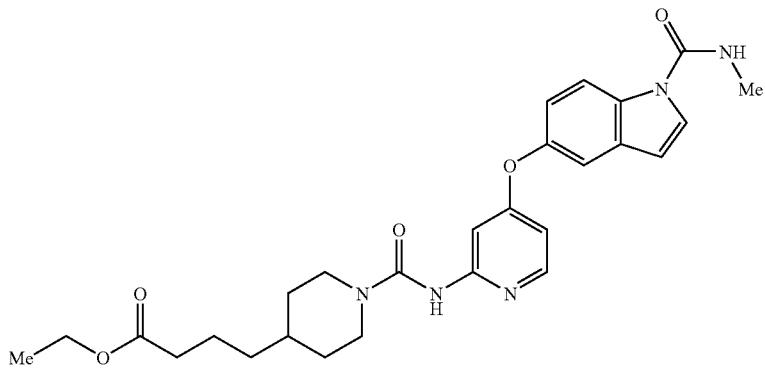
PRODUCTION
EXAMPLE 43-4
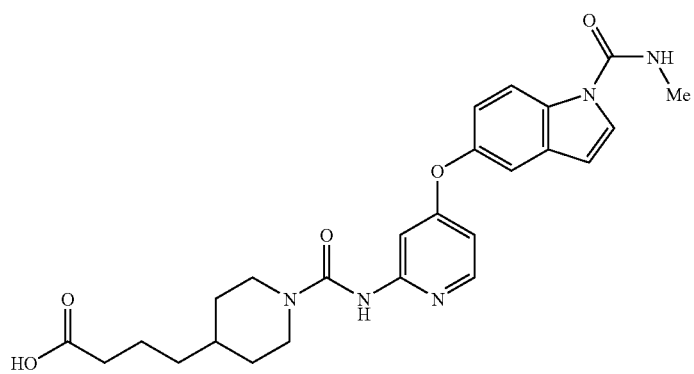
PRODUCTION
EXAMPLE 44-1
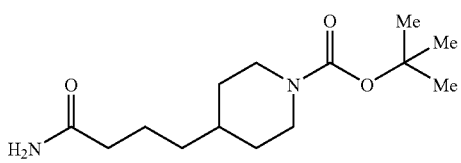
PRODUCTION
EXAMPLE 44-2
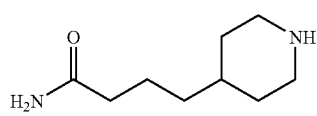
PRODUCTION
EXAMPLE 51-1
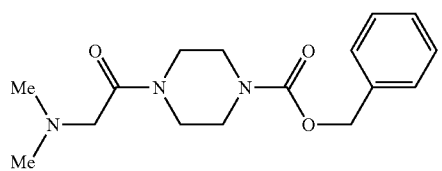

TABLE 3-continued
PRODUCTION
EXAMPLE 51-2
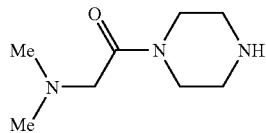
PRODUCTION
EXAMPLE 54-1
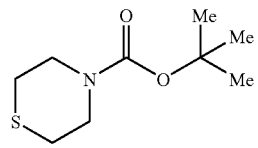
PRODUCTION
EXAMPLE 54-2
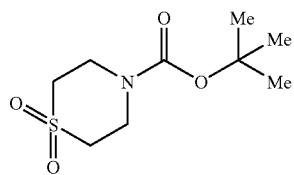
PRODUCTION
EXAMPLE 54-3
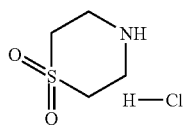
PRODUCTION
EXAMPLE 55-1
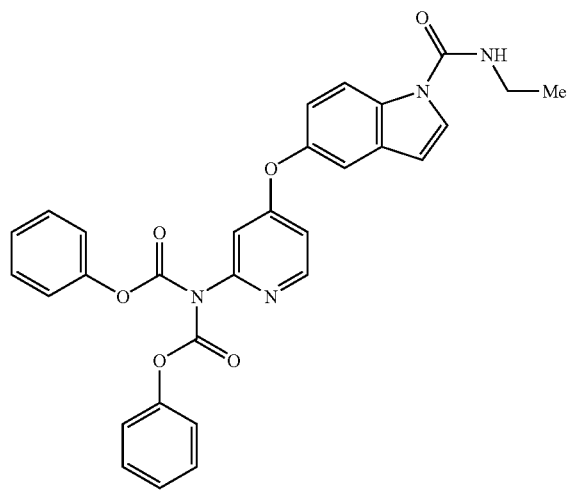

TABLE 3-continued
PRODUCTION EXAMPLE 59-1
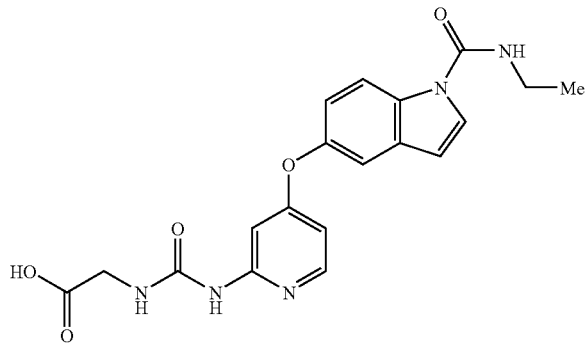
PRODUCTION EXAMPLE 90-1
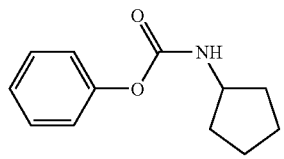
PRODUCTION EXAMPLE 90-2
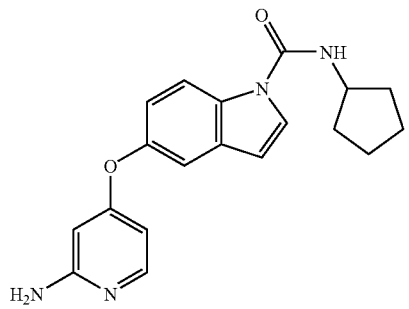
TABLE 4
PRODUCTION EXAMPLE 90-3
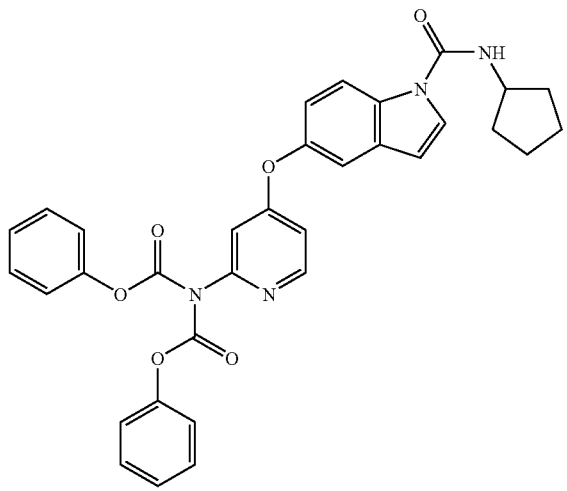

TABLE 4-continued
PRODUCTION
EXAMPLE 93-1
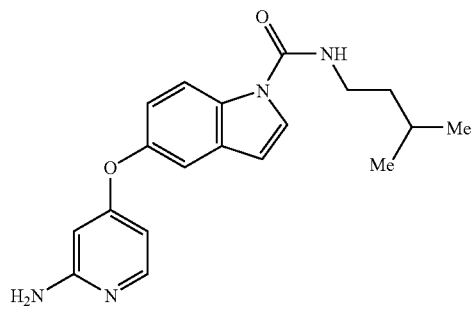
PRODUCTION
EXAMPLE 93-2
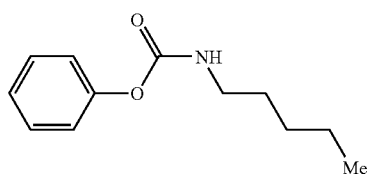
PRODUCTION
EXAMPLE 96-1
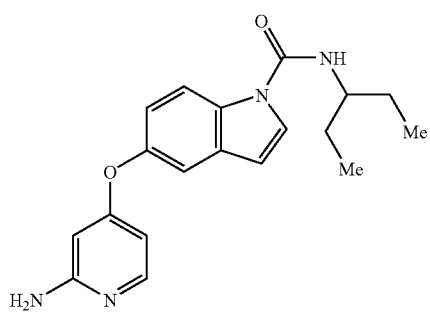
PRODUCTION
EXAMPLE 96-2
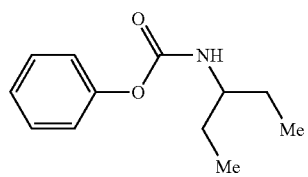
PRODUCTION
EXAMPLE 99-1
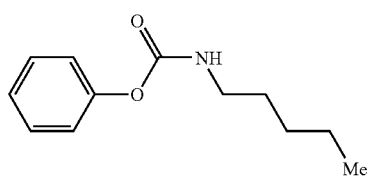

TABLE 4-continued
PRODUCTION EXAMPLE 99-2
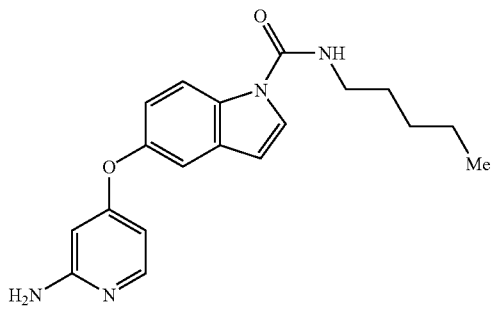
PRODUCTION EXAMPLE 99-3
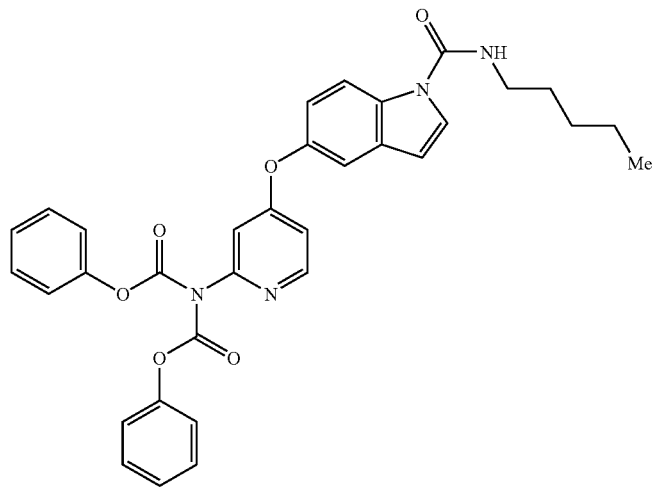
PRODUCTION EXAMPLE 102-1
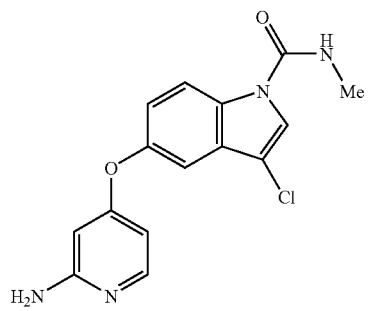

TABLE 4-continued
PRODUCTION EXAMPLE 102-2
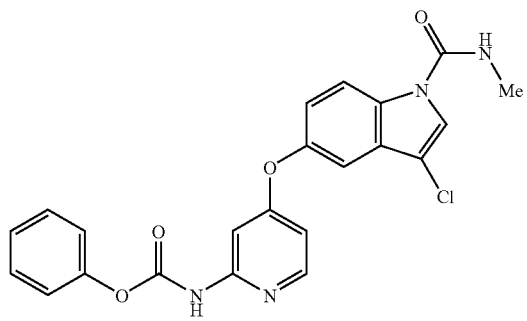
PRODUCTION EXAMPLE 105-1
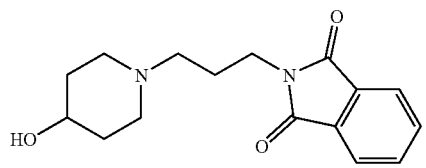
PRODUCTION EXAMPLE 105-2
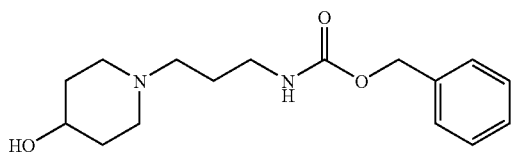
PRODUCTION EXAMPLE 105-3
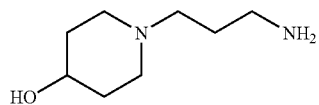
PRODUCTION EXAMPLE 109-1
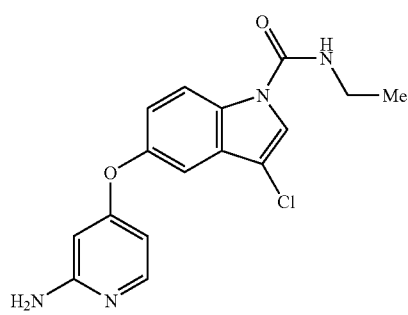

TABLE 4-continued
PRODUCTION EXAMPLE 112-1
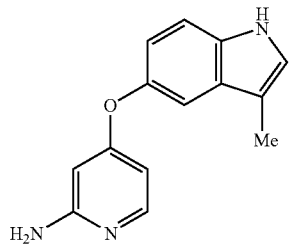
PRODUCTION EXAMPLE 112-2
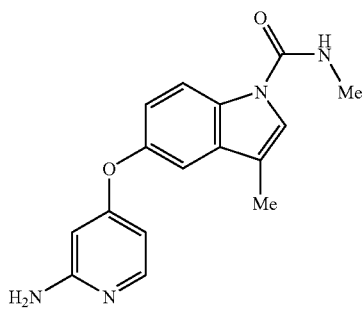
PRODUCTION EXAMPLE 114-1
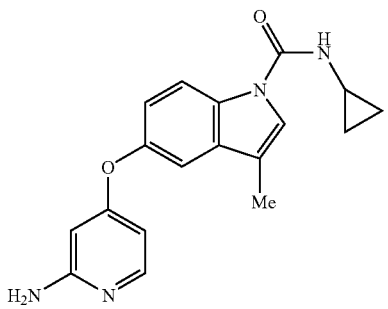
TABLE 5
PRODUCTION EXAMPLE 131-1
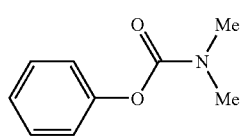
TABLE 5-continued
PRODUCTION EXAMPLE 131-2
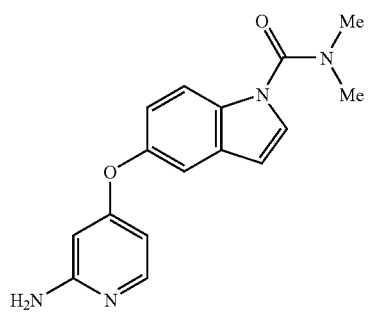

TABLE 5-continued
PRODUCTION EXAMPLE 134-1
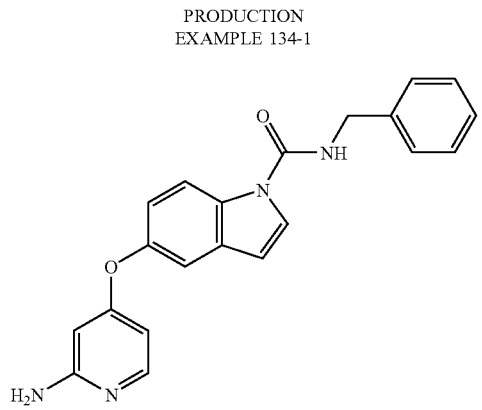
PRODUCTION EXAMPLE 135-1
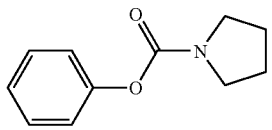
PRODUCTION EXAMPLE 135-2
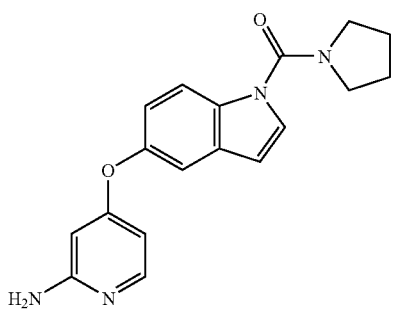
PRODUCTION EXAMPLE 137-1
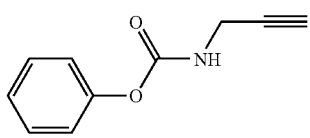
PRODUCTION EXAMPLE 137-2
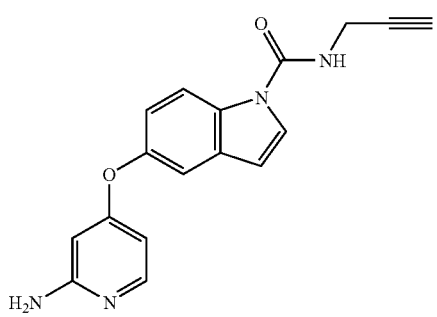
TABLE 5-continued
PRODUCTION EXAMPLE 140-1
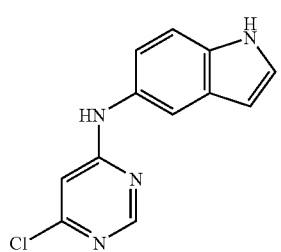
PRODUCTION EXAMPLE 140-2
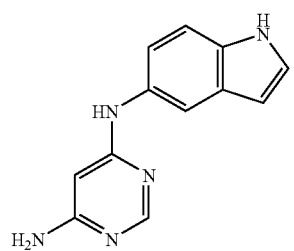
PRODUCTION EXAMPLE 140-3
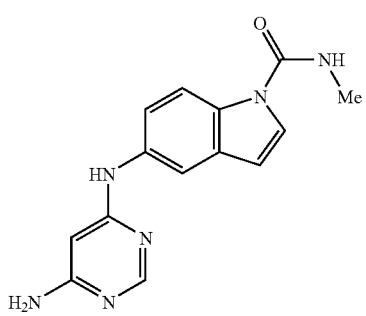
PRODUCTION EXAMPLE 146-1
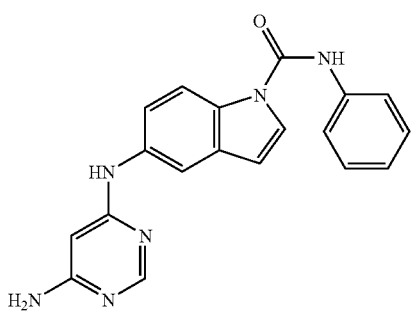

TABLE 5-continued
PRODUCTION EXAMPLE 149-1
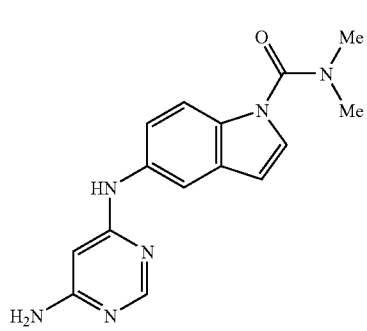
PRODUCTION EXAMPLE 151-1
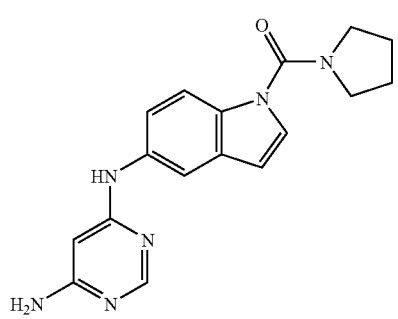
PRODUCTION EXAMPLE 156-1
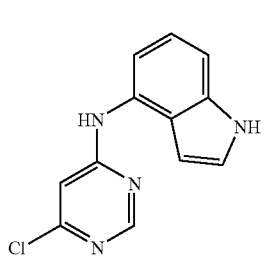
PRODUCTION EXAMPLE 156-2
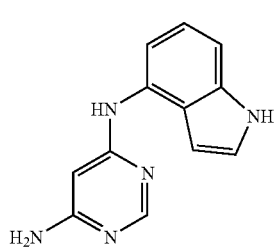
TABLE 5-continued
PRODUCTION EXAMPLE 156-3
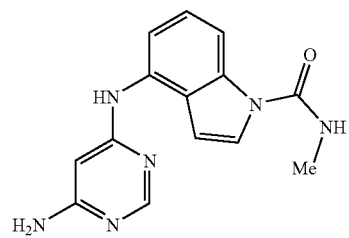
PRODUCTION EXAMPLE 159-1
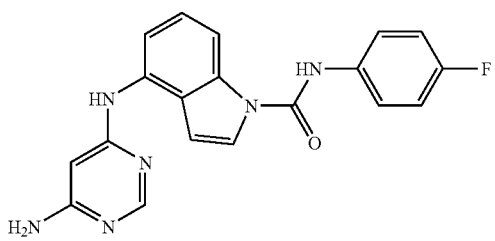
PRODUCTION EXAMPLE 161-1
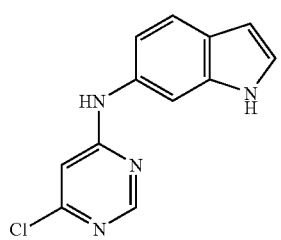
PRODUCTION EXAMPLE 161-2
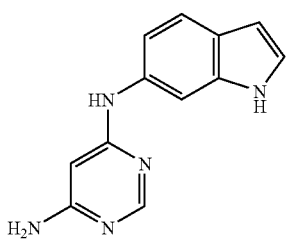
PRODUCTION EXAMPLE 161-3
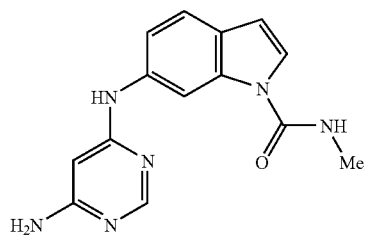

TABLE 5-continued
PRODUCTION EXAMPLE 163-1
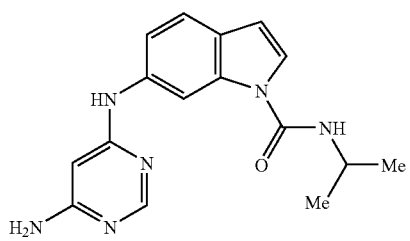
PRODUCTION EXAMPLE 165-1
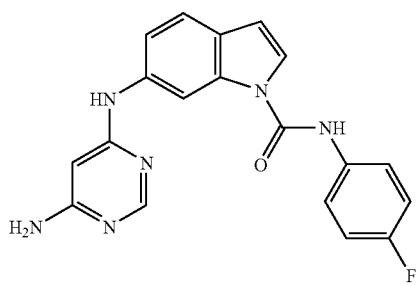
PRODUCTION EXAMPLE 167-1
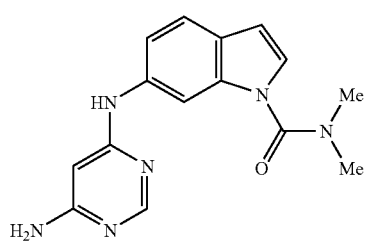
PRODUCTION EXAMPLE 168-1
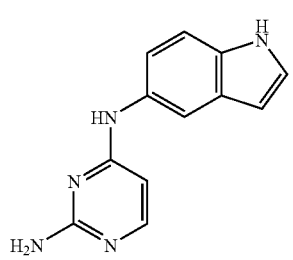
TABLE 5-continued
PRODUCTION EXAMPLE 168-2
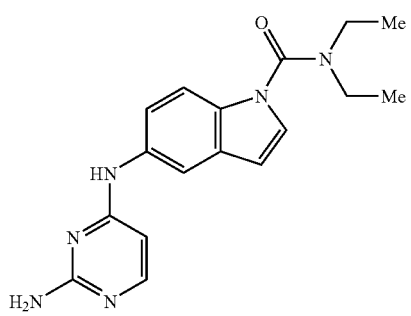
PRODUCTION EXAMPLE 169-1
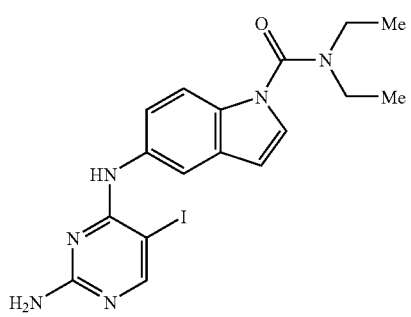
PRODUCTION EXAMPLE 170-1
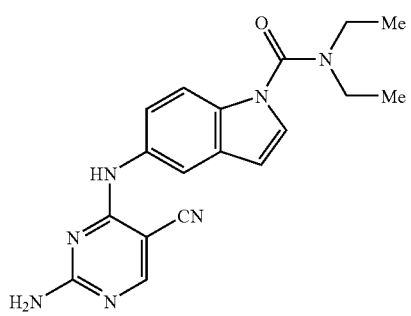
TABLE 6
PRODUCTION EXAMPLE 171-1
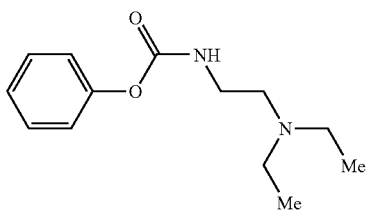

TABLE 6-continued
PRODUCTION EXAMPLE 172-1
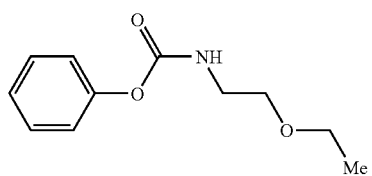
PRODUCTION EXAMPLE 172-2
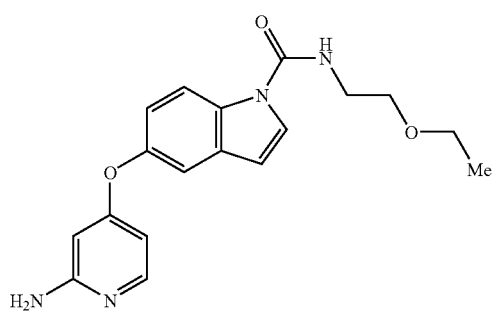
PRODUCTION EXAMPLE 174-1
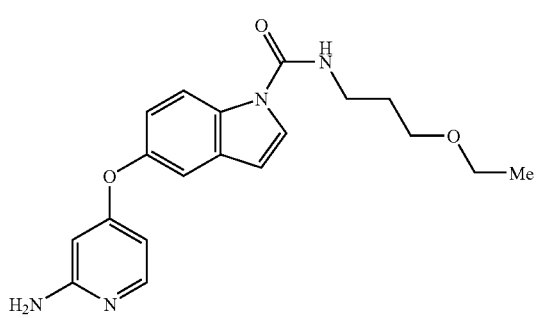
PRODUCTION EXAMPLE 176-1
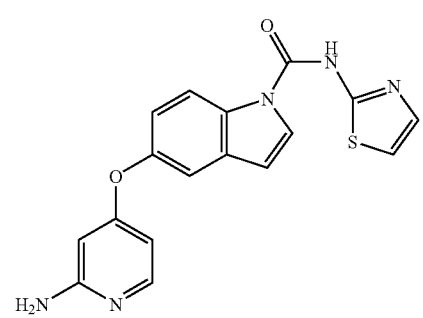
PRODUCTION EXAMPLE 178-1
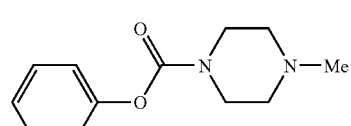
TABLE 6-continued
PRODUCTION EXAMPLE 178-2
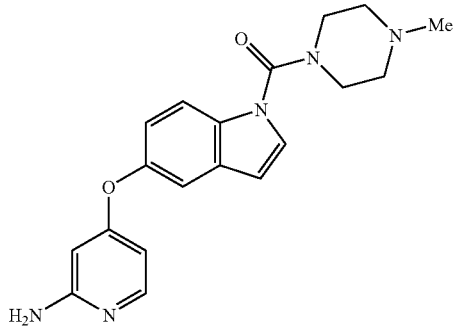
PRODUCTION EXAMPLE 179-1
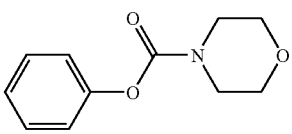
PRODUCTION EXAMPLE 179-2
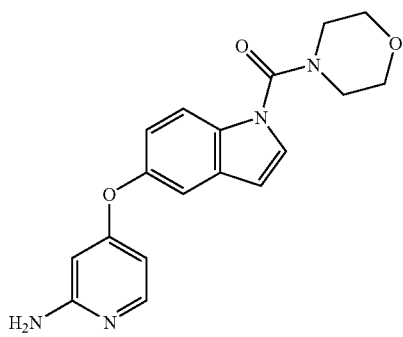
PRODUCTION EXAMPLE 181-1
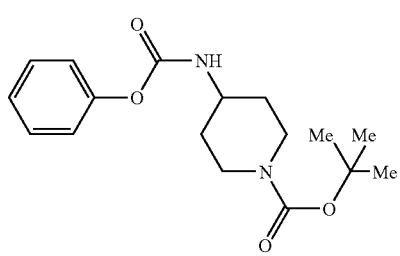

TABLE 6-continued
PRODUCTION EXAMPLE 183-1
PRODUCTION EXAMPLE 184-1
PRODUCTION EXAMPLE 187-1
PRODUCTION EXAMPLE 187-2
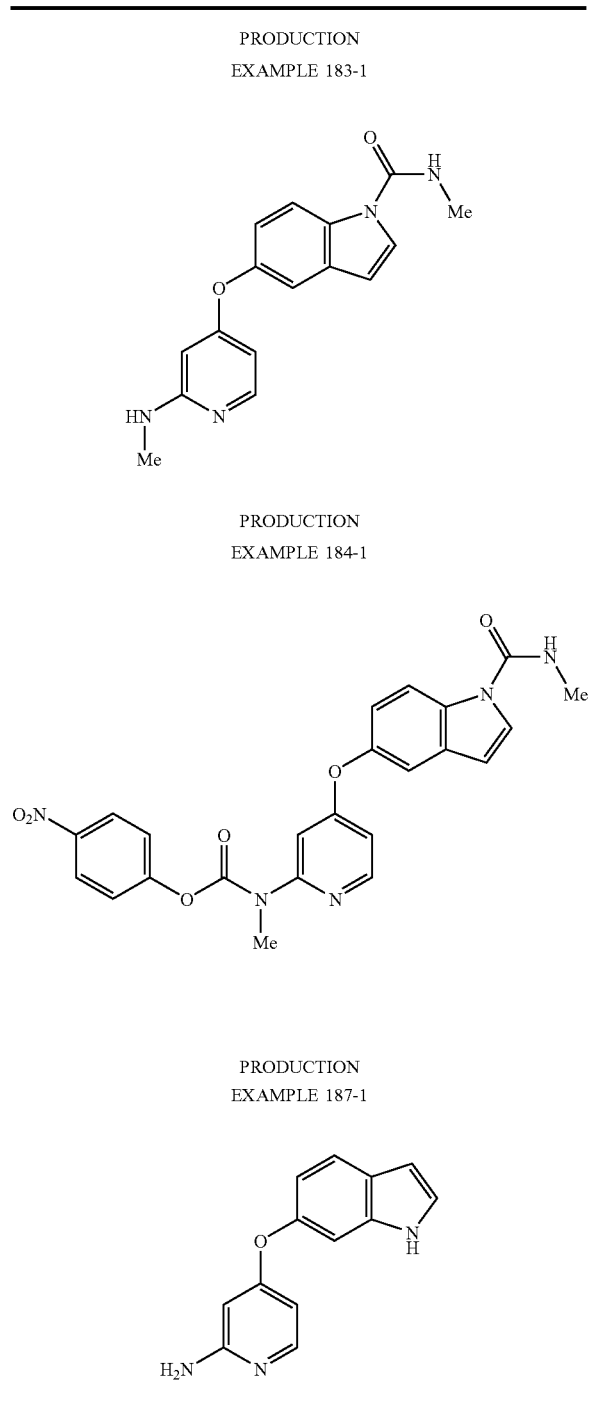
TABLE 6-continued
PRODUCTION EXAMPLE 187-3
PRODUCTION EXAMPLE 191-1
PRODUCTION EXAMPLE 191-2
PRODUCTION EXAMPLE 195-1
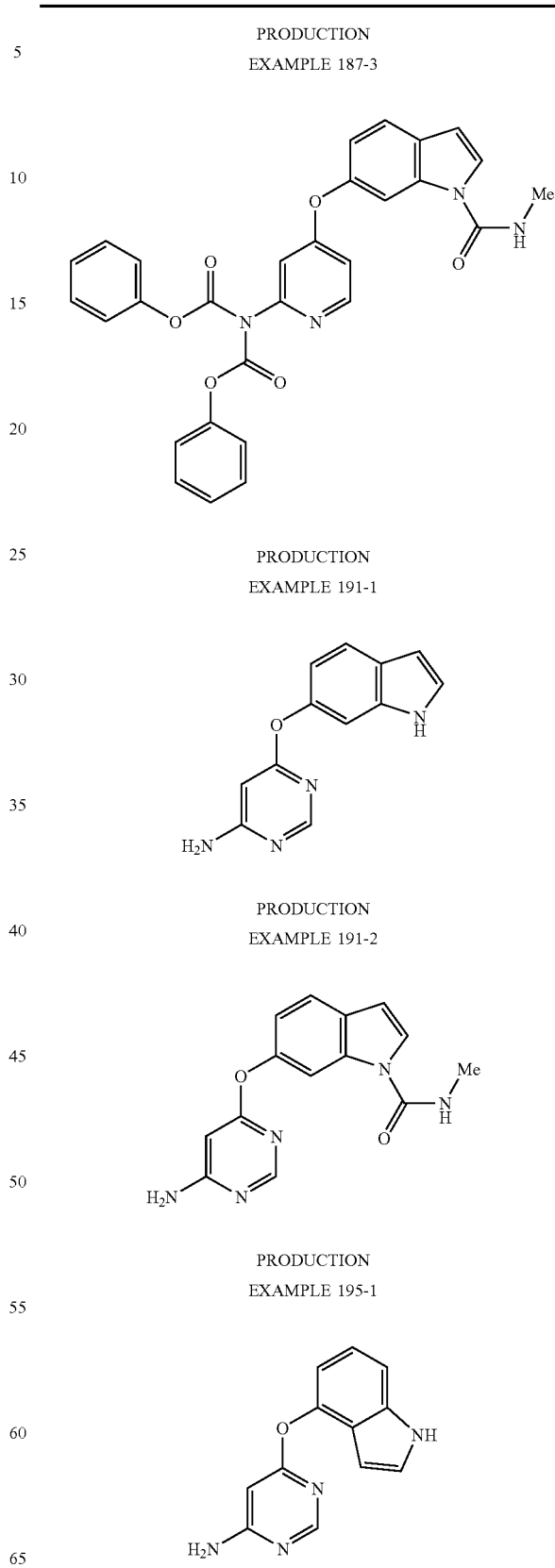

TABLE 6-continued
PRODUCTION EXAMPLE 195-2
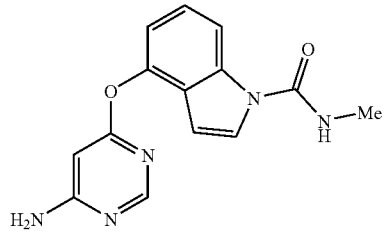
PRODUCTION EXAMPLE 199-1
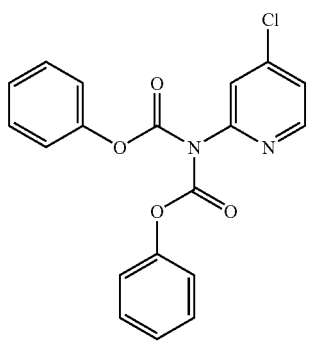
PRODUCTION EXAMPLE 199-2
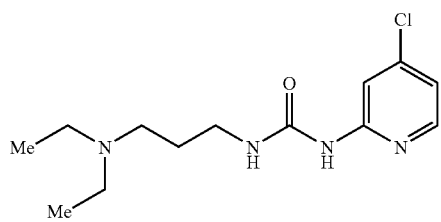
PRODUCTION EXAMPLE 200-1
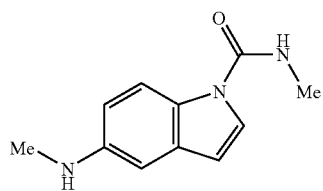
PRODUCTION EXAMPLE 201-1
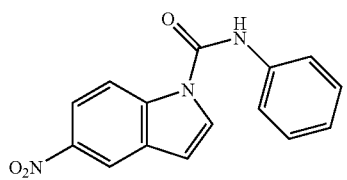
TABLE 6-continued
PRODUCTION EXAMPLE 202-2
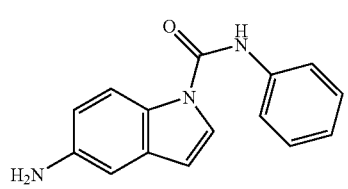
PRODUCTION EXAMPLE 201-3
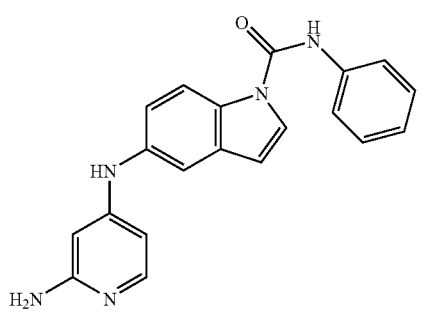
PRODUCTION EXAMPLE 203-1
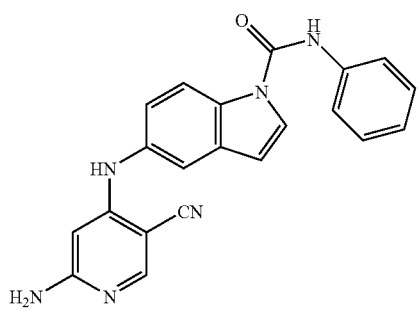
PRODUCTION EXAMPLE 205-1
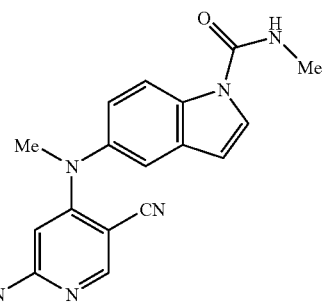

TABLE 7
PRODUCTION EXAMPLE 213-1
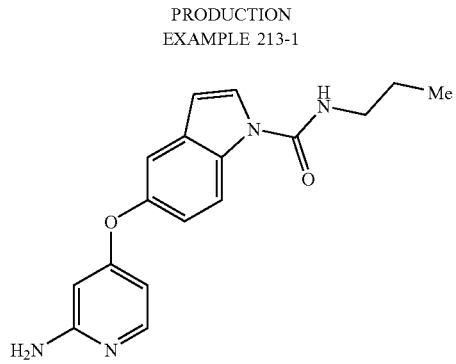
PRODUCTION EXAMPLE 214-1
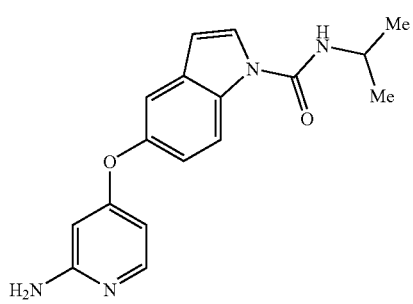
PRODUCTION EXAMPLE 215-1
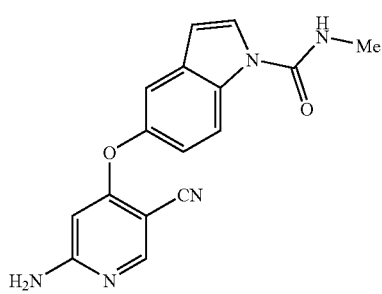
PRODUCTION EXAMPLE 215-2
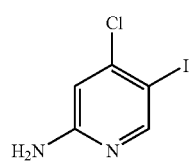
PRODUCTION EXAMPLE 215-3
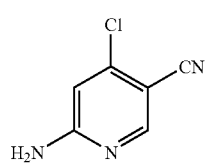
TABLE 7-continued
PRODUCTION EXAMPLE 215-4
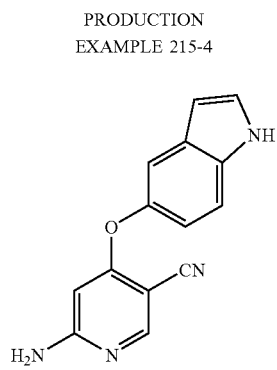
PRODUCTION EXAMPLE 218-1
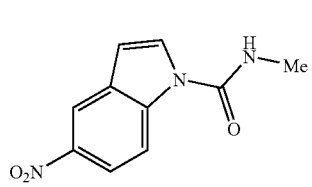
PRODUCTION EXAMPLE 218-2
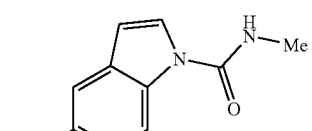
PRODUCTION EXAMPLE 218-3
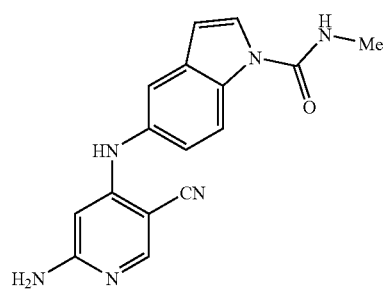
PRODUCTION EXAMPLE 220-1
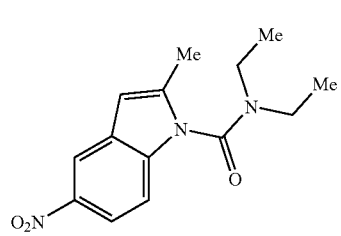

TABLE 7-continued
PRODUCTION EXAMPLE 220-2
PRODUCTION EXAMPLE 220-3
PRODUCTION EXAMPLE 221-1
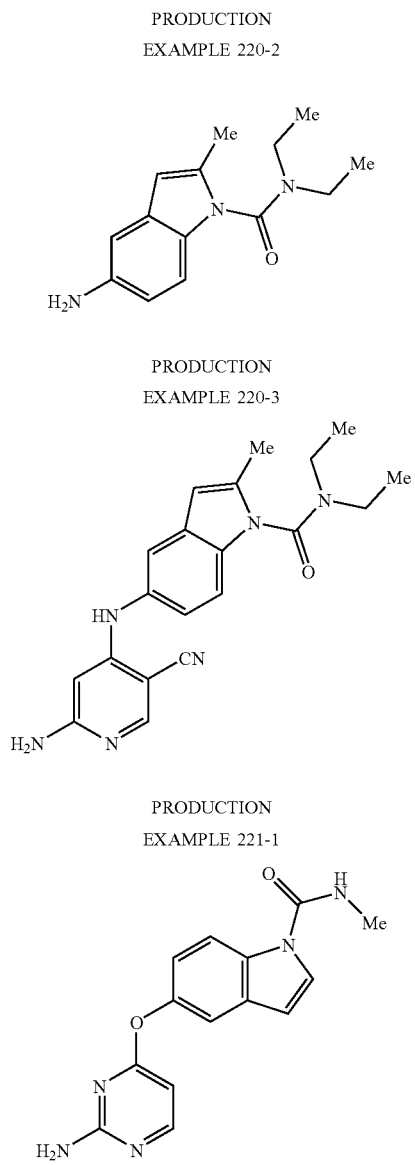
TABLE 7-continued
PRODUCTION EXAMPLE 221-2
PRODUCTION EXAMPLE 221-3
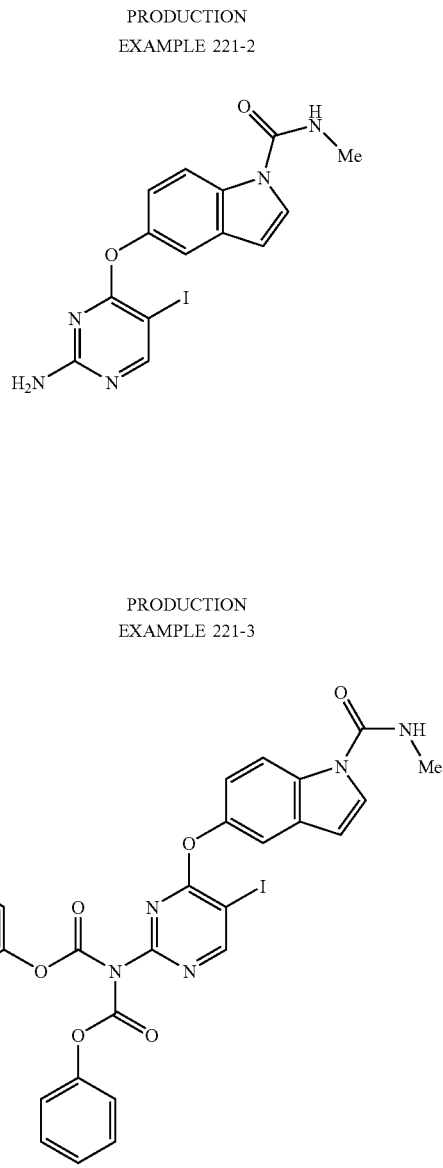
TABLE 8
EXAMPLE 1
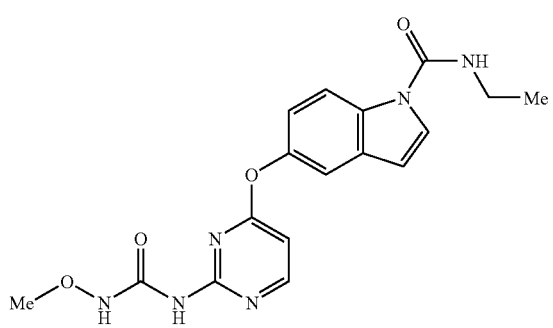

TABLE 8-continued
EXAMPLE 2
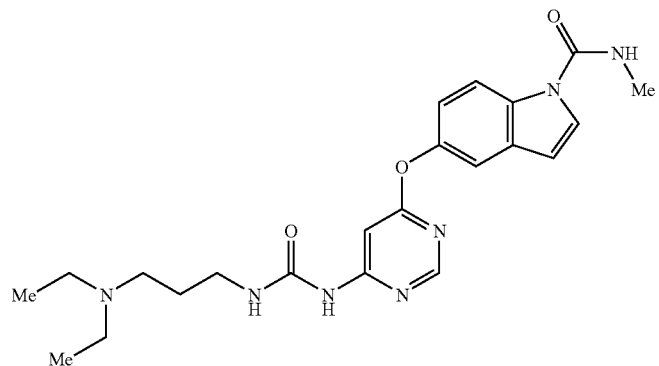
EXAMPLE 3
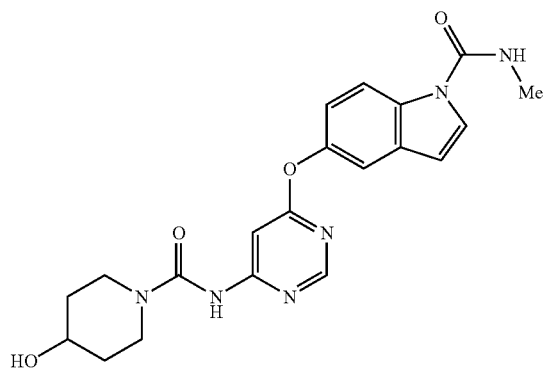
EXAMPLE 4
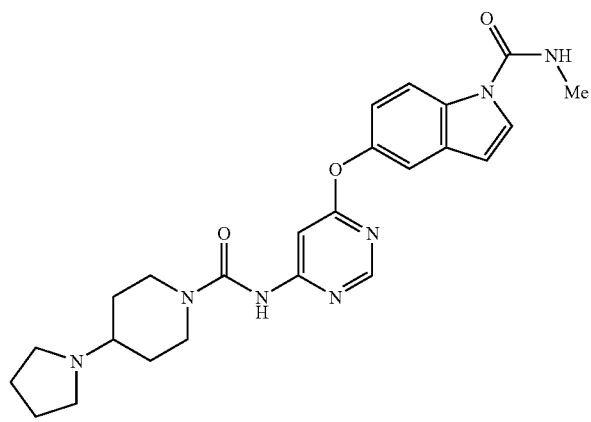

TABLE 8-continued
EXAMPLE 5
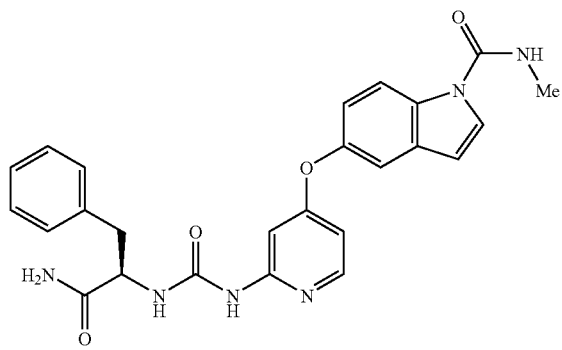
EXAMPLE 6
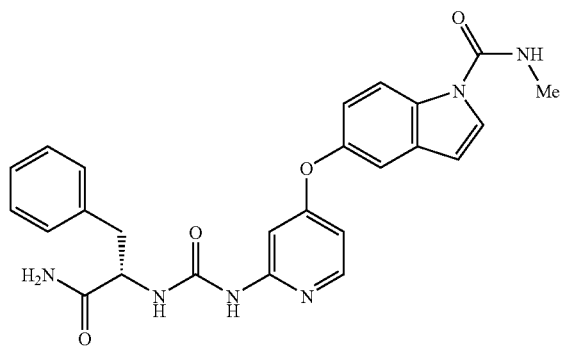
EXAMPLE 7
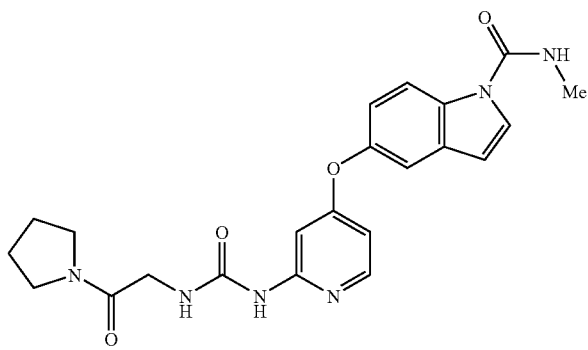
EXAMPLE 8
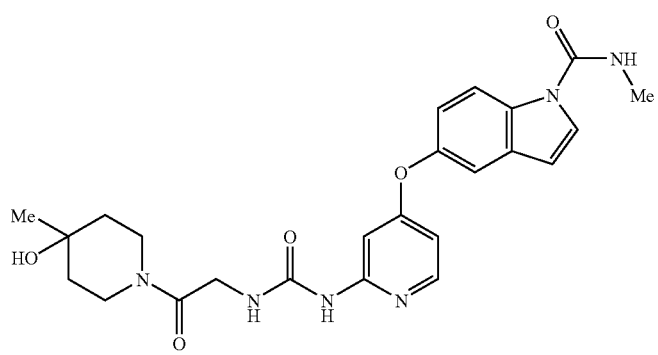

TABLE 8-continued
EXAMPLE 9
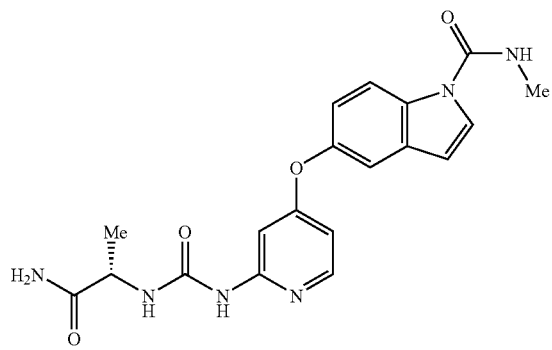
EXAMPLE 10
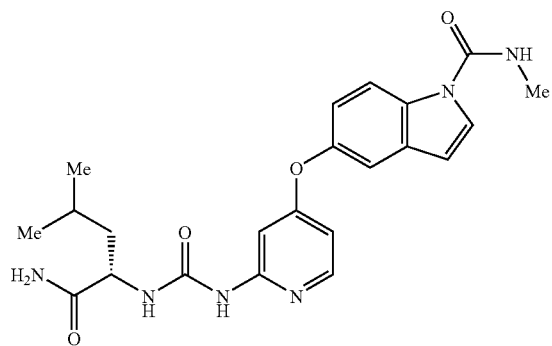
EXAMPLE 11
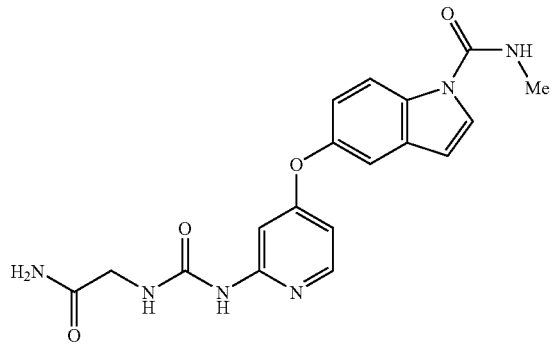
EXAMPLE 12
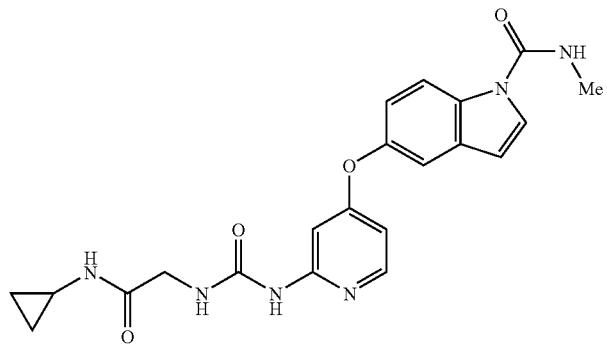

TABLE 8-continued
EXAMPLE 13
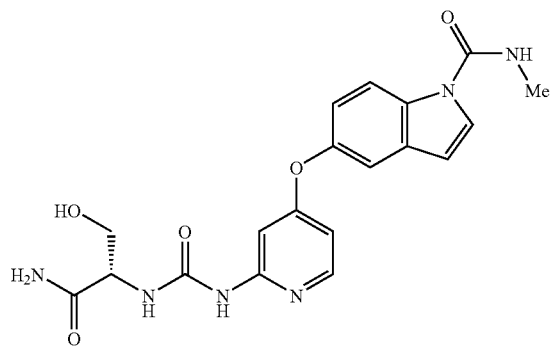
EXAMPLE 14
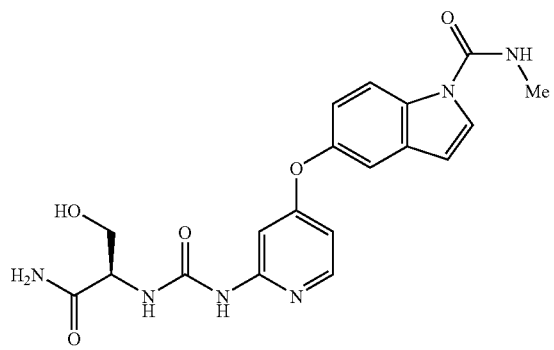
EXAMPLE 15
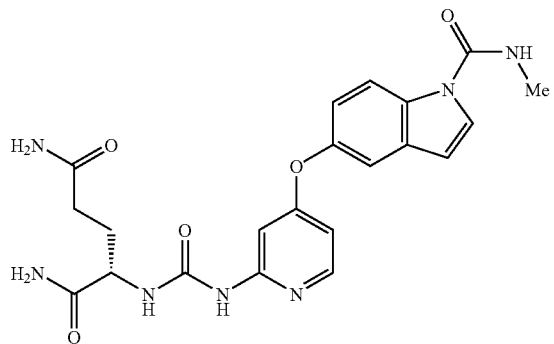
EXAMPLE 16
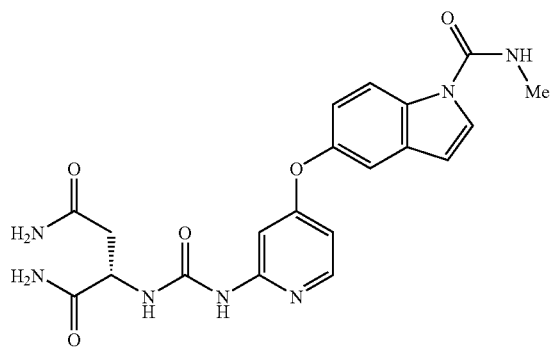

TABLE 8-continued
EXAMPLE 17
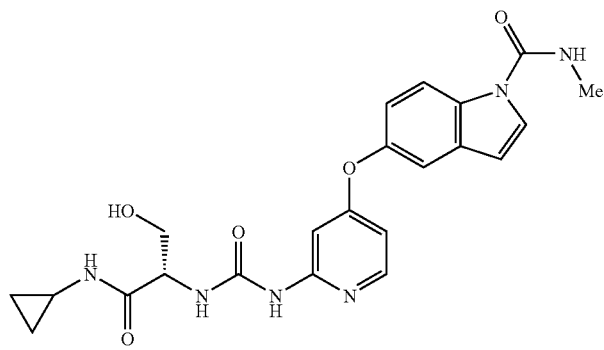
EXAMPLE 18
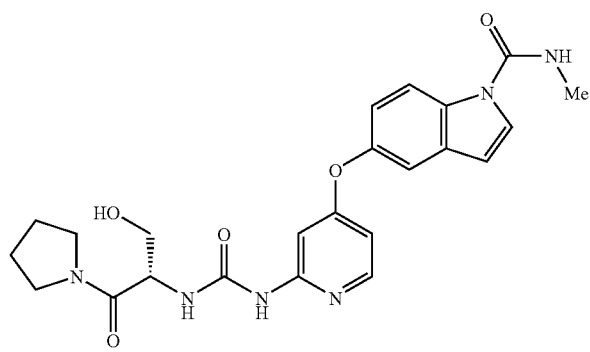
EXAMPLE 19
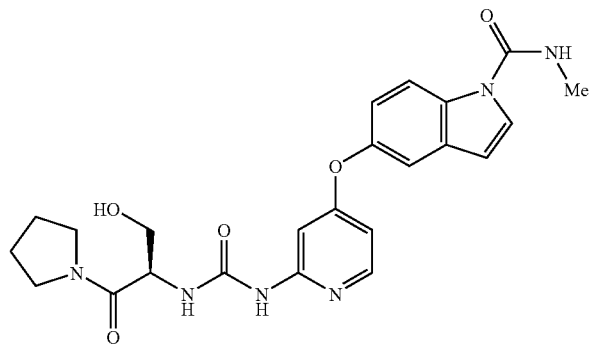
EXAMPLE 20
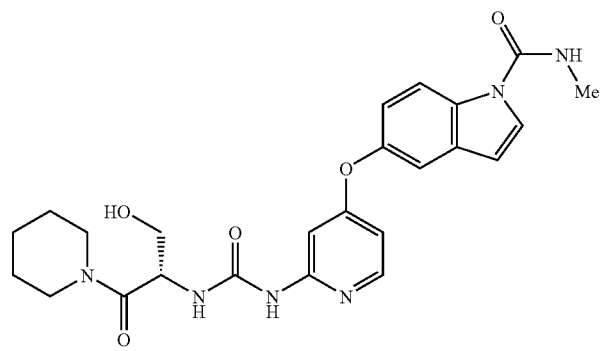

TABLE 8-continued
EXAMPLE 21
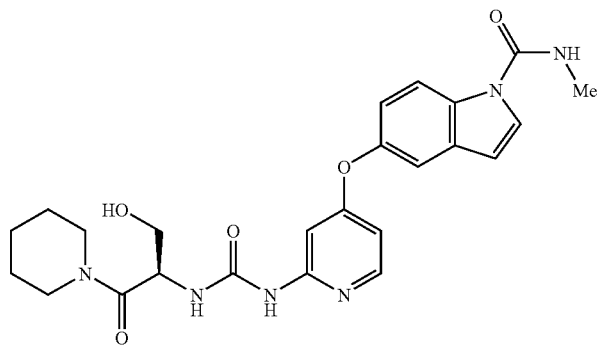
EXAMPLE 22
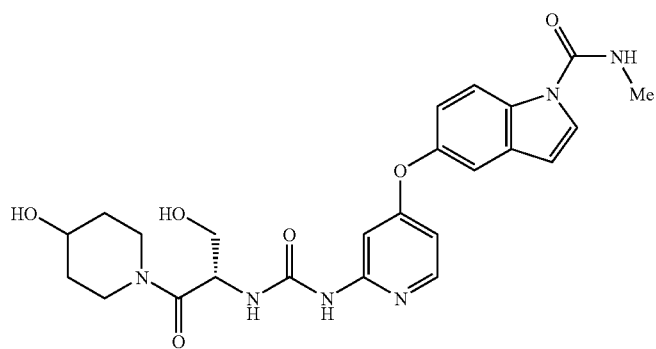
EXAMPLE 23
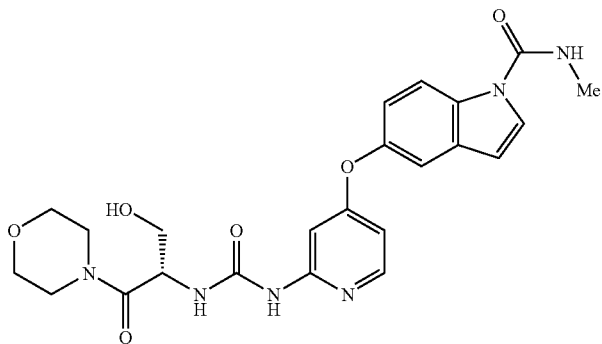
EXAMPLE 24
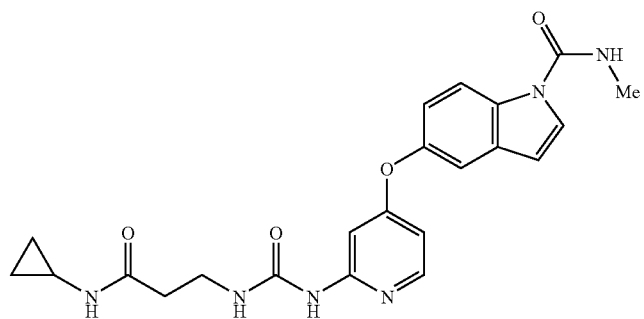

TABLE 8-continued
EXAMPLE 25
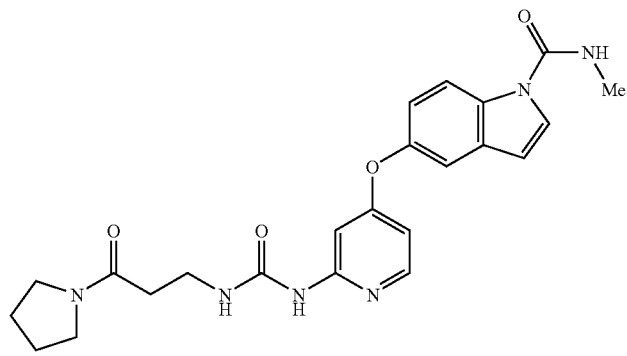
EXAMPLE 26
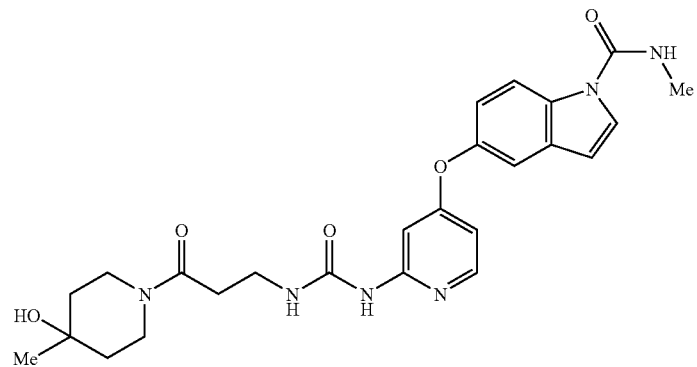
EXAMPLE 27
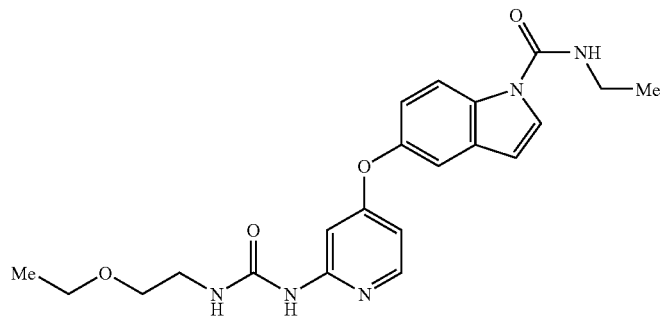

TABLE 8-continued
EXAMPLE 28
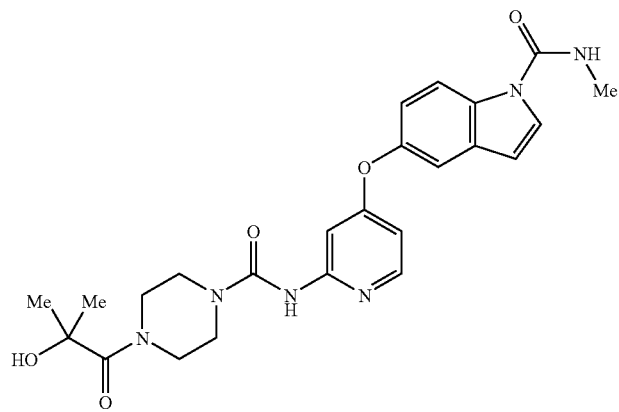
EXAMPLE 29
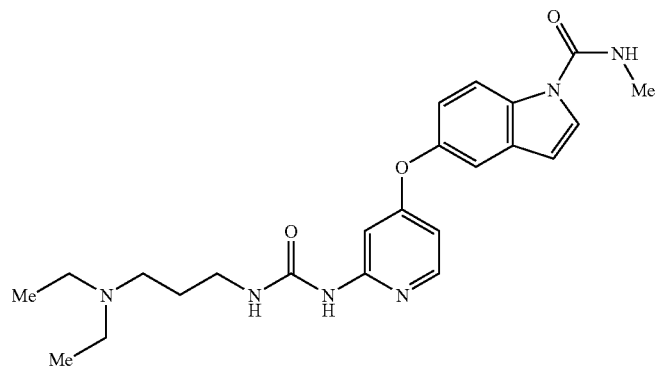
EXAMPLE 30
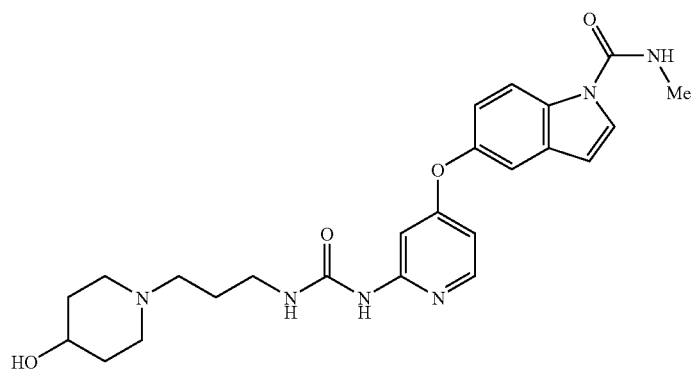

TABLE 8-continued
EXAMPLE 31
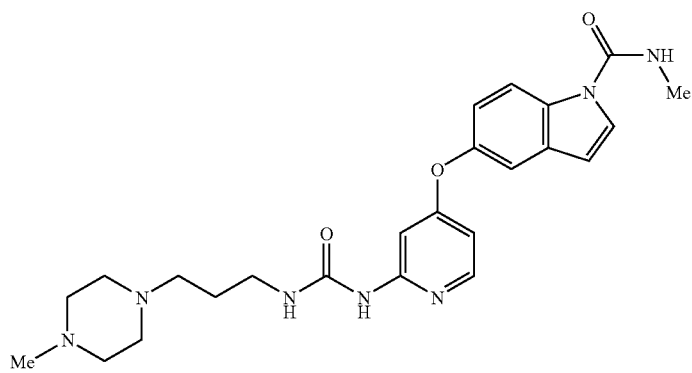
EXAMPLE 32
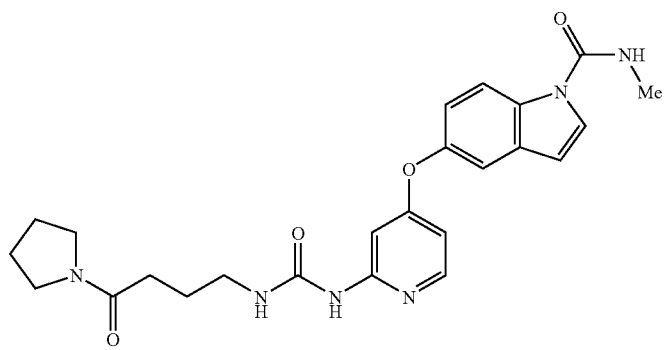
EXAMPLE 33
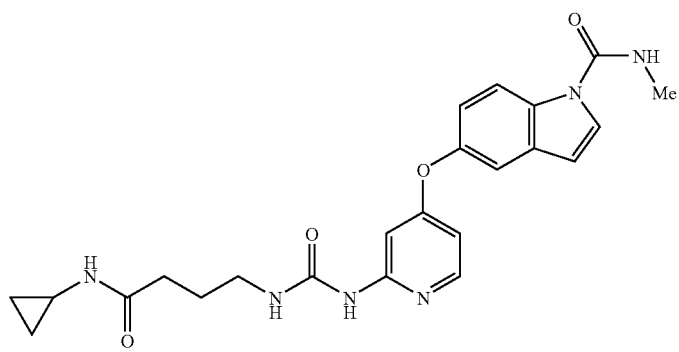
EXAMPLE 34
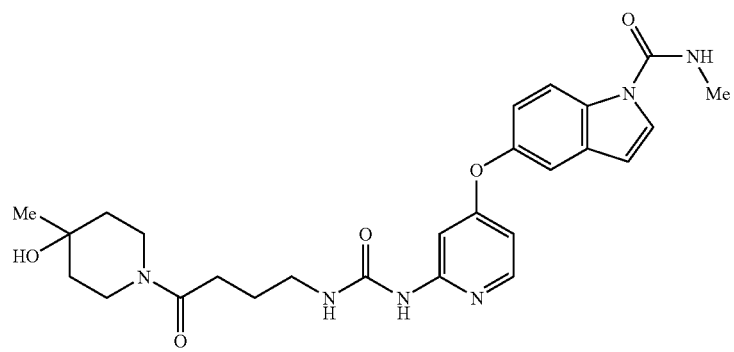

TABLE 8-continued
EXAMPLE 35
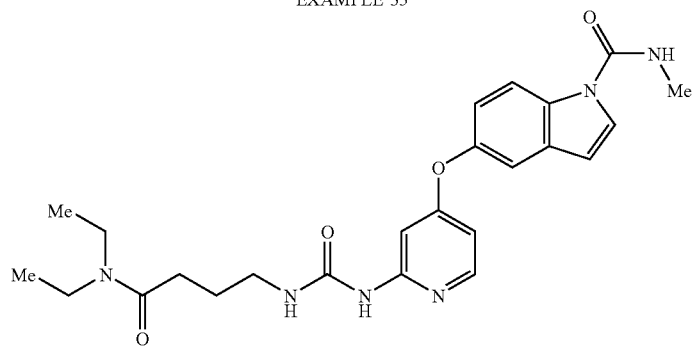
EXAMPLE 36
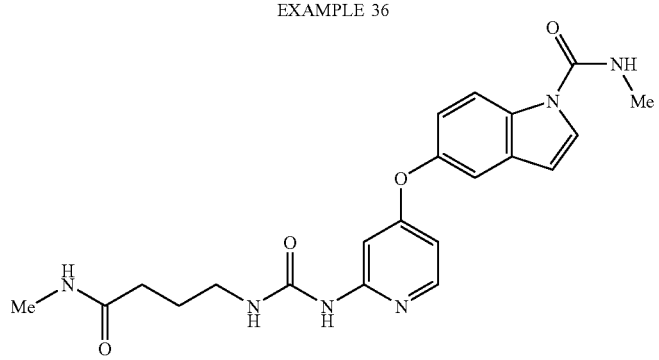
TABLE 9
EXAMPLE 73
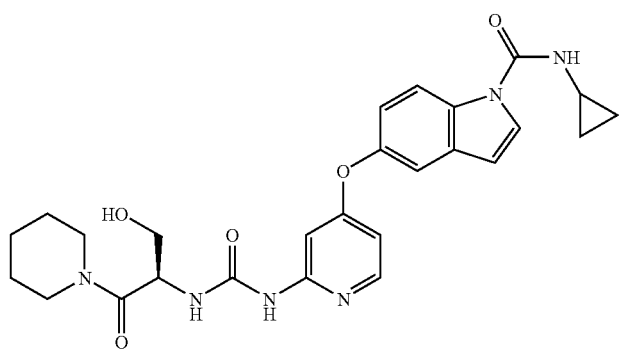
EXAMPLE 74
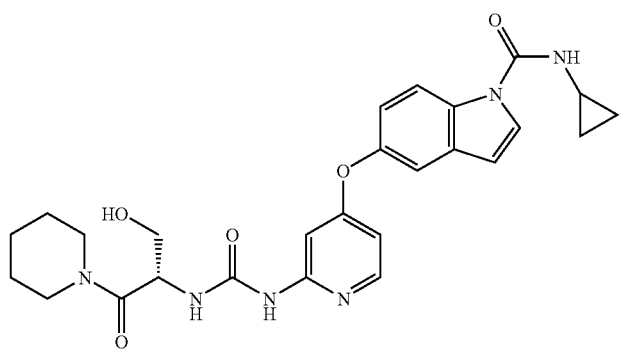

TABLE 9-continued
EXAMPLE 75
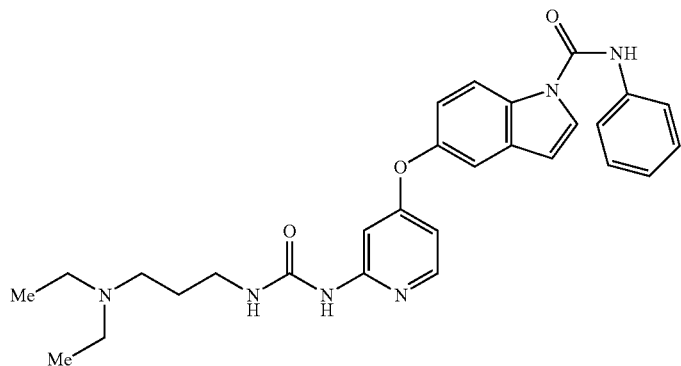
EXAMPLE 76
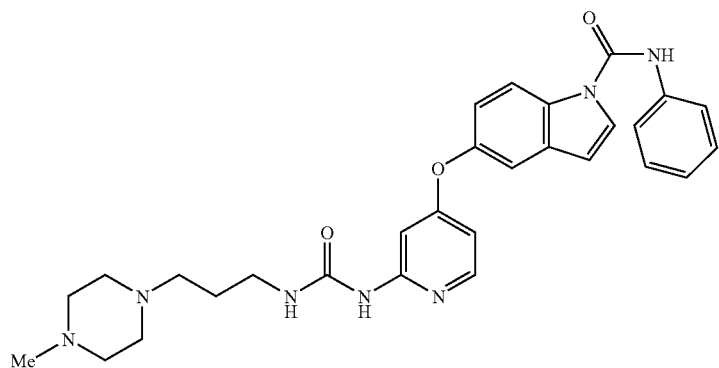
EXAMPLE 77
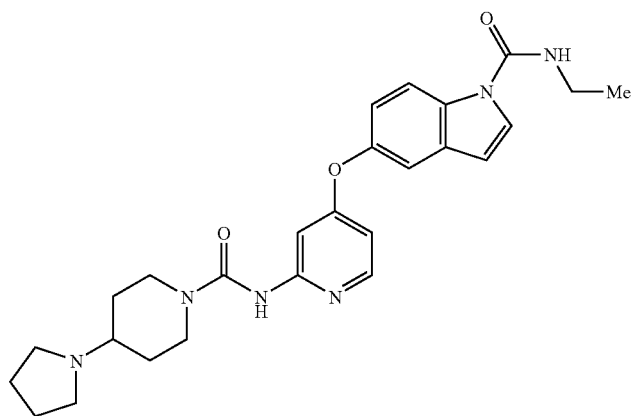

TABLE 9-continued
EXAMPLE 78
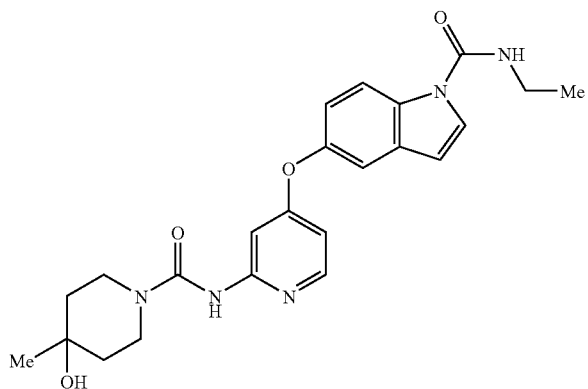
EXAMPLE 79
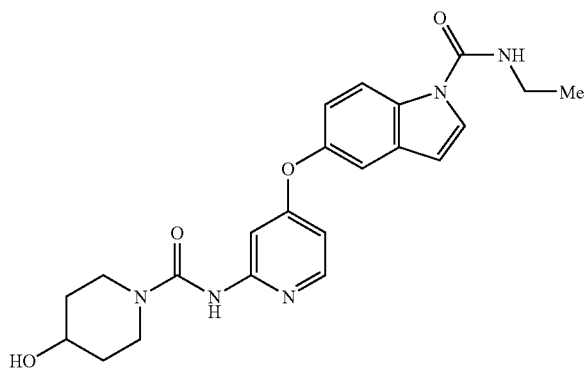
EXAMPLE 80
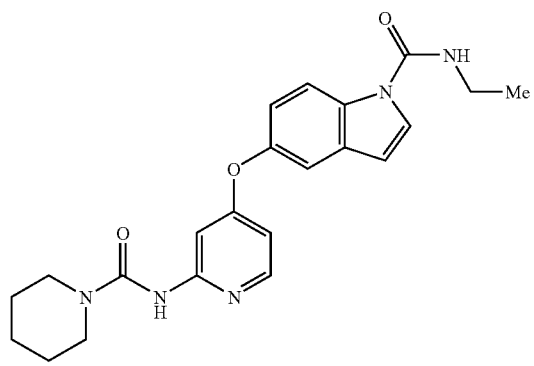

TABLE 9-continued
EXMIPLE 81
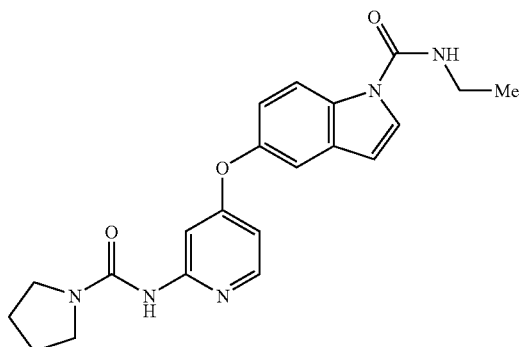
EXAMPLE 82
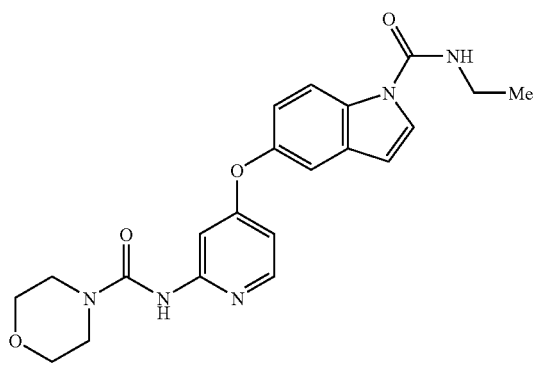
EXAMPLE 83
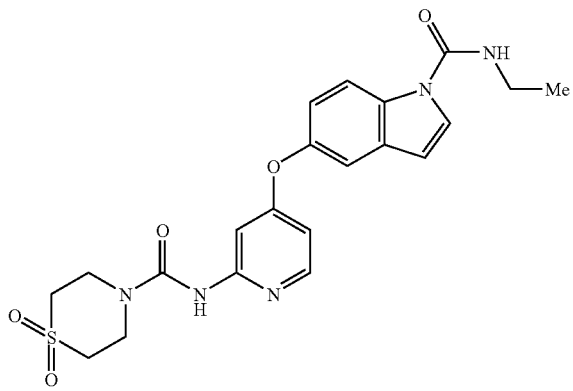
EXAMPLE 84
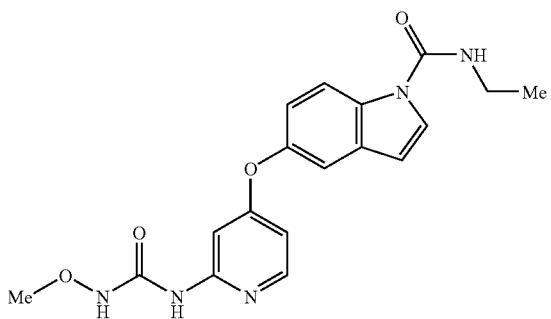

TABLE 9-continued
EXAMPLE 85
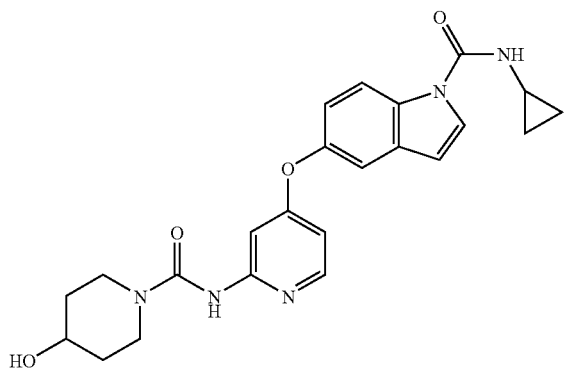
EXAMPLE 86
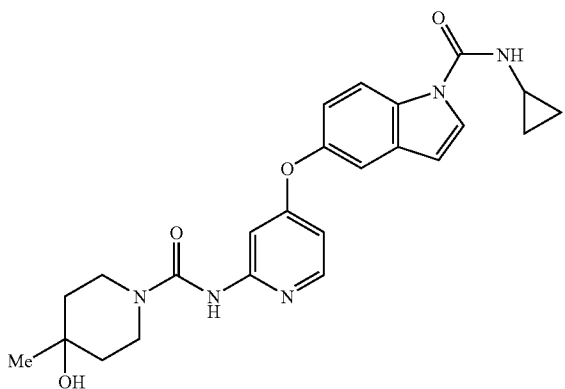
EXAMPLE 87
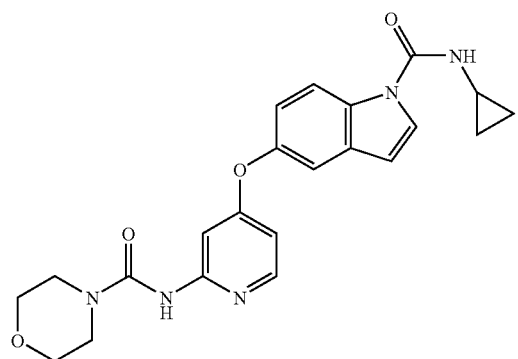

TABLE 9-continued
EXAMPLE 88
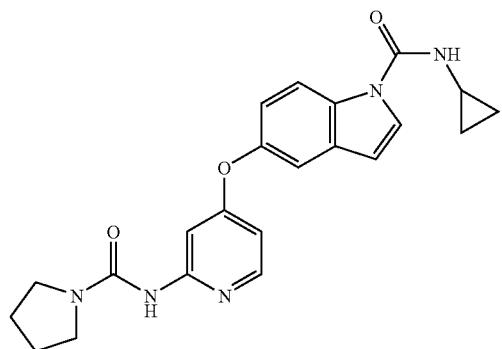
EXAMPLE 89
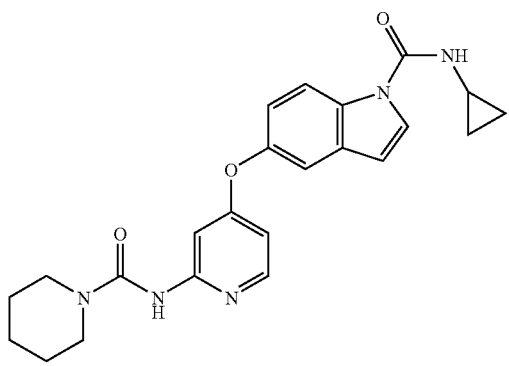
EXAMPLE 90
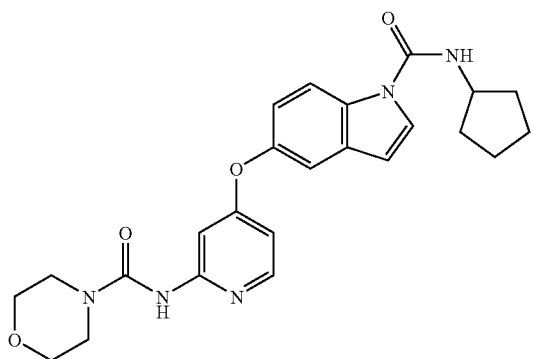
EXAMPLE 91
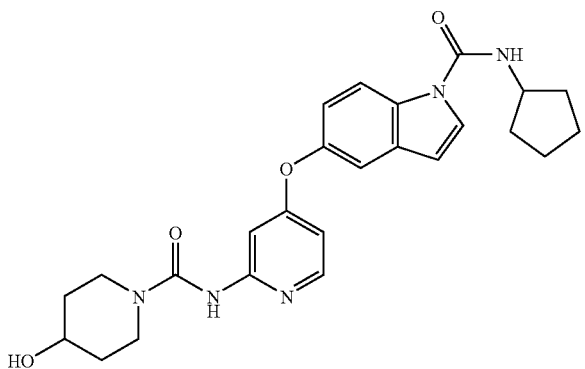

TABLE 9-continued
EXAMPLE 92
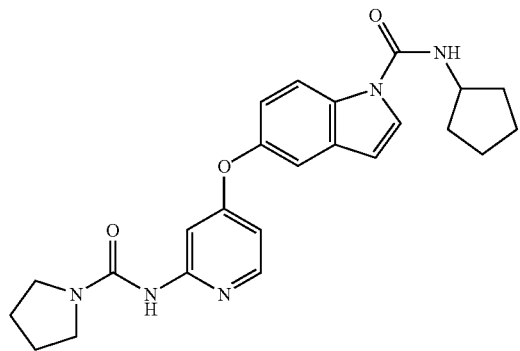
EXAMPLE 93
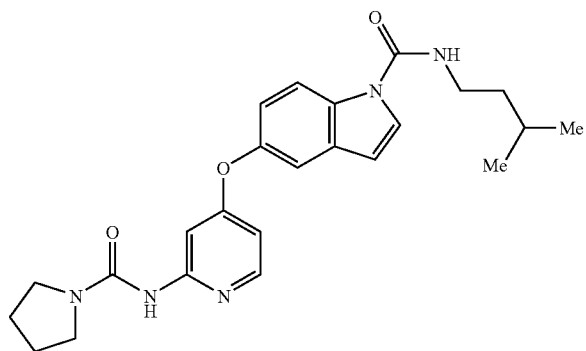
EXAMPLE 94
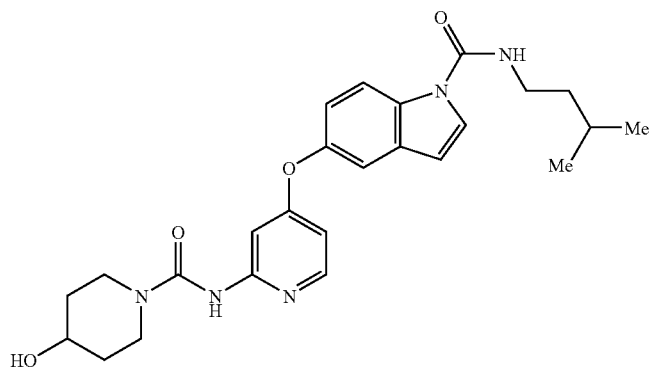

TABLE 9-continued
EXAMPLE 95
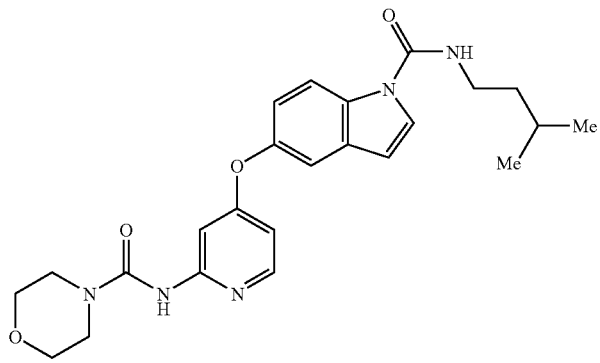
EXAMPLE 96
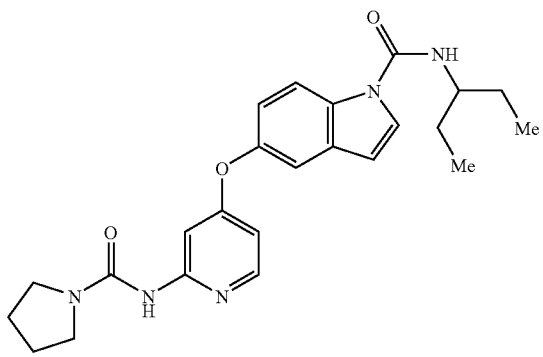
EXAMPLE 97
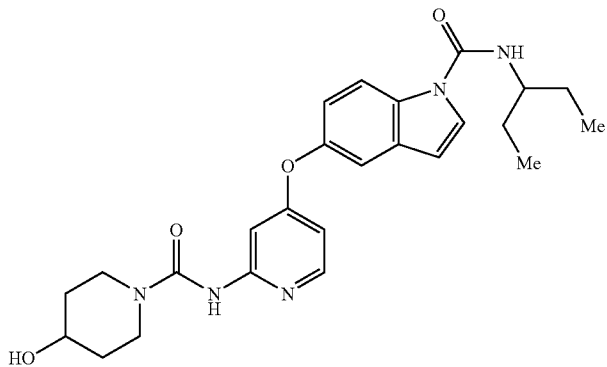
EXAMPLE 98
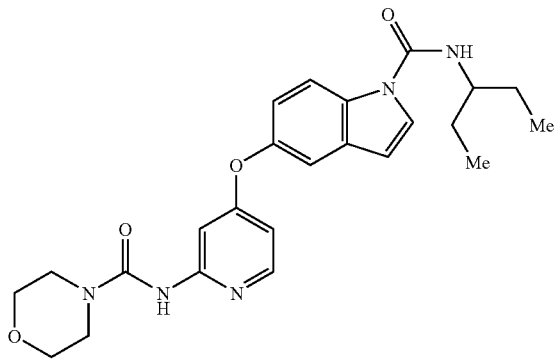

TABLE 9-continued
EXAMPLE 99
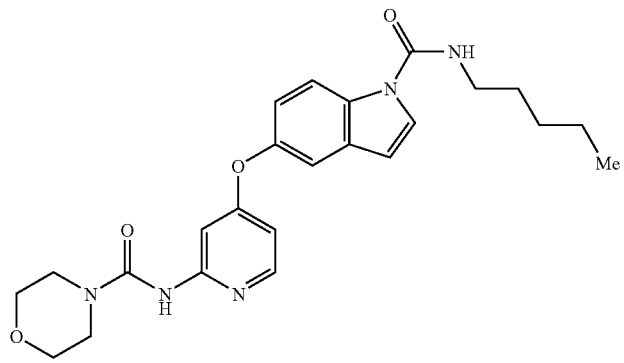
EXAMPLE 100
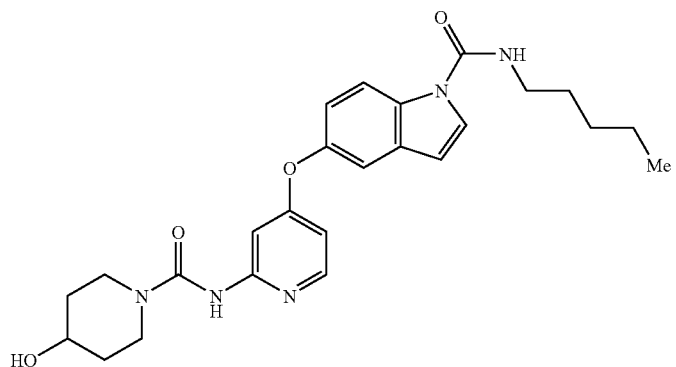
EXAMPLE 101
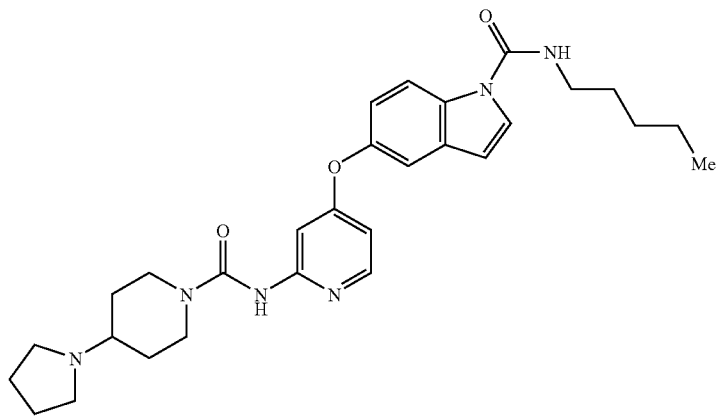

TABLE 9-continued
EXAMPLE 102
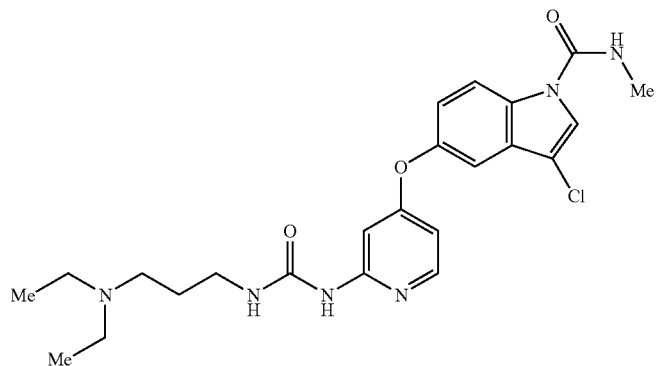
EXAMPLE 103
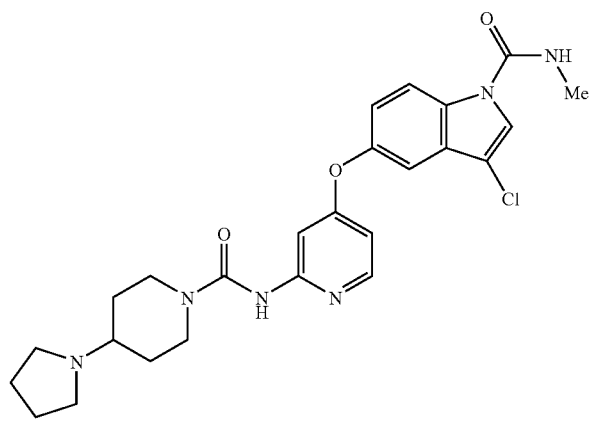
EXAMPLE 104
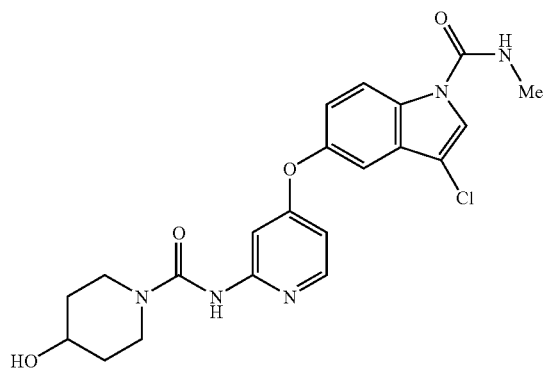

TABLE 9-continued
EXAMPLE 105
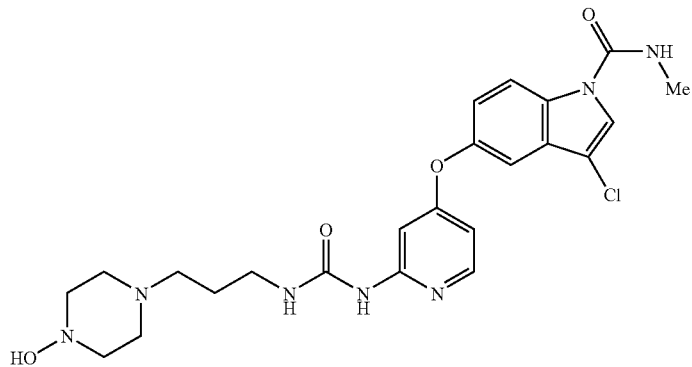
EXAMPLE 106
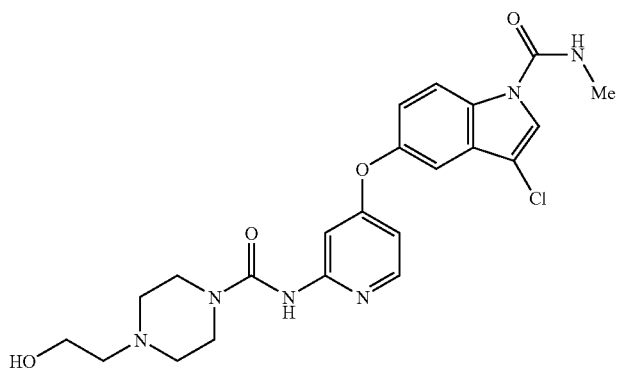
EXAMPLE 107
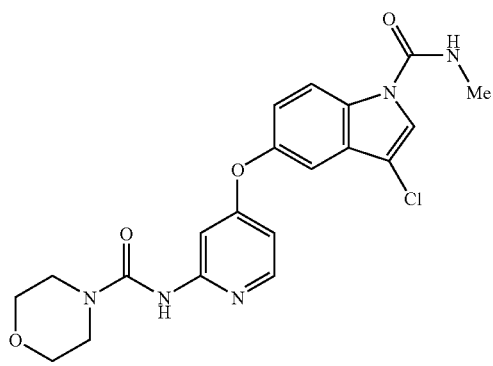

TABLE 9-continued
EXAMPLE 108
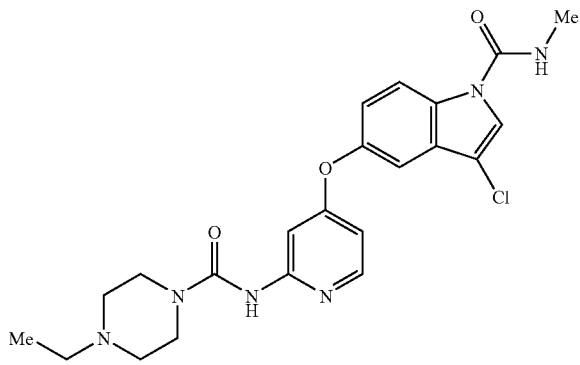
TABLE 10
EXAMPLE 73
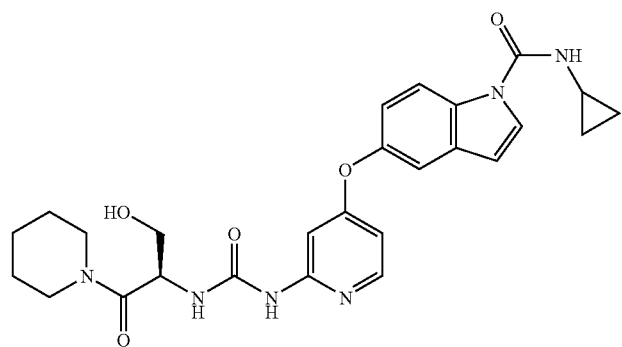
EXAMPLE 74
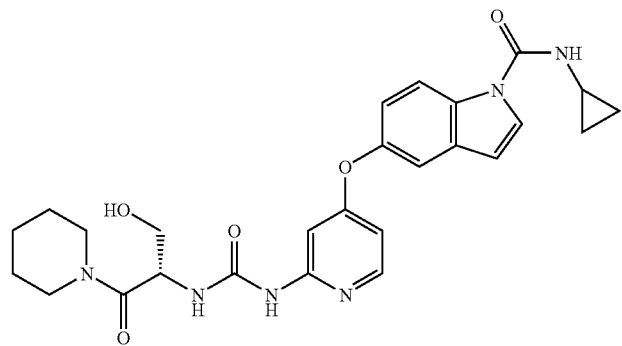

TABLE 10-continued
EXAMPLE 75
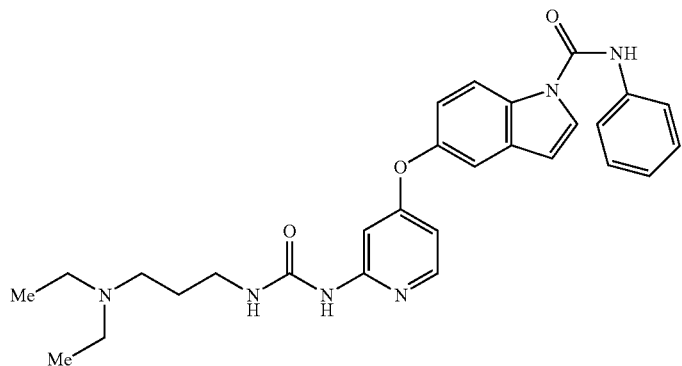
EXAMPLE 76
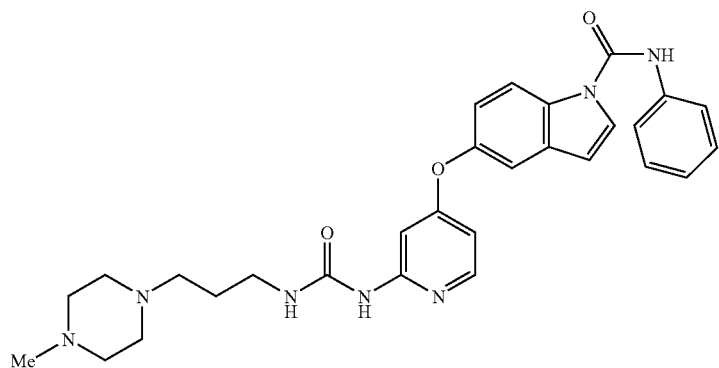
EXAMPLE 77
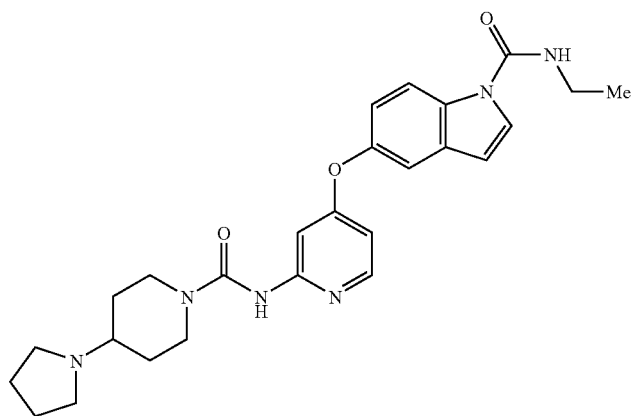

TABLE 10-continued
EXAMPLE 78
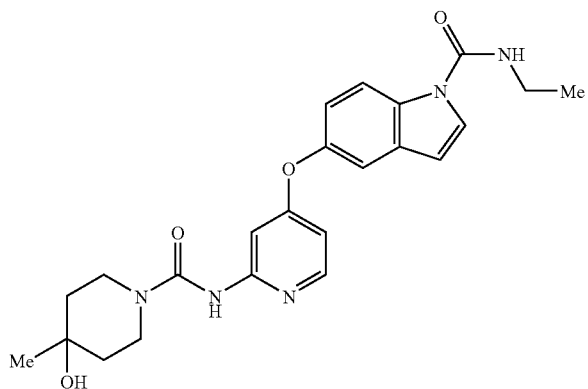
EXAMPLE 79
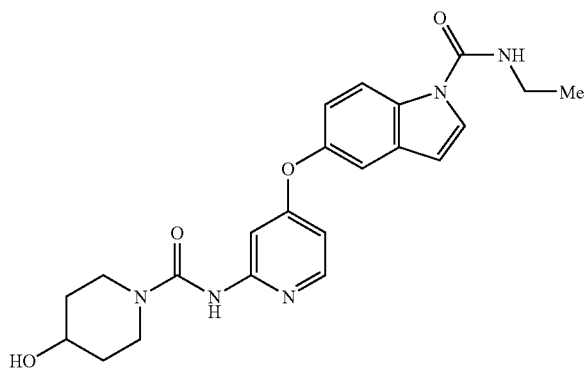
EXAMPLE 80
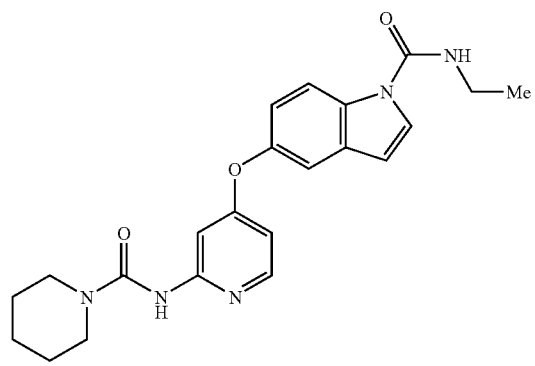

TABLE 10-continued
EXMIPLE 81
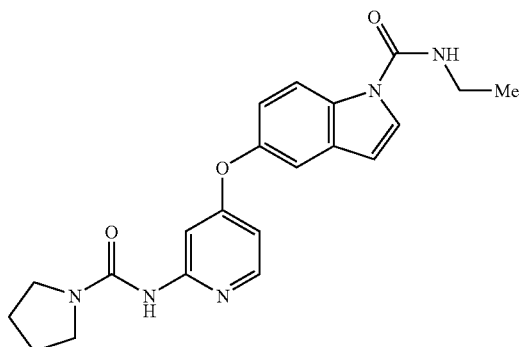
EXAMPLE 82
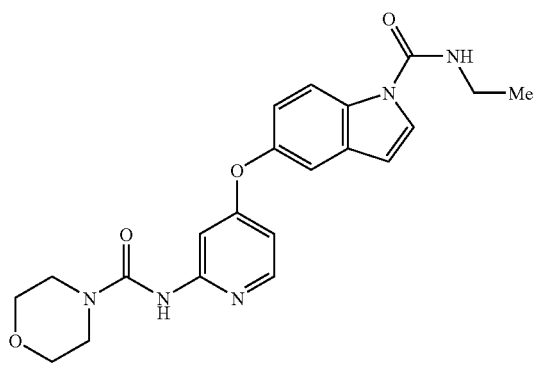
EXAMPLE 83
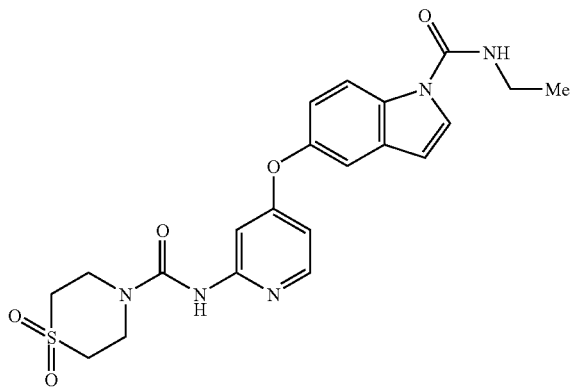
EXAMPLE 84
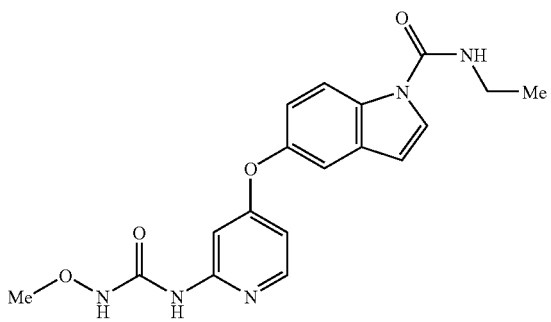

TABLE 10-continued
EXAMPLE 85
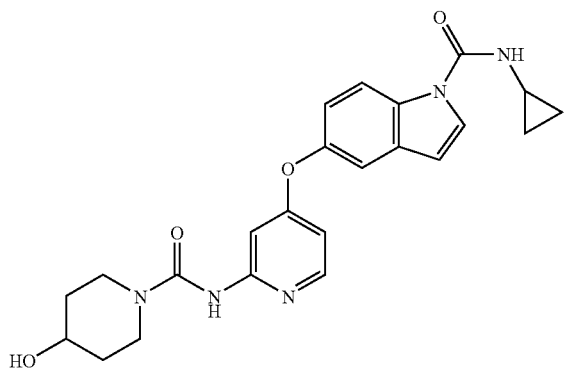
EXAMPLE 86
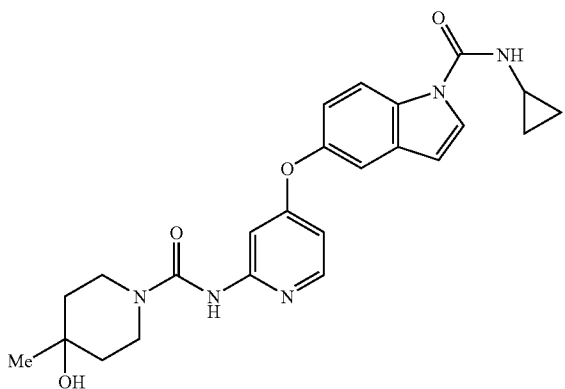
EXAMPLE 87
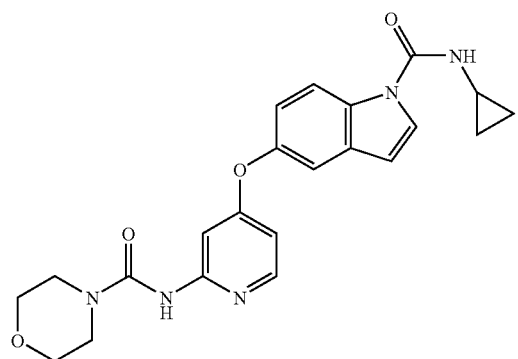

TABLE 10-continued
EXAMPLE 88
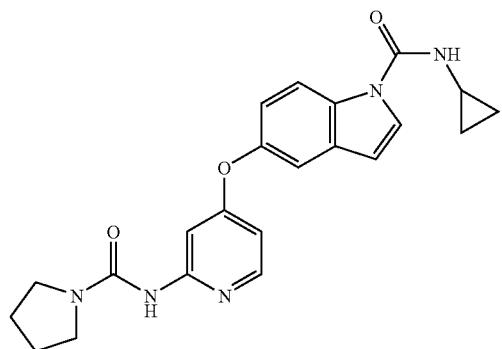
EXAMPLE 89
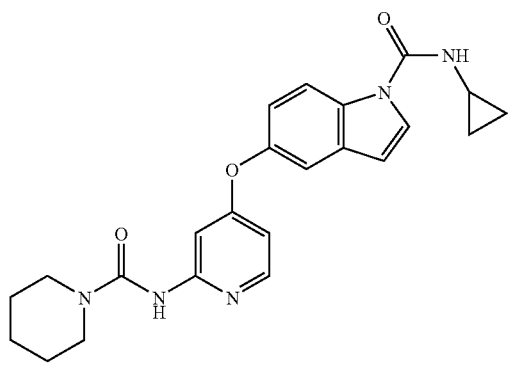
EXAMPLE 90
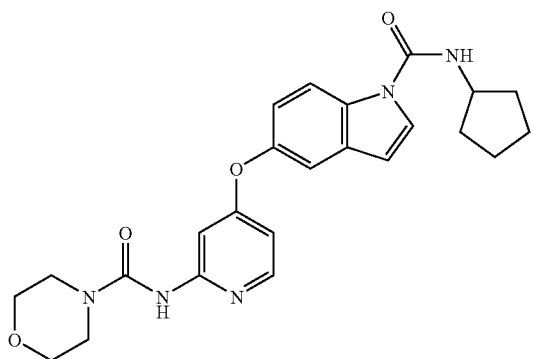
EXAMPLE 91
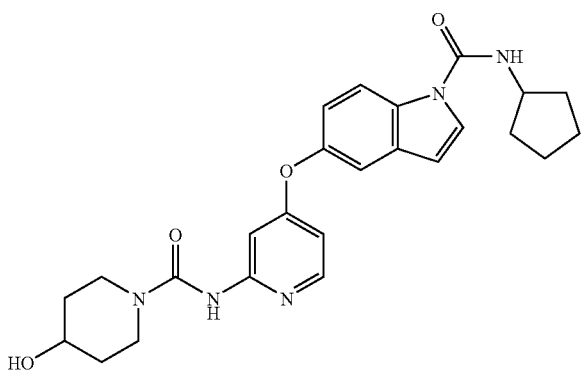

TABLE 10-continued
EXAMPLE 92
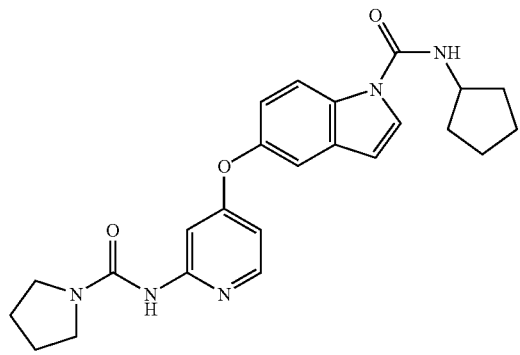
EXAMPLE 93
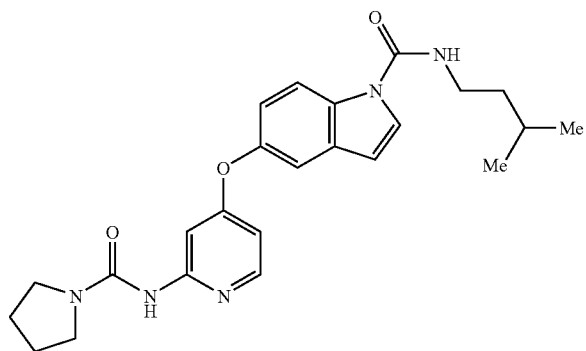
EXAMPLE 94
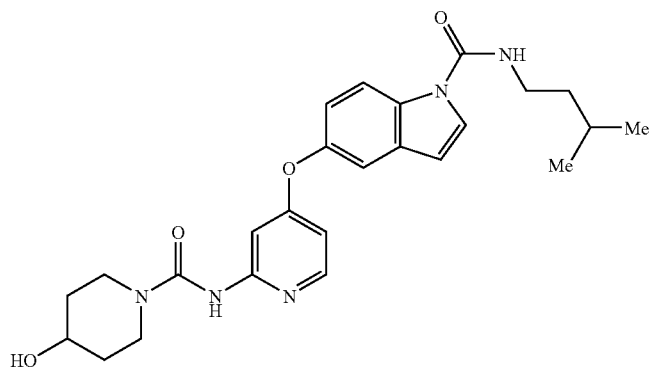

TABLE 10-continued
EXAMPLE 95
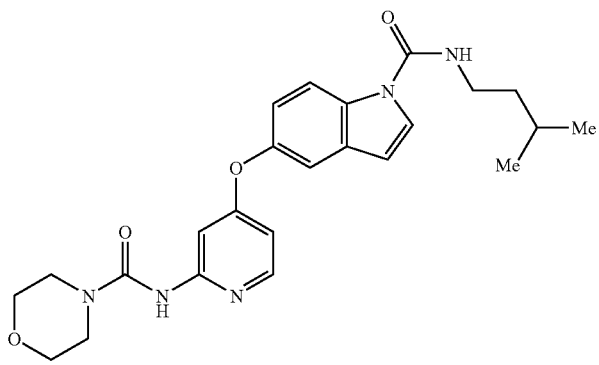
EXAMPLE 96
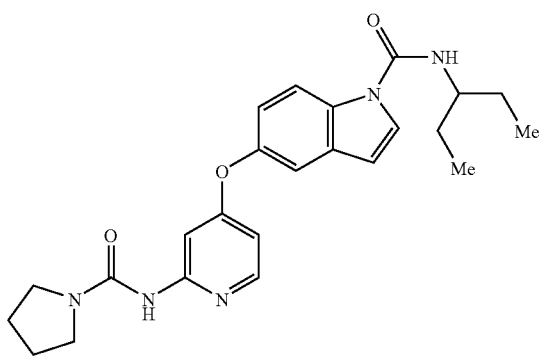
EXAMPLE 97
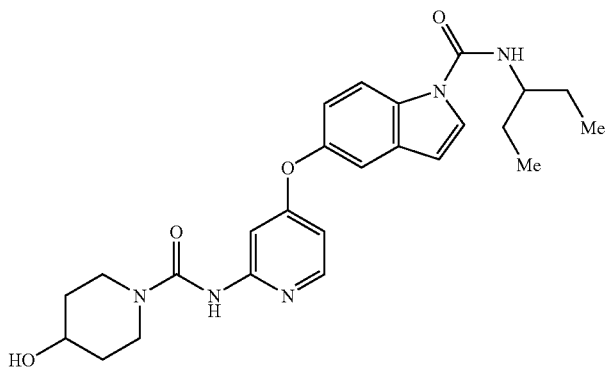
EXAMPLE 98
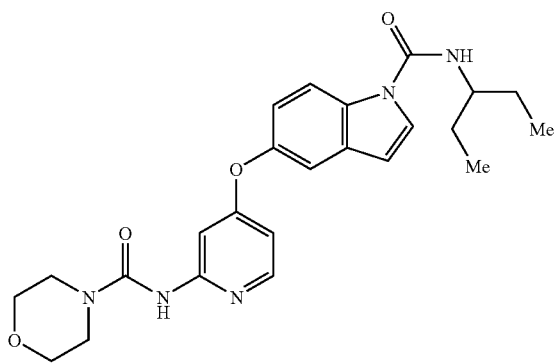

TABLE 10-continued
EXAMPLE 99
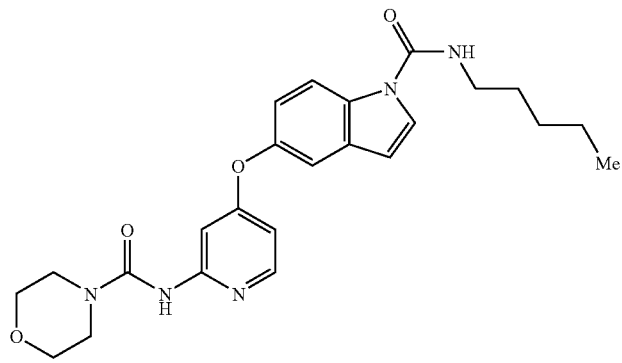
EXAMPLE 100
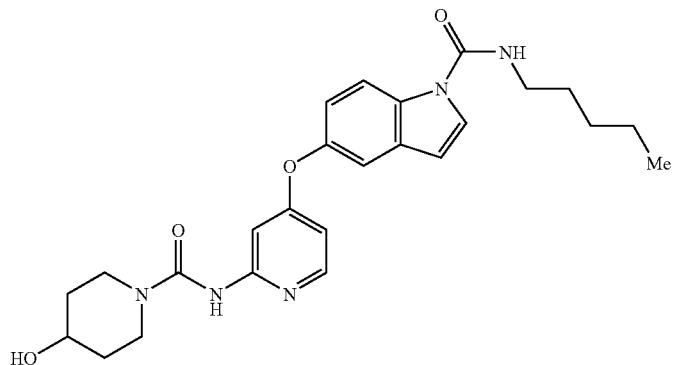
EXAMPLE 101
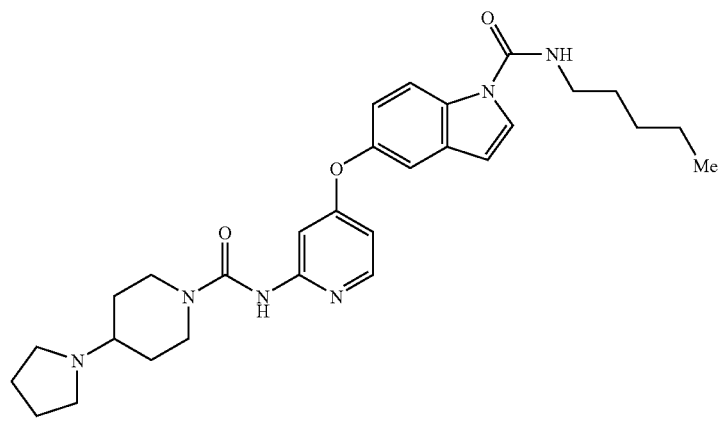

TABLE 10-continued
EXAMPLE 102
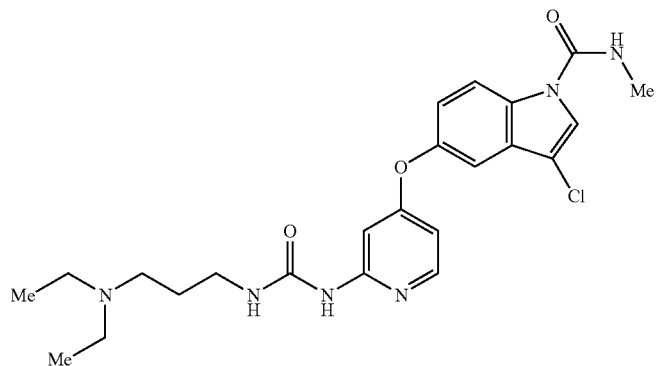
EXAMPLE 103
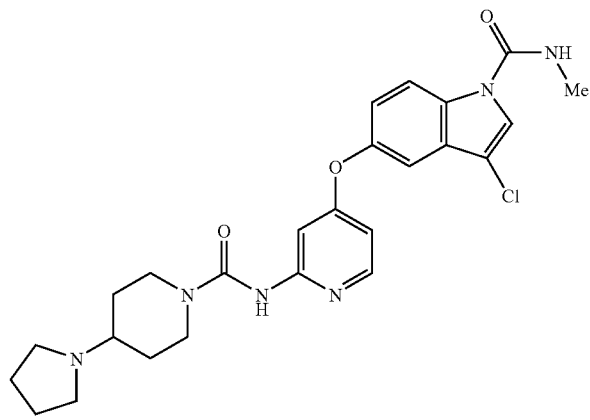
EXAMPLE 104
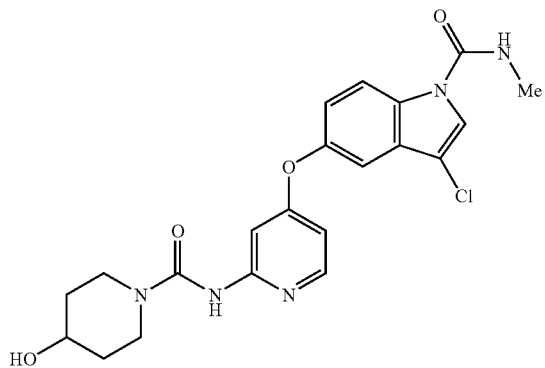

TABLE 10-continued
EXAMPLE 105
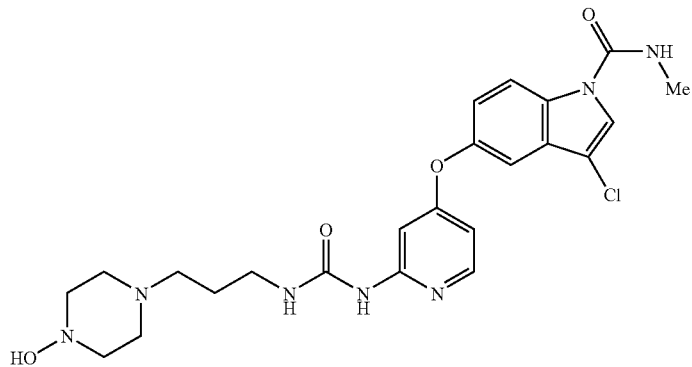
EXAMPLE 106
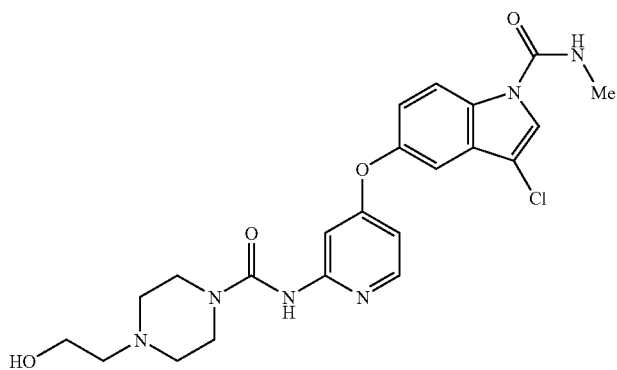
EXAMPLE 107
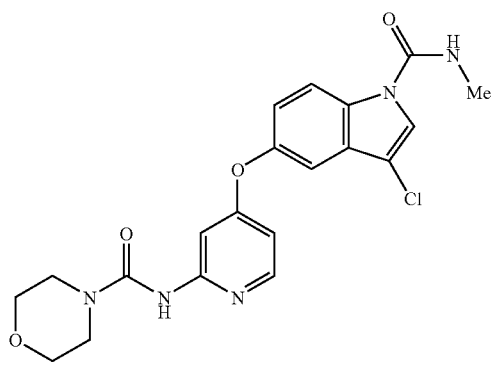

TABLE 10-continued
EXAMPLE 108
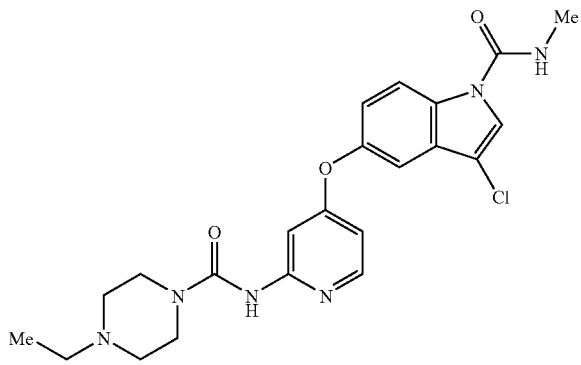
TABLE 11
EXAMPLE 109
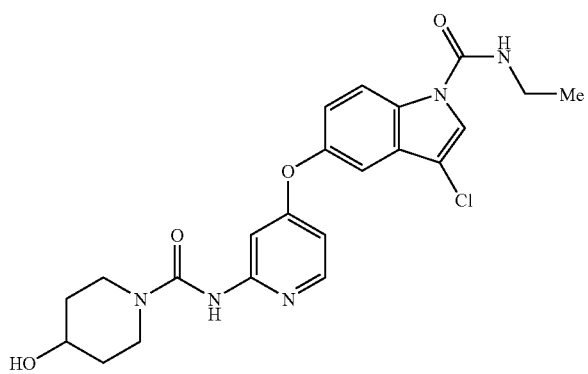
EXAMPLE 110
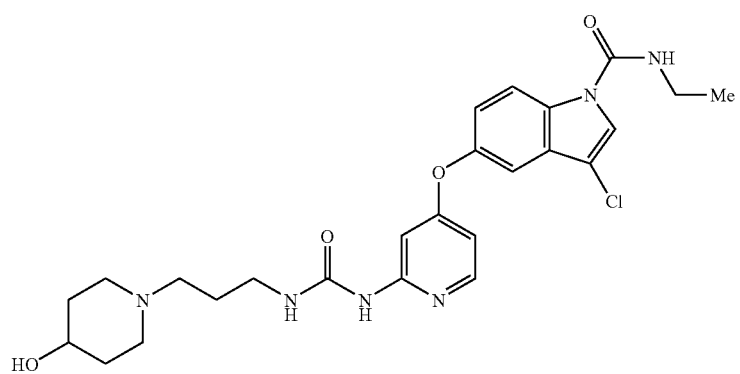

TABLE 11-continued
EXAMPLE 111
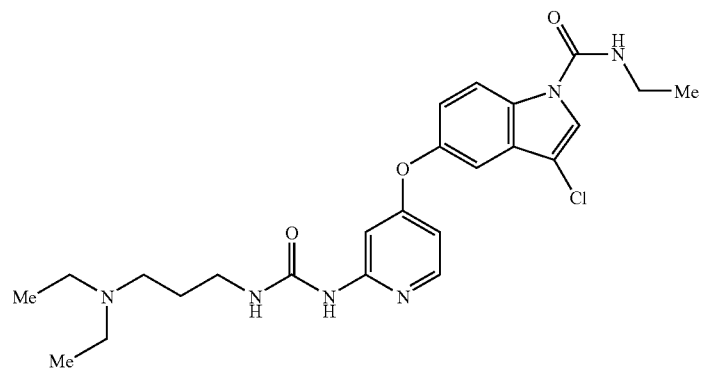
EXAMPLE 112
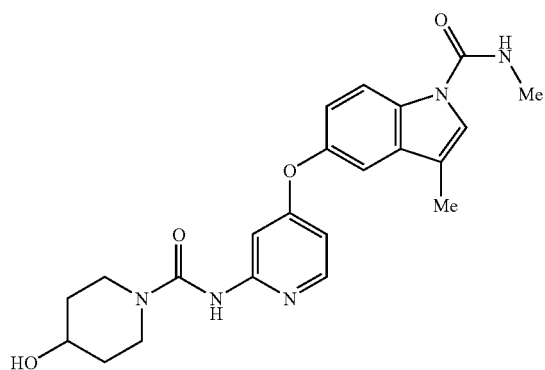
EXAMPLE 113
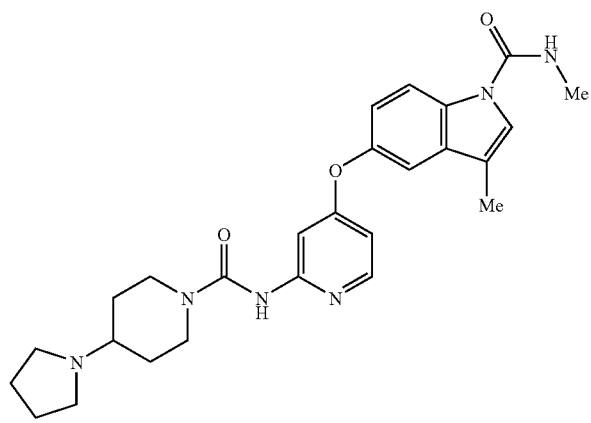

TABLE 11-continued
EXAMPLE 114
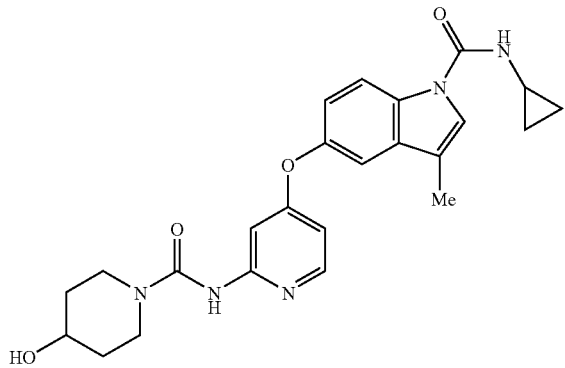
EXAMPLE 115
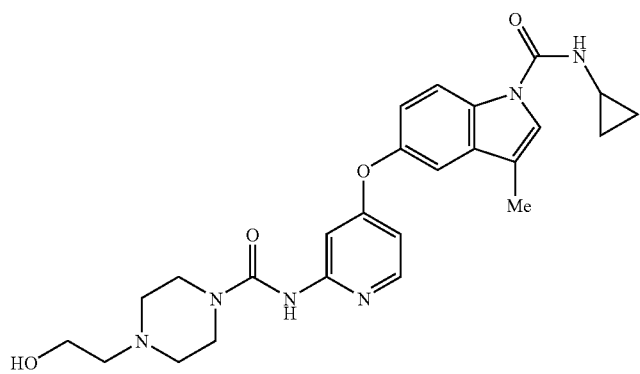
TABLE 12
EXAMPLE 116
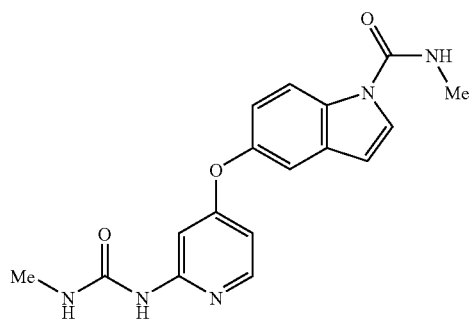

TABLE 12-continued
EXAMPLE 117
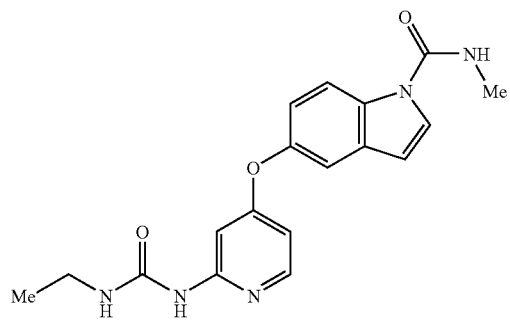
EXAMPLE 118
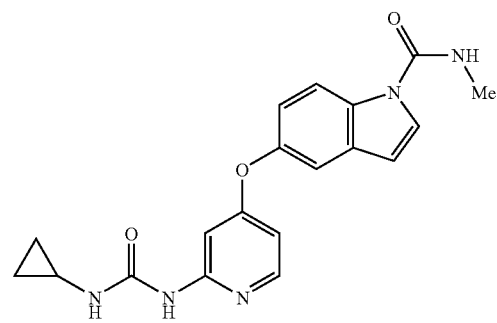
EXAMPLE 119
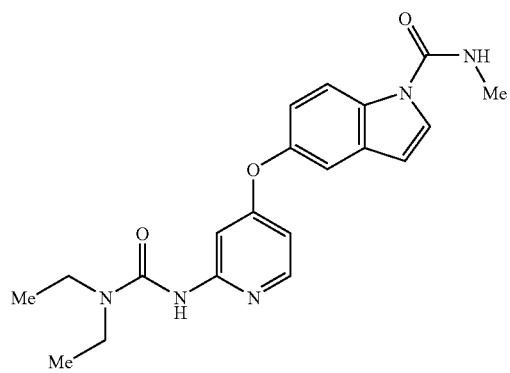
EXAMPLE 120
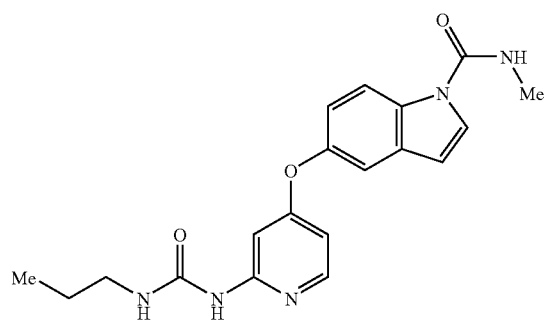

TABLE 12-continued
EXAMPLE 121
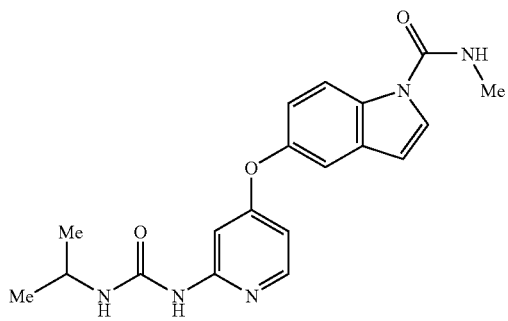
EXAMPLE 122
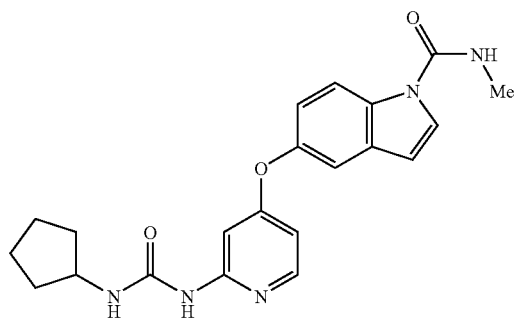
EXAMPLE 123
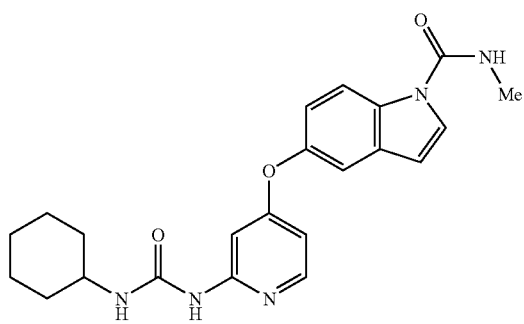
EXAMPLE 124
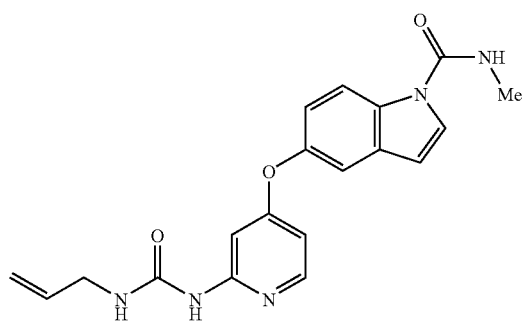

TABLE 12-continued
EXAMPLE 125
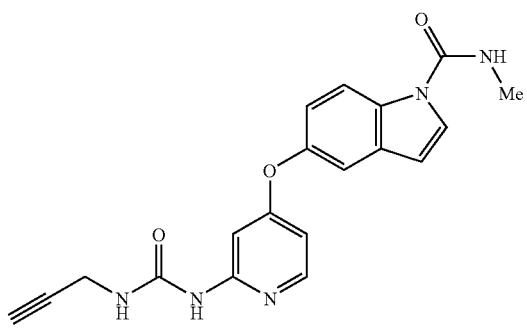
EXAMPLE 126
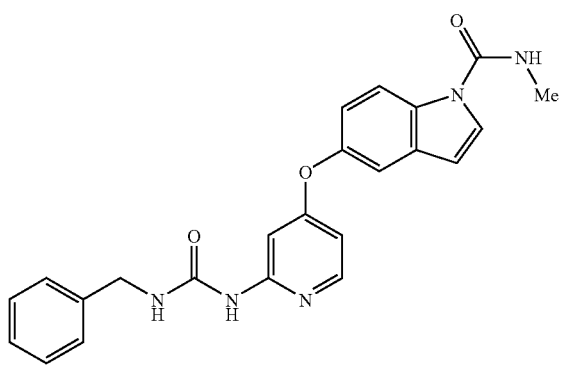
EXAMPLE 127
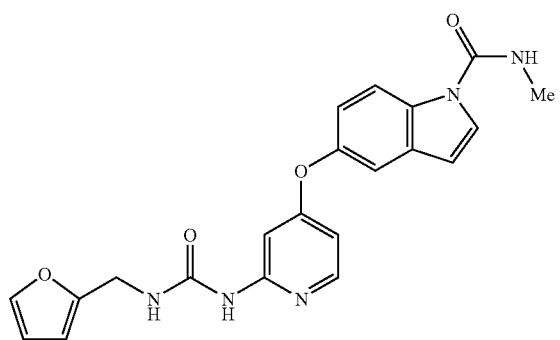
EXAMPLE 128
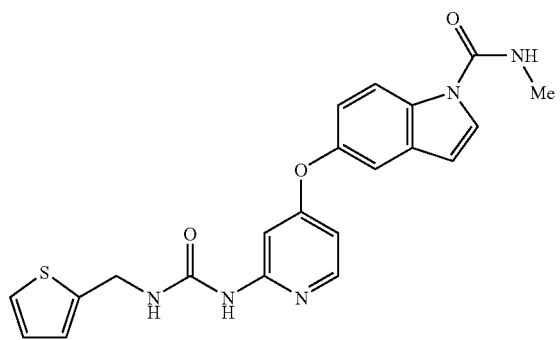

TABLE 12-continued
EXAMPLE 129
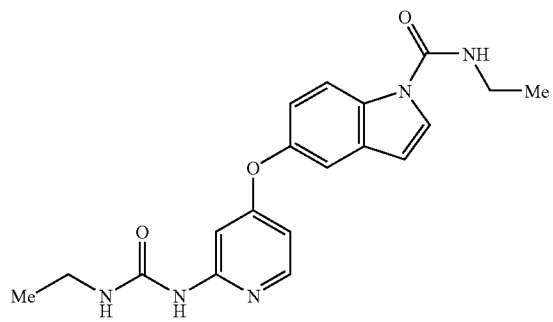
EXAMPLE 130
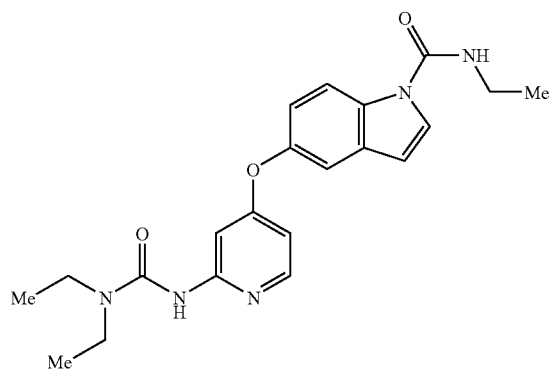
EXAMPLE 131
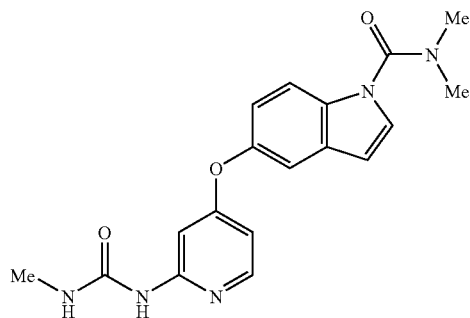
EXAMPLE 132
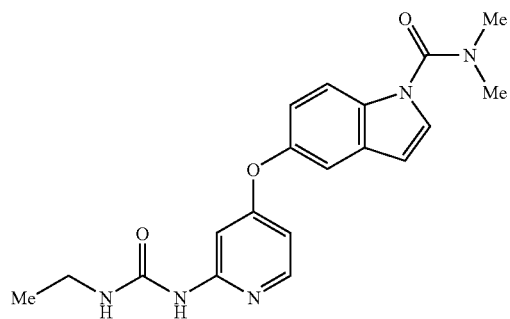

TABLE 12-continued
EXAMPLE 133
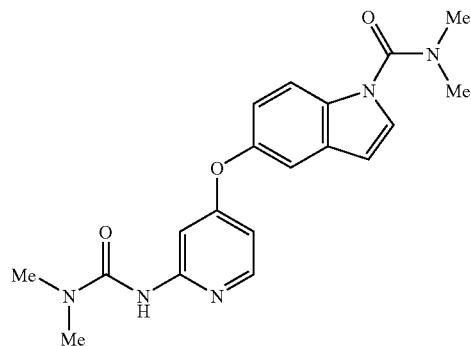
EXAMPLE 134
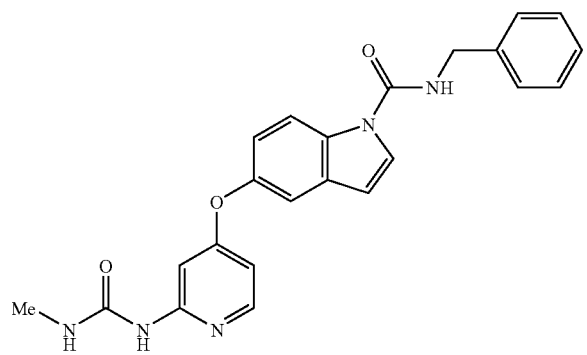
EXAMPLE 135
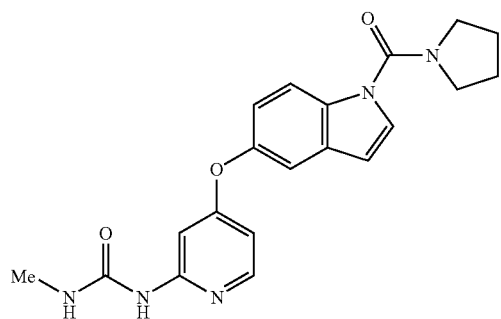
EXAMPLE 136
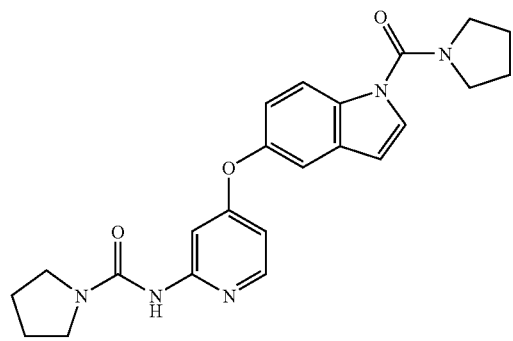

TABLE 12-continued
EXAMPLE 137
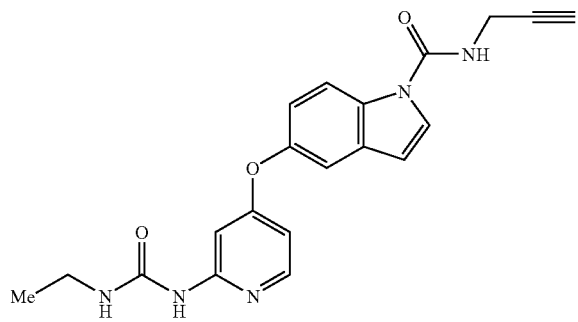
EXAMPLE 138
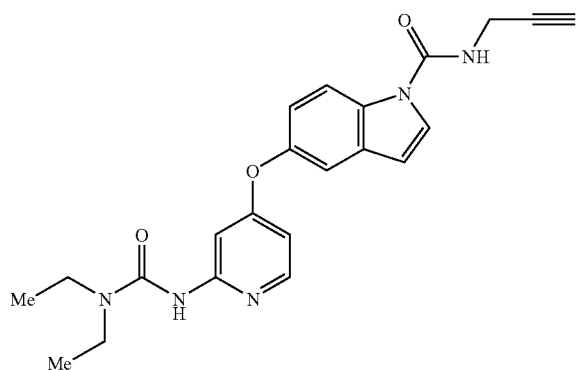
EXAMPLE 139
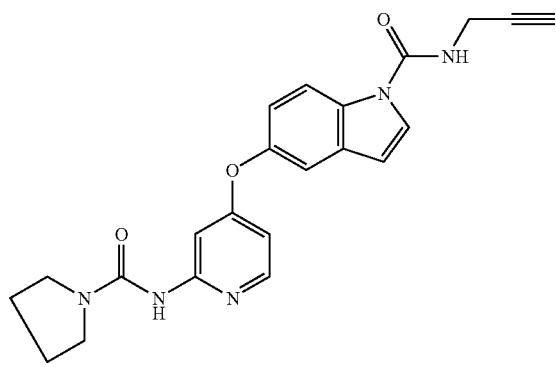
EXAMPLE 140
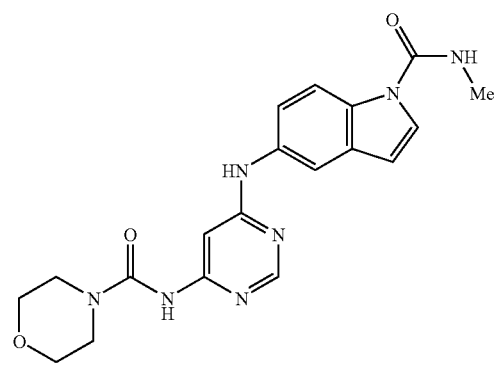

TABLE 12-continued
EXAMPLE 141
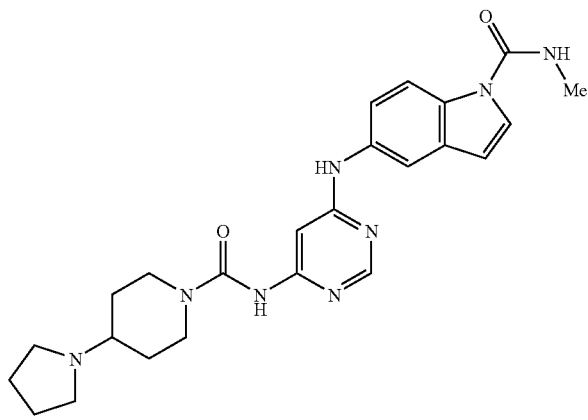
EXAMPLE 142
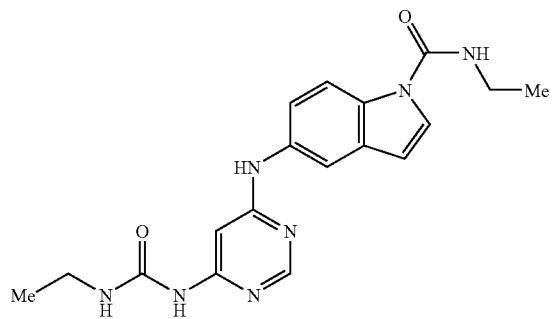
EXAMPLE 143
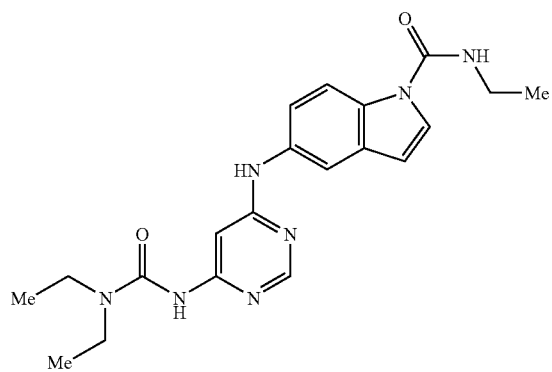

TABLE 12-continued
EXAMPLE 144
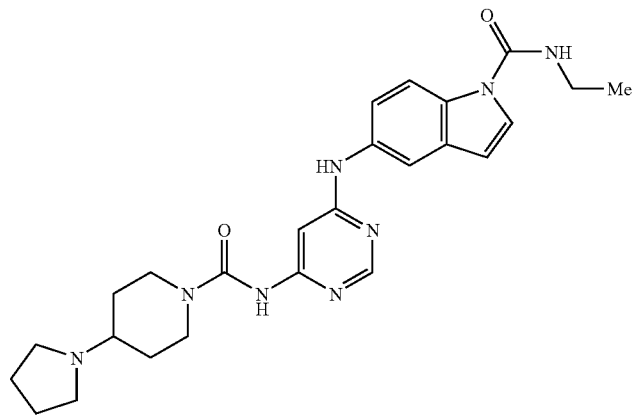
EXAMPLE 145
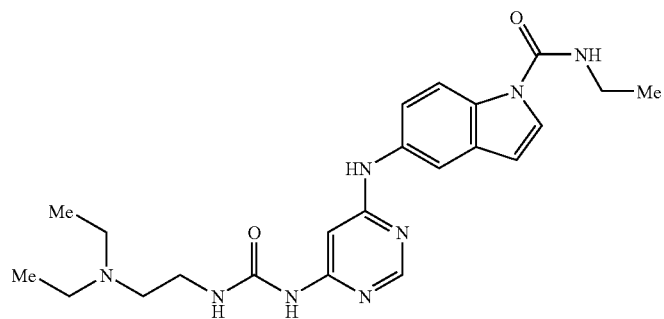
EXAMPLE 146
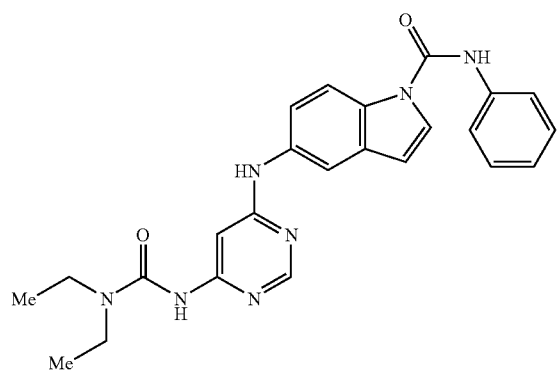

TABLE 12-continued
EXAMPLE 147
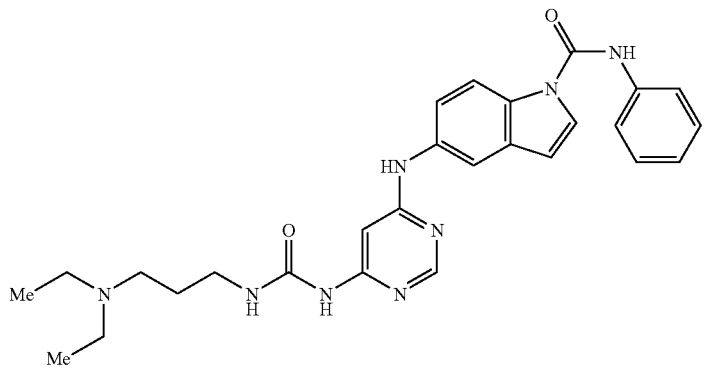
EXAMPLE 148
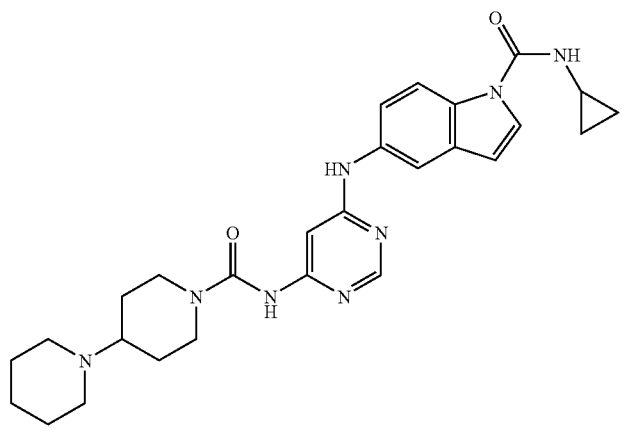
EXAMPLE 149
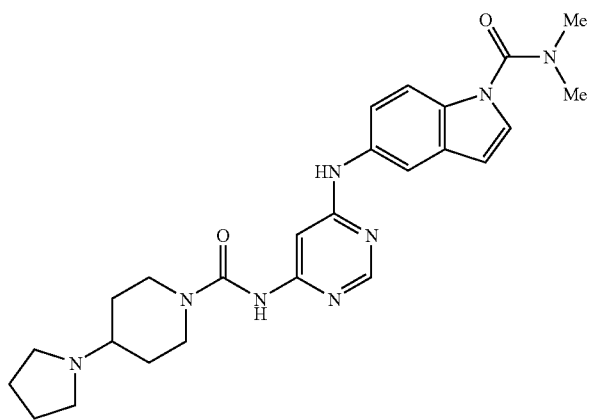

TABLE 12-continued
EXAMPLE 150
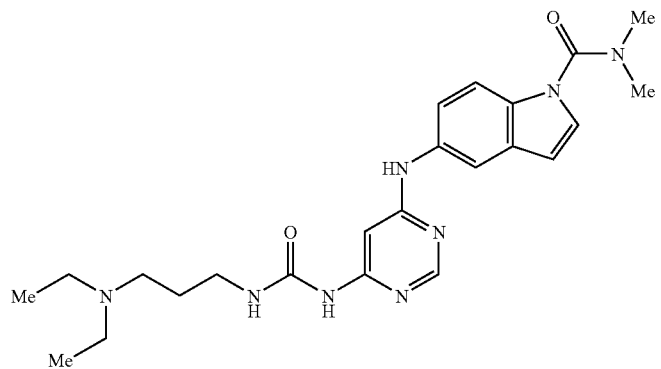
EXAMPLE 151
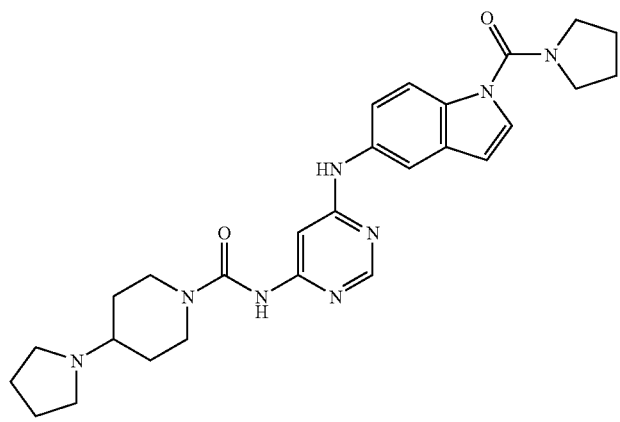
TABLE 13
EXAMPLE 152
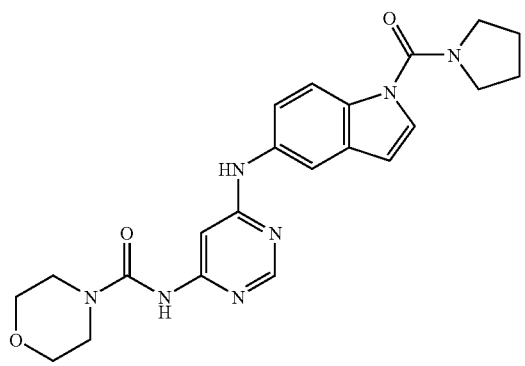

TABLE 13-continued
EXAMPLE 153
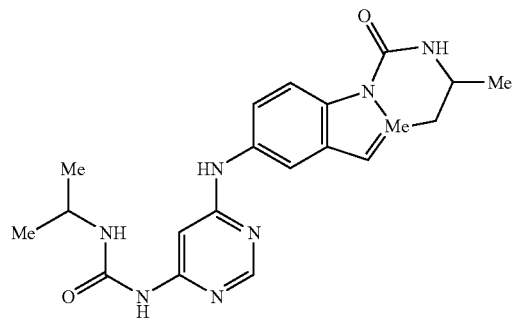
EXAMPLE 154
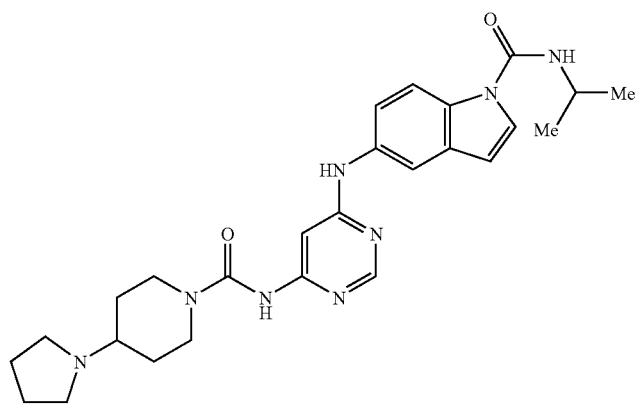
EXAMPLE 155
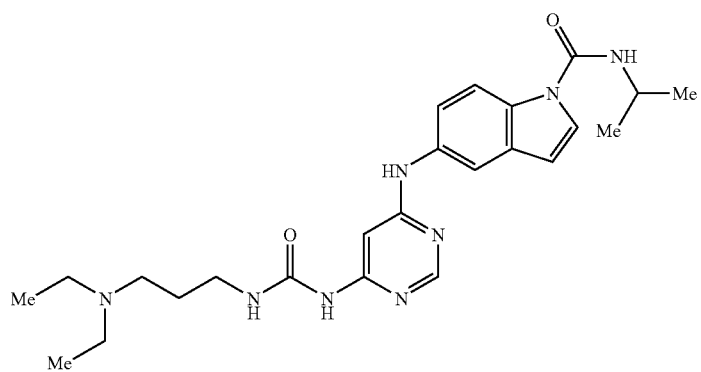
EXAMPLE 156
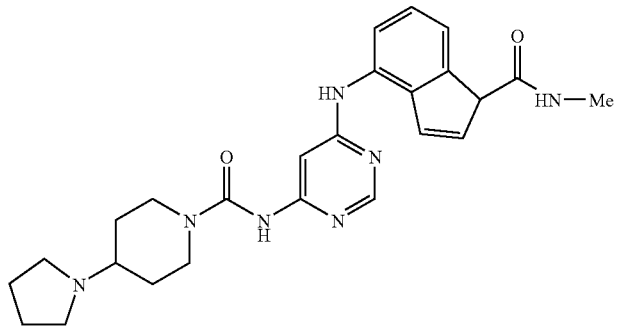

TABLE 13-continued
EXAMPLE 157
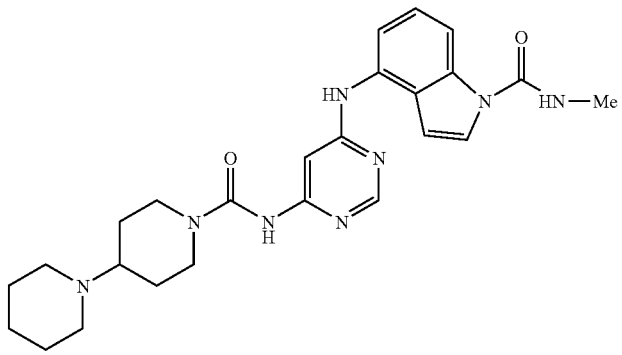
EXAMPLE 158
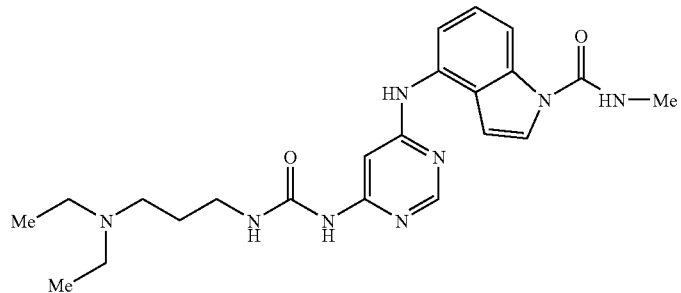
EXAMPLE 159
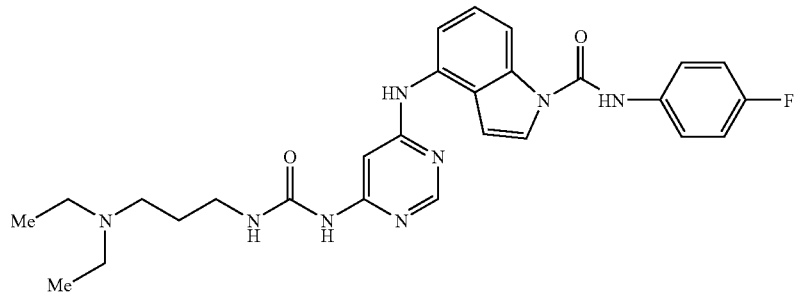
EXAMPLE 160
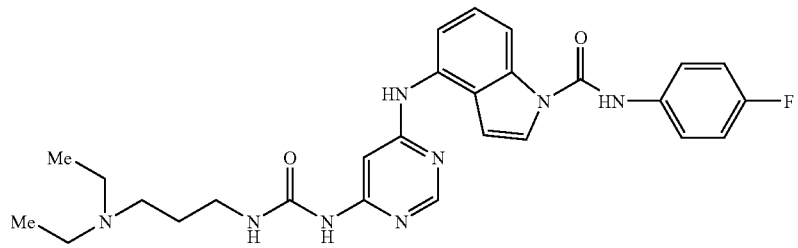

TABLE 13-continued
EXAMPLE 161
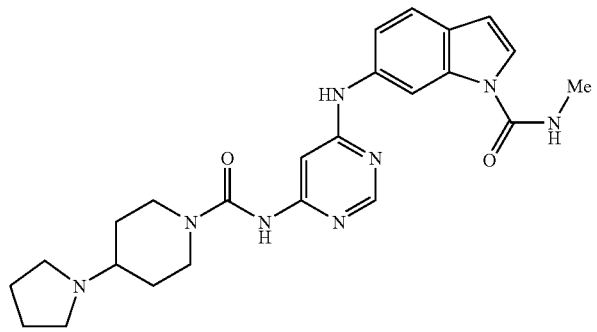
EXAMPLE 162
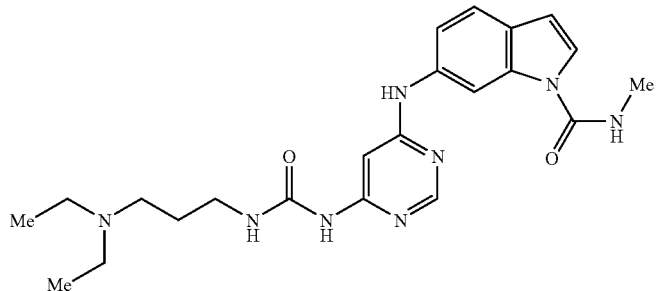
EXAMPLE 163
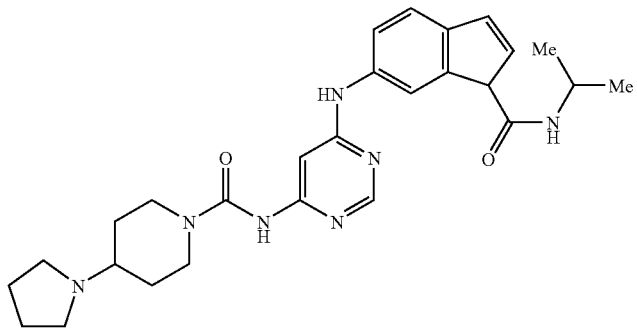
EXAMPLE 164
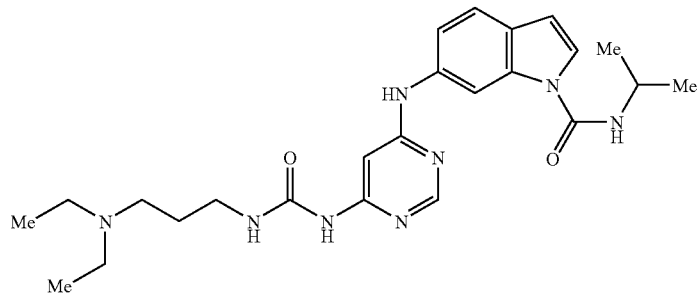

TABLE 13-continued
EXAMPLE 165
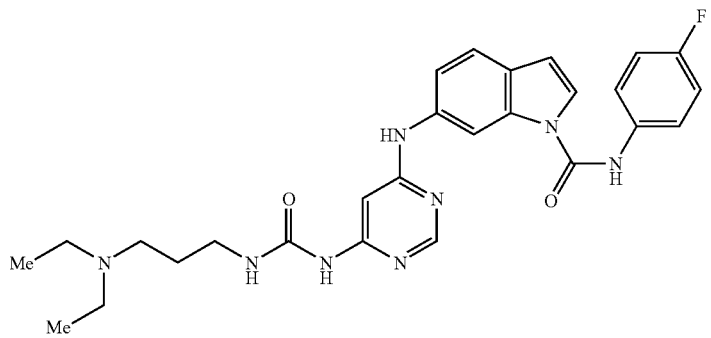
EXAMPLE 166
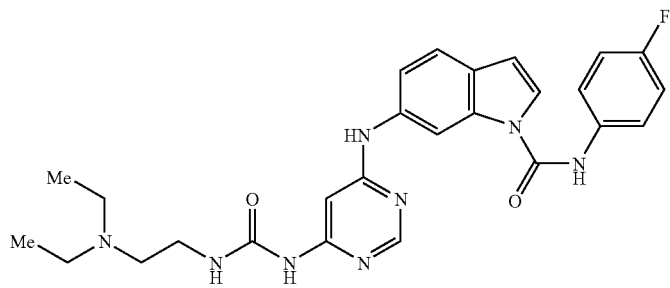
EXAMPLE 167
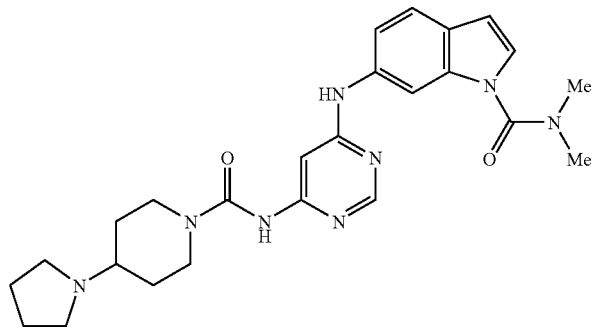
EXAMPLE 168
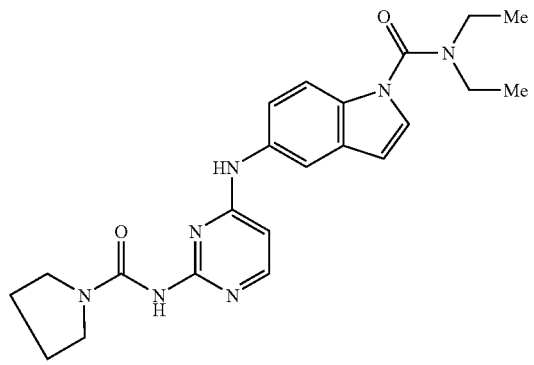

TABLE 13-continued
EXAMPLE 169
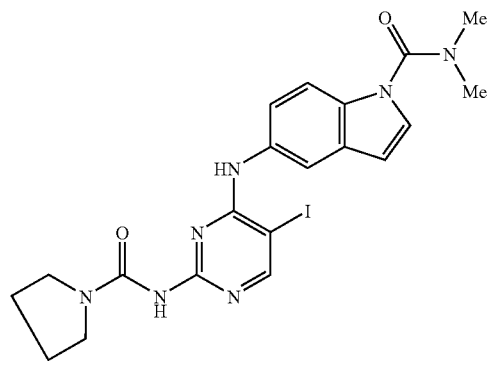
EXAMPLE 170
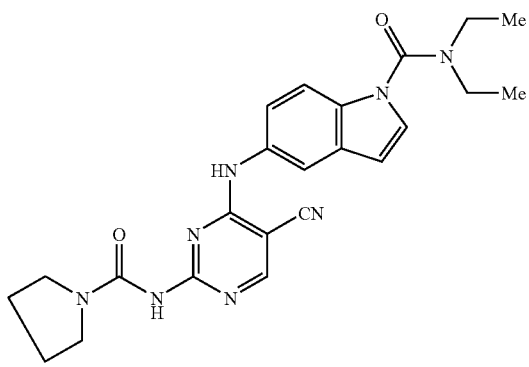
TABLE 14
EXAMPLE 171
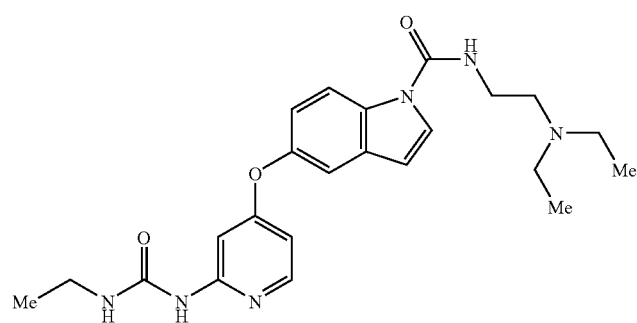

TABLE 14-continued
EXAMPLE 172
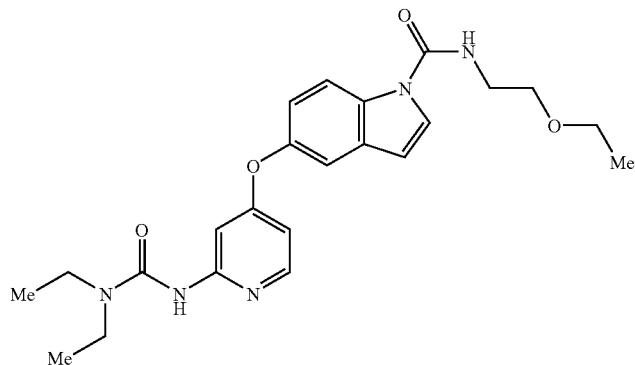
EXAMPLE 173
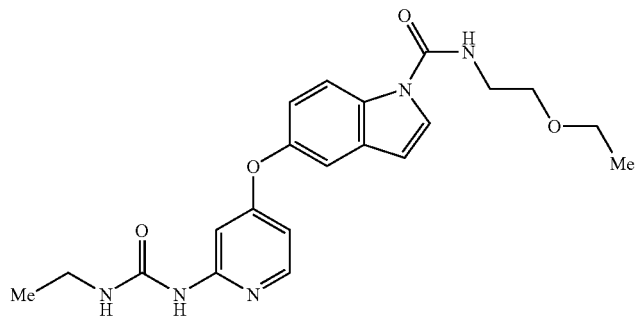
EXAMPLE 174
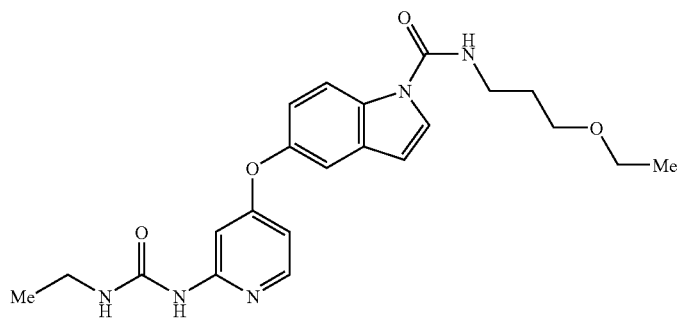
EXAMPLE 175
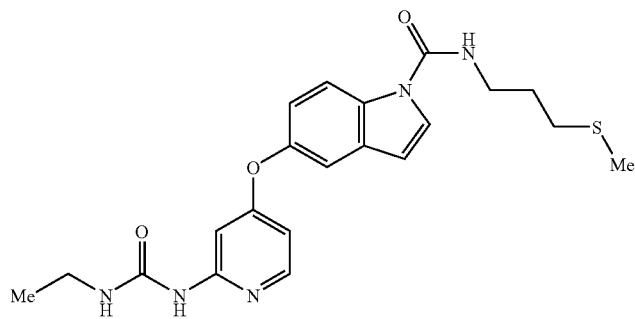

TABLE 14-continued
EXAMPLE 176
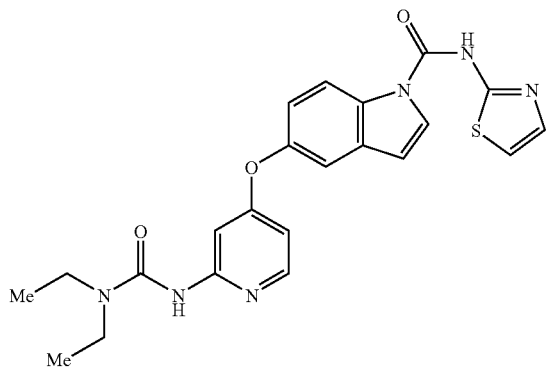
EXAMPLE 177
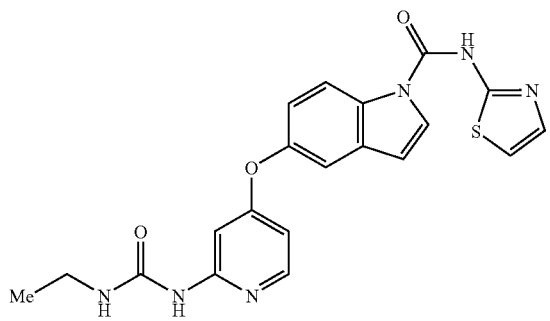
EXAMPLE 178
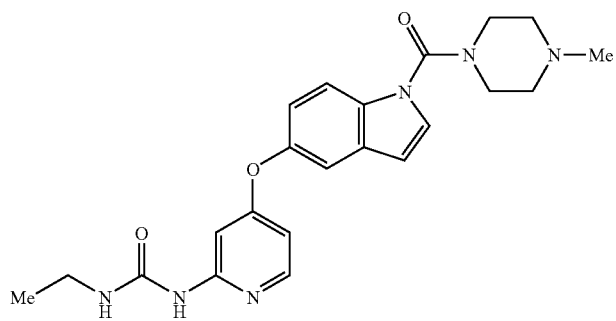
EXAMPLE 179
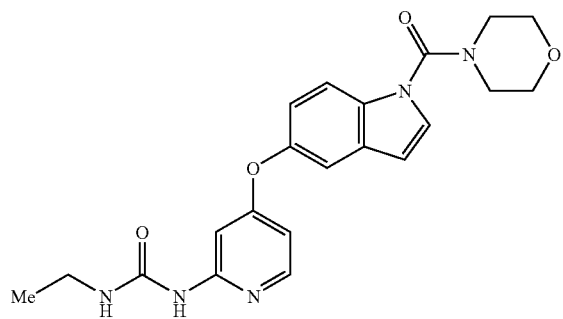

TABLE 14-continued
EXAMPLE 180
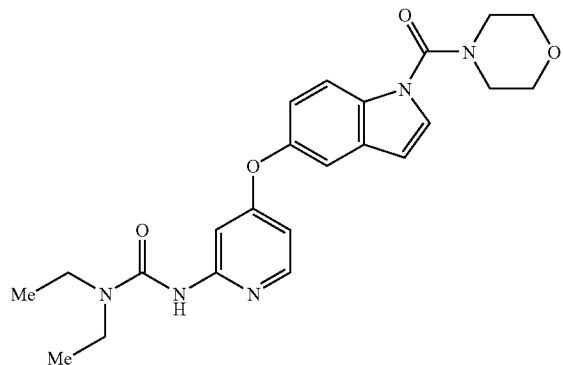
EXAMPLE 181
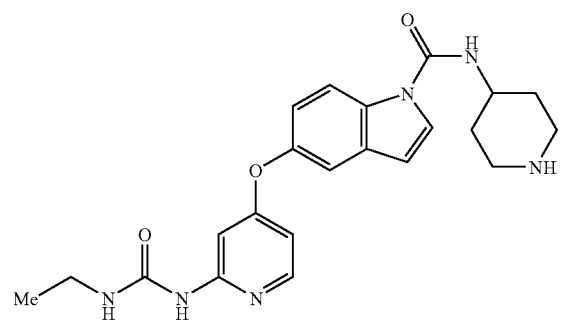
EXAMPLE 182
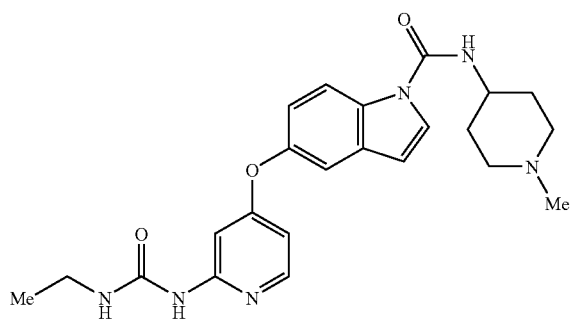
EXAMPLE 183
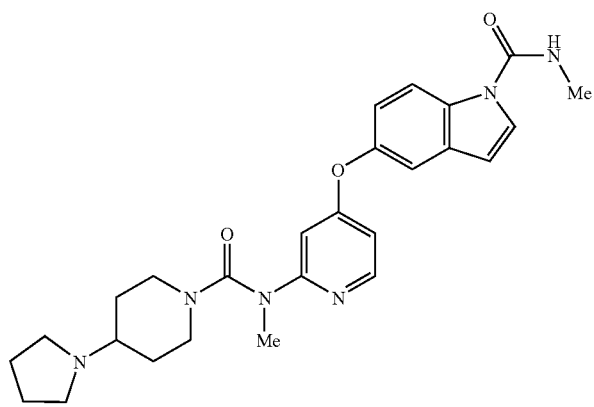

TABLE 14-continued
EXAMPLE 184
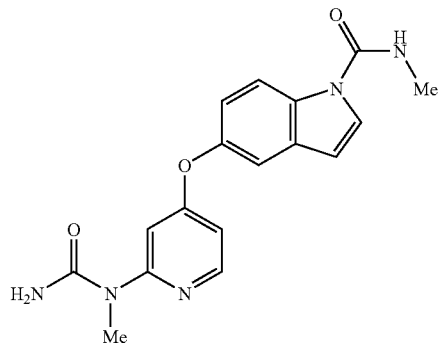
EXAMPLE 185
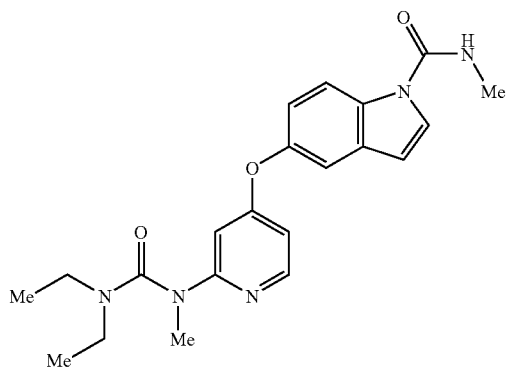
EXAMPLE 186
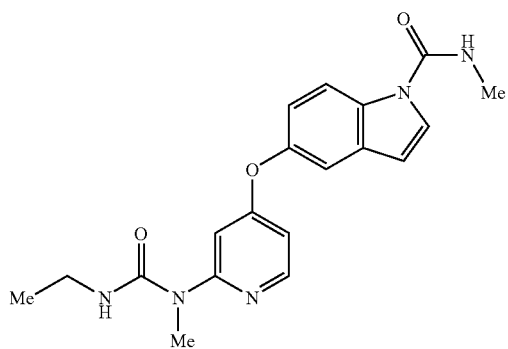
EXAMPLE 187
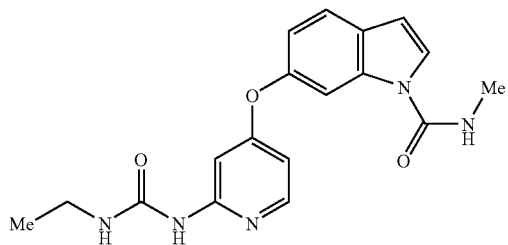

TABLE 14-continued
EXAMPLE 188
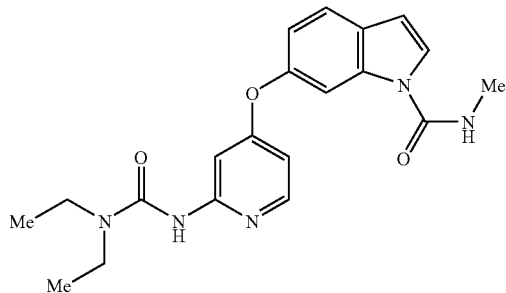
EXAMPLE 189
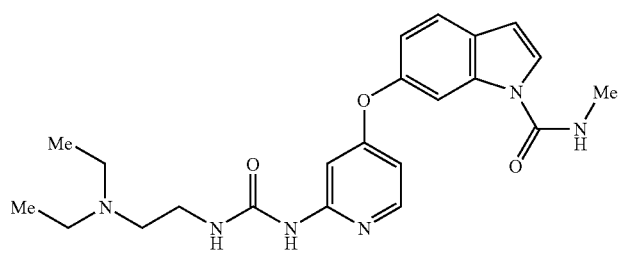
EXAMPLE 190
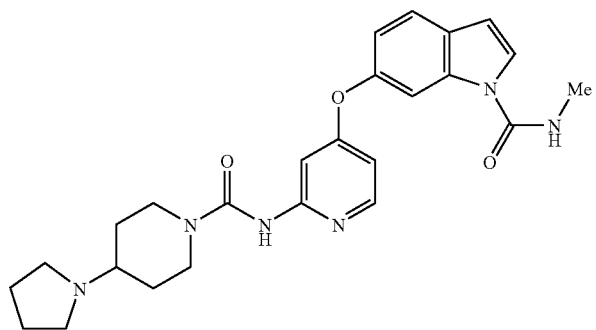
EXAMPLE 191
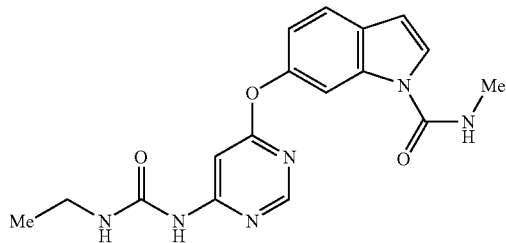

TABLE 14-continued
EXAMPLE 192
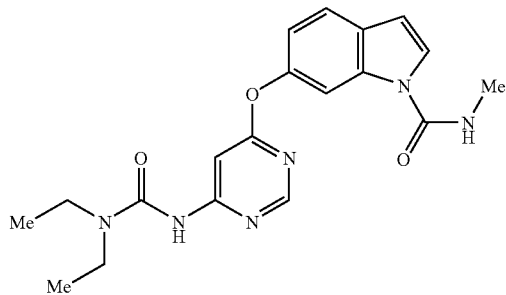
EXAMPLE 193
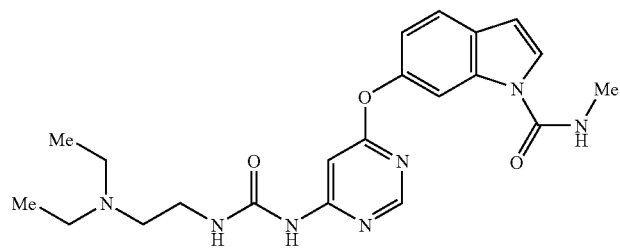
EXAMPLE 194
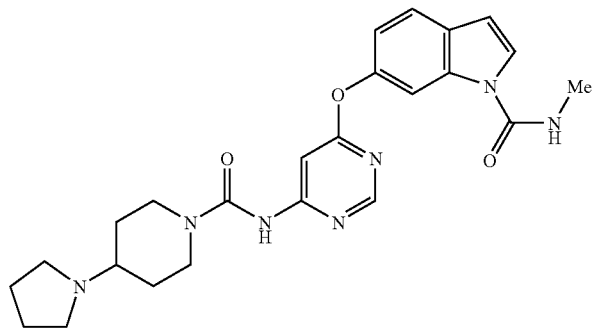
EXAMPLE 195
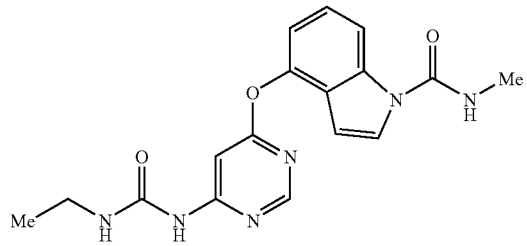

TABLE 14-continued
EXAMPLE 196
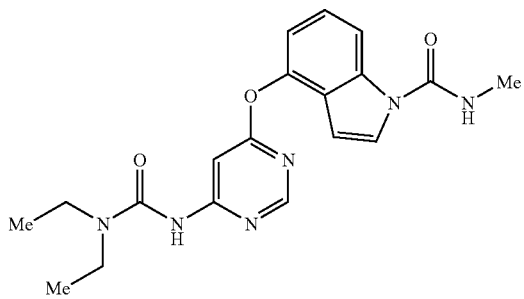
EXAMPLE 197
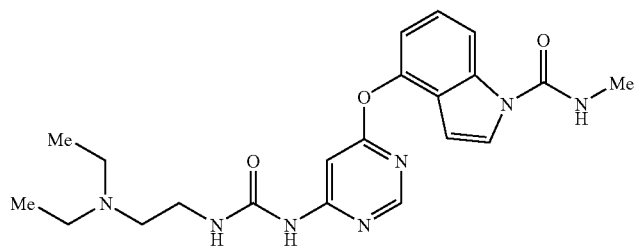
EXAMPLE 198
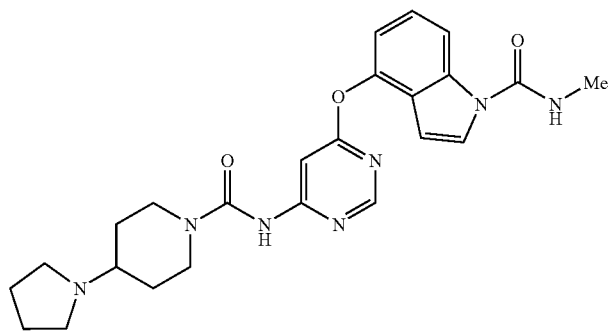
EXAMPLE 199
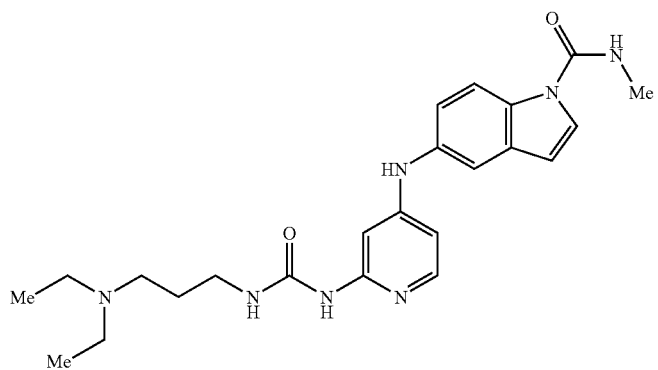

TABLE 14-continued
EXAMPLE 200
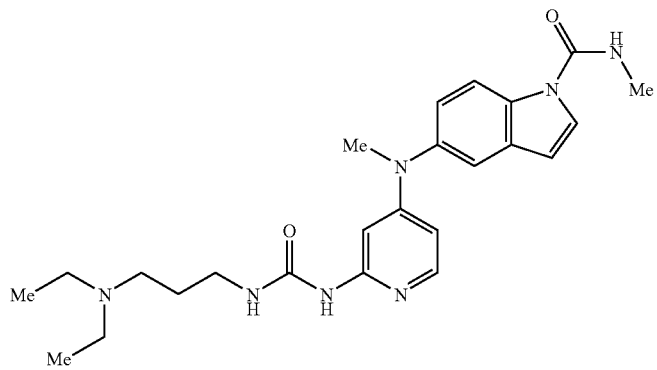
EXAMPLE 201
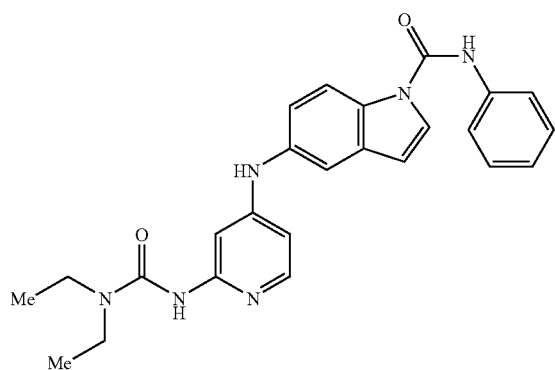
EXAMPLE 202
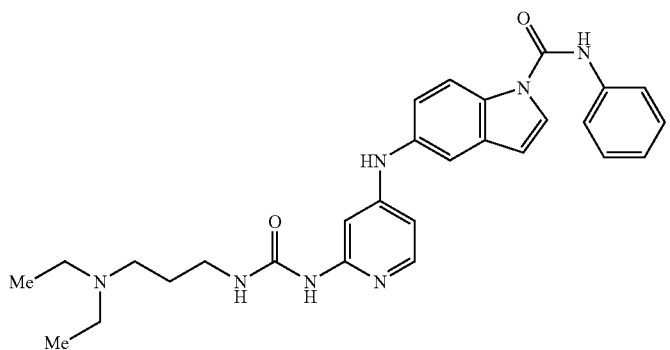
EXAMPLE 203
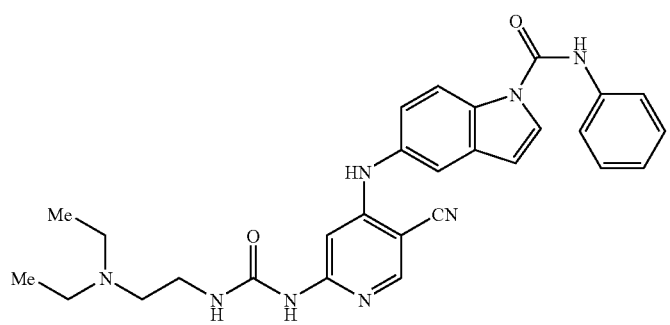

TABLE 14-continued
EXAMPLE 204
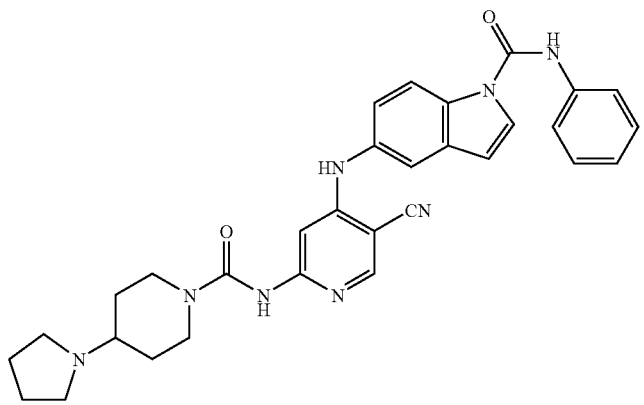
EXAMPLE 205
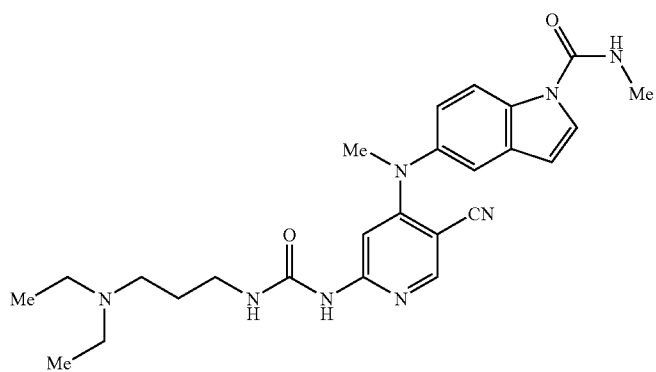
TABLE 15
EXAMPLE 206
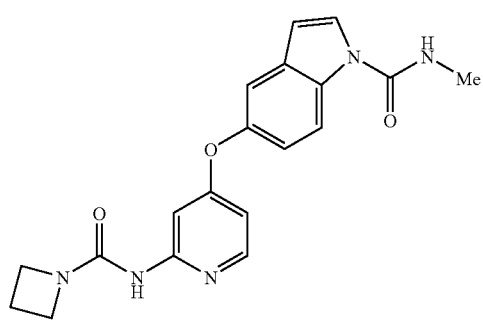

TABLE 15-continued
EXAMPLE 207
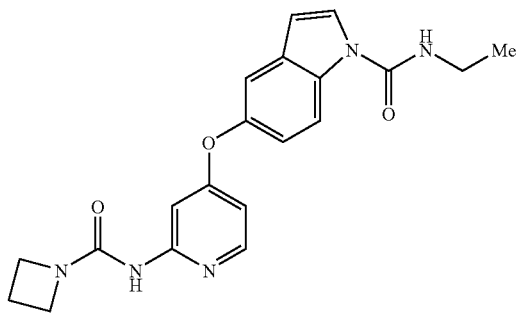
EXAMPLE 208
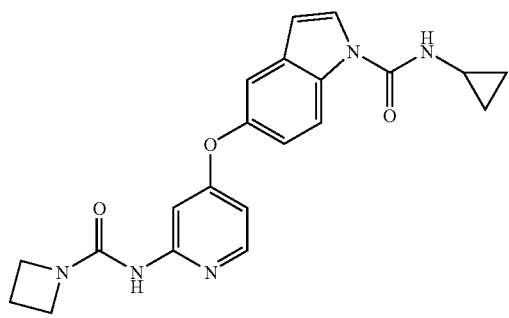
EXAMPLE 209
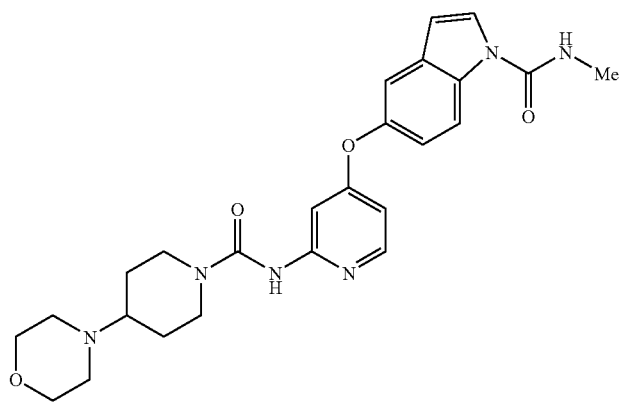
EXAMPLE 210
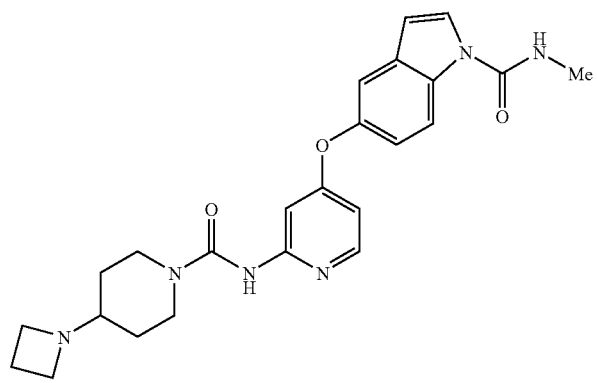

TABLE 15-continued
EXAMPLE 211
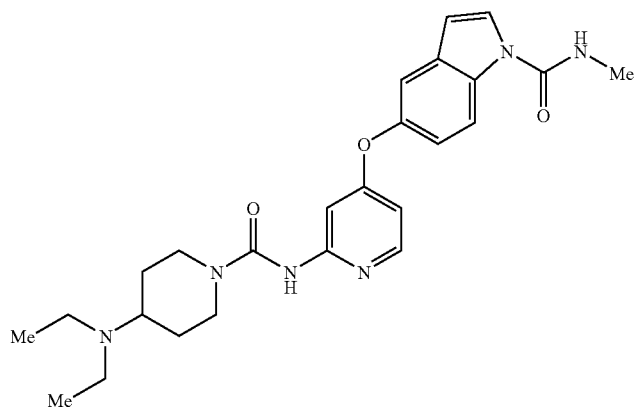
EXAMPLE 212
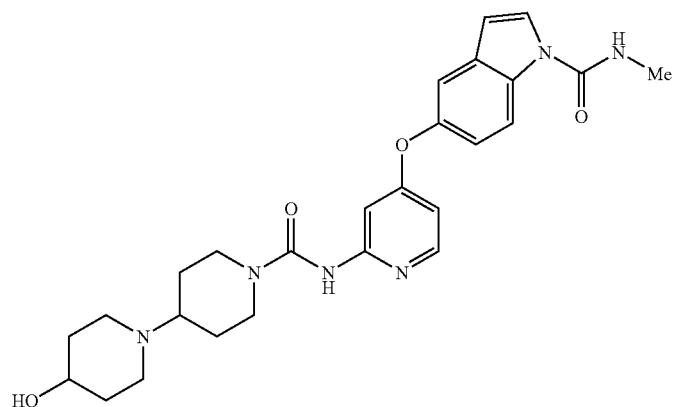
EXAMPLE 213
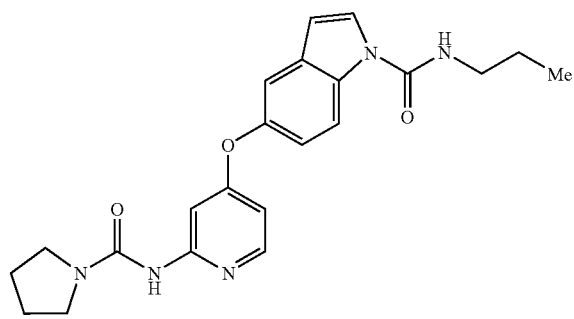
EXAMPLE 214
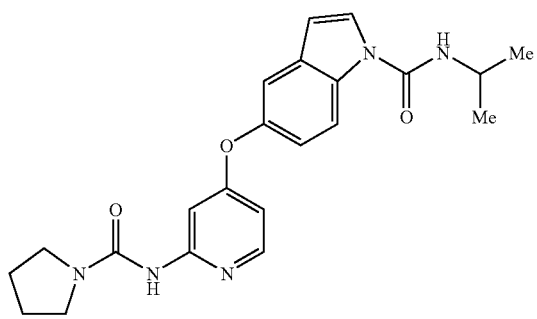

TABLE 15-continued
EXAMPLE 215
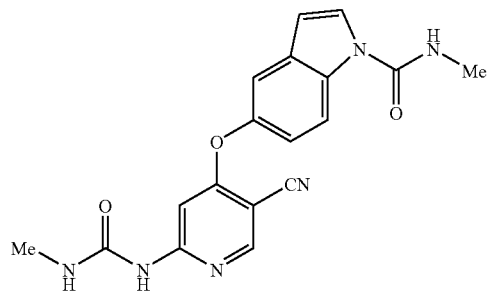
EXAMPLE 216
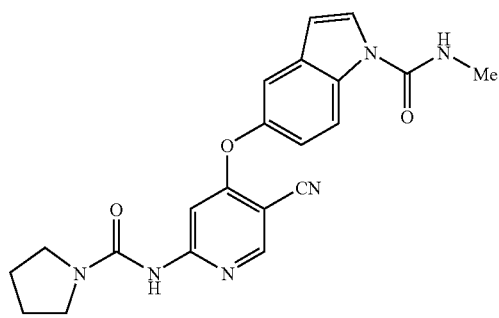
EXAMPLE 217
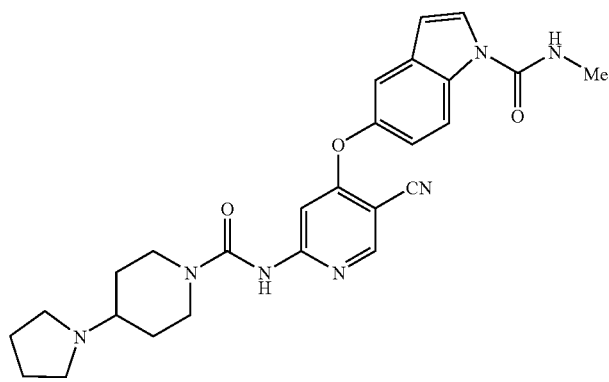
EXAMPLE 218
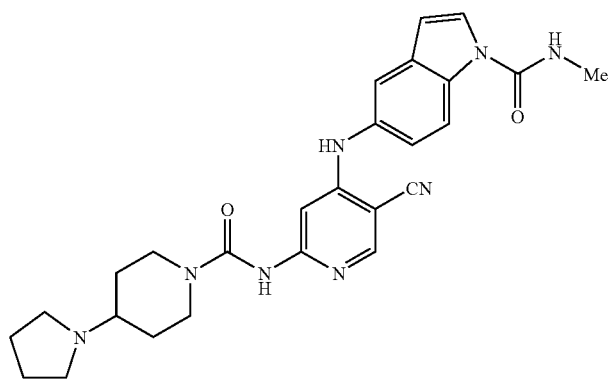

TABLE 15-continued

EXAMPLE 219

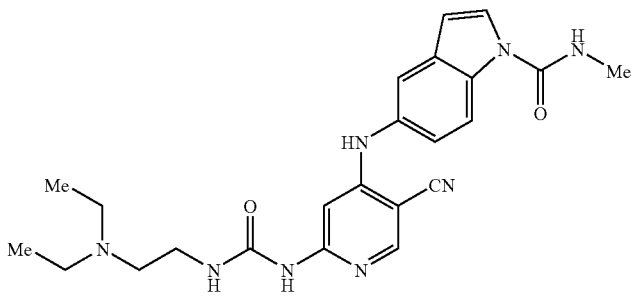

EXAMPLE 220

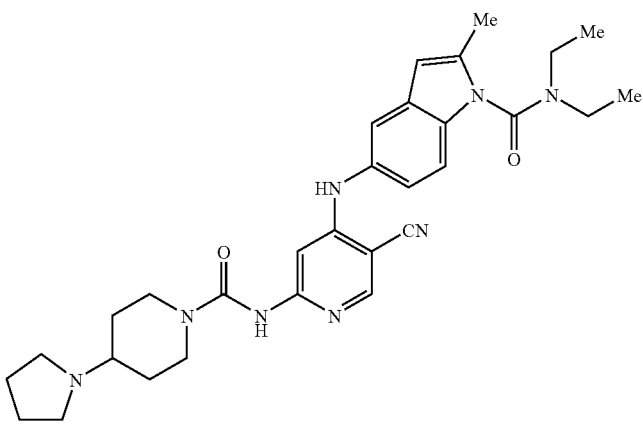

EXAMPLE 221

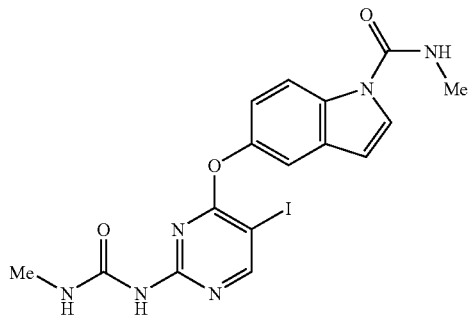

EFFECTS OF THE INVENTION

According to the present invention, it is possible to provide novel compounds that exhibit (1) powerful inhibitory action against tube formation by vascular endothelial cells induced by VEGF or FGF and (2) powerful inhibitory action against receptor kinases for VEGF or FGF, and which are highly useful as medicines.

It should be noted that the tube formation of vascular endothelial cells is an important process in angiogenesis, and a compound having inhibitory action therefor has angiogenesis inhibitory action. In addition, it is know that angiogenesis in body progresses by the additive/synergistic effect of a plurality of angiogenic factors represented by VEGF and FGF (Koolwijk P, van Erck M G M, de Vree W J A, Vermeer M A, Weich H A, Hance maaijer R, van Hinsberg V W M,. Cooperative effect of TNF-alpha, bFGF and VEGF on the formation of tubular structures of human microvascular endothelial cells in a fibrin matrix. Role of urokinase activity. J. Cell Biol., 132 P. 1177-1188, (1996)).

Therefore, the compounds of the invention which inhibit tube formation induced by VEGF or FGF produced by cancer cells and the like are expected to exhibit powerful angiogenesis inhibition in vivo, and should be highly useful as angiogenesis inhibitors. Moreover, the compounds of the invention are highly useful as angiogenesis inhibitors, and are aloso useful as prophylactic or therapeutic agents for diseases for which angiogenesis inhibition is effective, angiogenesis inhibitors, antitumor agents, therapeutic agents for angioma, cancer metastasis inhibitors, therapeutic agents for retinal neovascularization, therapeutic agents for diabetic retinopathy, therapeutic agents for inflammatory disease, therapeutic agents for inflammatory disease selected from deformant arthritis, rheumatoid arthritis, psoriasis or delayed hypersensitivity reaction, therapeutic agents for atherosclerosis, and angiogenesis inhibition-based antitumor agents.

SEQUENCE LISTING

```
<110> Eisai Co., Ltd.
<120> Nitrogen-containing aromatic derivatives
<130> EP02EE0801
<160> 2
<210> 1
<211> 23
<212> DNA
<213> Artifical Sequence
<400> 1 ccggatccatgaactttctgctg 23
<210> 2
<211> 21
<212> DNA
<213> Artifical Sequence
<400> 2 gtgaattctgtatcgatcgtt 21
``` wherein $X_1$ represents a group represented by the formula —$CR_{10}$=, $X_2$ represents a group represented by the formula —$CR_{11}$=;

Y represents an oxygen atom, a sulfur atom, a sulfinyl group, a sulfonyl group, or a group represented by the formula —$NR_Y$— (wherein $R_Y$ represents a hydrogen atom or a $C_{1-6}$ alkyl group);

$R_1$ represents an optionally substituted $C_{1-6}$ alkoxy group, an optionally substituted $C_{6-10}$ aryloxy group, a group represented by the formula —$NR_{12a}R_{12b}$, a group represented by the formula:

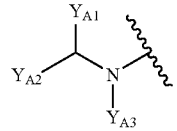

(VIII)

(wherein $Y_{A1}$ and $Y_{A2}$ each independently represent a group represented by the formula —$A_{10}$—$A_{11}$—$A_{12}$ (wherein $A_{10}$ represents a single bond or an optionally substituted $C_{1-6}$ alkylene; $A_{11}$ represents a single bond, an oxygen atom, a carbonyl group or a sulfonyl group; and $A_{12}$ represents a hydrogen atom, a $C_{1-6}$ alkyl group,

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 1
ccggatccat gaactttctg ctg                                            23

<210> SEQ ID NO 2
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 2
gtgaattctg tatcgatcgt t                                              21
```

What is claimed is:

1. A compound represented by the general formula:

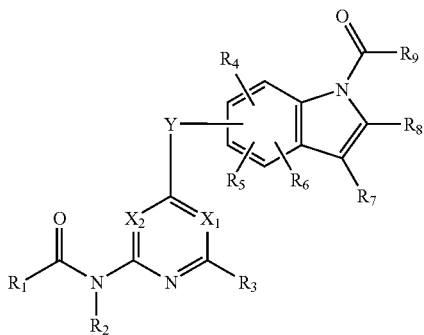

(I)

a $C_{2-6}$ alkenyl group, a $C_{2-6}$ alkynyl group, a $C_{3-8}$ cycloalkyl group, a $C_{6-10}$ aryl group, a 5- to 10-membered heteroaryl group, a group represented by the formula —$NR_{410}R_{411}$, a group represented by the formula —$OR_{412}$ (wherein $R_{410}$, $R_{411}$ and $R_{412}$ each independently represent a hydrogen atom, a C1–6 alkyl group or $C_{3-8}$ cycloalkyl group) or a group represented by the formula:

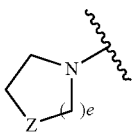

(wherein e represents 1 or 2; Z represents an oxygen atom, a group represented by the formula —CR$_{X7}$R$_{X8}$— or a group represented by the formula —NR$_{X9}$—; R$_{X7}$, R$_{X8}$ and R$_{X9}$ each independently represent a hydrogen atom, a hydroxyl group or a C$_{1-6}$ alkyl group)); and Y$_{A3}$ represents a hydrogen atom or an optionally substituted C$_{1-6}$ alkyl group) or a group represented by the formula:

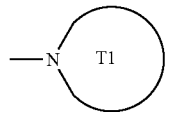

(wherein T1 represents an optionally substituted 5- to 10-membered aromatic heterocycle which may have X in the ring or an optionally substituted 3- to 10-membered heterocycle which may have X in the ring);

R$_2$, R$_3$, R$_4$, R$_5$, R$_6$, R$_7$, and R$_8$ each represent a hydrogen atom;

R$_{10}$ and R$_{11}$ each independently represent a hydrogen atom, a halogen atom, a cyano group, an optionally substituted C$_{1-6}$ alkyl group, an optionally substituted C$_{2-6}$ alkenyl group, an optionally substituted C$_{2-6}$ alkynyl group, an optionally substituted C$_{3-8}$ cycloalkyl group, a group represented by the formula —CO—R$_{13}$, a group represented by the formula —NR$_{14}$—CO—R$_{13}$, a group represented by the formula —SO$_2$—R$_{15}$, a group represented by the formula —NR$_{14}$—SO$_2$—R$_{15}$, or a group represented by the formula —NR$_{16a}$R$_{16b}$;

R$_9$ represents a group represented by the formula —NR$_{16a}$R$_{16b}$

R$_{12a}$ and R$_{12b}$ each independently represent a hydrogen atom, an optionally substituted C$_{1-6}$ alkyl group, an optionally substituted C$_{3-6}$ alkenyl group, an optionally substituted C$_{3-6}$ alkynyl group, an optionally substituted C$_{3-8}$ cycloalkyl group, an optionally substituted 3- to 10-membered heterocyclic group, or an optionally substituted C$_{1-6}$ alkoxy group;

R$_{13}$ represents a hydrogen atom, an optionally substituted C$_{1-6}$ alkyl group, an optionally substituted C$_{2-6}$ alkenyl group, an optionally substituted C$_{2-6}$ alkynyl group, an optionally substituted C$_{3-8}$ cycloalkyl group, an optionally substituted C$_{6-10}$ aryl group, an optionally substituted 5- to 10-membered heteroaryl group, an optionally substituted 3- to 10-membered heterocyclic group, an optionally substituted C$_{1-6}$ alkoxy group, an optionally substituted C$_{6-10}$ aryloxy group, a group represented by the formula —NR$_{12a}$R$_{12b}$, or a group represented by the formula:

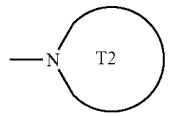

(wherein T2 represents an optionally substituted 5- to 10-membered aromatic heterocycle or an optionally substituted 3- to 10-membered heterocycle);

R$_{14}$ represents a hydrogen atom, an optionally substituted C$_{1-6}$ alkyl group, an optionally substituted C$_{2-6}$ alkenyl group, an optionally substituted C$_{2-6}$ alkynyl group, an optionally substituted C$_{3-8}$ cycloalkyl group, or a group represented by the formula —CO—R$_{13}$;

R$_{15}$ represents an optionally substituted C$_{1-6}$ alkyl group, an optionally substituted C$_{2-6}$ alkenyl group, an optionally substituted C$_{2-6}$ alkynyl group, an optionally substituted C$_{3-8}$ cycloalkyl group, an optionally substituted C$_{6-10}$ aryl group, an optionally substituted 5- to 10-membered heteroaryl group, or an optionally substituted 3- to 10-membered heterocyclic group;

R$_{16a}$ and R$_{16b}$ each independently represent a hydrogen atom, an optionally substituted C$_{1-6}$ alkyl group, an optionally substituted C$_{3-6}$ alkenyl group, an optionally substituted C$_{3-6}$ alkynyl group, an optionally substituted C$_{3-8}$ cycloalkyl group, an optionally substituted C$_{6-10}$ aryl group, or an optionally substituted C$_{1-6}$ alkoxy group; and X represents an oxygen atom, a sulfur atom, a carbonyl group, a sulfonyl group, a group represented by the formula —CR$_{X1}$R$_{X2}$—, or a group represented by the formula —NR$_{X3}$— (wherein R$_{X1}$, R$_{X2}$ and R$_{X3}$ each independently represent a hydrogen atom or a group represented by the formula —A$_1$—A$_2$—A$_3$ (wherein A$_1$ and A$_2$ each independently represent a single bond, an optionally substituted C$_{1-6}$ alkylene group or a carbonyl group; and A$_3$ represents a hydrogen atom, a C$_{3-8}$ cycloalkyl group, a group represented by the formula —NR$_{A1}$R$_{A2}$, or the formula —OR$_{A3}$ (wherein, R$_{A1}$, R$_{A2}$ and R$_{A3}$ each independently represent a hydrogen atom or a C$_{1-6}$ alkyl group), or an optionally substituted group represented by the formula:

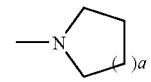

(wherein a represents 1 or 2))), a salt thereof, or a hydrate of the foregoing.

2. A compound represented by the general formula:

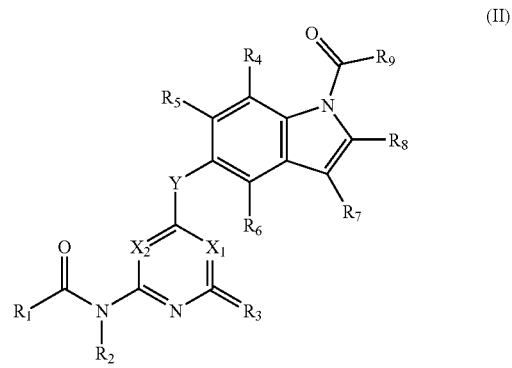

(II)

wherein X$_1$ represents a group represented by the formula —CR$_{10}$=, X$_2$ represents a group represented by the formula —CR$_{11}$=;

Y represents an oxygen atom, a sulfur atom, a sulfinyl group, a sulfonyl group, or a group represented by the formula —NR$_Y$— (wherein R$_Y$ represents a hydrogen atom or a C$_{1-6}$ alkyl group);

R$_1$ represents an optionally substituted C$_{1-6}$ alkoxy group, an optionally substituted C$_{6-10}$ aryloxy group, a group represented by the formula —NR$_{12a}$R$_{12b}$, a group represented by the formula:

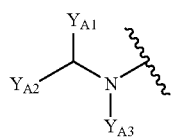

(VIII)

(wherein $Y_{A1}$ and $Y_{A2}$ each independently represent a group represented by the formula —$A_{10}$—$A_{11}$—$A_{12}$ (wherein $A_{10}$ represents a single bond or an optionally substituted $C_{1-6}$ alkylene; $A_{11}$ represents a single bond, an oxygen atom, a carbonyl group or a sulfonyl group; and $A_{12}$ represents a hydrogen atom, a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a 5- to 10-membered heteroaryl group, a group represented by the formula —$NR_{A10}R_{A11}$, a group represented by the formula —$OR_{A12}$ (wherein $R_{A10}$, $R_{A11}$ and $R_{A12}$ each independently represent a hydrogen atom, a $C_{1-6}$ alkyl group or $C_{3-8}$ cycloalkyl group) or a group represented by the formula:

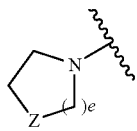

(wherein e represents 1 or 2; Z represents an oxygen atom, a group represented by the formula —$CR_{X7}R_{X8}$— or a group represented by the formula —$NR_{X9}$—; $R_{X7}$, $R_{X8}$ and $R_{X9}$ each independently represent a hydrogen atom, a hydroxyl group or a $C_{1-6}$ alkyl group)); and $Y_{A3}$ represents a hydrogen atom or an optionally substituted $C_{1-6}$ alkyl group) or a group represented by the formula:

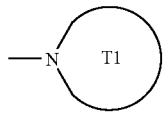

(wherein T1 represents an optionally substituted 5- to 10-membered aromatic heterocycle which may have X in the ring or an optionally substituted 3- to 10-membered heterocycle which may have X in the ring);

$R_2$, $R_3$, $R_4$, $R_5$, $R_6$, $R_7$, and $R_8$ each represent a hydrogen atom;

$R_{10}$ and $R_{11}$ each independently represent a hydrogen atom, a halogen atom, a cyano group, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, a group represented by the formula —CO—$R_{13}$, a group represented by the formula —$NR_{14}$—CO—$R_{13}$, a group represented by the formula —$SO_2$—$R_{15}$, a group represented by the formula —$NR_{14}$—$SO_2$—$R_{15}$, or a group represented by the formula —$NR_{16a}R_{16b}$;

$R_9$ represents a group represented by the formula —$NR_{16a}R_{16b}$;

$R_{12a}$ and $R_{12b}$ each independently represent a hydrogen atom, an optionally substituted $C_{1-6}$ alkyl group, an optionally substituted $C_{3-6}$ alkenyl group, an optionally substituted $C_{3-6}$ alkynyl group, an optionally substituted $C_{3-8}$ cycloalkyl group, an optionally substituted 3- to 10-membered heterocyclic group, or an optionally substituted $C_{1-6}$ alkoxy group;

$R_{13}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group, an optionally substituted 3- to 10-membered heterocyclic group, an optionally substituted $C_{1-6}$ alkoxy group, an optionally substituted $C_{6-10}$ aryloxy group, a group represented by the formula —$NR_{12a}R_{12b}$, or a group represented by the formula:

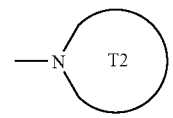

(wherein T2 represents an optionally substituted 5- to 10-membered aromatic heterocycle or an optionally substituted 3- to 10-membered heterocycle);

$R_{14}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, or a group represented by the formula —CO—$R_{13}$;

$R_{15}$ represents an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5- to 10-membered heteroaryl group, or an optionally substituted 3- to 10-membered heterocyclic group;

$R_{16a}$ and $R_{16b}$ each independently represent a hydrogen atom, an optionally substituted $C_{1-6}$ alkyl group, an optionally substituted $C_{3-6}$ alkenyl group, an optionally substituted $C_{3-6}$ alkynyl group, an optionally substituted $C_{3-8}$ cycloalkyl group, an optionally substituted $C_{6-10}$ aryl group, or an optionally substituted $C_{1-6}$ alkoxy group; and X represents an oxygen atom, a sulfur atom, a carbonyl group, a sulfonyl group, a group represented by the formula —$CR_{X1}R_{X2}$—, or a group represented by the formula —$NR_{X3}$— (wherein $R_{X1}$, $R_{X2}$ and $R_{X3}$ each independently represent a hydrogen atom or a group represented by the formula —$A_1$—$A_2$—$A_3$ (wherein $A_1$ and $A_2$ each independently represent a single bond, an optionally substituted $C_{1-6}$ alkylene group or a carbonyl group; and $A_3$ represents a hydrogen atom, a $C_{3-8}$ cycloalkyl group, a group represented by the formula —$NR_{A1}R_{A2}$, or the formula —$OR_{A3}$ (wherein, $R_{A1}$, $R_{A2}$ and $R_{A3}$ each independently represent a hydrogen atom or a $C_{1-6}$ alkyl group), or an optionally substituted group represented by the formula:

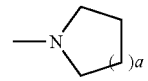

(wherein a represents 1 or 2))), a salt thereof, or a hydrate of the foregoing.

3. A compound according to claim 1 or 2, a salt of the compound, or a hydrate of the foregoing, wherein Y represents an oxygen atom, a group represented by the formula —NH—, or a group represented by the formula —N(CH$_3$)—.

4. A compound according to claim 1 or 2, a salt of the compound, or a hydrate of the foregoing, wherein Y represents an oxygen atom.

5. A compound according to claims 1 or 2, a salt of the compound, or a hydrate of the foregoing, wherein both $X_1$ and $X_2$ represent a group represented by the formula —CH═.

6. A compound according to claims 1 or 2, a salt of the compound, or a hydrate of the foregoing, wherein $R_9$ represents a group represented by the formula —NHR$_{17}$ (wherein $R_{17}$ represents an optionally substituted $C_{1-6}$ alkyl group, a $C_{3-6}$ alkynyl group, a $C_{3-8}$ cycloalkyl group, or an optionally substituted $C_{6-10}$ aryl group).

7. A compound according to claims 1 or 2, a salt of the compound, or a hydrate of the foregoing, wherein $R_9$ represents a group represented by the formula —NR$_{18a}$R$_{18b}$ (wherein $R_{18a}$ and $R_{18b}$ each independently represent a $C_{1-6}$ alkyl group).

8. A compound according to claims 1 or 2, a salt of the compound, or a hydrate of the foregoing, wherein $R_9$ represents a group represented by the formula —NHR$_{19}$ (wherein $R_{19}$ represents a $C_{1-6}$ alkyl group, a $C_{3-6}$ alkynyl group, a $C_{3-8}$ cycloalkyl group or a $C_{6-10}$ aryl group).

9. A compound according to claims 1 or 2, a salt of the compound, or a hydrate of the foregoing, wherein $R_9$ represents a group represented by the formula —NHR$_{20}$ (wherein $R_{20}$ represents a methyl group, an ethyl group or a cyclopropyl group).

10. A compound according to claims 1 or 2, a salt of the compound, or a hydrate of the foregoing, wherein $R_9$ represents a group represented by the formula —NH(CH$_3$).

11. A compound according to claims 1 or 2, a salt of the compound, or a hydrate of the foregoing, wherein $R_1$ represents a further optionally substituted group represented by the formula:

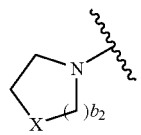

(III′)

(wherein $b_2$ represents 0, 1 or 2; and X represents an oxygen atom, a sulfur atom, a carbonyl group, a sulfonyl group, a group represented by the formula —CR$_{X1}$R$_{X2}$—, or a group represented by the formula —NR$_{X3}$— (wherein $R_{X1}$, $R_{X2}$ and $R_{X3}$ each independently represent a hydrogen atom or a group represented by the formula —A$_1$—A$_2$—A$_3$ (wherein A$_1$ and A$_2$ each independently represent a single bond, an optionally substituted $C_{1-6}$ alkylene group or a carbonyl group; and A$_3$ represents a hydrogen atom, a $C_{3-8}$ cycloalkyl group, a group represented by the formula —NR$_{A1}$R$_{A2}$, or the formula —OR$_{A3}$ (wherein, $R_{A1}$, $R_{A2}$ and $R_{A3}$ each independently represent a hydrogen atom or a $C_{1-6}$ alkyl group), or an optionally substituted group represented by the formula:

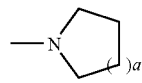

(wherein a represents 1 or 2))).

12. A compound according to claims 1 or 2, a salt of the compound, or a hydrate of the foregoing, wherein $R_1$ represents a group represented by the formula:

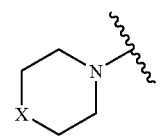

(IV)

(wherein X represents an oxygen atom, a sulfur atom, a carbonyl group, a sulfonyl group, a group represented by the formula —CR$_{X1}$R$_{X2}$—, or a group represented by the formula —NR$_{X3}$— (wherein $R_{X1}$, $R_{X2}$ and $R_{X3}$ each independently represent a hydrogen atom or a group represented by the formula —A$_1$—A$_2$—A$_3$ (wherein A$_1$ and A$_2$ each independently represent a single bond, an optionally substituted $C_{1-6}$ alkylene group or a carbonyl group; and A$_3$ represents a hydrogen atom, a $C_{3-8}$ cycloalkyl group, a group represented by the formula —NR$_{A1}$R$_{A2}$, or the formula —OR$_{A3}$ (wherein, $R_{A1}$, $R_{A2}$ and $R_{A3}$ each independently represent a hydrogen atom or a $C_{1-6}$ alkyl group), or an optionally substituted group represented by the formula:

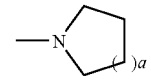

(wherein a represents 1 or 2))).

13. A compound according to claim 12, a salt of the compound, or a hydrate of the foregoing, wherein X in the formula (IV) represents an oxygen atom.

14. A compound according to claim 12, a salt of the compound, or a hydrate of the foregoing, wherein X in the formula (IV) represents a group represented by the formula:

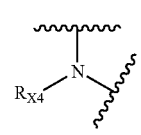

(V)

(wherein $R_{X4}$ represents a hydrogen atom or a group represented by the formula —A$_4$—A$_5$—A$_6$ (wherein A$_4$ and A$_5$ each independently represent a single bond, an optionally substituted $C_{1-6}$ alkylene or a carbonyl group; and A$_6$ represents a hydrogen atom, a $C_{3-8}$ cycloalkyl group or a group represented by the formula —NR$_{44}$R$_{45}$ or the formula —OR$_{46}$ (wherein $R_{44}$, $R_{45}$ and $R_{46}$ each independently represent a hydrogen atom or a $C_{1-6}$ alkyl group))).

15. A compound according to claim 12, a salt of the compound, or a hydrate of the foregoing, wherein X in the formula (IV) represents a group represented by the formula:

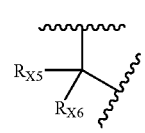

(VI)

(wherein $R_{X5}$ and $R_{X6}$ each independently represent a hydrogen atom or a group represented by the formula —$A_7$—$A_8$—$A_9$ (wherein $A_7$ and $A_8$ each independently represent a single bond, an optionally substituted $C_{1-6}$ alkylene group or a carbonyl group; and $A_9$ represents a hydrogen atom, a $C_{3-8}$ cycloalkyl group, a group represented by the formula —$NR_{47}R_{48}$, or the formula —$OR_{49}$ (wherein $R_{47}$, $R_{48}$, and $R_{49}$ each independently represent a hydrogen atom or a $C_{1-6}$ alkyl group), or a group represented by the formula:

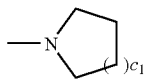

(wherein $c_1$ represents 0, 1 or 2))).

16. A compound according to claim 15, a salt of the compound, or a hydrate of the foregoing, wherein one of $R_{X5}$ and $R_{X6}$ in the formula (VI) represents a hydroxyl group and the other represents a hydrogen atom or a $C_{1-6}$ alkyl group.

17. A compound according to claim 15, a salt of the compound, or a hydrate of the foregoing, wherein one of $R_{X5}$ or $R_{X6}$ in the formula (VI) represents a hydrogen atom and the other represents a group represented by the formula:

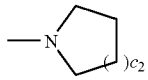

(wherein $c_2$ represents 1 or 2).

18. A compound according to claims 1 or 2, a salt of the compound, or a hydrate of the foregoing, wherein $R_1$ represents a group represented by the formula:

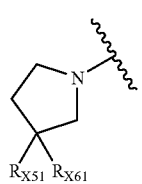

(VII)

(wherein $R_{X51}$ and $R_{X61}$ each independently represent a hydrogen atom or a group represented by the formula —$A_{71}$—$A_{81}$—$A_{91}$ (wherein $A_{71}$ and $A_{81}$ each independently represent a single bond, an optionally substituted $C_{1-6}$ alkylene group or a carbonyl group; and $A_{91}$ represents a hydrogen atom, a $C_{3-8}$ cycloalkyl group, a group represented by the formula —$NR_{471}R_{481}$, or the formula —$OR_{491}$ (wherein $R_{471}$, $R_{481}$, and $R_{491}$ each independently represent a hydrogen atom or a $C_{1-6}$ alkyl group), or a group represented by the formula:

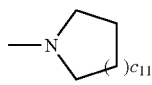

(wherein $c_{11}$ represents 0, 1 or 2))).

19. A compound according to claims 1 or 2, a salt of the compound, or a hydrate of the foregoing, wherein $R_1$ represents a group represented by the formula:

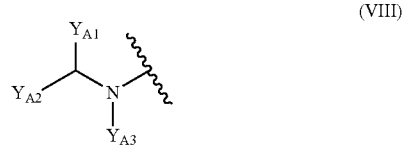

(VIII)

(wherein $Y_{A1}$ and $Y_{A2}$ each independently represent a group represented by the formula —$A_{10}$—$A_{11}$—$A_{12}$ (wherein $A_{10}$ represents a single bond or an optionally substituted $C_{1-6}$ alkylene group; $A_{11}$ represents a single bond, an oxygen atom, a carbonyl group, or a sulfonyl group; and $A_{12}$ represents a hydrogen atom, a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a 5- to 10-membered heteroaryl group, a group represented by the formula —$NR_{A10}R_{A11}$, or the formula —$OR_{A12}$ (wherein, $R_{A10}$, $R_{A11}$ and $R_{A12}$ each independently represent a hydrogen atom, a $C_{1-6}$ alkyl group or a $C_{3-8}$ cycloalkyl group), or a group represented by the formula:

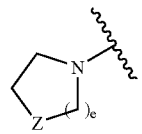

(wherein e represents 1 or 2; and Z represents an oxygen atom or a group represented by the formula —$CR_{X7}R_{X8}$— or the formula —$NR_{X9}$— (wherein $R_{X7}$, $R_{X8}$ and $R_{X9}$ each independently represent a hydrogen atom, a hydroxyl group or a $C_{1-6}$ alkyl group))); and $Y_{A3}$ represents a hydrogen atom or an optionally substituted $C_{1-6}$ alkyl group).

20. A compound according to claim 19, a salt of the compound, or a hydrate of the foregoing, wherein one of $Y_{A1}$ and $Y_{A2}$ in the formula (VIII) represents a hydrogen atom and the other represents a group represented by the formula —$(CH_2)_2$—$A_{13}$—$A_{14}$ (wherein $A_{13}$ represents a single bond, a carbonyl group or a sulfonyl group; and $A_{14}$ represents a $C_{1-6}$ alkyl group, a group represented by the formula —$NR_{A13}R_{A14}$ (wherein $R_{A13}$ and $R_{A14}$ each independently represent a hydrogen atom, a $C_{1-6}$ alkyl group or a $C_{3-8}$ cycloalkyl group), or a group represented by the formula:

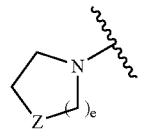

(wherein e represents 1 or 2; and Z represents an oxygen atom or a group represented by the formula —$CR_{X7}R_{X8}$— or the formula —$NR_{X9}$— (wherein $R_{X7}$, $R_{X8}$ and $R_{X9}$ each independently represent a hydrogen atom, a hydroxyl group or a $C_{1-6}$ alkyl group))); and $Y_{A3}$ in the formula (VIII) represents a hydrogen atom.

21. A compound according to claims 1 or 2, a salt of the compound, or a hydrate of the foregoing, wherein $R_1$ represents a group represented by the formulas:

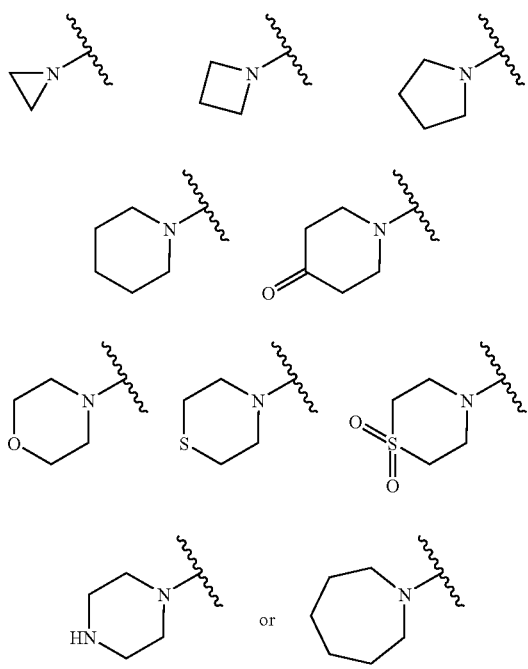

(each of the foregoing members being optionally substituted with a group selected from Substituent Group Alpha, wherein Substituent Group Alpha is a group consisting of a halogen atom, a hydroxyl group, a thiol group, a nitro group, a cyano group, a carboxyl group, an amino group, a $C_{1-6}$ alkyl group, a $C_{3-8}$ cycloalkyl group, and a group represented by the formulas:

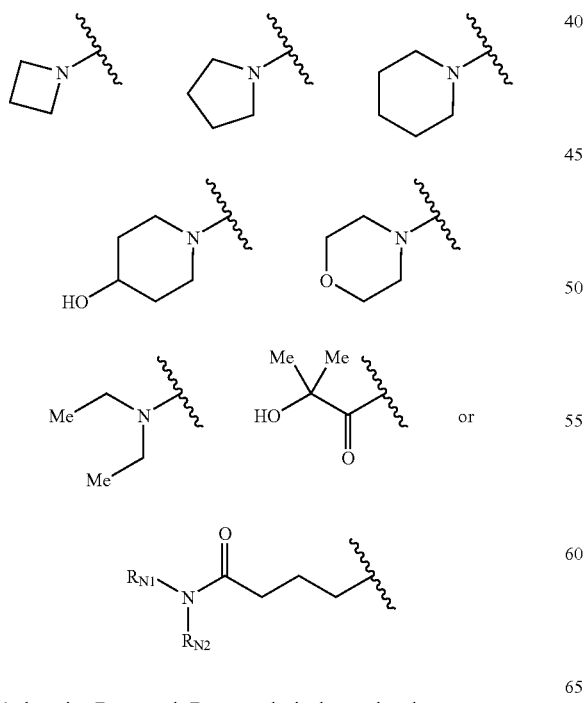

(wherein $R_{N1}$ and $R_{N2}$ each independently represent a hydrogen atom or a $C_{1-6}$ alkyl group)).

22. A compound according to claims 1 or 2, a salt of the compound, or a hydrate of the foregoing, wherein $R_1$ represents a group represented by the formulas:

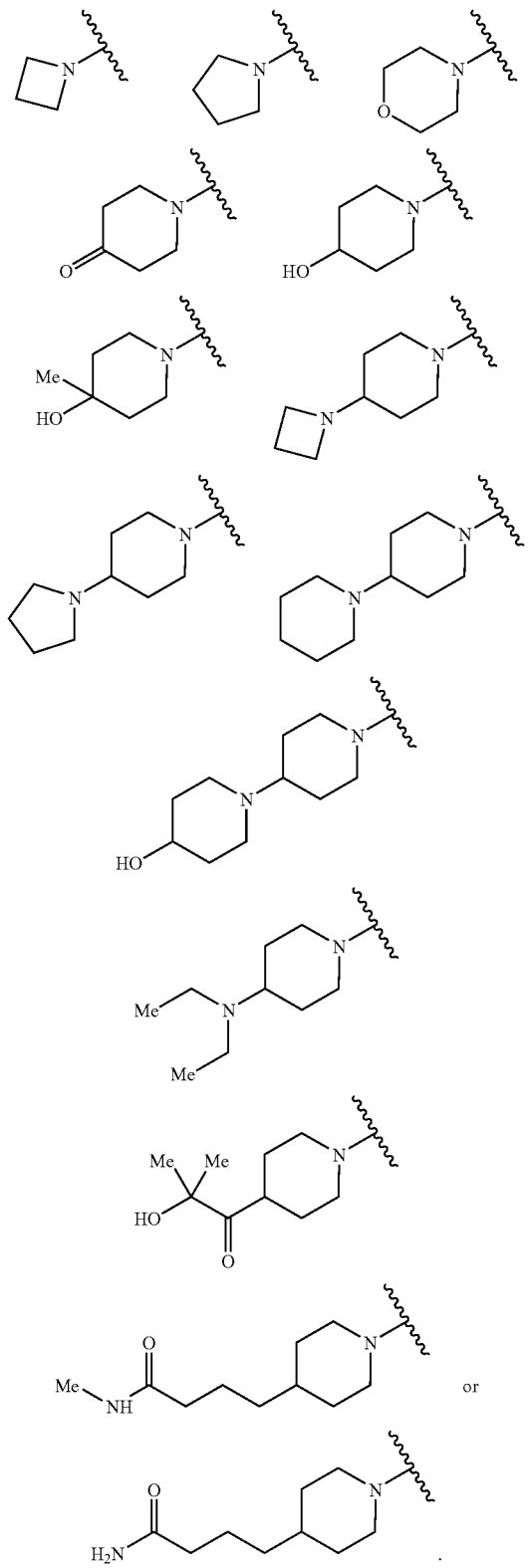

23. A compound according to claims 1 or 2, a salt of the compound, or a hydrate of the foregoing, wherein $R_1$ represents a group represented by the formulas:

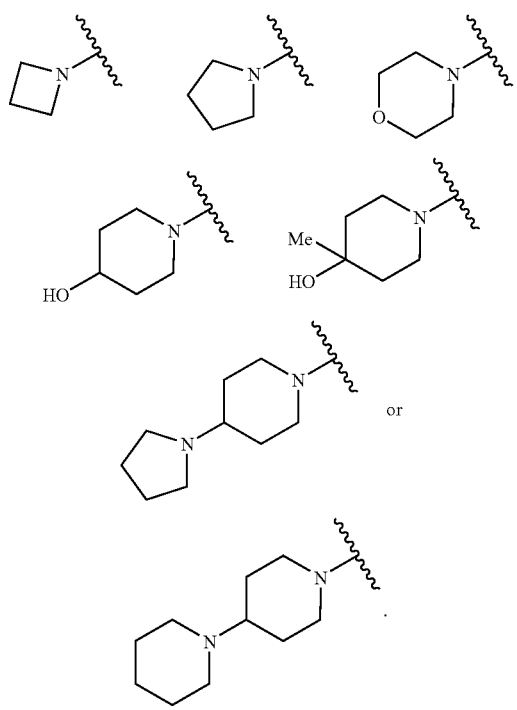

or

24. A compound according to claims 1 or 2, a salt of the compound, or a hydrate of the foregoing, wherein $R_1$ represents a group represented by the formulas:

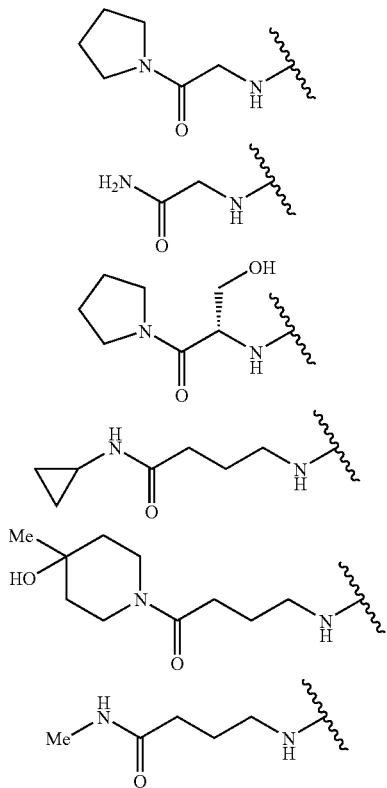

-continued

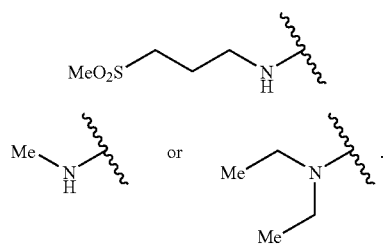

25. A compound according to claim 1 or 2, a salt of the compound, or a hydrate of the foregoing, wherein the compound is represented by the general formula:

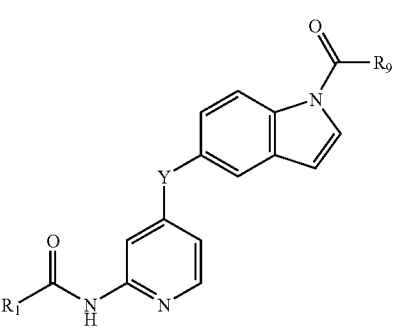

(IX)

(wherein $R_1$ represents a group represented by the formulas:

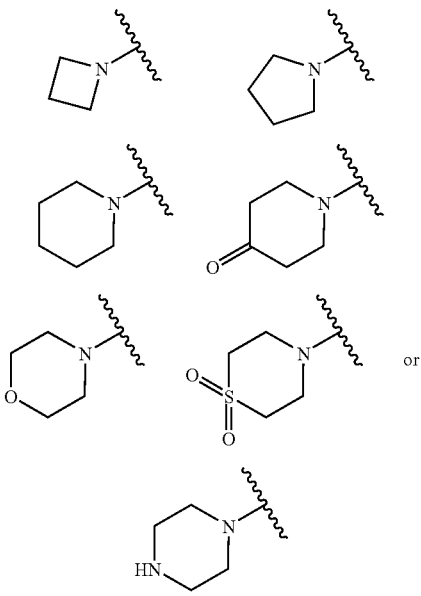

or (each of the foregoing members being optionally substituted with a group selected from Substituent Group Beta, wherein Substituent Group Beta is a group consisting of a hydroxyl group, a $C_{1-6}$ alkyl group, a $C_{3-8}$ cycloalkyl group, and a group represented by the formulas:

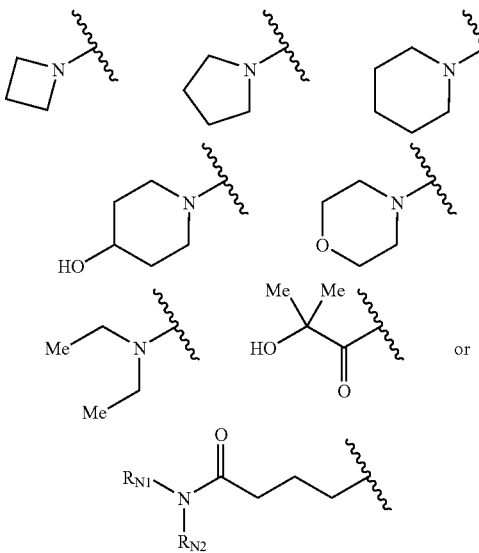

(wherein $R_{N1}$ and $R_{N2}$ each independently represent a hydrogen atom or a $C_{1-6}$ alkyl group)); and $R_9$ represents a group represented by the formula —$NHR_{20}$ (wherein $R_{20}$ represents a methyl group, an ethyl group or a cyclopropyl group)).

26. A compound according to claim 1, a salt of the compound, or a hydrate of the foregoing, wherein the compound is a compound selected from a group consisting of (5) 5-(2-(3-((1R)-1-carbamoyl-2-phenylethyl)ureido)pyridin-4-yloxy)-1H-indole-1-carboxylic acid methylamide;

(6) 5-(2-(3-((1S)-1-carbamoyl-2-phenylethyl)ureido)pyridin-4-yloxy)-1H-indole-1-carboxylic acid methylamide;

(7) 5-(2-(3-(2-oxo-2-(pyrrolidin-1-yl)ethyl)ureido)pyridin-4-yloxy)-1H-indole-1-carboxylic acid methylamide;

(8) 5-(2-(3-(2-(4-hydroxy-4-methylpiperidin-1-yl)-2-oxoethyl)ureido)pyridin-4-yloxy)-1H-indole-1-carboxylic acid methylamide;

(9) 5-(2-(3-((1 S)-1-carbamoylethyl)ureido)pyridin-4-yloxy)-1H-indole-1-carboxylic acid methylamide;

(10) 5-(2-(3-((1S)-1-carbamoyl-3-methylbutyl)ureido)pyridin-4-yloxy)-1H-indole-1-carboxylic acid methylamide;

(11) 5-(2-(3-carbamoylmethylureido)pyridin-4-yloxy)-1H-indole-1-carboxylic acid methylamide;

(12) 5-(2-(3-cyclopropylcarbamoylmethylureido)pyridin-4-yloxy)-1H-indole-1-carboxylic acid methylamide;

(13) 5-(2-(3-((1S)-1-carbamoyl-2-hydroxyethyl)ureido)pyridin-4-yloxy)-1H-indole-1-carboxylic acid methylamide;

(14) 5-(2-(3-((1R)-1-carbamoyl-2-hydroxyethyl)ureido)pyridin-4-yloxy)-1H-indole-1-carboxylic acid methylamide;

(15) (2S)-2-(3-(4-(1-methylcarbamoyl-1H-indol-5-yloxy)pyridin-2-yl)ureido)-1,5-pentanedicarboxylic acid diamide;

(16) (2S)-2-(3-(4-(1-methylcarbamoyl-1H-indol-5-yloxy)pyridin-2-yl)ureido)succinamide;

(17) 5-(2-(3-((1 S)-1-cyclopropylcarbamoyl-2-hydroxyethyl)ureido)pyridin-4-yloxy)-1H-indole-1-carboxylic acid methylamide;

(18) 5-(2-(3-((1 S)-1-hydroxymethyl-2-oxo-2-pyrrolidin-1-ylethyl)ureido)pyridin-4-yloxy)-1H-indole-1-carboxylic acid methylamide;

(19) 5-(2-(3-((1R)-1-hydroxymethyl-2-oxo-2-pyrrolidin-1-ylethyl)ureido)pyridin-4-yloxy)-1H-indole-1-carboxylic acid methylamide;

(20) 5-(2-(3-((1S)-1-hydroxymethyl-2-oxo-2-piperidin-1-ylethyl)ureido)pyridin-4-yloxy)-1H-indole-1-carboxylic acid methylamide;

(21) 5-(2-(3-((1R)-1-hydroxymethyl-2-oxo-2-piperidin-1-ylethyl)ureido)pyridin-4-yloxy)-1H-indole-1-carboxylic acid methylamide;

(22) 5-(2-(3-((1S)-1-hydroxymethyl-2-(4-hydroxypiperidin-1-yl)-2-oxoethyl)ureido)pyridin-4-yloxy)-1H-indole-1-carboxylic acid methylamide;

(23) 5-(2-(3-((1S)-1-hydroxymethyl-2-(morpholin-4-yl)-2-oxoethyl)ureido)pyridin-4-yloxy)-1H-indole-1-carboxylic acid methylamide;

(24) 5-(2-(3-(2-cyclopropylcarbamoylethyl)ureido)pyridin-4-yloxy)-1H-indole-1-carboxylic acid methylamide;

(25) 5-(2-(3-(3-oxo-3-(pyrrolidin-1-yl)propyl)ureido)pyridin-4-yloxy)-1H-indole-1-carboxylic acid methylamide;

(26) 5-(2-(3-(3-(4-hydroxy-4-methylpiperidin-1-yl)-3-oxopropyl)ureido)pyridin-4-yloxy)-1H-indole-1-carboxylic acid methylamide;

(27) N1-ethyl-5-(2-(((2-ethoxyethyl)amino)carbonyl)amino-4-pyridyl)oxy-1H-1-indolecarboxamide;

(28) N1-methyl-5-(2-((4-(2-hydroxy-2-methylpropionyl)piperazin-1-yl)carbonyl)amino-4-pyridyl)oxy-1H-1-indolecarboxamide;

(29) N1-methyl-5-(2-((3-(diethylamino)propylamino)carbonyl)amino-4-pyridyl)oxy-1H-1-indolecarboxamide;

(30) N1-methyl-5-(2-(((3-(4-hydroxypiperidino)propyl)amino)carbonyl)amino-4-pyridyl)oxy-1H-1-indolecarboxamide;

(31) N1-methyl-5-(2-(((3-(4-methylpiperazin-1-yl)propyl)amino)carbonyl)amino-4-pyridyl)oxy-1H-1-indolecarboxamide;

(32) 5-(2-(3-(4-oxo-4-(pyrrolidin-1-yl)butyl)ureido)pyridin-4-yloxy)-1H-indole-1-carboxylic acid methylamide;

(33) 5-(2-(3-(3-(cyclopropylcarbamoyl)propyl)ureido)pyridin-4-yloxy)-1H-indole-1-carboxylic acid methylamide;

(34) 5-(2-(3-(4-(4-hydroxy-4-methylpiperidin-1-yl)-4-oxobutyl)ureido)pyridin-4-yloxy)-1H-indole-1-carboxylic acid methylamide;

(35) 5-(2-(3-(3-(diethylcarbamoyl)propyl)ureido)pyridin-4-yloxy)-1H-indole-1-carboxylic acid methylamide;

(36) 5-(2-(3-(3-(methylcarbamoyl)propyl)ureido)pyridin-4-yloxy)-1H-indole-1-carboxylic acid methylamide;

(37) N1-methyl-5-(2-(pyrrolidin-1-ylcarbonyl)amino-4-pyridyl)oxy-1H-1-indolecarboxamide;

(38) N1-methyl-5-(2-(piperidin-1-ylcarbonyl)amino-4-pyridyl)oxy-1H-1-indolecarboxamide;

(39) N1-methyl-5-(2-((4-hydroxypiperidino)carbonyl)amino-4-pyridyl)oxy-1H-1-indolecarboxamide;

(40) N1-methyl-5-(2-(4-oxopiperidin-1-ylcarbonyl)amino-4-pyridyl)oxy-1H-1-indolecarboxamide;

(41) 5-(2-(((4-hydroxy-4-methylpiperidin-1-yl)carbonyl)amino)pyridin-4-yloxy)-1H-indole-1-carboxylic acid methylamide;

(42) N1-methyl-5-(2-((4-(1-hydroxy-1-methylethyl)piperidino)carbonyl)amino-4-pyridyl)oxy-1H-1-indolecarboxamide;
(43) 5-(2-(((4-(3-methylcarbamoylpropyl)piperidin-1-yl)carbonyl)amino)pyridin-4-yloxy)-1H-indole-1-carboxylic acid methylamide;
(44) 5-(2-(((4-(3-carbamoylpropyl)piperidin-1-yl)carbonyl)amino)pyridin-4-yloxy)-1H-indole-1-carboxylic acid methylamide;
(45) 5-(2-((4-((pyrrolidin-1-yl)carbonyl)piperidin-1-yl)carbonylamino)pyridin-4-yloxy)-1H-indole-1-carboxylic acid methylamide;
(46) N1-methyl-5-(2-(((4-(pyrrolidin-1-yl)piperidin-1-yl)carbonyl)amino)pyridin-4-yloxy)-1H-1-indolecarboxamide;
(47) N1-methyl-5-(2-(((4-(piperidin-1-yl)piperidin-1-yl)carbonyl)amino)pyridin-4-yloxy)-1H-1-indolecarboxamide;
(48) N1-methyl-5-(2-((4-ethylpiperazin-1-yl)carbonyl)amino-4-pyridyl)oxy-1H-1-indolecarboxamide;
(49) N1-methyl-5-(2-((4-(2-hydroxyethyl)piperazin-1-yl)carbonyl)amino-4-pyridyl)oxy-1H-1-indolecarboxamide;
(50) N1-methyl-5-(2-((3-methylsulfonylpropylamino)carbonyl)amino-4-pyridyl)oxy-1H-1-indolecarboxamide;
(51) N1-methyl-5-(2-((4-(2-dimethylaminoacetyl)piperazin-1-yl)carbonyl)amino-4-pyridyl)oxy-1H-1-indolecarboxamide;
(52) N1-methyl-5-(2-((4-cyclohexylpiperazin-1-yl)carbonyl)amino-4-pyridyl)oxy-1H-1-indolecarboxamide;
(53) N4-(4-(1-(methylamino)carbonyl-1H-5-indolyl)oxy-2-pyridyl)-4-morpholinecarboxamide;
(54) N1-methyl-5-(2-((1,1-dioxothiomorpholin-4-ylcarbonyl)amino)pyridin-4-yloxy)-1H-1-indolecarboxamide;
(55) 5-(2-(3-((1R)-1-hydroxymethyl-2-oxo-2-pyrrolidin-1-ylethyl)ureido)pyridin-4-yloxy)-1H-indole-1-carboxylic acid ethylamide;
(56) 5-(2-(3-((1S)-1-hydroxymethyl-2-oxo-2-pyrrolidin-1-ylethyl)ureido)pyridin-4-yloxy)-1H-indole-1-carboxylic acid ethylamide;
(57) 5-(2-(3-((1R)-1-hydroxymethyl-2-oxo-2-pyrrolidin-1-ylethyl)ureido)pyridin-4-yloxy)-1H-indole-1-carboxylic acid ethylamide;
(58) 5-(2-(3-((1S)-1-hydroxymethyl-2-oxo-2-piperidin-1-ylethyl)ureido)pyridin-4-yloxy)-1H-indole-1-carboxylic acid ethylamide;
(59) 5-(2-(3-(2-(4-hydroxy-4-methylpiperidin-1-yl)-2-oxoethyl)ureido)pyridin-4-yloxy)-1H-indole-1-carboxylic acid ethylamide;
(60) N1-ethyl-5-(2-((((1-methyl-4-piperidyl)methyl)amino)carbonyl)amino-4-pyridyl)oxy-1H-1-indolecarboxamide;
(61) N1-ethyl-5-(2-(((2-diethylamino)ethyl)amino)carbonyl)amino-4-pyridyl)oxy-1H-1-indolecarboxamide;
(62) N1-ethyl-5-(2-(((2-(morpholin-4-yl)ethyl)amino)carbonyl)amino-4-pyridyl)oxy-1H-1-indolecarboxamide;
(63) N1-ethyl-5-(2-(((2-(4-hydroxypiperidino)ethyl)amino)carbonyl)amino-4-pyridyl)oxy-1H-1-indolecarboxamide;
(64) N1-methyl-5-(2-(((2-(4-hydroxypiperidino)ethyl)amino)carbonyl)amino-4-pyridyl)oxy-1H-1-indolecarboxamide;
(65) N1-ethyl-5-(2-((3-(diethylamino)propylamino)carbonyl)amino-4-pyridyl)oxy-1H-1-indolecarboxamide;
(66) N1-ethyl-5-(2-(((3-(morpholin-4-yl)propyl)amino)carbonyl)amino-4-pyridyl)oxy-1H-1-indolecarboxamide;
(67) N1-ethyl-5-(2-(((3-(4-methylpiperazin-1-yl)propyl)amino)carbonyl)amino-4-pyridyl)oxy-1H-1-indolecarboxamide;
(68) N1-cyclopropyl-5-(2-(((4-(pyrrolidin-1-yl)piperidin-1-yl)carbonyl)amino)pyridin-4-yloxy)-1H-1-indolecarboxamide;
(69) 5-(2-(3-((1R)-1-hydroxymethyl-2-oxo-2-pyrrolidin-1-ylethyl)ureido)pyridin-4-yloxy)-1H-indole-1-carboxylic acid cyclopropylamide;
(70) 5-(2-(3-((1 S)-1-hydroxymethyl-2-oxo-2-pyrrolidin-1-ylethyl)ureido)pyridin-4-yloxy)-1H-indole-1-carboxylic acid cyclopropylamide;
(71) 5-(2-(3-(2-oxo-2-(pyrrolidin-1-yl)ethyl)ureido)pyridin-4-yloxy)-1H-indole-1-carboxylic acid cyclopropylamide;
(72) 5-(2-(3-(3-oxo-3-(pyrrolidin-1-yl)propyl)ureido)pyridin-4-yloxy)-1H-indole-1-carboxylic acid cyclopropylamide;
(73) 5-(2-(3-((1R)-1-hydroxymethyl-2-oxo-2-piperidin-1-ylethyl)ureido)pyridin-4-yloxy)-1H-indole-1-carboxylic acid cyclopropylamide;
(74) 5-(2-(3-((1 S)-1-hydroxymethyl-2-oxo-2-piperidin-1-ylethyl)ureido)pyridin-4-yloxy)-1H-indole-1-carboxylic acid cyclopropylamide;
(75) N1-phenyl-5-(2-(((3-(diethylamino)propyl)amino)carbonyl)amino-4-pyridyl)oxy-1H-1-indolecarboxamide;
(76) N1-phenyl-5-(2-(((3-(4-methylpiperazin-1-yl)propyl)amino)carbonyl)amino-4-pyridyl)oxy-1H-1-indolecarboxamide;
(77) N1-ethyl-5-(2-(((4-(pyrrolidin-1-yl)piperidin-1-yl)carbonyl)amino)pyridin-4-yloxy)-1H-1-indolecarboxamide;
(78) 5-(2-(((4-hydroxy-4-methylpiperidin-1-yl)carbonyl)amino)pyridin-4-yloxy)-1H-indole-1-carboxylic acid ethylamide;
(79) N1-ethyl-5-(2-((4-hydroxypiperidin-1-yl)carbonyl)amino-4-pyridyl)oxy-1H-1-indolecarboxamide;
(80) N1-ethyl-5-(2-(piperidin-1-ylcarbonyl)amino-4-pyridyl)oxy-1H-1-indolecarboxamide;
(81) N1-ethyl-5-((2-((pyrrolidin-1-ylcarbonyl)amino)-4-pyridyl)oxy)-1H-1-indolecarboxamide;
(82) N4-(4-((1-(ethylamino)carbonyl-1H-5-indolyl)oxy)-2-pyridyl)-4-morpholinecarboxamide;
(83) N1-ethyl-5-(2-((1,1-dioxothiomorpholin-4-ylcarbonyl)amino)pyridin-4-yloxy)-1H-1-indolecarboxamide;
(84) N1-ethyl-5-(2-((methoxylamino)carbonyl)amino-4-pyridyl)oxy-1H-1-indolecarboxamide;
(85) N1-cyclopropyl-5-(2-((4-hydroxypiperidino)carbonyl)amino-4-pyridyl)oxy-1H-1-indolecarboxamide;
(86) N1-cyclopropyl-5-(2-(((4-hydroxy-4-methylpiperidin-1-yl)carbonyl)amino)pyridin-4-yloxy)-1H-1-indolecarbox-amide;
(87) N4-(4-(1-(cyclopropylamino)carbonyl-1H-5-indolyl)oxy-2-pyridyl)-4-morpholinecarboxamide;
(88) N1-cyclopropyl-5-(2-((pyrrolidin-1-ylcarbonyl)amino)-4-pyridyl)oxy-1H-1-indolecarboxamide;
(89) N1-cyclopropyl-5-(2-(piperidin-1-ylcarbonyl)amino-4-pyridyl)oxy-1H-1-indolecarboxamide;
(90) N4-(4-(1-(cyclopentylamino)carbonyl-1H-5-indolyl)oxy-2-pyridyl)-4-morpholinecarboxamide;
(91) 5-(2-(((4-hydroxypiperidin-1-yl)carbonyl)amino)pyridin-4-yloxy)-1H-indole-1-carboxylic acid cyclopentylamide;

(92) N1-cyclopentyl-5-(2-((4-(pyrrolidin-1-yl)piperidin-1-ylcarbonyl)amino)pyridin-4-yloxy)-1H-1-indolecarboxamide;

(93) N1-(3-methylbutyl)-5-(2-(((4-(pyrrolidin-1-yl)piperidin-1-yl)carbonyl)amino)pyridin-4-yloxy)-1H-1-indolecarboxamide;

(94) N1-(3-methylbutyl)-5-(2-((4-(hydroxypiperidino)carbonyl)amino-4-pyridyl)oxy-1H-1-indolecarboxamide;

(95) N4-(4-(1-(((3-methylbutyl)amino)carbonyl-1H-5-indolyl)oxy-2-pyridyl)-4-morpholinecarboxamide;

(96) N1-(1-ethylpropyl)-5-(2-(((4-(pyrrolidin-1-yl)piperidin-1-yl)carbonyl)amino)pyridin-4-yloxy)-1H-1-indolecarboxamide;

(97) N1-(1-ethylpropyl)-5-(2-((4-hydroxypiperidino)carbonyl)amino-4-pyridyl)oxy-1H-1-indolecarboxamide;

(98) N4-(4-(1-((1-ethylpropyl)amino)carbonyl-1H-5-indolyl)oxy-2-pyridyl)-4-morpholinecarboxamide;

(99) N4-(4-(1-((1-pentyl)amino)carbonyl-1H-5-indolyl)oxy-2-pyridyl)-4-morpholinecarboxamide;

(100) N1-(1-pentyl)-5-(2-(((4-hydroxypiperidin-1-yl)carbonyl)amino)pyridin-4-yloxy)-1H-1-indolecarboxamide;

(101) N1-(1-pentyl)-5-(2-((4-(pyrrolidin-1-yl)piperidin-1-ylcarbonyl)amino)pyridin-4-yloxy)-1H-1-indolecarboxamide;

(116) N1-methyl-5-(2-((methylamino)carbonyl)amino-4-pyridyl)oxy-1H-1-indolecarboxamide;

(117) N1-methyl-5-(2-((diethylamino)carbonyl)amino-4-pyridyl)oxy-1H-1-indolecarboxamide;

(118) N1-(2-propynyl)-5-(2-((pyrrolidin-1-yl)carbonyl)amino-4-pyridyl)oxy-1H-1-indolecarboxamide;

(119) N1-methyl-5-(2-(azetidin-1-ylcarbonyl)amino-4-pyridyl)oxy-1H-1-indolecarboxamide;

(120) N1-ethyl-5-(2-(azetidin-1-ylcarbonyl)amino-4-pyridyl)oxy-1H-1-indolecarboxamide;

(121) N1-cyclopropyl-5-(2-(azetidin-1-ylcarbonyl)amino-4-pyridyl)oxy-1H-1-indolecarboxamide;

(122) N1-methyl-5-(2-(((4-(morpholin-4-yl)piperidin-1-yl)carbonyl)amino)pyridin-4-yloxy)-1H-1-indolecarboxamide;

(123) N1-methyl-5-(2-(((4-(azetidin-1-yl)piperidin-1-yl)carbonyl)amino)pyridin-4-yloxy)-1H-1-indolecarboxamide;

(124) N1-methyl-5-(2-(((4-(diethylamino)piperidin-1-yl)carbonyl)amino)pyridin-4-yloxy)-1H-1-indolecarboxamide;

(125) N1-methyl-5-(2-(((4-(4-hydroxypiperidin-1-yl)piperidin-1-yl)carbonyl)amino)pyridin-4-yloxy)-1H-1-indolecarboxamide; and (126) N1-propyl-5-(2-(pyrrolidin-1-ylcarbonyl)amino-4-pyridyl)oxy-1H-1-indolecarboxamide.

27. A compound according to claim 1, a salt of the compound, or a hydrate of the foregoing, wherein the compound is a compound selected from a group consisting of (1) 5-(2-(3-(2-oxo-2-(pyrrolidin-1-yl)ethyl)ureido)pyridin-4-yloxy)-1H-indole-1-carboxylic acid methylamide;

(2) 5-(2-(3-carbamoylmethylureido)pyridin-4-yloxy)-1H-indole-1-carboxylic acid methylamide;

(3) 5-(2-(3-((1S)-1-hydroxymethyl-2-oxo-2-pyrrolidin-1-ylethyl)ureido)pyridin-4-yloxy)-1H-indole-1-carboxylic acid methylamide;

(4) N1-methyl-5-(2-((4-(2-hydroxy-2-methylpropionyl)piperazin-1-yl)carbonyl)amino-4-pyridyl)oxy-1H-1-indolecarboxamide;

(5) 5-(2-(3-(4-oxo-4-(pyrrolidin-1-yl)butyl)ureido)pyridin-4-yloxy)-1H-indole-1-carboxylic acid methylamide;

(6) 5-(2-(3-(3-(cyclopropylcarbamoyl)propyl)ureido)pyridin-4-yloxy)-1H-indole-1-carboxylic acid methylamide;

(7) 5-(2-(3-(4-(4-hydroxy-4-methylpiperidin-1-yl)-4-oxobutyl)ureido)pyridin-4-yloxy)-1H-indole-1-carboxylic acid methylamide;

(8) 5-(2-(3-(3-(methylcarbamoyl)propyl)ureido)pyridin-4-yloxy)-1H-indole-1-carboxylic acid methylamide;

(9) N1-methyl-5-(2-(pyrrolidin-1-ylcarbonyl)amino-4-pyridyl)oxy-1H-1-indolecarboxamide;

(10) N1-methyl-5-(2-((4-hydroxypiperidino)carbonyl)amino-4-pyridyl)oxy-1H-1-indolecarboxamide;

(11) N1-methyl-5-(2-(4-oxopiperidin-1-ylcarbonyl)amino-4-pyridyl)oxy-1H-1-indolecarboxamide;

(12) 5-(2-(((4-hydroxy-4-methylpiperidin-1-yl)carbonyl)amino)pyridin-4-yloxy)-1H-indole-1-carboxylic acid methylamide;

(13) 5-(2-(((4-(3-methylcarbamoylpropyl)piperidin-1-yl)carbonyl)amino)pyridin-4-yloxy)-1H-indole-1-carboxylic acid methylamide;

(14) 5-(2-(((4-(3-carbamoylpropyl)piperidin-1-yl)carbonyl)amino)pyridin-4-yloxy)-1H-indole-1-carboxylic acid methylamide;

(15) N1-methyl-5-(2-(((4-(pyrrolidin-1-yl)piperidin-1-yl)carbonyl)amino)pyridin-4-yloxy)-1H-1-indolecarboxamide;

(16) N1-methyl-5-(2-(((4-(piperidin-1-yl)piperidin-1-yl)carbonyl)amino)pyridin-4-yloxy)-1H-1-indolecarboxamide;

(17) N1-methyl-5-(2-((3-methylsulfonylpropylamino)carbonyl)amino-4-pyridyl)oxy-1H-1-indolecarboxamide;

(18) N4-(4-(1-(methylamino)carbonyl-1H-5-indolyl)oxy-2-pyridyl)-4-morpholinecarboxamide;

(19) N1-cyclopropyl-5-(2-(((4-(pyrrolidin-1-yl)piperidin-1-yl)carbonyl)amino)pyridin-4-yloxy)-1H-1-indolecarboxamide;

(20) 5-(2-(((4-hydroxy-4-methylpiperidin-1-yl)carbonyl)amino)pyridin-4-yloxy)-1H-indole-1-carboxylic acid ethylamide;

(21) N1-ethyl-5-(2-((4-hydroxypiperidin-1-yl)carbonyl)amino-4-pyridyl)oxy-1H-1-indolecarboxamide;

(22) N1-ethyl-5-((2-((pyrrolidin-1-ylcarbonyl)amino)-4-pyridyl)oxy)-1H-1-indolecarboxamide;

(23) N4-(4-((1-(ethylamino)carbonyl-1H-5-indolyl)oxy)-2-pyridyl)-4-morpholinecarboxamide;

(24) N1-cyclopropyl-5-(2-((pyrrolidin-1-ylcarbonyl)amino)-4-pyridyl)oxy-1H-1-indolecarboxamide;

(26) N1-methyl-5-(2-((methylamino)carbonyl)amino-4-pyridyl)oxy-1H-1-indolecarboxamide;

(27) N1-methyl-5-(2-((diethylamino)carbonyl)amino-4-pyridyl)oxy-1H-1-indolecarboxamide;

(28) N1-(2-propynyl)-5-(2-((pyrrolidin-1-yl)carbonyl)amino-4-pyridyl)oxy-1H-1-indolecarboxamide;

(29) N1-methyl-5-(2-(azetidin-1-ylcarbonyl)amino-4-pyridyl)oxy-1H-1-indolecarboxamide;

(30) N1-ethyl-5-(2-(azetidin-1-ylcarbonyl)amino-4-pyridyl)oxy-1H-1-indolecarboxamide;

(31) N1-cyclopropyl-5-(2-(azetidin-1-ylcarbonyl)amino-4-pyridyl)oxy-1H-1-indolecarboxamide;

(32) N1-methyl-5-(2-(((4-(morpholin-4-yl)piperidin-1-yl)carbonyl)amino)pyridin-4-yloxy)-1H-1-indolecarboxamide;

(33) N1-methyl-5-(2-(((4-(azetidin-1-yl)piperidin-1-yl)carbonyl)amino)pyridin-4-yloxy)-1H-1-indolecarboxamide;

(34) N1-methyl-5-(2-(((4-(diethylamino)piperidin-1-yl)carbonyl)amino)pyridin-4-yloxy)-1H-1-indolecarboxamide;

(35) N1-methyl-5-(2-(((4-(4-hydroxypiperidin-1-yl)piperidin-1-yl)carbonyl)amino)pyridin-4-yloxy)-1H-1-indolecarboxamide; and

(36) N1-propyl-5-(2-(pyrrolidin-1-ylcarbonyl)amino-4-pyridyl)oxy-1H-1-indolecarboxamide.

28. A compound according to claim 1, a salt of the compound, or a hydrate of the foregoing, wherein the compound is a compound selected from a group consisting of (1) 5-(2-(((4-hydroxy-4-methylpiperidin-1-yl)carbonyl)amino)pyridin-4-yloxy)-1H-indole-1-carboxylic acid methylamide;

(2) N1-methyl-5-(2-((4-hydroxypiperidino)carbonyl)amino-4-pyridyl)oxy-1H-1-indolecarboxamide;

(3) N1-methyl-5-(2-(((4-(pyrrolidin-1-yl)piperidin-1-yl)carbonyl)amino)pyridin-4-yloxy)-1H-1-indolecarboxamide;

(4) N1-methyl-5-(2-(((4-(piperidin-1-yl)piperidin-1-yl)carbonyl)amino)pyridin-4-yloxy)-1H-1-indolecarboxamide; and (5) N4-(4-(1-(methylamino)carbonyl-1H-5-indolyl)oxy-2-pyridyl)-4-morpholinecarboxamide.

29. A pharmaceutical composition comprising a compound according to claims 1 or 2 and a pharmaceutical adjuvant.

30. A compound according to claim 1, a salt or hydrate thereof, wherein the compound is N1-methyl-5-(2-(((4-(pyrrolidin-1-yl)piperidin-1-yl)carbonyl)amino)pyridin-4-yloxy)-1H-1-indolecarboxamide.

31. A compound according to claim 1, a salt or hydrate thereof, wherein the compound is N1-methyl-5-(2-(((4-(piperidin-1-yl)piperidin-1-yl)carbonyl)amino)pyridin-4-yloxy)-1H-1-indolecarboxamide.

32. A compound according to claim 1, a salt or hydrate thereof, wherein the compound is N4-(4-(1-(methylamino)carbonyl-1H-5-indolyl)oxy-2-pyridyl)-4-morpholinecarboxamide.

* * * * *